United States Patent
Gahman et al.

(10) Patent No.: US 10,752,612 B2
(45) Date of Patent: Aug. 25, 2020

(54) PLK4 INHIBITORS

(71) Applicant: LUDWIG INSTITUTE FOR CANCER RESEARCH LTD, Zurich (CH)

(72) Inventors: Timothy Gahman, Encinitas, CA (US); Andrew Shiau, San Diego, CA (US)

(73) Assignee: LUDWIG INSTITUTE FOR CANCER RESEARCH LTD, Zurich (CH)

(*) Notice: Subject to any disclaimer, the term of this patent is extended or adjusted under 35 U.S.C. 154(b) by 0 days.

(21) Appl. No.: 15/567,012

(22) PCT Filed: Apr. 15, 2016

(86) PCT No.: PCT/IB2016/000594
§ 371 (c)(1),
(2) Date: Oct. 16, 2017

(87) PCT Pub. No.: WO2016/166604
PCT Pub. Date: Oct. 20, 2016

(65) Prior Publication Data
US 2018/0086739 A1    Mar. 29, 2018

Related U.S. Application Data

(60) Provisional application No. 62/149,292, filed on Apr. 17, 2015.

(51) Int. Cl.
*C07D 403/12* (2006.01)
*C07D 451/14* (2006.01)
*C07D 417/12* (2006.01)
*C07D 401/14* (2006.01)

(52) U.S. Cl.
CPC ......... *C07D 403/12* (2013.01); *C07D 401/14* (2013.01); *C07D 417/12* (2013.01); *C07D 451/14* (2013.01)

(58) Field of Classification Search
CPC .................................................. C07D 403/12
See application file for complete search history.

(56) References Cited

U.S. PATENT DOCUMENTS

| 7,531,536 B2 | 5/2009 | Bebbington et al. |
| 7,951,820 B2 | 5/2011 | Bebbington et al. |
| 8,455,507 B2 | 6/2013 | Studley et al. |

FOREIGN PATENT DOCUMENTS

| JP | 2007-145828 A | | 6/2007 | |
| JP | 2007145828 A | * | 6/2007 | |
| WO | WO-2004/000833 A1 | | 12/2003 | |
| WO | WO-2008/013807 A2 | | 1/2008 | |
| WO | WO-2008/013807 A3 | | 1/2008 | |
| WO | WO-2008/115973 A2 | | 9/2008 | |
| WO | WO-2008/115973 A3 | | 9/2008 | |
| WO | WO-2008/131103 A2 | | 10/2008 | |
| WO | WO-2008/131103 A3 | | 10/2008 | |
| WO | WO-2008131103 A2 | * | 10/2008 | ............. C12Q 1/485 |

OTHER PUBLICATIONS

Adams, P.D. et al. (Feb. 2010, e-published Jan. 22, 2010). "PHENIX: a comprehensive Python-based system for macromolecular structure solution," *Acta Crystallogr D Biol Crystallogr* 66(Pt 2):213-221.
Akritopoulou-Zanze, I et al. (Mar. 2009, e-published Jan. 21, 2009). "Kinase-targeted libraries: the design and synthesis of novel, potent, and selective kinase inhibitors," *Drug Discov Today* 14(5-6):291-297.
Bartolini, F. et al. (Oct. 15, 2006). "Generation of noncentrosomal microtubule arrays," *J Cell Sci* 119(Pt 20):4155-4163.
Basto, R. et al. (Jun. 30, 2006). "Flies without centrioles," *Cell* 125(7):1375-1386.
Bazzi, H. et al. (Apr. 15, 2014, e-published Mar. 31, 2014). "Acentriolar mitosis activates a p53-dependent apoptosis pathway in the mouse embryo," *PNAS USA* 111(15):E1491-1500.
Bebbington, D. et al. (Jul. 1, 2009, e-published May 3, 2009). "The discovery of the potent aurora inhibitor MK-0457 (VX-680)," *Bioorg Med Chem Lett* 19(13):3586-3592.
Berdougo, E. et al. (2009). "Functional dissection of mitotic regulators through gene targeting in human somatic cells," *Methods Mol Biol* 545:21-37.
Bettincourt-Dias, M. et al. (Dec. 20, 2005, e-published Dec. 1, 2005). "SAK/PLK4 is required for centriole duplication and flagella development," *Curr Biol* 15(24):2199-2207.
Blaydes, J.P. et al. (Feb. 2001, e-published Nov. 14, 2000). "Stoichiometric phosphorylation of human p53 at Ser315 stimulates p53-dependent transcription," *J Biol Chem* 276(7):4699-4708.
Brito, D.A. et al. (Feb. 2012, e-published Feb. 8, 2012). "Deconstructing the centriole: structure and number control," *Curr Opin Cell Biol* 24(1):4-13.
CAS Registry No. 1292015-89-4, (Apr. 9, 2011), 1 page.
CAS Registry No. 1303731-78-3 (Jun. 1, 2011), 1 page.
CAS Registry No. 1513691-66-1 (Jan. 7, 2014), 1 page.
CAS Registry No. 2007:640321 (2007), 2 pages.
Cheng, Y. et al. (Dec. 1973). "Relationship between the inhibition constant (K1) and the concentration of inhibitor which causes 50 per cent inhibition (I50) of an enzymatic reaction," *Biochem Pharmacol* 22(23):3099-3108.
Copeland, R.A. et al. (Oct. 20, 1995). "Recombinant human dihydroorotate dehydrogenase: expression, purification, and characterization of a catalytically functional truncated enzyme," *Arch Biochem Biophys* 323(10):79-86.
Cox, M.L. et al. (Mar. 2010). "Phosphorylation of serine 392 in p53 is a common and integral event during p53 induction by diverse stimuli," *Cell Signal* 22(3):564-571.
Davis, M.I. et al. (Oct. 30, 2011). "Comprehensive analysis of kinase inhibitor selectivity," *Nat Biotechnol* 29(11):1046-1051.

(Continued)

*Primary Examiner* — Mark L Shibuya
*Assistant Examiner* — Laura M Daniel
(74) *Attorney, Agent, or Firm* — Mintz, Levin, Cohn, Ferris, Glovsky and Popeo, P.C.; Irina E. Britva

(57) ABSTRACT

Provided herein, inter alia, are compounds and methods for inhibiting PLK4 and for treating cancer in a subject in need thereof.

20 Claims, 37 Drawing Sheets

Specification includes a Sequence Listing.

(56) References Cited

OTHER PUBLICATIONS

Dehring, D.A. et al. (Oct. 14, 2013, e-published Sep. 26, 2013). "Deuterosome-mediated centriole biogenesis," *Dev Cell* 27(1):103-112.
Drummond, I.A. et al. (Feb. 2012, e-published Jan. 4, 2012). "Cilia functions in development," *Curr Opin Cell Biol* 24(1):24-30.
Firat-Karalar, E.N. et al (2014). "The centriole duplication cycle," *Philosophical Transactions of The Royal Society B* 369:20130460.
Ganem, N.J. et al. (Jul. 9, 2009, e-published Jun. 7, 2009). "A mechanism linking extra centrosomes to chromosomal instability," *Nature* 460(7252):278-282.
Ganem, N.J. et al. (Aug. 14, 2014). "Cytokinesis failure triggers hippo tumor suppressor pathway activation," *Cell* 158(4):833-848.
Godinho, S.A. et al. (Jun. 5, 2014, e-published Apr. 13, 2014). "Oncogene-like induction of cellular invasion from centrosome amplification," *Nature* 510(7503):167-171.
Godinho, S.A. et al. (Sep. 5, 2014). "Causes and consequences of centrosome abnormalities in cancer," *Philos Trans R Soc Lond B Biol Sci* 369(1650).
Gorbsky, G.J. (Nov. 18, 2013). "Cohesion fatigue," *Curr Biol* 23(22):R986-R988.
Habedanck, R. et al. (Nov. 2005). "The Polo kinase Plk4 functions in centriole duplication," *Nat Cell Biol* 7(11):140-1146.
Higashimoto, Y. et al. (Jul. 28, 2000). "Human p53 is phosphorylated on serines 6 and 9 in response to DNA damage-inducing agents," *J Biol Chem* 275(30):23199-23203.
Holland, A.J. et al. (Jan. 25, 2010). "Polo-like kinase 4 kinase activity limits centrosome overduplication by autoregulating its own stability," *J Cell Biol* 188(2):191-198.
International Search Report dated Sep. 19, 2016 for PCT Application No. PCT/IB2016/000594, filed Apr. 15, 2016, 9 pages.
Izquierdo, D. et al. (Aug. 21, 2014, e-published Aug. 14, 2014). "Stabilization of cartwheel-less centrioles for duplication requires CEP295-mediated centriole-to-centrosome conversion," *Cell Rep* 8(4):957-965.
Jenkins, L.M. et al. (Aug. 2012, e-published Apr. 12, 2012). "p53 N-terminal phosphorylation: a defining layer of complex regulation," *Carcinogensis* 33(8):1441-1449.
Johnson, E.F. et al. (Aug. 21, 2007, e-published Jul. 27, 2007). "Pharmacological and functional comparison of the polo-like kinase family: insight into inhibitor and substrate specificity," *Biochemistry* 46(33):9551-9563.
Kabsch, W. (Feb. 2010, e-published Jan. 22, 2010). "XDS," *Acta Crystallogr D Biol Crystallogr* 66(Pt 2):125-132.
Karplus, P.A. et al. (May 25, 2012). "Linking crystallographic model and data quality," *Science* 336(6084):1030-1033.
Khodjakov, A. et al. (Apr. 2, 2001). "Centrosomes enhance the fidelity of cytokinesis in vertebrates and are required for cell cycle progression," *J Cell Biol* 153(1):237-242.
Kleylein-Sohn, J. et al. (Aug. 2007). "Plk4-induced centriole biogenesis in human cells," *Dev Cell* 13(2):190-202.
Kothe, M. et al. (Dec. 2007, e-published Nov. 13, 2007). "Selectivity-determining residues in Plk1," *Chem Biol Drug Des* 70(6):540-546.
Lakin, N.D. et al. (Dec. 13, 1999). "Regulation of p53 in response to DNA damage," *Oncogene* 18(53):7644-7655.
Lawo, S. et al. (Nov. 2012, e-published Oct. 21, 2012). "Subdiffraction imaging of centrosomes reveals higher-order organizational features of pericentriolar material," *Nat Cell Biol* 14(11):1148-1158.
Leonhardt, H. et al. (Apr. 17, 2000). "Dynamics of DNA replication factories in living cells," *J Cell Biol* 149(2):271-280.
Mason, J.M. et al. (Aug. 2014, e-published Jul. 17, 2014). "Functional characterization of CFI-400945, a Polo-like kinase 4 inhibitor, as a potential anticancer agent," *Cancer Cell* 26(2):163-176.
Mccoy, A.J. et al. (Aug. 1, 2007, e-published Jul. 13, 2007). "Phaser crystallographic software," *J Appl Crystallogr* 40(Pt 4):658-674.
Mueller, K. et al. (1988). "Complex Heterocyclic Structures—A Challenge for Computer-Assisted Molecular Modeling," *Bull Soc Chim Belg* 97:655-667.
Nigg, E.A. et al. (Aug. 1, 2014, e-published Jun. 18, 2014). "The centrosome duplication cycle in health and disease," *FEBS Lett* 588(15):2366-2372.
O'Connell, K.F. et al. (May 18, 2001). "The C. elegans zyg-1 gene encodes a regulator of centrosome duplication with distinct maternal and paternal roles in the embryo," *Cell* 105(4):547-558.
Peel, N. et al. (May 15, 2007, e-published May 3, 2007). "Overexpressing centriole-replication proteins in vivo induces centriole overduplication and de novo formation," *Curr Biol* 17(10):834-843.
Ran, F.A. et al. (Nov. 2013, e-published Oct. 24, 2013). "Genome engineering using the CRISPR-Cas9 system," *Nat Protoc* 8(11):2281-2308.
Rios, R.M. (Sep. 5, 2014). "The centrosome-Golgi apparatus nexus," *Philos Trans R Soc Lond B Biol Sci* 369(1650).
Sakaguchi, K. et al. (Sep. 15, 1998). "DNA damage activates p53 through a phosphorylation-acetylation cascade," *Genes Dev* 12(18):2831-2841.
Sampson, P.B. et al. (Jan. 8, 2015). "The discovery of Polo-like kinase 4 inhibitors: identification of (1R,2S).2-(3-((E).4-(((cis).2,6-dimethylmorpholino)methyl)styryl). 1H.indazol-6-yl)-5'-methoxyspiro[cyclopropane-1,3'-indolin]-2'-one (CFI-400945) as a potent, orally active antitumor agent." *J Med Chem* 58(1):147-169.
Schatten, H. (Jun. 2008, e-published Apr. 24, 2008). "The mammalian centrosome and its functional significance," *Histochem Cell Biol* 129(6):667-686.
Shen, H. et al. (2011). "Pharmacologic activation of p53 by small-molecule MDM2 antagonists," *Curr Pharm Des* 17(6):560-568.
Shieh, S.Y. et al. (Oct. 31, 1997). "DNA damage-induced phosphorylation of p53 alleviates inhibition by MDM2," *Cell* 91(3):325-334.
Silkworth, W.T. et al. (Aug. 10, 2009). "Multipolar spindle pole coalescence is a major source of kinetochore mis-attachment and chromosome mis-segregation in cancer cells," *PLoS One* 4(8):e6564.
Sir, J.H. et al. (Dec. 9, 2013, e-published Dec. 2, 2013). "Loss of centrioles causes chromosomal instability in vertebrate somatic cells," *J Cell Biol* 203(5):747-756.
Sloane, D.A. et al. (Jun. 18, 2010). "Drug-resistant aurora A mutants for cellular target validation of the small molecule kinase inhibitors MLN8054 and MLN8237," *ACS Chem Biol* 5(6):563-576.
Sonnen, K.F. et al. (2012). "3D-structured illumination microscopy provides novel insight into architecture of human centrosomes," *Biology Open* 1 965-976.
Stiess, M. et al. (Feb. 5, 2010, e-published Jan. 7, 2010). "Axon extension occurs independently of centrosomal microtubule nucleation," *Science* 327(5966):704-707.
Stubbs, J.L. et al. (Jan. 8, 2012). "Multicilin promotes centriole assembly and ciliogenesis during multiciliate cell differentiation," *Nat Cell Biol* 14(2):140-147.
Sumigray, K.D. et al. (Sep. 1, 2011). "Control of cortical microtubule organization and desmosome stability by centrosomal proteins," *Bioarchitecture* 1(5):221-224.
Uetake, Y. et al. (Jan. 15, 2007). "Cell cycle progression and de novo centriole assembly after centrosomal removal in untransformed human cells," *J Cell Biol* 176(2):173-182.
Uetake, Y. et al. (Sep. 28, 2010, e-published Sep. 9, 2010). "Prolonged prometaphase blocks daughter cell proliferation despite normal completion of mitosis," *Curr Biol* 20(18):1666-1671.
Winn, M.D. et al. (Apr. 2011, e-published Mar. 18, 2011). "Overview of the CCP4 suite and current developments," *Acta Crystallogr D Biol Crystallogr* 67 (Pt 4):235-242.
Written Opinion dated Sep. 19, 2016 for PCT Application No. PCT/IB2016/000594, filed Apr. 15, 2016, 9 pages.
Yang, Z. et al. (May 2014, e-published Feb. 18, 2014). "Screening with a novel cell-based assay for TAZ activators identifies a compound that enhances myogenesis in C2C12 cells and facilitates muscle repair in a muscle injury model," *Mol Cell Biol* 34(9):1607-1621.
Zitouni, S. et al. (Jul. 2014). "Polo-like kinases: structural variations lead to multiple functions," *Nat Rev Mol Cell Biol* 15(7):433-452.

* cited by examiner

PLK4 INHIBITORS

CROSS-REFERENCES TO RELATED APPLICATIONS

This application claims the benefit of US Provisional Application No. 62/149,292, filed Apr. 17, 2015, which is incorporated herein by reference in its entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 48518-501001WO-ST25.TXT, created on Apr. 14, 2016, 8,800 bytes, machine format IBM-PC, MS-Windows operating system, is hereby incorporated by reference.

BACKGROUND OF THE INVENTION

Centrioles play a role in cytokinesis. Polo-like kinase (PLK4) is one regulator of centriole biogenesis. PLK4 overexpression may trigger centriole overduplication which can lead to cancer. PLK4 shares active site homology with other kinases, including Aurora kinases. Thus, there is a need in art for selective kinase inhibitors for PLK4. Described herein are solutions to these and other problems in the art.

BRIEF SUMMARY OF THE INVENTION

Provided herein, inter alia, are compounds and methods of using the compounds for inhibiting PLK4 and cancer.

In one aspect are compounds having the formula:

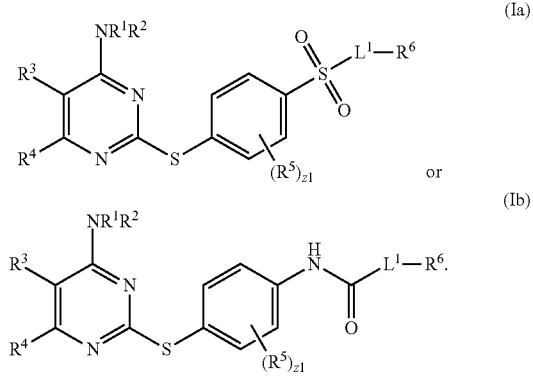

$L^1$ is a bond, —C(O)—, —C(O)O—, —O—, —S—, —$NR^{13}$—, —C(O)$NR^{13}$—, —$NR^{13}$C(O)—, —S(O)$_2$—, —S(O)$NR^{13}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, —$N_3$, —$CF_3$, —$CCl_3$, —$CBr_3$, —$CI_3$, —CN, —$COR^{1A}$, —$OR^{1A}$, —$NR^{1A}R^{1B}$, —C(O)$OR^{1A}$, —C(O)$NR^{1A}R^{1B}$, —$NO_2$, —$SR^{1A}$, —S(O)$_{n1}R^{1A}$, —S(O)$_{n1}OR^{1A}$, —S(O)$_{n1}NR^{1A}R^{1B}$, —$NHNR^{1A}R^{1B}$, —$ONR^{1A}R^{1B}$, —NHC(O)$NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, —$N_3$, —$CF_3$, —$CCl_3$, —$CBr_3$, —$CI_3$, —CN, —$COR^{2A}$, —$OR^{2A}$, —$NR^{2A}R^{2B}$, —C(O)$OR^{2A}$, —C(O)$NR^{2A}R^{2B}$, —$NO_2$, —$SR^{2A}$, —S(O)$_{n2}R^{2A}$, —S(O)$_{n2}OR^{2A}$, —S(O)$_{n2}NR^{2A}R^{2B}$, —$NHNR^{2A}R^{2B}$, —$ONR^{2A}R^{2B}$, —NHC(O)$NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, —$N_3$, —$CF_3$, —$CCl_3$, —$CBr_3$, —$CI_3$, —CN, —$COR^{3A}$, —$OR^{3A}$, —$N^{3A}R^{3B}$, —C(O)$OR^{3A}$, —C(O)$NR^{3A}R^{3B}$, —$NO_2$, —$SR^{3A}$, —S(O)$_{n3}R^{3A}$, —S(O)$_{n3}R^{3A}$, —S(O)$_{n3}NR^{3A}R^{3B}$, —$NHNR^{3A}R^{3B}$, —$ONR^{3A}R^{3B}$, —NHC(O)$NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is hydrogen, halogen, —$N_3$, —$CF_3$, —$CCl_3$, —$CBr_3$, —$CI_3$, —CN, —$COR^{4A}$, —$OR^{4A}$, —$NR^{4A}R^{4B}$, —C(O)$OR^{4A}$, —C(O)$NR^{4A}R^{4B}$, —$NO_2$, —$SR^{4A}$, —S(O)$_{n4}R^{4A}$, —S(O)$_{n4}OR^{4A}$, —S(O)$_{n4}NR^{4A}R^{4B}$, —$NHNR^{4A}R^{4B}$, —$ONR^{4A}R^{4B}$, —NHC(O)$NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^3$ and $R^4$ are optionally combined to form a substituted or unsubstituted cycloalkyl, substituted or unsubstituted heterocycloalkyl, substituted or unsubstituted aryl, or substituted or unsubstituted heteroaryl. $R^5$ is independently hydrogen, halogen, —$N_3$, —$CF_3$, —$CCl_3$, —$CBr_3$, —$CI_3$, —CN, —$COR^{5A}$, —$OR^{5A}$, —$R^{5A}R^{5B}$, —C(O)$OR^{5A}$, —C(O)$NR^{5A}R^{5B}$, —$NO_2$, —$SR^{5A}$, —S(O)$_{n5}R^{5A}$, —S(O)$_{n5}OR^{5A}$, —S(O)$_{n5}NR^{5A}R^{5B}$, —$NHNR^{5A}R^{5B}$, —$ONR^{5A}R^{5B}$, —NHC(O)$NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is hydrogen, oxo, halogen, —$N_3$, —$CF_3$, —$CCl_3$, —$CBr_3$, —$CI_3$, —CN, —CHO, —$OR^{6A}$, —$NR^{6A}R^{6B}$, —C(O)$OR^{6A}$, —C(O)$NR^{6A}R^{6B}$, —$NO_2$, —$SR^{6A}$, —S(O)$_{n6}R^{6A}$, —S(O)$_{n6}OR^{6A}$, —S(O)$_{n6}NR^{6A}R^{6B}$, —$NHNR^{6A}R^{6B}$, —$ONR^{6A}R^{6B}$, —NHC(O)$NHNR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. They symbols n1, n2, n3, n4, n5, and n6 are independently 1 or 2. The symbol z1 is 1, 2, 3, or 4. $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$, and $R^{13}$ are independently hydrogen, oxo, halogen, —$CF_3$, —CN, —OH, —$NH_2$, —COOH, —$CONH_2$, —$NO_2$, —SH, —S(O)$_2$Cl, —S(O)$_3$H, —S(O)$_4$H, —S(O)$_2NH_2$, —$NHNH_2$, —$ONH_2$, —NHC(O)$NHNH_2$, —NHC(O)$NH_2$, —NHS(O)$_2$H, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Also provided herein are compounds having the formula:

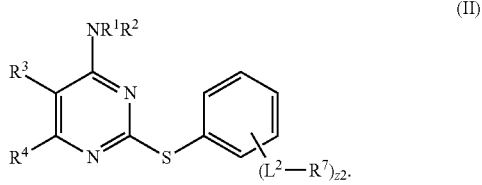

(II)

In a first aspect of formula (II), $L^1$ is a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ is independently a bond, —C(O)—, —C(O)O—, —O—, —S—, —NR$^{14}$—, —C(O)NR$^{14}$—, —NR$^{14}$C(O)—, —S(O)—, —S(O)$_2$—, —S(O)NR$^{14}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, —N$_3$, —CF$_3$, —CCl$_3$, —CBr$_3$, —CI$_3$, —CN, —COR$^{1A}$, —OR$^{1A}$, —NR$^{1A}$R$^{1B}$, —C(O)OR$^{1A}$, —C(O)NR$^{1A}$R$^{1B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, —N$_3$, —CF$_3$, —CCl$_3$, —CBr$_3$, —CI$_3$, —CN, —COR$^{2A}$, —OR$^{2A}$, —N$^{2A}$R$^{2B}$, —C(O)OR$^{2A}$, —C(O)NR$^{2A}$R$^{2B}$, —NO$_2$, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is halogen, —N$_3$, —CF$_3$, —CCl$_3$, —CBr$_3$, —CI$_3$, —CN, —COR$^{3A}$, —OR$^{3A}$, —NR$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is halogen, —N$_3$, —CF$_3$, —CCl$_3$, —CBr$_3$, —CI$_3$, —CN, —COR$^{4A}$, —OR$^{4A}$, —NR$^{4A}$R$^{4B}$, —C(O)OR$^{4A}$, —C(O)NR$^{4A}$R$^{4B}$, —NO$_2$, —SR$^{4A}$, —S(O)$_{n4}$R$^{4A}$, —S(O)$_{n4}$OR$^{4A}$, —S(O)$_{n4}$NR$^{4A}$R$^{4B}$, —NHNR$^{4A}$R$^{4B}$, —ONR$^{4A}$R$^{4B}$, —NHC(O)NHNR$^{4A}$R$^{4B}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is independently hydrogen, oxo, halogen, —N$_3$, —CF$_3$, —CCl$_3$, —CBr$_3$, —CI$_3$, —CN, —COR$^{7A}$, —OR$^{7A}$, —NR$^{7A}$R$^{7B}$, —C(O)OR$^{7A}$, —C(O)NR$^{7A}$R$^{7B}$, —NO$_2$, —SR$^{1A}$, —S(O)$_{n7}$R$^{7A}$, —S(O)$_{n7}$OR$^{7A}$, —S(O)$_{n7}$NR$^{7A}$R$^{7B}$, —NHNR$^{7A}$R$^{7B}$, —ONR$^{7A}$R$^{7B}$, —NHC(O)NHNR$^{7A}$R$^{7B}$, -L$^1$-R$^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is hydrogen, oxo, halogen, —N$_3$, —CF$_3$, —CCl$_3$, —CBr$_3$, —CI$_3$, —CN, —CHO, —OR$^{6A}$, —NR$^{6A}$R$^{6B}$, —C(O)OR$^{6A}$, —C(O)NR$^{6A}$R$^{6B}$, —NO$_2$, —SR$^{6A}$, —S(O)$_{n6}$R$^{6A}$, —S(O)$_{n6}$OR$^{6A}$, —S(O)$_{n6}$NR$^{6A}$R$^{6B}$, —NHNR$^{6A}$R$^{6B}$, —ONR$^{6A}$R$^{6B}$, —NHC(O)NHNR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1, n2, n3, n4, n6, and n7 are independently 1 or 2. The symbol z2 is 1, 2, 3, 4, or 5. $R^{1A}$, $R^{1B}$, $R^{2A}$, $R^{2B}$, $R^{3A}$, $R^{3B}$, $R^{4A}$, $R^{4B}$, $R^{6A}$, $R^{6B}$, $R^{7A}$, $R^{7B}$, $R^{13}$, and $R^{14}$ are independently hydrogen, oxo, halogen, —CF$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In a second aspect of formula (II), compounds are provided in which $L^1$ is a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ is independently a bond, —C(O)—, —C(O)O—, —O—, —S—, —NR$^{14}$—, —C(O)NR$^{14}$—, —NR$^{14}$C(O)—, —S(O)$_2$—, —S(O)NR$^{14}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, —N$_3$, —CF$_3$, —CCl$_3$, —CBr$_3$, —CI$_3$, —CN, —COR$^{1A}$, —OR$^{1A}$, —NR$^{1A}$R$^{1B}$, —C(O)OR$^{1A}$, —C(O)NR$^{1A}$R$^{1B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, —N$_3$, —CF$_3$, —CCl$_3$, —CBr$_3$, —CI$_3$, —CN, —COR$^{2A}$, —OR$^{2A}$, —NR$^{2A}$R$^{2B}$, —C(O)OR$^{2A}$, —C(O)NR$^{2A}$R$^{2B}$, —NO$_2$, —SR$^{2A}$, —S(O)$_{n2}$R$^{2A}$, —S(O)$_{n2}$R$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is —N$_3$, —CF$_3$, —CCl$_3$, —CBr$_3$, —CI$_3$, —CN, —COR$^{3A}$, —OR$^{3A}$, —NR$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is hydrogen, halogen, —N$_3$, —CF$_3$, —CCl$_3$, —CBr$_3$, —CI$_3$, —CN, —COR$^{4A}$, —OR$^{4A}$, —NR$^{4A}$R$^{4B}$, —C(O)OR$^{4A}$, —C(O)NR$^{4A}$R$^{4B}$, —NO$_2$, —SR$^{4A}$, —S(O)$_{n4}$R$^{4A}$, —S(O)$_{n4}$OR$^{4A}$, —S(O)$_{n4}$NR$^{4A}$R$^{4B}$, —NHNR$^{4A}$R$^{4B}$, —ONR$^{4A}$R$^{4B}$, —NHC(O)NHNR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^7$ is independently hydrogen, oxo, halogen, —N$_3$, —CF$_3$, —CCl$_3$, —CBr$_3$, —CI$_3$, —CN, —COR$^{7A}$, —OR$^{7A}$, —NR$^{7A}$R$^{7B}$, —C(O)OR$^{7A}$, —C(O)NR$^{7A}$R$^{7B}$, —NO$_2$, —SR$^{7A}$, —S(O)$_{n7}$R$^{7A}$, —S(O)$_{n7}$OR$^{7A}$, —S(O)$_{n7}$NR$^{7A}$R$^{7B}$, —NHNR$^{7A}$R$^{7B}$, —ONR$^{7A}$R$^{7B}$, —NHC(O)NHNR$^{7A}$R$^{7B}$, -L$^1$-R$^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^6$ is hydrogen, oxo, halogen, —N$_3$, —CF$_3$, —CCl$_3$, —CBr$_3$, —CI$_3$, —CN, —CHO, —OR$^{6A}$, —NR$^{6A}$R$^{6B}$, —C(O)OR$^{6A}$, —C(O)NR$^{6A}$R$^{6B}$, —NO$_2$, —SR$^{6A}$, —S(O)$_{n6}$R$^{6A}$, —S(O)$_{n6}$OR$^{6A}$, —S(O)$_{n6}$NR$^{6A}$R$^{6B}$, —NHNR$^{6A}$R$^{6B}$, —ONR$^{6A}$R$^{6B}$, —NHC(O)NHNR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1, n2, n3, n4, n6, and n7 are independently 1 or 2. The symbol z2 is 1, 2, 3, 4, or 5. R$^{1A}$, R$^{1B}$, R$^{2A}$, R$^{2B}$, R$^{3A}$, R$^{3B}$, R$^{4A}$, R$^{4B}$, R$^{6A}$, R$^{6B}$, R$^{7A}$, R$^{7B}$, R$^{13}$, and R$^{14}$ are independently hydrogen, oxo, halogen, —CF$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Provided herein are pharmaceutical compositions that include a compound described herein and a pharmaceutically acceptable excipient.

Methods of inhibiting a PLK4 kinase are provided herein. In one aspect, is a method of inhibiting a PLK4 kinase by contacting the PLK4 kinase with a compound described herein and allowing the compound to bind to the PLK4 kinase, thereby inhibiting the PLK4 kinase.

Methods of treating cancer in a subject in need thereof are also provided. In one aspect is a method of treating cancer in a subject in need thereof, by administering to the subject a therapeutically effective amount of a compound described herein. In another aspect is a method of treating basal cell carcinoma, medulloblastoma, pancreatic cancer, small cell lung cancer, gastric cancer, colon cancer, or chondrosarcoma in a subject in need thereof, by administering to the subject a therapeutically effective amount of a compound described herein. In another aspect, the method is a method of treating cancer in a subject in need thereof by administering to the subject a therapeutically effective amount of a compound having formula:

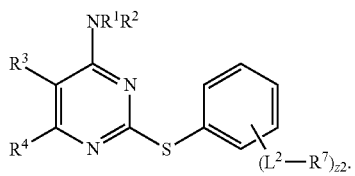

(II)

L$^1$ is a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. L$^2$ is independently a bond, —C(O)—, —C(O)O—, —O—, —S—, —NR$^{14}$—, —C(O)NR$^{14}$—, —NR$^{14}$C(O)—, —S(O)$_2$—, —S(O)NR$^{14}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. R$^1$ is hydrogen, halogen, —N$_3$, —CF$_3$, —CCl$_3$, —CBr$_3$, —CI$_3$, —CN, —COR$^{1A}$, —OR$^{1A}$, —NR$^{1A}$R$^{1B}$, —C(O)OR$^{1A}$, —C(O)NR$^{1A}$R$^{1B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ is hydrogen, halogen, —N$_3$, —CF$_3$, —CCl$_3$, —CBr$_3$, —CI$_3$, —CN, —COR$^{2A}$, —OR$^{2A}$, —NR$^{2A}$R$^{2B}$, —C(O)OR$^{2A}$, —C(O)NR$^{2A}$R$^{2B}$, —NO$_2$, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is halogen, —N$_3$, —CF$_3$, —CCl$_3$, —CBr$_3$, —CI$_3$, —CN, —COR$^{3A}$, —OR$^{3A}$, —NR$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ is hydrogen, halogen, —N$_3$, —CF$_3$, —CCl$_3$, —CBr$_3$, —CI$_3$, —CN, —COR$^{4A}$, —OR$^{4A}$, —NR$^{4A}$R$^{4B}$, —C(O)OR$^{4A}$, —C(O)NR$^{4A}$R$^{4B}$, —NO$_2$, —SR$^{4A}$, —S(O)$_{n4}$R$^{4A}$, —S(O)$_{n4}$OR$^{4A}$, —S(O)$_4$NR$^{4A}$R$^{4B}$, —NHNR$^{4A}$R$^{4B}$, —ONR$^{4A}$R$^{4B}$, —NHC(O)NHNR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^7$ is independently hydrogen, oxo, halogen, —N$_3$, —CF$_3$, —CCl$_3$, —CBr$_3$, —CI$_3$, —CN, —COR$^{7A}$, —OR$^{7A}$, —NR$^{7A}$R$^{7B}$, —C(O)OR$^{7A}$, —C(O)NR$^{7A}$R$^{7B}$, —NO$_2$, —SR$^{7A}$, —S(O)$_{n7}$R$^{7A}$, —S(O)$_{n7}$OR$^{7A}$, —S(O)$_{n7}$NR$^{7A}$R$^{7B}$, —NHNR$^{7A}$R$^{7B}$, —ONR$^{7A}$R$^{7B}$, —NHC(O)NHNR$^{7A}$R$^{7B}$, -L$^1$-R$^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^6$ is hydrogen, oxo, halogen, —N$_3$, —CF$_3$, —CCl$_3$, —CBr$_3$, —CI$_3$, —CN, —CHO, —OR$^{6A}$, —NR$^{6A}$R$^{6B}$, —C(O)OR$^{6A}$, —C(O)NR$^{6A}$R$^{6B}$, —NO$_2$, —SR$^{6A}$, —S(O)$_{n6}$R$^{6A}$, —S(O)$_{n6}$OR$^{6A}$, —S(O)$_{n6}$NR$^{6A}$R$^{6B}$, —NHNR$^{6A}$R$^{6B}$, —ONR$^{6A}$R$^{6B}$, —NHC(O)NHNR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1, n2, n3, n4, n6, and n7 are independently 1 or 2. The symbol z2 is 1, 2, 3, 4, or 5. $R^{1A}$, $R^{1B}$, $R^{2A}$, $R^{2B}$, $R^{3A}$, $R^{3B}$, $R^{4A}$, $R^{4B}$, $R^{6A}$, $R^{6B}$, $R^{7A}$, $R^{7B}$, $R^{13}$, and $R^{14}$ are independently hydrogen, oxo, halogen, —$CF_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —NHC(O)$NHNH_2$, —NHC(O)$NH_2$, —NHS(O)$_2H$, —NHC(O)H, —NHC(O)OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

BRIEF DESCRIPTION OF THE DRAWINGS

(FIG. 1A) Chemical structures, $K_i$ values, and selectivities [Plk4 versus Aurora A/B; $K_i$(kinase)/$K_i$(Plk4)] of the centrinones and VX-680. (FIG. 1B) Crystal structure of the centrinone-Plk4 kinase domain complex (highlighted αC helix). (FIG. 1C) Close-up of centrinone in the Plk4 active site. The aminopyrazole moiety of centrinone hydrogen bonds (dashes) with the main chain carbonyl of Glu 90 and the carbonyl and amide nitrogen of Cys 92. The 5-methoxy substituent (spheres) packs against the Met 91 side chain (stick and gray spheres). The benzylsulfone moiety (surface) wraps around Lys 41. (FIG. 1D) HeLa cells 7 days after centrinone addition and 10 days after centrinone washout (insets 3.3× magnified). Scale bar, 10 μm. Schematic shows progressive centrosome depletion following Plk4 inhibition. Bar graph shows the centrosome number distribution after centrinone addition and washout. (FIG. 1E) γ-tubulin foci in NIH/3T3 cells induced to overexpress wild-type or centrinone-resistant (G95L) Plk4-GFP. Scale bar, 5 μm. Data in D-E are mean+/−SD (N=3).

(FIG. 2A) Proliferation curves of HeLa and NIH/3 T3 cells immediately following addition of centrinone or DMSO (control). (FIG. 2B) Proliferation curves after chronic (>2 weeks) centrinone treatment (left), or after chronic centrinone treatment followed by drug washout for >2 weeks (right). (FIG. 2C) Proliferation curves after chronic (>2 weeks) centrinone treatment in cell lines with varying degrees of centrosome amplification. Numbers in parentheses are percent of cells exhibiting centrosome amplification in untreated population. Data in A-C are mean+/−SEM (N=3). (FIG. 2D) G1+S and G2 durations measured in HeLa and NIH/3T3 cells co-expressing GFP-PCNA and H2B-RFP (see FIG. 10A-10D). Data are mean+/−SD. (FIG. 2E) Percentage of cells exhibiting mitotic defects measured in HeLa and NIH/3T3 cells co-expressing centrin-GFP and H2B-RFP (see FIGS. 11A-11C). (FIG. 2F) Percentage of cells undergoing cell death in HeLa and NIH/3T3 cells, measured using a fluorescent caspase substrate. Data are mean+/−SD (N=2). (FIG. 2G) Graphs showing centrosome number distribution over time after centrinone washout from long-term (>2 weeks) treated HeLa, BT-549 and N1E-115-1 cells. The centrosome number distribution in untreated cells ("Pre" bars) is also shown for each cell line. Data are mean+/−SD (N=3).

(FIG. 3A) Centrosome number distribution (left; data are mean+/−SD; N=3) and proliferation (right, data are mean+/−SEM; N=3) of RPE1 cells following centrinone addition. (FIG. 3B) (left) Centrosome number distribution in RPE1 cells expressing WT or centrinone-resistant G95L (homozygous knock-in at the endogenous locus) Plk4. (right) Passaging assay on RPE1 Plk4 G95L cells. Data are mean+/−SD (N=2). (FIG. 3C) Lineage analysis showing the percentage of RPE1 cells with the indicated number of centrosomes arresting in each generation after centrinone addition (N=2). Cells co-expressing centrin-GFP and H2B-RFP were initially filmed in both GFP and RFP channels to count centrosomes and monitor mother cell mitosis. Daughter cell fate was subsequently tracked using RFP only. Arrest was the inability to enter mitosis within 48 hours of cell birth. (FIG. 3D) Western Blot of p53 and p21 in RPE1 cells. (FIG. 3E) Western Blot of RPE1 cells expressing control or p53 shRNA, and passaging assay of RPE1 cells expressing control or p53 shRNA following centrinone addition. Data are mean+/−SD (N=2).

(FIG. 4A) Western Blot for p53 phosphoepitopes associated with DNA damage in RPE1 cells treated with centrinone or doxorubicin as a positive control. (FIG. 4B) Quantification of γ-H2A.X foci in RPE1 nuclei. Data are mean+/−SD (N=3). (FIG. 4C) Western Blot of activated p38 in RPE1 cells. (FIG. 4D) Passaging assay of RPE1 cells expressing LATS1/2 microRNA, following addition of centrinone. (FIG. 4E) Daughter cell fate in RPE1 cells co-expressing centrin-GFP and H2B-RFP. Vertical bars represent measurements from individual daughter cells. Bar height is the time their mother spent in mitosis and color indicates arrest or division. Asterisks indicate chromosome missegregation in the mother cell. Daughter cell fate following nocodazole treatment of mother cells with a normal 2-centrosome complement (left) confirms existence of a mitotic duration sensor that arrests daughter cells if the mother cell spends more than ~84 minutes (black dashed lines on allplots) in mitosis. (FIG. 4F) Western Blot of RPE1 cells treated with centrinone or R7112. (FIG. 4G) Passaging assay of RPE1 cells following addition (Day 0) and washout (Day 8) of centrinone or R7112. Data in FIG. 4D and FIG. 4G are mean+/−SD (N=2).

(FIG. 5A) Deconvolved wide-field images of HeLa cells treated for 3 days with DMSO, centrinone, centrinone-B, or CFI-400945. Cells were fixed and stained for γ-tubulin and Cep192. Images are maximum intensity projections. Cell boundaries are outlined in gray. Insets are 3.4× magnified. Scale bar, 10 μm. (FIG. 5B) Quantification of γ-tubulin/Cep192 foci from cells in A. Data are mean+/−SD (N=3). Results similar to those described in A and B for HeLa cells were also observed in mouse NIH/3T3 fibroblasts as well as human breast (MDA-MB-231 and MDA-MB-468) and colon (HCT-116) carcinoma cells. (FIG. 5C) Western Blot of DLD-1 cells induced to overexpress full-length mouse Plk4-YFP (53), treated with the indicated centrinone or CFI-400945 concentrations for 24 hours. In untreated cells, levels of overexpressed Plk4-YFP are limited by autophosphorylation-induced degradation. Inhibition of Plk4 kinase activity leads to Plk4-YFP stabilization. At 250 nM CFI-400945, only slight Plk4-YFP stabilization is observed compared to the more substantial stabilization seen in the presence of 25 nM or 100 nM centrinone.

(FIG. 6A) Selection of VX-680 as the lead compound and selectivity design strategy. Inspection of a previously deposited structure of the Plk4 kinase domain bound to AMP-PNP (PDB:3COK) revealed an uncommon residue (Met 91) in the hinge region connecting the two kinase domain lobes. Hinge interactions can account for 40-60% of the binding energy of certain classes of ATP-competitive kinase inhibitors (54), and this region has previously been successfully targeted to generate selective inhibitors (e.g. the Plk1 inhibitor BI2356; 55). Modeling of reported biochemical Plk4 inhibitors predicted that the Aurora kinase inhibitor VX-680 would bind with its pyrimidine ring adjacent to Met 91. We hypothesized that selectivity for Plk4 could be introduced into this scaffold by adding substituents to the C5 ring position that would be accommodated by the flexible Met 91 of Plk4, but not by the bulkier tyrosine residues at the equivalent positions in human Aurora A/B/C. The image shown here was generated by superimposing the structure of human Aurora A bound to VX-680 (PDB:3E5A) over that of Plk4 bound to AMPPNP (PDB:3COK). The C5 position of VX-680 (gray sphere), Tyr 212 of Aurora A (gray sticks and surface), and Met 91 of Plk4 (sticks) are highlighted. (FIG. 6B) Flowchart illustrating the centrinone development process. Using VX-680 as a starting point, inhibitor analogs were iteratively synthesized based on the structure-activity relationship (SAR) results from cellular centrosome depletion and biochemical Plk4 and Aurora A/B kinase inhibition assays. Only one of the 133 compounds that robustly inhibited Plk4 in vitro (LCR-015) depleted centrosomes from both human and mouse cells at <10 µM. This result validated our approach of monitoring cellular activity in parallel with biochemical potency. LCR-015 was further optimized for potency and selectivity, resulting in centrinone and centrinone-B. (FIG. 6C) Stereo diagram of centrinone in the Plk4 active site showing a Ca trace of the Plk4 main chain, and residues whose side chains form nonpolar contacts with centrinone. The Ca of Gly 95 (sphere) is packed against centrinone. Mutation of this residue to a bulky leucine preserves in vitro catalytic activity but severely compromises centrinone binding. The benzylsulfone moiety inserts itself between the side chain of the catalytic lysine (Lys 41) and the aspartic acid (Asp 154) of the DFG motif. The side chain of Asp 154 is not visible in the electron density so it has been modeled as an alanine. (FIG. 6D) HeLa cells treated with DMSO, VX-680, or centrinone for 7 hours. Cells were fixed and stained for p-LATS2(S83) and p-H3(S10), which are reporters of Aurora A and Aurora B activity, respectively. Scale bar, 5 µm. The mean intensities of p-LATS2 and p-H3 staining were quantified for the three conditions. Values are normalized to DMSO. Data are mean+/−SD (N=3). (FIG. 6E) Quantification of the number of cells with detectable foci in HeLa cells stained for centriolar (centrin, SAS-6, CPAP) and pericentriolar material (γ-tubulin, Cep192, PCNT) proteins. Centrinone treatment resulted in loss of all markers from cells.

(FIG. 7A) Serum-starved DMSO- and centrinone-treated NIH/3T3 cells stained for γ-tubulin and the ciliary marker IFT88. Inset is 3.4× magnified. Scale bar, 10 µm. The mean percentage of cells with cilia was quantified. Data are mean+/−SD (N=3). (FIG. 7B) Deconvolved wide-field images of DMSO- and centrinone-treated NIH/3T3 cells either untreated, in the presence of 16 µM nocodazole or 5 minutes after nocodazole washout. Maximum intensity projections are shown. In the absence of centrosomes, short microtubules form throughout the cytoplasm after nocodazole washout, instead of focused asters. Insets are 3.3× magnified. Scale bar, 10 µm. The mean percentage of cells with visible asters 5 minutes after nocodazole washout was quantified. Data are mean+/−SD (N=3). (FIG. 7C) Golgi staining in NIH/3T3 cells treated with DMSO or centrinone for 10 days. Nocodazole treatment was used as a positive control for Golgi dispersal. Scale bar, 5 µm. Similar results were obtained in HeLa cells.

(FIG. 8A) Fluorescence confocal images of multiciliated cells treated with DMSO (control) or 10 µM centrinone expressing GFP-xCCDC78 and Centrin4-RFP and stained with Phalloidin to mark cell boundaries indicate that deuterosomes are present in centrinone-treated cells. Scale bar, 5 µm. (FIG. 8B) Fluorescence confocal images of DMSO, centrinone, and centrinone-B-treated multiciliated cells expressing Centrin4-GFP and stained with Phalloidin. Boxed regions are 3× magnified. Scale bars, 10 µm. Graph quantifying centriole density after treatment with DMSO or the indicated concentrations of centrinone or centrionone-B. Centrinone-treated cells exhibit dramatically reduced centriole numbers, suggesting that centriole assembly in multiciliated cells is Plk-dependent. Data are mean+/−SD (N=3).

(FIG. 9A) Centrosome depletion kinetics immediately following centrinone addition to NIH/3T3 cells. Data are mean+/−SD (N=3). (FIG. 9B) Passaging assay of HeLa and NIH/3T3 cells beginning immediately after centrinone addition. Cells were passaged at the indicated intervals. Centrinone-treated cells continue proliferating indefinitely, albeit at a slower rate than control cells. Data are mean+/−SD (N=2).

(FIG. 10A) Confocal images (maximum intensity projections) illustrating how cell cycle intervals (G1+S and G2) were measured. Times in the bottom left of each panel are in minutes relative to the beginning of G1 (chromosome decondensation). Scale bar, 10 µm. (FIG. 10B) Plots showing G1+S and G2 durations in DMSO- and centrinone-treated HeLa and NIH/3T3 cells co-expressing GFP-PCNA and H2B-RFP. Horizontal bars represent measurements from individual cells, ordered by total interphase duration. N=2. (FIG. 10C) Confocal images (maximum intensity projections) of HeLa cells treated with DMSO or centrinone for 8 days, then stained for apoptotic cells using a fluorescent caspase-3/7 activity reporter substrate. Scale bar, 50 µm. The percentage of dying cells is underestimated by this assay because it does not account for the fragile cells that have detached from the surface (in particular, those that die during or shortly after mitosis while the cell is loosely adherent). (FIG. 10D) Theoretical proliferation curves (black) for HeLa and NIH/3T3 cells with the indicated percentages of cell death, compared to measurements of centrinone-treated cells (squares; data reproduced from FIG. 2B). The equations used to generate the curves are shown above each plot (50,000=starting cell number; n=generation number). The doubling times were calculated by best-fit exponential regression of proliferation data from DMSO-treated cells adjusted as shown for increased time spent in mitosis. The curves indicate that the reduced proliferation rate of centrosome-less HeLa and NIH/3T3 cells can be explained by 25% and 15% cell death per generation, respectively.

(FIG. 11A) Schematic of the staggered treatment regime used to capture pioneer 2-, 1- and 0-centrosome mitoses. (FIG. 11B) Representative confocal images (maximum intensity projections) of 2-, 1- and 0-centrosome mitosis in NIH/3T3 cells co-expressing centrin-GFP and H2B-RFP. Arrowheads indicate centrin foci. Times in the bottom left of each panel are in minutes relative to NEBD. Scale bar, 10 m. (FIG. 11C) Plots of mitotic duration for NIH/3T3 and HeLa cells expressing centrin-GFP and H2B-RFP. Horizontal bars represent measurements from individual cells, ordered by the duration of NEBD to anaphase onset (N=2). Specific mitotic outcomes and associated percentages are indicated to the right of each box. Times in brackets are mean+/−SD of NEBD to anaphase onset. As centrosomes were lost, NIH/3T3 cells exhibited increases in chromosome missegregation and cytokinesis failure, and HeLa cells exhibited increases in chromosome missegregation and mitotic arrest, likely due to cohesion fatigue (57). These errors lead to cell death in mitosis or via apoptosis in the ensuing G1 (see FIG. 2F and FIG. 10D).

(FIG. 13A) Representative confocal images (maximum intensity projections) from a centrinone washout experiment in HeLa cells co-expressing centrin-GFP and H2B-RFP; only the GFP channel is shown. Yellow arrowheads mark centrin foci. Each frame was acquired at NEBD when the centrosomes are optimally distributed for counting. Times in the bottom left of each panel are in minutes relative to NEBD in the mother cell. Scale bar, 10 µm. (FIG. 13B) Histogram of mitotic outcomes for HeLa cells with <2, 2 or >2 centrosomes. The fates of daughter cells arising from 2-centrosome bipolar mitosis, multi-centrosome bipolar mitosis, and multi-centrosome multipolar mitosis are shown below. Data are mean+/−SD (N=2). (FIG. 13C) Plots of the number of centrin foci in the mother cell (x-axis) versus the sum of the centrin foci in her two daughter cells (y-axis) are shown for 3 different time intervals after centrinone washout (N=2). Intervals are based on the time of NEBD in the mother cells. The diagonal line represents the 2:1 ratio expected under normal conditions; points above or below this line correspond to over- or under-duplication, respectively. (FIG. 13D) Representative images of HeLa cells that were untreated, treated with 125 nM centrinone for 8 hours, or treated with centrinone for 8 hours followed by a 24-hour washout. Boxed regions are magnified 2.3× in panels below. Scale bar, 5 am. The Plk4 intensity at centrosomes was quantified and normalized to the intensity in untreated cells. Data are mean+/−SD (N=3). An 8-hour centrinone treatment was sufficient to double the measured levels of Plk4 at the centrosome.

(FIG. 14A) DNA content analysis of DMSO- and centrinone-treated RPE1 cells. The percentage of cells in G1 is indicated. (FIG. 14B) Passaging assay showing growth of primary fibroblasts immediately following addition of centrinone or DMSO as a control. Data are mean+/−SD (N=2). (FIG. 14C) Western Blot of p53 and p21 in primary fibroblasts after treatment with DMSO or centrinone for 8 days. (FIG. 14D) DNA content analysis of DMSO- and centrinone-treated primary fibroblasts. The percentage of cells in G1 is indicated. (FIG. 14E) Wide-field images of RPE1 cells and primary fibroblasts treated with centrinone for 1-3 days. Maximum intensity projections are shown. Nuclear boundaries are outlined in gray. A fraction of 1- and 0-centrosome cells exhibit increased nuclear p53 staining. Scale bar, 10 µm. (FIG. 14F) Quantification of p53-positive cells following centrinone addition to RPE1 and primary fibroblasts. Data are mean+/−SD (N=3).

(FIG. 16A) Western Blot of p53 post-translational modifications from RPE1 cells treated with the indicated compounds. Ser9, Ser33, Ser37, Ser315 and Ser392 have been demonstrated to be phosphorylated in response to DNA damage (58-62), which also triggers acetylation of Lys382 (57). A 16-hour treatment with 0.5 µM doxorubicin was used as a positive control for induction of DNA damage. (FIG. 16B) Deconvolved wide-field images of γ-H2A.X foci in RPE1 cells treated with DMSO or centrinone for 4 days, or 0.5 µM doxorubicin as a control. The presence or absence (centrinone) of centrosomes in imaged cells was confirmed by γ-tubulin staining. Scale bar, 5 µm. (FIG. 16C) Passaging assays of RPE1 cells treated with the indicated inhibitors of the DNA damage response pathway, beginning immediately after centrinone addition. Data are mean+/−SD (N=2). (FIG. 16D) Western Blot of phospho-MAPKAPK-2 after induction of osmotic stress, in the presence or absence of the p38 MAPK inhibitor SB203580. SB203580 blocks phosphorylation of MAP-KAPK-2 by p38. (FIG. 16E) Passaging assay of RPE1 cells treated with the p38 inhibitor SB203580, beginning immediately after centrinone addition. Data are mean+/−SD (N=2). (FIG. 16F) Western Blot of p53 and p21 in RPE1 cells treated with DMSO or centrinone for 8 days, or treated with centrinone for 8 days and then washed out for another 8 days. p53 and p21 levels remain elevated after centrinone washout.

(FIG. 17A) Western Blot of LATS2, YAP and phospho-YAP(Ser127) in diploid and tetraploid RPE1 cells. Knockdown of LATS2 results in decreased YAP phosphorylation, even in tetraploid (4n) cells generated by induction of cytokinesis failure. (FIG. 17B) Passaging assay of RPE1 cells expressing constitutively-active (S5A) YAP that cannot be phosphorylated by LATS2, following addition of centrinone. Data are mean+/−SD (N=2). (FIG. 17C) Quantification of the percentage of YAP-expressing RPE1 Fucci cells in G1, 12 hours after drug washout. Diploid cells measurements were obtained from cells treated with DMSO for 24 hours before washout, whereas tetraploid cell measurements were obtained from cells treated with 4 μM cytochalasin D (to induce cytokinesis failure) for 24 hours before washout. Tetraploid cells expressing wild-type YAP are arrested at G1, whereas cells expressing constitutively-active (S5A) YAP bypass the arrest. Data are mean+/−SD (N=3).

(FIG. 18A) Cells treated with DMSO or centrinone. Asterisks (*) mark cases in which the mother cell had visible chromosome missegregation. The percentage of daughters not dividing within 48 hours=3.5% (DMSO) and 1.5% (centrinone). (FIG. 18B) Cells treated with the Mps1 inhibitor NMS-P715. Only mitotic events with clear missegregation (lagging chromosomes and subsequent formation of daughter cells with micronuclei) were analyzed. The percentage of daughters not dividing within 48 hours=11.4%.

DETAILED DESCRIPTION OF THE INVENTION

Figure 1A:
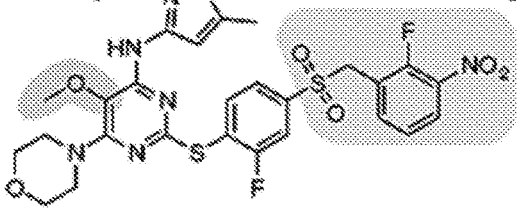
FIGS. 1A-1E. Centrinone is a selective Plk4 inhibitor that reversibly depletes centrioles from cells.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g. selected from the group consisting of O, N, P, Si, and S, and wherein the nitrogen and sulfur atoms may optionally be oxidized, and the nitrogen heteroatom may optionally be quaternized). The heteroatom(s) O, N, P, S, B, As, and Si may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. The ring-forming substituents may be attached to adjacent members of the base structure. For example, two ring-forming substituents attached to adjacent members of a cyclic base structure create a fused ring structure. The ring-forming substituents may be attached to a single member of the base structure. For example, two ring-forming substituents attached to a single member of a cyclic base structure create a spirocyclic structure. The ring-forming substituents may be attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and each substituted or unsubstituted heterocycloalkyl is a substituted or unsubstituted 3 to 7 membered heterocycloalkyl.

Each substituted group described in the compounds herein may be substituted with at least one substituent group. More specifically, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein may be substituted with at least one substituent group. At least one or all of these groups may be substituted with at least one size-limited substituent group. At least one or all of these groups may be substituted with at least one lower substituent group.

Each substituted or unsubstituted alkyl may be a substituted or unsubstituted C$_1$-C$_{20}$ alkyl, each substituted or unsubstituted heteroalkyl may be a substituted or unsubstituted 2 to 20 membered heteroalkyl, each substituted or unsubstituted cycloalkyl may be a substituted or unsubstituted C$_3$-C$_8$ cycloalkyl, and/or each substituted or unsubstituted heterocycloalkyl may be a substituted or unsubstituted 3 to 8 membered heterocycloalkyl. Each substituted or unsubstituted alkylene may be a substituted or unsubstituted C$_1$-C$_{20}$ alkylene, each substituted or unsubstituted heteroalkylene may be a substituted or unsubstituted 2 to 20 membered heteroalkylene, each substituted or unsubstituted cycloalkylene may be a substituted or unsubstituted C$_3$-C$_8$ cycloalkylene, and/or each substituted or unsubstituted heterocycloalkylene may be a substituted or unsubstituted 3 to 8 membered heterocycloalkylene.

Each substituted or unsubstituted alkyl may be a substituted or unsubstituted C$_1$-C$_8$ alkyl, each substituted or unsubstituted heteroalkyl may be a substituted or unsubstituted 2 to 8 membered heteroalkyl, each substituted or unsubstituted cycloalkyl may be a substituted or unsubstituted C$_3$-C$_7$ cycloalkyl, and/or each substituted or unsubstituted heterocycloalkyl may be a substituted or unsubstituted 3 to 7 membered heterocycloalkyl. Each substituted or unsubstituted alkylene may be a substituted or unsubstituted C$_1$-C$_8$ alkylene, each substituted or unsubstituted heteroalkylene may be a substituted or unsubstituted 2 to 8 membered heteroalkylene, each substituted or unsubstituted cycloalkylene may be a substituted or unsubstituted C$_3$-C$_7$ cycloalkylene, and/or each substituted or unsubstituted heterocycloalkylene may be a substituted or unsubstituted 3 to 7 membered heterocycloalkylene.

Certain compounds herein possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)-or (S)-or, as (D)- or (L)- for amino acids, and individual isomers are encompassed within the scope of the compounds described herein. The compounds described herein do not include those which are known in art to be too unstable to synthesize and/or isolate. The compounds described herein also are meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds described herein may exist in tautomeric forms, and that all such tautomeric forms of the compounds may be considered within the scope of the compounds described herein.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds, generally recognized as stable by those skilled in the art, are within the scope of the compounds described herein.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the compounds described herein.

The compounds described herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds described herein, whether radioactive or not, are encompassed within the scope of the compounds described herein.

The symbol "⌇" denotes the point of attachment of a chemical moiety to the remainder of a molecule or chemical formula.

Where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman decimal symbol may be used to distinguish each appearance of that particular R group. For example, where multiple $R^{13}$ substituents are present, each $R^{13}$ substituent may be distinguished as $R^{13.1}$, $R^{13.2}$, $R^{13.3}$, $R^{13.4}$, etc., wherein each of $R^{13.1}$, $R^{13.2}$, $R^{13.3}$, $R^{13.4}$, etc. is defined within the scope of the definition of $R^{13}$ and optionally differently.

Description of compounds described herein is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "VX-680," "tozasertib," and "MK-0457" as used herein refer to the compound having the formula:

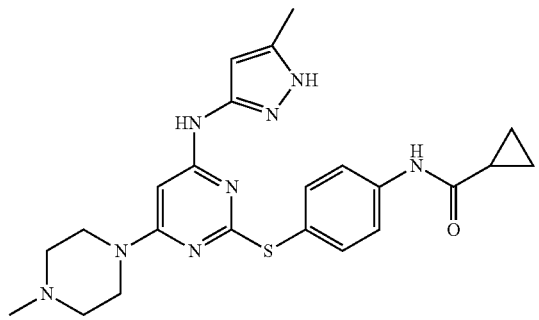

The term "pharmaceutically acceptable salts" is meant to include salts of the active compounds that are prepared with relatively nontoxic acids or bases, depending on the particular substituents found on the compounds described herein. When compounds described herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds described herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds described herein contain both basic and acidic functionalities that allow the compounds to be converted into either base or acid addition salts.

Thus, the compounds described herein may exist as salts, such as with pharmaceutically acceptable acids. The compounds described herein include such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the compounds described herein may be provided in a prodrug form. Prodrugs of the compounds described herein include those compounds that readily undergo chemical or enzymatic changes under physiological conditions to provide the compounds described herein. Additionally, prodrugs can be converted to the compounds described herein by chemical or biochemical methods in an ex vivo environment. For example, prodrugs can be slowly converted to the compounds described herein when placed in a transdermal patch reservoir with a suitable enzyme or chemical reagent.

Certain compounds described herein can exist in unsolvated forms as well as solvated forms, including hydrated forms. In general, the solvated forms are equivalent to unsolvated forms and are encompassed within the scope of the compounds described herein. Certain compounds described herein may exist in multiple crystalline or amorphous forms.

As used herein, the term "salt" refers to acid or base salts of the compounds described herein. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, or reduce one or more symptoms of a disease or condition). An example of an "effective amount" is an amount sufficient to contribute to the treatment, prevention, or reduction of a symptom or symptoms of a disease, which herein is referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the compounds described herein should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. A control may be the measurement of the activity of a protein in the absence of a compound as described herein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. Contacting may include allowing a compound described herein to interact with a protein or enzyme that is involved in a signaling pathway.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. Inhibition may refer to negatively affecting (e.g. decreasing) the concentration or level of the protein relative to the concentration or level of the protein in the absence of the inhibitor. Inhibition may refer reduction of a disease or symptoms of disease. Inhibition may refer to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

"PLK4" is used according to its common, ordinary meaning and refers to proteins of the same or similar names and functional fragments and homologs thereof. The term includes recombinant or naturally occurring forms of PLK4 (e.g. Polo-like Kinase 4; GI No: 160113150, SEQ ID NO:2), or variants thereof that maintain PLK4 activity (e.g. within at least 30%, 40%, 50%, 60%, 70%, 80%, 90%, 95%, or 100% activity compared to PLK4).

The term "modulator" refers to a composition that increases or decreases the level of a target molecule or the function of a target molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the compounds described herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds described herein. One of skill in the art will recognize that other pharmaceutical excipients are useful in combination with the compounds described herein.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route compatible with the selected compound preparation, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The pharmaceutical compositions described herein may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). The formulations of the compositions of the compounds described herein can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the compounds described herein into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein) is contained in a therapeutically effective amount, i.e., in an amount effective to achieve its intended purpose.

The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds described herein. Adjustment and manipulation of established dosages (e.g., frequency and duration) are well within the ability of those skilled in the art.

The compounds and complexes described herein can be used in combination with one another, with other active drugs known to be useful in treating a disease (e.g. anticancer agents) or with adjunctive agents that may not be effective alone, but may contribute to the efficacy of the active agent.

By "co-administer" it is meant that a composition described herein is administered at the same time, just prior to, or just after the administration of one or more additional therapies, for example an anti-cancer agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g. anti-cancer agents).

Co-administration includes administering one active agent (e.g. a compound described herein) within 0.5, 1, 2, 4, 6, 8, 10, 12, 16, 20, or 24 hours of a second active agent (e.g. anti-cancer agents). Co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. The active agents can be formulated separately. The active and/or adjunctive agents may be linked or conjugated to one another. The compounds described herein may be combined with treatments for cancer such as chemotherapy or radiation therapy.

The term "associated" or "associated with" in the context of a substance or substance activity or function associated with a disease means that the disease is caused by or characterized by (in whole or in part), a symptom of the disease is caused by or characterized by (in whole or in part) the substance or substance activity or function, or a side-effect of the compound (e.g. toxicity) is caused by or characterized by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. A patient may be a human.

"Disease" or "condition" refer to a state of being or health status of a patient or subject capable of being treated with the compounds or methods provided herein. Disease as used herein may refer to cancer.

As used herein, the term "cancer" refers to all types of cancer, neoplasm, malignant or benign tumors found in mammals, including leukemia, carcinomas and sarcomas. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

"Anti-cancer agent" is used in accordance with its plain and ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. An anti-cancer agent may be an agent approved by the FDA or similar regulatory agency of a country other than the USA, for treating cancer.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine;

dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Cancer model organism", as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

"Analog," or "analogue" are used in accordance with plain ordinary meaning within Chemistry and Biology and refer to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analogue is a compound that is similar or comparable in function and appearance but not in structure or origin to a reference compound.

I. Compounds

Provided herein are compounds having the formula:

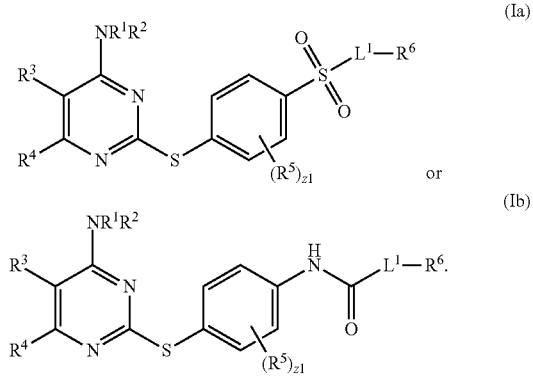

$L^1$ is a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, —N$_3$, —CF$_3$, —CCl$_3$, —CBr$_3$, —CI$_3$, —CN, —COR$^{1A}$, —OR$^{1A}$, —NR$^{1A}$R$^{1B}$, —C(O)OR$^{1A}$, —C(O)NR$^{1A}$R$^{1B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, —N$_3$, —CF$_3$, —CCl$_3$, —CBr$_3$, —CI$_3$, —CN, —COR$^{2A}$, —OR$^{2A}$, —NR$^{2A}$R$^{2B}$, —C(O)OR$^{2A}$, —C(O)NR$^{2A}$R$^{2B}$, —NO$_2$, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, —N$_3$, —CF$_3$, —CCl$_3$, —CBr$_3$, —CI$_3$, —CN, —COR$^{3A}$, —OR$^{3A}$, —N$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is hydrogen, halogen, —N$_3$, —CF$_3$, —CCl$_3$, —CBr$_3$, —CI$_3$, —CN, —COR$^{4A}$, —OR$^{4A}$, —NR$^{4A}$R$^{4B}$, —C(O)OR$^{4A}$, —C(O)NR$^{4A}$R$^{4B}$, —NO$_2$, —SR$^{4A}$, —S(O)$_{n4}$R$^{4A}$, —S(O)$_{n4}$OR$^{4A}$, —S(O)$_{n4}$NR$^{4A}$R$^{4B}$, —NHNR$^{4A}$R$^{4B}$, —ONR$^{4A}$R$^{4B}$, —NHC(O)NHNR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^3$ and $R^4$ are optionally combined to form a substituted or unsubstituted cycloalkyl (e.g. $R^{3C}$-substituted or unsubstituted cycloalkyl), substituted or unsubstituted heterocycloalkyl (e.g. $R^{3C}$-substituted or unsubstituted heterocycloalkyl), substituted or unsubstituted aryl (e.g. $R^{3C}$-substituted or unsubstituted aryl), or substituted or unsubstituted heteroaryl (e.g. $R^{3C}$-substituted or unsubstituted heteroaryl). $R^5$ is independently hydrogen, halogen, —N$_3$, —CF$_3$, —CCl$_3$, —CBr$_3$, —CI$_3$, —CN, —COR$^{5A}$, —OR$^{5A}$, —NR$^{5A}$R$^{5B}$, —C(O)OR$^{5A}$, —C(O)NR$^{5A}$R$^{5B}$, —NO$_2$, —SR$^{5A}$, —S(O)$_{n5}$R$^{5A}$, —S(O)$_{n5}$OR$^{5A}$, —S(O)$_{n5}$NR$^{5A}$R$^{5B}$, —NHNR$^{5A}$R$^{5B}$, —ONR$^{5A}$R$^{5B}$, —NHC(O)NHNR$^{5A}$R$^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is hydrogen, oxo, halogen, —N$_3$, —CF$_3$, —CCl$_3$, —CBr$_3$, —CI$_3$, —CN, —CHO, —OR$^{6A}$, —NR$^{6A}$R$^{6B}$, —C(O)OR$^{6A}$, —C(O)NR$^{6A}$R$^{6B}$, —NO$_2$, —SR$^{6A}$, —S(O)$_{n6}$R$^{6A}$, —S(O)$_{n6}$OR$^{6A}$, —S(O)$_{n6}$NR$^{6A}$R$^{6B}$, —NHNR$^{6A}$R$^{6B}$, —ONR$^{6A}$R$^{6B}$, —NHC(O)NHNR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1, n2, n3, n4, n5, and n6 are independently 1 or 2. The symbol z1 is 1, 2, 3, or 4. $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$, and $R^{13}$ are independently hydrogen, oxo, halogen, —CF$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the compound is not VX-680. In embodiments of formula Ib, $R^4$ is not a para-methyl piperidinyl. In embodiments of formula Ib, $R^4$ is not a para-ethyl piperidinyl. In embodiments of formula Ib, $R^4$ is not a para-propyl piperidinyl. In embodiments of formula Ib, $R^4$ is not a piperidinyl substituted with a methyl. In embodiments of formula Ib, $R^4$ is not a piperidinyl substituted with a ethyl. In embodiments of formula Ib, $R^4$ is not a piperidinyl substituted with a propyl. In embodiments of formula Ib, $R^4$ is not a piperidinyl substituted with an unsubstituted alkyl at the para position. In embodiments of formula Ib, $R^4$ is not a piperidinyl substituted with an unsubstituted alkyl. In embodiments of formula Ib, $R^4$ is not a piperidinyl substituted with a substituted or unsubstituted alkyl. In embodiments of formula Ib, $R^4$ is not a substituted or unsubstituted piperidinyl. In embodiments of formula Ib, $R^4$ is not a substituted heterocycloalkyl. In embodiments of formula Ib, $R^4$ is not a substituted or unsubstituted heterocycloalkyl. In embodiments of formula Ia, $R^4$ is not a para-methyl piperidinyl. In embodiments of formula Ib, $R^4$ is not a para-ethyl piperidinyl. In embodiments of formula Ib, $R^4$ is not a para-propyl piperidinyl. In embodiments of formula Ib, $R^4$ is not a piperidinyl substituted with a methyl. In embodiments of formula Ib, $R^4$ is not a piperidinyl substituted with a ethyl. In embodiments of formula Ib, $R^4$ is not a piperidinyl substituted with a propyl. In embodiments of formula Ia, $R^4$ is not a piperidinyl substituted with an unsubstituted alkyl at the para position. In embodiments of formula Ia, $R^4$ is not a piperidinyl substituted with an unsubstituted alkyl. In embodiments of formula Ia, $R^4$ is not a piperidinyl substituted with a substituted or unsubstituted alkyl. In embodiments of formula Ia, $R^4$ is not a substituted or unsubstituted piperidinyl. In embodiments of formula Ia, $R^4$ is not a substituted heterocycloalkyl. In embodiments of formula Ia, $R^4$ is not a substituted or unsubstituted heterocycloalkyl. In embodiments, the provisos set forth in the embodiments of the paragraph apply only when -$L^1$-$R^6$ is cyclopropyl. The embodiments in this paragraph are equally applicable to all other appropriate formulae set forth herein.

In embodiments of formula Ib, -$L^1$-$R^6$ is not cyclopropyl. In embodiments of formula Ia, -$L^1$-$R^6$ is not cyclopropyl. In embodiments of formula Ib, -$L^1$-$R^6$ is not cyclopropyl when $R^4$ is piperidinyl. In embodiments of formula Ib, -$L^1$-$R^6$ is not cyclopropyl when $R^4$ is piperidinyl substituted with substituted or unsubstituted alkyl. In embodiments of formula Ib, -$L^1$-$R^6$ is not cyclopropyl when $R^4$ is piperidinyl substituted with unsubstituted alkyl. In embodiments of formula Ib, -$L^1$-$R^6$ is not cyclopropyl when $R^4$ is piperidinyl substituted with methyl, ethyl or propyl. In embodiments of formula Ib, -$L^1$-$R^6$ is not cyclopropyl when $R^4$ is piperidinyl substituted with para methyl, para ethyl or para propyl. In embodiments of formula Ia, -$L^1$-$R^6$ is not cyclopropyl when $R^4$ is piperidinyl. In embodiments of formula Ia, -$L^1$-$R^6$ is not cyclopropyl when $R^4$ is piperidinyl substituted with substituted or unsubstituted alkyl. In embodiments of formula Ia, -$L^1$-$R^6$ is not cyclopropyl when $R^4$ is piperidinyl substituted with unsubstituted alkyl. In embodiments of formula Ia, -$L^1$-$R^6$ is not cyclopropyl when $R^4$ is piperidinyl substituted with methyl, ethyl or propyl. In embodiments of formula Ia, -$L^1$-$R^6$ is not cyclopropyl when $R^4$ is piperidinyl substituted with para methyl, para ethyl or para propyl. The embodiments in this paragraph are equally applicable to all other appropriate formulae set forth herein.

The compound may be a compound of formula:

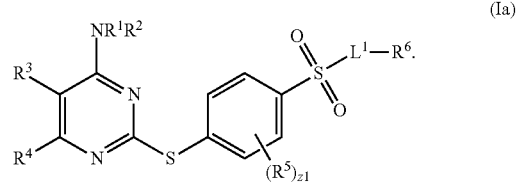

(Ia)

The compound may be a compound of formula:

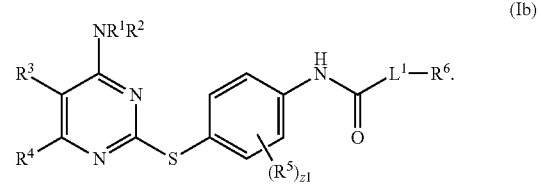

(Ib)

In embodiments, the compound of formula (Ib) is not,

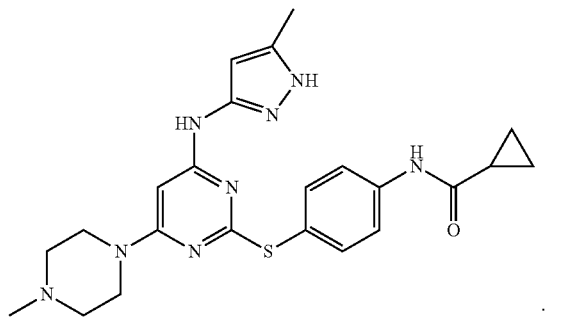 [SMILES: Cc1cc(Nc2cc(N3CCN(C)CC3)nc(Sc3ccc(NC(=O)C4CC4)cc3)n2)n[nH]1]

(VX-680)

$R^1$ may be hydrogen, halogen, —$N_3$, —$CF_3$, —$CCl_3$, —$CBr_3$, —$CI_3$, —CN, —$COR^{14}$, —$OR^{14}$, —$NR^{14}R^{1B}$, —C(O)$OR^{14}$, or —C(O)$NR^{14}R^{1B}$. $R^1$ may be hydrogen, halogen, —$N_3$, —$CF_3$, —$CCl_3$, —$CBr_3$, —$CI_3$, —CN, —$COR^{14}$, —$OR^{14}$, —$NR^{14}R^{1B}$, —C(O)$OR^{14}$, or —C(O)$NR^{14}R^{1B}$ where $R^{14}$ and $R^{1B}$ are independently hydrogen, oxo, halogen, —$CF_3$, —OH, —$NH_2$, —COOH, —$CONH_2$, substituted or unsubstituted alkyl, or substituted or unsubstituted aryl. $R^1$ may be hydrogen. $R^1$ may be hydrogen or substituted or unsubstituted alkyl.

$R^1$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^1$ may be substituted or unsubstituted alkyl. $R^1$ may be substituted alkyl. $R^1$ may be unsubstituted alkyl. $R^1$ may be substituted or unsubstituted $C_1$-$C_{20}$ alkyl. $R^1$ may be substituted $C_1$-$C_{20}$ alkyl. $R^1$ may be unsubstituted $C_1$-$C_{20}$ alkyl. $R^1$ may be substituted or unsubstituted $C_1$-$C_{10}$ alkyl. $R^1$ may be substituted $C_1$-$C_{10}$ alkyl. $R^1$ may be unsubstituted $C_1$-$C_{10}$ alkyl. $R^1$ may be substituted or unsubstituted $C_1$-$C_5$ alkyl. $R^1$ may be unsubstituted $C_1$-$C_5$ alkyl. $R^1$ may be substituted $C_1$-$C_5$ alkyl. $R^1$ may be methyl, substituted or unsubstituted ethyl, or substituted or unsubstituted propyl. $R^1$ may be methyl. $R^1$ may be ethyl.

$R^1$ may be $R^{1C}$-substituted or unsubstituted alkyl. $R^1$ may be $R^{1C}$-substituted alkyl. $R^1$ may be $R^{1C}$-substituted or unsubstituted $C_1$-$C_{20}$ alkyl. $R^1$ may be $R^{1C}$-substituted $C_1$-$C_{20}$ alkyl. $R^1$ may be $R^{1C}$-substituted or unsubstituted $C_1$-$C_{10}$ alkyl. $R^1$ may be $R^{1C}$-substituted $C_1$-$C_{10}$ alkyl. $R^1$ may be $R^{1C}$-substituted or unsubstituted $C_1$-$C_5$ alkyl. $R^1$ may be $R^{1C}$-substituted $C_1$-$C_5$ alkyl. $R^1$ may be methyl, $R^{1C}$-substituted or unsubstituted ethyl, or $R^{1C}$-substituted or unsubstituted propyl.

$R^1$ may be substituted or unsubstituted heteroalkyl. $R^1$ may be substituted heteroalkyl. $R^1$ may be unsubstituted heteroalkyl. $R^1$ may be substituted or unsubstituted 2 to 20 membered heteroalkyl. $R^1$ may be substituted 2 to 20 membered heteroalkyl. $R^1$ may be substituted or unsubstituted 2 to 10 membered heteroalkyl. $R^1$ may be substituted 2 to 10 membered heteroalkyl. $R^1$ may be substituted or unsubstituted 2 to 6 membered heteroalkyl. $R^1$ may be substituted 2 to 6 membered heteroalkyl.

$R^1$ may be $R^{1C}$-substituted or unsubstituted heteroalkyl. $R^1$ may be $R^{1C}$-substituted heteroalkyl. $R^1$ may be $R^{1C}$-substituted or unsubstituted 2 to 20 membered heteroalkyl. $R^1$ may be $R^{1C}$-substituted 2 to 20 membered heteroalkyl. $R^1$ may be $R^{1C}$-substituted or unsubstituted 2 to 10 membered heteroalkyl. $R^1$ may be $R^{1C}$-substituted 2 to 10 membered heteroalkyl. $R^1$ may be $R^{1C}$-substituted or unsubstituted 2 to 6 membered heteroalkyl. $R^1$ may be $R^{1C}$-substituted 2 to 6 membered heteroalkyl.

$R^1$ may be substituted or unsubstituted cycloalkyl. $R^1$ may be substituted cycloalkyl. $R^1$ may be unsubstituted cycloalkyl. $R^1$ may be substituted or unsubstituted 3 to 20 membered cycloalkyl. $R^1$ may be substituted 3 to 20 membered cycloalkyl. $R^1$ may be substituted or unsubstituted 3 to 10 membered cycloalkyl. $R^1$ may be substituted 3 to 10 membered cycloalkyl. $R^1$ may be substituted or unsubstituted 3 to 6 membered cycloalkyl. $R^1$ may be substituted 3 to 6 membered cycloalkyl.

$R^1$ may be $R^{1C}$-substituted or unsubstituted cycloalkyl. $R^1$ may be $R^{1C}$-substituted cycloalkyl. $R^1$ may be $R^{1C}$-substituted or unsubstituted 3 to 20 membered cycloalkyl. $R^1$ may be $R^{1C}$-substituted 3 to 20 membered cycloalkyl. $R^1$ may be $R^{1C}$-substituted or unsubstituted 3 to 10 membered cycloalkyl. $R^1$ may be $R^{1C}$-substituted 3 to 10 membered cycloalkyl. $R^1$ may be $R^{1C}$-substituted or unsubstituted 3 to 6 membered cycloalkyl. $R^1$ may be $R^{1C}$-substituted 3 to 6 membered cycloalkyl.

$R^1$ may be substituted or unsubstituted heterocycloalkyl. $R^1$ may be substituted heterocycloalkyl. $R^1$ may be unsubstituted heterocycloalkyl. $R^1$ may be substituted or unsubstituted 3 to 20 membered heterocycloalkyl. $R^1$ may be substituted 3 to 20 membered heterocycloalkyl. $R^1$ may be substituted or unsubstituted 3 to 10 membered heterocycloalkyl. $R^1$ may be substituted 3 to 10 membered heterocycloalkyl. $R^1$ may be substituted or unsubstituted 3 to 6 membered heterocycloalkyl. $R^1$ may be substituted 3 to 6 membered heterocycloalkyl.

$R^1$ may be $R^{1C}$-substituted or unsubstituted heterocycloalkyl. $R^1$ may be $R^{1C}$-substituted heterocycloalkyl. $R^1$ may be $R^{1C}$-substituted or unsubstituted 3 to 20 membered heterocycloalkyl. $R^1$ may be $R^{1C}$-substituted 3 to 20 membered heterocycloalkyl. $R^1$ may be $R^{1C}$-substituted or unsubstituted 3 to 10 membered heterocycloalkyl. $R^1$ may be $R^{1C}$-substituted 3 to 10 membered heterocycloalkyl. $R^1$ may be $R^{1C}$-substituted or unsubstituted 3 to 6 membered heterocycloalkyl. $R^1$ may be $R^{1C}$-substituted 3 to 6 membered heterocycloalkyl.

$R^1$ may be substituted or unsubstituted aryl. $R^1$ may be substituted aryl. $R^1$ may be unsubstituted aryl. $R^1$ may be substituted or unsubstituted 5 to 20 membered aryl. $R^1$ may be substituted 5 to 20 membered aryl. $R^1$ may be substituted or unsubstituted 5 to 8 membered aryl (e.g. phenyl). $R^1$ may be substituted 5 to 8 membered aryl. $R^1$ may be substituted or unsubstituted 5 or 6 membered aryl. $R^1$ may be substituted 5 or 6 membered aryl.

$R^1$ may be $R^{1C}$-substituted or unsubstituted aryl. $R^1$ may be $R^{1C}$-substituted aryl. $R^1$ may be $R^{1C}$-substituted or unsubstituted 5 to 20 membered aryl. $R^1$ may be $R^{1C}$-substituted 5 to 20 membered aryl. $R^1$ may be $R^{1C}$-substituted or unsubstituted 5 to 8 membered aryl. $R^1$ may be $R^{1C}$-substituted 5 to 8 membered aryl. $R^1$ may be $R^{1C}$-substituted or unsubstituted 5 or 6 membered aryl. $R^1$ may be $R^{1C}$-substituted 5 or 6 membered aryl (e.g. phenyl).

$R^1$ may be substituted or unsubstituted heteroaryl. $R^1$ may be substituted heteroaryl. $R^1$ may be unsubstituted heteroaryl. $R^1$ may be substituted or unsubstituted 5 to 20 membered heteroaryl. $R^1$ may be substituted 5 to 20 membered heteroaryl. $R^1$ may be substituted or unsubstituted 5 to 8 membered heteroaryl. $R^1$ may be substituted 5 to 8 membered heteroaryl. $R^1$ may be substituted or unsubstituted 5 or 6 membered heteroaryl. $R^1$ may be substituted 5 or 6 membered heteroaryl.

$R^1$ may be $R^{1C}$-substituted or unsubstituted heteroaryl. $R^1$ may be $R^{1C}$-substituted heteroaryl. $R^1$ may be $R^{1C}$-substituted or unsubstituted 5 to 20 membered heteroaryl. $R^1$ may be $R^{1C}$-substituted 5 to 20 membered heteroaryl. $R^1$ may be $R^{1C}$-substituted or unsubstituted 5 to 8 membered heteroaryl. $R^1$ may be $R^{1C}$-substituted 5 to 8 membered heteroaryl. $R^1$ may be $R^{1C}$-substituted or unsubstituted 5 or 6 membered heteroaryl. $R^1$ may be $R^{1C}$-substituted 5 or 6 membered heteroaryl.

$R^{1A}$ may independently be hydrogen, halogen, oxo, $N_3$, —$CF_3$, —$CCl_3$, —$CBr_3$, —$CI_3$, —CN, —$OR^{1D}$, —$COR^{1D}$, —$NR^{1D}R^{1E}$, —$COOR^{1D}$, —$CONR^{1D}R^{1E}$, —$NO_2$, —$SR^{1D}$, —$S(O)_2R^{1D}$, —$S(O)_3R^{1D}$, —$S(O)_4R^{1D}$, —$S(O)_2NR^{1D}R^{1E}$, —$NHNR^{1D}R^{1E}$, —$ONR^{1D}R^{1E}$, —$NHC(O)NHNR^{1D}R^{1E}$, —$NHC(O)NR^{1D}R^{1E}$, —$NHS(O)_2R^{1D}$, —$NHC(O)R^{1D}$, —$NHC(O)$—$OR^{1D}$, —$NHOR^{1D}$, —$OCF_3$, —$OCHF_2$, $R^{1C}$-substituted or unsubstituted alkyl, $R^{1C}$-substituted or unsubstituted heteroalkyl, $R^{1C}$-substituted or unsubstituted cycloalkyl, $R^{1C}$-substituted or unsubstituted heterocycloalkyl, $R^{1C}$-substituted or unsubstituted aryl, or $R^{1C}$-substituted or unsubstituted heteroaryl.

$R^{1C}$ is independently halogen, oxo, $N_3$, —$CF_3$, —$CCl_3$, —$CBr_3$, —$CI_3$, —CN, —OH, —$COR^{1D}$, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{1C}$ may independently be halogen, oxo, $N_3$, —$CF_3$, —$CCl_3$, —$CBr_3$, —$CI_3$, —CN, —OH, —COH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{1B}$ may independently be hydrogen, halogen, oxo, $N_3$, —$CF_3$, —$CCl_3$, —$CBr_3$, —$CI_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

$R^{1D}$ and $R^{1E}$ are independently hydrogen, halogen, oxo, N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted heteroalkyl, unsubstituted cycloalkyl, unsubstituted heterocycloalkyl, unsubstituted aryl, or unsubstituted heteroaryl.

$R^2$ may be hydrogen, halogen, —N$_3$, —CF$_3$, —CCl$_3$, —CBr$_3$, —CI$_3$, —CN, —COR$^{2A}$, —OR$^{2A}$, —NR$^{2A}$R$^{2B}$, —C(O)OR$^{2A}$, or —C(O)NR$^{2A}$R$^{2B}$. $R^2$ may be hydrogen, halogen, —N$_3$, —CF$_3$, —CCl$_3$, —CBr$_3$, —CI$_3$, —CN, —COR$^{2A}$, —OR$^{2A}$, —NR$^{2A}$R$^{2B}$, —C(O)OR$^{2A}$, or —C(O)NR$^{2A}$R$^{2B}$ where $R^{2A}$ and $R^{2B}$, are independently hydrogen, oxo, halogen, —CF$_3$, —OH, —NH$_2$, —COOH, —CONH$_2$, substituted or unsubstituted cycloalkyl, substituted or unsubstituted heterocycloalkyl, substituted or unsubstituted aryl, or substituted or unsubstituted heteroaryl.

$R^2$ may be substituted or unsubstituted cycloalkyl, substituted or unsubstituted heterocycloalkyl, substituted or unsubstituted aryl, or substituted or unsubstituted heteroaryl. $R^2$ may be $R^{2A}$-substituted or unsubstituted cycloalkyl, $R^{2A}$-substituted or unsubstituted heterocycloalkyl, $R^{2A}$-substituted or unsubstituted aryl, or $R^{2A}$-substituted or unsubstituted heteroaryl. $R^2$ may be substituted or unsubstituted heterocycloalkyl, substituted or unsubstituted aryl, or substituted or unsubstituted heteroaryl. $R^2$ may be $R^{2A}$-substituted or unsubstituted heterocycloalkyl, $R^{2A}$-substituted or unsubstituted aryl, or $R^{2A}$-substituted or unsubstituted heteroaryl.

$R^2$ may be $R^{2C}$-substituted or unsubstituted alkyl, $R^{2C}$-substituted or unsubstituted heteroalkyl, $R^{2C}$-substituted or unsubstituted cycloalkyl, $R^{2C}$-substituted or unsubstituted heterocycloalkyl, $R^{2C}$-substituted or unsubstituted aryl, or $R^{2C}$-substituted or unsubstituted heteroaryl. In embodiments, $R^2$ is substituted with an alkyl, heteroalkyl, cycloalkyl, heterocycloalkyl, aryl or heteroaryl, wherein said alkyl, heteroalkyl, cycloalkyl, heterocycloalkyl, aryl or heteroaryl is substituted with a substituent selected from —N$_3$, —CF$_3$, —CCl$_3$, —CBr$_3$, —CI$_3$, —CN, —OH, —NH$_2$, —C(O)OH, —C(O)NH$_2$, —NO$_2$, —SH, substituted or unsubstituted alkyl, and substituted or unsubstituted heteroalkyl.

$R^2$ may be substituted or unsubstituted alkyl. $R^2$ may be substituted alkyl. $R^2$ may be unsubstituted alkyl. $R^2$ may be substituted or unsubstituted C$_1$-C$_{20}$ alkyl. $R^2$ may be substituted C$_1$-C$_{20}$ alkyl. $R^2$ may be unsubstituted C$_1$-C$_{20}$ alkyl. $R^2$ may be substituted or unsubstituted C$_1$-C$_{10}$ alkyl. $R^2$ may be substituted C$_1$-C$_{10}$ alkyl. $R^2$ may be unsubstituted C$_1$-C$_{10}$ alkyl. $R^2$ may be substituted or unsubstituted C$_1$-C$_5$ alkyl. $R^2$ may be unsubstituted C$_1$-C$_5$ alkyl. $R^2$ may be substituted C$_1$-C$_5$ alkyl. $R^2$ may be methyl, substituted or unsubstituted ethyl, or substituted or unsubstituted propyl. $R^2$ may be methyl. $R^2$ may be ethyl.

$R^2$ may be $R^{2C}$-substituted or unsubstituted alkyl. $R^2$ may be $R^{2C}$-substituted alkyl. $R^2$ may be $R^{2C}$-substituted or unsubstituted C$_1$-C$_{20}$ alkyl. $R^2$ may be $R^{2C}$-substituted C$_1$-C$_{20}$ alkyl. $R^2$ may be $R^{2C}$-substituted or unsubstituted C$_1$-C$_{10}$ alkyl. $R^2$ may be $R^{2C}$-substituted C$_1$-C$_{10}$ alkyl. $R^2$ may be $R^{2C}$-substituted or unsubstituted C$_1$-C$_5$ alkyl. $R^2$ may be $R^{2C}$-substituted C$_1$-C$_5$ alkyl. $R^2$ may be methyl, $R^{2C}$-substituted or unsubstituted ethyl, or $R^{2C}$-substituted or unsubstituted propyl.

$R^2$ may be substituted or unsubstituted heteroalkyl. $R^2$ may be substituted heteroalkyl. $R^2$ may be unsubstituted heteroalkyl. $R^2$ may be substituted or unsubstituted 2 to 20 membered heteroalkyl. $R^2$ may be substituted 2 to 20 membered heteroalkyl. $R^2$ may be unsubstituted 2 to 20 membered heteroalkyl. $R^2$ may be substituted or unsubstituted 2 to 10 membered heteroalkyl. $R^2$ may be substituted 2 to 10 membered heteroalkyl. $R^2$ may be unsubstituted 2 to 10 membered heteroalkyl. $R^2$ may be substituted or unsubstituted 2 to 6 membered heteroalkyl. $R^2$ may be substituted 2 to 6 membered heteroalkyl. $R^2$ may be unsubstituted 2 to 6 membered heteroalkyl.

$R^2$ may be $R^{2C}$-substituted or unsubstituted heteroalkyl. $R^2$ may be $R^{2C}$-substituted heteroalkyl. $R^2$ may be $R^{2C}$-substituted or unsubstituted 2 to 20 membered heteroalkyl. $R^2$ may be $R^{2C}$-substituted 2 to 20 membered heteroalkyl. $R^2$ may be $R^{2C}$-substituted or unsubstituted 2 to 10 membered heteroalkyl. $R^2$ may be $R^{2C}$-substituted 2 to 10 membered heteroalkyl. $R^2$ may be $R^{2C}$-substituted or unsubstituted 2 to 6 membered heteroalkyl. $R^2$ may be $R^{2C}$-substituted 2 to 6 membered heteroalkyl.

$R^2$ may be substituted or unsubstituted cycloalkyl. $R^2$ may be substituted cycloalkyl. $R^2$ may be unsubstituted cycloalkyl. $R^2$ may be substituted or unsubstituted 3 to 20 membered cycloalkyl. $R^2$ may be substituted 3 to 20 membered cycloalkyl. $R^2$ may be unsubstituted 3 to 20 membered cycloalkyl. $R^2$ may be substituted or unsubstituted 3 to 10 membered cycloalkyl. $R^2$ may be substituted 3 to 10 membered cycloalkyl. $R^2$ may be unsubstituted 3 to 10 membered cycloalkyl. $R^2$ may be substituted or unsubstituted 3 to 6 membered cycloalkyl. $R^2$ may be substituted 3 to 6 membered cycloalkyl. $R^2$ may be unsubstituted 3 to 6 membered cycloalkyl.

$R^2$ may be $R^{2C}$-substituted or unsubstituted cycloalkyl. $R^2$ may be $R^{2C}$-substituted cycloalkyl. $R^2$ may be $R^{2C}$-substituted or unsubstituted 3 to 20 membered cycloalkyl. $R^2$ may be $R^{2C}$-substituted 3 to 20 membered cycloalkyl. $R^2$ may be $R^{2C}$-substituted or unsubstituted 3 to 10 membered cycloalkyl. $R^2$ may be $R^{2C}$-substituted 3 to 10 membered cycloalkyl. $R^2$ may be $R^{2C}$-substituted or unsubstituted 3 to 6 membered cycloalkyl. $R^2$ may be $R^{2C}$-substituted 3 to 6 membered cycloalkyl.

$R^2$ may be substituted or unsubstituted heterocycloalkyl. $R^2$ may be substituted heterocycloalkyl. $R^2$ may be unsubstituted heterocycloalkyl. $R^2$ may be substituted or unsubstituted 3 to 20 membered heterocycloalkyl. $R^2$ may be substituted 3 to 20 membered heterocycloalkyl. $R^2$ may be unsubstituted 3 to 20 membered heterocycloalkyl. $R^2$ may be substituted or unsubstituted 3 to 10 membered heterocycloalkyl. $R^2$ may be substituted 3 to 10 membered heterocycloalkyl. $R^2$ may be unsubstituted 3 to 10 membered heterocycloalkyl. $R^2$ may be substituted or unsubstituted 3 to 6 membered heterocycloalkyl. $R^2$ may be substituted 3 to 6 membered heterocycloalkyl. $R^2$ may be unsubstituted 3 to 6 membered heterocycloalkyl.

$R^2$ may be $R^{2C}$-substituted or unsubstituted heterocycloalkyl. $R^2$ may be $R^{2C}$-substituted heterocycloalkyl. $R^2$ may be $R^{2C}$-substituted or unsubstituted 3 to 20 membered heterocycloalkyl. $R^2$ may be $R^{2C}$-substituted 3 to 20 membered heterocycloalkyl. $R^2$ may be $R^{2C}$-substituted or unsubstituted 3 to 10 membered heterocycloalkyl. $R^2$ may be $R^{2C}$-substituted 3 to 10 membered heterocycloalkyl. $R^2$ may be $R^{2C}$-substituted or unsubstituted 3 to 6 membered heterocycloalkyl. $R^2$ may be $R^{2C}$-substituted 3 to 6 membered heterocycloalkyl.

$R^2$ may be substituted or unsubstituted aryl. $R^2$ may be substituted aryl. $R^2$ may be unsubstituted aryl. $R^2$ may be substituted or unsubstituted 5 to 20 membered aryl. $R^2$ may be substituted 5 to 20 membered aryl. $R^2$ may be unsubstituted 5 to 20 membered aryl. $R^2$ may be substituted or unsubstituted 5 to 8 membered aryl (e.g. phenyl). $R^2$ may be substituted 5 to 8 membered aryl. $R^2$ may be substituted or unsubstituted 5 or 6 membered aryl. $R^2$ may be unsubstituted 5 to 8 membered aryl (e.g. phenyl). $R^2$ may be substituted 5 or 6 membered aryl. $R^2$ may be unsubstituted 5 or 6 membered aryl.

$R^2$ may be $R^{2C}$-substituted or unsubstituted aryl. $R^2$ may be $R^{2C}$-substituted aryl. $R^2$ may be $R^{2C}$-substituted or unsubstituted 5 to 20 membered aryl. $R^2$ may be $R^{2C}$-substituted 5 to 20 membered aryl. $R^2$ may be $R^{2C}$-substituted or unsubstituted 5 to 8 membered aryl. $R^2$ may be $R^{2C}$-substituted 5 to 8 membered aryl. $R^2$ may be $R^{2C}$-substituted or unsubstituted 5 or 6 membered aryl. $R^2$ may be $R^{2C}$-substituted 5 or 6 membered aryl (e.g. phenyl).

$R^2$ may be substituted or unsubstituted heteroaryl. $R^2$ may be substituted heteroaryl. $R^2$ may be unsubstituted heteroaryl. $R^2$ may be substituted or unsubstituted 5 to 20 membered heteroaryl. $R^2$ may be substituted 5 to 20 membered heteroaryl. $R^2$ may be unsubstituted 5 to 20 membered heteroaryl. $R^2$ may be substituted or unsubstituted 5 to 8 membered heteroaryl. $R^2$ may be substituted 5 to 8 membered heteroaryl. $R^2$ may be unsubstituted 5 to 8 membered heteroaryl. $R^2$ may be substituted or unsubstituted 5 or 6 membered heteroaryl. $R^2$ may be substituted 5 or 6 membered heteroaryl. $R^2$ may be unsubstituted 5 or 6 membered heteroaryl.

$R^2$ may be $R^{2C}$-substituted or unsubstituted heteroaryl. $R^2$ may be $R^{2C}$-substituted heteroaryl. $R^2$ may be $R^{2C}$-substituted or unsubstituted 5 to 20 membered heteroaryl. $R^2$ may be $R^{2C}$-substituted 5 to 20 membered heteroaryl. $R^2$ may be $R^{2C}$-substituted or unsubstituted 5 to 8 membered heteroaryl. $R^2$ may be $R^{2C}$-substituted 5 to 8 membered heteroaryl. $R^2$ may be $R^{2C}$-substituted or unsubstituted 5 or 6 membered heteroaryl. $R^2$ may be $R^{2C}$-substituted 5 or 6 membered heteroaryl.

$R^{2A}$ may independently be hydrogen, halogen, oxo, $N_3$, —$CF_3$, —$CCl_3$, —$CBr_3$, —$CI_3$, —CN, —OH, —$COR^{2C}$, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —NHC(O)$NHNH_2$, —NHC(O)$NH_2$, —NHS(O)$_2H$, —NHC(O)H, —NHC(O)—OH, —NHOH, —$OCF_3$, —$OCHF_2$, $R^{2C}$-substituted or unsubstituted alkyl, $R^{2C}$-substituted or unsubstituted heteroalkyl, $R^{2C}$-substituted or unsubstituted cycloalkyl, $R^{2C}$-substituted or unsubstituted heterocycloalkyl, $R^{2C}$-substituted or unsubstituted aryl, or $R^{2C}$-substituted or unsubstituted heteroaryl. $R^{2A}$ may independently be substituted or unsubstituted $C_1$-$C_5$ alkyl. $R^{2A}$ may independently be methyl.

$R^{2C}$ is independently hydrogen, halogen, oxo, $N_3$, —$CF_3$, —$CCl_3$, —$CBr_3$, —$CI_3$, —CN, —$OR^{2D}$, —$COR^{2D}$, —$NR^{2D}R^{2E}$, —$COOR^{2D}$, —$CONR^{2D}R^{2E}$, —$NO_2$, —SH, —$S(O)_2R^{2D}$, —$S(O)_3R^{2D}$, —$S(O)_4R^{2D}$, —$S(O)_2NR^{2D}R^{2E}$, —$NHNR^{2D}R^{2E}$, —$ONR^{2D}R^{2E}$, —NHC(O)$NHNR^{2D}R^{2E}$, —NHC(O)$NR^{2D}R^{2E}$, —NHS(O)$_2R^{2D}$, —NHC(O)$R^{2D}$, —NHC(O)—$OR^{2D}$, —$NHOR^{2D}$, —$OCF_3$, —$OCHF_2$, $R^{2D}$-substituted or unsubstituted alkyl, $R^{2D}$-substituted or unsubstituted heteroalkyl, $R^{2D}$-substituted or unsubstituted cycloalkyl, $R^{2D}$-substituted or unsubstituted heterocycloalkyl, $R^{2D}$-substituted or unsubstituted aryl, or $R^{2D}$-substituted or unsubstituted heteroaryl.

$R^{2C}$ may independently be hydrogen, halogen, oxo, $N_3$, —$CF_3$, —$CCl_3$, —$CBr_3$, —$CI_3$, —CN, —OH, —$COR^{2D}$, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —NHC(O)$NHNH_2$, —NHC(O)$NH_2$, —NHS(O)$_2H$, —NHC(O)H, —NHC(O)—OH, —NHOH, —$OCF_3$, —$OCHF_2$, $R^{2D}$-substituted or unsubstituted alkyl, $R^{2D}$-substituted or unsubstituted heteroalkyl, $R^{2D}$-substituted or unsubstituted cycloalkyl, $R^{2D}$-substituted or unsubstituted heterocycloalkyl, $R^{2D}$-substituted or unsubstituted aryl, or $R^{2D}$-substituted or unsubstituted heteroaryl.

$R^{2B}$ may independently be hydrogen, halogen, oxo, $N_3$, —$CF_3$, —$CCl_3$, —$CBr_3$, —$CI_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —NHC(O) $NHNH_2$, —NHC(O)$NH_2$, —NHS(O)$_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{2D}$ and $R^{2E}$ are independently hydrogen, halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —NHC(O)$NHNH_2$, —NHC(O)$NH_2$, —NHS(O)$_2H$, —NHC(O)H, —NHC(O)—OH, —NHOH, —$OCF_3$, —$OCHF_2$, unsubstituted heteroalkyl, unsubstituted cycloalkyl, unsubstituted heterocycloalkyl, unsubstituted aryl, or unsubstituted heteroaryl.

$R^2$ may be $R^{2A}$-substituted or unsubstituted heteroaryl where $R^{2A}$ is —$N_3$, —$CF_3$, —$CCl_3$, —$CBr_3$, —$CI_3$, —CN, —OH, —$NH_2$, —C(O)OH, —C(O)$NH_2$, —$NO_2$, —SH, substituted or unsubstituted alkyl, substituted or unsubstituted heteroalkyl. $R^2$ may be $R^{2A}$-substituted or unsubstituted heteroaryl where $R^{2A}$ is —$CF_3$, —CN, —OH, —$NH_2$, —C(O)OH, —C(O)$NH_2$, —$NO_2$, or substituted or unsubstituted alkyl. $R^{2A}$ may be substituted or unsubstituted $C_1$-$C_5$ alkyl. $R^{2A}$ may be methyl.

$R^2$ may be substituted or unsubstituted furanyl, substituted or unsubstituted pyrroyl, substituted or unsubstituted thiophenyl, substituted or unsubstituted imidazoyl, substituted or unsubstituted pyrazolyl, substituted or unsubstituted oxazoyl, substituted or unsubstituted isoxazolyl, substituted or unsubstituted thiazolyl, substituted or unsubstituted pyridinyl, substituted or unsubstituted pyrazinyl, substituted or unsubstituted pyrimidinyl, or substituted or unsubstituted pyridazinyl. $R^2$ may be substituted or unsubstituted furanyl. $R^2$ may be substituted or unsubstituted pyrroyl. $R^2$ may be substituted or unsubstituted thiophenyl. $R^2$ may be substituted or unsubstituted imidazoyl. $R^2$ may be substituted or unsubstituted pyrazolyl. $R^2$ may be substituted or unsubstituted oxazoyl. $R^2$ may be substituted or unsubstituted isoxazolyl. $R^2$ may be substituted or unsubstituted thiazolyl. $R^2$ may be substituted or unsubstituted pyridinyl. $R^2$ may be substituted or unsubstituted pyrazinyl. $R^2$ may be substituted or unsubstituted pyrimidinyl. $R^2$ may be substituted or unsubstituted pyridazinyl.

$R^2$ may be $R^{2A}$-substituted or unsubstituted furanyl, substituted or unsubstituted pyrroyl, substituted or unsubstituted thiophenyl, substituted or unsubstituted imidazoyl, substituted or unsubstituted pyrazolyl, substituted or unsubstituted oxazoyl, substituted or unsubstituted isoxazolyl, substituted or unsubstituted thiazolyl, substituted or unsubstituted pyridinyl, substituted or unsubstituted pyrazinyl, substituted or unsubstituted pyrimidinyl, or substituted or unsubstituted pyridazinyl. $R^2$ may be $R^{2A}$-substituted or unsubstituted furanyl. $R^2$ may be $R^{2A}$-substituted or unsubstituted pyrrolyl. $R^2$ may be $R^{2A}$-substituted or unsubstituted thiophenyl. $R^2$ may be $R^{2A}$-substituted or unsubstituted imidazoyl. $R^2$ may be $R^{2A}$-substituted or unsubstituted pyrazolyl. $R^2$ may be $R^{2A}$-substituted or unsubstituted pyrazolyl where $R^{2A}$ is $-N_3$, $-CF_3$, $-CCl_3$, $-CBr_3$, $-CI_3$, $-CN$, $-OH$, $-NH_2$, $-C(O)OH$, $-C(O)NH_2$, $-NO_2$, $-SH$, substituted or unsubstituted alkyl, or substituted or unsubstituted heteroalkyl. $R^2$ may be $R^{2A}$-substituted or unsubstituted oxazoyl. $R^2$ may be $R^{2A}$-substituted or unsubstituted isoxazolyl. $R^2$ may be $R^{2A}$-substituted or unsubstituted thiazolyl. $R^2$ may be $R^{2A}$-substituted or unsubstituted pyridinyl. $R^2$ may be $R^{2A}$-substituted or unsubstituted pyrazinyl. $R^2$ may be $R^{2A}$-substituted or unsubstituted pyrimidinyl. $R^2$ may be $R^{2A}$-substituted or unsubstituted pyridazinyl. $R^2$ may be 5-methyl-1H-pyrazolyl.

$R^3$ may be hydrogen, halogen, $-N_3$, $-CF_3$, $-CCl_3$, $-CBr_3$, $-CI_3$, $-CN$, $-COR^{3A}$, $-OR^{3A}$, $-NR^{3A}R^{3B}$, $-C(O)OR^{3A}$, $-C(O)NR^{3A}R^{3B}$, $-NO_2$, $-SR^{3A}$, $-S(O)_{n3}R^{3A}$, $-S(O)_{n3}OR^{3A}$, $-S(O)_3NR^{3A}R^{3B}$, $-NHNR^{3A}R^{3B}$, $-ONR^{3A}R^{3B}$, $-NHC(O)NHNR^{3A}R^{3B}$, substituted or unsubstituted alkyl, or optionally combined with $R^4$ to form a substituted or unsubstituted cycloalkyl where $R^{3A}$ and $R^{3B}$ are independently hydrogen, oxo, halogen, $-CF_3$, $-OH$, $-NH_2$, $-COOH$, $-CONH_2$, substituted or unsubstituted alkyl, or substituted or unsubstituted aryl.

$R^3$ may be hydrogen, halogen, $-OR^{3A}$, or substituted or unsubstituted alkyl, where $R^{3A}$ is as defined herein. $R^3$ may be hydrogen, halogen, $-OR^{3A}$, or $R^{3C}$-substituted or unsubstituted alkyl, where $R^{3A}$ and $R^{3C}$ are as defined herein. $R^3$ may be hydrogen, halogen, $-OR^{3A}$, or substituted or unsubstituted alkyl where $R^{3A}$ is substituted or unsubstituted alkyl. $R^3$ may be hydrogen, halogen, $-OR^{3A}$, or $R^{3C}$-substituted or unsubstituted alkyl where $R^{3A}$ is substituted or unsubstituted alkyl and $R^{3C}$ is as defined herein. $R^3$ may be hydrogen, halogen, $-OR^{3A}$, or substituted or unsubstituted alkyl where $R^{3A}$ is $R^{3C}$-substituted or unsubstituted alkyl. $R^3$ may be hydrogen, halogen, $-OR^{3A}$, or $R^{3C}$-substituted or unsubstituted alkyl where $R^{3A}$ is $R^{3C}$-substituted or unsubstituted alkyl and $R^{3C}$ is as defined herein.

$R^3$ may be $-Cl$, $-I$, or $-Br$. $R^3$ may be $-Cl$. $R^3$ may be $-Br$. $R^3$ may be $-I$. $R^3$ may be $-F$. $R^3$ may be $-OR^{3A}$, where $R^{3A}$ is as defined herein. $R^3$ may be $-OR^{3A}$ where $R^{3A}$ is substituted or unsubstituted alkyl. $R^3$ may be $-OR^{3A}$ where $R^{3A}$ is substituted or unsubstituted $C_1$-$C_5$ alkyl. $R^3$ may be $-OR^{3A}$ where $R^{3A}$ is $R^{3C}$-substituted or unsubstituted $C_1$-$C_5$ alkyl. $R^3$ may be $-OCH_3$. $R^3$ may be $-OCH_2CH_3$. $R^3$ may be $-OR^{3A}$ where $R^{3A}$ is substituted or unsubstituted $C_5$-$C_6$ aryl.

$R^3$ may be substituted or unsubstituted alkyl. $R^3$ may be substituted alkyl. $R^3$ may be unsubstituted alkyl. $R^3$ may be substituted or unsubstituted $C_1$-$C_{20}$ alkyl. $R^3$ may be substituted $C_1$-$C_{20}$ alkyl. $R^3$ may be unsubstituted $C_1$-$C_{20}$ alkyl. $R^3$ may be substituted or unsubstituted $C_1$-$C_{10}$ alkyl. $R^3$ may be substituted $C_1$-$C_{10}$ alkyl. $R^3$ may be unsubstituted $C_1$-$C_{10}$ alkyl. $R^3$ may be substituted or unsubstituted $C_1$-$C_5$ alkyl. $R^3$ may be unsubstituted $C_1$-$C_5$ alkyl. $R^3$ may be substituted $C_1$-$C_5$ alkyl. $R^3$ may be methyl, substituted or unsubstituted ethyl, or substituted or unsubstituted propyl. $R^3$ may be methyl. $R^3$ may be ethyl.

$R^3$ may be $R^{3C}$-substituted or unsubstituted alkyl. $R^3$ may be $R^{3C}$-substituted alkyl. $R^3$ may be $R^{3C}$-substituted or unsubstituted $C_1$-$C_{20}$ alkyl. $R^3$ may be $R^{3C}$-substituted $C_1$-$C_{20}$ alkyl. $R^3$ may be $R^{3C}$-substituted or unsubstituted $C_1$-$C_{10}$ alkyl. $R^3$ may be $R^{3C}$-substituted $C_1$-$C_{10}$ alkyl. $R^3$ may be $R^{3C}$-substituted or unsubstituted $C_1$-$C_5$ alkyl. $R^3$ may be $R^{3C}$-substituted $C_1$-$C_5$ alkyl. $R^3$ may be methyl, $R^{3C}$-substituted or unsubstituted ethyl, or $R^{3C}$-substituted or unsubstituted propyl.

$R^3$ may be substituted or unsubstituted heteroalkyl. $R^3$ may be substituted heteroalkyl. $R^3$ may be unsubstituted heteroalkyl. $R^3$ may be substituted or unsubstituted 2 to 20 membered heteroalkyl. $R^3$ may be substituted 2 to 20 membered heteroalkyl. $R^3$ may be unsubstituted 2 to 20 membered heteroalkyl. $R^3$ may be substituted or unsubstituted 2 to 10 membered heteroalkyl. $R^3$ may be substituted 2 to 10 membered heteroalkyl. $R^3$ may be unsubstituted 2 to 10 membered heteroalkyl. $R^3$ may be substituted or unsubstituted 2 to 6 membered heteroalkyl. $R^3$ may be substituted 2 to 6 membered heteroalkyl. $R^3$ may be unsubstituted 2 to 6 membered heteroalkyl.

$R^3$ may be $R^{3C}$-substituted or unsubstituted heteroalkyl. $R^3$ may be $R^{3C}$-substituted heteroalkyl. $R^3$ may be $R^{3C}$-substituted or unsubstituted 2 to 20 membered heteroalkyl. $R^3$ may be $R^{3C}$-substituted 2 to 20 membered heteroalkyl. $R^3$ may be $R^{3C}$-substituted or unsubstituted 2 to 10 membered heteroalkyl. $R^3$ may be $R^{3C}$-substituted 2 to 10 membered heteroalkyl. $R^3$ may be $R^{3C}$-substituted or unsubstituted 2 to 6 membered heteroalkyl. $R^3$ may be $R^{3C}$-substituted 2 to 6 membered heteroalkyl.

$R^3$ may be substituted or unsubstituted cycloalkyl. $R^3$ may be substituted cycloalkyl. $R^3$ may be unsubstituted cycloalkyl. $R^3$ may be substituted or unsubstituted 3 to 20 membered cycloalkyl. $R^3$ may be substituted 3 to 20 membered cycloalkyl. $R^3$ may be unsubstituted 3 to 20 membered cycloalkyl. $R^3$ may be substituted or unsubstituted 3 to 10 membered cycloalkyl. $R^3$ may be substituted 3 to 10 membered cycloalkyl. $R^3$ may be unsubstituted 3 to 10 membered cycloalkyl. $R^3$ may be unsubstituted 3 to 6 membered cycloalkyl. $R^3$ may be substituted 3 to 6 membered cycloalkyl.

$R^3$ may be $R^{3C}$-substituted or unsubstituted cycloalkyl. $R^3$ may be $R^{3C}$-substituted cycloalkyl. $R^3$ may be $R^{3C}$-substituted or unsubstituted 3 to 20 membered cycloalkyl. $R^3$ may be $R^{3C}$-substituted 3 to 20 membered cycloalkyl. $R^3$ may be $R^{3C}$-substituted or unsubstituted 3 to 10 membered cycloalkyl. $R^3$ may be $R^{3C}$-substituted 3 to 10 membered cycloalkyl. $R^3$ may be $R^{3C}$-substituted or unsubstituted 3 to 6 membered cycloalkyl. $R^3$ may be $R^{3C}$-substituted 3 to 6 membered cycloalkyl.

$R^3$ may be substituted or unsubstituted heterocycloalkyl. $R^3$ may be substituted heterocycloalkyl. $R^3$ may be unsubstituted heterocycloalkyl. $R^3$ may be substituted or unsubstituted 3 to 20 membered heterocycloalkyl. $R^3$ may be substituted 3 to 20 membered heterocycloalkyl. $R^3$ may be unsubstituted 3 to 20 membered heterocycloalkyl. $R^3$ may be substituted or unsubstituted 3 to 10 membered heterocycloalkyl. $R^3$ may be substituted 3 to 10 membered heterocycloalkyl. $R^3$ may be unsubstituted 3 to 10 membered heterocycloalkyl. $R^3$ may be substituted or unsubstituted 3 to 6 membered heterocycloalkyl. $R^3$ may be substituted 3 to 6 membered heterocycloalkyl. $R^3$ may be unsubstituted 3 to 6 membered heterocycloalkyl.

R$^3$ may be R$^{3C}$-substituted or unsubstituted heterocycloalkyl. R$^3$ may be R$^{3C}$-substituted heterocycloalkyl. R$^3$ may be R$^{3C}$-substituted or unsubstituted 3 to 20 membered heterocycloalkyl. R$^3$ may be R$^{3C}$-substituted 3 to 20 membered heterocycloalkyl. R$^3$ may be R$^{3C}$-substituted or unsubstituted 3 to 10 membered heterocycloalkyl. R$^3$ may be R$^{3C}$-substituted 3 to 10 membered heterocycloalkyl. R$^3$ may be R$^{3C}$-substituted or unsubstituted 3 to 6 membered heterocycloalkyl. R$^3$ may be R$^{3C}$-substituted 3 to 6 membered heterocycloalkyl.

R$^3$ may be substituted or unsubstituted aryl. R$^3$ may be substituted aryl. R$^3$ may be unsubstituted aryl. R$^3$ may be substituted or unsubstituted 5 to 20 membered aryl. R$^3$ may be substituted 5 to 20 membered aryl. R$^3$ may be unsubstituted 5 to 20 membered aryl. R$^3$ may be substituted or unsubstituted 5 to 8 membered aryl (e.g. phenyl). R$^3$ may be substituted 5 to 8 membered aryl. R$^3$ may be substituted or unsubstituted 5 or 6 membered aryl. R$^3$ may be unsubstituted 5 to 8 membered aryl (e.g. phenyl). R$^3$ may be substituted 5 or 6 membered aryl. R$^3$ may be unsubstituted 5 or 6 membered aryl.

R$^3$ may be R$^{3C}$-substituted or unsubstituted aryl. R$^3$ may be R$^{3C}$-substituted aryl. R$^3$ may be R$^{3C}$-substituted or unsubstituted 5 to 20 membered aryl. R$^3$ may be R$^{3C}$-substituted 5 to 20 membered aryl. R$^3$ may be R$^{3C}$-substituted or unsubstituted 5 to 8 membered aryl. R$^3$ may be R$^{3C}$-substituted 5 to 8 membered aryl. R$^3$ may be R$^{3C}$-substituted or unsubstituted 5 or 6 membered aryl. R$^3$ may be R$^{3C}$-substituted 5 or 6 membered aryl (e.g. phenyl).

R$^3$ may be substituted or unsubstituted heteroaryl. R$^3$ may be substituted heteroaryl. R$^3$ may be unsubstituted heteroaryl. R$^3$ may be substituted or unsubstituted 5 to 20 membered heteroaryl. R$^3$ may be substituted 5 to 20 membered heteroaryl. R$^3$ may be unsubstituted 5 to 20 membered heteroaryl. R$^3$ may be substituted or unsubstituted 5 to 8 membered heteroaryl. R$^3$ may be substituted 5 to 8 membered heteroaryl. R$^3$ may be unsubstituted 5 to 8 membered heteroaryl. R$^3$ may be substituted or unsubstituted 5 or 6 membered heteroaryl. R$^3$ may be substituted 5 or 6 membered heteroaryl. R$^3$ may be unsubstituted 5 or 6 membered heteroaryl.

R$^3$ may be R$^{3C}$-substituted or unsubstituted heteroaryl. R$^3$ may be R$^{3C}$-substituted heteroaryl. R$^3$ may be R$^{3C}$-substituted or unsubstituted 5 to 20 membered heteroaryl. R$^3$ may be R$^{3C}$-substituted 5 to 20 membered heteroaryl. R$^3$ may be R$^{3C}$-substituted or unsubstituted 5 to 8 membered heteroaryl. R$^3$ may be R$^{3C}$-substituted 5 to 8 membered heteroaryl. R$^3$ may be R$^{3C}$-substituted or unsubstituted 5 or 6 membered heteroaryl. R$^3$ may be R$^{3C}$-substituted 5 or 6 membered heteroaryl.

R$^{3A}$ may independently be hydrogen, halogen, oxo, N$_3$, —CF$_3$, —CCl$_3$, —CBr$_3$, —CI$_3$, —CN, —COR$^{3C}$, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{3C}$-substituted or unsubstituted alkyl, R$^{3C}$-substituted or unsubstituted heteroalkyl, R$^{3C}$-substituted or unsubstituted cycloalkyl, R$^{3C}$-substituted or unsubstituted heterocycloalkyl, R$^{3C}$-substituted or unsubstituted aryl, or R$^{3C}$-substituted or unsubstituted heteroaryl.

R$^{3C}$ is independently hydrogen, halogen, oxo, N$_3$, —CF$_3$, —CCl$_3$, —CBr$_3$, —CI$_3$, —CN, —COR$^{3D}$, —OR$^{3D}$, —NR$^{3D}$R$^{3E}$, —COOR$^{3D}$, —CONR$^{3D}$R$^{3E}$, —NO$_2$, —SR$^{3D}$, —S(O)$_2$R$^{3D}$, —S(O)$_3$R$^{3D}$, —S(O)$_4$R$^{3D}$, —S(O)$_2$R$^{3D}$R$^{3E}$, —NHNR$^{3D}$R$^{3E}$, —ONR$^{3D}$R$^{3E}$, —NHC(O)NHNR$^{3D}$R$^{3E}$, —NHC(O)NR$^{3D}$R$^{3E}$, —NHS(O)$_2$R$^{3D}$, —NHC(O)R$^{3D}$, —NHC(O)—OR$^D$, —NHOR$^{3D}$, —OCF$_3$, —OCHF$_2$, R$^{3D}$-substituted or unsubstituted alkyl, R$^{3D}$-substituted or unsubstituted heteroalkyl, R$^{3D}$-substituted or unsubstituted cycloalkyl, R$^{3D}$-substituted or unsubstituted heterocycloalkyl, R$^{3D}$-substituted or unsubstituted aryl, or R$^{3D}$-substituted or unsubstituted heteroaryl.

R$^{3C}$ may independently be hydrogen, halogen, oxo, N$_3$, —CF$_3$, —CCl$_3$, —CBr$_3$, —CI$_3$, —CN, —COR$^{3D}$, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{3D}$-substituted or unsubstituted alkyl, R$^{3D}$-substituted or unsubstituted heteroalkyl, R$^{3D}$-substituted or unsubstituted cycloalkyl, R$^{3D}$-substituted or unsubstituted heterocycloalkyl, R$^{3D}$-substituted or unsubstituted aryl, or R$^{3D}$-substituted or unsubstituted heteroaryl.

R$^{3B}$ may independently be hydrogen, halogen, oxo, N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

R$^{3D}$ is independently hydrogen, halogen, oxo, N$_3$, —CF$_3$, —CCl$_3$, —CBr$_3$, —CI$_3$, —CN, —OH, —COR$^{3F}$, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{3F}$-substituted or unsubstituted heteroalkyl, R$^{3F}$-substituted or unsubstituted cycloalkyl, R$^{3F}$-substituted or unsubstituted heterocycloalkyl, R$^{3F}$-substituted or unsubstituted aryl, or R$^{3F}$-substituted or unsubstituted heteroaryl.

R$^{3D}$ may independently be hydrogen, halogen, oxo, N$_3$, —CF$_3$, —CCl$_3$, —CBr$_3$, —CI$_3$, —CN, —OH, —COH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted heteroalkyl, unsubstituted cycloalkyl, unsubstituted heterocycloalkyl, unsubstituted aryl, or unsubstituted heteroaryl.

R$^{3E}$ and R$^{3F}$ are independently hydrogen, halogen, oxo, N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

R$^3$ and R$^4$ may together form a substituted or unsubstituted cycloalkyl. R$^3$ and R$^4$ may together form a R$^{3C}$-substituted or unsubstituted cycloalkyl. R$^3$ and R$^4$ may together form an unsubstituted cycloalkyl. R$^3$ and R$^4$ may together form an unsubstituted C$_3$-C$_6$ cycloalkyl. R$^3$ and R$^4$ may together form an unsubstituted saturated C$_3$-C$_6$ cycloalkyl. R$^3$ and R$^4$ may together form an C$_3$-C$_6$ unsubstituted unsaturated cycloalkyl. R$^3$ and R$^4$ may together form an R$^{3C}$-substituted saturated C$_3$-C$_6$ cycloalkyl where R$^{3C}$ is as defined herein. R$^{3C}$ may be halogen, —COR$^{3D}$, unsubstituted C$_1$-C$_5$ alkyl, substituted or unsubstituted cycloalkyl, or substituted or unsubstituted heterocycloalkyl. R$^{3C}$ may be methyl, unsubstituted ethyl, or unsubstituted propyl. R$^{3C}$ may be substituted or unsubstituted $C_3$-$C_6$ cycloalkyl. $R^{3C}$ may be unsubstituted $C_3$-$C_6$ cycloalkyl. $R^{3C}$ may be substituted $C_3$-$C_6$ cycloalkyl. $R^{3C}$ may be $R^{3D}$-substituted cycloalkyl, where $R^{3D}$ is as defined herein. $R^{3C}$ may be substituted or unsubstituted $C_3$-$C_6$ heterocycloalkyl. $R^{3C}$ may be unsubstituted $C_3$-$C_6$ heterocycloalkyl. $R^{3C}$ may be substituted $C_3$-$C_6$ heterocycloalkyl. $R^{3C}$ may be $R^{3D}$-substituted heterocycloalkyl, where $R^{3D}$ is as defined herein. $R^{3D}$ may be —$COR^{3E}$, substituted or unsubstituted alkyl or substituted or unsubstituted heterocycloalkyl.

$R^4$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ may be substituted or unsubstituted cycloalkyl, substituted or unsubstituted heterocycloalkyl, substituted or unsubstituted aryl, or substituted or unsubstituted heteroaryl.

$R^4$ may be substituted or unsubstituted alkyl. $R^4$ may be substituted alkyl. $R^4$ may be unsubstituted alkyl. $R^4$ may be substituted or unsubstituted $C_1$-$C_{20}$ alkyl. $R^4$ may be substituted $C_1$-$C_{20}$ alkyl. $R^4$ may be unsubstituted $C_1$-$C_{20}$ alkyl. $R^4$ may be substituted or unsubstituted $C_1$-$C_{10}$ alkyl. $R^4$ may be substituted $C_1$-$C_{10}$ alkyl. $R^4$ may be unsubstituted $C_1$-$C_{10}$ alkyl. $R^4$ may be substituted or unsubstituted $C_1$-$C_5$ alkyl. $R^4$ may be substituted $C_1$-$C_5$ alkyl. $R^4$ may be unsubstituted $C_1$-$C_5$ alkyl. $R^4$ may be methyl, substituted or unsubstituted ethyl, or substituted or unsubstituted propyl.

$R^4$ may be $R^{40}$-substituted or unsubstituted alkyl. $R^4$ may be $R^{40}$-substituted alkyl. $R^4$ may be $R^{40}$-substituted or unsubstituted $C_1$-$C_{20}$ alkyl. $R^4$ may be $R^{40}$-substituted $C_1$-$C_{20}$ alkyl. $R^4$ may be $R^{40}$-substituted or unsubstituted $C_1$-$C_{10}$ alkyl. $R^4$ may be $R^{40}$-substituted $C_1$-$C_{10}$ alkyl. $R^4$ may be $R^{40}$-substituted or unsubstituted $C_1$-$C_5$ alkyl. $R^4$ may be $R^{40}$-substituted $C_1$-$C_5$ alkyl. $R^4$ may be methyl, $R^{40}$-substituted or unsubstituted ethyl, or $R^{40}$-substituted or unsubstituted propyl.

$R^4$ may be substituted or unsubstituted heteroalkyl. $R^4$ may be substituted heteroalkyl. $R^4$ may be unsubstituted heteroalkyl. $R^4$ may be substituted or unsubstituted 2 to 20 membered heteroalkyl. $R^4$ may be substituted 2 to 20 membered heteroalkyl. $R^4$ may be unsubstituted 2 to 20 membered heteroalkyl. $R^4$ may be substituted or unsubstituted 2 to 10 membered heteroalkyl. $R^4$ may be substituted 2 to 10 membered heteroalkyl. $R^4$ may be unsubstituted 2 to 10 membered heteroalkyl. $R^4$ may be substituted or unsubstituted 2 to 6 membered heteroalkyl. $R^4$ may be substituted 2 to 6 membered heteroalkyl. $R^4$ may be unsubstituted 2 to 6 membered heteroalkyl.

$R^4$ may be $R^{40}$-substituted or unsubstituted heteroalkyl. $R^4$ may be $R^{40}$-substituted heteroalkyl. $R^4$ may be $R^{40}$-substituted or unsubstituted 2 to 20 membered heteroalkyl. $R^4$ may be $R^{40}$-substituted 2 to 20 membered heteroalkyl. $R^4$ may be $R^{40}$-substituted or unsubstituted 2 to 10 membered heteroalkyl. $R^4$ may be $R^{40}$-substituted 2 to 10 membered heteroalkyl. $R^4$ may be $R^{40}$-substituted or unsubstituted 2 to 6 membered heteroalkyl. $R^4$ may be $R^{40}$-substituted 2 to 6 membered heteroalkyl.

$R^4$ may be substituted or unsubstituted cycloalkyl. $R^4$ may be substituted cycloalkyl. $R^4$ may be unsubstituted cycloalkyl. $R^4$ may be substituted or unsubstituted 3 to 20 membered cycloalkyl. $R^4$ may be substituted 3 to 20 membered cycloalkyl. $R^4$ may be unsubstituted 3 to 20 membered cycloalkyl. $R^4$ may be substituted or unsubstituted 3 to 10 membered cycloalkyl. $R^4$ may be substituted 3 to 10 membered cycloalkyl. $R^4$ may be unsubstituted 3 to 10 membered cycloalkyl. $R^4$ may be substituted or unsubstituted 3 to 6 membered cycloalkyl. $R^4$ may be substituted 3 to 6 membered cycloalkyl. $R^4$ may be unsubstituted 3 to 6 membered cycloalkyl.

$R^4$ may be $R^{40}$-substituted or unsubstituted cycloalkyl. $R^4$ may be $R^{40}$-substituted cycloalkyl. $R^4$ may be $R^{40}$-substituted or unsubstituted 3 to 20 membered cycloalkyl. $R^4$ may be $R^{40}$-substituted 3 to 20 membered cycloalkyl. $R^4$ may be $R^{40}$-substituted or unsubstituted 3 to 10 membered cycloalkyl. $R^4$ may be $R^{40}$-substituted 3 to 10 membered cycloalkyl. $R^4$ may be $R^{40}$-substituted or unsubstituted 3 to 6 membered cycloalkyl. $R^4$ may be $R^{40}$-substituted 3 to 6 membered cycloalkyl.

$R^4$ may be substituted or unsubstituted heterocycloalkyl. $R^4$ may be substituted heterocycloalkyl. $R^4$ may be unsubstituted heterocycloalkyl. $R^4$ may be substituted or unsubstituted 3 to 20 membered heterocycloalkyl. $R^4$ may be substituted 3 to 20 membered heterocycloalkyl. $R^4$ may be unsubstituted 3 to 20 membered heterocycloalkyl. $R^4$ may be substituted or unsubstituted 3 to 10 membered heterocycloalkyl. $R^4$ may be substituted 3 to 10 membered heterocycloalkyl. $R^4$ may be unsubstituted 3 to 10 membered heterocycloalkyl. $R^4$ may be substituted or unsubstituted 3 to 6 membered heterocycloalkyl. $R^4$ may be substituted 3 to 6 membered heterocycloalkyl. $R^4$ may be unsubstituted 3 to 6 membered heterocycloalkyl.

$R^4$ may be $R^{40}$-substituted or unsubstituted heterocycloalkyl. $R^4$ may be $R^{40}$-substituted heterocycloalkyl. $R^4$ may be $R^{40}$-substituted or unsubstituted 3 to 20 membered heterocycloalkyl. $R^4$ may be $R^{40}$-substituted 3 to 20 membered heterocycloalkyl. $R^4$ may be $R^{40}$-substituted or unsubstituted 3 to 10 membered heterocycloalkyl. $R^4$ may be $R^{40}$-substituted 3 to 10 membered heterocycloalkyl. $R^4$ may be $R^{40}$-substituted or unsubstituted 3 to 6 membered heterocycloalkyl. $R^4$ may be $R^{40}$-substituted 3 to 6 membered heterocycloalkyl.

$R^4$ may be substituted or unsubstituted aryl. $R^4$ may be substituted aryl. $R^4$ may be unsubstituted aryl. $R^4$ may be substituted or unsubstituted 5 to 20 membered aryl. $R^4$ may be substituted 5 to 20 membered aryl. $R^4$ may be unsubstituted 5 to 20 membered aryl. $R^4$ may be substituted or unsubstituted 5 to 8 membered aryl. $R^4$ may be substituted 5 to 8 membered aryl. $R^4$ may be unsubstituted 5 to 8 membered aryl. $R^4$ may be substituted or unsubstituted 5 or 6 membered aryl. $R^4$ may be substituted 5 or 6 membered aryl (e.g. phenyl). $R^4$ may be unsubstituted 5 or 6 membered aryl.

$R^4$ may be $R^{40}$-substituted or unsubstituted aryl. $R^4$ may be $R^{40}$-substituted aryl. $R^4$ may be $R^{40}$-substituted or unsubstituted 5 to 20 membered aryl. $R^4$ may be $R^{40}$-substituted 5 to 20 membered aryl. $R^4$ may be $R^{40}$-substituted or unsubstituted 5 to 8 membered aryl. $R^4$ may be $R^{40}$-substituted 5 to 8 membered aryl. $R^4$ may be $R^{40}$-substituted or unsubstituted 5 or 6 membered aryl. $R^4$ may be $R^{40}$-substituted 5 or 6 membered aryl (e.g. phenyl).

$R^4$ may be substituted or unsubstituted aryl. $R^4$ may be substituted heteroaryl. $R^4$ may be unsubstituted heteroaryl. $R^4$ may be substituted or unsubstituted 5 to 20 membered heteroaryl. $R^4$ may be substituted 5 to 20 membered aryl. $R^4$ may be unsubstituted 5 to 20 membered heteroaryl. $R^4$ may be substituted or unsubstituted 5 to 8 membered heteroaryl. $R^4$ may be substituted 5 to 8 membered heteroaryl. $R^4$ may be unsubstituted 5 to 8 membered heteroaryl. $R^4$ may be substituted or unsubstituted 5 or 6 membered heteroaryl. $R^4$ may be substituted 5 or 6 membered heteroaryl. $R^4$ may be unsubstituted 5 or 6 membered heteroaryl.

$R^4$ may be $R^{40}$-substituted or unsubstituted heteroaryl. $R^4$ may be $R^{40}$-substituted heteroaryl. $R^4$ may be $R^{40}$-substituted or unsubstituted 5 to 20 membered heteroaryl. $R^4$ may be $R^{40}$-substituted 5 to 20 membered heteroaryl. $R^4$ may be $R^{40}$-substituted or unsubstituted 5 to 8 membered heteroaryl. $R^4$ may be $R^{40}$-substituted 5 to 8 membered heteroaryl. $R^4$ may be $R^{40}$-substituted or unsubstituted 5 or 6 membered heteroaryl. $R^4$ may be $R^{40}$-substituted 5 or 6 membered heteroaryl.

$R^4$ may be $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl. $R^4$ may be $R^{40}$-substituted or unsubstituted cycloalkyl. $R^4$ may be $R^{40}$-substituted or unsubstituted aryl. $R^4$ may be $R^{40}$-substituted or unsubstituted heteroaryl.

$R^4$ may be $R^{40}$-substituted or unsubstituted heterocycloalkyl. $R^4$ may be substituted or unsubstituted 5 to 8 membered heterocycloalkyl. $R^4$ may be $R^{40}$-substituted or unsubstituted 5 to 8 membered heterocycloalkyl. $R^4$ may be substituted or unsubstituted 5 to 8 membered heterocycloalkyl having at least one ring nitrogen. $R^4$ may be $R^{40}$-substituted or unsubstituted 5 to 8 membered heterocycloalkyl having at least one ring nitrogen.

$R^4$ may be substituted or unsubstituted piperidinyl, substituted or unsubstituted piperazinyl, substituted or unsubstituted morpholino, or substituted or unsubstituted pyrrolidinyl. $R^4$ may be substituted or unsubstituted piperidinyl. $R^4$ may be substituted or unsubstituted piperazinyl. $R^4$ may be substituted or unsubstituted morpholino. $R^4$ may be substituted or unsubstituted pyrrolidinyl.

$R^4$ may be $R^{40}$-substituted or unsubstituted piperidinyl, $R^{40}$-substituted or unsubstituted piperazinyl, $R^{40}$-substituted or unsubstituted morpholino, or $R^{40}$-substituted or unsubstituted pyrrolidinyl. $R^4$ may be $R^{40}$-substituted or unsubstituted piperidinyl. $R^4$ may be $R^{40}$-substituted or unsubstituted piperazinyl. $R^4$ may be $R^{40}$-substituted or unsubstituted morpholino. $R^4$ may be $R^{40}$-substituted or unsubstituted pyrrolidinyl.

$R^{40}$ is independently oxo, halogen, $-N_3$, $-CF_3$, $-CCl_3$, $-CBr_3$, $-CI_3$, $-CN$, $-COR^{40A}$, $-OR^{40A}$, $-NR^{40A}R^{40B}$, $-C(O)OR^{40A}$, $-C(O)NR^{40A}R^{40B}$, $-NO_2$, $-SR^{40A}$, $-S(O)_2R^{40A}$, $-S(O)_2OR^{40A}$, $-S(O)_2N^{40A}R^{40B}$, $-NHNR^{40A}R^{40B}$, $-ONR^{40A}R^{40B}$, $-NHC(O)NHNR^{40A}R^{40B}$, $R^{40A}$-substituted or unsubstituted alkyl, $R^{40A}$-substituted or unsubstituted heteroalkyl, $R^{40A}$-substituted or unsubstituted cycloalkyl, $R^{40A}$-substituted or unsubstituted heterocycloalkyl, $R^{40A}$-substituted or unsubstituted aryl, or $R^{40A}$-substituted or unsubstituted heteroaryl.

$R^{40}$ may independently be oxo, halogen, $-N_3$, $-CF_3$, $-CCl_3$, $-CBr_3$, $-CI_3$, $-CN$, $-COR^{40A}$, $-OR^{40A}$, $-NR^{40A}R^{40B}$, $-C(O)OR^{40A}$, $-C(O)NR^{40A}R^{40B}$, $-NO_2$, $-SR^{40A}$, $-S(O)_2R^{40A}$, $-S(O)_2OR^{40A}$, $-S(O)_2NR^{40A}R^{40B}$, $-NHNR^{40A}R^{40B}$, $-ONR^{40A}R^{40B}$, $-NHC(O)NHNR^{40A}R^{40B}$, unsubstituted alkyl, unsubstituted heteroalkyl, unsubstituted cycloalkyl, unsubstituted heterocycloalkyl, unsubstituted aryl, or unsubstituted heteroaryl.

$R^{40}$ may independently be oxo, halogen, $-N_3$, $-CF_3$, $-CCl_3$, $-CBr_3$, $-CI_3$, $-CN$, $-OH$, $-NH_2$, $-C(O)OH$, $-C(O)NH_2$, $-COH$, $-COCH_3$, $-NO_2$, $-SH$, $-S(O)_2H$, $-S(O)_2OH$, $-S(O)_2NH_2$, $-NHNH_2$, $-ONH_2$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^{40A}$ is independently hydrogen, oxo, halogen, $-N_3$, $-CF_3$, $-CCl_3$, $-CBr_3$, $-CI_3$, $-CN$, $-OR^{41}$, $-NR^{41A}R^{40C}$, $-COR^{41}$, $-COOR^{41}$, $-CONR^{41A}R^{40C}$, $-NO_2$, $-SR^{41}$, $-S(O)_2R^{41}$, $-S(O)_3R^{41}$, $-S(O)_2NR^{41}R^{40C}$, $S(O)_4R^{41}$, $-NHNR^{41}R^{40C}$, $-ONR^{41}R^{40C}$, $-NHC(O)NHNR^{41}R^{40C}$, $-NHC(O)NR^{41A}R^{40C}$, $-NHS(O)_2R^{41}$, $-NHC(O)R^{41}$, $-NHC(O)-OR^{41}$, $-NHOR^{41}$, $-OCF_3$, $-OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^{40A}$ may independently be hydrogen, oxo, halogen, $-N_3$, $-CF_3$, $-CCl_3$, $-CBr_3$, $-CI_3$, $-CN$, $-OH$, $-NH_2$, $-COR^{41}$, $-COOH$, $-CONH_2$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^{40A}$ may independently be hydrogen, oxo, halogen, $-N_3$, $-CF_3$, $-CCl_3$, $-CBr_3$, $-CI_3$, $-CN$, $-OH$, $-NH_2$, $-COOH$, $-CONH_2$, $-COH$, $-COCH_3$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{41}$ is independently hydrogen, halogen, $-N_3$, $-CF_3$, $-CCl_3$, $-CBr_3$, $-CI_3$, $-CN$, $-COR^{41A}$, $-OR^{41A}$, $-NR^{41A}R^{41B}$, $-C(O)OR^{41A}$, $-C(O)NR^{41A}R^{41B}$, $-NO_2$, $-SR^{41A}$, $-S(O)_2R^{41A}$, $-S(O)_2OR^{41A}$, $-S(O)_2NR^{41A}R^{41B}$, $-NHNR^{41A}R^{41B}$, $-ONR^{41A}R^{41B}$, $-NHC(O)NHNR^{41A}R^{41B}$, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl.

$R^{41}$ may independently be hydrogen, oxo, halogen, $-N_3$, $-CF_3$, $-CCl_3$, $-CBr_3$, $-CI_3$, $-CN$, $-OH$, $-NH_2$, $-COOH$, $-CONH_2$, $-COH$, $-COCH_3$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{42}$ is independently oxo, halogen, $-N_3$, $-CF_3$, $-CCl_3$, $-CBr_3$, $-CI_3$, $-CN$, $-OH$, $-NH_2$, $-COOH$, $-CONH_2$, $-COH$, $-COCH_3$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl.

$R^{42}$ may independently be oxo, halogen, $-N_3$, $-CF_3$, $-CCl_3$, $-CBr_3$, $-CI_3$, $-CN$, $-OH$, $-NH_2$, $-COOH$, $-CONH_2$, $-COH$, $-COCH_3$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{43}$ is independently oxo, halogen, $-N_3$, $-CF_3$, $-CCl_3$, $-CBr_3$, $-CI_3$, $-CN$, $-OH$, $-NH_2$, $-COOH$, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{44}$-substituted or unsubstituted alkyl, R$^{44}$-substituted or unsubstituted heteroalkyl, R$^{44}$-substituted or unsubstituted cycloalkyl, R$^{44}$-substituted or unsubstituted heterocycloalkyl, R$^{44}$-substituted or unsubstituted aryl, or R$^{44}$-substituted or unsubstituted heteroaryl.

R$^{41A}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{41C}$-substituted or unsubstituted heteroalkyl, R$^{41C}$-substituted or unsubstituted cycloalkyl, R$^{41C}$-substituted or unsubstituted heterocycloalkyl, R$^{41C}$-substituted or unsubstituted aryl, or R$^{41C}$-substituted or unsubstituted heteroaryl.

R$^{41C}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{41D}$-substituted or unsubstituted alkyl, R$^{41D}$-substituted or unsubstituted heteroalkyl, R$^{41D}$-substituted or unsubstituted cycloalkyl, R$^{41D}$-substituted or unsubstituted heterocycloalkyl, R$^{41D}$-substituted or unsubstituted aryl, or R$^{41D}$-substituted or unsubstituted heteroaryl.

R$^{41B}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{41E}$-substituted or unsubstituted alkyl, R$^{41E}$-substituted or unsubstituted heteroalkyl, R$^{41E}$-substituted or unsubstituted cycloalkyl, R$^{41E}$-substituted or unsubstituted heterocycloalkyl, R$^{41E}$-substituted or unsubstituted aryl, or R$^{41E}$-substituted or unsubstituted heteroaryl.

R$^{41E}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{41F}$-substituted or unsubstituted alkyl, R$^{41F}$-substituted or unsubstituted heteroalkyl, R$^{41F}$-substituted or unsubstituted cycloalkyl, R$^{41F}$-substituted or unsubstituted heterocycloalkyl, R$^{41F}$-substituted or unsubstituted aryl, or R$^{41F}$-substituted or unsubstituted heteroaryl.

R$^{40B}$ is independently hydrogen, oxo, halogen, —N$_3$, —CF$_3$, —CCl$_3$, —CBr$_3$, —CI$_3$, —CN, —OR$^{45}$, —NR$^{45}$R$^{40D}$, —COR$^{45}$, —COOR$^{45}$, —CONR$^{45}$R$^{40D}$, —NO$_2$, —SR$^{45}$, —S(O)$_2$R$^{45}$, —S(O)$_3$R$^{45}$, —S(O)$_4$R$^{45}$, —S(O)$_2$NR$^{45}$R$^{40D}$, —NHNR$^{45}$R$^{40D}$, —ONR$^{45}$R$^{40D}$, —NHC(O)NHNR$^{45}$R$^{40D}$, —NHC(O)NR$^{45}$R$^{40D}$, —NHS(O)$_2$R$^{45}$, —NHC(O)R$^{45}$, —NHC(O)—OR$^{45}$, —NHOR$^{45}$, —OCF$_3$, —OCHF$_2$, R$^{45}$-substituted or unsubstituted heteroalkyl, R$^{45}$-substituted or unsubstituted cycloalkyl, R$^{45}$-substituted or unsubstituted heterocycloalkyl, R$^{45}$-substituted or unsubstituted aryl, or R$^{45}$-substituted or unsubstituted heteroaryl.

R$^{40B}$ may independently be hydrogen, oxo, halogen, —N$_3$, —CF$_3$, —CCl$_3$, —CBr$_3$, —CI$_3$, —CN, —OH, —NH$_2$, —COR$^{45}$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{45}$-substituted or unsubstituted heteroalkyl, R$^{45}$-substituted or unsubstituted cycloalkyl, R$^{45}$-substituted or unsubstituted heterocycloalkyl, R$^{45}$-substituted or unsubstituted aryl, or R$^{45}$-substituted or unsubstituted heteroaryl.

R$^{40B}$ may independently be hydrogen, oxo, halogen, —N$_3$, —CF$_3$, —CCl$_3$, —CBr$_3$, —CI$_3$, —CN, —OH, —NH$_2$, —COOH, —COH, —COCH$_3$, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

R$^{45}$ is independently hydrogen, halogen, oxo, —N$_3$, —CF$_3$, —CCl$_3$, —CBr$_3$, —CI$_3$, —CN, —COR$^{45A}$, —OR$^{45A}$, —NR$^{45A}$R$^{45B}$, —C(O)OR$^{45A}$, —C(O)NR$^{45A}$R$^{45B}$, —NO$_2$, —SR$^{45A}$, —S(O)$_2$R$^{45A}$, —S(O)$_2$OR$^{45A}$, —S(O)$_2$NR$^{45A}$R$^{45B}$, —NHNR$^{45A}$R$^{45B}$, —ONR$^{45A}$R$^{45B}$, —NHC(O)NHNR$^{45A}$R$^{45B}$, R$^{46}$-substituted or unsubstituted alkyl, R$^{46}$-substituted or unsubstituted heteroalkyl, R$^{46}$-substituted or unsubstituted cycloalkyl, R$^{46}$-substituted or unsubstituted heterocycloalkyl, R$^{46}$-substituted or unsubstituted aryl, or R$^{46}$-substituted or unsubstituted heteroaryl.

R$^{45A}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{45C}$-substituted or unsubstituted heteroalkyl, R$^{45C}$-substituted or unsubstituted cycloalkyl, R$^{45C}$-substituted or unsubstituted heterocycloalkyl, R$^{45C}$-substituted or unsubstituted aryl, or R$^{45C}$-substituted or unsubstituted heteroaryl.

R$^{45C}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{45D}$-substituted or unsubstituted alkyl, R$^{45D}$-substituted or unsubstituted heteroalkyl, R$^{45D}$-substituted or unsubstituted cycloalkyl, R$^{45D}$-substituted or unsubstituted heterocycloalkyl, R$^{45D}$-substituted or unsubstituted aryl, or R$^{45D}$-substituted or unsubstituted heteroaryl.

R$^{45B}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{45E}$-substituted or unsubstituted alkyl, R$^{45E}$-substituted or unsubstituted heteroalkyl, R$^{45E}$-substituted or unsubstituted cycloalkyl, R$^{45E}$-substituted or unsubstituted heterocycloalkyl, R$^{45E}$-substituted or unsubstituted aryl, or R$^{45E}$-substituted or unsubstituted heteroaryl.

R$^{45E}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{45F}$-substituted or unsubstituted alkyl, R$^{45F}$-substituted or unsubstituted heteroalkyl, R$^{45F}$-substituted or unsubstituted cycloalkyl, R$^{45F}$-substituted or unsubstituted heterocycloalkyl, R$^{45F}$-substituted or unsubstituted aryl, or R$^{45F}$-substituted or unsubstituted heteroaryl.

R$^{46}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{47}$-substituted or unsubstituted alkyl, R$^{47}$-substituted or unsubstituted heteroalkyl, R$^{47}$-substituted or unsubstituted cycloalkyl, R$^{47}$-substituted or unsubstituted heterocycloalkyl, R$^{47}$-substituted or unsubstituted aryl, or R$^{47}$-substituted or unsubstituted heteroaryl.

R$^{40C}$, R$^{40D}$, R$^{41D}$, R$^{41F}$, and R$^{45D}$ are independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

R$^{45F}$, R$^{44}$, and R$^{47}$ are independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl R$^4$ may be —NR$^{4A}$R$^{4B}$. R$^{4A}$ and R$^{4B}$ are as defined herein. R$^{4A}$ may be hydrogen, R$^{41}$-substituted or unsubstituted alkyl, or R$^{41}$-substituted or unsubstituted heteroalkyl, where R$^{41}$ is as defined herein. R$^{4A}$ may be hydrogen, R$^{41}$-substituted or unsubstituted alkyl, or R$^{41}$-substituted or unsubstituted heteroalkyl, where R$^{41}$ is hydrogen, halogen, —CF$_3$, —OR$^{41A}$, —NR$^{41A}$R$^{41B}$, R$^{42}$-substituted or unsubstituted alkyl, R$^{42}$-substituted or unsubstituted heteroalkyl, or R$^{42}$-substituted or unsubstituted aryl. R$^{4A}$ may be hydrogen, R$^{41}$-substituted or unsubstituted alkyl, or R$^{41}$-substituted or unsubstituted heteroalkyl, where R$^{41}$ is hydrogen, halogen, —CF$_3$, —OR$^{41A}$, —NR$^{41A}$R$^{41B}$, R$^{42}$-substituted or unsubstituted alkyl, R$^{42}$-substituted or unsubstituted heteroalkyl, or R$^{42}$-substituted or unsubstituted aryl, R$^{41A}$ and R$^{41B}$ are independently hydrogen or unsubstituted C$_1$-C$_5$ alkyl, and R$^{42}$ is as described herein.

R$^{4B}$ may be hydrogen, R$^{45}$-substituted or unsubstituted alkyl, or R$^{45}$-substituted or unsubstituted heteroalkyl, where R$^{45}$ is as defined herein. R$^{4B}$ may be hydrogen, R$^{45}$-substituted or unsubstituted alkyl, or R$^{45}$-substituted or unsubstituted heteroalkyl, where R$^{45}$ is hydrogen, halogen, CF$_3$, —OR$^{45A}$, —NR$^{45A}$R$^{45B}$, R$^{46}$-substituted or unsubstituted alkyl, R$^{46}$-substituted or unsubstituted heteroalkyl, or R$^{46}$-substituted or unsubstituted aryl. R$^{4B}$ may be hydrogen, R$^{45}$-substituted or unsubstituted alkyl, or R$^{45}$-substituted or unsubstituted heteroalkyl, where R$^{45}$ is hydrogen, halogen, CF$_3$, —OR$^{45A}$, —N$^{45A}$R$^{45B}$, R$^{46}$-substituted or unsubstituted alkyl, R$^{46}$-substituted or unsubstituted heteroalkyl, or R$^{46}$-substituted or unsubstituted aryl, R$^{45A}$ and R$^{45B}$ are independently hydrogen or unsubstituted C$_1$-C$_5$ alkyl and R$^{46}$ is as defined herein.

R$^{4A}$ may independently be hydrogen, oxo, halogen, —N$_3$, —CF$_3$, —CCl$_3$, —CBr$_3$, —CI$_3$, —CN, —OR$^{41}$, —NR$^{41}$R$^{40C}$, —COR$^{41}$, —COOR$^{41}$, —CONR$^{41}$R$^{40C}$, —NO$_2$, —SR$^{41}$, —S(O)$_2$R$^{41}$, —S(O)$_3$R$^{41}$, —S(O)$_4$R$^{41}$, —NHNR$^{41A}$R$^{40C}$, —ONR$^{41A}$R$^{40C}$, —NHC(O)NHNR$^{41}$R$^{40C}$, —NHC(O)NR$^{41A}$R$^{40C}$, —NHS(O)$_2$R$^{41}$, —NHC(O)R$^{41}$, —NHC(O)—OR$^{41}$, —NHOR$^{41}$, —OCF$_3$, —OCHF$_2$, R$^{41}$-substituted or unsubstituted alkyl, R$^{41}$-substituted or unsubstituted heteroalkyl, R$^{41}$-substituted or unsubstituted cycloalkyl, R$^{41}$-substituted or unsubstituted heterocycloalkyl, R$^{41}$-substituted or unsubstituted aryl, or R$^{41}$-substituted or unsubstituted heteroaryl.

R$^{4A}$ may independently be hydrogen, oxo, halogen, —N$_3$, —CF$_3$, —CCl$_3$, —CBr$_3$, —CI$_3$, —CN, —OH, —NH$_2$, —COR$^{41}$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{41}$-substituted or unsubstituted alkyl, R$^{41}$-substituted or unsubstituted heteroalkyl, R$^{41}$-substituted or unsubstituted cycloalkyl, R$^{41}$-substituted or unsubstituted heterocycloalkyl, R$^{41}$-substituted or unsubstituted aryl, or R$^{41}$-substituted or unsubstituted heteroaryl.

R$^{4A}$ may independently be hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{41}$-substituted or unsubstituted alkyl, R$^{41}$-substituted or unsubstituted heteroalkyl, R$^{41}$-substituted or unsubstituted cycloalkyl, R$^{41}$-substituted or unsubstituted heterocycloalkyl, R$^{41}$-substituted or unsubstituted aryl, or R$^{41}$-substituted or unsubstituted heteroaryl.

R$^{4B}$ may independently be hydrogen, oxo, halogen, —N$_3$, —CF$_3$, —CCl$_3$, —CBr$_3$, —CI$_3$, —CN, —OR$^{45}$, —NR$^{45}$R$^{40D}$, —COR$^{45}$, —COOR$^{45}$, —CONR$^{45}$R$^{40D}$, —NO$_2$, —SR$^{45}$, —S(O)$_2$R$^{45}$, —S(O)$_3$R$^{45}$, —S(O)$_4$R$^{45}$, —S(O)$_2$NR$^{45}$R$^{40D}$, —NHNR$^{45}$R$^{40D}$, —ONR$^{45}$R$^{40D}$, —NHC(O)NHNR$^{45}$R$^{40D}$, —NHC(O)NR$^{45}$R$^{40D}$, —NHS(O)$_2$R$^{45}$, —NHC(O)R$^{45}$, —NHC(O)—OR$^{45}$, —NHOR$^{45}$, —OCF$_3$, —OCHF$_2$, R$^{45}$-substituted or unsubstituted heteroalkyl, R$^{45}$-substituted or unsubstituted cycloalkyl, R$^{45}$-substituted or unsubstituted heterocycloalkyl, R$^{45}$-substituted or unsubstituted aryl, or R$^{45}$-substituted or unsubstituted heteroaryl.

R$^{4B}$ may independently be oxo, halogen, —CF$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{45}$-substituted or unsubstituted alkyl, R$^{45}$-substituted or unsubstituted heteroalkyl, R$^{45}$-substituted or unsubstituted cycloalkyl, R$^{45}$-substituted or unsubstituted heterocycloalkyl, R$^{45}$-substituted or unsubstituted aryl, or R$^{45}$-substituted or unsubstituted heteroaryl.

The compound of formula (Ia) may have the formula:

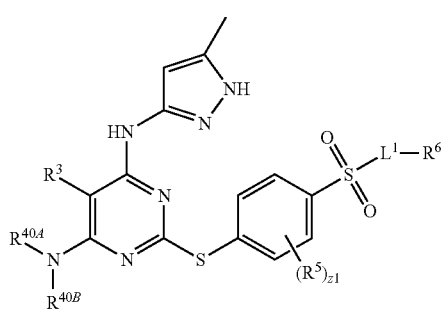

(Ia1)

where L$^1$, z1, R$^3$, R$^5$, R$^6$, R$^{40A}$, and R$^{40B}$ are as described herein.

The compound of formula (Ib) may have the formula:

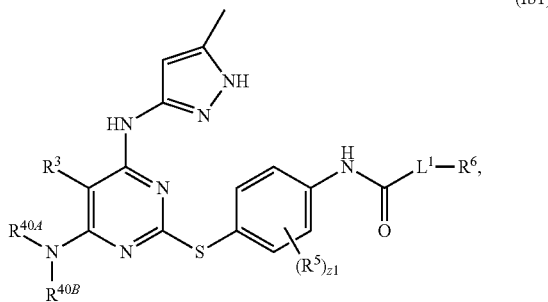

(Ib1)

where $L^1$, z1, $R^3$, $R^5$, $R^6$, $R^{40A}$, and $R^{40B}$ are as described herein.

$R^5$ may independently be hydrogen, halogen, —$N_3$, —$CF_3$, —$CCl_3$, —$CBr_3$, —$CI_3$, —CN, —$COR^{5A}$, —$OR^{5A}$, —$NR^{5A}R^{5B}$, —C(O)$OR^{5A}$, —C(O)$NR^{5A}R^{5B}$, —$NO_2$, —$SR^{5A}$, —S(O)$_{n5}R^{5A}$, —S(O)$_{n5}OR^{5A}$, —S(O)$_{n5}NR^{5A}R^{5B}$, —$NHNR^{5A}R^{5B}$, —$ONR^{5A}R^{5B}$, or —NHC(O)$NHNR^{5A}R^{5B}$. $R^5$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ may be hydrogen or halogen. $R^5$ may be hydrogen or —Cl, —I, or —Br. $R^5$ may be hydrogen or —Cl or —F. $R^5$ may be hydrogen. $R^5$ may be —Cl. $R^5$ may be —I. $R^5$ may be —Br. $R^5$ may be —F. The symbol z1 may be 1, 2, or 3. The symbol z1 may be 1 or 2. $R^5$ may be hydrogen or —Cl or —F where the symbol z1 is 1 or 2.

$R^5$ may be substituted or unsubstituted alkyl. $R^5$ may be substituted alkyl. $R^5$ may be unsubstituted alkyl. $R^5$ may be substituted or unsubstituted $C_1$-$C_{20}$ alkyl. $R^5$ may be substituted $C_1$-$C_{20}$ alkyl. $R^5$ may be unsubstituted $C_1$-$C_{20}$ alkyl. $R^5$ may be substituted or unsubstituted $C_1$-$C_{10}$ alkyl. $R^5$ may be substituted $C_1$-$C_{10}$ alkyl. $R^5$ may be unsubstituted $C_1$-$C_{10}$ alkyl. $R^5$ may be substituted or unsubstituted $C_1$-$C_5$ alkyl. $R^5$ may be unsubstituted $C_1$-$C_5$ alkyl. $R^5$ may be substituted $C_1$-$C_5$ alkyl. $R^5$ may be methyl, substituted or unsubstituted ethyl, or substituted or unsubstituted propyl. $R^5$ may be methyl. $R^5$ may be ethyl.

$R^5$ may be $R^{5C}$-substituted or unsubstituted alkyl. $R^5$ may be $R^{5C}$-substituted alkyl. $R^5$ may be $R^{5C}$-substituted or unsubstituted $C_1$-$C_{20}$ alkyl. $R^5$ may be $R^{5C}$-substituted $C_1$-$C_{20}$ alkyl. $R^5$ may be $R^{5C}$-substituted or unsubstituted $C_1$-$C_{10}$ alkyl. $R^5$ may be $R^{5C}$-substituted $C_1$-$C_{10}$ alkyl. $R^5$ may be $R^{5C}$-substituted or unsubstituted $C_1$-$C_5$ alkyl. $R^5$ may be $R^{5C}$-substituted $C_1$-$C_5$ alkyl. $R^5$ may be methyl, $R^{5C}$-substituted or unsubstituted ethyl, or $R^{5C}$-substituted or unsubstituted propyl.

$R^5$ may be substituted or unsubstituted heteroalkyl. $R^5$ may be substituted heteroalkyl. $R^5$ may be unsubstituted heteroalkyl. $R^5$ may be substituted or unsubstituted 2 to 20 membered heteroalkyl. $R^5$ may be substituted 2 to 20 membered heteroalkyl. $R^5$ may be substituted or unsubstituted 2 to 10 membered heteroalkyl. $R^5$ may be substituted 2 to 10 membered heteroalkyl. $R^5$ may be substituted or unsubstituted 2 to 6 membered heteroalkyl. $R^5$ may be substituted 2 to 6 membered heteroalkyl.

$R^5$ may be $R^{5C}$-substituted or unsubstituted heteroalkyl. $R^5$ may be $R^{5C}$-substituted heteroalkyl. $R^5$ may be $R^{5C}$-substituted or unsubstituted 2 to 20 membered heteroalkyl. $R^5$ may be $R^{5C}$-substituted 2 to 20 membered heteroalkyl. $R^5$ may be $R^{5C}$-substituted or unsubstituted 2 to 10 membered heteroalkyl. $R^5$ may be $R^{5C}$-substituted 2 to 10 membered heteroalkyl. $R^5$ may be $R^{5C}$-substituted or unsubstituted 2 to 6 membered heteroalkyl. $R^5$ may be $R^{5C}$-substituted 2 to 6 membered heteroalkyl.

$R^5$ may be substituted or unsubstituted cycloalkyl. $R^5$ may be substituted cycloalkyl. $R^5$ may be unsubstituted cycloalkyl. $R^5$ may be substituted or unsubstituted 3 to 20 membered cycloalkyl. $R^5$ may be substituted 3 to 20 membered cycloalkyl. $R^5$ may be substituted or unsubstituted 3 to 10 membered cycloalkyl. $R^5$ may be substituted 3 to 10 membered cycloalkyl. $R^5$ may be substituted or unsubstituted 3 to 6 membered cycloalkyl. $R^5$ may be substituted 3 to 6 membered cycloalkyl.

$R^5$ may be $R^{5C}$-substituted or unsubstituted cycloalkyl. $R^5$ may be $R^{5C}$-substituted cycloalkyl. $R^5$ may be $R^{5C}$-substituted or unsubstituted 3 to 20 membered cycloalkyl. $R^5$ may be $R^{5C}$-substituted 3 to 20 membered cycloalkyl. $R^5$ may be $R^{5C}$-substituted or unsubstituted 3 to 10 membered cycloalkyl. $R^5$ may be $R^{5C}$-substituted 3 to 10 membered cycloalkyl. $R^5$ may be $R^{5C}$-substituted or unsubstituted 3 to 6 membered cycloalkyl. $R^5$ may be $R^{5C}$-substituted 3 to 6 membered cycloalkyl.

$R^5$ may be substituted or unsubstituted heterocycloalkyl. $R^5$ may be substituted heterocycloalkyl. $R^5$ may be unsubstituted heterocycloalkyl. $R^5$ may be substituted or unsubstituted 3 to 20 membered heterocycloalkyl. $R^5$ may be substituted 3 to 20 membered heterocycloalkyl. $R^5$ may be substituted or unsubstituted 3 to 10 membered heterocycloalkyl. $R^5$ may be substituted 3 to 10 membered heterocycloalkyl. $R^5$ may be substituted or unsubstituted 3 to 6 membered heterocycloalkyl. $R^5$ may be substituted 3 to 6 membered heterocycloalkyl.

$R^5$ may be $R^{5C}$-substituted or unsubstituted heterocycloalkyl. $R^5$ may be $R^{5C}$-substituted heterocycloalkyl. $R^5$ may be $R^{5C}$-substituted or unsubstituted 3 to 20 membered heterocycloalkyl. $R^5$ may be $R^{5C}$-substituted 3 to 20 membered heterocycloalkyl. $R^5$ may be $R^{5C}$-substituted or unsubstituted 3 to 10 membered heterocycloalkyl. $R^5$ may be $R^{5C}$-substituted 3 to 10 membered heterocycloalkyl. $R^5$ may be $R^{5C}$-substituted or unsubstituted 3 to 6 membered heterocycloalkyl. $R^5$ may be $R^{5C}$-substituted 3 to 6 membered heterocycloalkyl.

$R^5$ may be substituted or unsubstituted aryl. $R^5$ may be substituted aryl. $R^5$ may be unsubstituted aryl. $R^5$ may be substituted or unsubstituted 5 to 20 membered aryl. $R^5$ may be substituted 5 to 20 membered aryl. $R^5$ may be substituted or unsubstituted 5 to 8 membered aryl (e.g. phenyl). $R^5$ may be substituted 5 to 8 membered aryl. $R^5$ may be substituted or unsubstituted 5 or 6 membered aryl. $R^5$ may be substituted 5 or 6 membered aryl.

$R^5$ may be $R^{5C}$-substituted or unsubstituted aryl. $R^5$ may be $R^{5C}$-substituted aryl. $R^5$ may be $R^{5C}$-substituted or unsubstituted 5 to 20 membered aryl. $R^5$ may be $R^{5C}$-substituted 5 to 20 membered aryl. $R^5$ may be $R^{5C}$-substituted or unsubstituted 5 to 8 membered aryl. $R^5$ may be $R^{5C}$-substituted 5 to 8 membered aryl. $R^5$ may be $R^{5C}$-substituted or unsubstituted 5 or 6 membered aryl. $R^5$ may be $R^{5C}$-substituted 5 or 6 membered aryl (e.g. phenyl).

$R^5$ may be substituted or unsubstituted heteroaryl. $R^5$ may be substituted heteroaryl. $R^5$ may be unsubstituted heteroaryl. $R^5$ may be substituted or unsubstituted 5 to 20 membered heteroaryl. $R^5$ may be substituted 5 to 20 membered heteroaryl. $R^5$ may be substituted 5 to 8 membered heteroaryl. $R^5$ may be substituted 5 to 8 membered heteroaryl. $R^5$ may be substituted or unsubstituted 5 or 6 membered heteroaryl. $R^5$ may be substituted 5 or 6 membered heteroaryl.

$R^5$ may be $R^{5C}$-substituted or unsubstituted heteroaryl. $R^5$ may be $R^{5C}$-substituted heteroaryl. $R^5$ may be $R^{5C}$-substituted or unsubstituted 5 to 20 membered heteroaryl. $R^5$ may be $R^{5C}$-substituted 5 to 20 membered heteroaryl. $R^5$ may be $R^{5C}$-substituted or unsubstituted 5 to 8 membered heteroaryl. $R^5$ may be $R^{5C}$-substituted 5 to 8 membered heteroaryl. $R^5$ may be $R^{5C}$-substituted or unsubstituted 5 or 6 membered heteroaryl. $R^5$ may be $R^{5C}$-substituted 5 or 6 membered heteroaryl.

$R^{5A}$ may independently be hydrogen, halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —NHC(O)—OH, —NHOH, —$OCF_3$, —$OCHF_2$, $R^{5C}$-substituted or unsubstituted alkyl, $R^{5C}$-substituted or unsubstituted heteroalkyl, $R^{5C}$-substituted or unsubstituted cycloalkyl, $R^{5C}$-substituted or unsubstituted heterocycloalkyl, $R^{5C}$-substituted or unsubstituted aryl, or $R^{5C}$-substituted or unsubstituted heteroaryl.

$R^{5C}$ is independently halogen, oxo, $N_3$, —$CF_3$, —$CCl_3$, —$CBr_3$, —$CI_3$, —CN, —OH, —$COR^{5D}$, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —NHC(O)—OH, —NHOH, —$OCF_3$, —$OCHF_2$, $R^{5D}$-substituted or unsubstituted alkyl, $R^{5D}$-substituted or unsubstituted heteroalkyl, $R^{5D}$-substituted or unsubstituted cycloalkyl, $R^{5D}$-substituted or unsubstituted heterocycloalkyl, $R^{5D}$-substituted or unsubstituted aryl, or $R^{5D}$-substituted or unsubstituted heteroaryl.

$R^{5B}$ may independently be hydrogen, halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{5D}$ is independently halogen, oxo, $N_3$, —$CF_3$, —$CCl_3$, —$CBr_3$, —$CI_3$, —CN, —OH, —$COR^{5E}$, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —NHC(O)—OH, —NHOH, —$OCF_3$, —$OCHF_2$, $R^{5E}$-substituted or unsubstituted heteroalkyl, $R^{5E}$-substituted or unsubstituted cycloalkyl, $R^{5E}$-substituted or unsubstituted heterocycloalkyl, $R^{5E}$-substituted or unsubstituted aryl, or $R^{5E}$-substituted or unsubstituted heteroaryl.

$R^{5E}$ is independently halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^6$ may be hydrogen, —$NH_2$, —$CF_3$, —$NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ may be hydrogen, —$CF_3$, —$NR^{6A}R^{6B}$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl.

$R^6$ may be substituted or unsubstituted cycloalkyl, substituted or unsubstituted heterocycloalkyl, substituted or unsubstituted aryl, or substituted or unsubstituted heteroaryl.

$R^6$ may be substituted or unsubstituted alkyl. $R^6$ may be substituted alkyl. $R^6$ may be unsubstituted alkyl. $R^6$ may be substituted or unsubstituted $C_1$-$C_{20}$ alkyl. $R^6$ may be substituted $C_1$-$C_{20}$ alkyl. $R^6$ may be unsubstituted $C_1$-$C_{20}$ alkyl. $R^6$ may be substituted or unsubstituted $C_1$-$C_{10}$ alkyl. $R^6$ may be substituted $C_1$-$C_{10}$ alkyl. $R^6$ may be unsubstituted $C_1$-$C_{10}$ alkyl. $R^6$ may be substituted or unsubstituted $C_1$-$C_5$ alkyl. $R^6$ may be substituted $C_1$-$C_5$ alkyl. $R^6$ may be unsubstituted $C_1$-$C_5$ alkyl. $R^6$ may be methyl, substituted or unsubstituted ethyl, or substituted or unsubstituted propyl. $R^6$ may be hydrogen, methyl, ethyl or propyl. $R^6$ may be hydrogen. $R^6$ may be methyl.

$R^6$ may be $R^{60}$-substituted or unsubstituted alkyl. $R^6$ may be $R^{60}$-substituted alkyl. $R^6$ may be $R^{60}$-substituted or unsubstituted $C_1$-$C_{20}$ alkyl. $R^6$ may be $R^{60}$-substituted $C_1$-$C_{20}$ alkyl. $R^6$ may be $R^{60}$-substituted or unsubstituted $C_1$-$C_{10}$ alkyl. $R^6$ may be $R^{60}$-substituted $C_1$-$C_{10}$ alkyl. $R^6$ may be $R^{60}$-substituted or unsubstituted $C_1$-$C_5$ alkyl. $R^6$ may be $R^{60}$-substituted $C_1$-$C_5$ alkyl. $R^6$ may be methyl, $R^{60}$-substituted or unsubstituted ethyl, or $R^{60}$-substituted or unsubstituted propyl.

$R^6$ may be substituted or unsubstituted heteroalkyl. $R^6$ may be substituted heteroalkyl. $R^6$ may be unsubstituted heteroalkyl. $R^6$ may be substituted 2 to 20 membered heteroalkyl. $R^6$ may be substituted 2 to 20 membered heteroalkyl. $R^6$ may be unsubstituted 2 to 20 membered heteroalkyl. $R^6$ may be substituted or unsubstituted 2 to 10 membered heteroalkyl. $R^6$ may be substituted 2 to 10 membered heteroalkyl. $R^6$ may be unsubstituted 2 to 10 membered heteroalkyl. $R^6$ may be substituted or unsubstituted 2 to 6 membered heteroalkyl. $R^6$ may be substituted 2 to 6 membered heteroalkyl. $R^6$ may be unsubstituted 2 to 6 membered heteroalkyl.

$R^6$ may be $R^{60}$-substituted or unsubstituted heteroalkyl. $R^6$ may be $R^{60}$-substituted heteroalkyl. $R^6$ may be $R^{60}$-substituted or unsubstituted 2 to 20 membered heteroalkyl. $R^6$ may be $R^{60}$-substituted 2 to 20 membered heteroalkyl. $R^6$ may be $R^{60}$-substituted or unsubstituted 2 to 10 membered heteroalkyl. $R^6$ may be $R^{60}$-substituted 2 to 10 membered heteroalkyl. $R^6$ may be $R^{60}$-substituted or unsubstituted 2 to 6 membered heteroalkyl. $R^6$ may be $R^{60}$-substituted 2 to 6 membered heteroalkyl.

$R^6$ may be substituted or unsubstituted cycloalkyl. $R^6$ may be substituted cycloalkyl. $R^6$ may be unsubstituted cycloalkyl. $R^6$ may be substituted or unsubstituted 3 to 20 membered cycloalkyl. $R^6$ may be substituted 3 to 20 membered cycloalkyl. $R^6$ may be unsubstituted 3 to 20 membered cycloalkyl. $R^6$ may be substituted or unsubstituted 3 to 10 membered cycloalkyl. $R^6$ may be substituted 3 to 10 membered cycloalkyl. $R^6$ may be unsubstituted 3 to 10 membered cycloalkyl. $R^6$ may be substituted or unsubstituted 3 to 6 membered cycloalkyl. $R^6$ may be substituted 3 to 6 membered cycloalkyl. $R^6$ may be unsubstituted 3 to 6 membered cycloalkyl.

$R^6$ may be $R^{60}$-substituted or unsubstituted cycloalkyl. $R^6$ may be $R^{60}$-substituted cycloalkyl. $R^6$ may be $R^{60}$-substituted or unsubstituted 3 to 20 membered cycloalkyl. $R^6$ may be $R^{60}$-substituted 3 to 20 membered cycloalkyl. $R^6$ may be $R^{60}$-substituted or unsubstituted 3 to 10 membered cycloalkyl. $R^6$ may be $R^{60}$-substituted 3 to 10 membered cycloalkyl. $R^6$ may be $R^{60}$-substituted or unsubstituted 3 to 6 membered cycloalkyl. $R^6$ may be $R^{60}$-substituted 3 to 6 membered cycloalkyl.

$R^6$ may be substituted or unsubstituted heterocycloalkyl. $R^6$ may be substituted heterocycloalkyl. $R^6$ may be unsubstituted heterocycloalkyl. $R^6$ may be substituted or unsubstituted 3 to 20 membered heterocycloalkyl. $R^6$ may be substituted 3 to 20 membered heterocycloalkyl. $R^6$ may be unsubstituted 3 to 20 membered heterocycloalkyl. $R^6$ may be substituted or unsubstituted 3 to 10 membered heterocycloalkyl. $R^6$ may be substituted 3 to 10 membered heterocycloalkyl. $R^6$ may be unsubstituted 3 to 10 membered heterocycloalkyl. $R^6$ may be substituted or unsubstituted 3 to 6 membered heterocycloalkyl. $R^6$ may be substituted 3 to 6 membered heterocycloalkyl. $R^6$ may be unsubstituted 3 to 6 membered heterocycloalkyl.

$R^6$ may be $R^{60}$-substituted or unsubstituted heterocycloalkyl. $R^6$ may be $R^{60}$-substituted heterocycloalkyl. $R^6$ may be $R^{60}$-substituted or unsubstituted 3 to 20 membered heterocycloalkyl. $R^6$ may be $R^{60}$-substituted 3 to 20 membered heterocycloalkyl. $R^6$ may be $R^{60}$-substituted or unsubstituted 3 to 10 membered heterocycloalkyl. $R^6$ may be $R^{60}$-substituted 3 to 10 membered heterocycloalkyl. $R^6$ may be $R^{60}$-substituted or unsubstituted 3 to 6 membered heterocycloalkyl. $R^6$ may be $R^{60}$-substituted 3 to 6 membered heterocycloalkyl.

$R^6$ may be substituted or unsubstituted aryl. $R^6$ may be substituted aryl. $R^6$ may be unsubstituted aryl. $R^6$ may be substituted or unsubstituted 5 to 20 membered aryl. $R^6$ may be substituted 5 to 20 membered aryl. $R^6$ may be unsubstituted 5 to 20 membered aryl. $R^6$ may be substituted or unsubstituted 5 to 8 membered aryl. $R^6$ may be substituted 5 to 8 membered aryl. $R^6$ may be unsubstituted 5 to 8 membered aryl. $R^6$ may be substituted or unsubstituted 5 or 6 membered aryl. $R^6$ may be substituted 5 or 6 membered aryl (e.g. phenyl). $R^6$ may be unsubstituted 5 or 6 membered aryl (e.g. phenyl).

$R^6$ may be $R^{60}$-substituted or unsubstituted aryl. $R^6$ may be $R^{60}$-substituted aryl. $R^6$ may be $R^{60}$-substituted or unsubstituted 5 to 20 membered aryl. $R^6$ may be $R^{60}$-substituted 5 to 20 membered aryl. $R^6$ may be $R^{60}$-substituted or unsubstituted 5 to 8 membered aryl. $R^6$ may be $R^{60}$-substituted 5 to 8 membered aryl. $R^6$ may be $R^{60}$-substituted or unsubstituted 5 or 6 membered aryl. $R^6$ may be $R^{60}$-substituted 5 or 6 membered aryl (e.g. phenyl).

$R^6$ may be substituted or unsubstituted heteroaryl. $R^6$ may be substituted heteroaryl. $R^6$ may be unsubstituted heteroaryl. $R^6$ may be substituted or unsubstituted 5 to 20 membered heteroaryl. $R^6$ may be substituted 5 to 20 membered heteroaryl. $R^6$ may be unsubstituted 5 to 20 membered heteroaryl. $R^6$ may be substituted or unsubstituted 5 to 8 membered heteroaryl. $R^6$ may be substituted 5 to 8 membered heteroaryl. $R^6$ may be unsubstituted 5 to 8 membered heteroaryl. $R^6$ may be substituted or unsubstituted 5 or 6 membered heteroaryl. $R^6$ may be substituted 5 or 6 membered heteroaryl. $R^6$ may be unsubstituted 5 or 6 membered heteroaryl.

$R^6$ may be $R^{60}$-substituted or unsubstituted heteroaryl. $R^6$ may be $R^{60}$-substituted heteroaryl. $R^6$ may be $R^{60}$-substituted or unsubstituted 5 to 20 membered heteroaryl. $R^6$ may be $R^{60}$-substituted 5 to 20 membered heteroaryl. $R^6$ may be $R^{60}$-substituted or unsubstituted 5 to 8 membered heteroaryl. $R^6$ may be $R^{60}$-substituted 5 to 8 membered heteroaryl. $R^6$ may be $R^{60}$-substituted or unsubstituted 5 or 6 membered heteroaryl. $R^6$ may be $R^{60}$-substituted 5 or 6 membered heteroaryl.

$R^6$ may be $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl.

$R^6$ may be $R^{60}$-substituted or unsubstituted $C_3$ cycloalkyl. $R^6$ may be unsubstituted $C_3$ cycloalkyl. $R^6$ may be $R^{60}$-substituted or unsubstituted $C_4$ cycloalkyl. $R^6$ may be unsubstituted $C_4$ cycloalkyl. $R^6$ may be $R^{60}$-substituted or unsubstituted $C_5$ cycloalkyl. $R^6$ may be unsubstituted $C_5$ cycloalkyl. $R^6$ may be $R^{60}$-substituted or unsubstituted saturated $C_3$ cycloalkyl. $R^6$ may be unsubstituted saturated $C_3$ cycloalkyl. $R^6$ may be $R^{60}$-substituted or unsubstituted saturated $C_4$ cycloalkyl. $R^6$ may be $R^{60}$-substituted or unsubstituted saturated $C_5$ cycloalkyl. $R^6$ may be unsubstituted saturated $C_5$ cycloalkyl.

$R^6$ may $R^{60}$-substituted or unsubstituted aryl where $R^{60}$ is as defined herein, $R^{60A}$ is hydrogen, halogen, —$NO_2$, —$CF_3$, —CN, —$COR^{61}$, $R^{61}$-substituted or unsubstituted alkyl, $R^{61}$-substituted or unsubstituted heteroalkyl, or $R^{61}$-substituted or unsubstituted aryl, where $R^{61}$ is as defined herein and $R^{60B}$ is hydrogen, halogen, or unsubstituted alkyl.

$R^6$ may be $R^{60}$-substituted or unsubstituted heteroaryl where $R^{60}$ is halogen, —$CF_3$, —$NR^{60A}R^{60B}$, —$NO_2$, —$OR^{60A}$, —$COOR^{60A}$, —$COR^{61}$, $R^{61}$-substituted or unsubstituted alkyl, $R^{61}$-substituted or unsubstituted heteroalkyl, or $R^{61}$-substituted or unsubstituted aryl, where $R^{61}$ is —$NR^{61A}R^{61B}$, and $R^{60A}$, $R^{60B}$, $R^{61A}$, and $R^{61B}$ are independently hydrogen or unsubstituted $C_1$-$C_5$ unsubstituted alkyl.

$R^6$ may be substituted or unsubstituted thiophenyl, substituted or unsubstituted thiazolyl, substituted or unsubstituted imidazolyl, or substituted or unsubstituted oxazolyl. $R^6$ may be substituted or unsubstituted thiophenyl. $R^6$ may be substituted or unsubstituted thiazolyl. $R^6$ may be substituted or unsubstituted imidazolyl. $R^6$ may be substituted or unsubstituted oxazolyl.

$R^6$ may be $R^{60}$-substituted or unsubstituted thiophenyl, $R^{60}$-substituted or unsubstituted thiazolyl, $R^{60}$-substituted or unsubstituted imidazolyl, or $R^{60}$-substituted or unsubstituted oxazolyl. $R^6$ may be $R^{60}$-substituted or unsubstituted thiophenyl. $R^6$ may be $R^{60}$-substituted or unsubstituted thiazolyl. $R^6$ may be $R^{60}$-substituted or unsubstituted imidazolyl. $R^6$ may be $R^{60}$-substituted or unsubstituted oxazolyl.

$R^{60}$ is independently hydrogen, halogen, —$N_3$, —$CF_3$, —$CCl_3$, —$CBr_3$, —$CI_3$, —CN, —$COR^{61}$, —$OR^{60A}$, —$NR^{60A}R^{60B}$, —$C(O)OR^{60A}$, —$C(O)NR^{60A}R^{60B}$, —$NO_2$, —$SR^{60A}$, —$S(O)_2H$, —$S(O)_2OH$, —$S(O)_2NH_2$, —$NHNH_2$, —$ONH_2$, —$NHC(O)NHNR^{60A}R^{6B}$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl.

$R^{60}$ may independently be oxo, halogen, —$N_3$, —$CF_3$, —$CCl_3$, —$CBr_3$, —$CI_3$, —CN, —COH, —$COCH_3$, —OH, —$NH_2$, —C(O)OH, —$C(O)NH_2$, —$NO_2$, —SH, —$S(O)_2H$, —$S(O)_2OH$, —$S(O)_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^{60A}$ is independently hydrogen, oxo, halogen, —$N_3$, —$CF_3$, —$CCl_3$, —$CBr_3$, —$CI_3$, —CN, —$OR^{61}$, —$NR^{61}R^{60C}$, —$COOR^{61}$, —$CONR^{61}R^{60C}$, —$COR^{61}$, —$NO_2$, —$SR^{61}$, —$S(O)_2R^{61}$, —$S(O)_3R^{61}$, —$S(O)_4R^{61}$, —$S(O)_2R^{61}R^{60C}$, —$NHNR^{61}R^{60C}$, —$ONR^{61}R^{60C}$, —NHC (O)NHNR$^{61}$R$^{60C}$, —NHC(O)NR$^{61}$R$^{60C}$, —NHS(O)$_2$R$^{61}$, —NHC(O)R$^{61}$, —NHC(O)—OR$^{61}$, —NHOR$^{61}$, —OCF$_3$, —OCHF$_2$, R$^{61}$-substituted or unsubstituted alkyl, R$^{61}$-substituted or unsubstituted heteroalkyl, R$^{61}$-substituted or unsubstituted cycloalkyl, R$^{61}$-substituted or unsubstituted heterocycloalkyl, R$^{61}$-substituted or unsubstituted aryl, or R$^{61}$-substituted or unsubstituted heteroaryl.

R$^{60A}$ may independently be hydrogen, oxo, halogen, —N$_3$, —CF$_3$, —CCl$_3$, —CBr$_3$, —CI$_3$, —CN, —OH, —NH$_2$, —COOH, —CONH$_2$, —COR$^{61}$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{61}$-substituted or unsubstituted alkyl, R$^{61}$-substituted or unsubstituted heteroalkyl, R$^{61}$-substituted or unsubstituted cycloalkyl, R$^{61}$-substituted or unsubstituted heterocycloalkyl, R$^{61}$-substituted or unsubstituted aryl, or R$^{61}$-substituted or unsubstituted heteroaryl.

R$^{60A}$ may independently be hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. R$^{60A}$ may independently be hydrogen or unsubstituted C$_1$-C$_5$ alkyl. R$^{60A}$ may independently be hydrogen. R$^{60A}$ may independently be methyl or unsubstituted ethyl. R$^{60A}$ may independently be methyl.

R$^{61}$ is independently hydrogen, halogen, —N$_3$, —CF$_3$, —CCl$_3$, —CBr$_3$, —CI$_3$, —CN, —COR$^{61A}$, —OR$^{61A}$, —NR$^{61A}$R$^{61B}$, —C(O)OR$^{61A}$, —C(O)NR$^{61A}$R$^{61B}$, —NO$_2$, —SR$^{61A}$, —S(O)$_2$R$^{61A}$, —S(O)$_2$OR$^{61A}$, —S(O)$_2$NR$^{61A}$R$^{61B}$, —NHNHR$^{61A}$R$^{61B}$, —ONR$^{61A}$R$^{61B}$, —NHC(O)NHNR$^{61A}$R$^{61B}$, R$^{62}$-substituted or unsubstituted alkyl, R$^{62}$-substituted or unsubstituted heteroalkyl, R$^{62}$-substituted or unsubstituted cycloalkyl, R$^{62}$-substituted or unsubstituted heterocycloalkyl, R$^{62}$-substituted or unsubstituted aryl, or R$^{62}$-substituted or unsubstituted heteroaryl.

R$^{61}$ is independently hydrogen, halogen, —N$_3$, —CF$_3$, —CCl$_3$, —CBr$_3$, —CI$_3$, —CN, —COR$^{61A}$, —OR$^{61A}$, —NR$^{61A}$R$^{61B}$, —C(O)OR$^{61A}$, —C(O)NR$^{61A}$R$^{61B}$, —NO$_2$, —SR$^{61A}$, —S(O)$_2$H, —S(O)$_2$OH, —S(O)$_2$NH$_2$, —NHNH$_2$, —ONH$_2$, —NHC(O)NHNR$^{61A}$R$^{61B}$, R$^{62}$-substituted or unsubstituted alkyl, R$^{62}$-substituted or unsubstituted heteroalkyl, R$^{62}$-substituted or unsubstituted cycloalkyl, R$^{62}$-substituted or unsubstituted heterocycloalkyl, R$^{62}$-substituted or unsubstituted aryl, or R$^{62}$-substituted or unsubstituted heteroaryl.

R$^{61}$ may independently be hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

R$^{62}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{63}$-substituted or unsubstituted alkyl, R$^{63}$-substituted or unsubstituted heteroalkyl, R$^{63}$-substituted or unsubstituted cycloalkyl, R$^{63}$-substituted or unsubstituted heterocycloalkyl, R$^{63}$-substituted or unsubstituted aryl, or R$^{63}$-substituted or unsubstituted heteroaryl.

R$^{62}$ may independently be oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

R$^{63}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{64}$-substituted or unsubstituted alkyl, R$^{64}$-substituted or unsubstituted heteroalkyl, R$^{64}$-substituted or unsubstituted cycloalkyl, R$^{64}$-substituted or unsubstituted heterocycloalkyl, R$^{64}$-substituted or unsubstituted aryl, or R$^{64}$-substituted or unsubstituted heteroaryl.

R$^{61A}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{61C}$-substituted or unsubstituted heteroalkyl, R$^{61C}$-substituted or unsubstituted cycloalkyl, R$^{61C}$-substituted or unsubstituted heterocycloalkyl, R$^{61C}$-substituted or unsubstituted aryl, or R$^{61C}$-substituted or unsubstituted heteroaryl. R$^{61A}$ may independently be hydrogen or unsubstituted C$_1$-C$_5$ alkyl. R$^{61A}$ may independently be hydrogen. R$^{61A}$ may independently be methyl or unsubstituted ethyl. R$^{61A}$ may independently be methyl.

R$^{61C}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{61D}$-substituted or unsubstituted alkyl, R$^{61D}$-substituted or unsubstituted heteroalkyl, R$^{61D}$-substituted or unsubstituted cycloalkyl, R$^{61D}$-substituted or unsubstituted heterocycloalkyl, R$^{61D}$-substituted or unsubstituted aryl, or R$^{61D}$-substituted or unsubstituted heteroaryl.

R$^{61B}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{61E}$-substituted or unsubstituted alkyl, R$^{61E}$-substituted or unsubstituted heteroalkyl, R$^{61E}$-substituted or unsubstituted cycloalkyl, R$^{61E}$-substituted or unsubstituted heterocycloalkyl, R$^{61E}$-substituted or unsubstituted aryl, or R$^{61E}$-substituted or unsubstituted heteroaryl. R$^{61B}$ may independently be hydrogen or unsubstituted C$_1$-C$_5$ alkyl. R$^{61B}$ may independently be hydrogen. R$^{61B}$ may independently be methyl or unsubstituted ethyl. R$^{61B}$ may independently be methyl.

R$^{61E}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{61F}$-substituted or unsubstituted alkyl, R$^{61F}$-substituted or unsubstituted heteroalkyl, R$^{61F}$-substituted or unsubstituted cycloalkyl, R$^{61F}$-substituted or unsubstituted heterocycloalkyl, R$^{61F}$-substituted or unsubstituted aryl, or R$^{61F}$-substituted or unsubstituted heteroaryl.

R$^{60B}$ is independently hydrogen, oxo, halogen, —N$_3$, —CF$_3$, —CCl$_3$, —CBr$_3$, —CI$_3$, —CN, —OR$^{65}$, —NR$^{65}$R$^{60D}$, —COOR$^{65}$, —CONR$^{65}$R$^{6D}$, —COR$^{65}$, —NO$_2$, —SH, —S(O)$_2$R$^{65}$, —S(O)$_3$R$^{65}$, —S(O)$_4$R$^{65}$, —S(O)$_2$NR$^{65}$R$^{60D}$, —NHNR$^{65}$R$^{60D}$, —ONR$^{65}$R$^{60D}$, —NHC(O)NHNR$^{65}$R$^{60D}$, —NHC(O)NR$^{65}$R$^{60D}$, —NHS(O)$_2$R$^{65}$, —NHC(O)R$^{65}$, —NHC(O)—OR$^{65}$, —NHOR$^{65}$, —OCF$_3$, —OCHF$_2$, R$^{65}$-substituted or unsubstituted heteroalkyl, R$^{65}$-substituted or unsubstituted cycloalkyl, R$^{65}$-substituted or unsubstituted heterocycloalkyl, R$^{65}$-substituted or unsubstituted aryl, or R$^{65}$-substituted or unsubstituted heteroaryl. R$^{60B}$ may independently be hydrogen or unsubstituted C$_1$-C$_5$ alkyl. R$^{60B}$ may independently be hydrogen. R$^{60B}$ may independently be methyl or unsubstituted ethyl. R$^{60B}$ may independently be methyl.

R$^{60B}$ may independently be hydrogen, oxo, halogen, —N$_3$, —CF$_3$, —CCl$_3$, —CBr$_3$, —CI$_3$, —CN, —OH, —NH$_2$, —COOH, —CONH$_2$, —COR$^{65}$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{65}$-substituted or unsubstituted heteroalkyl, R$^{65}$-substituted or unsubstituted cycloalkyl, R$^{65}$-substituted or unsubstituted heterocycloalkyl, R$^{65}$-substituted or unsubstituted aryl, or R$^{65}$-substituted or unsubstituted heteroaryl. R$^{60B}$ may independently be hydrogen or unsubstituted C$_1$-C$_5$ alkyl. R$^{60B}$ may independently be hydrogen. R$^{60B}$ may independently be methyl or unsubstituted ethyl. R$^{60B}$ may independently be methyl.

R$^{60B}$ may independently be hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

R$^{65}$ is independently hydrogen, halogen, oxo, —N$_3$, —CF$_3$, —CCl$_3$, —CBr$_3$, —CI$_3$, —CN, —COR$^{65A}$, —OR$^{65A}$, —NR$^{65A}$R$^{65B}$, —C(O)OR$^{65A}$, —C(O)NR$^{65A}$R$^{65B}$, —NO$_2$, —SR$^{65A}$, —S(O)$_2$H, —S(O)$_2$OH, —S(O)$_2$NH$_2$, —NHNH$_2$, —ONH$_2$, —NHC(O)NHNR$^{65A}$R$^{65B}$, R$^{66}$-substituted or unsubstituted alkyl, R$^{66}$-substituted or unsubstituted heteroalkyl, R$^{66}$-substituted or unsubstituted cycloalkyl, R$^{66}$-substituted or unsubstituted heterocycloalkyl, R$^{66}$-substituted or unsubstituted aryl, or R$^{66}$-substituted or unsubstituted heteroaryl.

R$^{65A}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{65C}$-substituted or unsubstituted heteroalkyl, R$^{65C}$-substituted or unsubstituted cycloalkyl, R$^{65C}$-substituted or unsubstituted heterocycloalkyl, R$^{65C}$-substituted or unsubstituted aryl, or R$^{65C}$-substituted or unsubstituted heteroaryl. R$^{65A}$ may independently be hydrogen or unsubstituted C$_1$-C$_5$ alkyl. R$^{65A}$ may independently be hydrogen. R$^{65A}$ may independently be methyl or unsubstituted ethyl. R$^{65A}$ may independently be methyl.

R$^{65C}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{65D}$-substituted or unsubstituted alkyl, R$^{65D}$-substituted or unsubstituted heteroalkyl, R$^{65D}$-substituted or unsubstituted cycloalkyl, R$^{65D}$-substituted or unsubstituted heterocycloalkyl, R$^{65D}$-substituted or unsubstituted aryl, or R$^{65D}$-substituted or unsubstituted heteroaryl.

R$^{65B}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{65E}$-substituted or unsubstituted alkyl, R$^{65E}$-substituted or unsubstituted heteroalkyl, R$^{65E}$-substituted or unsubstituted cycloalkyl, R$^{65E}$-substituted or unsubstituted heterocycloalkyl, R$^{65E}$-substituted or unsubstituted aryl, or R$^{65E}$-substituted or unsubstituted heteroaryl. R$^{65B}$ may independently be hydrogen or unsubstituted C$_1$-C$_5$ alkyl. R$^{65B}$ may independently be hydrogen. R$^{65B}$ may independently be methyl or unsubstituted ethyl. R$^{65B}$ may independently be methyl.

R$^{65E}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{65F}$-substituted or unsubstituted alkyl, R$^{65F}$-substituted or unsubstituted heteroalkyl, R$^{65F}$-substituted or unsubstituted cycloalkyl, R$^{65F}$-substituted or unsubstituted heterocycloalkyl, R$^{65F}$-substituted or unsubstituted aryl, or R$^{65F}$-substituted or unsubstituted heteroaryl.

R$^{66}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{67}$-substituted or unsubstituted alkyl, R$^{67}$-substituted or unsubstituted heteroalkyl, R$^{67}$-substituted or unsubstituted cycloalkyl, R$^{67}$-substituted or unsubstituted heterocycloalkyl, R$^{67}$-substituted or unsubstituted aryl, or R$^{67}$-substituted or unsubstituted heteroaryl.

R$^{60C}$, R$^{60D}$, R$^{61D}$, R$^{61F}$, R$^{65D}$, R$^{65F}$, R$^{64}$, and R$^{67}$ are independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

R$^{64}$ may independently be hydrogen, oxo, halogen, —N$_3$, —CF$_3$, —CCl$_3$, —CBr$_3$, —CI$_3$, —CN, —OR$^{61}$, —NR$^{61}$R$^{60C}$, —COOR$^{61}$, —CONR$^{61}$R$^{60C}$, —COR$^{61}$, —NO$_2$, —SR$^{61}$, —S(O)$_2$R$^{61}$, —S(O)$_3$R$^{61}$, —S(O)$_4$R$^{61}$, —S(O)$_2$R$^{61}$R$^{60C}$, —NHNR$^{61}$R$^{60C}$, —ONR$^{61}$R$^{60C}$, —NHC(O)NHNR$^{61}$R$^{60C}$, —NHC(O)NR$^{61}$R$^{60C}$, —NHS(O)$_2$R$^{61}$, —NHC(O)R$^{61}$, —NHC(O)—OR$^{61}$, —NHOR$^{61}$, —OCF$_3$, —OCHF$_2$, R$^{61}$-substituted or unsubstituted alkyl, R$^{61}$-substituted or unsubstituted heteroalkyl, R$^{61}$-substituted or unsubstituted cycloalkyl, R$^{61}$-substituted or unsubstituted heterocycloalkyl, R$^{61}$-substituted or unsubstituted aryl, or R$^{61}$-substituted or unsubstituted heteroaryl.

R$^{6A}$ may independently be hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{61}$-substituted or unsubstituted alkyl, R$^{61}$-substituted or unsubstituted heteroalkyl, R$^{61}$-substituted or unsubstituted cycloalkyl, R$^{61}$-substituted or unsubstituted heterocycloalkyl, R$^{61}$-substituted or unsubstituted aryl, or R$^{61}$-substituted or unsubstituted heteroaryl.

R$^{6B}$ may independently be hydrogen, oxo, halogen, —N$_3$, —CF$_3$, —CCl$_3$, —CBr$_3$, —CI$_3$, —CN, —OR$^{65}$, —NR$^{65}$R$^{60D}$, —COOR$^{65}$, —CONR$^{65}$R$^{60D}$, —COR$^{65}$, —NO$_2$, —SH, —S(O)$_2$R$^{65}$, —S(O)$_3$R$^{65}$, —S(O)$_4$R$^{65}$, —S(O)$_2$NR$^{65}$R$^{60D}$, —NHNR$^{65}$R$^{60D}$, —ONR$^{65}$R$^{60D}$, —NHC(O)NHNR$^{65}$R$^{60D}$, —NHC(O)NR$^{65}$R$^{60D}$, —NHS(O)$_2$R$^{65}$, —NHC(O)R$^{65}$, —NHC(O)—OR$^{65}$, —NHOR$^{65}$, —OCF$_3$, —OCHF$_2$, R$^{65}$-substituted or unsubstituted heteroalkyl, R$^{65}$-substituted or unsubstituted cycloalkyl, R$^{65}$-substituted or unsubstituted heterocycloalkyl, R$^{65}$-substituted or unsubstituted aryl, or R$^{65}$-substituted or unsubstituted heteroaryl.

R$^{6B}$ may independently be oxo, halogen, —CF$_3$, —CN, —OH, —NH$_2$, —COOH, —CONH$_2$, —NO$_2$, —SH, —S(O)$_2$Cl, —S(O)$_3$H, —COH, —COCH$_3$, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{65}$-substituted or unsubstituted alkyl, R$^{65}$-substituted or unsubstituted heteroalkyl, R$^{65}$-substituted or unsubstituted cycloalkyl, R$^{65}$-substituted or unsubstituted heterocycloalkyl, R$^{65}$-substituted or unsubstituted aryl, or R$^{65}$-substituted or unsubstituted heteroaryl.

The compound of formula (Ia) may have the formula:

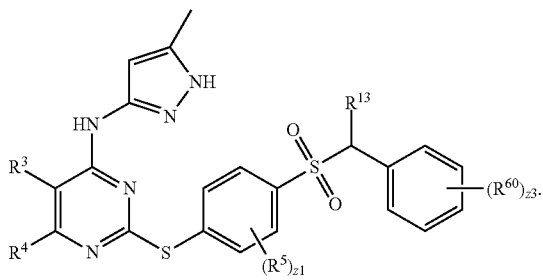

R$^3$, R$^4$, R$^5$, z1, R$^{13}$, and R$^{60}$ are as described herein. The symbol z3 is an integer of 0, 1, 2, 3, 4, or 5. The symbol z3 may be 1, 2, or 3. The symbol z3 may be 1. The symbol z3 may be 2. The symbol z3 may be 3.

R$^{60}$ may independently be hydrogen, halogen, —N$_3$, —CF$_3$, —CCl$_3$, —CBr$_3$, —CI$_3$, —CN, —COR$^{61}$, —OR$^{60A}$, —NR$^{60A}$R$^{60B}$, —C(O)OR$^{60A}$, —C(O)NR$^{60A}$R$^{60B}$, —NO$_2$, —SR$^{60A}$, —S(O)$_2$H, —S(O)$_2$OH, —S(O)$_2$NH$_2$, —NHNH$_2$, —ONH$_2$, —NHC(O)NHNR$^{60A}$R$^{60B}$, R$^{61}$-substituted or unsubstituted alkyl, R$^{61}$-substituted or unsubstituted heteroalkyl, R$^{61}$-substituted or unsubstituted cycloalkyl, R$^{61}$-substituted or unsubstituted heterocycloalkyl, R$^{61}$-substituted or unsubstituted aryl, or R$^{61}$-substituted or unsubstituted heteroaryl. R$^{60A}$ may independently be hydrogen, halogen, —NO$_2$, —CF$_3$, —CN, —COR$^{61}$, R$^{61}$-substituted or unsubstituted alkyl, R$^{61}$-substituted or unsubstituted heteroalkyl, or R$^{61}$-substituted or unsubstituted aryl. R$^{61}$ may independently be hydrogen, halogen, —N$_3$, —CF$_3$, —CCl$_3$, —CBr$_3$, —CI$_3$, —CN, —COR$^{61A}$, —OR$^{61A}$, —NR$^{61A}$R$^{61B}$, —C(O)OR$^{61A}$, —C(O)NR$^{61A}$R$^{61B}$, —NO$_2$, —SR$^{61A}$, —S(O)$_2$H, —S(O)$_2$OH, —S(O)$_2$NH$_2$, —NHNH$_2$, —ONH$_2$, —NHC(O)NHNR$^{61A}$R$^{61B}$, R$^{62}$-substituted or unsubstituted alkyl, R$^{62}$-substituted or unsubstituted heteroalkyl, R$^{62}$-substituted or unsubstituted cycloalkyl, R$^{62}$-substituted or unsubstituted heterocycloalkyl, R$^{62}$-substituted or unsubstituted aryl, or R$^{62}$-substituted or unsubstituted heteroaryl. R$^{62}$ may independently be hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. R$^{60B}$ may independently be hydrogen halogen, or unsubstituted alkyl.

The compound of formula (Ia) may have the formula:

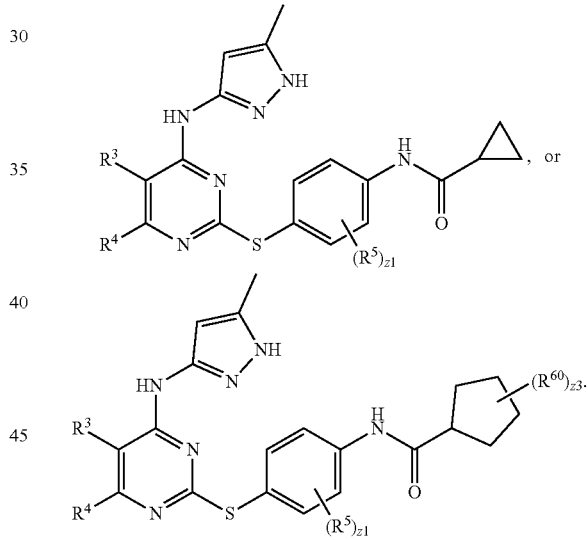

R$^3$, R$^4$, R$^5$, z1, z3, and R$^{60}$ are as described herein. R$^{60}$ may independently be hydrogen, halogen, —N$_3$, —CF$_3$, —CCl$_3$, —CBr$_3$, —CI$_3$, —CN, —COR$^{61}$, —OR$^{60A}$, —$^{60A}$R$^{60B}$, —C(O)OR$^{60A}$, —C(O)NR$^{60A}$R$^{60B}$, —NO$_2$, —SR$^{60A}$, —S(O)$_2$H, —S(O)$_2$OH, —S(O)$_2$NH$_2$, —NHNH$_2$, —ONH$_2$, —NHC(O)NHNR$^{60A}$R$^{6B}$, R$^{61}$-substituted or unsubstituted alkyl, R$^{61}$-substituted or unsubstituted heteroalkyl, R$^{61}$-substituted or unsubstituted cycloalkyl, R$^{61}$-substituted or unsubstituted heterocycloalkyl, R$^{61}$-substituted or unsubstituted aryl, or R$^{61}$-substituted or unsubstituted heteroaryl. R$^{60A}$ may independently be hydrogen, halogen, —NO$_2$, —CF$_3$, —CN, —COR$^{61}$, R$^{61}$-substituted or unsubstituted alkyl, R$^{61}$-substituted or unsubstituted heteroalkyl, or R$^{61}$-substituted or unsubstituted aryl; R$^{61}$ is independently hydrogen, halogen, or unsubstituted alkyl. R$^{60B}$ may independently be hydrogen halogen, or unsubstituted alkyl.

The compound of formula (Ia) may have the formula:

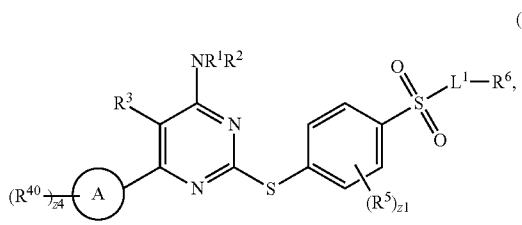

(Ia2)

where $L^1$, z1, $R^1$, $R^2$, $R^5$, $R^6$, and $R^{40}$ are as described herein. The symbol z4 is an integer of 0, 1, 2, 3, 4, 5, 6, or 7. Ring A is cycloalkyl or heterocycloalkyl. The compound of formula (Ia2) may have formula:

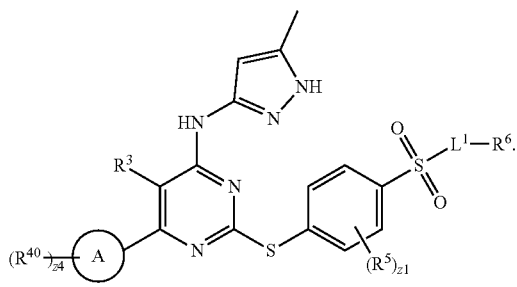

The compound of formula (Ia) may have the formula:

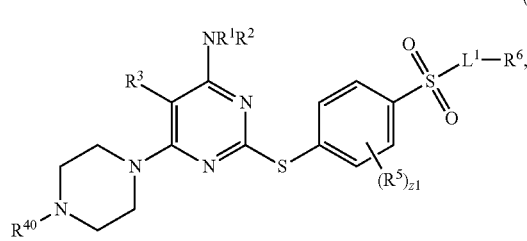

(Ia3)

where $L^1$, z1, $R^1$, $R^2$, $R^5$, $R^6$, and $R^{40}$ are as described herein. The compound of formula (Ia3) may have formula

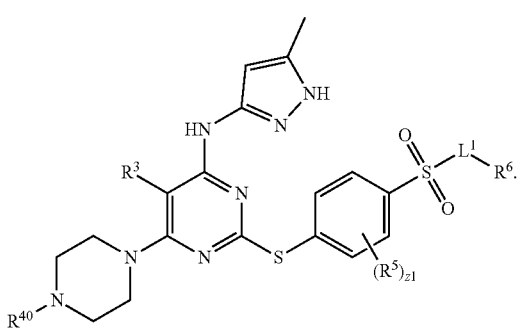

The compound of formula (Ia) may have the formula:

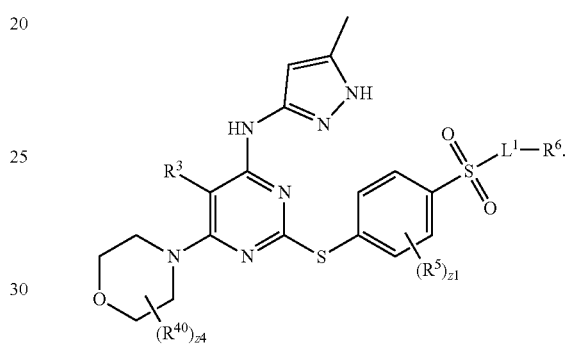

(Ia4)

where $L^1$, z1, $R^1$, $R^2$, $R^5$, $R^6$, and $R^{40}$ are as described herein and the symbol z4 is an integer of 0, 1, 2, 3, or 4. The compound of formula (Ia4) may have the formula

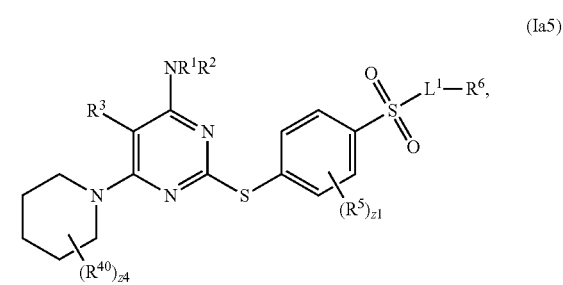

The compound of formula (Ia) may have the formula:

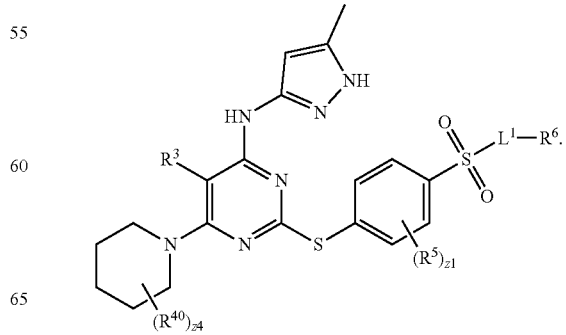

(Ia5)

where $L^1$, z1, z4, $R^1$, $R^2$, $R^5$, $R^6$, and $R^{40}$ are as described herein. The compound of formula (Ia5) may have the formula The compound of formula (Ia) may have the formula:

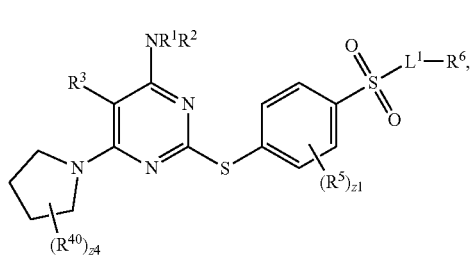

(Ia6)

where $L^1$, z1, $R^1$, $R^2$, $R^5$, $R^6$, and $R^{40}$ are as described herein and the symbol z4 is an integer of 0, 1, 2, 3, or 4. The compound of formula (Ia6) may have the formula

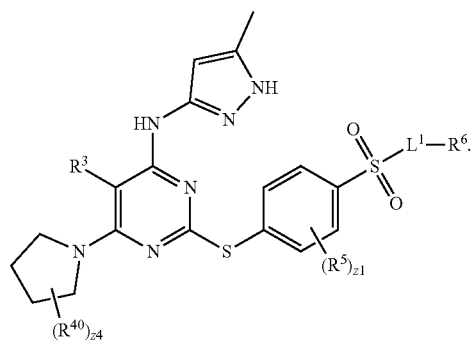

The compound of formula (Ib) may have the formula:

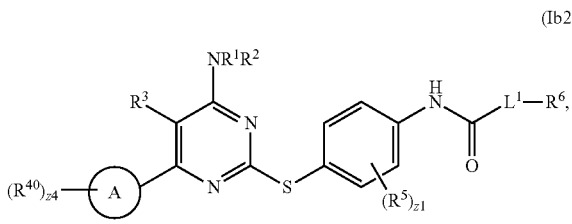

(Ib2)

where $L^1$, z1, z4, $R^1$, $R^2$, $R^5$, $R^6$, and $R^{40}$ are as described herein and the compound is not VX-680. Ring A is cycloalkyl or heterocycloalkyl. The compound of formula (Ib2) may have the formula:

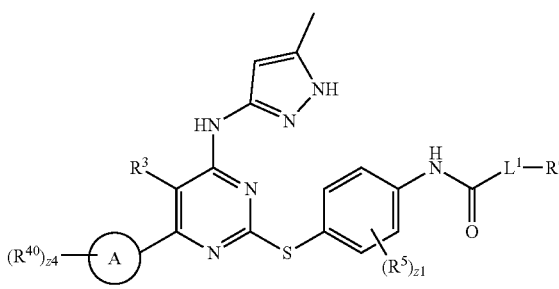

where the compound is not VX-680.

The compound of formula (Ib) may have the formula:

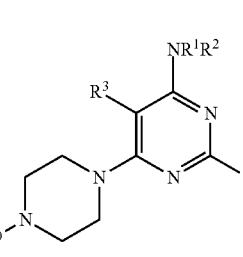

(Ib3)

where $L^1$, z1, $R^1$, $R^2$, $R^5$, $R^6$, and $R^{40}$ are as described herein and the compound is not VX-680. The compound of formula (Ib3) may have the formula:

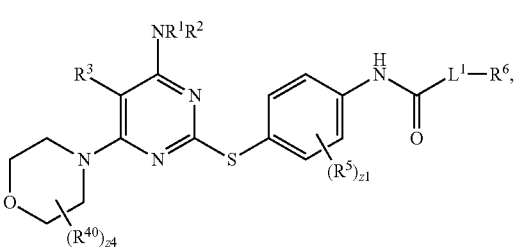

where the compound is not VX-680.

The compound of formula (Ib) may have the formula:

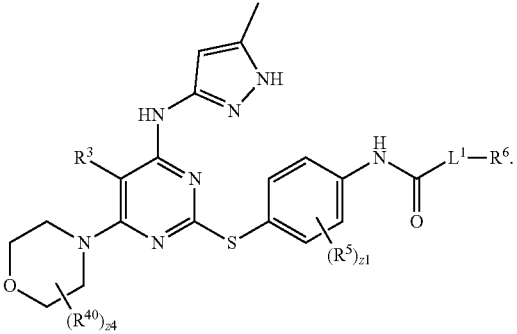

(Ib4)

where $L^1$, z1, $R^1$, $R^2$, $R^5$, $R^6$, and $R^{40}$ are as described herein and the symbol z4 is an integer of 0, 1, 2, 3, or 4. The compound of formula (Ib4) may have the formula The compound of formula (Ib) may have the formula:

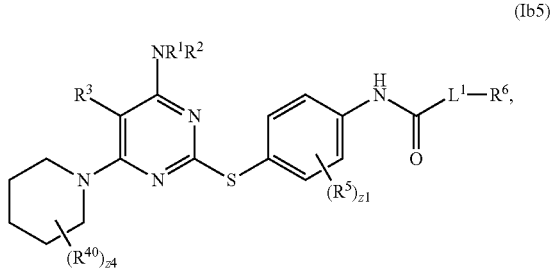
(Ib5)

where $L^1$, z1, $R^1$, $R^2$, $R^5$, $R^6$, and $R^{40}$ are as described herein and the symbol z4 is an integer of 0, 1, 2, 3, 4, or 5. The compound of formula (Ib5) may have the formula

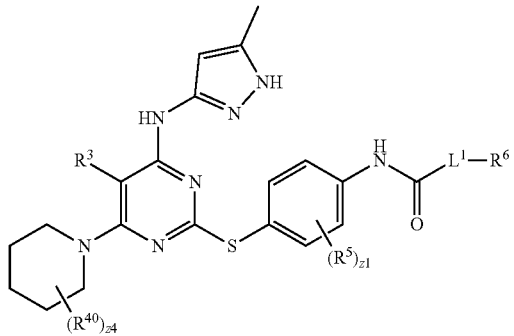

The compound of formula (Ib) may have the formula:

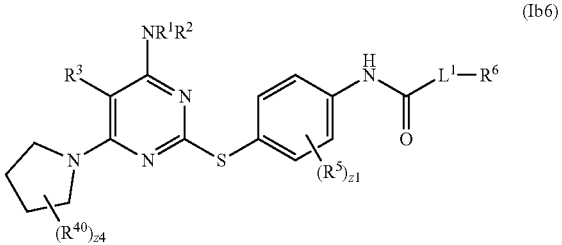
(Ib6)

where $L^1$, z1, $R^1$, $R^2$, $R^5$, $R^6$, and $R^{40}$ are as described herein and the symbol z4 is an integer of 0, 1, 2, 3, or 4. The compound of formula (Ib2) may have the formula

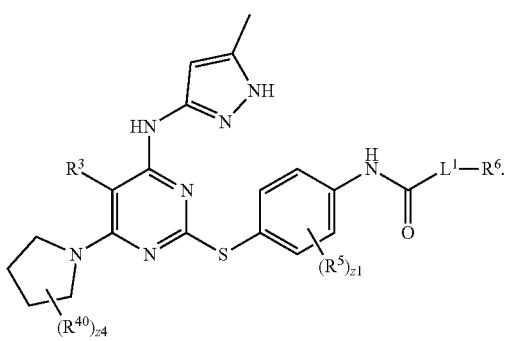

Further to any of Formulae (Ia) or (Ib), or embodiments thereof, $L^1$ may be a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—. $L^1$ may be a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^1$ may be a bond, substituted or unsubstituted alkylene, or substituted or unsubstituted heteroalkylene. $L^1$ may be a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—, substituted or unsubstituted alkylene, or substituted or unsubstituted heteroalkylene. $L^1$ may be a bond, —C(O)—, —C(O)O—, —O—, —S—, —NR$^{13}$—, —C(O)NR$^{13}$—, —NR$^{13}$C(O)—, —S(O)$_2$—, —S(O) NR$^{13}$—, substituted or unsubstituted alkylene, or substituted or unsubstituted heteroalkylene where $R^{13}$ is hydrogen or substituted or unsubstituted alkyl. $L^1$ may be a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—, $R^{13}$-substituted or unsubstituted alkylene, or $R^{13}$-substituted or unsubstituted heteroalkylene where $R^{13}$ is hydrogen or substituted or unsubstituted alkyl. $R^{13}$ may be unsubstituted alkyl.

$L^1$ may be a bond or substituted or unsubstituted alkylene. $L^1$ may be a bond or $R^{13}$-substituted or unsubstituted alkylene. $L^1$ may be a bond or $R^{13}$-substituted or unsubstituted alkylene where $R^{13}$ is hydrogen or substituted or unsubstituted alkyl. $L^1$ may be a bond or substituted or unsubstituted $C_1$-$C_5$ alkylene. $L^1$ may be a bond or $R^{13}$-substituted or unsubstituted $C_1$-$C_5$ alkylene. $L^1$ may be a bond or $R^{13}$-substituted or unsubstituted $C_1$-$C_5$ alkylene where $R^{13}$ is hydrogen or substituted or unsubstituted $C_1$-$C_5$ alkyl. $L^1$ may be $R^{13}$-substituted or unsubstituted alkylene where $R^{13}$ is hydrogen, halogen, or substituted or unsubstituted alkyl. In embodiments, $L^i$ may be unsubstituted alkylene. In embodiments, $L^1$ may be unsubstituted methylene. In embodiments, $L^1$ may be $R^{13}$-substituted methylene. In embodiments, $L^1$ may be methylene substituted with one $R^{13}$-substituent. In embodiments, the $R^{13}$-substituent may be halogen. In embodiments, $L^1$ may be methylene substituted with one fluoro substituent. In embodiments, $L^1$ may be methylene independently substituted with two $R^{13}$-substituents. In embodiments, $L^1$ may be methylene independently substituted with halogen substituents. In embodiments, the $R^{13}$-substituent may be alkyl. In embodiments, $L^1$ may be methylene mono substituted with substituted or unsubstituted alkyl. In embodiments, $L^1$ may be methylene disubstituted with substituted or unsubstituted alkyl. In embodiments, the two independent $R^{13}$-substitutents combine to form a substituted or unsubstituted cycloalkyl, or a substituted or unsubstituted heterocycloalkyl. In embodiments, $L^1$ may be methylene singly substituted with halogen or unsubstituted alkyl. In embodiments, $L^1$ may be methylene independently disubstituted with halogen or unsubstituted alkyl. In embodiments, $L^1$ may be methylene singly substituted with halogen or substituted alkyl. In embodiments, $L^1$ may be methylene independently disubstituted with halogen or substituted alkyl.

$R^{13}$ may independently be hydrogen, halogen, oxo, $N_3$, —CF$_3$, —CCl$_3$, —CBr$_3$, —CI$_3$, —CN, —OH, —COH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{13A}$-substituted or unsubstituted heteroalkyl, $R^{13A}$-substituted or unsubstituted cycloalkyl, $R^{13A}$-substituted or unsubstituted heterocycloalkyl, $R^{13A}$-substituted or unsubstituted aryl, or $R^{13A}$-substituted or unsubstituted heteroaryl.

$R^{13A}$ is independently halogen, oxo, $N_3$, —$CF_3$, —$CCl_3$, —$CBr_3$, —$CI_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, where $L^1$ is a substituted or unsubstituted cycloalkylene or heterocycloalkylene, a single carbon of the cycloalkylene or heterocycloalkylene is connected (bonded) to both the sulfonyl moiety and $R^6$. For example, in some embodiments, $L^1$ is:

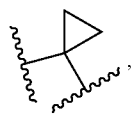

wherein the symbol $\sim\!\!\sim$ denotes the point of attachment to the sulfonyl moiety and $R^6$.

In embodiments, $L^1$ may be substituted or unsubstituted $C_1$-$C_5$ cycloalkylene. In embodiments, $L^1$ may be substituted or unsubstituted cyclopropylene. In embodiments, $L^1$ may be substituted or unsubstituted cyclobutylene. In embodiments, $L^1$ may be substituted or unsubstituted cyclopentylene. In embodiments, $L^1$ may be unsubstituted cyclopropylene. In embodiments, $L^1$ may be unsubstituted cyclobutylene. In embodiments, $L^1$ may be unsubstituted cyclopentylene. In embodiments, $L^1$ may be $C_1$-$C_5$ cycloalkylene substituted with halogen, or substituted or unsubstituted alkyl.

The compound of formula (Ia) may have the formula:

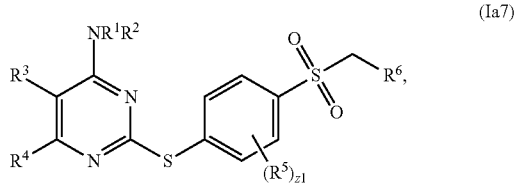
(Ia7)

where z1, $R^1$, $R^2$, $R^3$, $R^4$, $R^5$, and $R^6$ are as described herein. The compound of formula (Ia7) may have the formula:

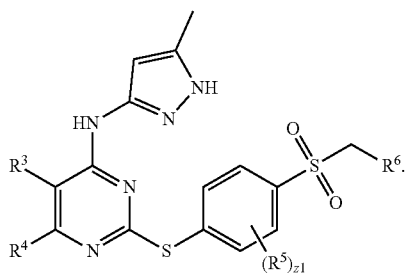

The compound of formula (Ia) may have the formula:

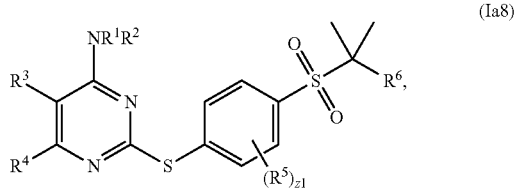
(Ia8)

where z1, $R^1$, $R^2$, $R^3$, $R^4$, $R^5$, and $R^6$ are as described herein.

The compound of formula (Ia8) may have the formula:

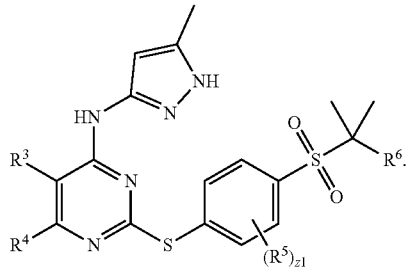

In embodiments, the compound of Formula (Ia) may have the structure of Formula (Ia9a) following:

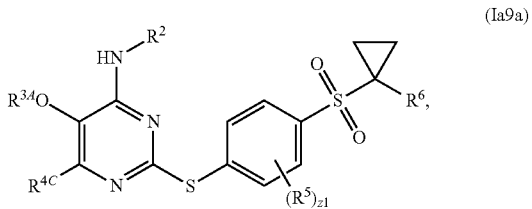
(Ia9a)

wherein $R^{3A}$ is substituted or unsubstituted alkyl, and $R^{4C}$ is substituted or unsubstituted heterocycloalkyl.

In embodiments, $R^2$ is substituted or unsubstituted heteroaryl. In embodiments, $R^2$ is unsubstituted heteroaryl. In embodiments, $R^2$ is substituted heteroaryl. In embodiments, $R^2$ is $R^{2C}$-substituted heteroaryl, wherein $R^{2C}$ is as defined herein. $R^2$ may be $R^{2C}$-substituted or unsubstituted 5 to 20 membered heteroaryl. $R^2$ may be $R^{2C}$-substituted 5 to 20 membered heteroaryl. $R^2$ may be $R^{2C}$-substituted or unsubstituted 5 to 8 membered heteroaryl. $R^2$ may be $R^{2C}$-substituted 5 to 8 membered heteroaryl. $R^2$ may be $R^{2C}$-substituted or unsubstituted 5 or 6 membered heteroaryl. $R^2$ may be $R^{2C}$-substituted 5 or 6 membered heteroaryl.

In embodiments, $R^2$ is substituted or unsubstituted pyrazolyl. In embodiments, $R^2$ is unsubstituted pyrazolyl. In embodiments, $R^2$ is substituted pyrazolyl. In embodiments, $R^2$ is pyrazolyl substituted with substituted or unsubstituted alkyl. In embodiments, $R^2$ is pyrazolyl substituted with unsubstituted alkyl. In embodiments, $R^2$ is pyrazolyl substituted with unsubstituted lower alkyl. In embodiments, $R^2$ is pyrazolyl substituted methyl, ethyl or propyl. In embodiments, $R^2$ is methyl substituted pyrazolyl.

In embodiments, $R^2$ is $R^{2C}$-substituted pyrazolyl. In embodiments, $R^2$ is $R^{2C}$-substituted pyrazolyl, wherein $R^{2C}$ is substituted or unsubstituted alkyl. In embodiments, $R^2$ is $R^{2C}$-substituted pyrazolyl, wherein $R^{2C}$ is unsubstituted alkyl. In embodiments, $R^2$ is $R^{2C}$-substituted pyrazolyl, wherein $R^{2C}$ is unsubstituted lower alkyl. In embodiments, $R^2$ is $R^{2C}$-substituted pyrazolyl, wherein $R^{2C}$ is unsubstituted methyl, ethyl or propyl. In embodiments, $R^2$ is $R^{2C}$-substituted pyrazolyl, wherein $R^{2C}$ is unsubstituted methyl.

In embodiments, the compound of Formula (Ia9a) may have a formula with structure of Formula (Ia9b):

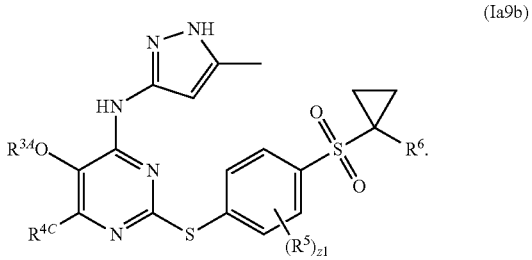
(Ia9b)

Further to any of Formulae (Ia9a)-(Ia9b), in embodiments $R^{3A}$ is substituted or unsubstituted alkyl. In embodiments $R^{3A}$ is unsubstituted alkyl. In embodiments, $R^{3A}$ is unsubstituted lower alkyl. In embodiments, $R^{3A}$ is methyl, ethyl or propyl. In embodiments, $R^{3A}$ is methyl. In embodiments, $R^{3A}$ is $R^{3C}$-substituted or unsubstituted alkyl, wherein $R^{3C}$ is as defined herein.

In embodiments, the compound of Formulae (Ia9a)-(Ia9b) may have the structure of Formula (Ia9c):

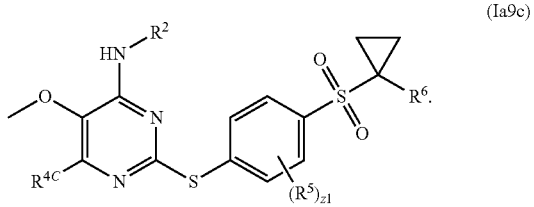

(Ia9c)

In embodiments, $R^{4C}$ is substituted or unsubstituted heterocycloalkyl. In embodiments, $R^{4C}$ is unsubstituted heterocycloalkyl. In embodiments, $R^{4C}$ is substituted heterocycloalkyl. In embodiments, $R^{3C}$ is $R^{40}$-substituted heterocycloalkyl, wherein $R^{40}$ is as defined herein.

In embodiments, the compound of Formulae (Ia9a)-(Ia9c) has the structure of Formula (Ia9d) following:

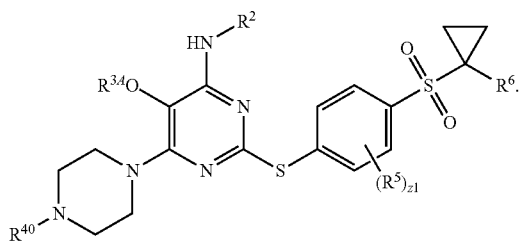

(Ia9d)

In formula (Ia9d), $R^{40}$ may be substituted or unsubstituted alkyl or substituted or unsubstituted heteroalkyl (e.g. —CH$_2$C(O)N(CH$_3$)$_2$).

Further to any of Formulae (Ia9a)-(Ia9d), in embodiments $R^5$ and z1 are as defined herein. In embodiments, $R^5$ is halogen, and z1 is 1. In embodiments, $R^5$ is fluoro.

Further to any of Formulae (Ia9a)-(Ia9d), in embodiments $R^6$ is substituted or unsubstituted aryl. In embodiments, $R^6$ is unsubstituted aryl. $R^6$ is aryl independently substituted one or more times with halogen or —NO$_2$.

In embodiments, the compound may have the structure of Formula (Ia9e):

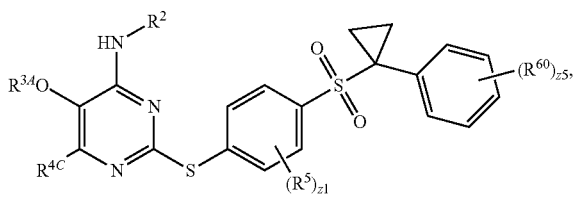

(Ia9f)

wherein $R^{60}$ and z5 are as defined herein. In embodiments, $R^{60}$ is halogen or —NO$_2$, and z5 is 1 or 2. In embodiments, z5 is 1. In embodiments, z5 is 2.

The compound of formula (Ib) may have the formula:

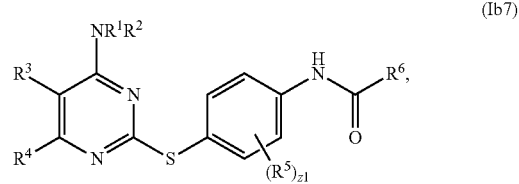

(Ib7)

wherein z1, $R^1$, $R^2$, $R^3$, $R^4$, $R^5$, and $R^6$ are as described herein and the compound is not VX-680.

The compound of formula (Ib7) may have the formula:

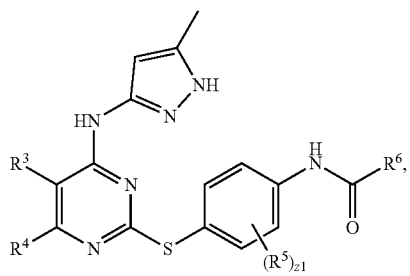

wherein the compound is not VX-680.

In embodiments, the compound provided herein has the formula:

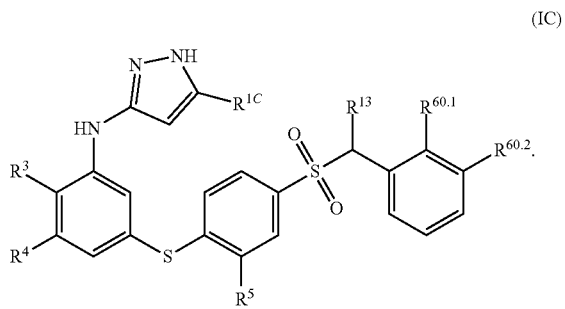

(IC)

In Formula (IC), $R^3$, $R^4$, $R^{1C}$, $R^5$ and $R^{13}$ are as defined herein, including all embodiments thereof. $R^{60.1}$ and $R^{60.2}$ are independently as defined for $R^{60}$. In embodiments, $R^{60.1}$ and $R^{60.2}$ are different. In embodiments, $R^{13}$ is hydrogen. In embodiments, $R^3$ is methoxy (—O—CH$_3$). In embodiments, $R^5$ is halogen (e.g. F). In embodiments, $R^{1C}$ is substituted or unsubstituted alkyl (e.g. methyl). In embodiments, $R^{60.1}$ is halogen (e.g. F). In embodiments, $R^{60.2}$ is nitro (—NO$_2$). In embodiments, $R^4$ is substituted or unsubstituted heterocycloalkyl (e.g. unsubstituted morphilino or unsubstituted piperidinyl). In embodiments, $R^4$ is substituted or unsubstituted heterocycloalkyl wherein the point of attachment to the remainder of the molecule is a ring nitrogen.

Also provided herein are compounds having the formula:

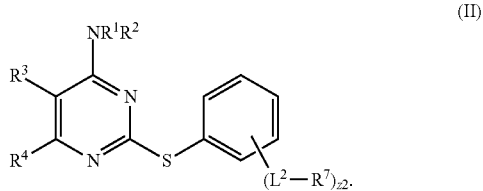

(II)

In a first aspect of formula (II), $L^2$ is independently a bond, —C(O)—, —C(O)O—, —O—, —S—, —NR$^{14}$—, —C(O)NR$^{14}$—, —NR$^{14}$C(O)—, —S(O)—, —S(O)$_2$—, —S(O)NR$^{14}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^7$ is independently hydrogen, oxo, halogen, —N$_3$, —CF$_3$, —CCl$_3$, —CBr$_3$, —CI$_3$, —CN, —COR$^{7A}$, —OR$^{7A}$, —NR$^{7A}$R$^{7B}$, —C(O)OR$^{7A}$, —C(O)NR$^{7A}$R$^{7B}$, —NO$_2$, —SR$^{14}$, —S(O)$_{n7}$R$^{7A}$, —S(O)$_{n7}$OR$^{7A}$, —S(O)$_{n7}$NR$^{7A}$R$^{7B}$, —NHNR$^{7A}$R$^{7B}$, —ONR$^{14}$R$^{1B}$, —NHC(O)NHNR$^{7A}$R$^{1B}$, -L$^1$-R$^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n7 is independently 1 or 2. The symbol z2 is 1, 2, 3, 4, or 5. $R^{7A}$, $R^{7B}$, $R^{13}$, and $R^{14}$ are independently hydrogen, oxo, halogen, —CF$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The compound is not VX-680.

$L^1$, $R^1$, $R^2$, and $R^6$ of the compound of formula (II) are as described hereinabove for compounds having formula (I), including all embodiments thereof.

$R^3$ of the compound of formula (II) is as described hereinabove for compounds of formula (I) with the proviso that $R^3$ is not hydrogen. Thus, $R^3$ may be halogen, —N$_3$, —CF$_3$, —CCl$_3$, —CBr$_3$, —CI$_3$, —CN, —COR$^{3A}$, —OR$^{3A}$, —NR$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, or substituted or unsubstituted alkyl, where $R^{3A}$, $R^{3B}$, and $R^{3C}$ are as described herein. $R^3$ may be halogen, —N$_3$, —CF$_3$, —CCl$_3$, —CBr$_3$, —CI$_3$, —CN, —COR$^{3A}$, —OR$^{3A}$, —NR$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, or substituted or unsubstituted alkyl, where $R^{3A}$, $R^{3B}$, and $R^{3C}$ are independently hydrogen, oxo, halogen, —CF$_3$, —OH, —NH$_2$, —COOH, —CONH$_2$, substituted or unsubstituted alkyl, or substituted or unsubstituted aryl. $R^3$ may be —OCH$_3$. $R^3$ may be —OCH$_3$CH$_3$.

$R^3$ may be halogen, —OR$^{3A}$, or substituted or unsubstituted alkyl. $R^3$ may be halogen, —OR$^{3A}$, or substituted or unsubstituted alkyl where f substituted or unsubstituted alkyl. $R^3$ may be —OR$^{3A}$. $R^3$ may be —OR$^{3A}$ where $R^{3A}$ is substituted or unsubstituted alkyl.

$R^4$ of the compound of formula (II) is as described hereinabove for compounds of formula (I) with the proviso that $R^4$ is not hydrogen or substituted or unsubstituted alkyl.

The compound of formula (II) may be compound having one of the formulae Ia, Ia1, Ia2, Ia3, Ia4, Ia5, Ia6, Ia7, Ia8, Ib, Ib1, Ib2, Ib3, Ib4, Ib5, Ib6, or Ib7.

$R^7$ may independently be hydrogen, halogen, —N$_3$, —CF$_3$, —CCl$_3$, —CBr$_3$, —CI$_3$, —CN, —COR$^{7A}$, —OR$^{7A}$, —NR$^{7A}$R$^{7B}$, —C(O)OR$^{7A}$, —C(O)NR$^{7A}$R$^{7B}$, —NO$_2$, —SR$^{7A}$, —S(O)$_{n7}$R$^{7A}$, —S(O)$_{n7}$OR$^{7A}$, —S(O)$_{n7}$NR$^{7A}$R$^{7B}$, —NHNR$^{7A}$R$^{7B}$, —ONR$^{7A}$R$^{7B}$, or —NHC(O)NHNR$^{7A}$R$^{7B}$. $R^7$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ may be hydrogen or halogen. $R^7$ may be hydrogen or —Cl, —I, or —Br. $R^7$ may be hydrogen or —Cl or —F. $R^7$ may be hydrogen. $R^7$ may be —Cl. $R^7$ may be —I. $R^7$ may be —I. $R^7$ may be —F. The symbol z1 may be 1, 2, or 3. The symbol z1 may be 1 or 2. $R^7$ may be hydrogen or —Cl or —F where the symbol z1 is 1 or 2.

$R^7$ may be substituted or unsubstituted alkyl. $R^7$ may be substituted alkyl. $R^7$ may be unsubstituted alkyl. $R^7$ may be substituted or unsubstituted $C_1$-$C_{20}$ alkyl. $R^7$ may be substituted $C_1$-$C_{20}$ alkyl. $R^7$ may be unsubstituted $C_1$-$C_{20}$ alkyl. $R^7$ may be substituted or unsubstituted $C_1$-$C_{10}$ alkyl. $R^7$ may be substituted $C_1$-$C_{10}$ alkyl. $R^7$ may be unsubstituted $C_1$-$C_{10}$ alkyl. $R^7$ may be substituted or unsubstituted $C_1$-$C_5$ alkyl. $R^7$ may be unsubstituted $C_1$-$C_5$ alkyl. $R^7$ may be substituted $C_1$-$C_5$ alkyl. $R^7$ may be methyl, substituted or unsubstituted ethyl, or substituted or unsubstituted propyl. $R^7$ may be methyl. $R^7$ may be ethyl.

$R^7$ may be $R^{7C}$-substituted or unsubstituted alkyl. $R^7$ may be $R^{7C}$-substituted alkyl. $R^7$ may be $R^{7C}$-substituted or unsubstituted $C_1$-$C_{20}$ alkyl. $R^7$ may be $R^{7C}$-substituted $C_1$-$C_{20}$ alkyl. $R^7$ may be $R^{7C}$-substituted or unsubstituted $C_1$-$C_{10}$ alkyl. $R^7$ may be $R^{7C}$-substituted $C_1$-$C_{10}$ alkyl. $R^7$ may be $R^{7C}$-substituted or unsubstituted $C_1$-$C_5$ alkyl. $R^7$ may be $R^{7C}$-substituted $C_1$-$C_5$ alkyl. $R^7$ may be methyl, $R^{7C}$-substituted or unsubstituted ethyl, or $R^{7C}$-substituted or unsubstituted propyl.

$R^7$ may be substituted or unsubstituted heteroalkyl. $R^7$ may be substituted heteroalkyl. $R^7$ may be unsubstituted heteroalkyl. $R^7$ may be substituted or unsubstituted 2 to 20 membered heteroalkyl. $R^7$ may be substituted 2 to 20 membered heteroalkyl. $R^7$ may be substituted or unsubstituted 2 to 10 membered heteroalkyl. $R^7$ may be substituted 2 to 10 membered heteroalkyl. $R^7$ may be substituted or unsubstituted 2 to 6 membered heteroalkyl. $R^7$ may be substituted 2 to 6 membered heteroalkyl.

$R^7$ may be $R^{7C}$-substituted or unsubstituted heteroalkyl. $R^7$ may be $R^{7C}$-substituted heteroalkyl. $R^7$ may be $R^{7C}$-substituted or unsubstituted 2 to 20 membered heteroalkyl. $R^7$ may be $R^{7C}$-substituted 2 to 20 membered heteroalkyl. $R^7$ may be $R^{7C}$-substituted or unsubstituted 2 to 10 membered heteroalkyl. $R^7$ may be $R^{7C}$-substituted 2 to 10 membered heteroalkyl. $R^7$ may be $R^{7C}$-substituted or unsubstituted 2 to 6 membered heteroalkyl. $R^7$ may be $R^{7C}$-substituted 2 to 6 membered heteroalkyl.

$R^7$ may be substituted or unsubstituted cycloalkyl. $R^7$ may be substituted cycloalkyl. $R^7$ may be unsubstituted cycloalkyl. $R^7$ may be substituted or unsubstituted 3 to 20 membered cycloalkyl. $R^7$ may be substituted 3 to 20 membered cycloalkyl. $R^7$ may be substituted or unsubstituted 3 to 10 membered cycloalkyl. $R^7$ may be substituted 3 to 10 membered cycloalkyl. $R^7$ may be substituted or unsubstituted 3 to 6 membered cycloalkyl. $R^7$ may be substituted 3 to 6 membered cycloalkyl.

$R^7$ may be $R^{7C}$-substituted or unsubstituted cycloalkyl. $R^7$ may be $R^{7C}$-substituted cycloalkyl. $R^7$ may be $R^{7C}$-substituted or unsubstituted 3 to 20 membered cycloalkyl. $R^7$ may be $R^{7C}$-substituted 3 to 20 membered cycloalkyl. $R^7$ may be $R^{7C}$-substituted or unsubstituted 3 to 10 membered cycloalkyl. $R^7$ may be $R^{7C}$-substituted 3 to 10 membered cycloalkyl. $R^7$ may be $R^{7C}$-substituted or unsubstituted 3 to 6 membered cycloalkyl. $R^7$ may be $R^{7C}$-substituted 3 to 6 membered cycloalkyl.

$R^7$ may be substituted or unsubstituted heterocycloalkyl. $R^7$ may be substituted heterocycloalkyl. $R^7$ may be unsubstituted heterocycloalkyl. $R^7$ may be substituted or unsubstituted 3 to 20 membered heterocycloalkyl. $R^7$ may be substituted 3 to 20 membered heterocycloalkyl. $R^7$ may be substituted or unsubstituted 3 to 10 membered heterocycloalkyl. $R^7$ may be substituted 3 to 10 membered heterocycloalkyl. $R^7$ may be substituted or unsubstituted 3 to 6 membered heterocycloalkyl. $R^7$ may be substituted 3 to 6 membered heterocycloalkyl.

$R^7$ may be $R^{7C}$-substituted or unsubstituted heterocycloalkyl. $R^7$ may be $R^{7C}$-substituted heterocycloalkyl. $R^7$ may be $R^{7C}$-substituted or unsubstituted 3 to 20 membered heterocycloalkyl. $R^7$ may be $R^{7C}$-substituted 3 to 20 membered heterocycloalkyl. $R^7$ may be $R^{7C}$-substituted or unsubstituted 3 to 10 membered heterocycloalkyl. $R^7$ may be $R^{7C}$-substituted 3 to 10 membered heterocycloalkyl. $R^7$ may be $R^{7C}$-substituted or unsubstituted 3 to 6 membered heterocycloalkyl. $R^7$ may be $R^{7C}$-substituted 3 to 6 membered heterocycloalkyl.

$R^7$ may be substituted or unsubstituted aryl. $R^7$ may be substituted aryl. $R^7$ may be unsubstituted aryl. $R^7$ may be substituted or unsubstituted 5 to 20 membered aryl. $R^7$ may be substituted 5 to 20 membered aryl. $R^7$ may be substituted or unsubstituted 5 to 8 membered aryl (e.g. phenyl). $R^7$ may be substituted 5 to 8 membered aryl. $R^7$ may be substituted or unsubstituted 5 or 6 membered aryl. $R^7$ may be substituted 5 or 6 membered aryl.

$R^7$ may be $R^{7C}$-substituted or unsubstituted aryl. $R^7$ may be $R^{7C}$-substituted aryl. $R^7$ may be $R^{7C}$-substituted or unsubstituted 5 to 20 membered aryl. $R^7$ may be $R^{7C}$-substituted 5 to 20 membered aryl. $R^7$ may be $R^{7C}$-substituted or unsubstituted 5 to 8 membered aryl. $R^7$ may be $R^{7C}$-substituted 5 to 8 membered aryl. $R^7$ may be $R^{7C}$-substituted or unsubstituted 5 or 6 membered aryl. $R^7$ may be $R^{7C}$-substituted 5 or 6 membered aryl (e.g. phenyl).

$R^7$ may be substituted or unsubstituted heteroaryl. $R^7$ may be substituted heteroaryl. $R^7$ may be unsubstituted heteroaryl. $R^7$ may be substituted or unsubstituted 5 to 20 membered heteroaryl. $R^7$ may be substituted 5 to 20 membered heteroaryl. $R^7$ may be substituted or unsubstituted 5 to 8 membered heteroaryl. $R^7$ may be substituted 5 to 8 membered heteroaryl. $R^7$ may be substituted or unsubstituted 5 or 6 membered heteroaryl. $R^7$ may be substituted 5 or 6 membered heteroaryl.

$R^7$ may be $R^{7C}$-substituted or unsubstituted heteroaryl. $R^7$ may be $R^{7C}$-substituted heteroaryl. $R^7$ may be $R^{7C}$-substituted or unsubstituted 5 to 20 membered heteroaryl. $R^7$ may be $R^{7C}$-substituted 5 to 20 membered heteroaryl. $R^7$ may be $R^{7C}$-substituted or unsubstituted 5 to 8 membered heteroaryl. $R^7$ may be $R^{7C}$-substituted 5 to 8 membered heteroaryl. $R^7$ may be $R^{7C}$-substituted or unsubstituted 5 or 6 membered heteroaryl. $R^7$ may be $R^{7C}$-substituted 5 or 6 membered heteroaryl.

$R^{7A}$ is independently hydrogen, halogen, oxo, $N_3$, —$CF_3$, —$CCl_3$, —$CBr_3$, —$CI_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —NHC(O)$NHNH_2$, —NHC(O)$NH_2$, —NHS(O)$_2H$, —NHC(O)H, —NHC(O)—OH, —NHOH, —$OCF_3$, —$OCHF_2$, $R^{7C}$-substituted or unsubstituted alkyl, $R^{7C}$-substituted or unsubstituted heteroalkyl, $R^{7C}$-substituted or unsubstituted cycloalkyl, $R^{7C}$-substituted or unsubstituted heterocycloalkyl, $R^{7C}$-substituted or unsubstituted aryl, or $R^{7C}$-substituted or unsubstituted heteroaryl.

$R^{7C}$ is independently halogen, oxo, $N_3$, —$CF_3$, —$CCl_3$, —$CBr_3$, —$CI_3$, —CN, —OH, —$COR^{7D}$, —$NR^{7D}R^{7E}$, —$COOR^{7D}$, —$CONR^{7D}R^{7E}$, —$NO_2$, —$SR^{7D}$, —$S(O)_2R^{7D}$, —$S(O)_3R^{7D}$, —$S(O)_4R^{7D}$, —$S(O)_2NR^{7D}R^{7E}$, —$NHNR^{7D}R^{7E}$, —$ONR^{7D}R^{7E}$, —NHC(O)$NHNR^{7D}R^{7E}$, —NHC(O)$NR^{7D}R^{7E}$, —NHS(O)$_2R^{7D}$, —NHC(O)$R^{7D}$, —NHC(O)—$OR^{7D}$, —$NHOR^{7D}$, —$OCF_3$, —$OCHF_2$, $R^{7D}$-substituted or unsubstituted alkyl, $R^{7D}$-substituted or unsubstituted heteroalkyl, $R^{7D}$-substituted or unsubstituted cycloalkyl, $R^{7D}$-substituted or unsubstituted heterocycloalkyl, $R^{7D}$-substituted or unsubstituted aryl, or $R^{7D}$-substituted or unsubstituted heteroaryl.

$R^{7C}$ may independently be halogen, oxo, $N_3$, —$CF_3$, —$CCl_3$, —$CBr_3$, —$CI_3$, —CN, —OH, —$NH_2$, —COOH, —$CONH_2$, —C(O)H, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —NHC(O)$NHNH_2$, —NHC(O)$NH_2$, —NHS(O)$_2H$, —NHC(O)H, —NHC(O)—OH, —NHOH, —$OCF_3$, —$OCHF_2$, $R^{7D}$-substituted or unsubstituted alkyl, $R^{7D}$-substituted or unsubstituted heteroalkyl, $R^{7D}$-substituted or unsubstituted cycloalkyl, $R^{7D}$-substituted or unsubstituted heterocycloalkyl, $R^{7D}$-substituted or unsubstituted aryl, or $R^{7D}$-substituted or unsubstituted heteroaryl.

$R^{7B}$ and $R^{7E}$ may independently be hydrogen, halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —NHC(O)$NHNH_2$, —NHC(O)$NH_2$, —NHS(O)$_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{7D}$ is independently hydrogen, halogen, oxo, $N_3$, —$CF_3$, —$CCl_3$, —$CBr_3$, —$CI_3$, —CN, —OH, —$COR^{7F}$, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —NHC(O)$NHNH_2$, —NHC(O)$NH_2$, —NHS(O)$_2H$, —NHC(O)H, —NHC(O)—OH, —NHOH, —$OCF_3$, —$OCHF_2$, $R^{7F}$-substituted or unsubstituted heteroalkyl, $R^{7F}$-substituted or unsubstituted cycloalkyl, $R^{7F}$-substituted or unsubstituted heterocycloalkyl, $R^{7F}$-substituted or unsubstituted aryl, or $R^{7F}$-substituted or unsubstituted heteroaryl.

$R^{7F}$ is independently halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —NHC(O)$NHNH_2$, —NHC(O)$NH_2$, —NHS(O)$_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^7$ may be -$L^1$-$R^6$, where $L^1$ and $R^6$ are independently as described herein. $R^7$ may be -$L^1$-$R^6$, where $L^1$ and $R^6$ are independently as described herein and $L^2$ is a bond, —$SO_2$, or —NHC(O)—.

L² may independently be a bond, —C(O)—, —C(O)O—, —O—, —S—, —NR¹⁴—, —C(O)NR¹⁴—, —NR¹⁴C(O)—, —S(O)—, —S(O)₂—, —S(O)NR¹⁴—. L² may independently be a bond, —S(O)₂—, or —NR¹⁴C(O)—, where R¹⁴ is hydrogen or unsubstituted $C_1$-$C_5$ alkyl. L² may independently be a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. L² may independently be a bond, substituted or unsubstituted alkylene, or substituted or unsubstituted heteroalkylene. L² may independently be a bond, —C(O)—, —C(O)O—, —O—, —S—, —NR¹⁴—, —C(O)NR¹⁴—, —NR¹⁴C(O)—, —S(O)₂—, —S(O)NR¹⁴—, substituted or unsubstituted alkylene, or substituted or unsubstituted heteroalkylene. L² may independently be a bond, —C(O)—, —C(O)O—, —O—, —S—, —NR¹⁴—, —C(O)NR¹⁴—, —NR¹⁴C(O)—, —S(O)₂—, —S(O)NR¹⁴—, substituted or unsubstituted alkylene, or substituted or unsubstituted heteroalkylene where R¹⁴ is hydrogen or substituted or unsubstituted alkyl. L² may independently be a bond, —C(O)—, —C(O)O—, —O—, —S—, —NR¹⁴—, —C(O)NR¹⁴—, —NR¹⁴C(O)—, —S(O)₂—, —S(O)NR¹⁴—, R¹⁴-substituted or unsubstituted alkylene, or R¹⁴-substituted or unsubstituted heteroalkylene where R¹⁴ is hydrogen or substituted or unsubstituted alkyl. R¹⁴ may be unsubstituted alkyl.

L² may independently be a bond or substituted or unsubstituted alkylene. L² may independently be a bond or R¹⁴-substituted or unsubstituted alkylene. L² may independently be a bond or R¹⁴-substituted or unsubstituted alkylene where R¹⁴ is hydrogen or substituted or unsubstituted alkyl. L² may independently be a bond or substituted or unsubstituted $C_1$-$C_5$ alkylene. L² may be a bond or R¹⁴-substituted or unsubstituted $C_1$-$C_5$ alkylene. L² may independently be a bond or R¹⁴-substituted or unsubstituted $C_1$-$C_5$ alkylene where R¹⁴ is hydrogen or substituted or unsubstituted $C_1$-$C_5$ alkyl. L² may independently be R¹⁴-substituted or unsubstituted alkylene where R¹⁴ is hydrogen, halogen, or substituted or unsubstituted alkyl. L² may independently be a bond. L² may independently be bond, —SO₂, or —NHC(O)— and R⁷ may be L¹-R⁶, where L¹ and R⁶ are as described herein.

R¹⁴ may independently be hydrogen, halogen, oxo, N₃, —CF₃, —CCl₃, —CBr₃, —CI₃, —CN, —OH, —COH, —NH₂, —COOH, —CONH₂, —COH, —COCH₃, —NO₂, —SH, —S(O)₂Cl, —S(O)₃H, —S(O)₄H, —S(O)₂NH₂, —NHNH₂, —ONH₂, —NHC(O)NHNH₂, —NHC(O)NH₂, —NHS(O)₂H, —NHC(O)H, —NHC(O)—OH, —NHOH, —OCF₃, —OCHF₂, R¹⁴ᴬ-substituted or unsubstituted heteroalkyl, R¹⁴ᴬ-substituted or unsubstituted cycloalkyl, R¹⁴ᴬ-substituted or unsubstituted heterocycloalkyl, R¹⁴ᴬ-substituted or unsubstituted aryl, or R¹⁴ᴬ-substituted or unsubstituted heteroaryl.

R¹⁴ᴬ is independently halogen, oxo, N₃, —CF₃, —CCl₃, —CBr₃, —CI₃, —CN, —OH, —NH₂, —COOH, —CONH₂, —COH, —COCH₃, —NO₂, —SH, —S(O)₂Cl, —S(O)₃H, —S(O)₄H, —S(O)₂NH₂, —NHNH₂, —ONH₂, —NHC(O)NHNH₂, —NHC(O)NH₂, —NHS(O)₂H, —NHC(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, or unsubstituted heteroaryl.

The compound of formula (II) may have the formula:

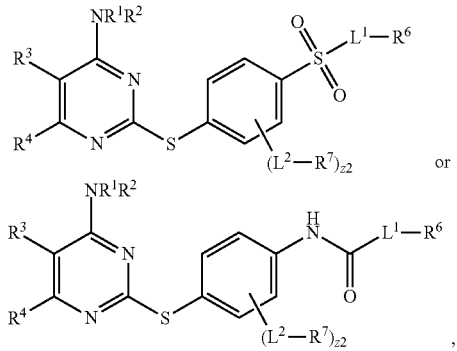

wherein z2a is 0, 1, 2, 3, or 4, and the compound is not VX-680. z2a may be 0, 1, or 2. z2a may be 0. z2a may be 1. z2a may be 2. z2a may be 3. z2a may be 4.

In a second aspect of formula (II), compounds are provided in which R¹, R², and R⁴ are as described hereinabove for compounds of formula (I). L², R⁷, and z2 are as described hereinabove for first aspect of the compound having formula (II). R⁷ may be -L¹-R⁶, where L¹ and R⁶ are independently as described herein. The compound is not VX-680.

R³ of the second aspect of the compound of formula (II) is as described hereinabove for compounds of formula (I) with the proviso that R³ is not hydrogen, halogen, or substituted or unsubstituted alkyl. R³ may be —N₃, —CF₃, —CCl₃, —CBr₃, —CI₃, —CN, —COR³ᴬ, —OR³ᴬ, —NR³ᴬR³ᴮ, —C(O)OR³ᴬ, —C(O)NR³ᴬR³ᴮ, —NO₂, —SR³ᴬ, —S(O)ₙ₃R³ᴬ, —S(O)ₙ₃OR³ᴬ, —S(O)ₙ₃NR³ᴬR³ᴮ, —NHNR³ᴬR³ᴮ, —ONR³ᴬR³ᴮ, —NHC(O)NHNR³ᴬR³ᴮ, where R³ᴬ, R³ᴮ, R³ᶜ, are as described herein. R³ may be —N₃, —CF₃, —CCl₃, —CBr₃, —CI₃, —CN, —COR³ᴬ, —OR³ᴬ, —NR³ᴬR³ᴮ, —C(O)OR³ᴬ, —C(O)NR³ᴬR³ᴮ, —NO₂, —SR³ᴬ, —S(O)ₙ₃R³ᴬ, —S(O)ₙ₃OR³ᴬ, —S(O)ₙ₃NR³ᴬR³ᴮ, —NHNR³ᴬR³ᴮ, —ONR³ᴬR³ᴮ, —NHC(O)NHNR³ᴬR³ᴮ, where R³ᴬ, R³ᴮ, R³ᶜ, are independently hydrogen, oxo, halogen, —CF₃, —OH, —NH₂, —COOH, —CONH₂, substituted or unsubstituted alkyl, or substituted or unsubstituted aryl. R³ may be —OCH₃.

R³ may be —OR³ᴬ. R³ may be —OR³ᴬ where R³ᴬ is substituted or unsubstituted alkyl.

The compound of formula (II) (e.g. the first or second aspect) may have the formula:

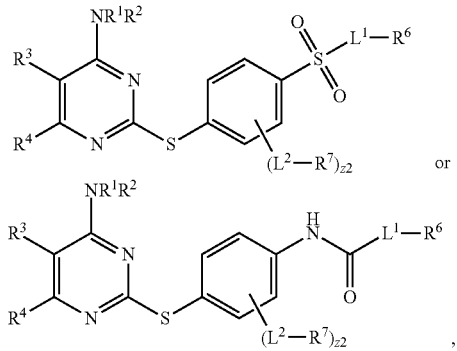

wherein z2a is 0, 1, 2, 3, or 4, and the compound is not VX-680. z2a may be 0, 1, or 2. z2a may be 0. z2a may be 1. z2a may be 2. z2a may be 3. z2a may be 4.

Further provided herein are compounds having the formula:

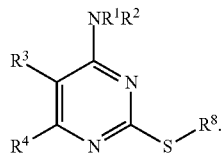

(III)

$R^1$, $R^2$, $R^3$, and $R^4$ are as described hereinabove for formula (I). In embodiments, $R^3$, and $R^4$ are as set forth hereinabove for formula (II) (including the first and second aspects). $R^8$ is unsubstituted $C_1$-$C_5$ alkyl. $R^8$ may be methyl, ethyl, or propyl. $R^8$ may be methyl.

The compound may be a compound set forth in Table 1. The compound may be a compound set forth in Table 1 having activity indicated as "XXX". The compound may be a compound set forth in Table 1, having the formula (I). The compound may be a compound set forth in Table 1, having the formula (I) and having activity indicated as "XXX". The compound may be a compound set forth in Table 1, having the formula (I) and having activity indicated as "XX". The compound may be a compound set forth in Table 1, having the formula (I) and having activity indicated as "X". The compound may be a compound set forth in Table 1, having the formula (II) (including the first or second aspect). The compound may be a compound set forth in Table 1, having the formula (II) (including the first or second aspect) and having activity indicated as "XXX". The compound may be a compound set forth in Table 1, having the formula (II) (including the first or second aspect) and having activity indicated as "XX". The compound may be a compound set forth in Table 1, having the formula (II) (including the first or second aspect) and having activity indicated as "X". The compound may be a compound set forth in Table 1, having the formula (III). The compound may be a compound set forth in Table 1, having the formula (III) and having activity indicated as "XXX". The compound may be a compound set forth in Table 1, having the formula (III) and having activity indicated as "XX". The compound may be a compound set forth in Table 1, having the formula (III) and having activity indicated as "X".

In embodiments the compound is not a compound set forth in U.S. Pat. No. 8,455,507, which is herein incorporated by reference in its entirety. In embodiments the compound is not a compound set forth in U.S. Pat. No. 7,531,536 which is herein incorporated by reference in its entirety. In embodiments the compound is not a compound set forth in U.S. Pat. No. 7,951,820 which is herein incorporated by reference in its entirety.

II. Pharmaceutical Compositions

Provided herein are pharmaceutical compositions of the compounds described herein. In one aspect is a pharmaceutical composition that includes a pharmaceutically acceptable excipient and a compound (e.g. formula (I), (II) (including the first or second aspect), (III), or a compound of Table 1 or Table 2) as described herein. The compound may be a compound having the formula (I) as described herein. The compound may be a compound having the formula (II) (including the first or second aspect) as described herein. The compound may be a compound having the formula (III) as described herein. The compound may be a compound set forth in Table 1. The compound may be a compound set forth in Table 2.

The pharmaceutical composition may include a second agent in a therapeutically effective amount. The pharmaceutical composition may include a second agent where the second agent treats cancer. The second agent may be an anti-cancer agent as described herein.

The pharmaceutical composition may be useful in treating cancer. The pharmaceutical composition may be used to treat basal cell carcinoma, medulloblastoma, pancreatic cancer, small cell lung cancer, gastric cancer, colon cancer, or chondrosarcoma in a subject in need thereof. When used for treating cancer, the pharmaceutical composition may be coadministered with an anti-cancer agent as described herein.

1. Formulations

The pharmaceutical composition may be prepared and administered in a wide variety of dosage formulations. Compounds described herein (e.g. formula (I), (II) (including the first or second aspect), (III) or a compound of Table 1 or Table 2) may be administered orally, rectally, or by injection (e.g. intravenously, intramuscularly, intracutaneously, subcutaneously, intraduodenally, or intraperitoneally).

For preparing pharmaceutical compositions from compounds having formula (I), (II) (including the first or second aspect), (III) or a compound of Table 1 or Table 2, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

For any compound described herein or combination thereof, the therapeutically effective amounts can be initially determined from cell culture assays. Target concentrations will be those concentrations of active compound(s) that are capable of increasing the extent of cancer cell death as measured, for example, using methods known in the art.

Therapeutically effective amounts for use in humans may be determined from animal models. For example, a dose for humans can be formulated to achieve a concentration that has been found to be effective in animals. The dosage in humans can be adjusted by monitoring response of the cancer to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

III. Methods Of Inhibiting PLK4

Also provided herein are methods of inhibiting a PLK4 kinase. In one aspect is a method of inhibiting a PLK4 kinase by contacting the PLK4 kinase with a compound described herein, including compounds exemplified by formula (I), (II) (including the first or second aspect), or (III), including compounds set forth in Table 1 or Table 2 and allowing the compound to bind to the PLK4 kinase, thereby inhibiting the PLK4 kinase. In embodiments, the compound is not VX-680.

The method of inhibiting may be performed in vitro. The method may be performed in vitro where the PLK4 kinase and a compound described herein are combined in a reaction vessel. The reaction vessel may be a multi-well (e.g. 6, 8, 12, 24, 48, 96, 192 well) plate. The reaction vessel may be a container used in high-throughput screening techniques known in the art.

The method of inhibiting may be performed in vivo. When performed in vivo, the contacting may be performed inside a cell. The cell may be a cancer-line cell as described herein. The cell may be a human cell. The cell may form part of an organism (e.g. a human).

IV. Methods Of Treating Cancer

Further provided herein are methods of treating cancer in a subject in need thereof. In one aspect, is a method of treating cancer in a subject in need thereof by administering to the subject a therapeutically effective amount of a compound described herein, including compounds exemplified by formula (I), (II) (including the first or second aspect), or (III) (including compounds set forth in Table 1 or Table 2). In embodiments, the compound is not VX-680.

The compound may be administered by one of the routes described herein. The compound may be co-administered with a second agent (e.g. an anti-cancer agent described herein). The compound may be a compound of formula (I). The compound may be a compound of formula (II) (including the first or second aspect). The compound may be a compound of formula (III). The compound may be a compound set forth in Table 1. The compound may be a compound set forth in Table 2.

The subject may be a mammal. The subject may be a human. The subject may be a cancer patient (e.g. a subject diagnosed with, or being treated for cancer).

The cancer may be basal cell carcinoma, medulloblastoma, pancreatic cancer, small cell lung cancer, gastric cancer, colon cancer, or chondrosarcoma.

Provided herein is a method of treating basal cell carcinoma, in a subject in need thereof, by administering to the subject a therapeutically effective amount of a compound described herein. Provided herein is a method of treating medulloblastoma, in a subject in need thereof, by administering to the subject a therapeutically effective amount of a compound described herein. Provided herein is a method of treating pancreatic cancer, in a subject in need thereof, by administering to the subject a therapeutically effective amount of a compound described herein. Provided herein is a method of treating small cell lung cancer, in a subject in need thereof, by administering to the subject a therapeutically effective amount of a compound described herein. Provided herein is a method of treating gastric cancer, in a subject in need thereof, by administering to the subject a therapeutically effective amount of a compound described herein. Provided herein is a method of treating colon cancer, in a subject in need thereof, by administering to the subject a therapeutically effective amount of a compound described herein. Also provided herein is a method of treating chondrosarcoma in a subject in need thereof, by administering to the subject a therapeutically effective amount of a compound described herein.

In embodiments, the cancer may be basal cell carcinoma, medulloblastoma, pancreatic cancer, small cell lung cancer, gastric cancer, colon cancer, chondrosarcoma or neuroblastoma. In embodiments, the cancer is neuroblastoma. Provided herein is a method of treating neuroblastoma in a subject in need thereof by administering to the subject a therapeutically effective amount of a compound described herein. In embodiments, the compound may be a compound with structure of Formulae (I), (II) (III), or an embodiment thereof disclosed herein. In embodiments, the compound is set forth in Table 1 or Table 2. In embodiments, the compound has the structure of any one of Formulae (Ia9a), (Ia9b), (Ia9c), (Ia9d), (Ia9e), or (Ia9f). In embodiments, the compound is not VX-680.

V. Examples

Example 1—Compounds

Table 1: Compounds of formula (I), (II), and (III). Activity denoted by X indicates compound has $IC_{50}$ value greater than about 1 µM. Activity denoted by XX indicates compound has $IC_{50}$ value of about 100 nM to about 1 µM. Activity denoted by X indicates compound has $IC_{50}$ value less than about 100 nM. All compounds were confirmed by mass spectroscopy and by $^1H$ and $^{13}C$ NMR.

TABLE 1
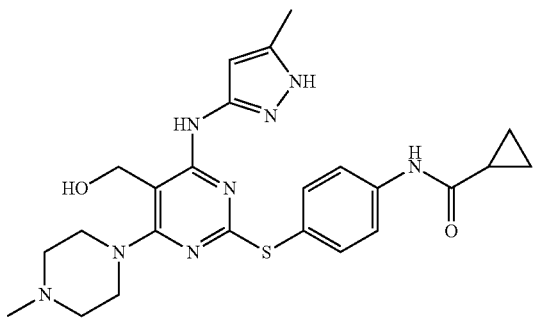 [SMILES: Cc1cc(Nc2nc(Sc3ccc(NC(=O)C4CC4)cc3)nc(N3CCN(C)CC3)c2CO)n[nH]1]
Activity XX
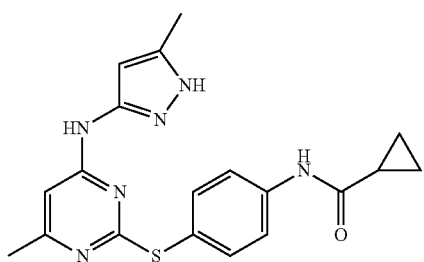 [SMILES: Cc1cc(Nc2cc(C)[nH]n2)nc(Sc2ccc(NC(=O)C3CC3)cc2)n1]
XXX
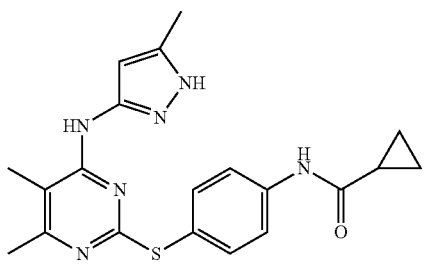 [SMILES: Cc1cc(Nc2nc(Sc3ccc(NC(=O)C4CC4)cc3)nc(C)c2C)n[nH]1]
XXX
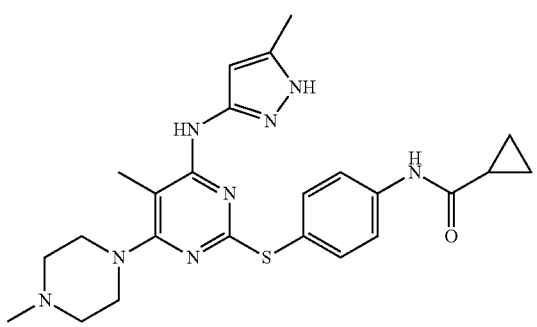 [SMILES: Cc1cc(Nc2nc(Sc3ccc(NC(=O)C4CC4)cc3)nc(N3CCN(C)CC3)c2C)n[nH]1]
XXX
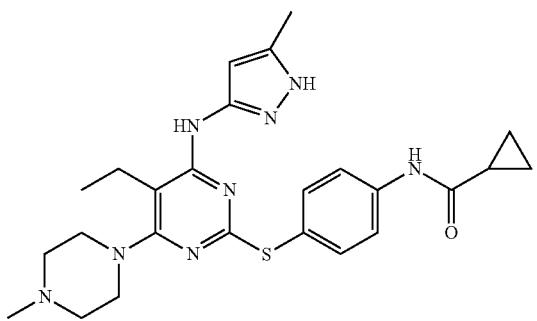
X TABLE 1-continued
| | Activity X |
|---|---|
| 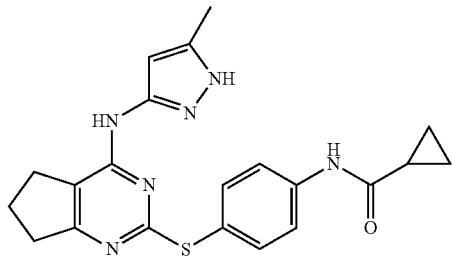 [SMILES: Cc1cc(Nc2nc(Sc3ccc(NC(=O)C4CC4)cc3)nc3c2CCC3)n[nH]1] | |
| 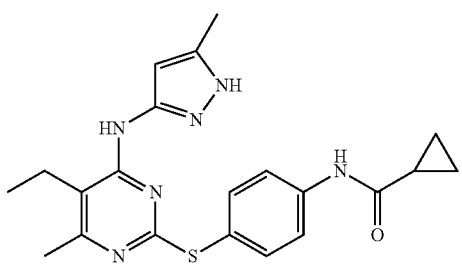 [SMILES: CCc1c(C)nc(Sc2ccc(NC(=O)C3CC3)cc2)nc1Nc1cc(C)[nH]n1] | X |
| 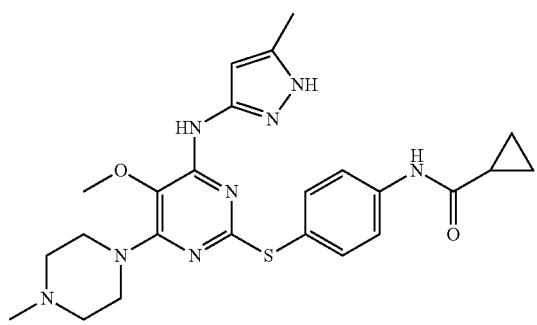 [SMILES: COc1c(Nc2cc(C)[nH]n2)nc(Sc2ccc(NC(=O)C3CC3)cc2)nc1N1CCN(C)CC1] | XXX |
| 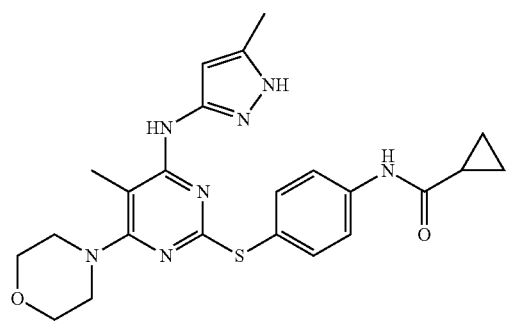 [SMILES: Cc1cc(Nc2nc(Sc3ccc(NC(=O)C4CC4)cc3)nc(N3CCOCC3)c2C)n[nH]1] | XXX |
| 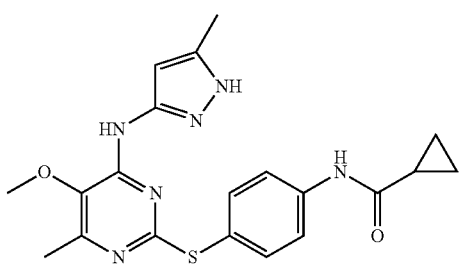 [SMILES: COc1c(C)nc(Sc2ccc(NC(=O)C3CC3)cc2)nc1Nc1cc(C)[nH]n1] | XXX |

TABLE 1-continued
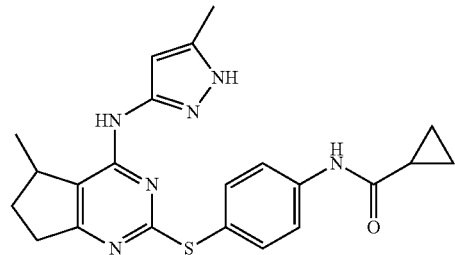 [SMILES: Cc1cc(Nc2nc(Sc3ccc(NC(=O)C4CC4)cc3)nc3c2C(C)CC3)n[nH]1] Activity XXX
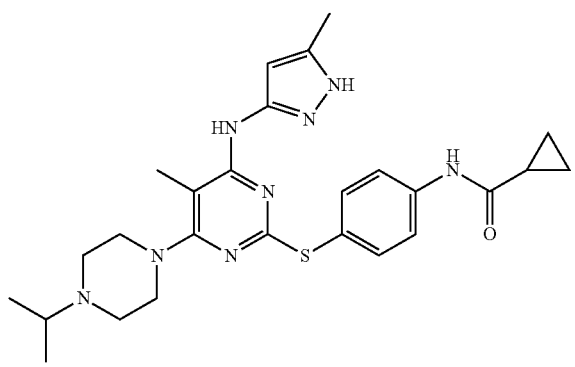 [SMILES: Cc1cc(Nc2nc(Sc3ccc(NC(=O)C4CC4)cc3)nc(N3CCN(C(C)C)CC3)c2C)n[nH]1] XXX
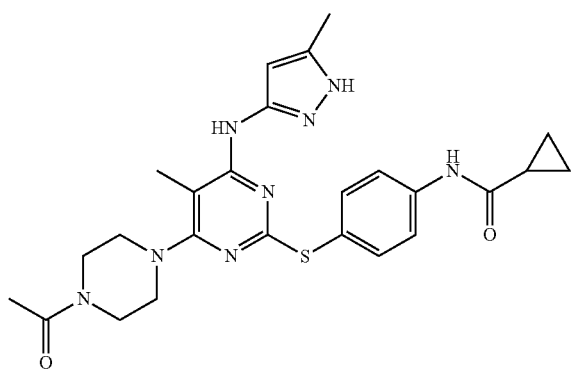 [SMILES: CC(=O)N1CCN(c2nc(Sc3ccc(NC(=O)C4CC4)cc3)nc(Nc3cc(C)[nH]n3)c2C)CC1] XXX
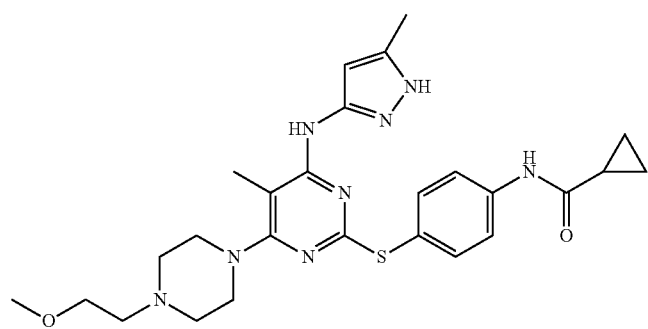 [SMILES: COCCN1CCN(c2nc(Sc3ccc(NC(=O)C4CC4)cc3)nc(Nc3cc(C)[nH]n3)c2C)CC1] XXX TABLE 1-continued
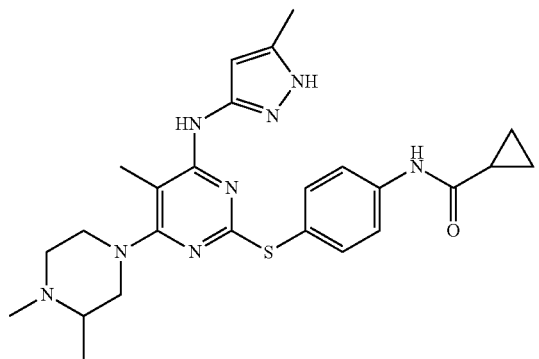 [SMILES: Cc1cc(Nc2nc(Sc3ccc(NC(=O)C4CC4)cc3)nc(N3CCN(C)C(C)C3)c2C)n[nH]1] XXX
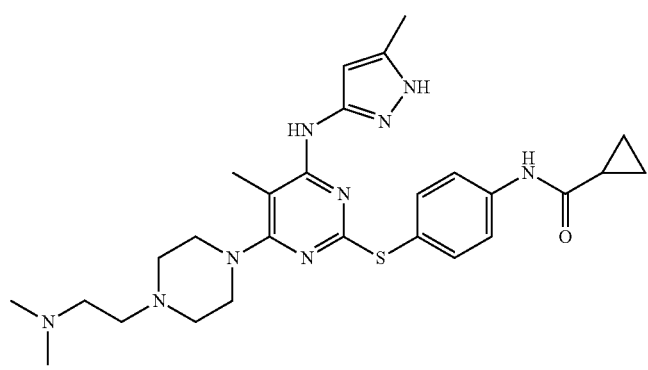 [SMILES: Cc1cc(Nc2nc(Sc3ccc(NC(=O)C4CC4)cc3)nc(N3CCN(CCN(C)C)CC3)c2C)n[nH]1] Activity XXX
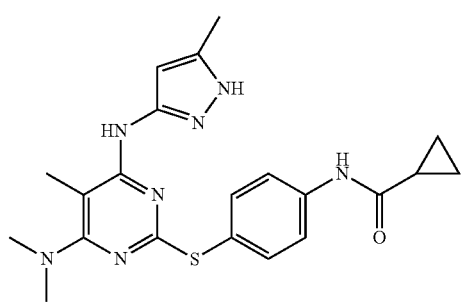 [SMILES: Cc1cc(Nc2nc(Sc3ccc(NC(=O)C4CC4)cc3)nc(N(C)C)c2C)n[nH]1] XXX
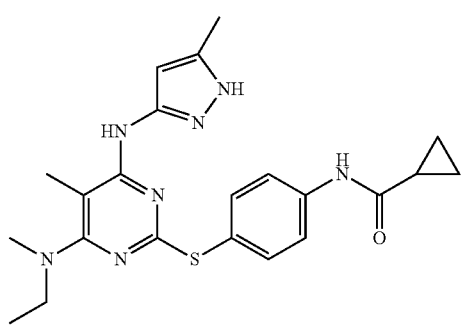 [SMILES: CCN(C)c1nc(Sc2ccc(NC(=O)C3CC3)cc2)nc(Nc2cc(C)[nH]n2)c1C] XXX TABLE 1-continued
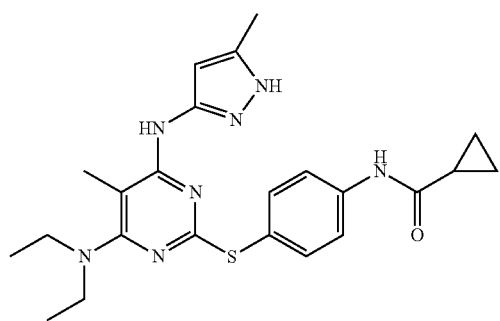 [SMILES: CCN(CC)c1nc(Sc2ccc(NC(=O)C3CC3)cc2)nc(Nc2cc(C)[nH]n2)c1C]
XXX
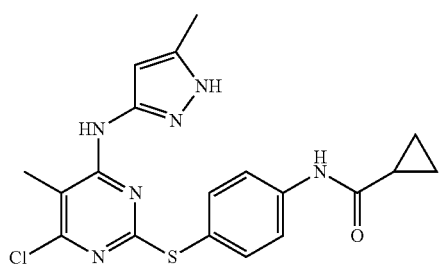 [SMILES: Cc1cc(Nc2nc(Sc3ccc(NC(=O)C4CC4)cc3)nc(Cl)c2C)n[nH]1]
XXX
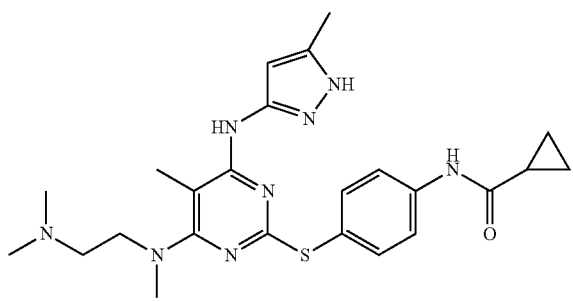 [SMILES: Cc1cc(Nc2nc(Sc3ccc(NC(=O)C4CC4)cc3)nc(N(C)CCN(C)C)c2C)n[nH]1]
Activity XXX
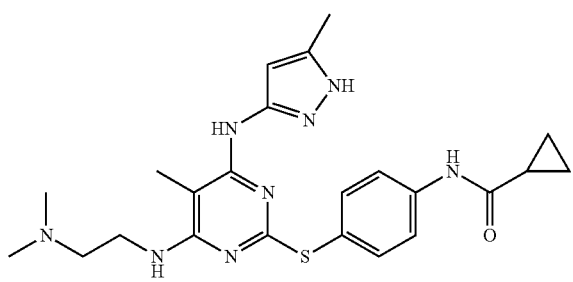 [SMILES: Cc1cc(Nc2nc(Sc3ccc(NC(=O)C4CC4)cc3)nc(NCCN(C)C)c2C)n[nH]1]
XXX
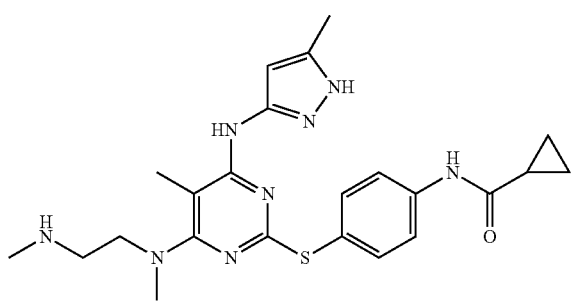 [SMILES: CNCCN(C)c1nc(Sc2ccc(NC(=O)C3CC3)cc2)nc(Nc2cc(C)[nH]n2)c1C]
XXX TABLE 1-continued
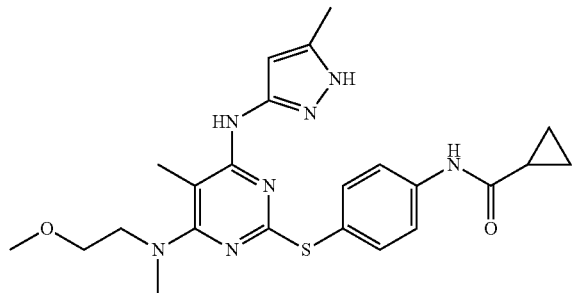 [SMILES: COCCN(C)c1nc(Sc2ccc(NC(=O)C3CC3)cc2)nc(Nc2cc(C)[nH]n2)c1C] XXX
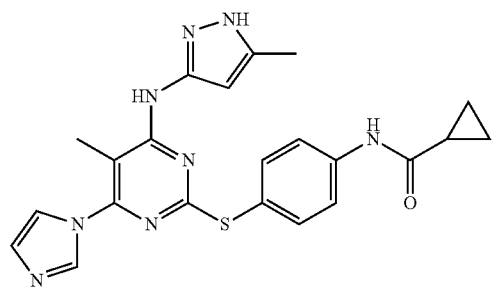 [SMILES: Cc1cc(Nc2nc(Sc3ccc(NC(=O)C4CC4)cc3)nc(-n3ccnc3)c2C)n[nH]1] XX
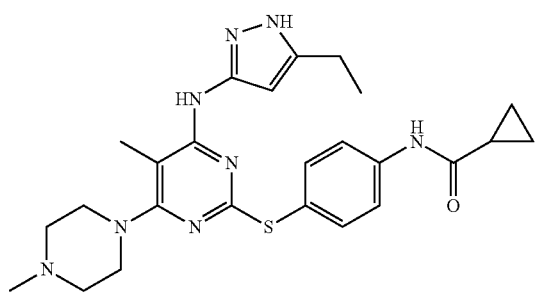 [SMILES: CCc1cc(Nc2nc(Sc3ccc(NC(=O)C4CC4)cc3)nc(N3CCN(C)CC3)c2C)n[nH]1] Activity X
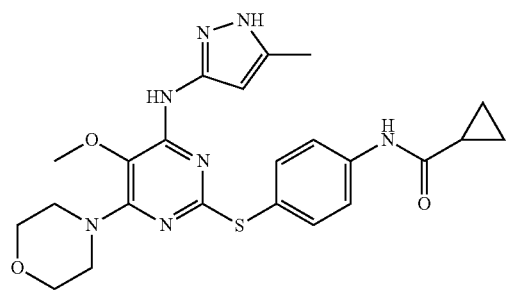 [SMILES: COc1c(Nc2cc(C)[nH]n2)nc(Sc2ccc(NC(=O)C3CC3)cc2)nc1N1CCOCC1] XXX
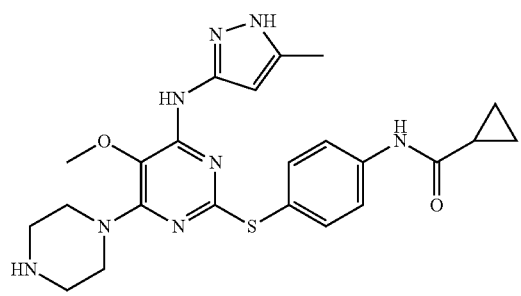 [SMILES: COc1c(Nc2cc(C)[nH]n2)nc(Sc2ccc(NC(=O)C3CC3)cc2)nc1N1CCNCC1] XXX TABLE 1-continued
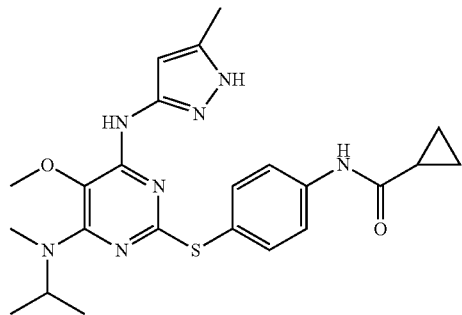 [SMILES: COc1c(Nc2cc(C)[nH]n2)nc(Sc2ccc(NC(=O)C3CC3)cc2)nc1N(C)C(C)C]
XX
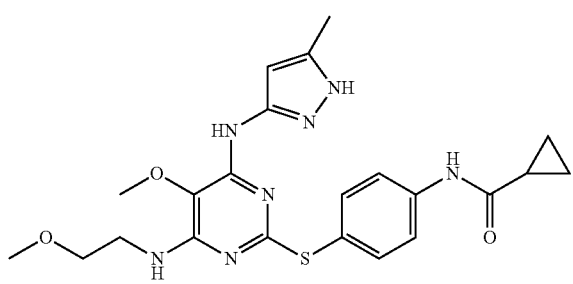 [SMILES: COCCNc1nc(Sc2ccc(NC(=O)C3CC3)cc2)nc(Nc2cc(C)[nH]n2)c1OC]
XXX
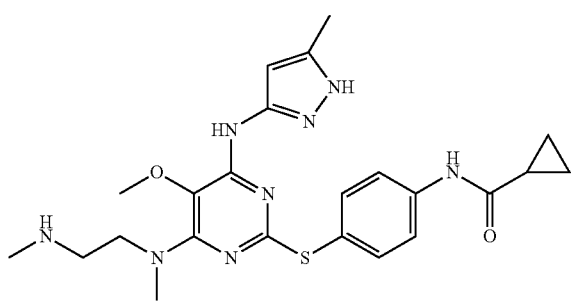 [SMILES: CNCCN(C)c1nc(Sc2ccc(NC(=O)C3CC3)cc2)nc(Nc2cc(C)[nH]n2)c1OC]
Activity XX
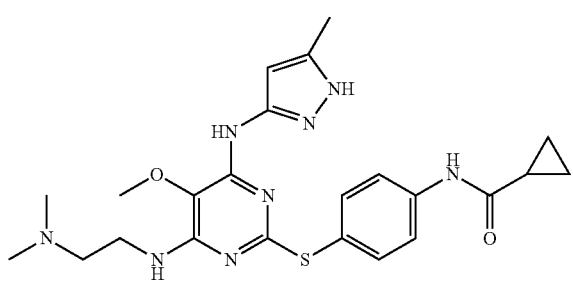 [SMILES: COc1c(NCCN(C)C)nc(Sc2ccc(NC(=O)C3CC3)cc2)nc1Nc1cc(C)[nH]n1]
XX
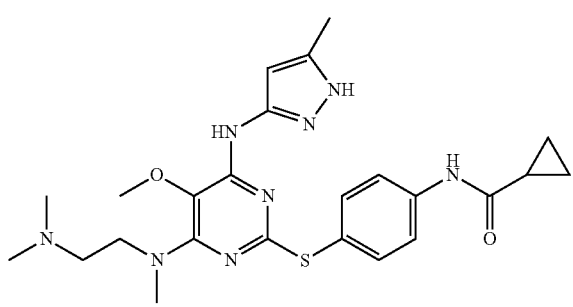 [SMILES: COc1c(Nc2cc(C)[nH]n2)nc(Sc2ccc(NC(=O)C3CC3)cc2)nc1N(C)CCN(C)C]
XX TABLE 1-continued
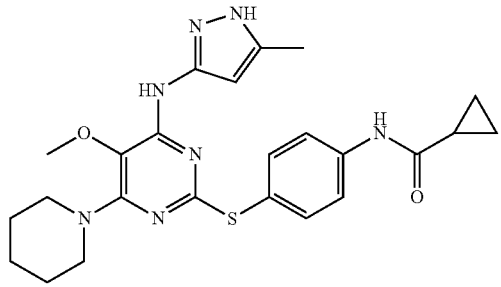 [SMILES: COc1c(Nc2cc(C)[nH]n2)nc(Sc2ccc(NC(=O)C3CC3)cc2)nc1N1CCCCC1] XXX
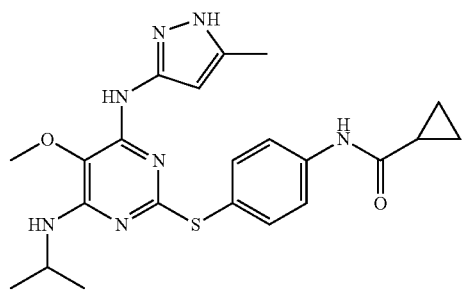 [SMILES: COc1c(Nc2cc(C)[nH]n2)nc(Sc2ccc(NC(=O)C3CC3)cc2)nc1NC(C)C] XXX
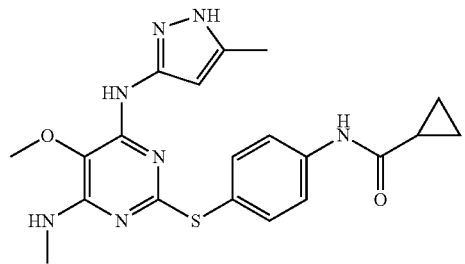 [SMILES: CNc1nc(Sc2ccc(NC(=O)C3CC3)cc2)nc(Nc2cc(C)[nH]n2)c1OC] Activity XXX
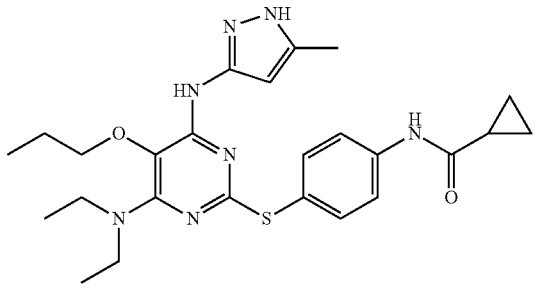 [SMILES: CCCOc1c(Nc2cc(C)[nH]n2)nc(Sc2ccc(NC(=O)C3CC3)cc2)nc1N(CC)CC] XX
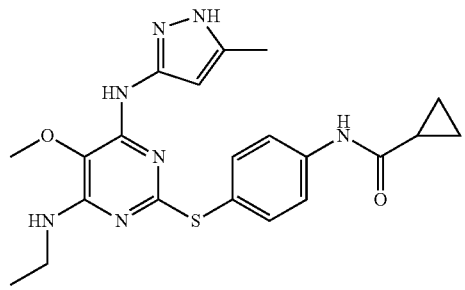 [SMILES: CCNc1nc(Sc2ccc(NC(=O)C3CC3)cc2)nc(Nc2cc(C)[nH]n2)c1OC] XXX TABLE 1-continued
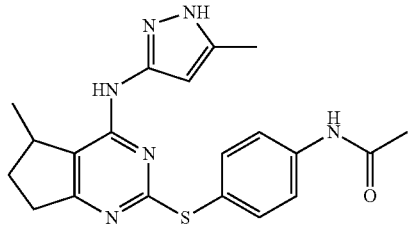 [SMILES: CC(=O)Nc1ccc(Sc2nc3c(c(Nc4cc(C)[nH]n4)n2)C(C)CC3)cc1] XXX
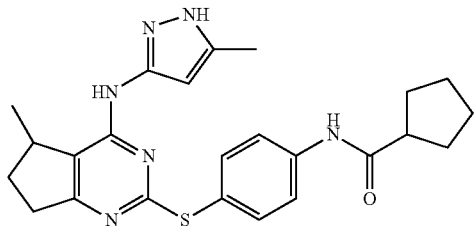 [SMILES: Cc1cc(Nc2nc(Sc3ccc(NC(=O)C4CCCC4)cc3)nc3c2C(C)CC3)n[nH]1] XXX
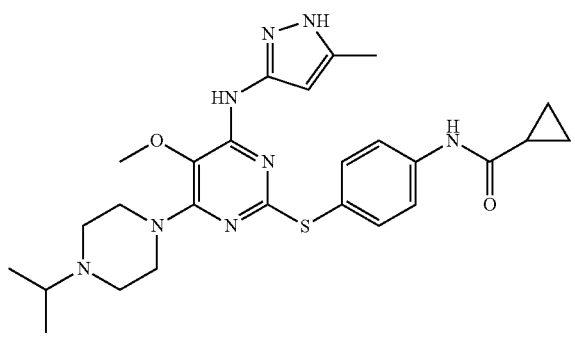 [SMILES: COc1c(Nc2cc(C)[nH]n2)nc(Sc2ccc(NC(=O)C3CC3)cc2)nc1N1CCN(C(C)C)CC1] Activity XXX
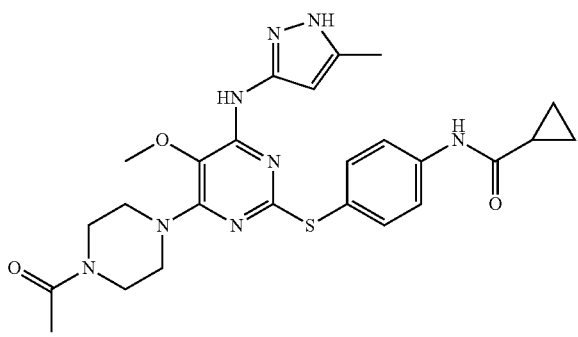 [SMILES: COc1c(Nc2cc(C)[nH]n2)nc(Sc2ccc(NC(=O)C3CC3)cc2)nc1N1CCN(C(C)=O)CC1] XXX
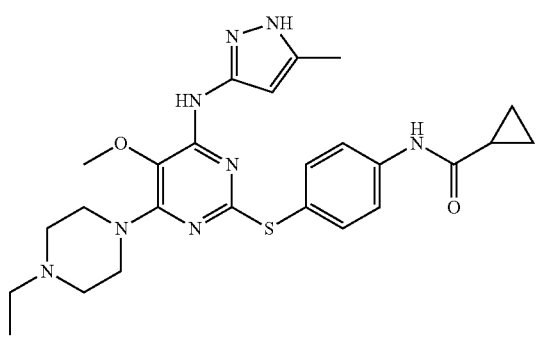 [SMILES: CCN1CCN(c2nc(Sc3ccc(NC(=O)C4CC4)cc3)nc(Nc3cc(C)[nH]n3)c2OC)CC1] XXX TABLE 1-continued
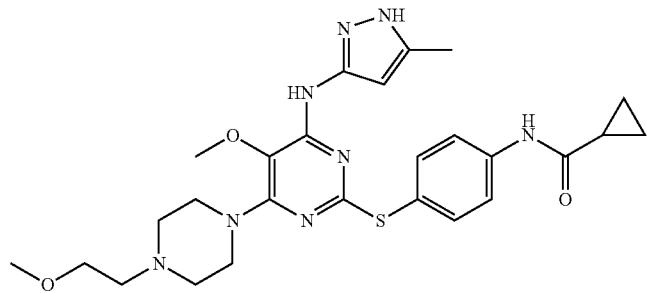 [SMILES: COCCN1CCN(c2nc(Sc3ccc(NC(=O)C4CC4)cc3)nc(Nc3cc(C)[nH]n3)c2OC)CC1]
XXX
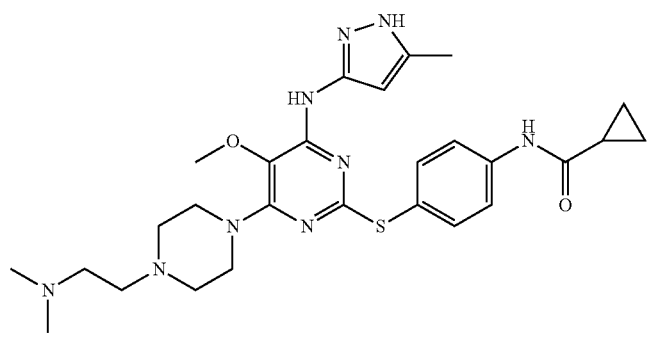 [SMILES: COc1c(Nc2cc(C)[nH]n2)nc(Sc2ccc(NC(=O)C3CC3)cc2)nc1N1CCN(CCN(C)C)CC1]
XXX
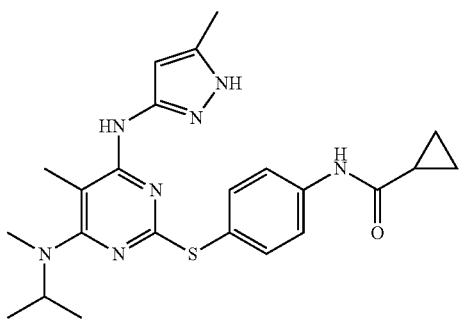
Activity XXX
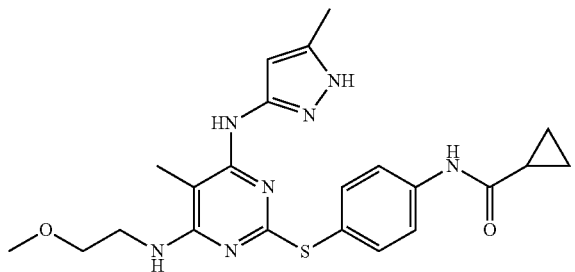 [SMILES: COCCNc1nc(Sc2ccc(NC(=O)C3CC3)cc2)nc(Nc2cc(C)[nH]n2)c1C]
XXX
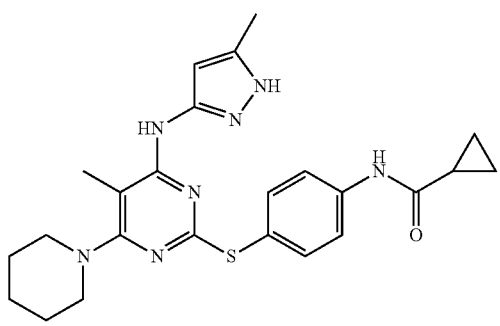 [SMILES: Cc1cc(Nc2nc(Sc3ccc(NC(=O)C4CC4)cc3)nc(N3CCCCC3)c2C)n[nH]1]
XXX TABLE 1-continued
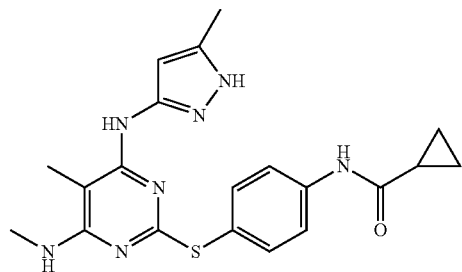 [SMILES: CNc1nc(Sc2ccc(NC(=O)C3CC3)cc2)nc(Nc2cc(C)[nH]n2)c1C] XXX
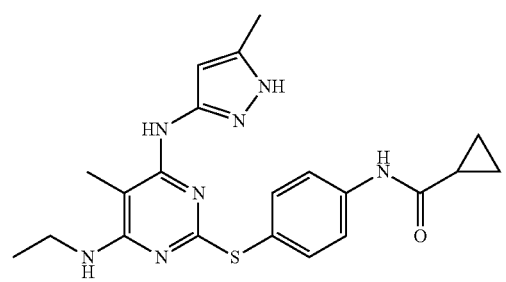 [SMILES: CCNc1nc(Sc2ccc(NC(=O)C3CC3)cc2)nc(Nc2cc(C)[nH]n2)c1C] XXX
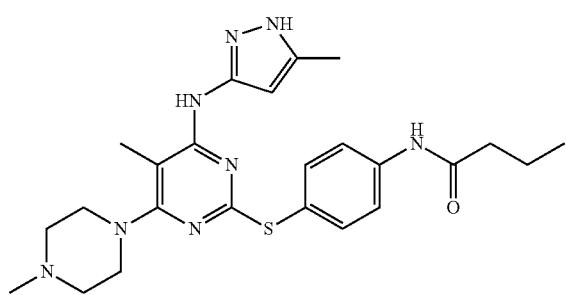 [SMILES: CCCC(=O)Nc1ccc(Sc2nc(Nc3cc(C)[nH]n3)c(C)c(N3CCN(C)CC3)n2)cc1] Activity XXX
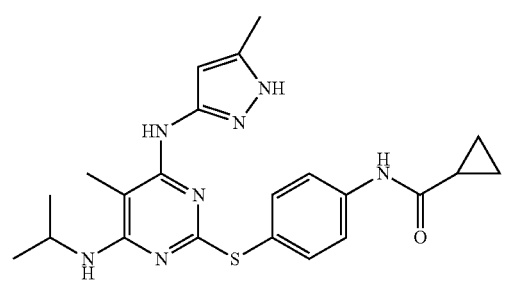 [SMILES: Cc1cc(Nc2nc(Sc3ccc(NC(=O)C4CC4)cc3)nc(NC(C)C)c2C)n[nH]1] XXX
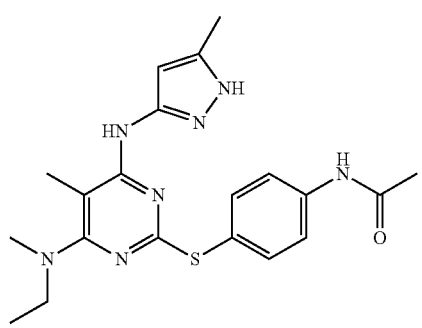 [SMILES: CCN(C)c1nc(Sc2ccc(NC(C)=O)cc2)nc(Nc2cc(C)[nH]n2)c1C] XXX TABLE 1-continued
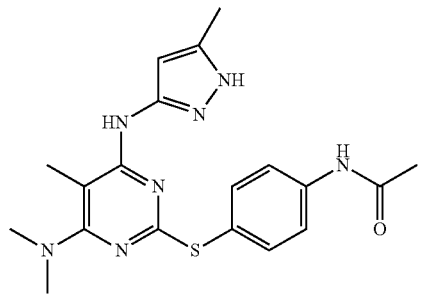 [SMILES: CC(=O)Nc1ccc(Sc2nc(Nc3cc(C)[nH]n3)c(C)c(N(C)C)n2)cc1] XXX
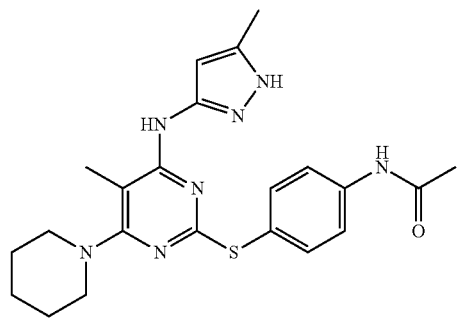 [SMILES: CC(=O)Nc1ccc(Sc2nc(Nc3cc(C)[nH]n3)c(C)c(N3CCCCC3)n2)cc1] XXX
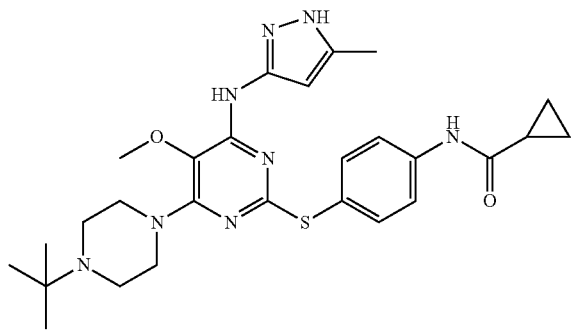 [SMILES: COc1c(Nc2cc(C)[nH]n2)nc(Sc2ccc(NC(=O)C3CC3)cc2)nc1N1CCN(C(C)(C)C)CC1] Activity X
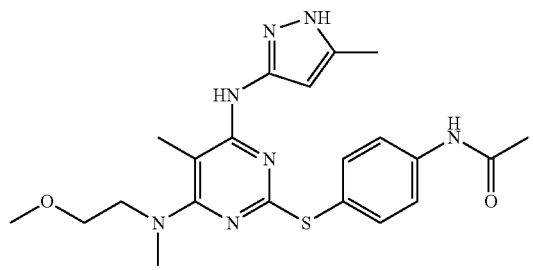 [SMILES: COCCN(C)c1nc(Sc2ccc(NC(C)=O)cc2)nc(Nc2cc(C)[nH]n2)c1C] XXX
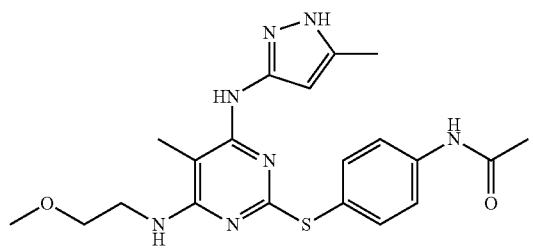 [SMILES: COCCNc1nc(Sc2ccc(NC(C)=O)cc2)nc(Nc2cc(C)[nH]n2)c1C] XXX TABLE 1-continued
| | |
|---|---|
| 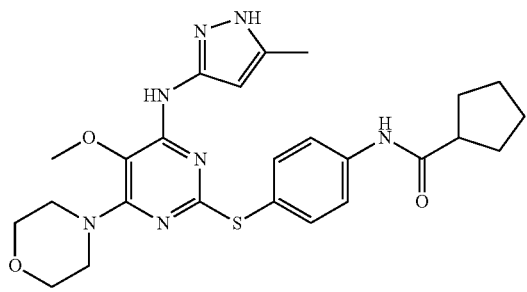 [SMILES: COc1c(Nc2cc(C)[nH]n2)nc(Sc2ccc(NC(=O)C3CCCC3)cc2)nc1N1CCOCC1] | XXX |
| 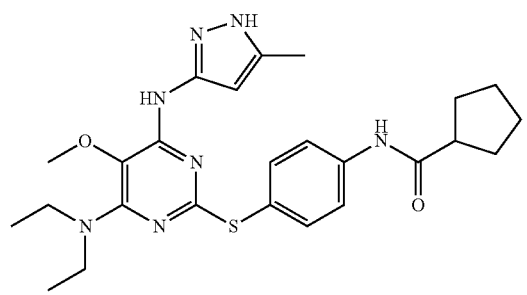 [SMILES: CCN(CC)c1nc(Sc2ccc(NC(=O)C3CCCC3)cc2)nc(Nc2cc(C)[nH]n2)c1OC] | XX |
| 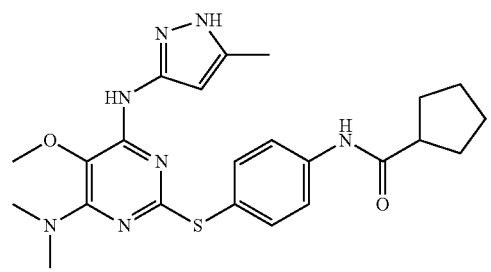 [SMILES: COc1c(Nc2cc(C)[nH]n2)nc(Sc2ccc(NC(=O)C3CCCC3)cc2)nc1N(C)C] | Activity XXX |
| 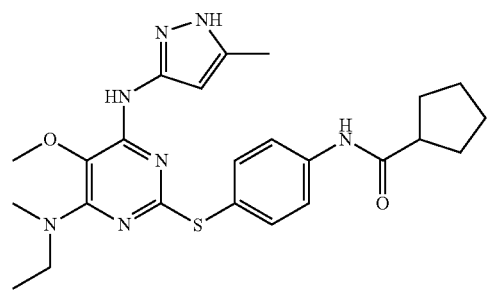 [SMILES: CCN(C)c1nc(Sc2ccc(NC(=O)C3CCCC3)cc2)nc(Nc2cc(C)[nH]n2)c1OC] | XX |
| 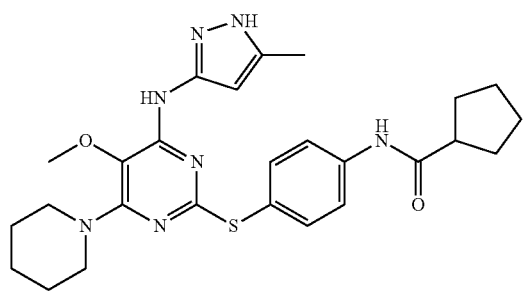 [SMILES: COc1c(Nc2cc(C)[nH]n2)nc(Sc2ccc(NC(=O)C3CCCC3)cc2)nc1N1CCCCC1] | XX |

TABLE 1-continued
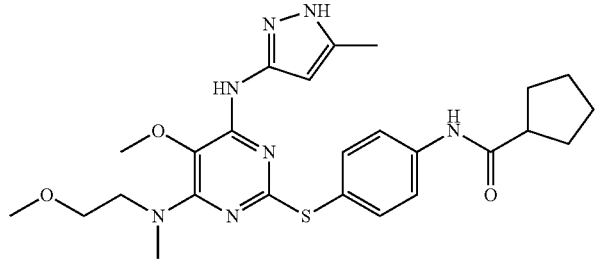 [SMILES: COCCN(C)c1nc(Sc2ccc(NC(=O)C3CCCC3)cc2)nc(Nc2cc(C)[nH]n2)c1OC]
XX
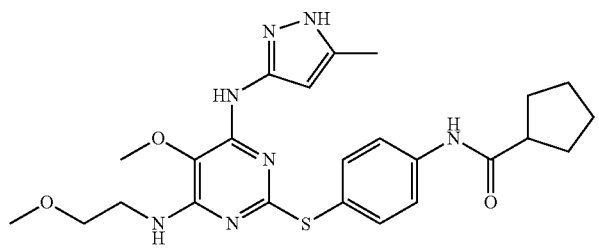 [SMILES: COCCNc1nc(Sc2ccc(NC(=O)C3CCCC3)cc2)nc(Nc2cc(C)[nH]n2)c1OC]
XXX
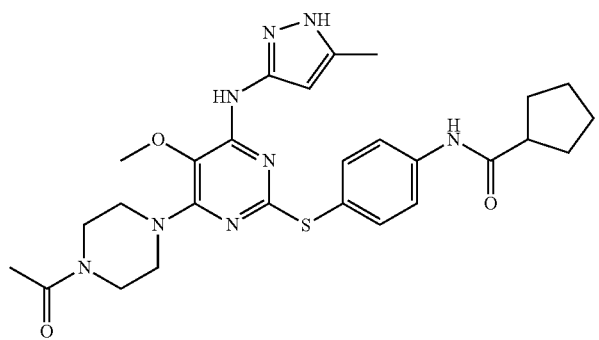 [SMILES: COc1c(Nc2cc(C)[nH]n2)nc(Sc2ccc(NC(=O)C3CCCC3)cc2)nc1N1CCN(C(C)=O)CC1]
Activity XXX
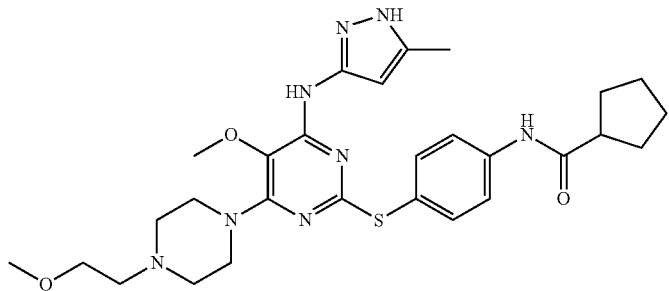 [SMILES: COCCN1CCN(c2nc(Sc3ccc(NC(=O)C4CCCC4)cc3)nc(Nc3cc(C)[nH]n3)c2OC)CC1]
XXX
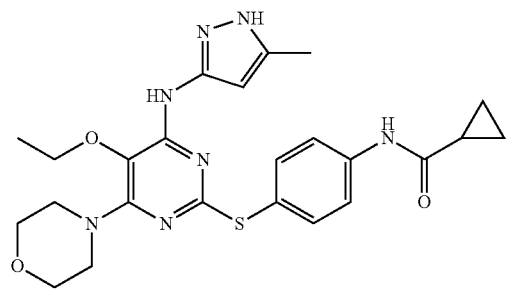 [SMILES: CCOc1c(Nc2cc(C)[nH]n2)nc(Sc2ccc(NC(=O)C3CC3)cc2)nc1N1CCOCC1]
XXX TABLE 1-continued
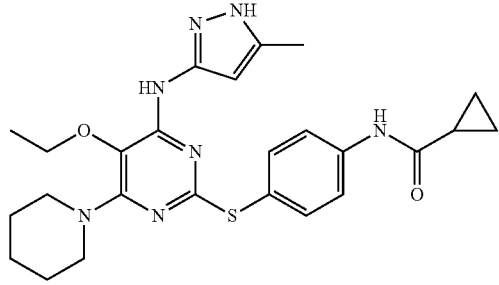 [SMILES: CCOc1c(Nc2cc(C)[nH]n2)nc(Sc2ccc(NC(=O)C3CC3)cc2)nc1N1CCCCC1]
XX
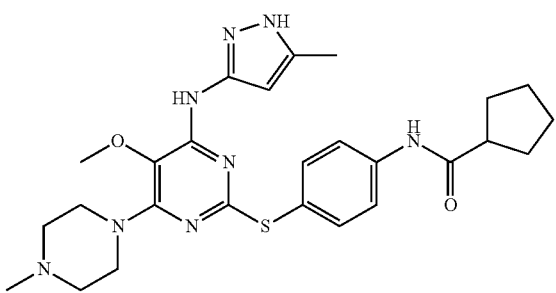 [SMILES: COc1c(Nc2cc(C)[nH]n2)nc(Sc2ccc(NC(=O)C3CCCC3)cc2)nc1N1CCN(C)CC1]
XXX
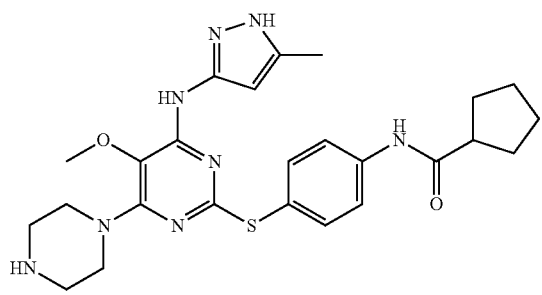 [SMILES: COc1c(Nc2cc(C)[nH]n2)nc(Sc2ccc(NC(=O)C3CCCC3)cc2)nc1N1CCNCC1]
Activity XXX
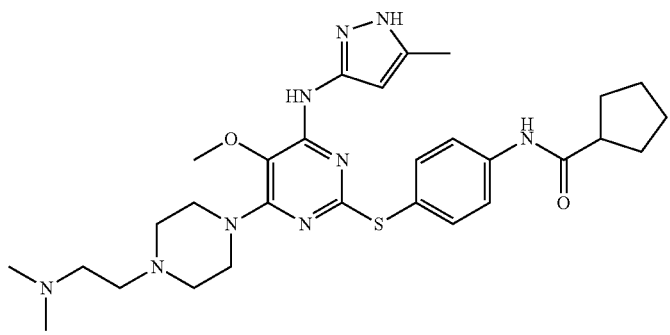 [SMILES: COc1c(Nc2cc(C)[nH]n2)nc(Sc2ccc(NC(=O)C3CCCC3)cc2)nc1N1CCN(CCN(C)C)CC1]
XXX
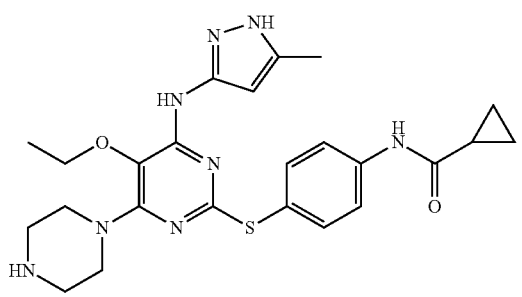 [SMILES: CCOc1c(Nc2cc(C)[nH]n2)nc(Sc2ccc(NC(=O)C3CC3)cc2)nc1N1CCNCC1]
XXX TABLE 1-continued
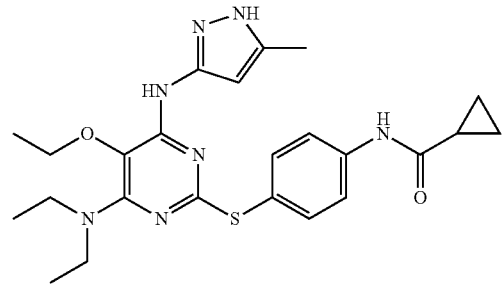 [SMILES: CCOc1c(Nc2cc(C)[nH]n2)nc(Sc2ccc(NC(=O)C3CC3)cc2)nc1N(CC)CC] XXX
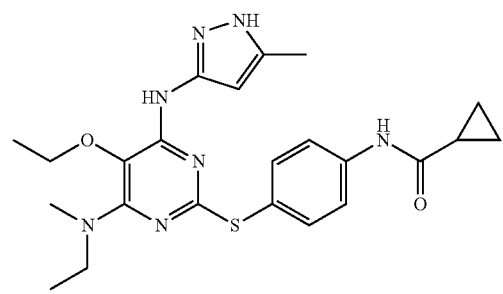 [SMILES: CCOc1c(Nc2cc(C)[nH]n2)nc(Sc2ccc(NC(=O)C3CC3)cc2)nc1N(C)CC] XXX
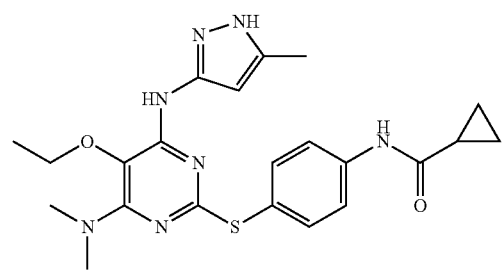 [SMILES: CCOc1c(Nc2cc(C)[nH]n2)nc(Sc2ccc(NC(=O)C3CC3)cc2)nc1N(C)C] Activity XXX
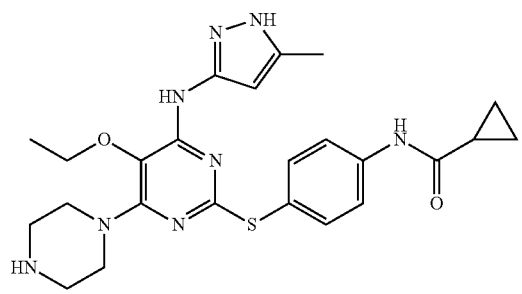 [SMILES: CCOc1c(Nc2cc(C)[nH]n2)nc(Sc2ccc(NC(=O)C3CC3)cc2)nc1N1CCNCC1] XX
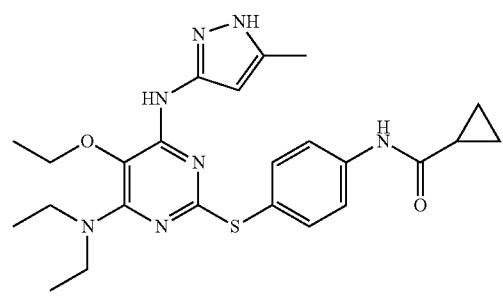 [SMILES: CCOc1c(Nc2cc(C)[nH]n2)nc(Sc2ccc(NC(=O)C3CC3)cc2)nc1N(CC)CC] XX TABLE 1-continued
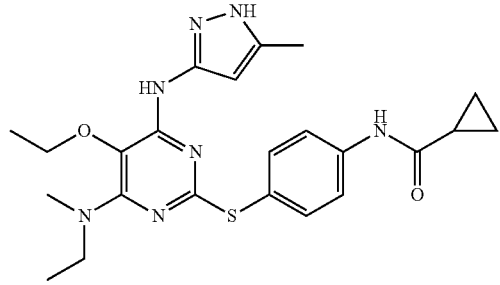 [SMILES: CCOc1c(Nc2cc(C)[nH]n2)nc(Sc2ccc(NC(=O)C3CC3)cc2)nc1N(C)CC] XX
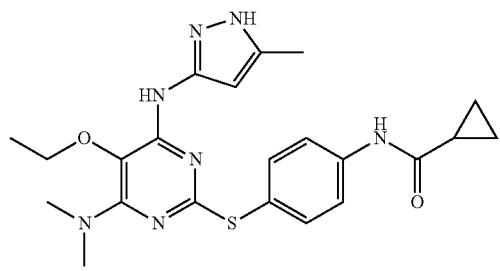 XX
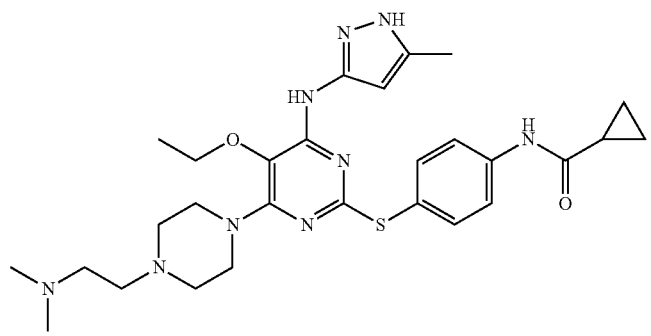 [SMILES: CCOc1c(Nc2cc(C)[nH]n2)nc(Sc2ccc(NC(=O)C3CC3)cc2)nc1N1CCN(CCN(C)C)CC1] Activity XX
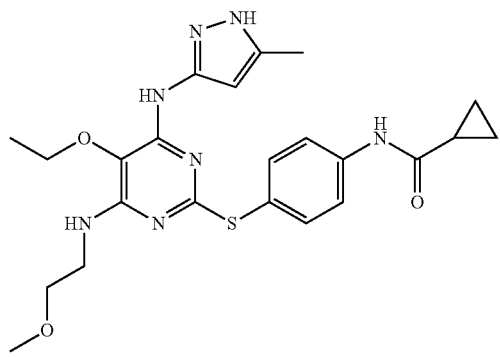 [SMILES: CCOc1c(NCCOC)nc(Sc2ccc(NC(=O)C3CC3)cc2)nc1Nc1cc(C)[nH]n1] XX
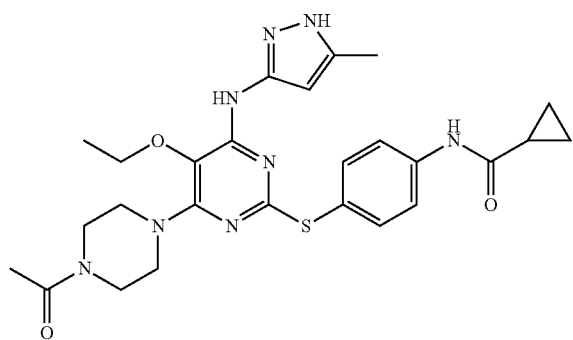 [SMILES: CCOc1c(Nc2cc(C)[nH]n2)nc(Sc2ccc(NC(=O)C3CC3)cc2)nc1N1CCN(C(C)=O)CC1] XX TABLE 1-continued
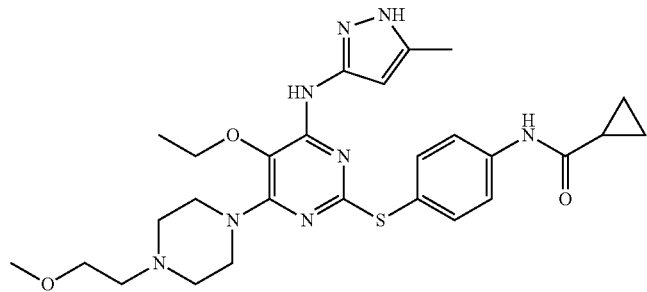 [SMILES: CCOc1c(Nc2cc(C)[nH]n2)nc(Sc2ccc(NC(=O)C3CC3)cc2)nc1N1CCN(CCOC)CC1] XX
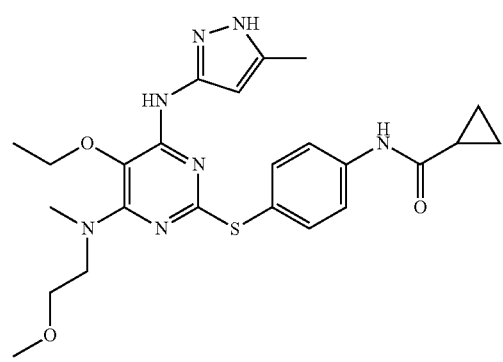 [SMILES: CCOc1c(Nc2cc(C)[nH]n2)nc(Sc2ccc(NC(=O)C3CC3)cc2)nc1N(C)CCOC] XX
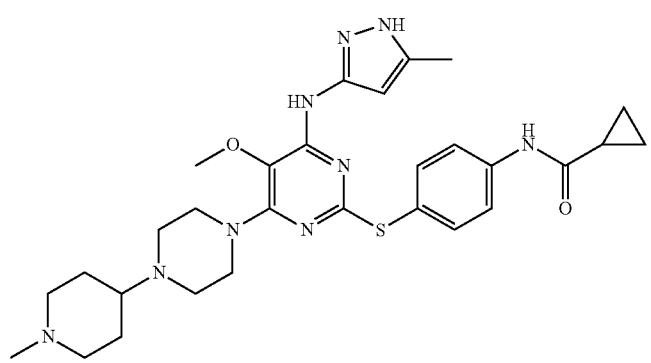 [SMILES: COc1c(Nc2cc(C)[nH]n2)nc(Sc2ccc(NC(=O)C3CC3)cc2)nc1N1CCN(C2CCN(C)CC2)CC1] Activity XXX
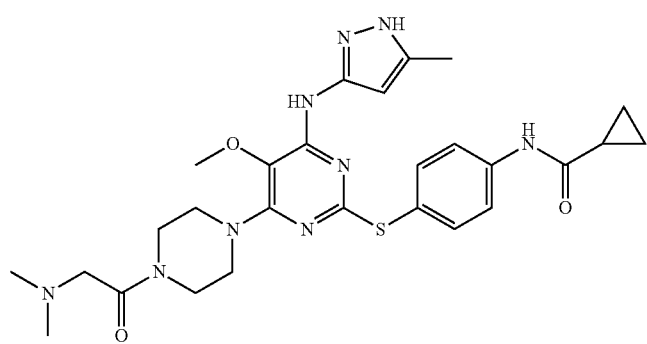 [SMILES: COc1c(Nc2cc(C)[nH]n2)nc(Sc2ccc(NC(=O)C3CC3)cc2)nc1N1CCN(C(=O)CN(C)C)CC1] XXX TABLE 1-continued
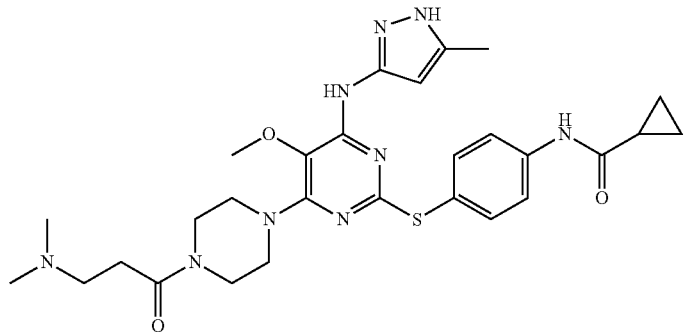 [SMILES: COc1c(Nc2cc(C)[nH]n2)nc(Sc2ccc(NC(=O)C3CC3)cc2)nc1N1CCN(C(=O)CCN(C)C)CC1] XXX
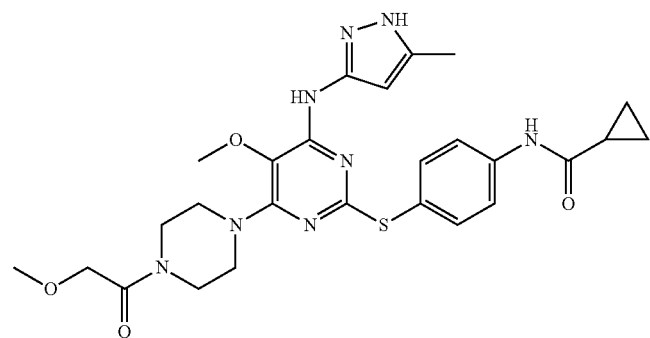 [SMILES: COCC(=O)N1CCN(c2nc(Sc3ccc(NC(=O)C4CC4)cc3)nc(Nc3cc(C)[nH]n3)c2OC)CC1] XXX
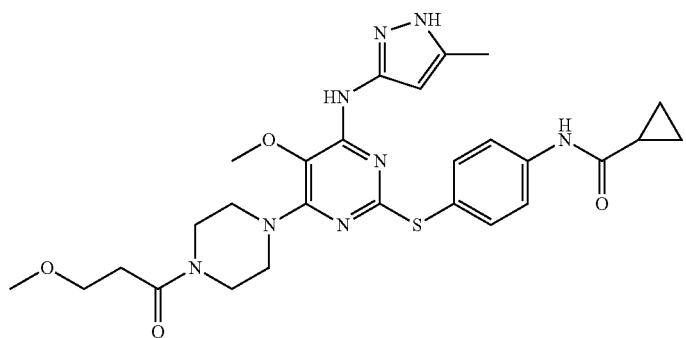 [SMILES: COCCC(=O)N1CCN(c2nc(Sc3ccc(NC(=O)C4CC4)cc3)nc(Nc3cc(C)[nH]n3)c2OC)CC1] XXX
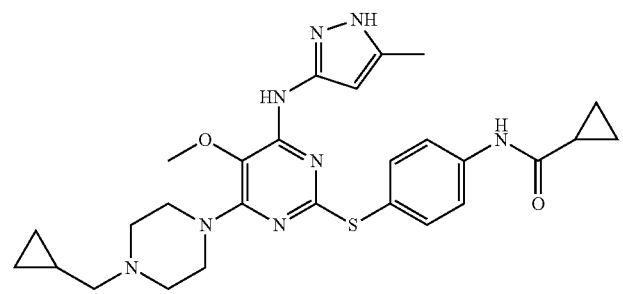 [SMILES: COc1c(Nc2cc(C)[nH]n2)nc(Sc2ccc(NC(=O)C3CC3)cc2)nc1N1CCN(CC2CC2)CC1] Activity XXX
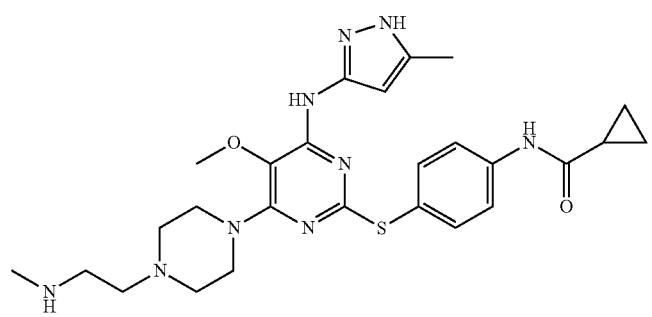 [SMILES: CNCCN1CCN(c2nc(Sc3ccc(NC(=O)C4CC4)cc3)nc(Nc3cc(C)[nH]n3)c2OC)CC1] XXX TABLE 1-continued
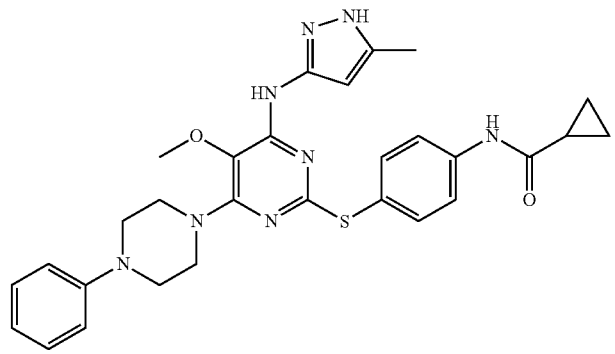 [SMILES: COc1c(Nc2cc(C)[nH]n2)nc(Sc2ccc(NC(=O)C3CC3)cc2)nc1N1CCN(c2ccccc2)CC1] XX
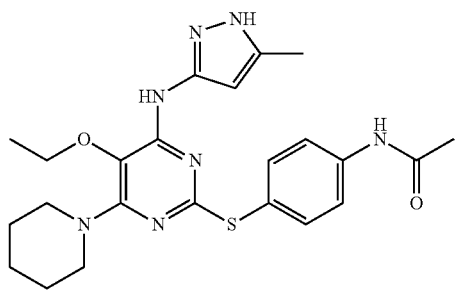 [SMILES: CCOc1c(Nc2cc(C)[nH]n2)nc(Sc2ccc(NC(C)=O)cc2)nc1N1CCCCC1] XX
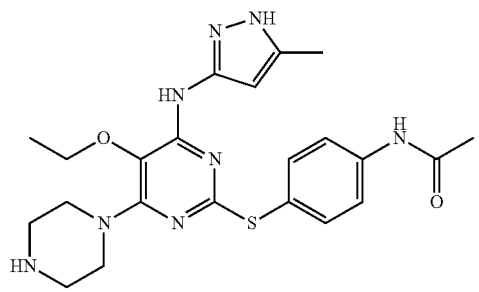 [SMILES: CCOc1c(Nc2cc(C)[nH]n2)nc(Sc2ccc(NC(C)=O)cc2)nc1N1CCNCC1] XX
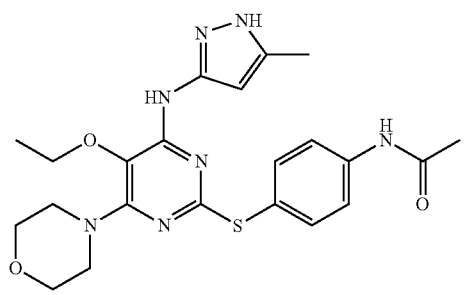 [SMILES: CCOc1c(Nc2cc(C)[nH]n2)nc(Sc2ccc(NC(C)=O)cc2)nc1N1CCOCC1] Activity XX
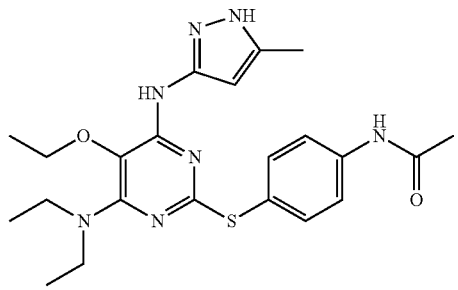 [SMILES: CCOc1c(Nc2cc(C)[nH]n2)nc(Sc2ccc(NC(C)=O)cc2)nc1N(CC)CC] XX TABLE 1-continued
| | |
|---|---|
| 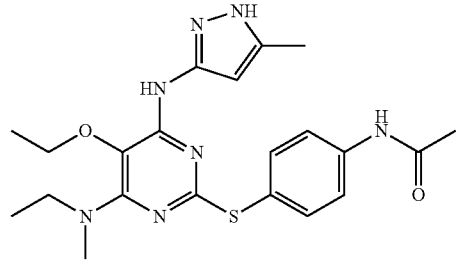 [SMILES: CCOc1c(Nc2cc(C)[nH]n2)nc(Sc2ccc(NC(C)=O)cc2)nc1N(C)CC] | XX |
| 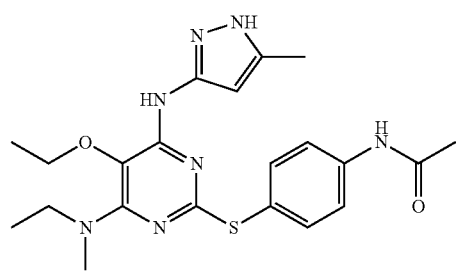 [SMILES: CCOc1c(Nc2cc(C)[nH]n2)nc(Sc2ccc(NC(C)=O)cc2)nc1N(C)CC] | XX |
| 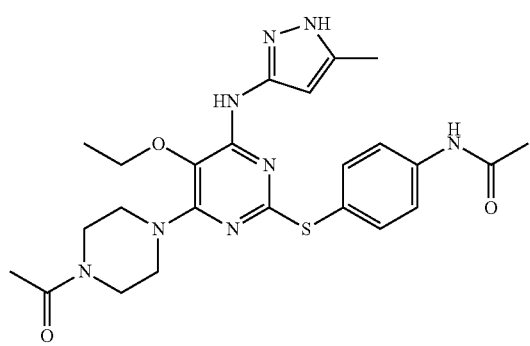 [SMILES: CCOc1c(Nc2cc(C)[nH]n2)nc(Sc2ccc(NC(C)=O)cc2)nc1N1CCN(C(C)=O)CC1] | XX |
| 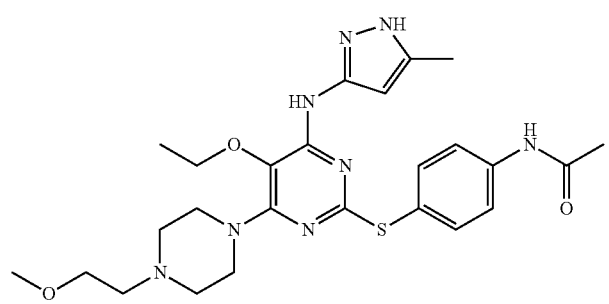 [SMILES: CCOc1c(Nc2cc(C)[nH]n2)nc(Sc2ccc(NC(C)=O)cc2)nc1N1CCN(CCOC)CC1] | Activity XX |
| 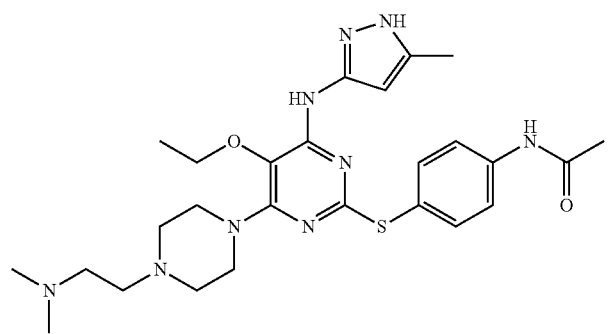 [SMILES: CCOc1c(Nc2cc(C)[nH]n2)nc(Sc2ccc(NC(C)=O)cc2)nc1N1CCN(CCN(C)C)CC1] | XX |

TABLE 1-continued
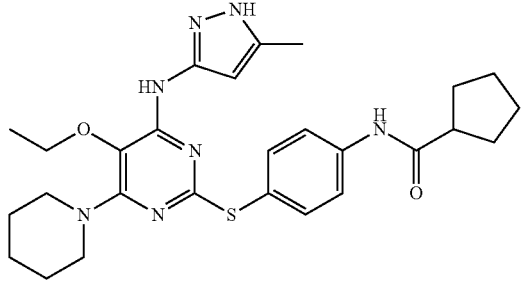 [SMILES: CCOc1c(Nc2cc(C)[nH]n2)nc(Sc2ccc(NC(=O)C3CCCC3)cc2)nc1N1CCCCC1] XX
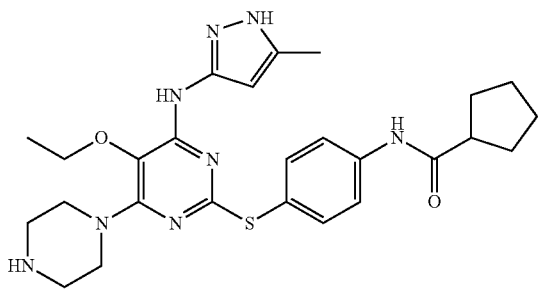 [SMILES: CCOc1c(Nc2cc(C)[nH]n2)nc(Sc2ccc(NC(=O)C3CCCC3)cc2)nc1N1CCNCC1] XX
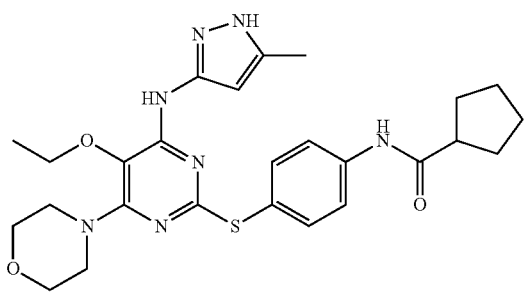 [SMILES: CCOc1c(Nc2cc(C)[nH]n2)nc(Sc2ccc(NC(=O)C3CCCC3)cc2)nc1N1CCOCC1] XX
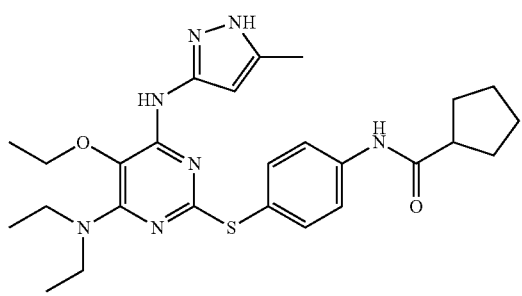 [SMILES: CCOc1c(Nc2cc(C)[nH]n2)nc(Sc2ccc(NC(=O)C3CCCC3)cc2)nc1N(CC)CC] Activity X
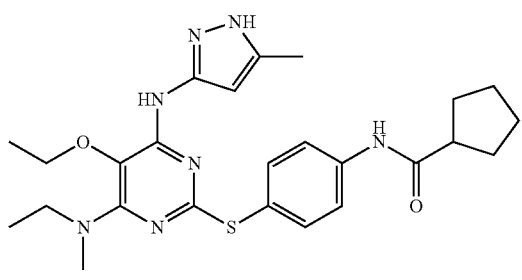 [SMILES: CCOc1c(Nc2cc(C)[nH]n2)nc(Sc2ccc(NC(=O)C3CCCC3)cc2)nc1N(C)CC] XX TABLE 1-continued
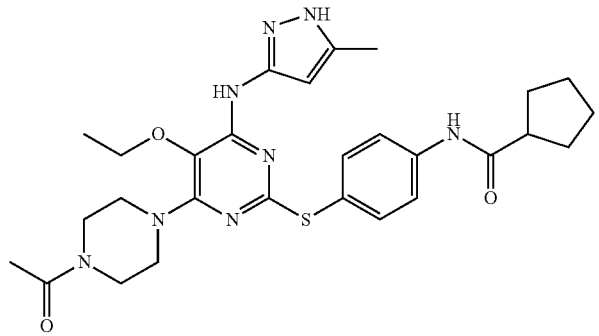 [SMILES: CCOc1c(Nc2cc(C)[nH]n2)nc(Sc2ccc(NC(=O)C3CCCC3)cc2)nc1N1CCN(C(C)=O)CC1] XX
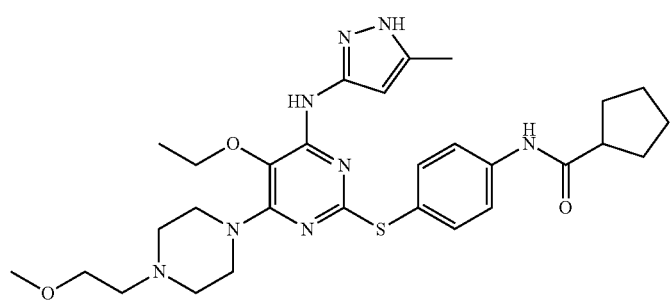 [SMILES: CCOc1c(Nc2cc(C)[nH]n2)nc(Sc2ccc(NC(=O)C3CCCC3)cc2)nc1N1CCN(CCOC)CC1] XX
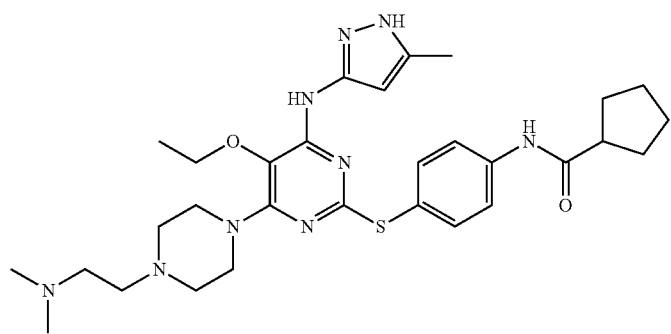 [SMILES: CCOc1c(Nc2cc(C)[nH]n2)nc(Sc2ccc(NC(=O)C3CCCC3)cc2)nc1N1CCN(CCN(C)C)CC1] XX
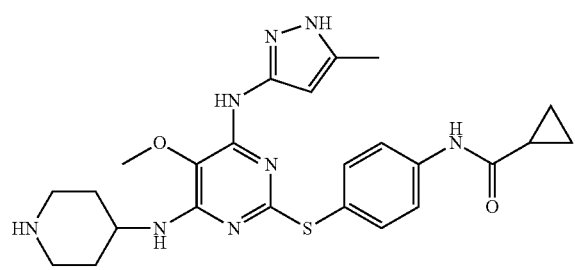 [SMILES: COc1c(Nc2cc(C)[nH]n2)nc(Sc2ccc(NC(=O)C3CC3)cc2)nc1NC1CCNCC1] Activity XX
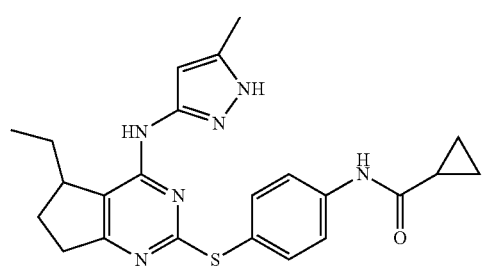 [SMILES: CCC1CCc2nc(Sc3ccc(NC(=O)C4CC4)cc3)nc(Nc3cc(C)[nH]n3)c21] XXX TABLE 1-continued
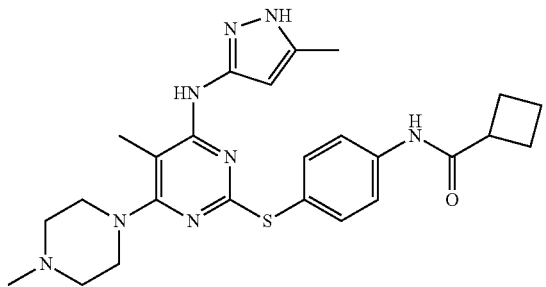 [SMILES: Cc1cc(Nc2nc(Sc3ccc(NC(=O)C4CCC4)cc3)nc(N3CCN(C)CC3)c2C)n[nH]1] XXX
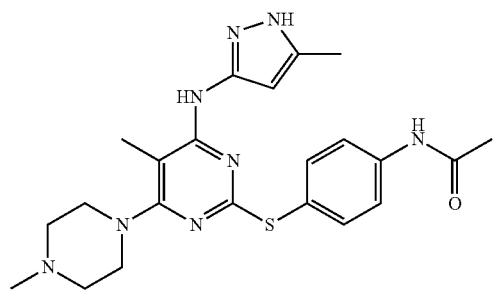 [SMILES: CC(=O)Nc1ccc(Sc2nc(Nc3cc(C)[nH]n3)c(C)c(N3CCN(C)CC3)n2)cc1] XXX
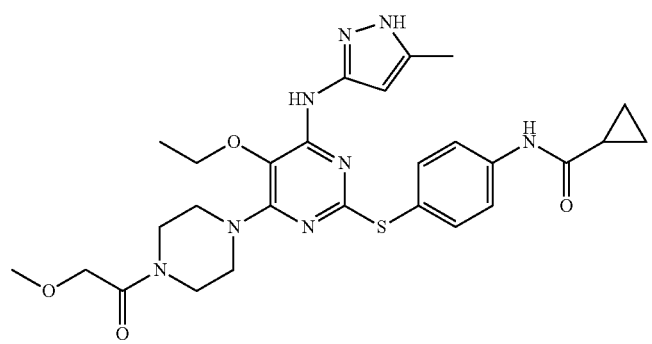 [SMILES: CCOc1c(Nc2cc(C)[nH]n2)nc(Sc2ccc(NC(=O)C3CC3)cc2)nc1N1CCN(C(=O)COC)CC1] XX
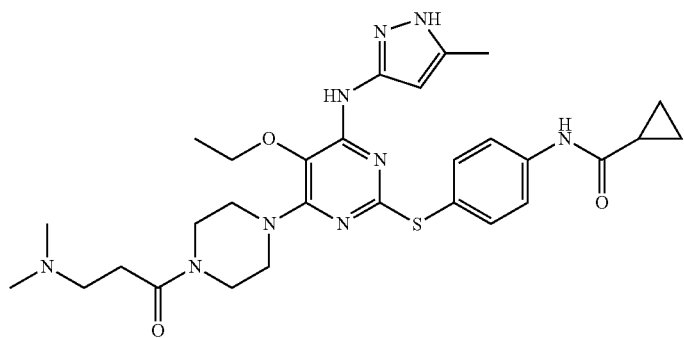 [SMILES: CCOc1c(Nc2cc(C)[nH]n2)nc(Sc2ccc(NC(=O)C3CC3)cc2)nc1N1CCN(C(=O)CCN(C)C)CC1] Activity XX
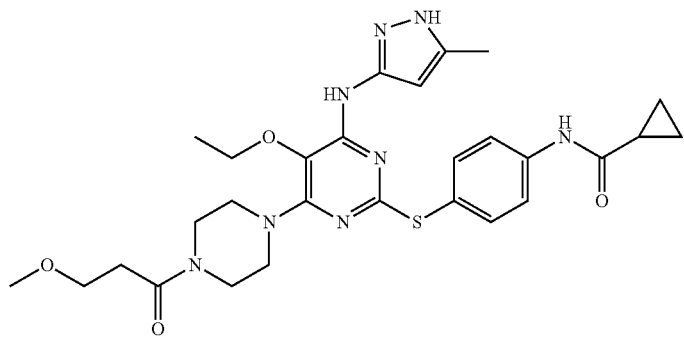 [SMILES: CCOc1c(Nc2cc(C)[nH]n2)nc(Sc2ccc(NC(=O)C3CC3)cc2)nc1N1CCN(C(=O)CCOC)CC1] XX TABLE 1-continued
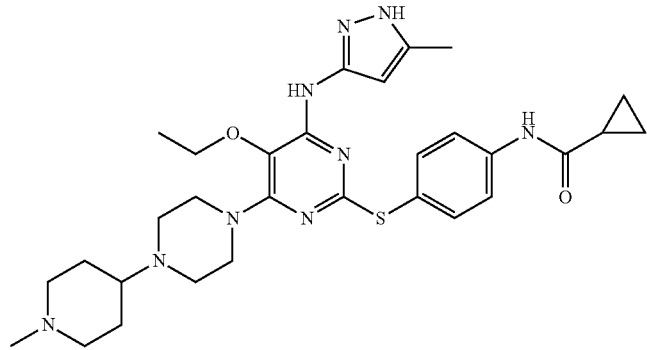 [SMILES: CCOc1c(Nc2cc(C)[nH]n2)nc(Sc2ccc(NC(=O)C3CC3)cc2)nc1N1CCN(C2CCN(C)CC2)CC1] XX
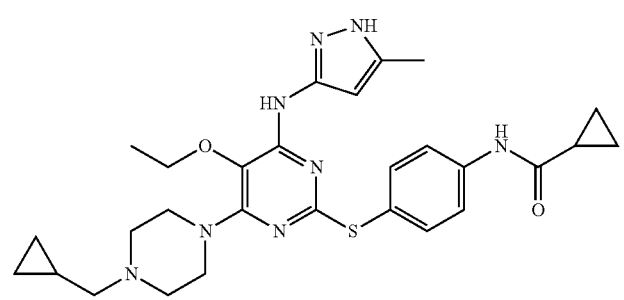 [SMILES: CCOc1c(Nc2cc(C)[nH]n2)nc(Sc2ccc(NC(=O)C3CC3)cc2)nc1N1CCN(CC2CC2)CC1] XX
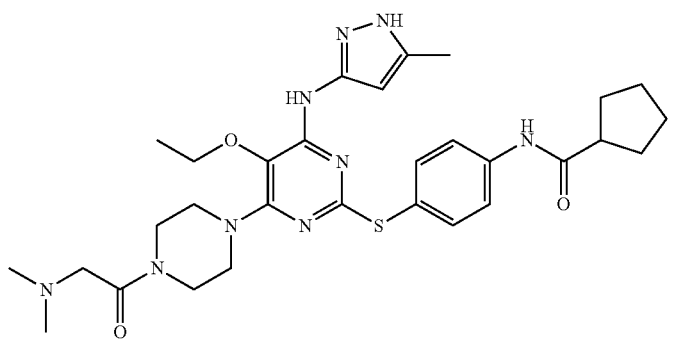 [SMILES: CCOc1c(Nc2cc(C)[nH]n2)nc(Sc2ccc(NC(=O)C3CCCC3)cc2)nc1N1CCN(C(=O)CN(C)C)CC1] Activity XX
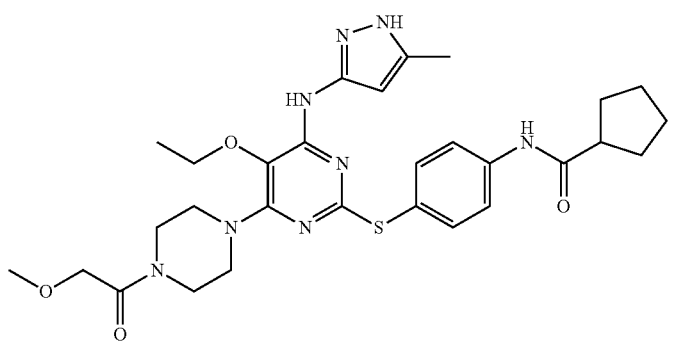 [SMILES: CCOc1c(Nc2cc(C)[nH]n2)nc(Sc2ccc(NC(=O)C3CCCC3)cc2)nc1N1CCN(C(=O)COC)CC1] XX TABLE 1-continued
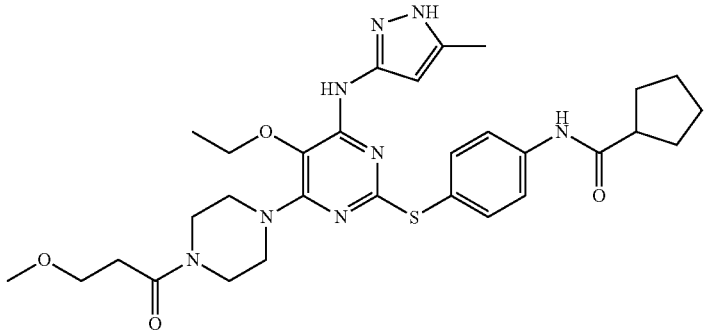 [SMILES: CCOc1c(Nc2cc(C)[nH]n2)nc(Sc2ccc(NC(=O)C3CCCC3)cc2)nc1N1CCN(C(=O)CCOC)CC1] XX
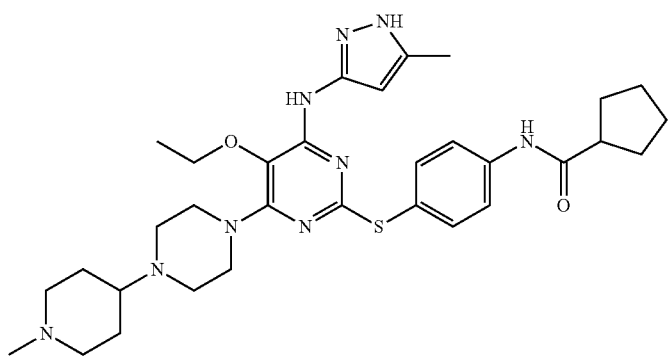 [SMILES: CCOc1c(Nc2cc(C)[nH]n2)nc(Sc2ccc(NC(=O)C3CCCC3)cc2)nc1N1CCN(C2CCN(C)CC2)CC1] XX
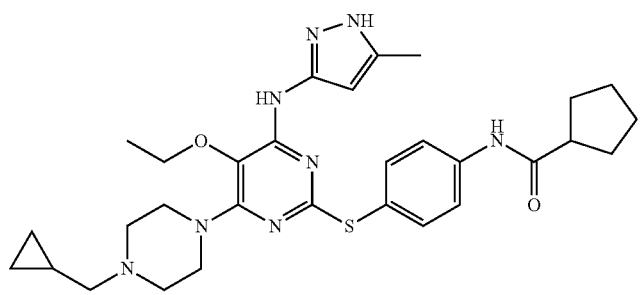 [SMILES: CCOc1c(Nc2cc(C)[nH]n2)nc(Sc2ccc(NC(=O)C3CCCC3)cc2)nc1N1CCN(CC2CC2)CC1] Activity XX
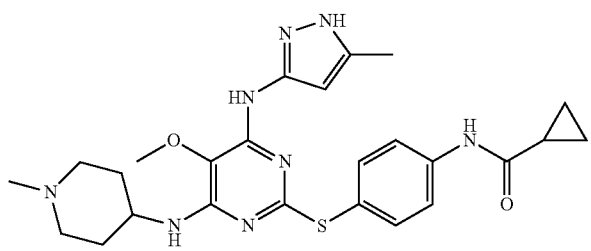 [SMILES: COc1c(Nc2cc(C)[nH]n2)nc(Sc2ccc(NC(=O)C3CC3)cc2)nc1NC1CCN(C)CC1] XX
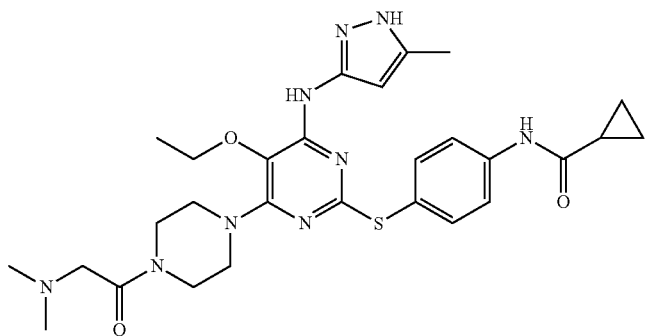 [SMILES: CCOc1c(Nc2cc(C)[nH]n2)nc(Sc2ccc(NC(=O)C3CC3)cc2)nc1N1CCN(C(=O)CN(C)C)CC1] XX TABLE 1-continued
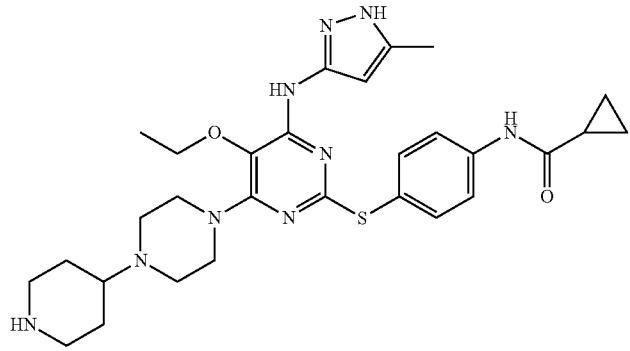 [SMILES: CCOc1c(Nc2cc(C)[nH]n2)nc(Sc2ccc(NC(=O)C3CC3)cc2)nc1N1CCN(C2CCNCC2)CC1] XX
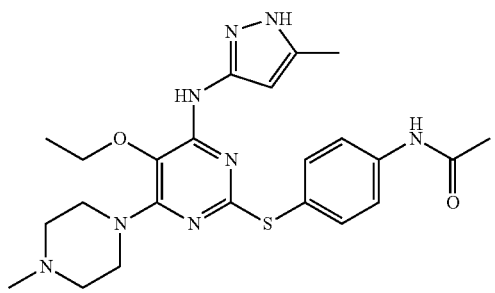 [SMILES: CCOc1c(Nc2cc(C)[nH]n2)nc(Sc2ccc(NC(C)=O)cc2)nc1N1CCN(C)CC1] Activity XX
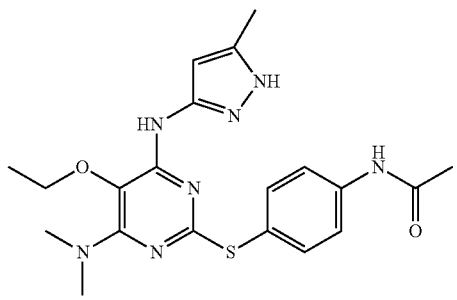 [SMILES: CCOc1c(Nc2cc(C)[nH]n2)nc(Sc2ccc(NC(C)=O)cc2)nc1N(C)C] XX
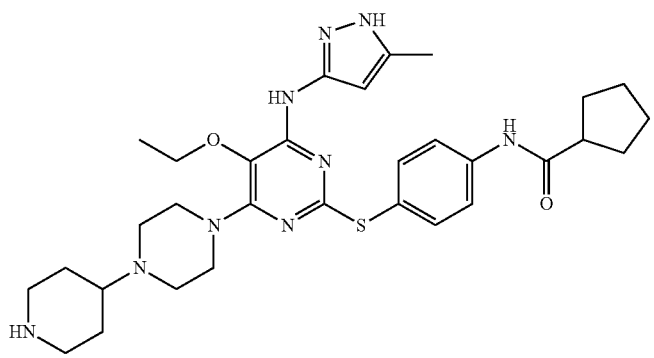 [SMILES: CCOc1c(Nc2cc(C)[nH]n2)nc(Sc2ccc(NC(=O)C3CCCC3)cc2)nc1N1CCN(C2CCNCC2)CC1] XX
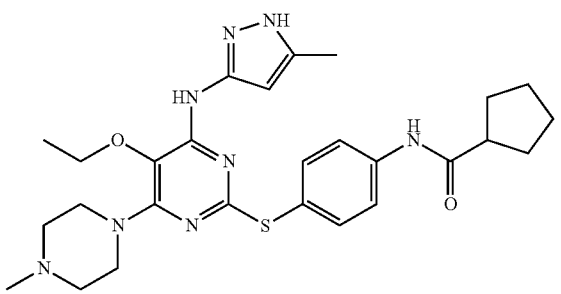 [SMILES: CCOc1c(Nc2cc(C)[nH]n2)nc(Sc2ccc(NC(=O)C3CCCC3)cc2)nc1N1CCN(C)CC1] XX TABLE 1-continued
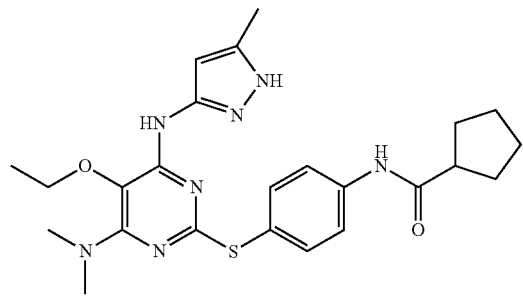 [SMILES: CCOc1c(Nc2cc(C)[nH]n2)nc(Sc2ccc(NC(=O)C3CCCC3)cc2)nc1N(C)C]
Activity XX
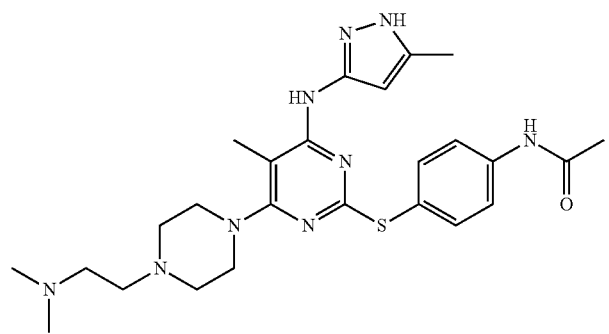 [SMILES: CC(=O)Nc1ccc(Sc2nc(Nc3cc(C)[nH]n3)c(C)c(N3CCN(CCN(C)C)CC3)n2)cc1]
XXX
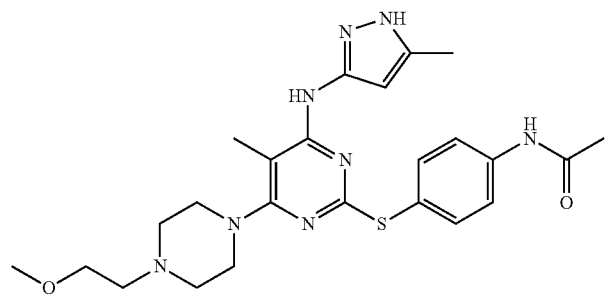 [SMILES: COCCN1CCN(c2nc(Sc3ccc(NC(C)=O)cc3)nc(Nc3cc(C)[nH]n3)c2C)CC1]
XXX
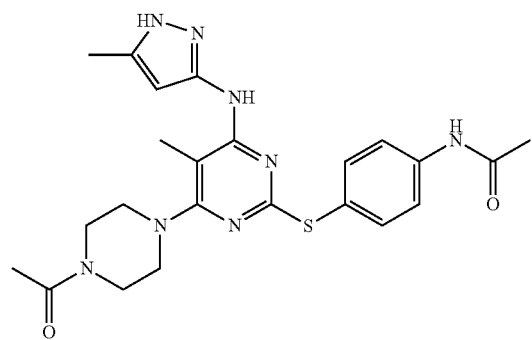 [SMILES: CC(=O)Nc1ccc(Sc2nc(Nc3cc(C)[nH]n3)c(C)c(N3CCN(C(C)=O)CC3)n2)cc1]
XXX
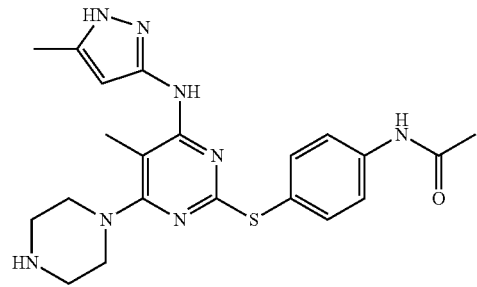 [SMILES: CC(=O)Nc1ccc(Sc2nc(Nc3cc(C)[nH]n3)c(C)c(N3CCNCC3)n2)cc1]
XXX TABLE 1-continued
| | |
|---|---|
| 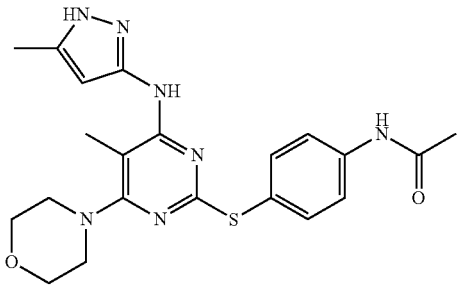 [SMILES: CC(=O)Nc1ccc(Sc2nc(Nc3cc(C)[nH]n3)c(C)c(N3CCOCC3)n2)cc1] | Activity XXX |
| 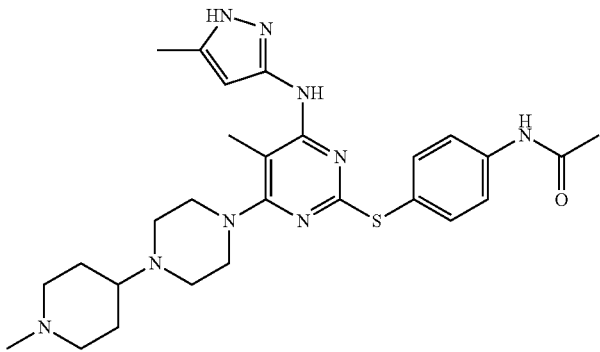 | XXX |
| 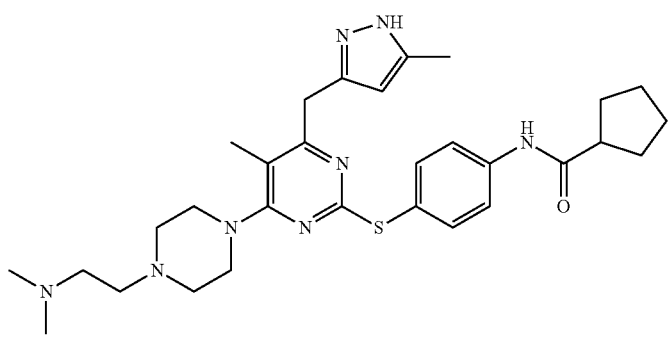 [SMILES: Cc1cc(Cc2nc(Sc3ccc(NC(=O)C4CCCC4)cc3)nc(N3CCN(CCN(C)C)CC3)c2C)n[nH]1] | XXX |
| 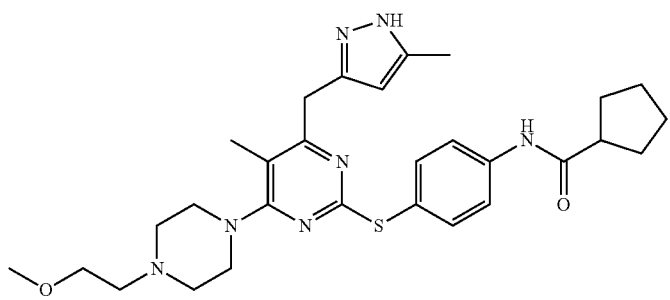 [SMILES: COCCN1CCN(c2nc(Sc3ccc(NC(=O)C4CCCC4)cc3)nc(Cc3cc(C)[nH]n3)c2C)CC1] | XXX |
| 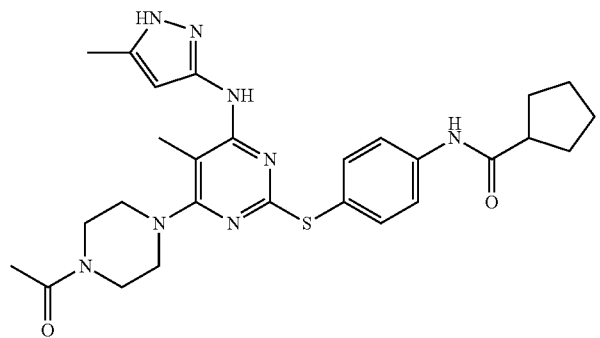 [SMILES: CC(=O)N1CCN(c2nc(Sc3ccc(NC(=O)C4CCCC4)cc3)nc(Nc3cc(C)[nH]n3)c2C)CC1] | XXX |

TABLE 1-continued
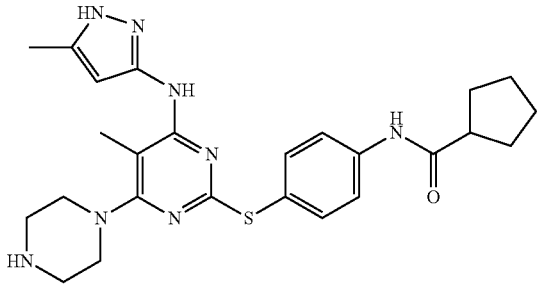 [SMILES: Cc1cc(Nc2nc(Sc3ccc(NC(=O)C4CCCC4)cc3)nc(N3CCNCC3)c2C)n[nH]1] Activity XXX
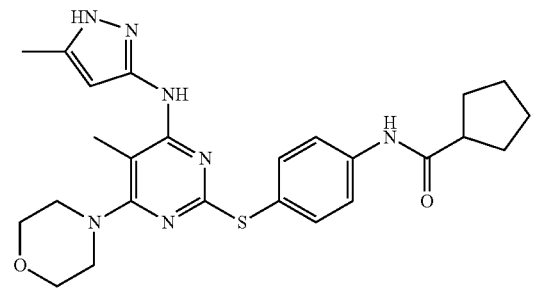 [SMILES: Cc1cc(Nc2nc(Sc3ccc(NC(=O)C4CCCC4)cc3)nc(N3CCOCC3)c2C)n[nH]1] XXX
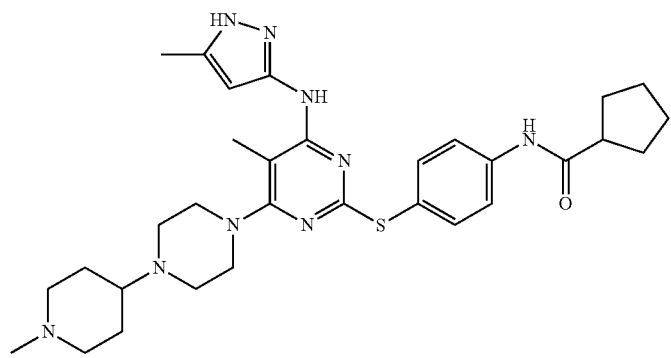 [SMILES: Cc1cc(Nc2nc(Sc3ccc(NC(=O)C4CCCC4)cc3)nc(N3CCN(C4CCN(C)CC4)CC3)c2C)n[nH]1] XXX
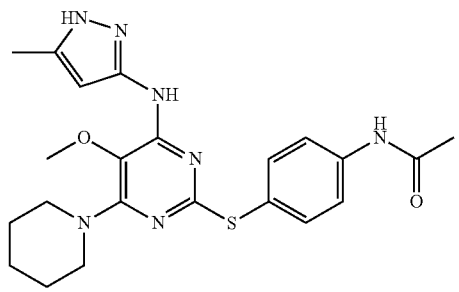 [SMILES: COc1c(Nc2cc(C)[nH]n2)nc(Sc2ccc(NC(C)=O)cc2)nc1N1CCCCC1] XXX
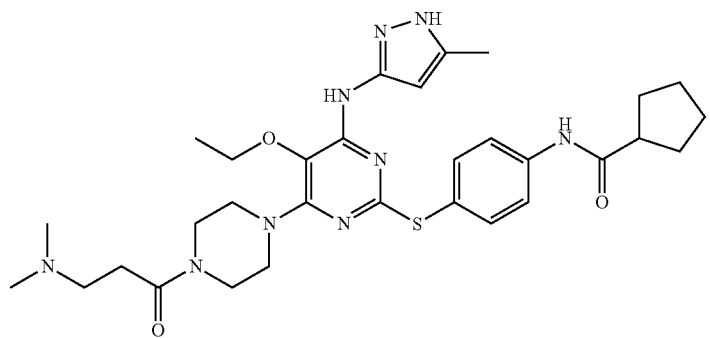 [SMILES: CCOc1c(Nc2cc(C)[nH]n2)nc(Sc2ccc(NC(=O)C3CCCC3)cc2)nc1N1CCN(C(=O)CCN(C)C)CC1] X TABLE 1-continued
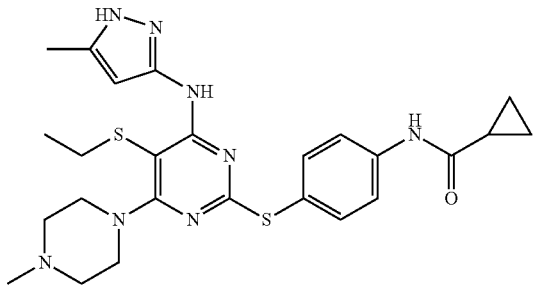 [SMILES: CCSc1c(Nc2cc(C)[nH]n2)nc(Sc2ccc(NC(=O)C3CC3)cc2)nc1N1CCN(C)CC1]
Activity XX
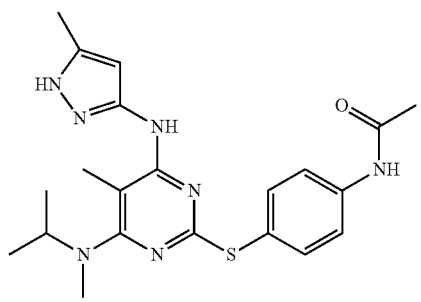 [SMILES: CC(=O)Nc1ccc(Sc2nc(Nc3cc(C)[nH]n3)c(C)c(N(C)C(C)C)n2)cc1]
XXX
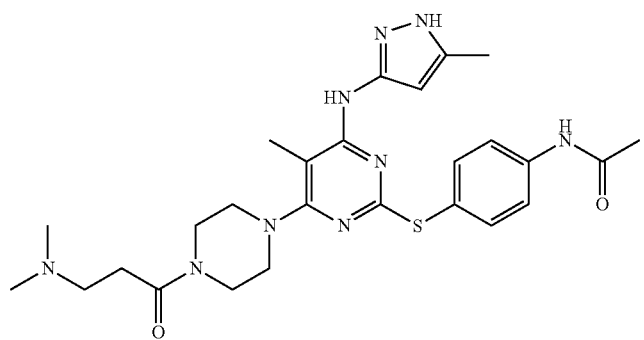 [SMILES: CC(=O)Nc1ccc(Sc2nc(Nc3cc(C)[nH]n3)c(C)c(N3CCN(C(=O)CCN(C)C)CC3)n2)cc1]
XXX
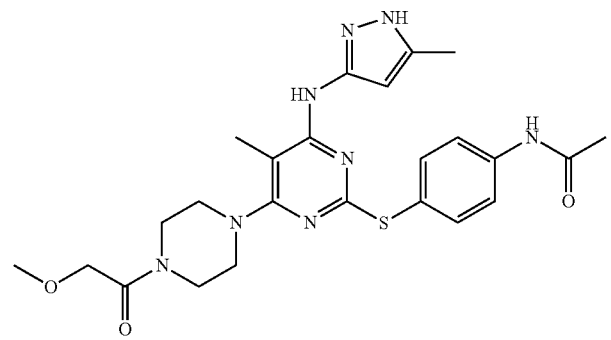
XXX
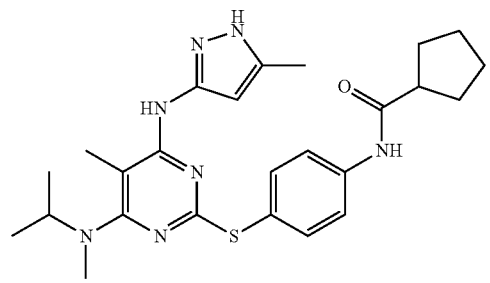 [SMILES: Cc1cc(Nc2nc(Sc3ccc(NC(=O)C4CCCC4)cc3)nc(N(C)C(C)C)c2C)n[nH]1]
XXX TABLE 1-continued
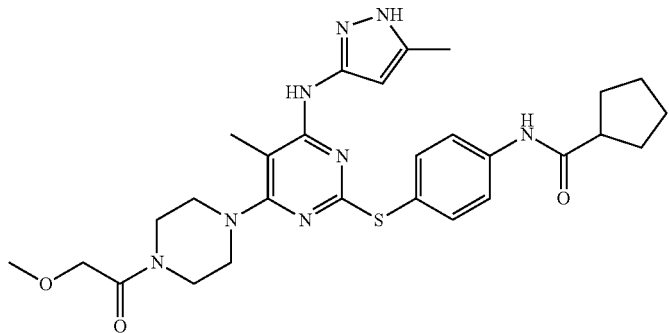 [SMILES: COCC(=O)N1CCN(c2nc(Sc3ccc(NC(=O)C4CCCC4)cc3)nc(Nc3cc(C)[nH]n3)c2C)CC1]
Activity XXX
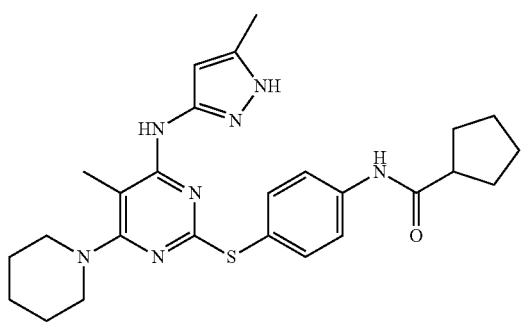 [SMILES: Cc1cc(Nc2nc(Sc3ccc(NC(=O)C4CCCC4)cc3)nc(N3CCCCC3)c2C)n[nH]1]
XXX
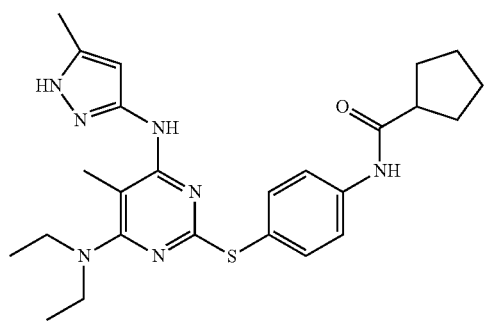 [SMILES: CCN(CC)c1nc(Sc2ccc(NC(=O)C3CCCC3)cc2)nc(Nc2cc(C)[nH]n2)c1C]
XX
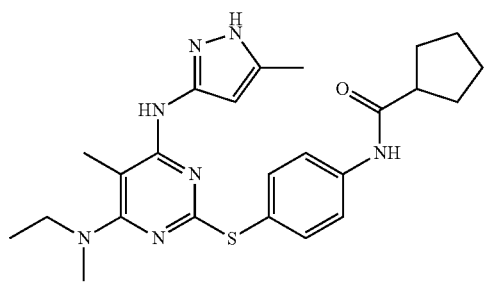 [SMILES: CCN(C)c1nc(Sc2ccc(NC(=O)C3CCCC3)cc2)nc(Nc2cc(C)[nH]n2)c1C]
XXX
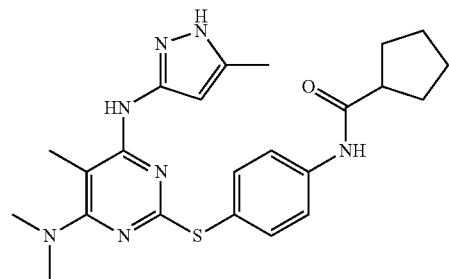 [SMILES: Cc1cc(Nc2nc(Sc3ccc(NC(=O)C4CCCC4)cc3)nc(N(C)C)c2C)n[nH]1]
XXX TABLE 1-continued
| | Activity XX |
|---|---|
| 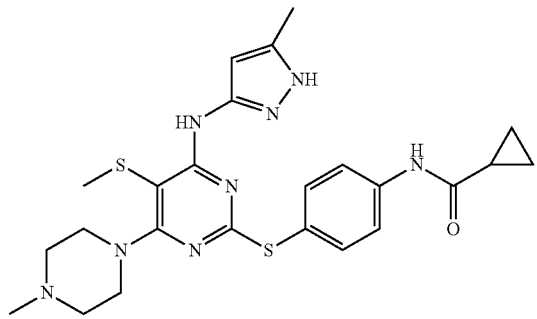 [SMILES: CSc1c(Nc2cc(C)[nH]n2)nc(Sc2ccc(NC(=O)C3CC3)cc2)nc1N1CCN(C)CC1] | |
| 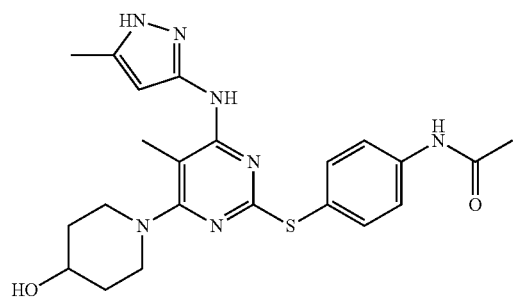 [SMILES: CC(=O)Nc1ccc(Sc2nc(Nc3cc(C)[nH]n3)c(C)c(N3CCC(O)CC3)n2)cc1] | XXX |
| 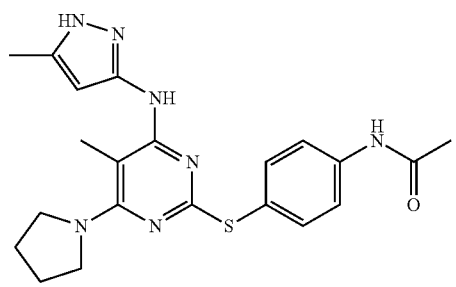 [SMILES: CC(=O)Nc1ccc(Sc2nc(Nc3cc(C)[nH]n3)c(C)c(N3CCCC3)n2)cc1] | XXX |
| 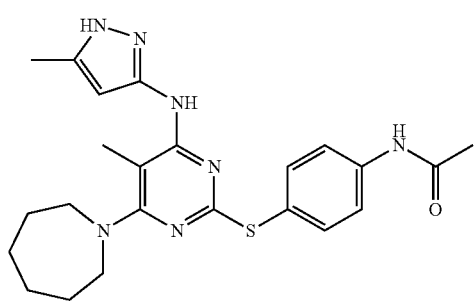 [SMILES: CC(=O)Nc1ccc(Sc2nc(Nc3cc(C)[nH]n3)c(C)c(N3CCCCCC3)n2)cc1] | XXX |
| 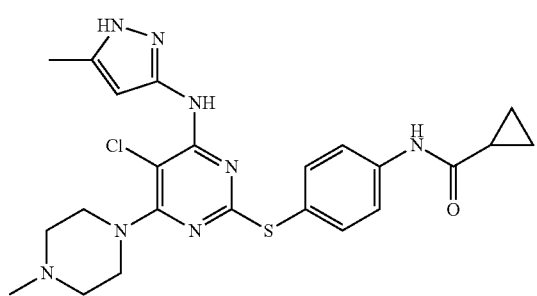 [SMILES: Cc1cc(Nc2nc(Sc3ccc(NC(=O)C4CC4)cc3)nc(N3CCN(C)CC3)c2Cl)n[nH]1] | XX |

TABLE 1-continued
| | |
|---|---|
| 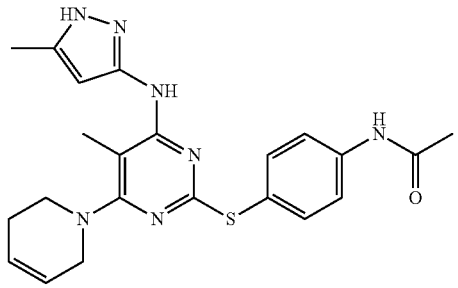 [SMILES: CC(=O)Nc1ccc(Sc2nc(Nc3cc(C)[nH]n3)c(C)c(N3CC=CCC3)n2)cc1] | Activity XXX |
| 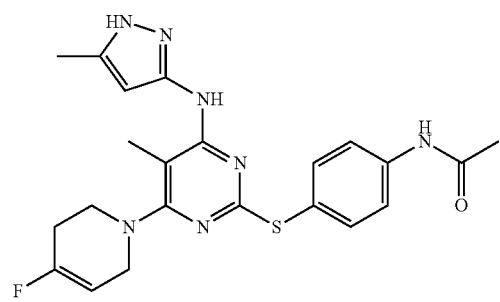 [SMILES: CC(=O)Nc1ccc(Sc2nc(Nc3cc(C)[nH]n3)c(C)c(N3CC=C(F)CC3)n2)cc1] | XXX |
| 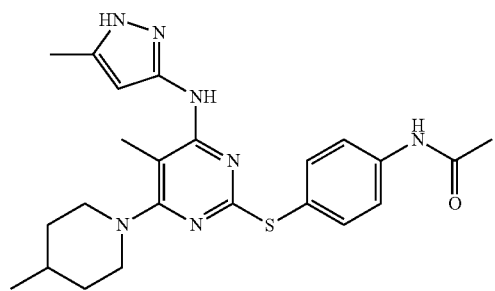 [SMILES: CC(=O)Nc1ccc(Sc2nc(Nc3cc(C)[nH]n3)c(C)c(N3CCC(C)CC3)n2)cc1] | XXX |
| 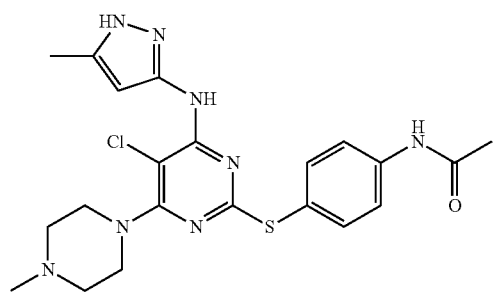 [SMILES: CC(=O)Nc1ccc(Sc2nc(Nc3cc(C)[nH]n3)c(Cl)c(N3CCN(C)CC3)n2)cc1] | XXX |
| 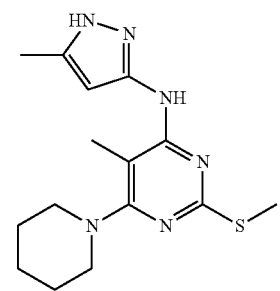 [SMILES: CSc1nc(Nc2cc(C)[nH]n2)c(C)c(N2CCCCC2)n1] | XXX |

TABLE 1-continued
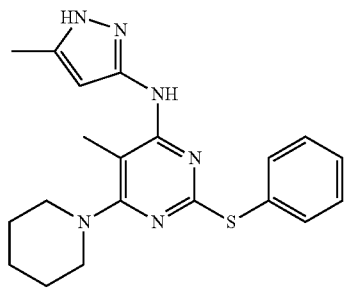 [SMILES: Cc1cc(Nc2nc(Sc3ccccc3)nc(N3CCCCC3)c2C)n[nH]1] Activity XXX
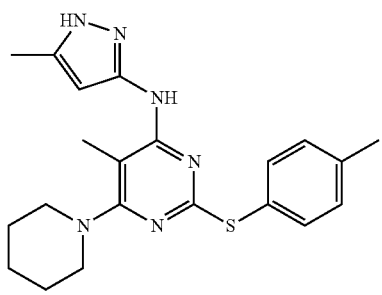 [SMILES: Cc1ccc(Sc2nc(Nc3cc(C)[nH]n3)c(C)c(N3CCCCC3)n2)cc1] XXX
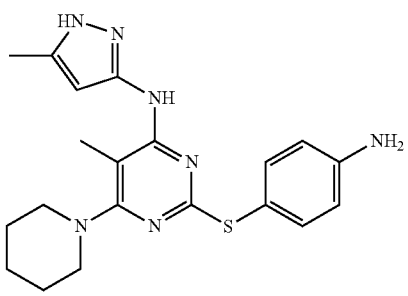 [SMILES: Cc1cc(Nc2nc(Sc3ccc(N)cc3)nc(N3CCCCC3)c2C)n[nH]1] XXX
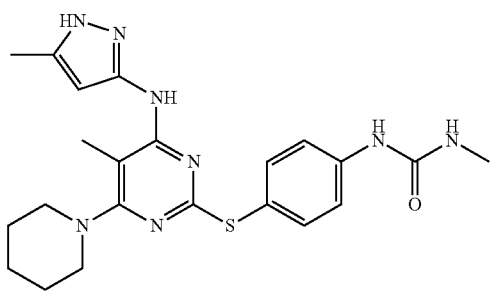 [SMILES: CNC(=O)Nc1ccc(Sc2nc(Nc3cc(C)[nH]n3)c(C)c(N3CCCCC3)n2)cc1] XXX
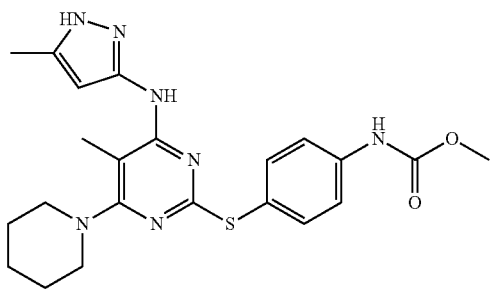 [SMILES: COC(=O)Nc1ccc(Sc2nc(Nc3cc(C)[nH]n3)c(C)c(N3CCCCC3)n2)cc1] XXX TABLE 1-continued
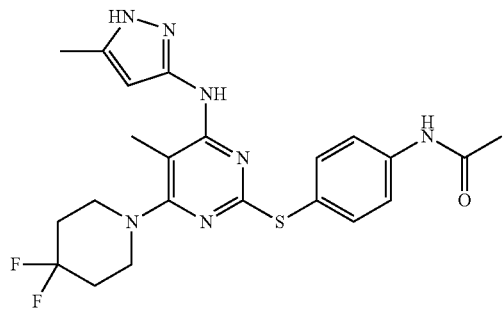 [SMILES: CC(=O)Nc1ccc(Sc2nc(Nc3cc(C)[nH]n3)c(C)c(N3CCC(F)(F)CC3)n2)cc1]
Activity XXX
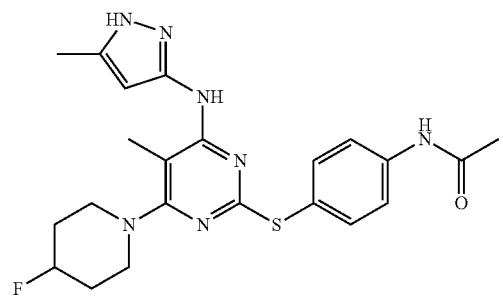 [SMILES: CC(=O)Nc1ccc(Sc2nc(Nc3cc(C)[nH]n3)c(C)c(N3CCC(F)CC3)n2)cc1]
XXX
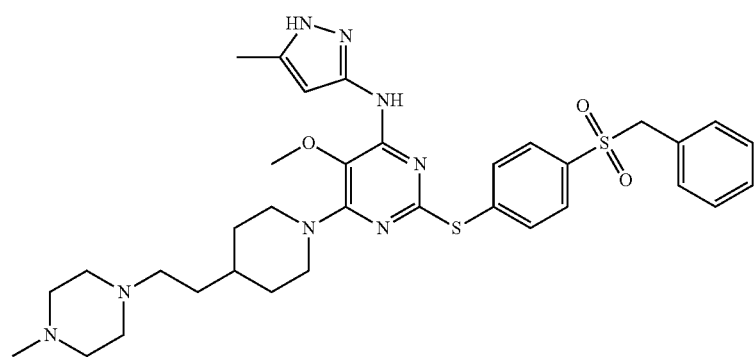
XXX
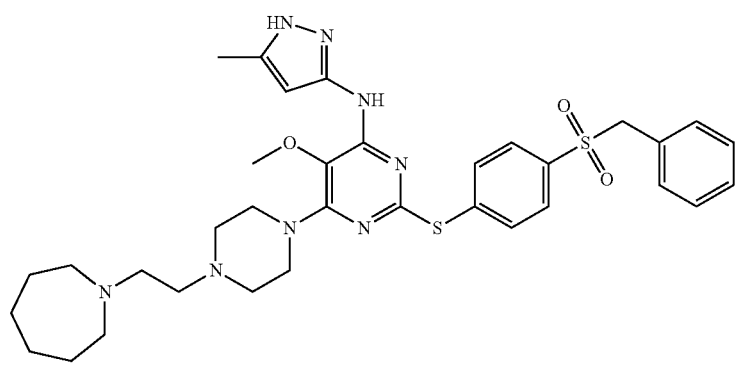 [SMILES: COc1c(Nc2cc(C)[nH]n2)nc(Sc2ccc(S(=O)(=O)Cc3ccccc3)cc2)nc1N1CCN(CCN2CCCCCC2)CC1]
XXX TABLE 1-continued
| | Activity |
|---|---|
| 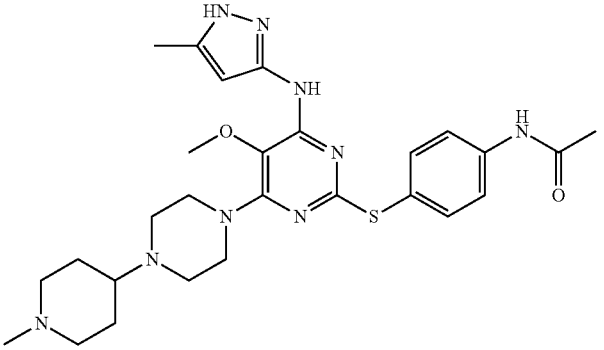 [SMILES: COc1c(Nc2cc(C)[nH]n2)nc(Sc2ccc(NC(C)=O)cc2)nc1N1CCN(C2CCN(C)CC2)CC1] | XXX |
| 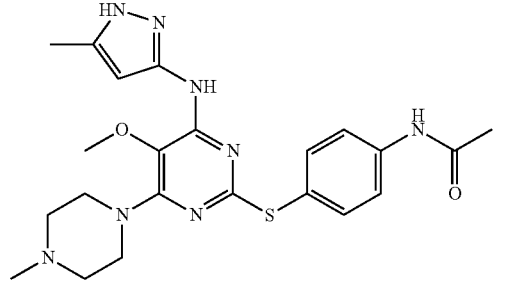 [SMILES: COc1c(Nc2cc(C)[nH]n2)nc(Sc2ccc(NC(C)=O)cc2)nc1N1CCN(C)CC1] | XXX |
| 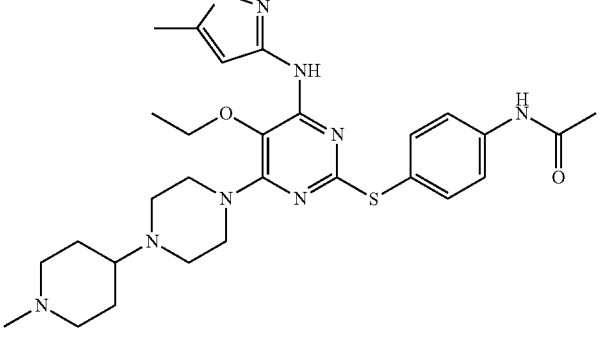 | XX |
| 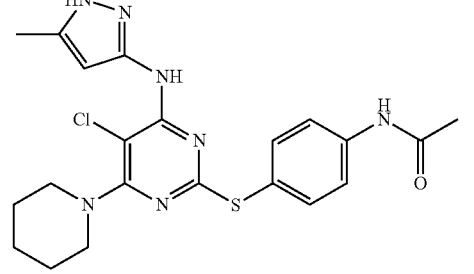 | XXX |
| 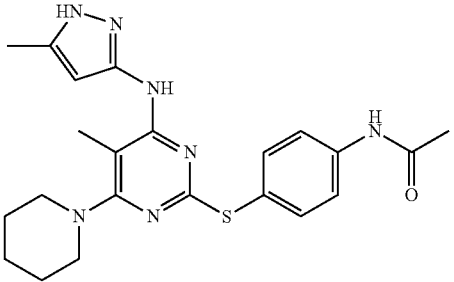 [SMILES: CC(=O)Nc1ccc(Sc2nc(Nc3cc(C)[nH]n3)c(C)c(N3CCCCC3)n2)cc1] | XXX |

| | |
|---|---|
| 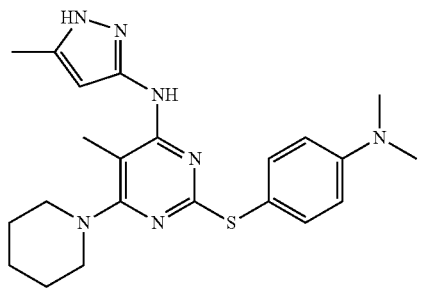 [SMILES: Cc1cc(Nc2nc(Sc3ccc(N(C)C)cc3)nc(N3CCCCC3)c2C)n[nH]1] | Activity XXX |
| 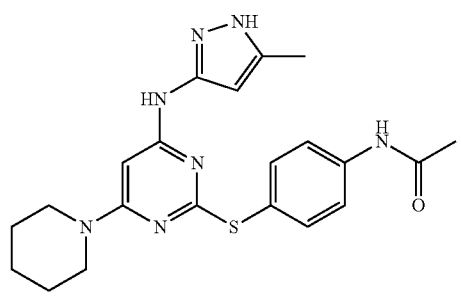 [SMILES: CC(=O)Nc1ccc(Sc2nc(Nc3cc(C)[nH]n3)cc(N3CCCCC3)n2)cc1] | XXX |
| 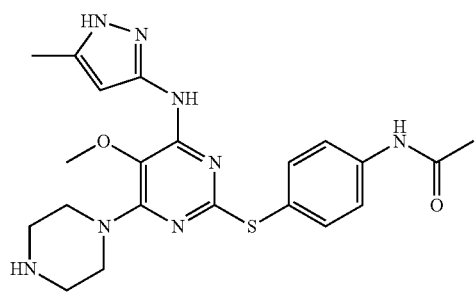 [SMILES: COc1c(Nc2cc(C)[nH]n2)nc(Sc2ccc(NC(C)=O)cc2)nc1N1CCNCC1] | XXX |
| 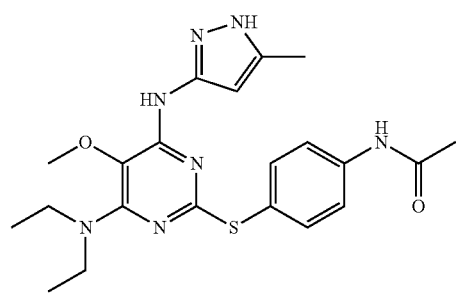 [SMILES: CCN(CC)c1nc(Sc2ccc(NC(C)=O)cc2)nc(Nc2cc(C)[nH]n2)c1OC] | XXX |
| 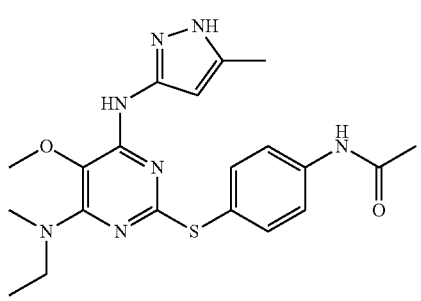 [SMILES: CCN(C)c1nc(Sc2ccc(NC(C)=O)cc2)nc(Nc2cc(C)[nH]n2)c1OC] | XXX |

TABLE 1-continued
| | |
|---|---|
| 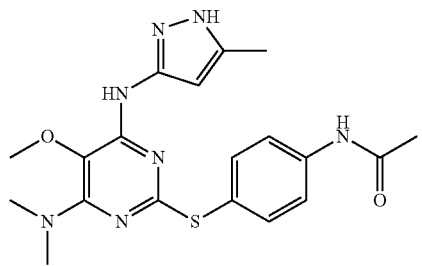 [SMILES: COc1c(Nc2cc(C)[nH]n2)nc(Sc2ccc(NC(C)=O)cc2)nc1N(C)C] | Activity XXX |
| 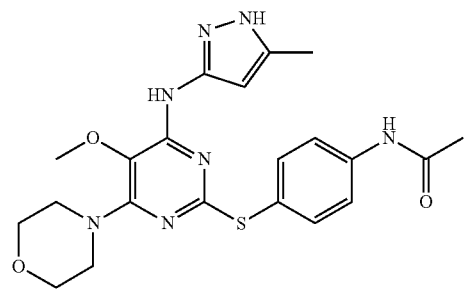 [SMILES: COc1c(Nc2cc(C)[nH]n2)nc(Sc2ccc(NC(C)=O)cc2)nc1N1CCOCC1] | XXX |
| 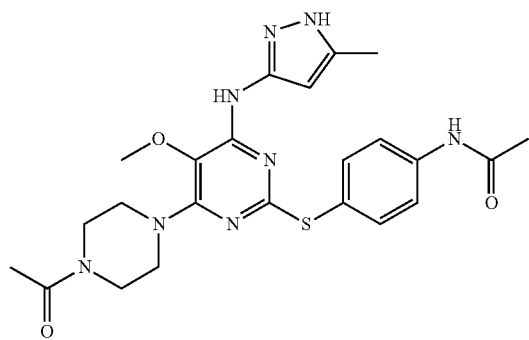 [SMILES: COc1c(Nc2cc(C)[nH]n2)nc(Sc2ccc(NC(C)=O)cc2)nc1N1CCN(C(C)=O)CC1] | XXX |
| 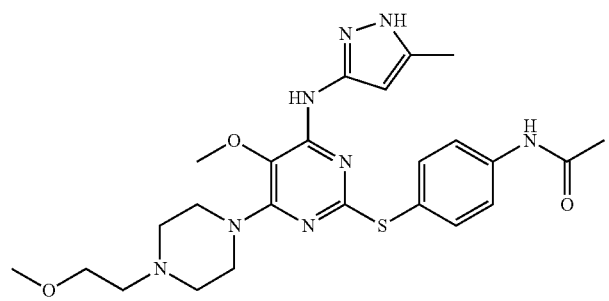 [SMILES: COCCN1CCN(c2nc(Sc3ccc(NC(C)=O)cc3)nc(Nc3cc(C)[nH]n3)c2OC)CC1] | XXX |
| 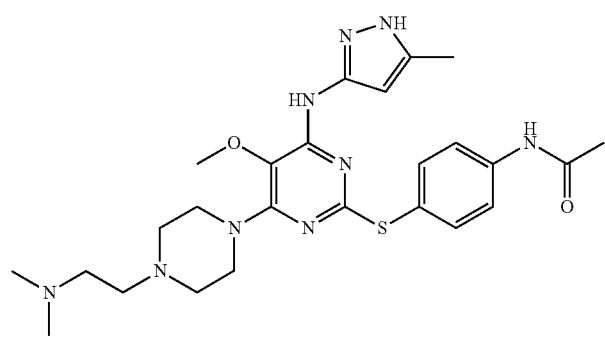 [SMILES: COc1c(Nc2cc(C)[nH]n2)nc(Sc2ccc(NC(C)=O)cc2)nc1N1CCN(CCN(C)C)CC1] | XXX |

TABLE 1-continued
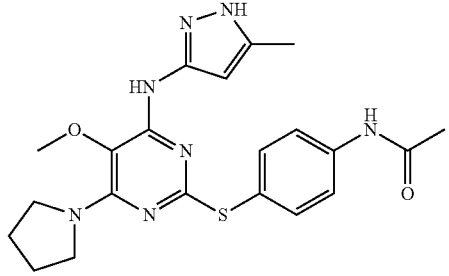 [SMILES: COc1c(Nc2cc(C)[nH]n2)nc(Sc2ccc(NC(C)=O)cc2)nc1N1CCCC1] Activity XXX
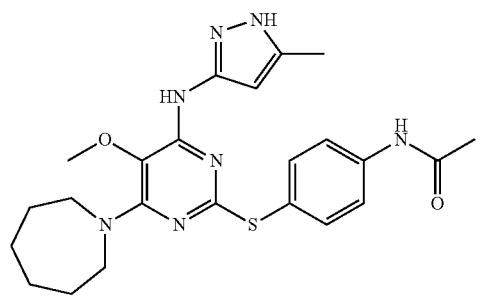 [SMILES: COc1c(Nc2cc(C)[nH]n2)nc(Sc2ccc(NC(C)=O)cc2)nc1N1CCCCCC1] XX
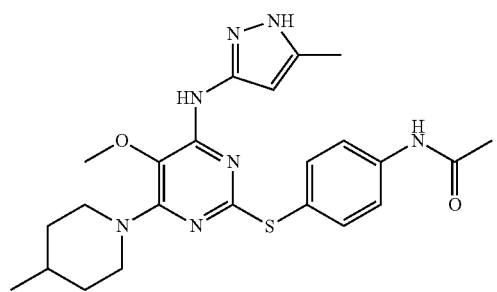 [SMILES: COc1c(Nc2cc(C)[nH]n2)nc(Sc2ccc(NC(C)=O)cc2)nc1N1CCC(C)CC1] XX
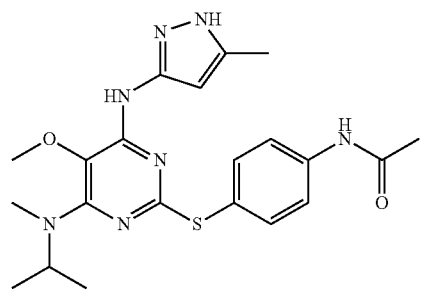 [SMILES: COc1c(Nc2cc(C)[nH]n2)nc(Sc2ccc(NC(C)=O)cc2)nc1N(C)C(C)C] Activity XXX
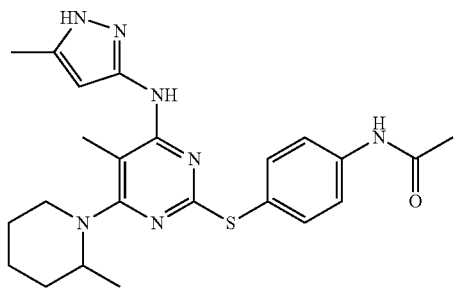 [SMILES: CC(=O)Nc1ccc(Sc2nc(Nc3cc(C)[nH]n3)c(C)c(N3CCCCC3C)n2)cc1] XXX TABLE 1-continued
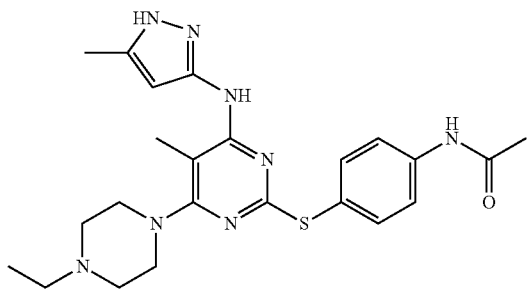 [SMILES: CCN1CCN(c2nc(Sc3ccc(NC(C)=O)cc3)nc(Nc3cc(C)[nH]n3)c2C)CC1] Activity XXX
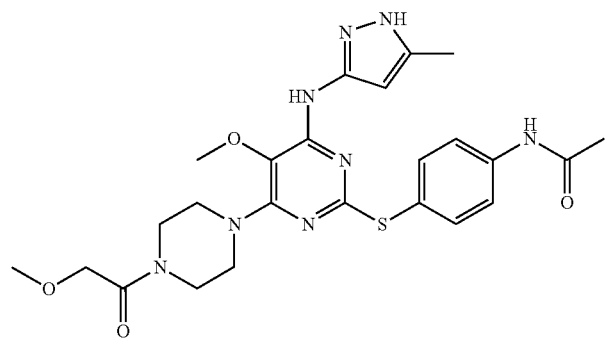 [SMILES: COCC(=O)N1CCN(c2nc(Sc3ccc(NC(C)=O)cc3)nc(Nc3cc(C)[nH]n3)c2OC)CC1] XXX
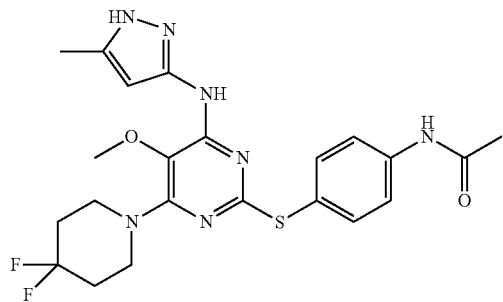 [SMILES: COc1c(Nc2cc(C)[nH]n2)nc(Sc2ccc(NC(C)=O)cc2)nc1N1CCC(F)(F)CC1] XXX
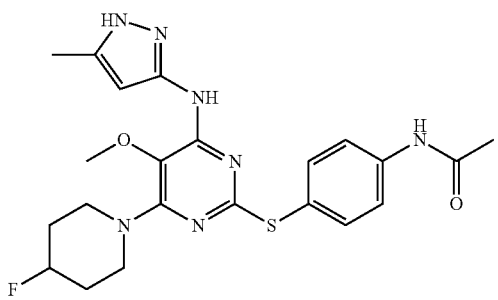 [SMILES: COc1c(Nc2cc(C)[nH]n2)nc(Sc2ccc(NC(C)=O)cc2)nc1N1CCC(F)CC1] XXX
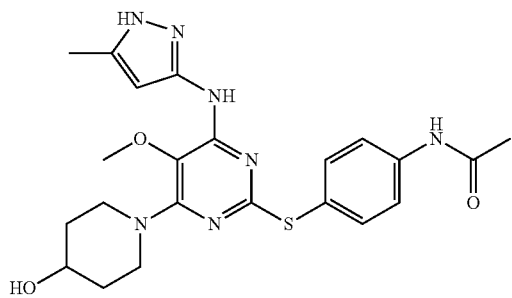 [SMILES: COc1c(Nc2cc(C)[nH]n2)nc(Sc2ccc(NC(C)=O)cc2)nc1N1CCC(O)CC1] XXX TABLE 1-continued
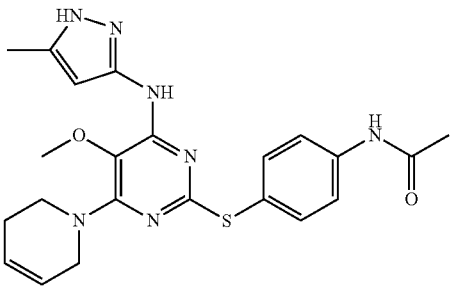 [SMILES: COc1c(Nc2cc(C)[nH]n2)nc(Sc2ccc(NC(C)=O)cc2)nc1N1CC=CCC1] Activity XXX
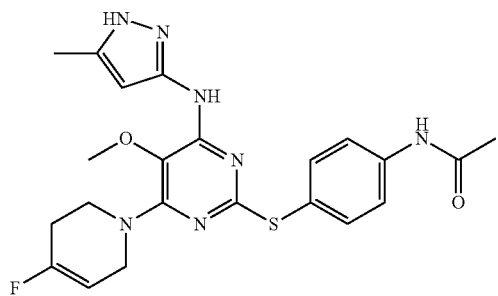 [SMILES: COc1c(Nc2cc(C)[nH]n2)nc(Sc2ccc(NC(C)=O)cc2)nc1N1CC=C(F)CC1] XXX
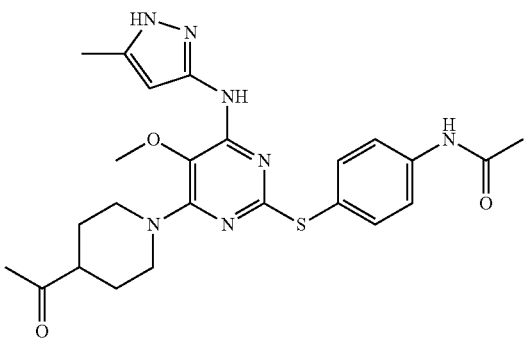 [SMILES: COc1c(Nc2cc(C)[nH]n2)nc(Sc2ccc(NC(C)=O)cc2)nc1N1CCC(C(C)=O)CC1] XXX
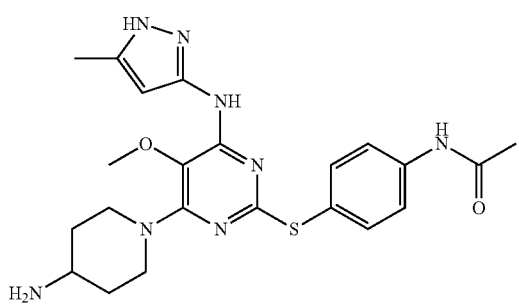 [SMILES: COc1c(Nc2cc(C)[nH]n2)nc(Sc2ccc(NC(C)=O)cc2)nc1N1CCC(N)CC1] XXX
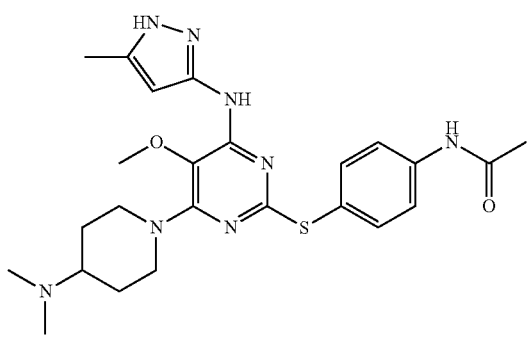 [SMILES: COc1c(Nc2cc(C)[nH]n2)nc(Sc2ccc(NC(C)=O)cc2)nc1N1CCC(N(C)C)CC1] XXX TABLE 1-continued
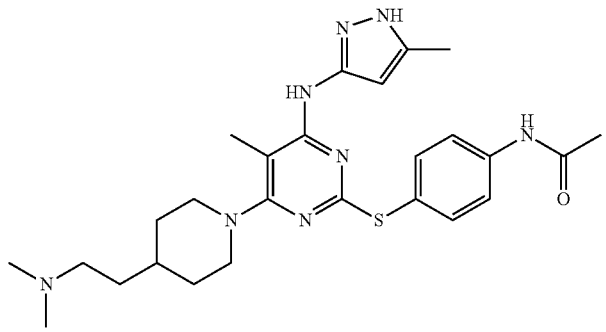 Activity XXX
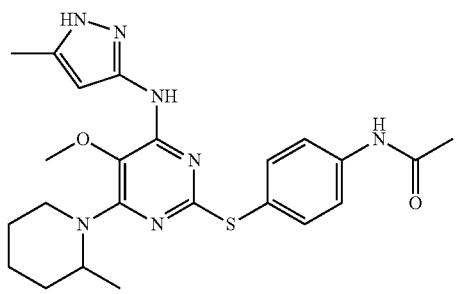 [SMILES: COc1c(Nc2cc(C)[nH]n2)nc(Sc2ccc(NC(C)=O)cc2)nc1N1CCCCC1C] XX
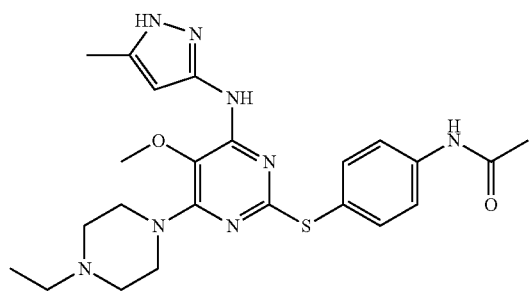 [SMILES: CCN1CCN(c2nc(Sc3ccc(NC(C)=O)cc3)nc(Nc3cc(C)[nH]n3)c2OC)CC1] XXX
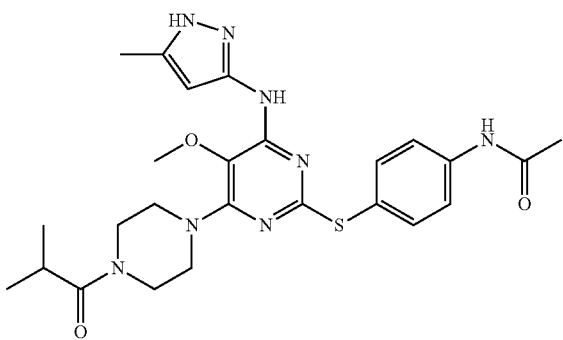 [SMILES: COc1c(Nc2cc(C)[nH]n2)nc(Sc2ccc(NC(C)=O)cc2)nc1N1CCN(C(=O)C(C)C)CC1] XXX
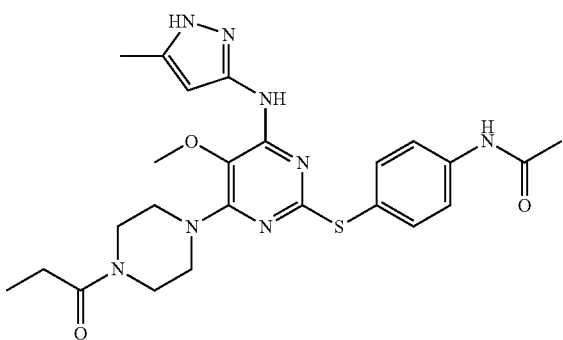 [SMILES: CCC(=O)N1CCN(c2nc(Sc3ccc(NC(C)=O)cc3)nc(Nc3cc(C)[nH]n3)c2OC)CC1] XXX TABLE 1-continued
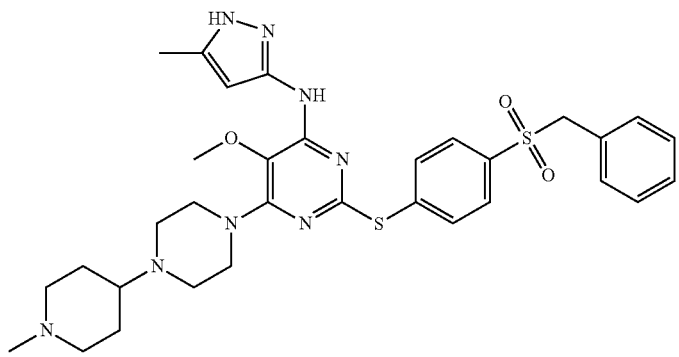 [SMILES: COc1c(Nc2cc(C)[nH]n2)nc(Sc2ccc(S(=O)(=O)Cc3ccccc3)cc2)nc1N1CCN(C2CCN(C)CC2)CC1] Activity XXX
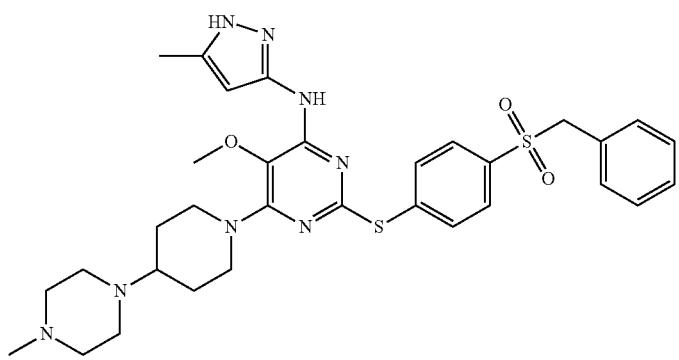 [SMILES: COc1c(Nc2cc(C)[nH]n2)nc(Sc2ccc(S(=O)(=O)Cc3ccccc3)cc2)nc1N1CCC(N2CCN(C)CC2)CC1] XXX
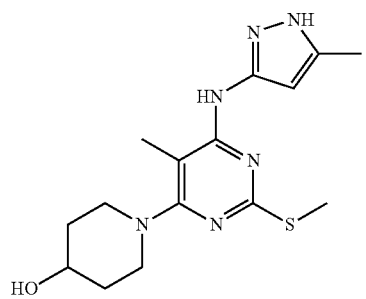 [SMILES: CSc1nc(Nc2cc(C)[nH]n2)c(C)c(N2CCC(O)CC2)n1] XXX
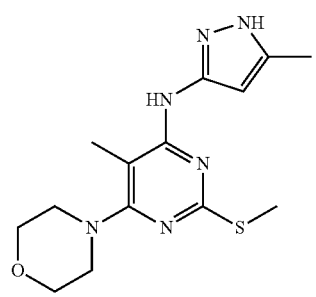 [SMILES: CSc1nc(Nc2cc(C)[nH]n2)c(C)c(N2CCOCC2)n1] XXX
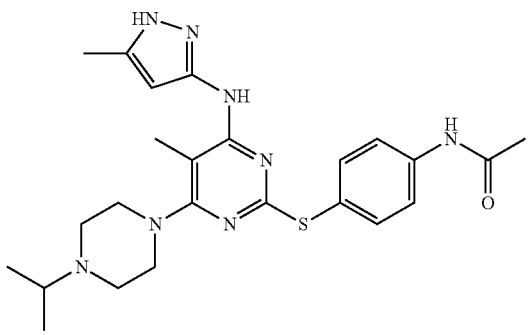 [SMILES: CC(=O)Nc1ccc(Sc2nc(Nc3cc(C)[nH]n3)c(C)c(N3CCN(C(C)C)CC3)n2)cc1] XXX TABLE 1-continued
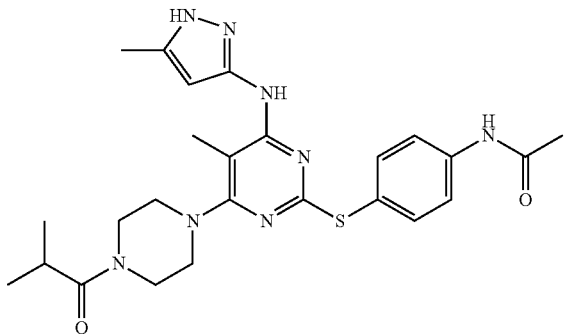 [SMILES: CC(=O)Nc1ccc(Sc2nc(Nc3cc(C)[nH]n3)c(C)c(N3CCN(C(=O)C(C)C)CC3)n2)cc1]
Activity XXX
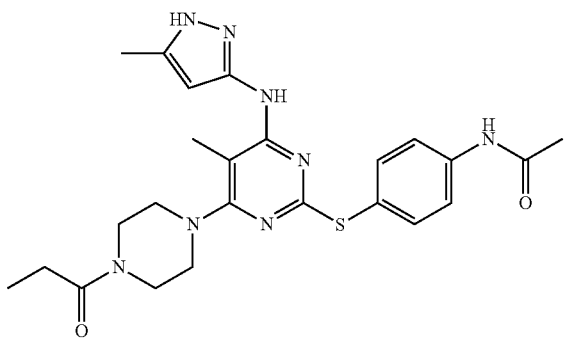 [SMILES: CCC(=O)N1CCN(c2nc(Sc3ccc(NC(C)=O)cc3)nc(Nc3cc(C)[nH]n3)c2C)CC1]
XXX
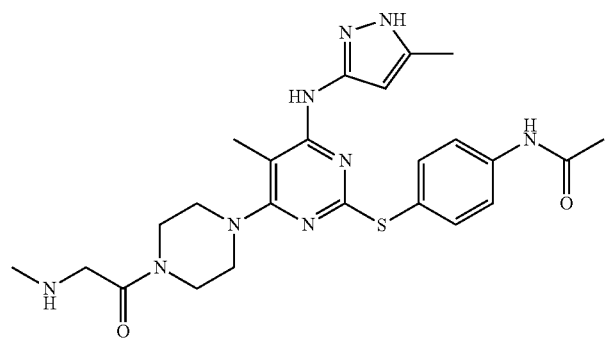
XXX
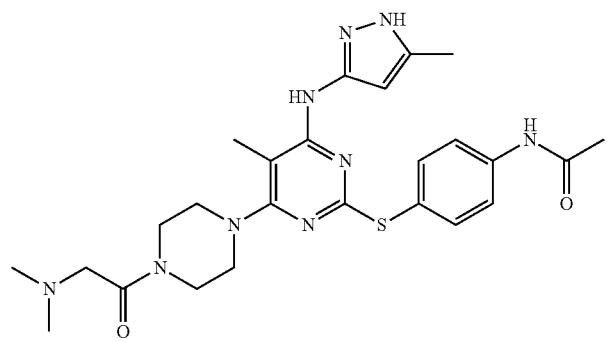 [SMILES: CC(=O)Nc1ccc(Sc2nc(Nc3cc(C)[nH]n3)c(C)c(N3CCN(C(=O)CN(C)C)CC3)n2)cc1]
XXX TABLE 1-continued
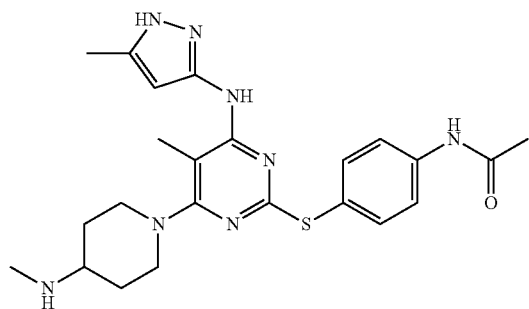 [SMILES: CNC1CCN(c2nc(Sc3ccc(NC(C)=O)cc3)nc(Nc3cc(C)[nH]n3)c2C)CC1]
XXX
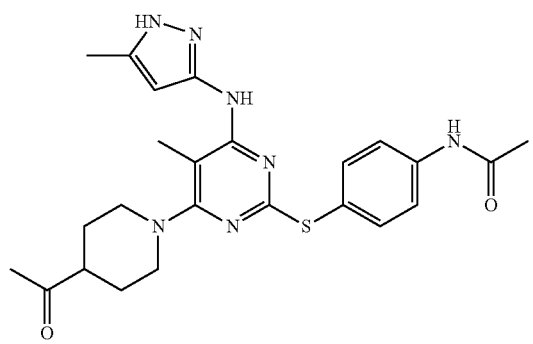
Activity XXX
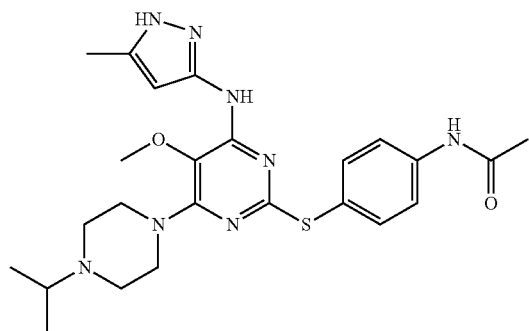 [SMILES: COc1c(Nc2cc(C)[nH]n2)nc(Sc2ccc(NC(C)=O)cc2)nc1N1CCN(C(C)C)CC1]
XXX
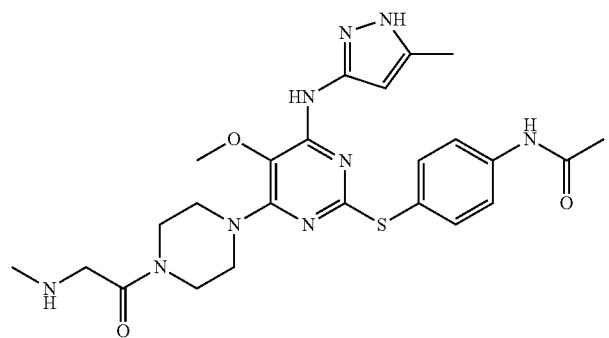 [SMILES: CNCC(=O)N1CCN(c2nc(Sc3ccc(NC(C)=O)cc3)nc(Nc3cc(C)[nH]n3)c2OC)CC1]
XXX TABLE 1-continued
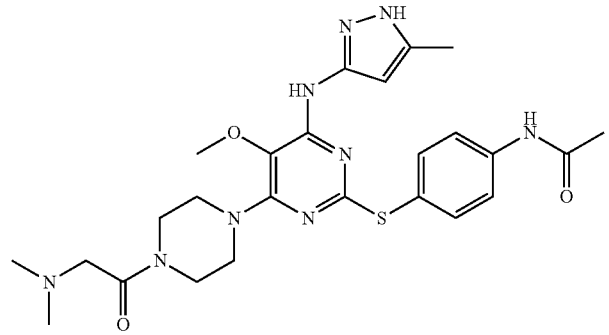 [SMILES: COc1c(Nc2cc(C)[nH]n2)nc(Sc2ccc(NC(C)=O)cc2)nc1N1CCN(C(=O)CN(C)C)CC1] XXX
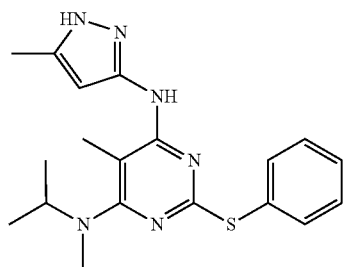 [SMILES: Cc1cc(Nc2nc(Sc3ccccc3)nc(N(C)C(C)C)c2C)n[nH]1] XXX
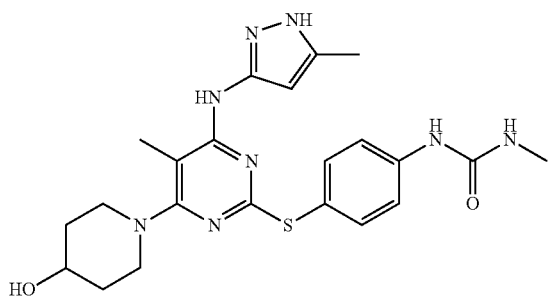 [SMILES: CNC(=O)Nc1ccc(Sc2nc(Nc3cc(C)[nH]n3)c(C)c(N3CCC(O)CC3)n2)cc1] Activity XXX
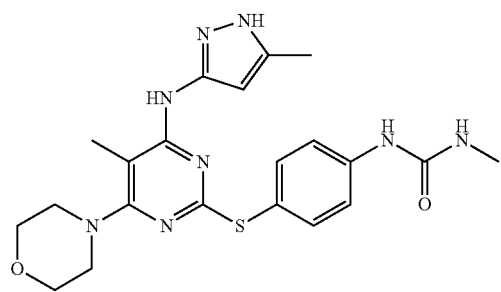 [SMILES: CNC(=O)Nc1ccc(Sc2nc(Nc3cc(C)[nH]n3)c(C)c(N3CCOCC3)n2)cc1] XXX
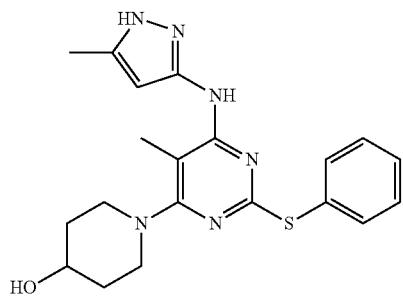 [SMILES: Cc1cc(Nc2nc(Sc3ccccc3)nc(N3CCC(O)CC3)c2C)n[nH]1] XXX TABLE 1-continued
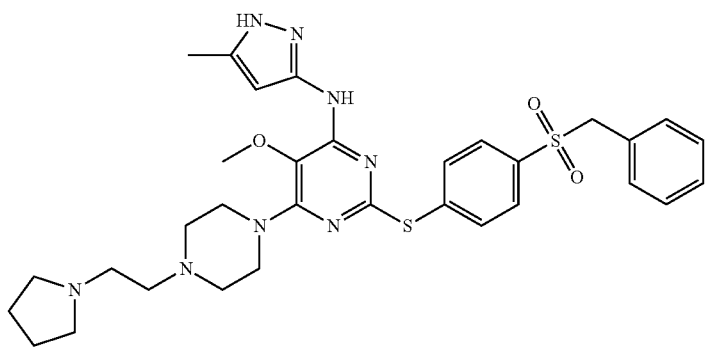 [SMILES: COc1c(Nc2cc(C)[nH]n2)nc(Sc2ccc(S(=O)(=O)Cc3ccccc3)cc2)nc1N1CCN(CCN2CCCC2)CC1] XXX
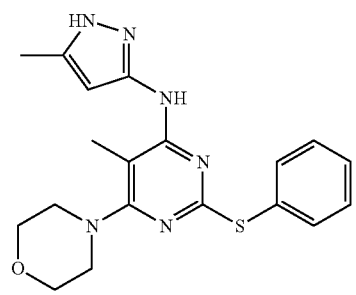 [SMILES: Cc1cc(Nc2nc(Sc3ccccc3)nc(N3CCOCC3)c2C)n[nH]1] XXX
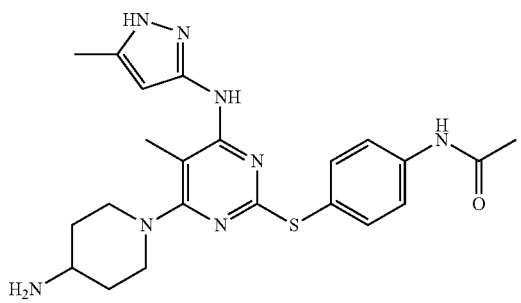 [SMILES: CC(=O)Nc1ccc(Sc2nc(Nc3cc(C)[nH]n3)c(C)c(N3CCC(N)CC3)n2)cc1] Activity XXX
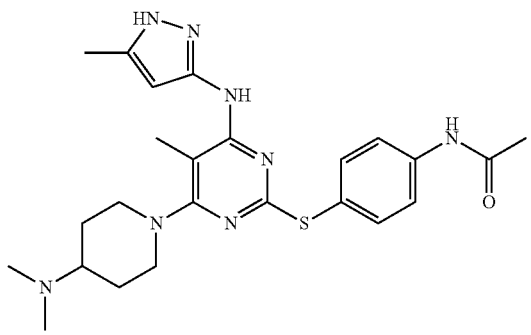 [SMILES: CC(=O)Nc1ccc(Sc2nc(Nc3cc(C)[nH]n3)c(C)c(N3CCC(N(C)C)CC3)n2)cc1] XXX
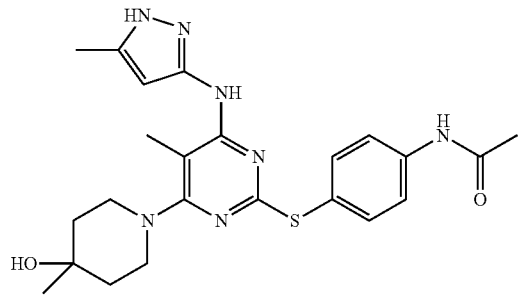 [SMILES: CC(=O)Nc1ccc(Sc2nc(Nc3cc(C)[nH]n3)c(C)c(N3CCC(C)(O)CC3)n2)cc1] XXX TABLE 1-continued
| | |
|---|---|
| 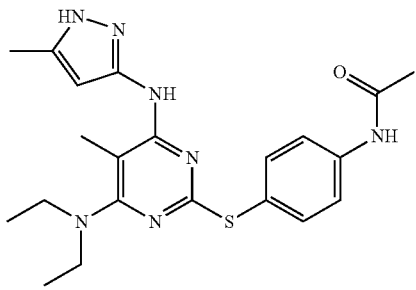 [SMILES: CCN(CC)c1nc(Sc2ccc(NC(C)=O)cc2)nc(Nc2cc(C)[nH]n2)c1C] | XXX |
| 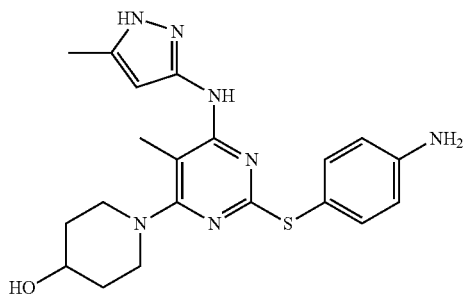 [SMILES: Cc1cc(Nc2nc(Sc3ccc(N)cc3)nc(N3CCC(O)CC3)c2C)n[nH]1] | XXX |
| 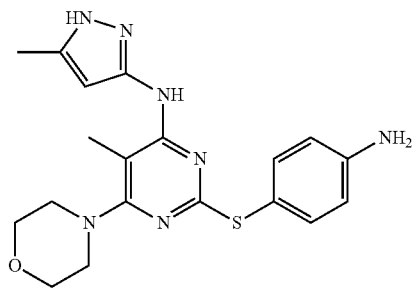 [SMILES: Cc1cc(Nc2nc(Sc3ccc(N)cc3)nc(N3CCOCC3)c2C)n[nH]1] | Activity XXX |
| 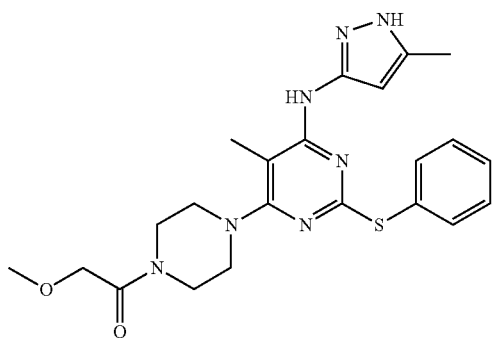 [SMILES: COCC(=O)N1CCN(c2nc(Sc3ccccc3)nc(Nc3cc(C)[nH]n3)c2C)CC1] | XXX |
| 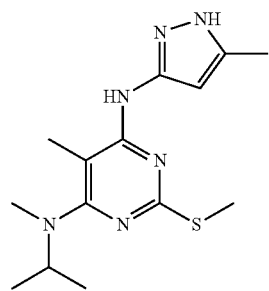 | XXX |

TABLE 1-continued
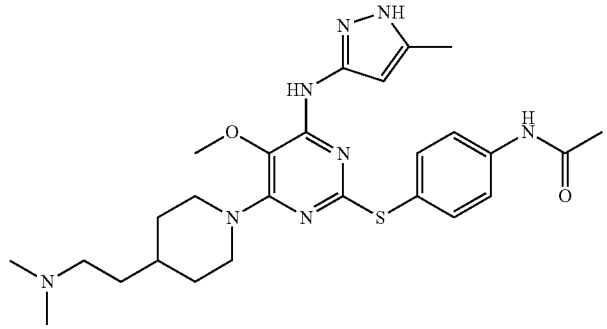 [SMILES: COc1c(Nc2cc(C)[nH]n2)nc(Sc2ccc(NC(C)=O)cc2)nc1N1CCC(CCN(C)C)CC1] XXX
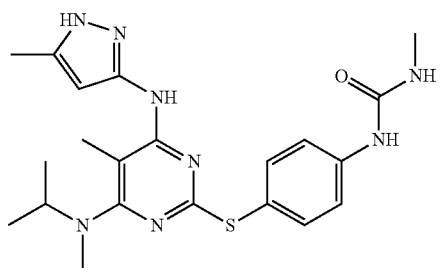 [SMILES: CNC(=O)Nc1ccc(Sc2nc(Nc3cc(C)[nH]n3)c(C)c(N(C)C(C)C)n2)cc1] XXX
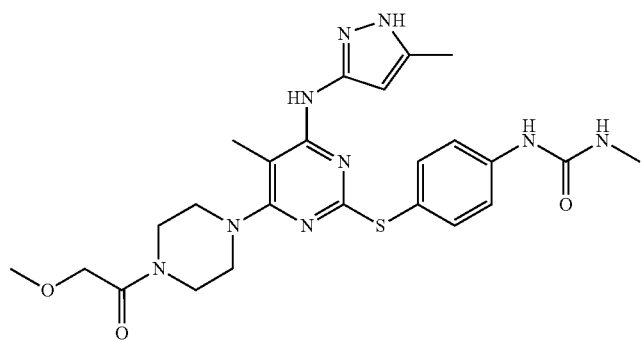 Activity XXX
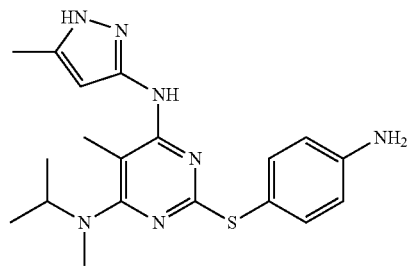 [SMILES: Cc1cc(Nc2nc(Sc3ccc(N)cc3)nc(N(C)C(C)C)c2C)n[nH]1] XXX
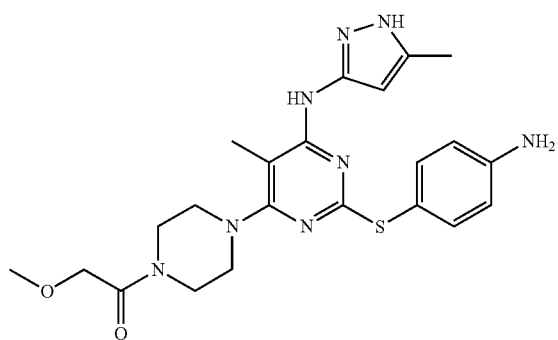 [SMILES: COCC(=O)N1CCN(c2nc(Sc3ccc(N)cc3)nc(Nc3cc(C)[nH]n3)c2C)CC1] XXX TABLE 1-continued
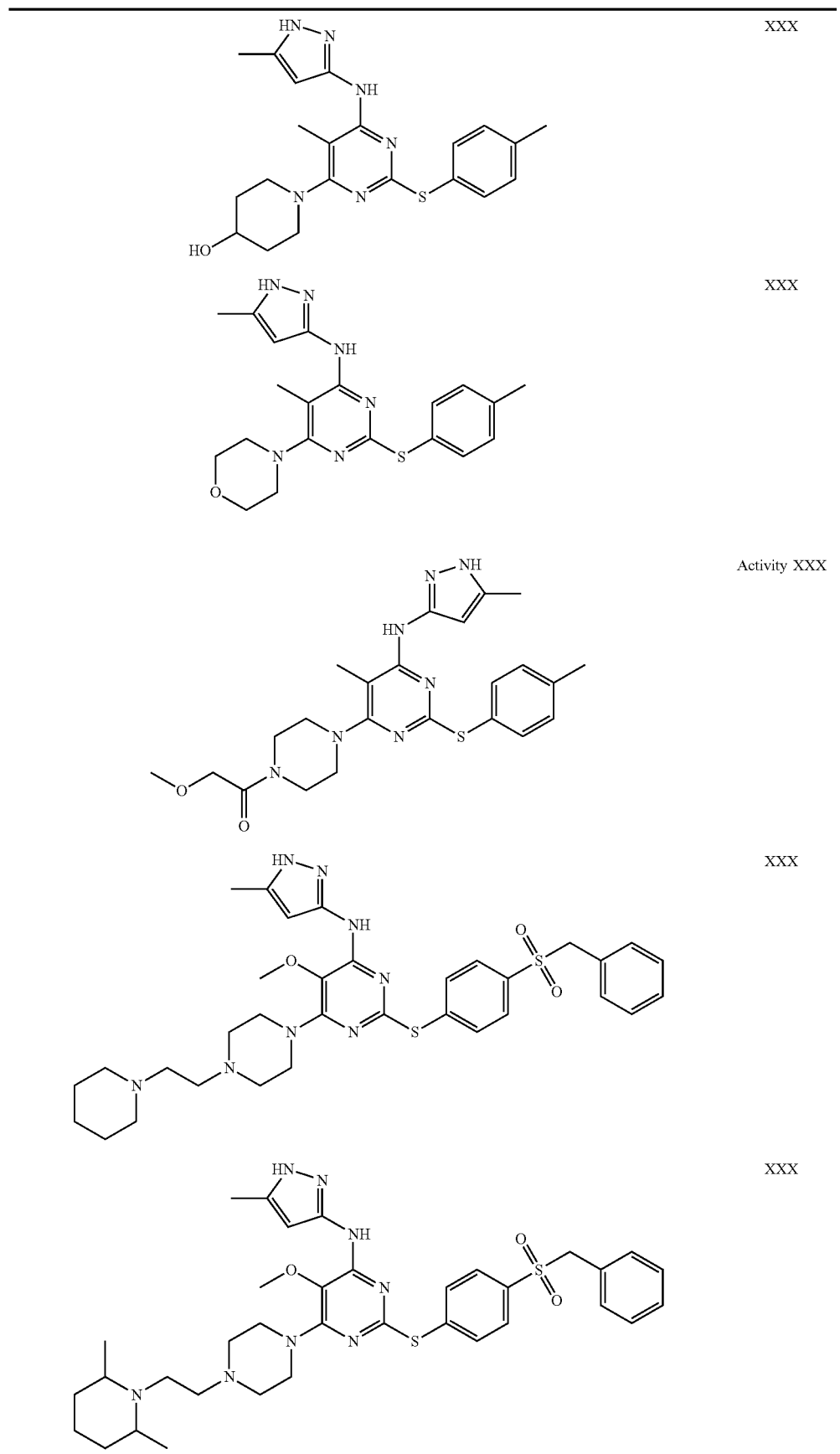
| | |
|---|---|
| | XXX |
| | XXX |
| | Activity XXX |
| | XXX |
| | XXX |

TABLE 1-continued
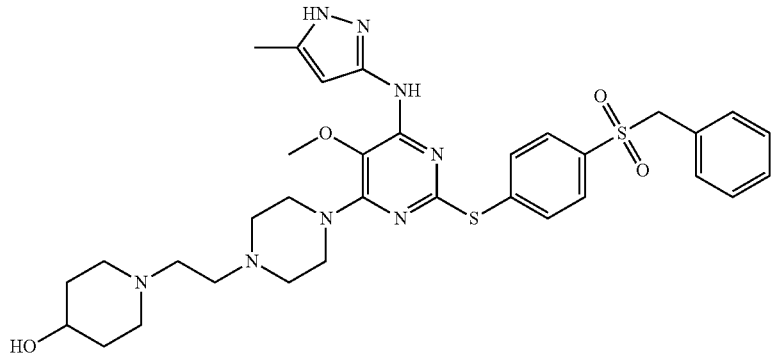 [SMILES: COc1c(Nc2cc(C)[nH]n2)nc(Sc2ccc(S(=O)(=O)Cc3ccccc3)cc2)nc1N1CCN(CCN2CCC(O)CC2)CC1] XXX
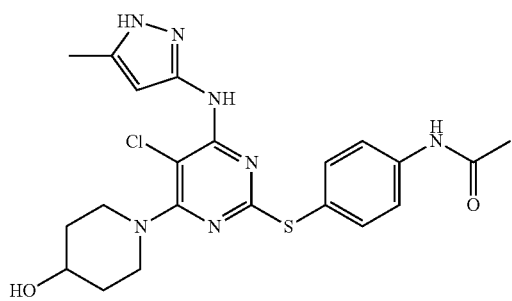 Activity XXX
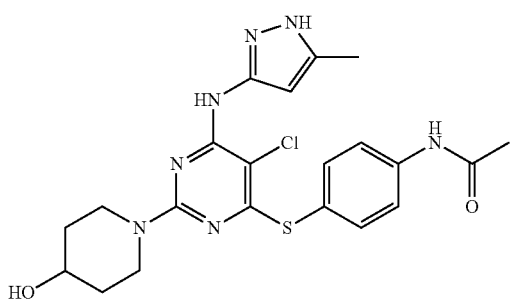 [SMILES: CC(=O)Nc1ccc(Sc2nc(N3CCC(O)CC3)nc(Nc3cc(C)[nH]n3)c2Cl)cc1] XXX
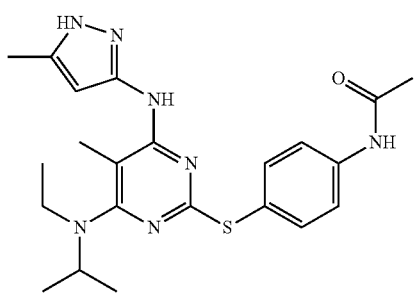 [SMILES: CCN(c1nc(Sc2ccc(NC(C)=O)cc2)nc(Nc2cc(C)[nH]n2)c1C)C(C)C] XXX
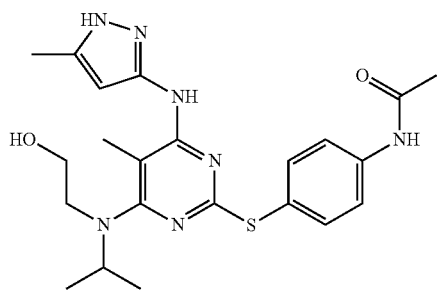 [SMILES: CC(=O)Nc1ccc(Sc2nc(Nc3cc(C)[nH]n3)c(C)c(N(CCO)C(C)C)n2)cc1] XXX

TABLE 1-continued
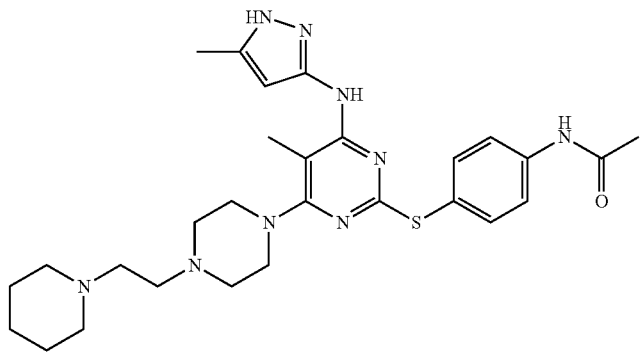 [SMILES: CC(=O)Nc1ccc(Sc2nc(Nc3cc(C)[nH]n3)c(C)c(N3CCN(CCN4CCCCC4)CC3)n2)cc1]
XXX
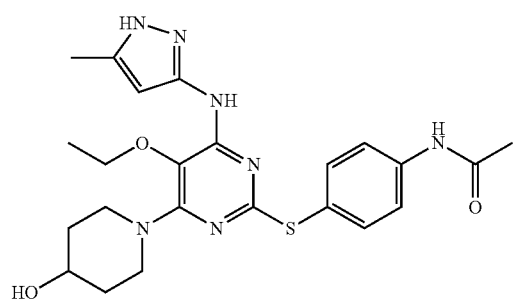 [SMILES: CCOc1c(Nc2cc(C)[nH]n2)nc(Sc2ccc(NC(C)=O)cc2)nc1N1CCC(O)CC1]
Activity XXX
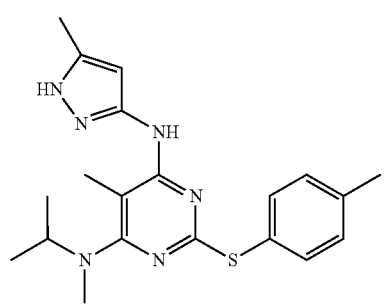 [SMILES: Cc1ccc(Sc2nc(Nc3cc(C)[nH]n3)c(C)c(N(C)C(C)C)n2)cc1]
XXX
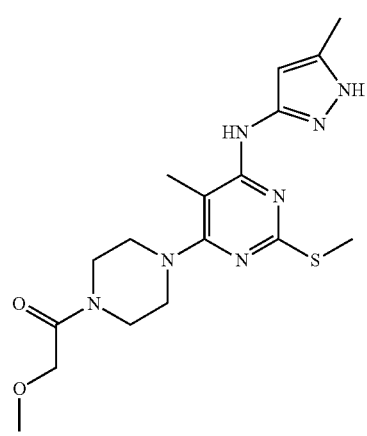 [SMILES: COCC(=O)N1CCN(c2nc(SC)nc(Nc3cc(C)[nH]n3)c2C)CC1]
XXX TABLE 1-continued
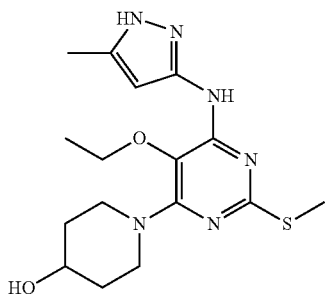 [SMILES: CCOc1c(Nc2cc(C)[nH]n2)nc(SC)nc1N1CCC(O)CC1] XX
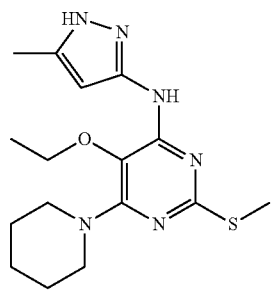 [SMILES: CCOc1c(Nc2cc(C)[nH]n2)nc(SC)nc1N1CCCCC1] XX
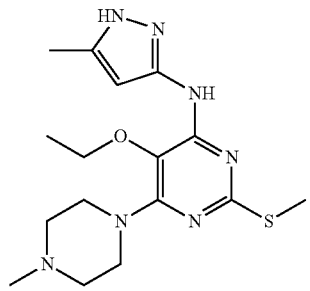 XX
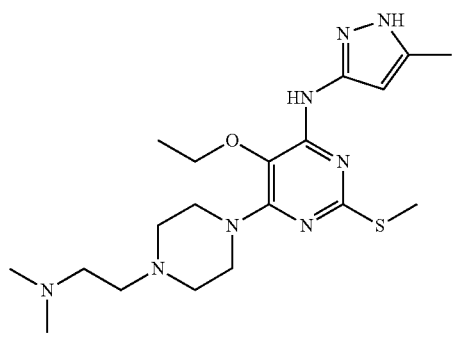 Activity XX
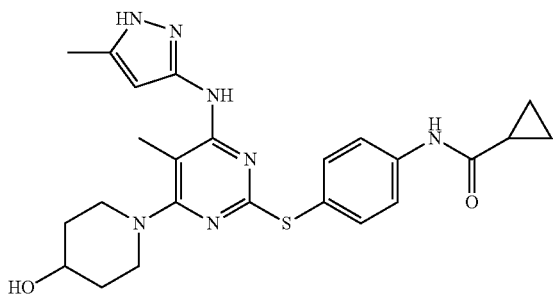 [SMILES: Cc1cc(Nc2nc(Sc3ccc(NC(=O)C4CC4)cc3)nc(N3CCC(O)CC3)c2C)n[nH]1] XXX TABLE 1-continued
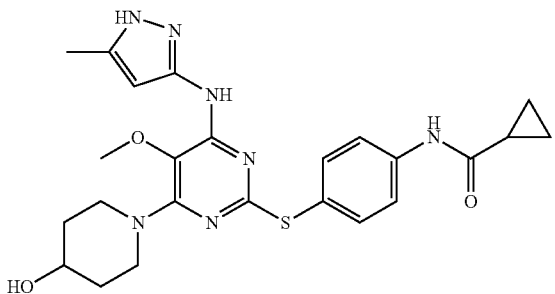 [SMILES: COc1c(Nc2cc(C)[nH]n2)nc(Sc2ccc(NC(=O)C3CC3)cc2)nc1N1CCC(O)CC1] XXX
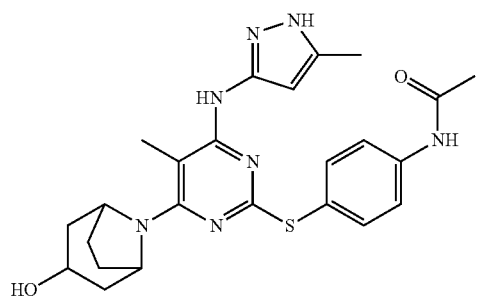 [SMILES: CC(=O)Nc1ccc(Sc2nc(Nc3cc(C)[nH]n3)c(C)c(N3C4CCC3CC(O)C4)n2)cc1] XXX
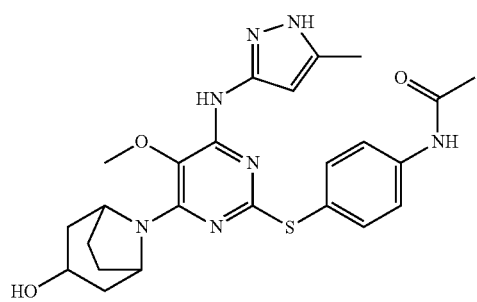 [SMILES: COc1c(Nc2cc(C)[nH]n2)nc(Sc2ccc(NC(C)=O)cc2)nc1N1C2CCC1CC(O)C2] XXX
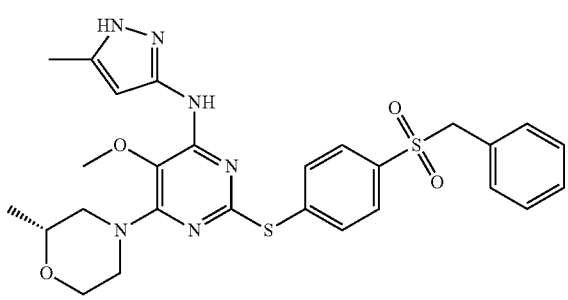 [SMILES: COc1c(Nc2cc(C)[nH]n2)nc(Sc2ccc(S(=O)(=O)Cc3ccccc3)cc2)nc1N1CCO[C@H](C)C1] Activity XXX
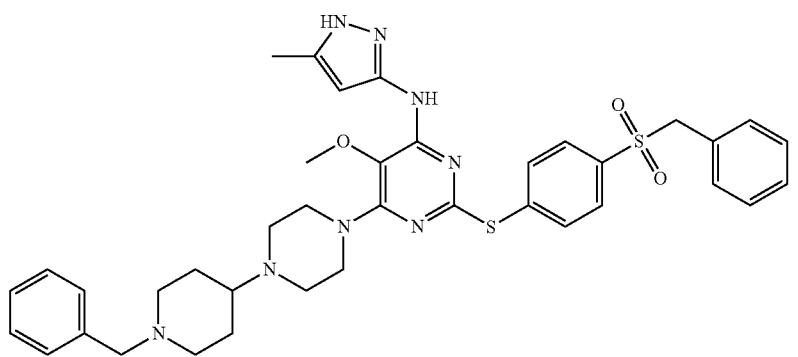 [SMILES: COc1c(Nc2cc(C)[nH]n2)nc(Sc2ccc(S(=O)(=O)Cc3ccccc3)cc2)nc1N1CCN(C2CCN(Cc3ccccc3)CC2)CC1] XXX TABLE 1-continued
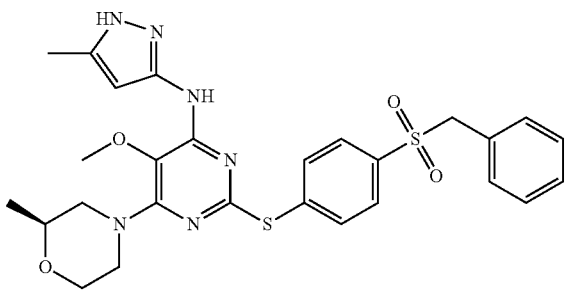 [SMILES: COc1c(Nc2cc(C)[nH]n2)nc(Sc2ccc(S(=O)(=O)Cc3ccccc3)cc2)nc1N1CCO[C@@H](C)C1]
XXX
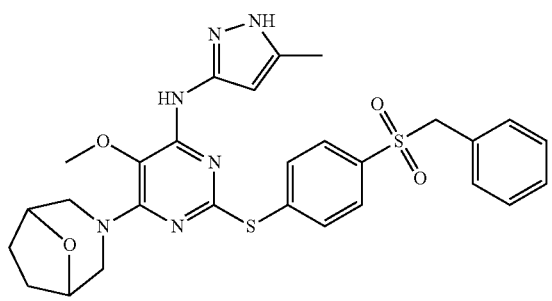 [SMILES: COc1c(Nc2cc(C)[nH]n2)nc(Sc2ccc(S(=O)(=O)Cc3ccccc3)cc2)nc1N1CC2CCC(C1)O2]
XXX
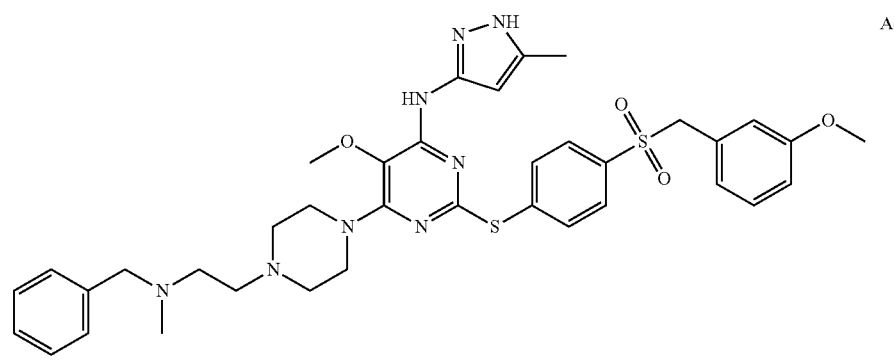
Activity XXX
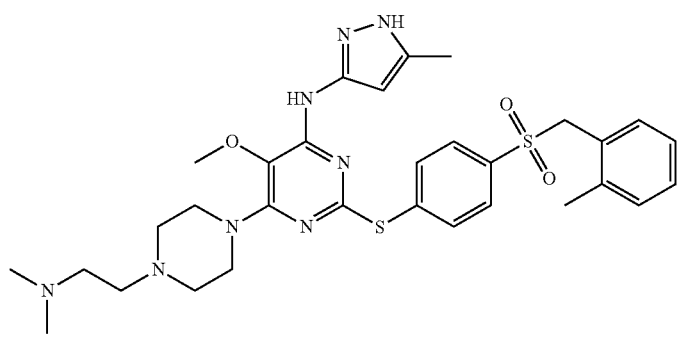 [SMILES: COc1c(Nc2cc(C)[nH]n2)nc(Sc2ccc(S(=O)(=O)Cc3ccccc3C)cc2)nc1N1CCN(CCN(C)C)CC1]
XXX
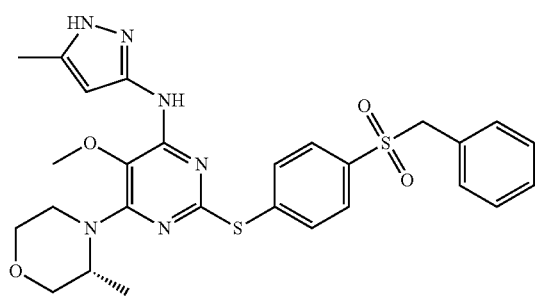 [SMILES: COc1c(Nc2cc(C)[nH]n2)nc(Sc2ccc(S(=O)(=O)Cc3ccccc3)cc2)nc1N1CCOC[C@H]1C]
XXX TABLE 1-continued
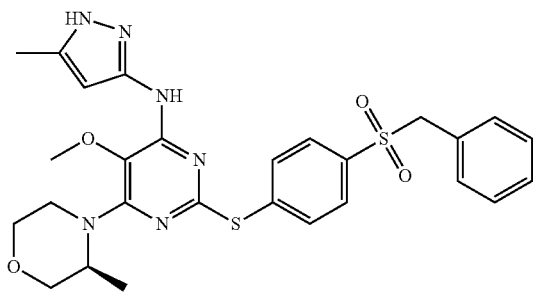 [SMILES: COc1c(Nc2cc(C)[nH]n2)nc(Sc2ccc(S(=O)(=O)Cc3ccccc3)cc2)nc1N1CCOC[C@@H]1C]
XXX
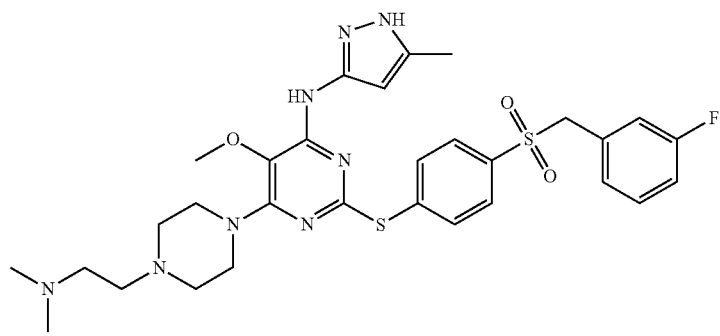 [SMILES: COc1c(Nc2cc(C)[nH]n2)nc(Sc2ccc(S(=O)(=O)Cc3cccc(F)c3)cc2)nc1N1CCN(CCN(C)C)CC1]
Activity XXX
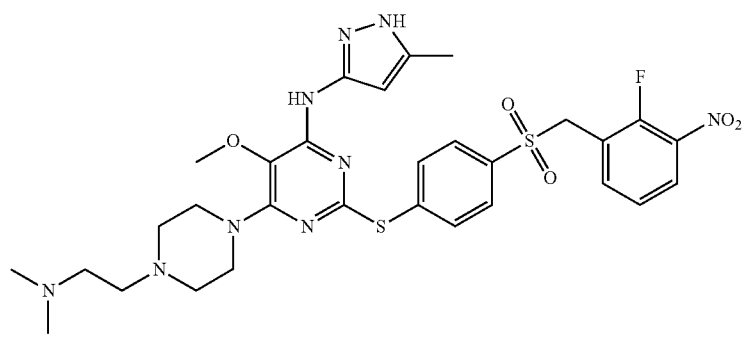 [SMILES: COc1c(Nc2cc(C)[nH]n2)nc(Sc2ccc(S(=O)(=O)Cc3cccc([N+](=O)[O-])c3F)cc2)nc1N1CCN(CCN(C)C)CC1]
XXX
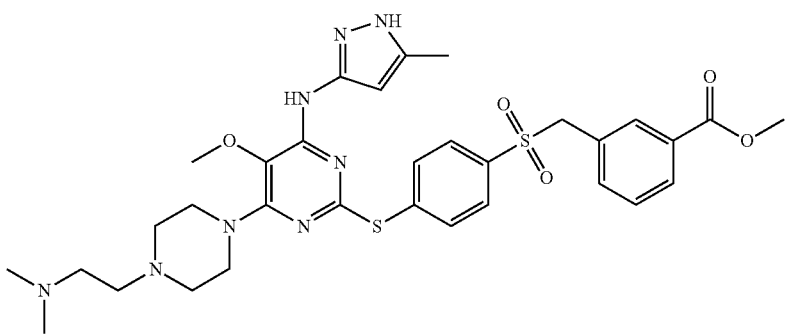
XXX
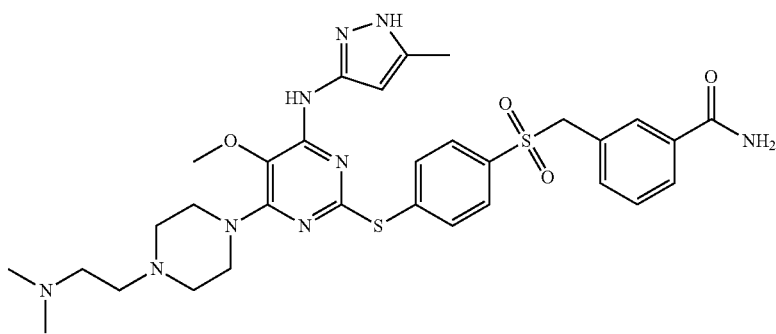 [SMILES: COc1c(Nc2cc(C)[nH]n2)nc(Sc2ccc(S(=O)(=O)Cc3cccc(C(N)=O)c3)cc2)nc1N1CCN(CCN(C)C)CC1]
XXX TABLE 1-continued
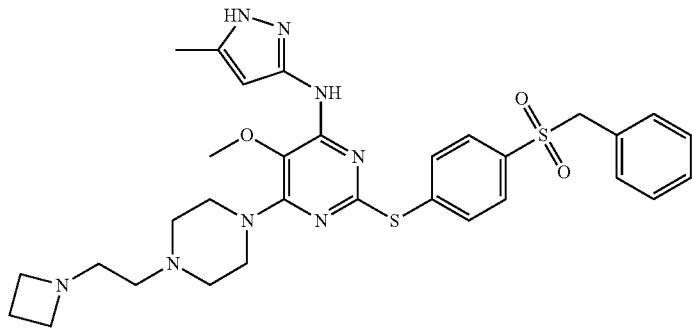 [SMILES: COc1c(Nc2cc(C)[nH]n2)nc(Sc2ccc(S(=O)(=O)Cc3ccccc3)cc2)nc1N1CCN(CCN2CCC2)CC1]
Activity XXX
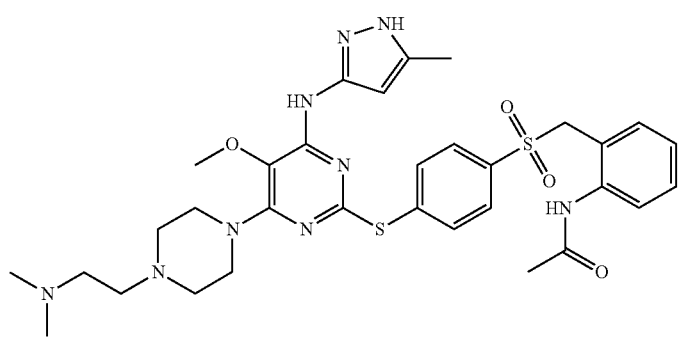 [SMILES: COc1c(Nc2cc(C)[nH]n2)nc(Sc2ccc(S(=O)(=O)Cc3ccccc3NC(C)=O)cc2)nc1N1CCN(CCN(C)C)CC1]
XXX
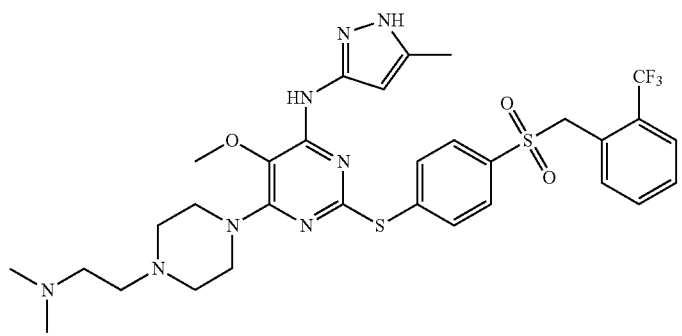 [SMILES: COc1c(Nc2cc(C)[nH]n2)nc(Sc2ccc(S(=O)(=O)Cc3ccccc3C(F)(F)F)cc2)nc1N1CCN(CCN(C)C)CC1]
XXX
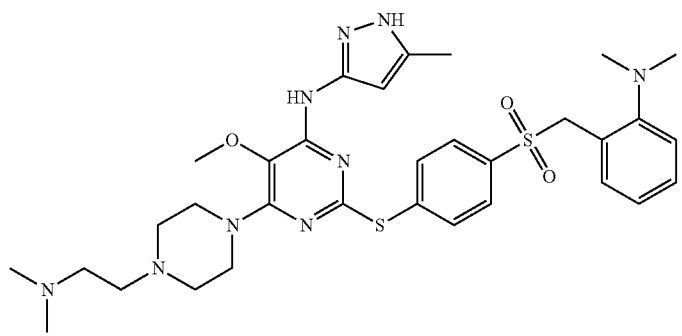
XXX TABLE 1-continued
| | |
|---|---|
| 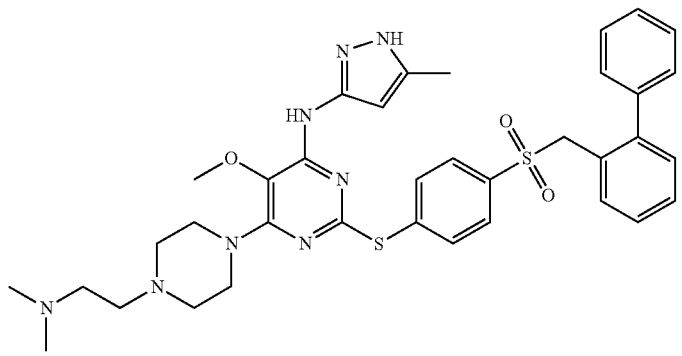 [SMILES: COc1c(Nc2cc(C)[nH]n2)nc(Sc2ccc(S(=O)(=O)Cc3ccccc3-c3ccccc3)cc2)nc1N1CCN(CCN(C)C)CC1] | Activity XXX |
| 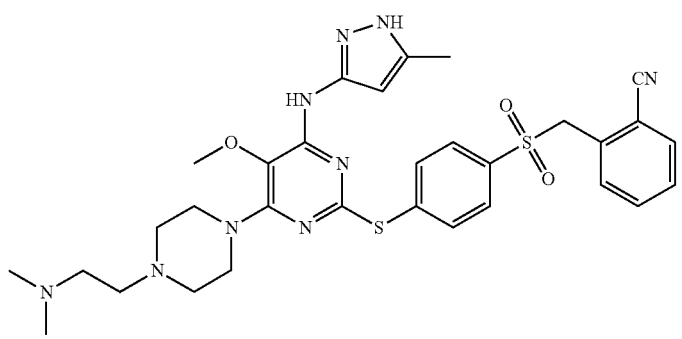 [SMILES: COc1c(Nc2cc(C)[nH]n2)nc(Sc2ccc(S(=O)(=O)Cc3ccccc3C#N)cc2)nc1N1CCN(CCN(C)C)CC1] | XXX |
| 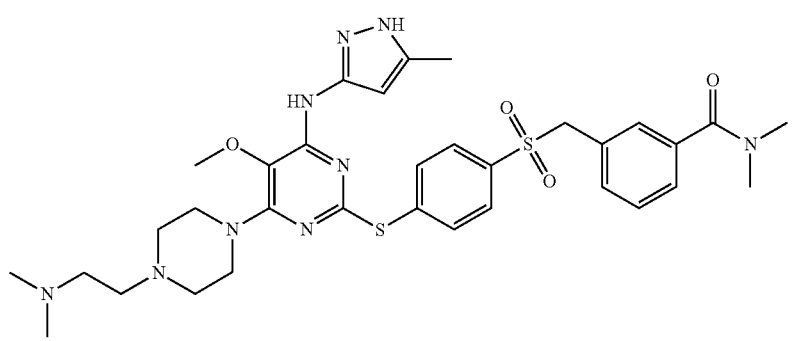 | XXX |
| 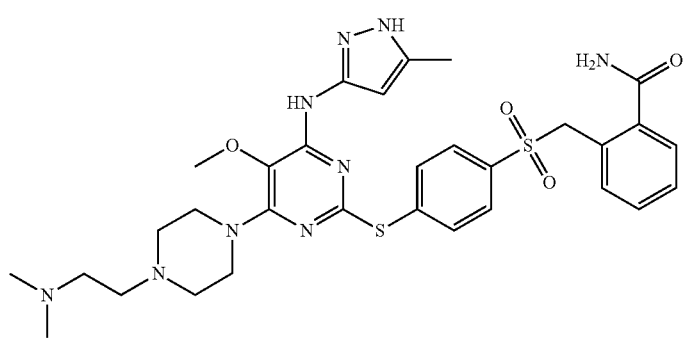 [SMILES: COc1c(Nc2cc(C)[nH]n2)nc(Sc2ccc(S(=O)(=O)Cc3ccccc3C(N)=O)cc2)nc1N1CCN(CCN(C)C)CC1] | XXX |

| | TABLE 1-continued | |
|---|---|---|
| 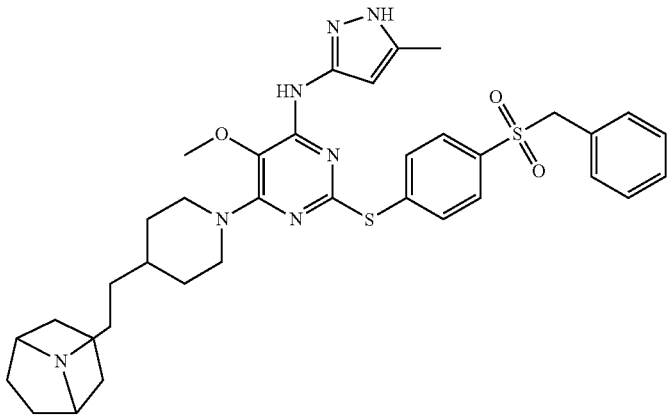 [SMILES: COc1c(Nc2cc(C)[nH]n2)nc(Sc2ccc(S(=O)(=O)Cc3ccccc3)cc2)nc1N1CCC(CCC23CC4CCC(C2)N43)CC1] | | Activity XXX |
| 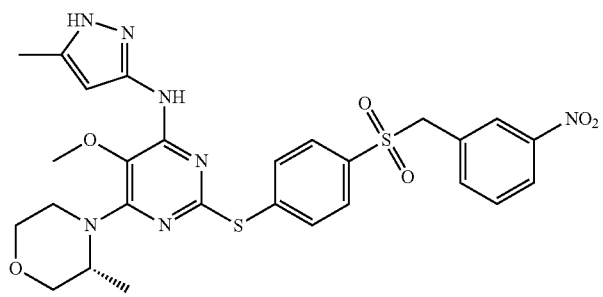 [SMILES: COc1c(Nc2cc(C)[nH]n2)nc(Sc2ccc(S(=O)(=O)Cc3cccc([N+](=O)[O-])c3)cc2)nc1N1CCOC[C@H]1C] | | XXX |
| 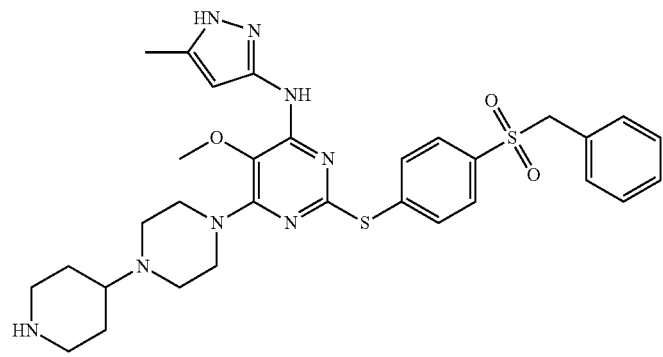 [SMILES: COc1c(Nc2cc(C)[nH]n2)nc(Sc2ccc(S(=O)(=O)Cc3ccccc3)cc2)nc1N1CCN(C2CCNCC2)CC1] | | XXX |
| 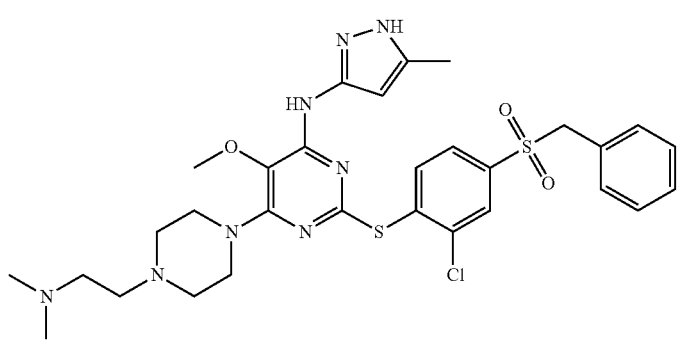 [SMILES: COc1c(Nc2cc(C)[nH]n2)nc(Sc2ccc(S(=O)(=O)Cc3ccccc3)cc2Cl)nc1N1CCN(CCN(C)C)CC1] | | XXX |

US 10,752,612 B2
TABLE 1-continued
| | |
|---|---|
| 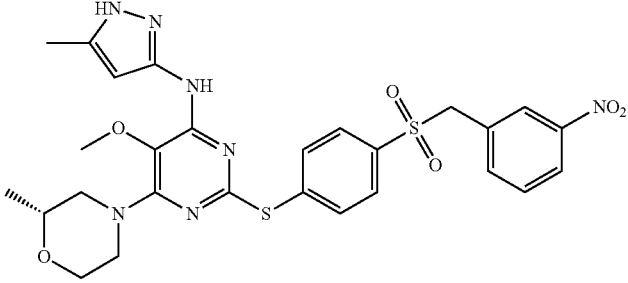 [SMILES: COc1c(Nc2cc(C)[nH]n2)nc(Sc2ccc(S(=O)(=O)Cc3cccc([N+](=O)[O-])c3)cc2)nc1N1CCO[C@H](C)C1] | Activity XXX |
| 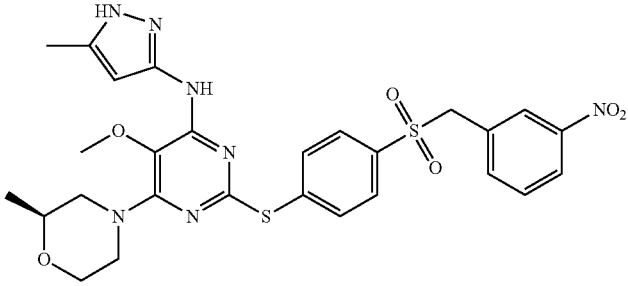 [SMILES: COc1c(Nc2cc(C)[nH]n2)nc(Sc2ccc(S(=O)(=O)Cc3cccc([N+](=O)[O-])c3)cc2)nc1N1CCO[C@@H](C)C1] | XXX |
| 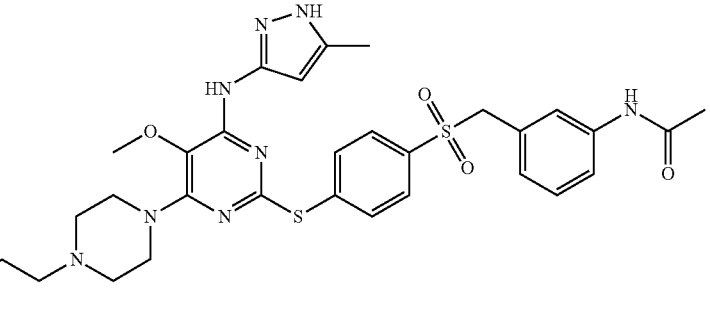 | XXX |
| 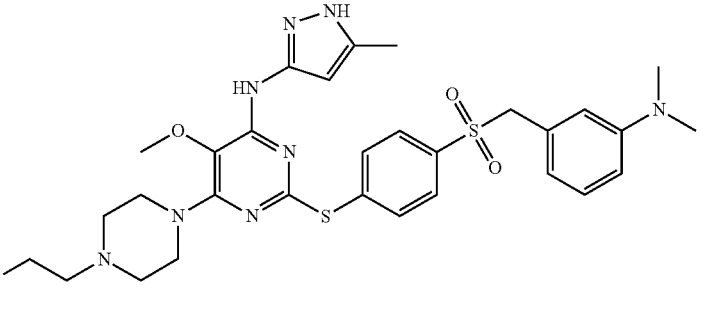 | XXX |
| 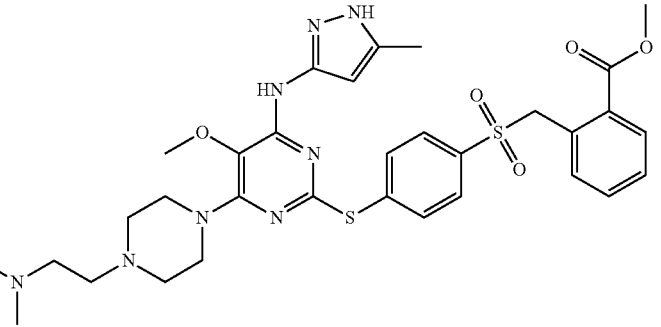 | Activity XXX |

TABLE 1-continued
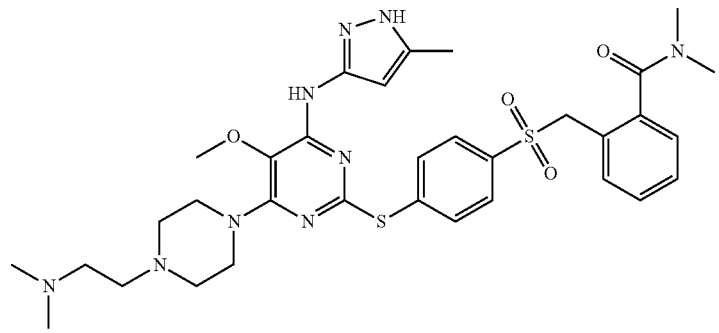
XXX
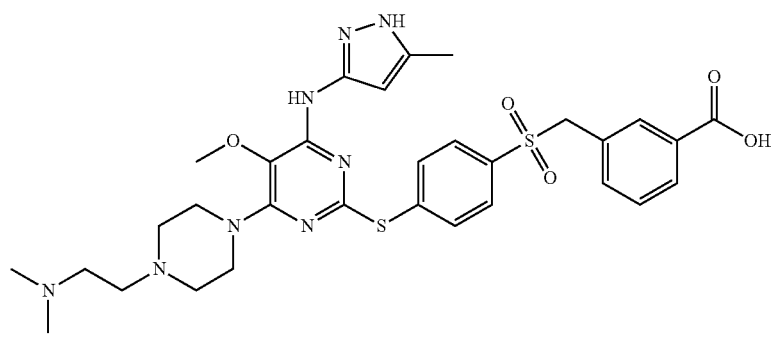 [SMILES: COc1c(Nc2cc(C)[nH]n2)nc(Sc2ccc(S(=O)(=O)Cc3cccc(C(=O)O)c3)cc2)nc1N1CCN(CCN(C)C)CC1]
XXX
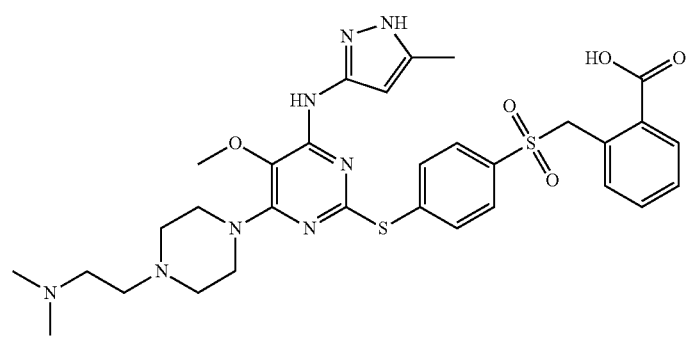 [SMILES: COc1c(Nc2cc(C)[nH]n2)nc(Sc2ccc(S(=O)(=O)Cc3ccccc3C(=O)O)cc2)nc1N1CCN(CCN(C)C)CC1]
XXX
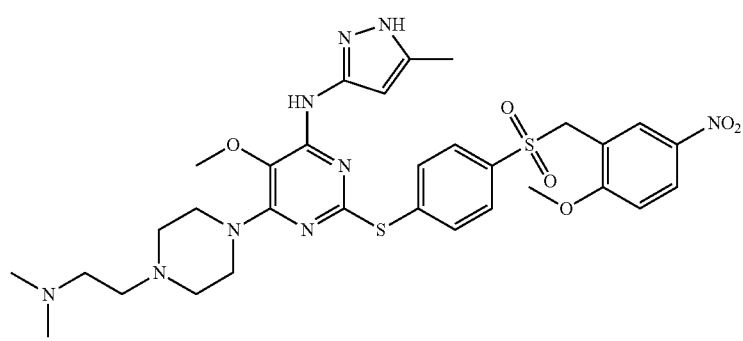 [SMILES: COc1ccc([N+](=O)[O-])cc1CS(=O)(=O)c1ccc(Sc2nc(Nc3cc(C)[nH]n3)c(OC)c(N3CCN(CCN(C)C)CC3)n2)cc1]
Activity XXX TABLE 1-continued
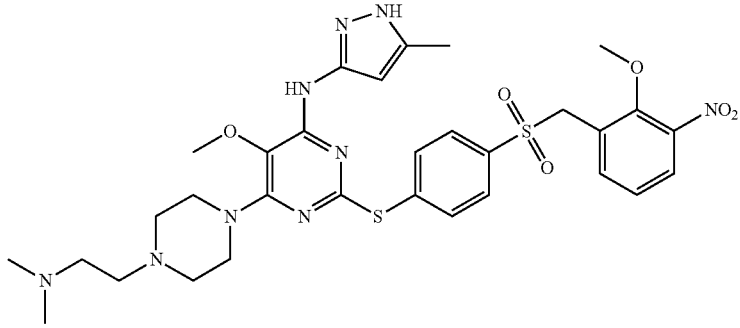 [SMILES: COc1c(CS(=O)(=O)c2ccc(Sc3nc(Nc4cc(C)[nH]n4)c(OC)c(N4CCN(CCN(C)C)CC4)n3)cc2)cccc1[N+](=O)[O-]] XXX
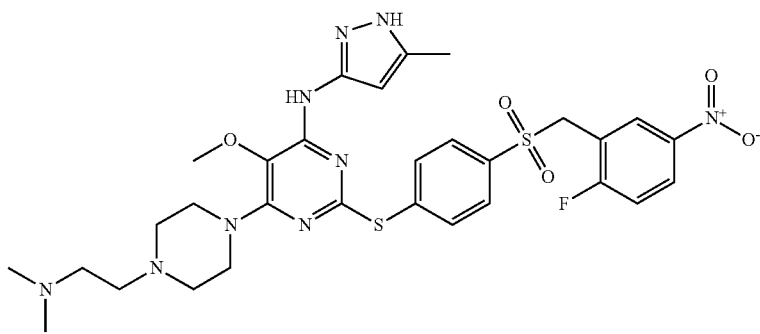 [SMILES: COc1c(Nc2cc(C)[nH]n2)nc(Sc2ccc(S(=O)(=O)Cc3cc([N+](=O)[O-])ccc3F)cc2)nc1N1CCN(CCN(C)C)CC1] XXX
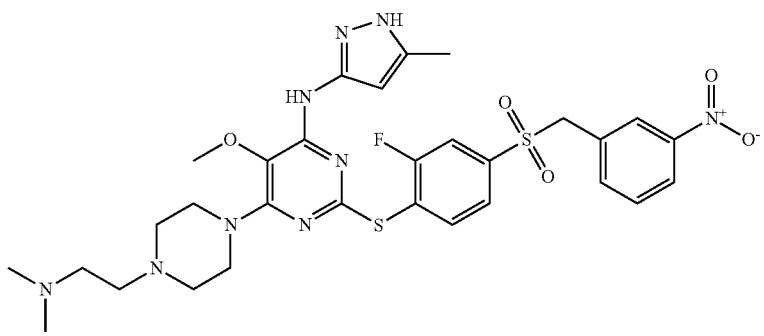 [SMILES: COc1c(Nc2cc(C)[nH]n2)nc(Sc2ccc(S(=O)(=O)Cc3cccc([N+](=O)[O-])c3)cc2F)nc1N1CCN(CCN(C)C)CC1] XXX
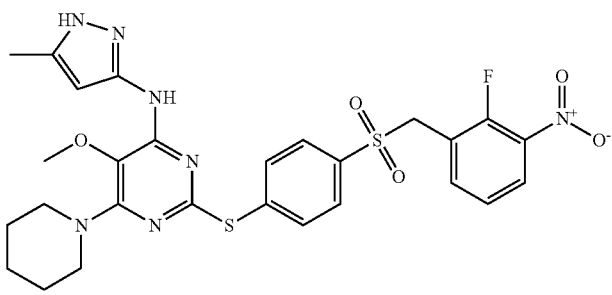 [SMILES: COc1c(Nc2cc(C)[nH]n2)nc(Sc2ccc(S(=O)(=O)Cc3cccc([N+](=O)[O-])c3F)cc2)nc1N1CCCCC1] Activity XXX
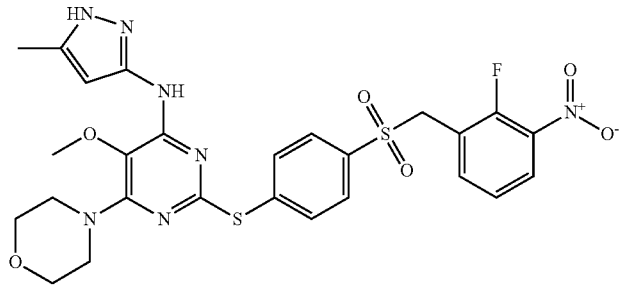 [SMILES: COc1c(Nc2cc(C)[nH]n2)nc(Sc2ccc(S(=O)(=O)Cc3cccc([N+](=O)[O-])c3F)cc2)nc1N1CCOCC1] XXX

| | |
|---|---|
| 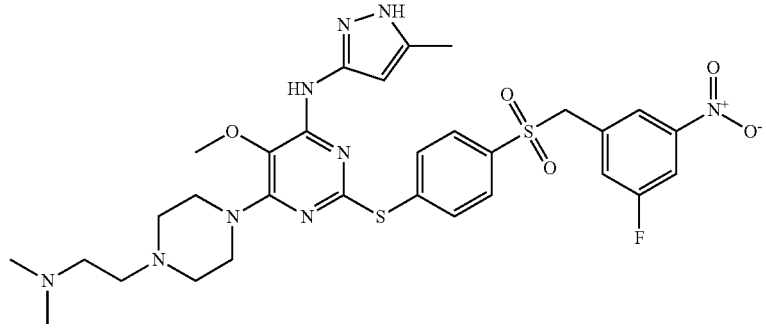 [SMILES: COc1c(Nc2cc(C)[nH]n2)nc(Sc2ccc(S(=O)(=O)Cc3cc(F)cc([N+](=O)[O-])c3)cc2)nc1N1CCN(CCN(C)C)CC1] | XXX |
| 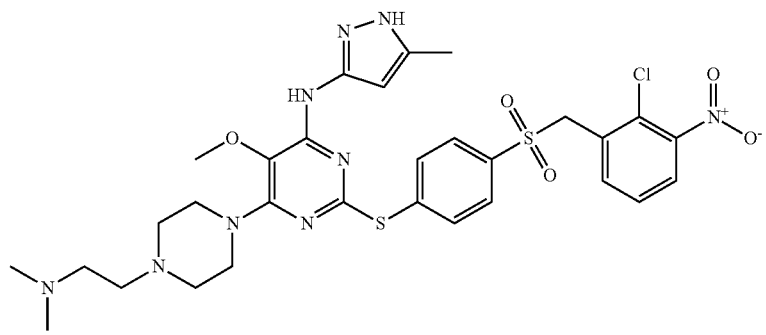 [SMILES: COc1c(Nc2cc(C)[nH]n2)nc(Sc2ccc(S(=O)(=O)Cc3cccc([N+](=O)[O-])c3Cl)cc2)nc1N1CCN(CCN(C)C)CC1] | XXX |
| 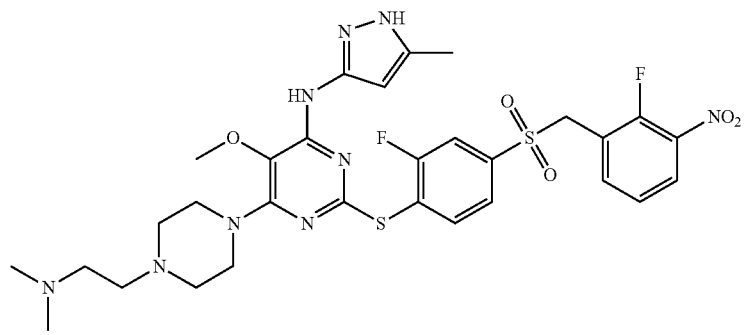 [SMILES: COc1c(Nc2cc(C)[nH]n2)nc(Sc2ccc(S(=O)(=O)Cc3cccc([N+](=O)[O-])c3F)cc2F)nc1N1CCN(CCN(C)C)CC1] | Activity XXX |
| 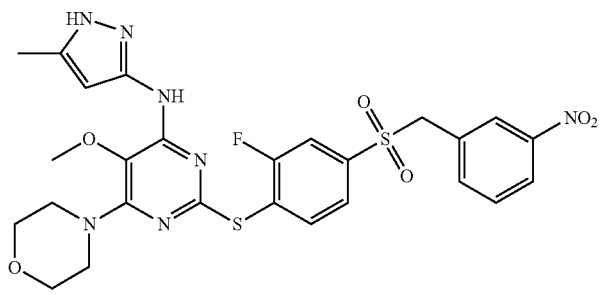 [SMILES: COc1c(Nc2cc(C)[nH]n2)nc(Sc2ccc(S(=O)(=O)Cc3cccc([N+](=O)[O-])c3)cc2F)nc1N1CCOCC1] | XXX |
| 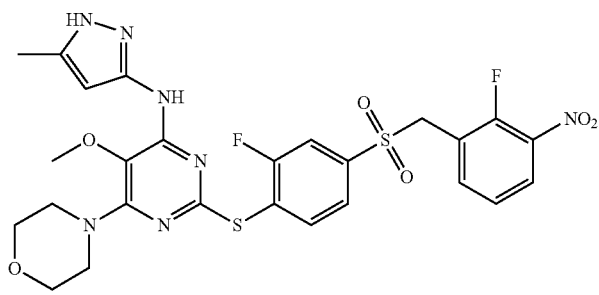 [SMILES: COc1c(Nc2cc(C)[nH]n2)nc(Sc2ccc(S(=O)(=O)Cc3cccc([N+](=O)[O-])c3F)cc2F)nc1N1CCOCC1] | XXX |

TABLE 1-continued
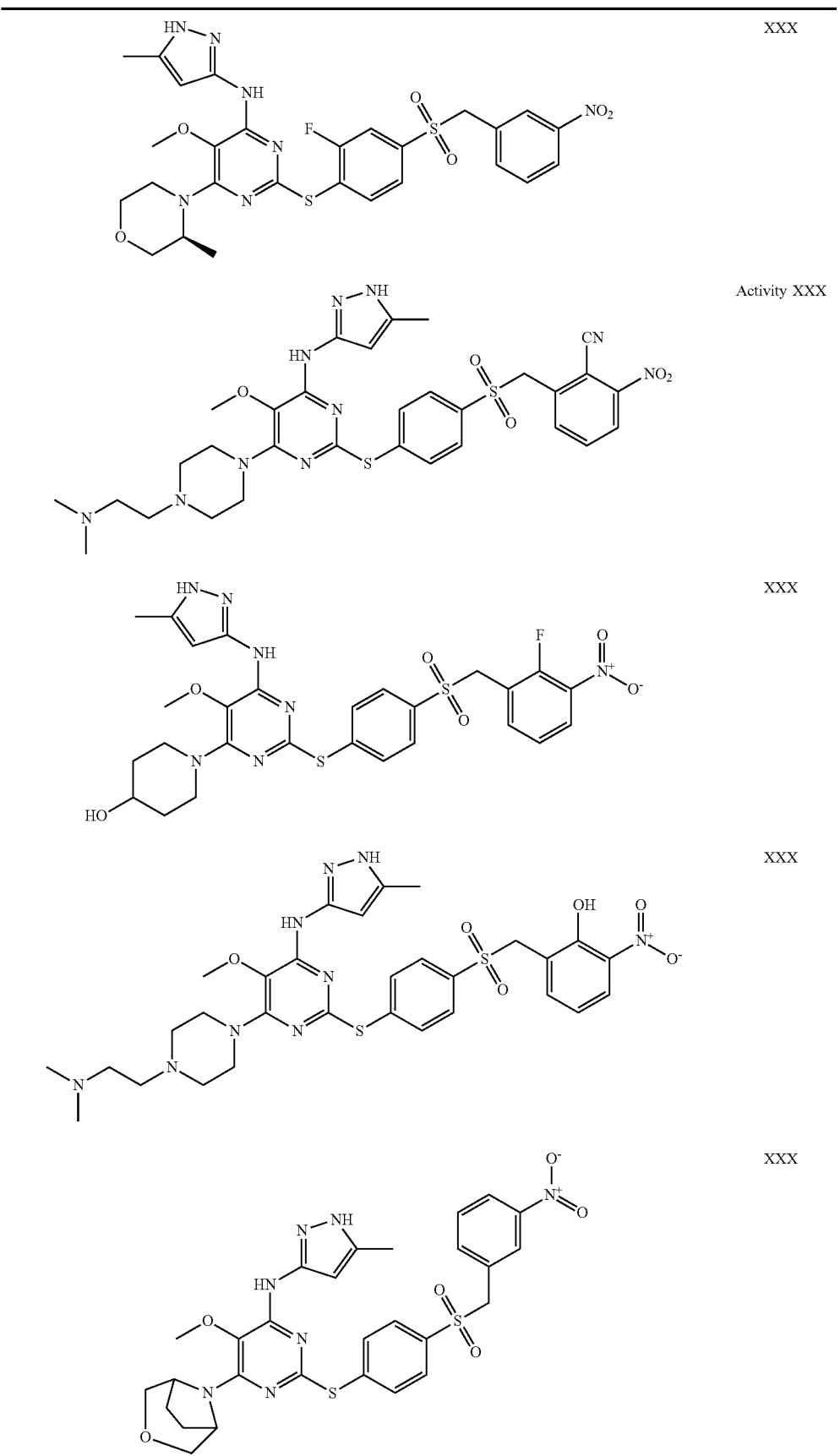
| | |
|---|---|
| | XXX |
| | Activity XXX |
| | XXX |
| | XXX |
| | XXX |

TABLE 1-continued
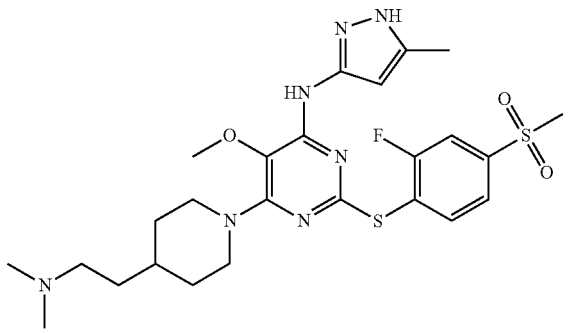 Activity XXX
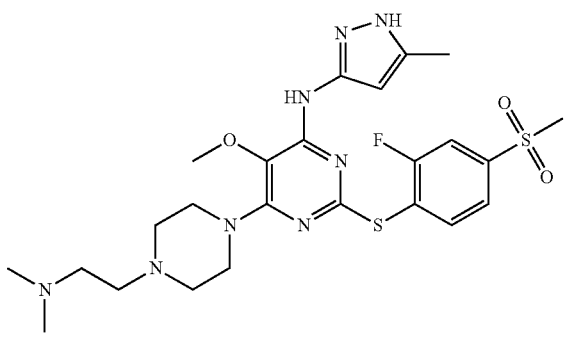 XXX
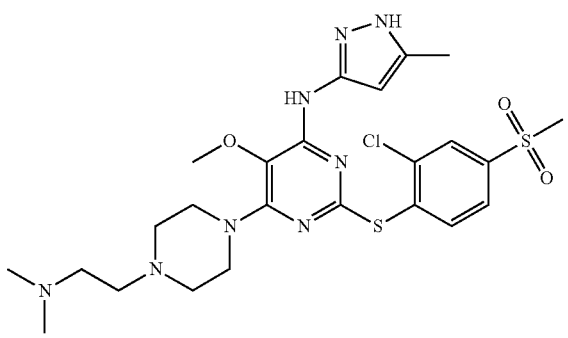 XXX
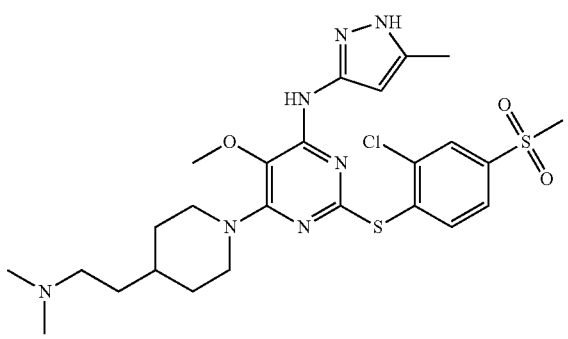 XXX
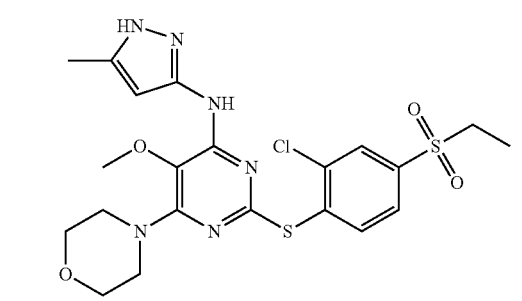 [SMILES: CCS(=O)(=O)c1ccc(Sc2nc(Nc3cc(C)[nH]n3)c(OC)c(N3CCOCC3)n2)c(Cl)c1] XXX TABLE 1-continued
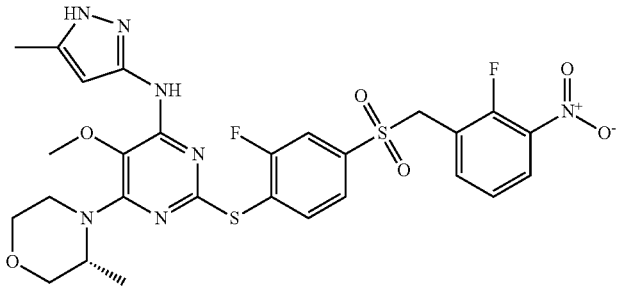 [SMILES: COc1c(Nc2cc(C)[nH]n2)nc(Sc2ccc(S(=O)(=O)Cc3cccc([N+](=O)[O-])c3F)cc2F)nc1N1CCOC[C@H]1C]
Activity XXX
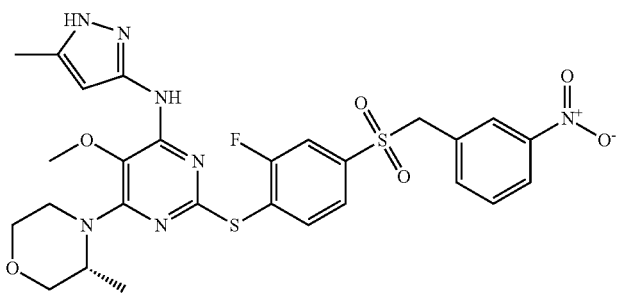 [SMILES: COc1c(Nc2cc(C)[nH]n2)nc(Sc2ccc(S(=O)(=O)Cc3cccc([N+](=O)[O-])c3)cc2F)nc1N1CCOC[C@H]1C]
XXX
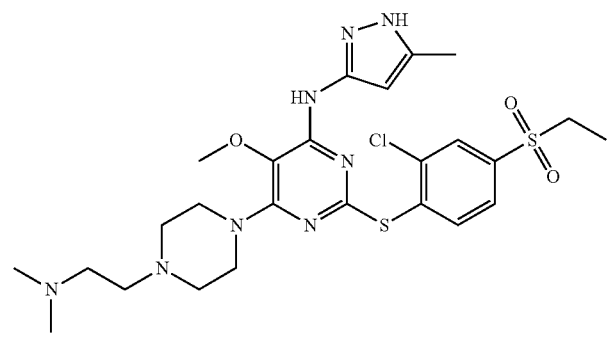
XXX
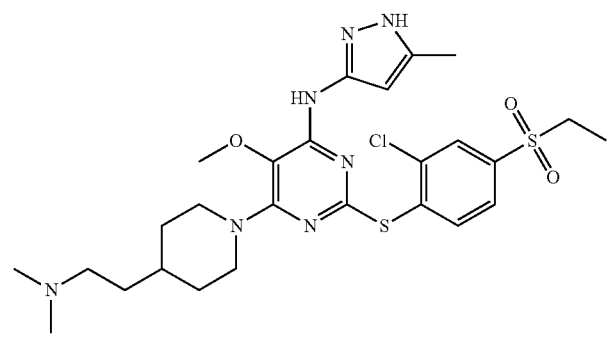
XXX
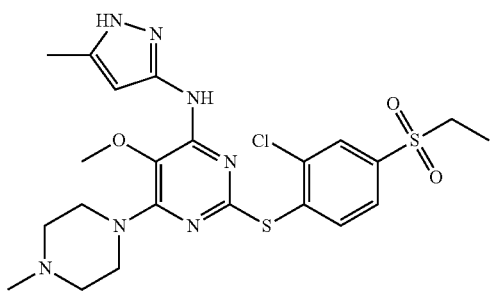 [SMILES: CCS(=O)(=O)c1ccc(Sc2nc(Nc3cc(C)[nH]n3)c(OC)c(N3CCN(C)CC3)n2)c(Cl)c1]
Activity XXX TABLE 1-continued
| | |
|---|---|
| 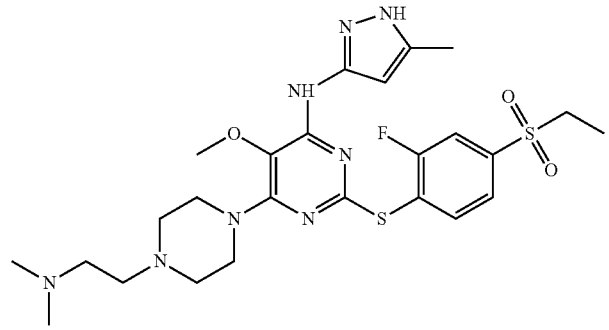 [SMILES: CCS(=O)(=O)c1ccc(Sc2nc(Nc3cc(C)[nH]n3)c(OC)c(N3CCN(CCN(C)C)CC3)n2)c(F)c1] | XXX |
| 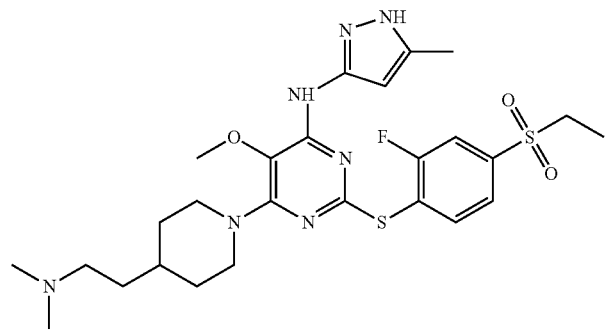 | XXX |
| 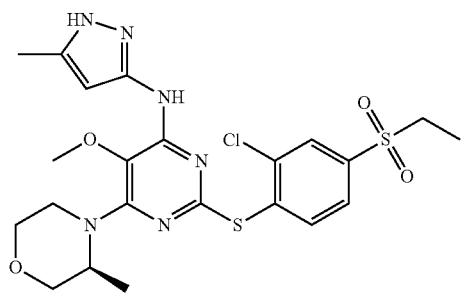 [SMILES: CCS(=O)(=O)c1ccc(Sc2nc(Nc3cc(C)[nH]n3)c(OC)c(N3CCOC[C@@H]3C)n2)c(Cl)c1] | XXX |
| 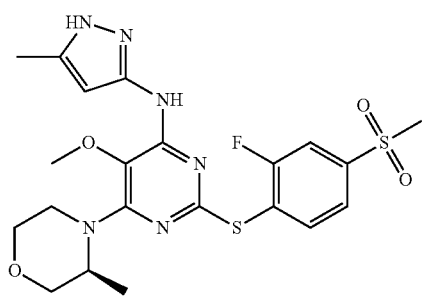 [SMILES: COc1c(Nc2cc(C)[nH]n2)nc(Sc2ccc(S(C)(=O)=O)cc2F)nc1N1CCOC[C@@H]1C] | XXX |
| 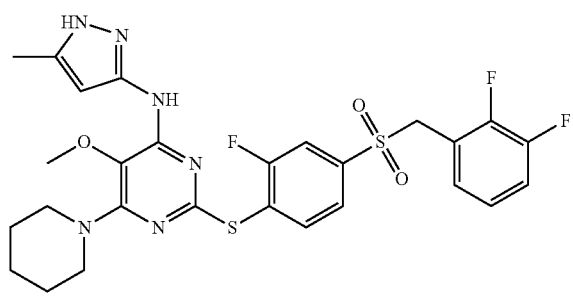 [SMILES: COc1c(Nc2cc(C)[nH]n2)nc(Sc2ccc(S(=O)(=O)Cc3cccc(F)c3F)cc2F)nc1N1CCCCC1] | Activity XXX |

TABLE 1-continued
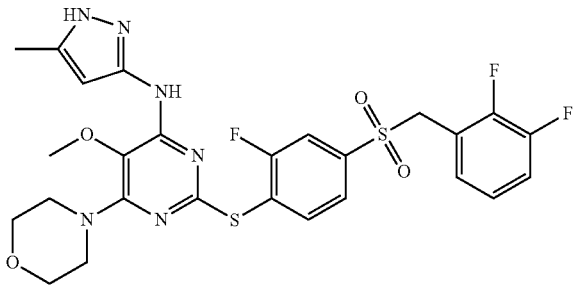 [SMILES: COc1c(Nc2cc(C)[nH]n2)nc(Sc2ccc(S(=O)(=O)Cc3cccc(F)c3F)cc2F)nc1N1CCOCC1] XXX
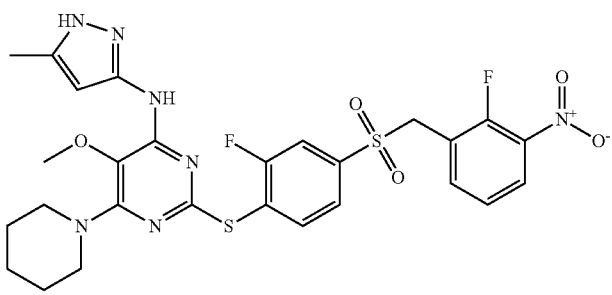 [SMILES: COc1c(Nc2cc(C)[nH]n2)nc(Sc2ccc(S(=O)(=O)Cc3cccc([N+](=O)[O-])c3F)cc2F)nc1N1CCCCC1] XXX
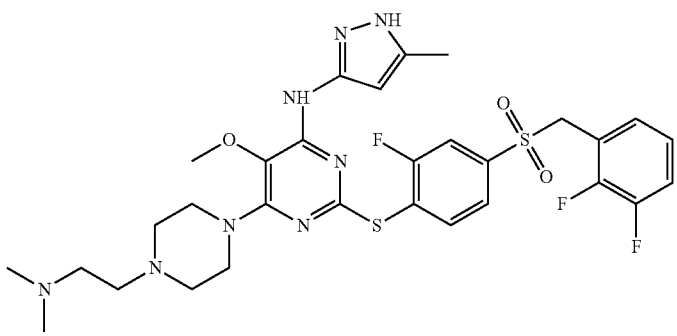 [SMILES: COc1c(Nc2cc(C)[nH]n2)nc(Sc2ccc(S(=O)(=O)Cc3cccc(F)c3F)cc2F)nc1N1CCN(CCN(C)C)CC1] XXX
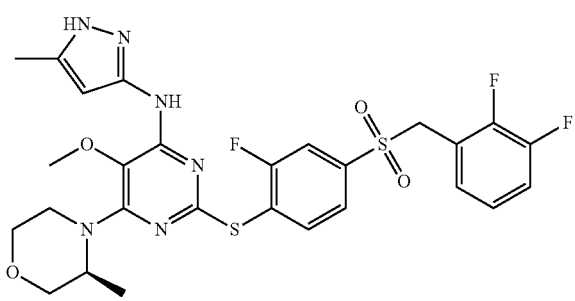 [SMILES: COc1c(Nc2cc(C)[nH]n2)nc(Sc2ccc(S(=O)(=O)Cc3cccc(F)c3F)cc2F)nc1N1CCOC[C@@H]1C] Activity XXX
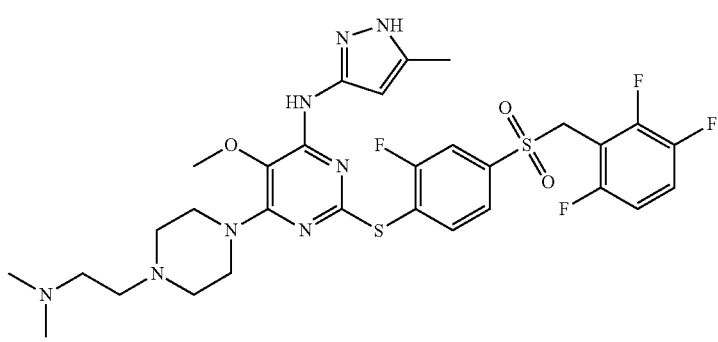 [SMILES: COc1c(Nc2cc(C)[nH]n2)nc(Sc2ccc(S(=O)(=O)Cc3c(F)ccc(F)c3F)cc2F)nc1N1CCN(CCN(C)C)CC1] XXX TABLE 1-continued
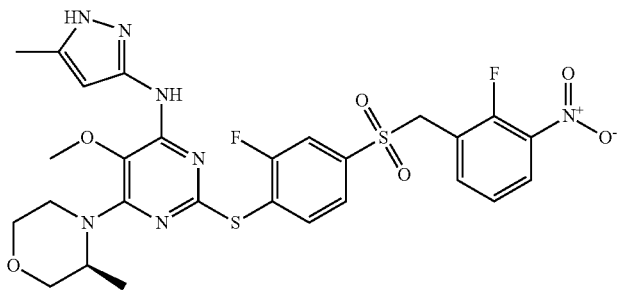 [SMILES: COc1c(Nc2cc(C)[nH]n2)nc(Sc2ccc(S(=O)(=O)Cc3cccc([N+](=O)[O-])c3F)cc2F)nc1N1CCOC[C@@H]1C] XXX
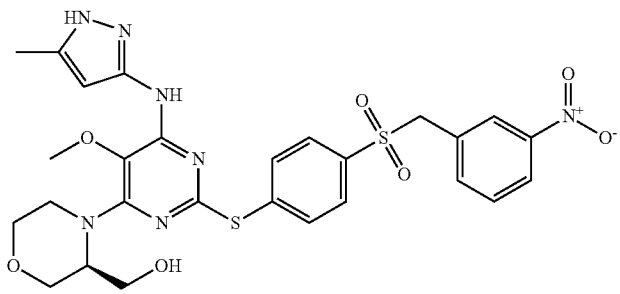 [SMILES: COc1c(Nc2cc(C)[nH]n2)nc(Sc2ccc(S(=O)(=O)Cc3cccc([N+](=O)[O-])c3)cc2)nc1N1CCOC[C@@H]1CO] XXX
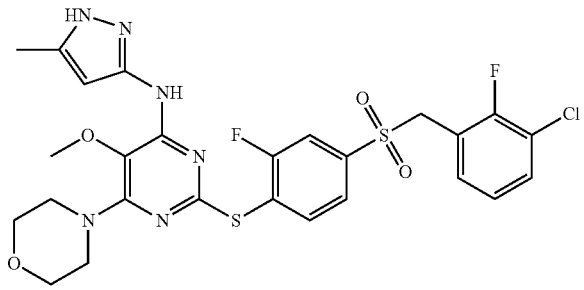 [SMILES: COc1c(Nc2cc(C)[nH]n2)nc(Sc2ccc(S(=O)(=O)Cc3cccc(Cl)c3F)cc2F)nc1N1CCOCC1] Activity XXX
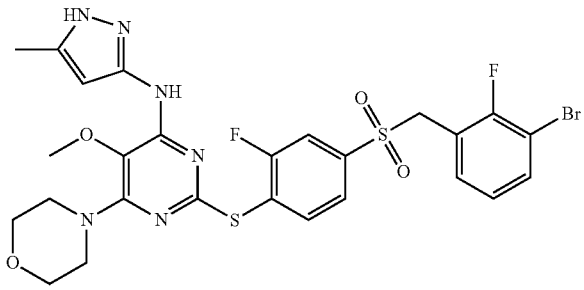 [SMILES: COc1c(Nc2cc(C)[nH]n2)nc(Sc2ccc(S(=O)(=O)Cc3cccc(Br)c3F)cc2F)nc1N1CCOCC1] XXX
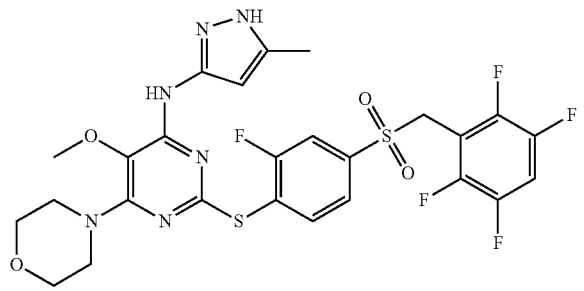 [SMILES: COc1c(Nc2cc(C)[nH]n2)nc(Sc2ccc(S(=O)(=O)Cc3c(F)c(F)cc(F)c3F)cc2F)nc1N1CCOCC1] XXX TABLE 1-continued
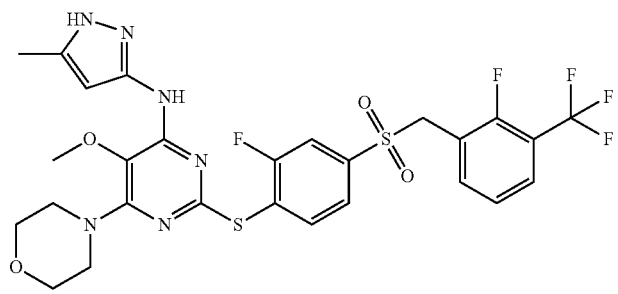 [SMILES: COc1c(Nc2cc(C)[nH]n2)nc(Sc2ccc(S(=O)(=O)Cc3cccc(C(F)(F)F)c3F)cc2F)nc1N1CCOCC1]
XXX
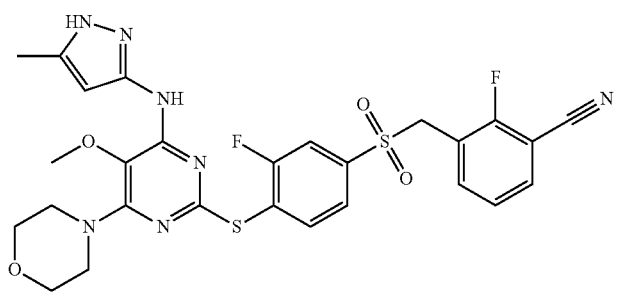 [SMILES: COc1c(Nc2cc(C)[nH]n2)nc(Sc2ccc(S(=O)(=O)Cc3cccc(C#N)c3F)cc2F)nc1N1CCOCC1]
Activity XXX
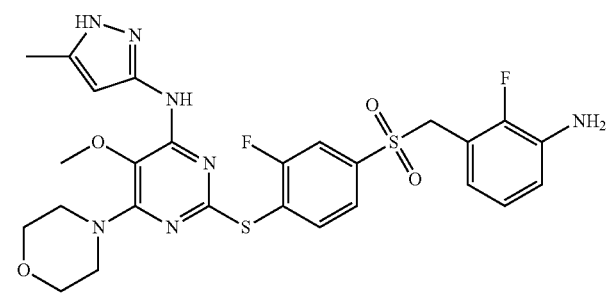
XXX
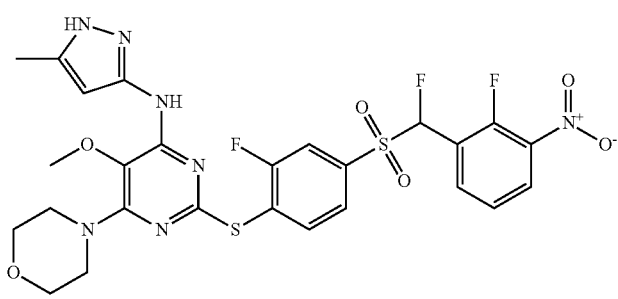 [SMILES: COc1c(Nc2cc(C)[nH]n2)nc(Sc2ccc(S(=O)(=O)C(F)c3cccc([N+](=O)[O-])c3F)cc2F)nc1N1CCOCC1]
XXX
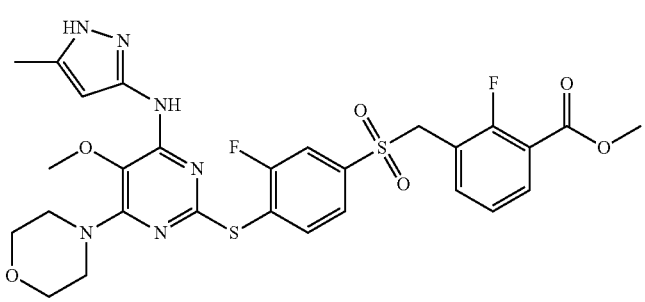
XXX

| | |
|---|---|
| 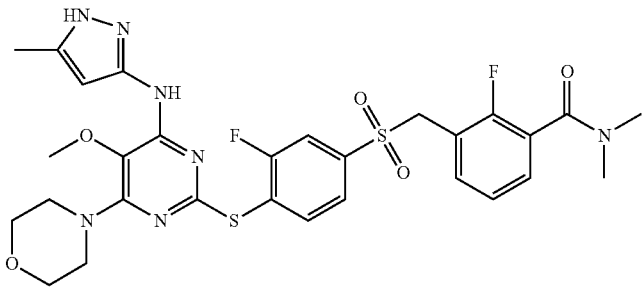 [SMILES: COc1c(Nc2cc(C)[nH]n2)nc(Sc2ccc(S(=O)(=O)Cc3cccc(C(=O)N(C)C)c3F)cc2F)nc1N1CCOCC1] | Activity XXX |
| 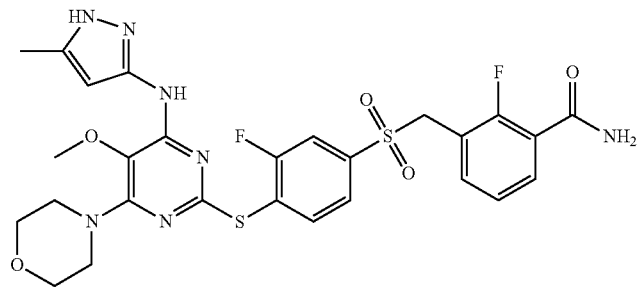 [SMILES: COc1c(Nc2cc(C)[nH]n2)nc(Sc2ccc(S(=O)(=O)Cc3cccc(C(N)=O)c3F)cc2F)nc1N1CCOCC1] | XXX |
| 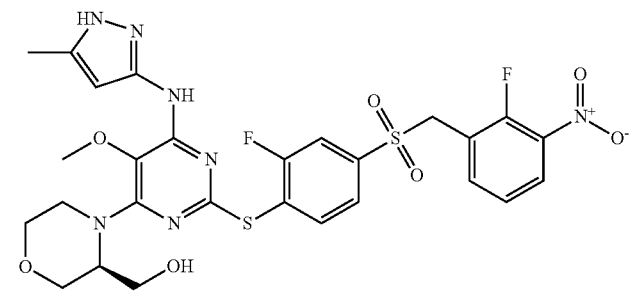 [SMILES: COc1c(Nc2cc(C)[nH]n2)nc(Sc2ccc(S(=O)(=O)Cc3cccc([N+](=O)[O-])c3F)cc2F)nc1N1CCOC[C@@H]1CO] | XXX |
| 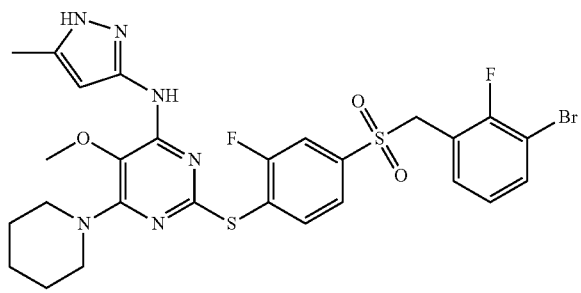 [SMILES: COc1c(Nc2cc(C)[nH]n2)nc(Sc2ccc(S(=O)(=O)Cc3cccc(Br)c3F)cc2F)nc1N1CCCCC1] | XXX |
| 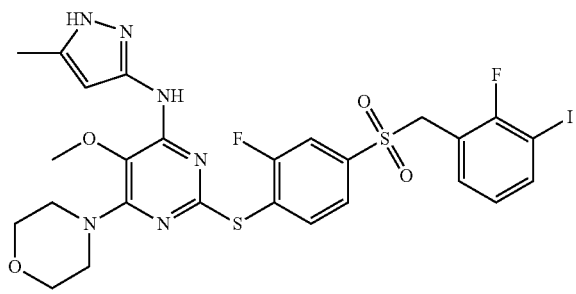 [SMILES: COc1c(Nc2cc(C)[nH]n2)nc(Sc2ccc(S(=O)(=O)Cc3cccc(I)c3F)cc2F)nc1N1CCOCC1] | Activity XXX |

TABLE 1-continued
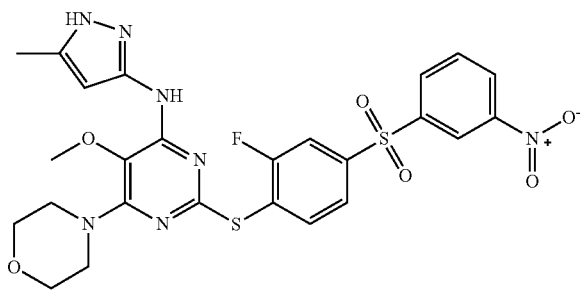 [SMILES: COc1c(Nc2cc(C)[nH]n2)nc(Sc2ccc(S(=O)(=O)c3cccc([N+](=O)[O-])c3)cc2F)nc1N1CCOCC1]
XXX
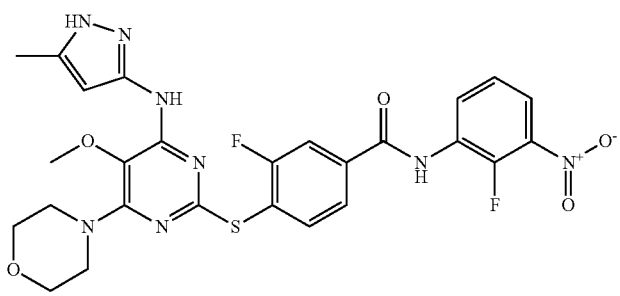 [SMILES: COc1c(Nc2cc(C)[nH]n2)nc(Sc2ccc(C(=O)Nc3cccc([N+](=O)[O-])c3F)cc2F)nc1N1CCOCC1]
XXX
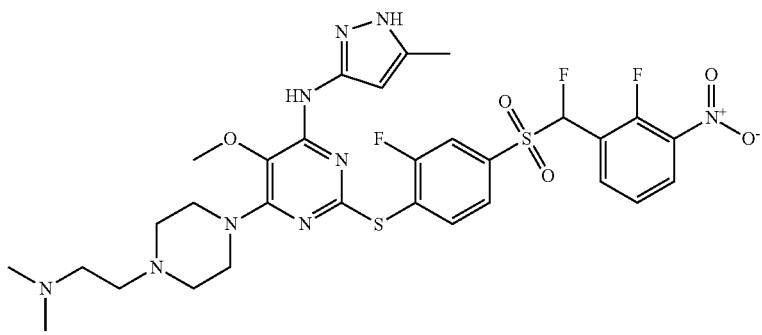
XXX
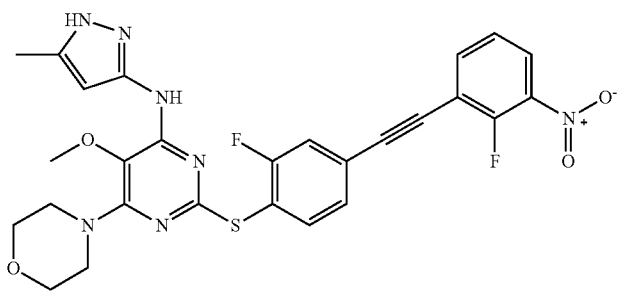 [SMILES: COc1c(Nc2cc(C)[nH]n2)nc(Sc2ccc(C#Cc3cccc([N+](=O)[O-])c3F)cc2F)nc1N1CCOCC1]
Activity XXX
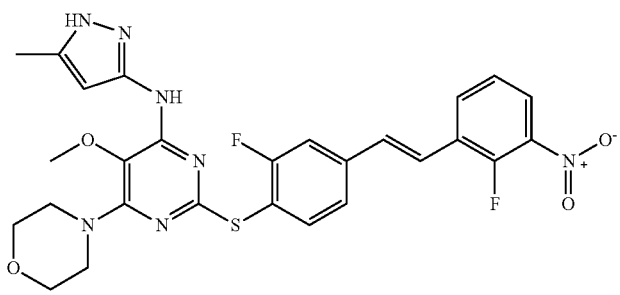 [SMILES: COc1c(Nc2cc(C)[nH]n2)nc(Sc2ccc(/C=C/c3cccc([N+](=O)[O-])c3F)cc2F)nc1N1CCOCC1]
XXX TABLE 1-continued
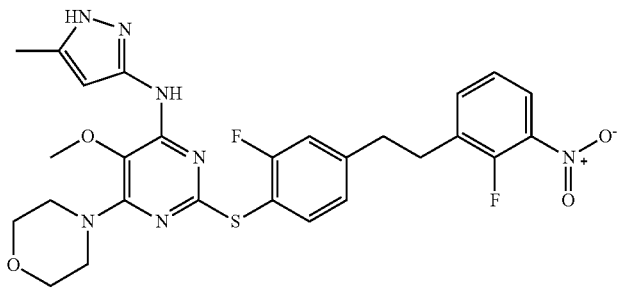 [SMILES: COc1c(Nc2cc(C)[nH]n2)nc(Sc2ccc(CCc3cccc([N+](=O)[O-])c3F)cc2F)nc1N1CCOCC1] XXX
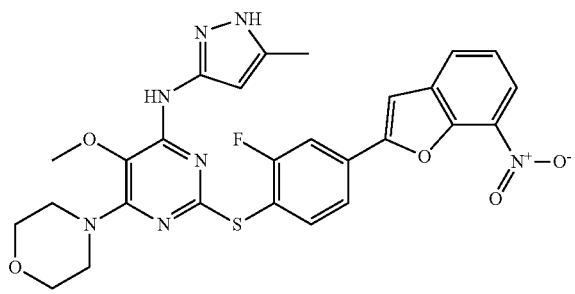 [SMILES: COc1c(Nc2cc(C)[nH]n2)nc(Sc2ccc(-c3cc4cccc([N+](=O)[O-])c4o3)cc2F)nc1N1CCOCC1] XXX
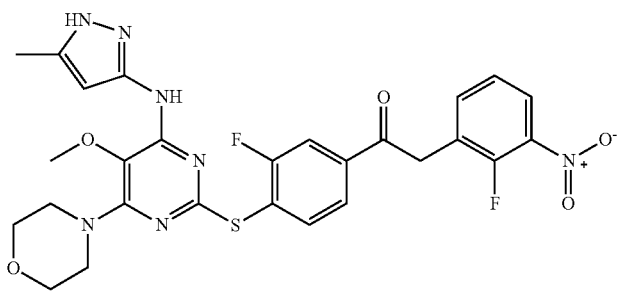 Activity XXX
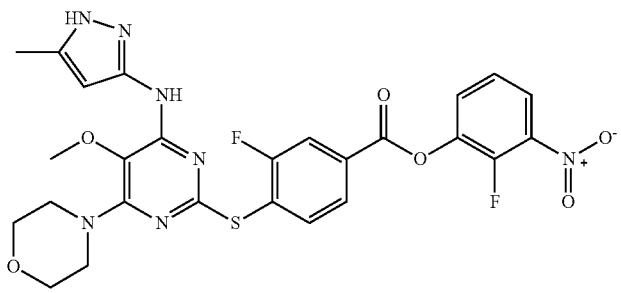 [SMILES: COc1c(Nc2cc(C)[nH]n2)nc(Sc2ccc(C(=O)Cc3cccc([N+](=O)[O-])c3F)cc2F)nc1N1CCOCC1] XXX
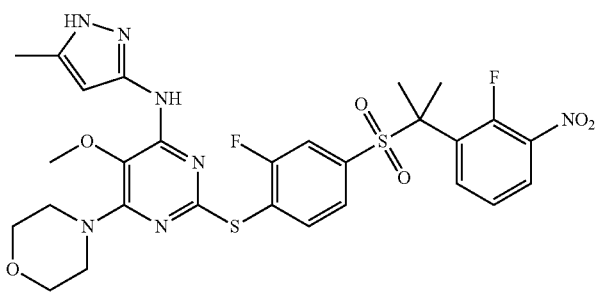 [SMILES: COc1c(Nc2cc(C)[nH]n2)nc(Sc2ccc(S(=O)(=O)C(C)(C)c3cccc([N+](=O)[O-])c3F)cc2F)nc1N1CCOCC1] XXX TABLE 1-continued
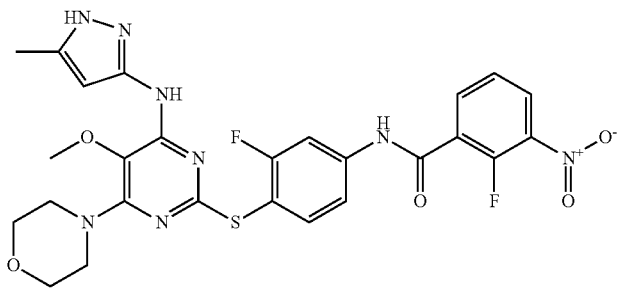 [SMILES: COc1c(Nc2cc(C)[nH]n2)nc(Sc2ccc(NC(=O)c3cccc([N+](=O)[O-])c3F)cc2F)nc1N1CCOCC1] XX
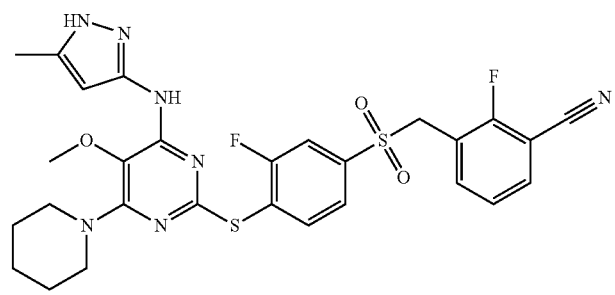 [SMILES: COc1c(Nc2cc(C)[nH]n2)nc(Sc2ccc(S(=O)(=O)Cc3cccc(C#N)c3F)cc2F)nc1N1CCCCC1] Activity XXX
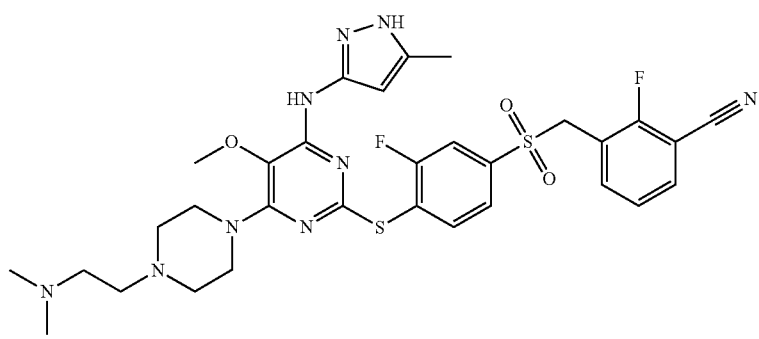 [SMILES: COc1c(Nc2cc(C)[nH]n2)nc(Sc2ccc(S(=O)(=O)Cc3cccc(C#N)c3F)cc2F)nc1N1CCN(CCN(C)C)CC1] XXX
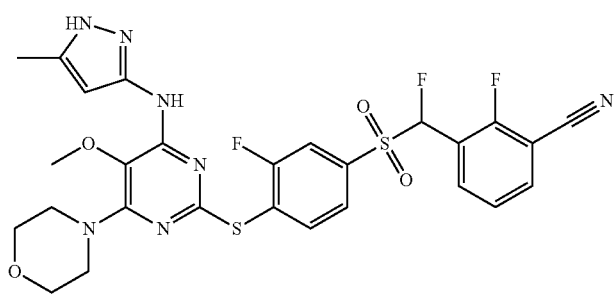 [SMILES: COc1c(Nc2cc(C)[nH]n2)nc(Sc2ccc(S(=O)(=O)C(F)c3cccc(C#N)c3F)cc2F)nc1N1CCOCC1] XXX
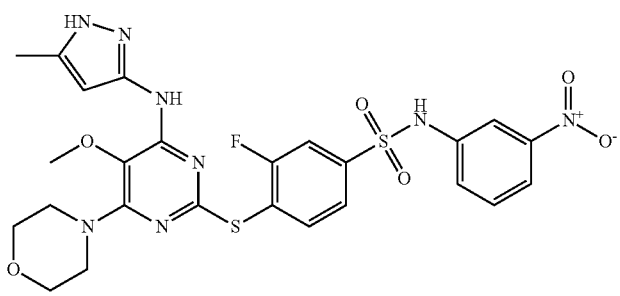 [SMILES: COc1c(Nc2cc(C)[nH]n2)nc(Sc2ccc(S(=O)(=O)Nc3cccc([N+](=O)[O-])c3)cc2F)nc1N1CCOCC1] XXX TABLE 1-continued
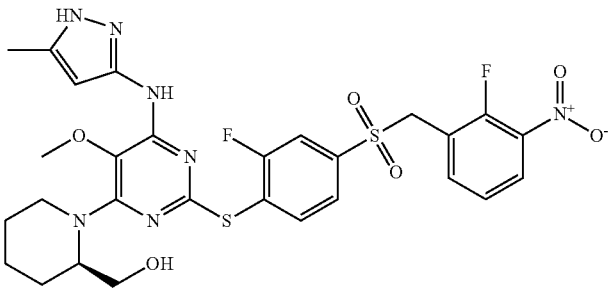 [SMILES: COc1c(Nc2cc(C)[nH]n2)nc(Sc2ccc(S(=O)(=O)Cc3cccc([N+](=O)[O-])c3F)cc2F)nc1N1CCCC[C@@H]1CO] Activity XXX
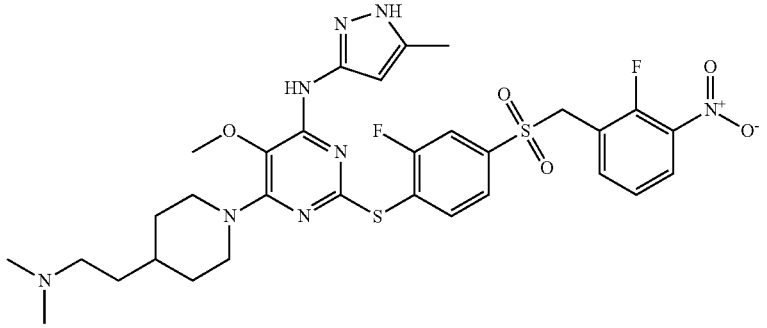 [SMILES: COc1c(Nc2cc(C)[nH]n2)nc(Sc2ccc(S(=O)(=O)Cc3cccc([N+](=O)[O-])c3F)cc2F)nc1N1CCC(CCN(C)C)CC1] XXX
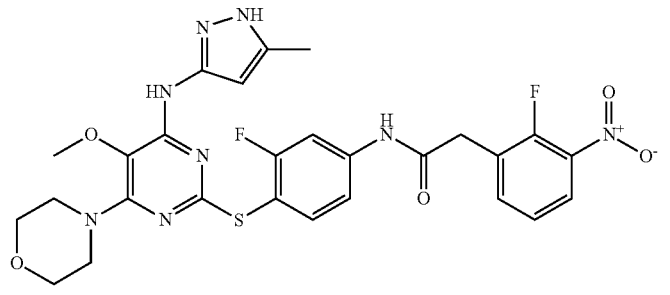 [SMILES: COc1c(Nc2cc(C)[nH]n2)nc(Sc2ccc(NC(=O)Cc3cccc([N+](=O)[O-])c3F)cc2F)nc1N1CCOCC1] XXX
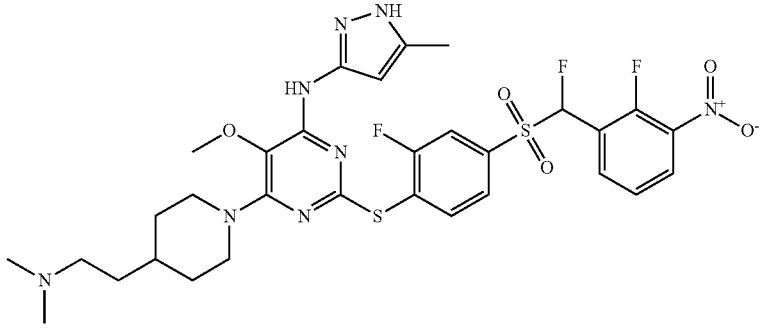 [SMILES: COc1c(Nc2cc(C)[nH]n2)nc(Sc2ccc(S(=O)(=O)C(F)c3cccc([N+](=O)[O-])c3F)cc2F)nc1N1CCC(CCN(C)C)CC1] XXX
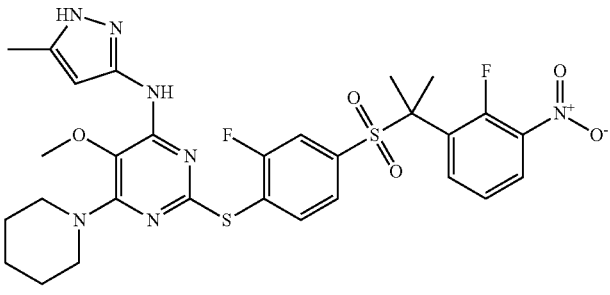 [SMILES: COc1c(Nc2cc(C)[nH]n2)nc(Sc2ccc(S(=O)(=O)C(C)(C)c3cccc([N+](=O)[O-])c3F)cc2F)nc1N1CCCCC1] Activity XXX TABLE 1-continued
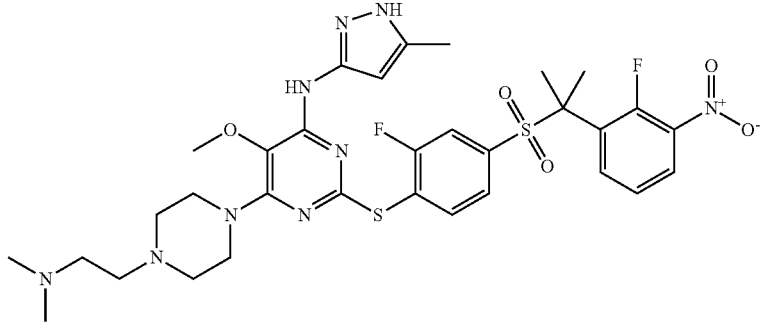 [SMILES: COc1c(Nc2cc(C)[nH]n2)nc(Sc2ccc(S(=O)(=O)C(C)(C)c3cccc([N+](=O)[O-])c3F)cc2F)nc1N1CCN(CCN(C)C)CC1] XXX
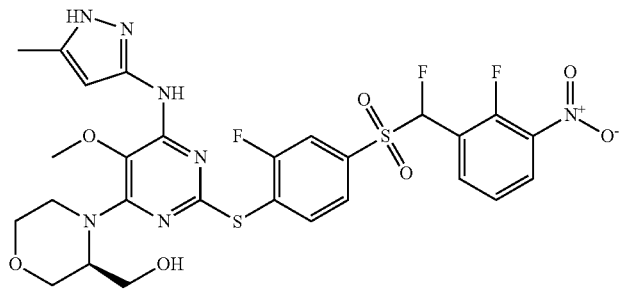 [SMILES: COc1c(Nc2cc(C)[nH]n2)nc(Sc2ccc(S(=O)(=O)C(F)c3cccc([N+](=O)[O-])c3F)cc2F)nc1N1CCOC[C@@H]1CO] XXX
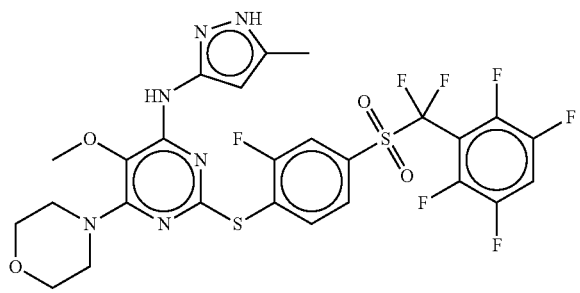 XXX
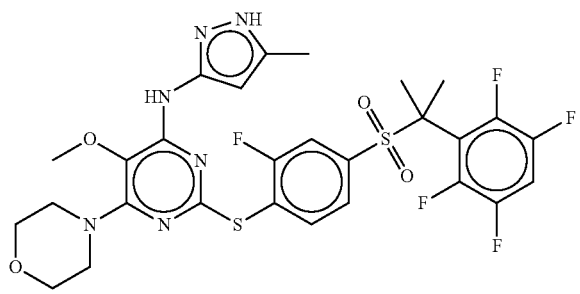 Activity XXX
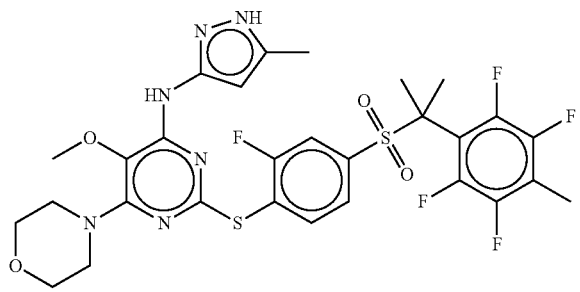 XXX TABLE 1-continued
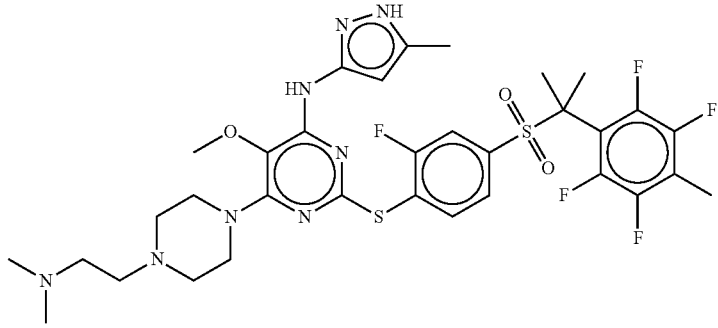
XXX
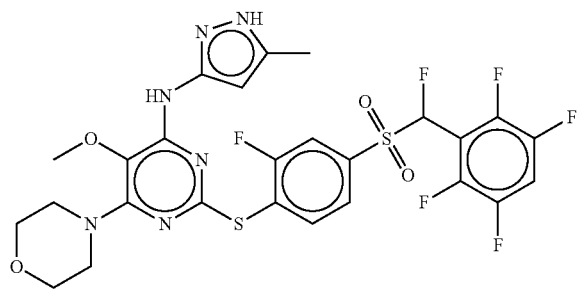
XXX
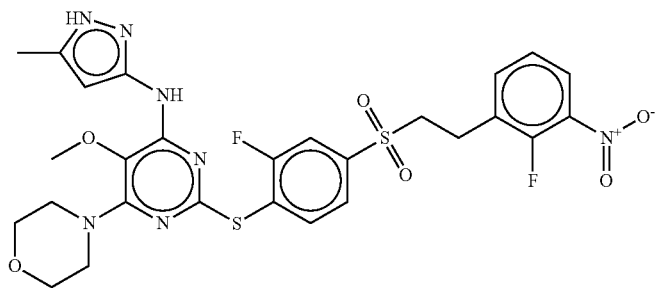
Activity XXX
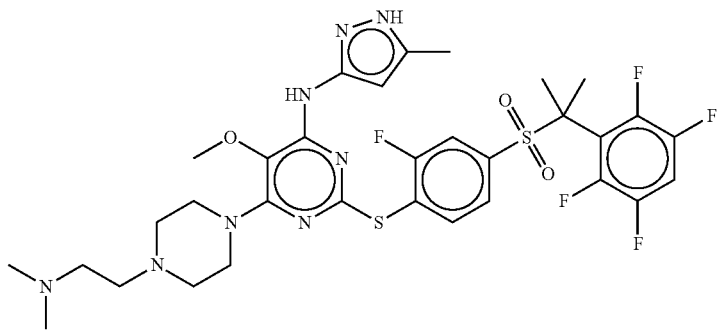
XXX
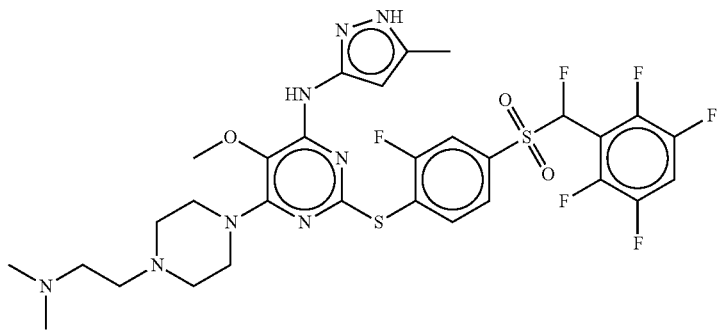
XXX

| | |
|---|---|
| 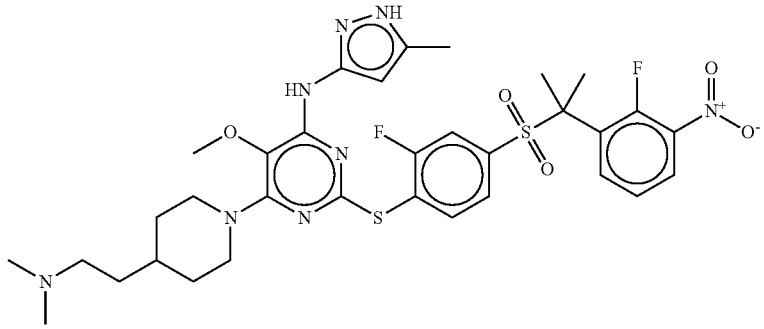 | XXX |
| 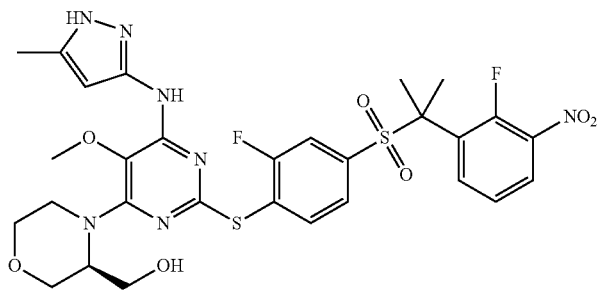 [SMILES: COc1c(Nc2cc(C)[nH]n2)nc(Sc2ccc(S(=O)(=O)C(C)(C)c3cccc([N+](=O)[O-])c3F)cc2F)nc1N1CCOC[C@@H]1CO] | Activity XXX |
| 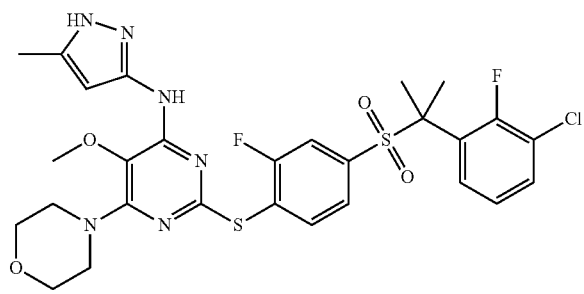 [SMILES: COc1c(Nc2cc(C)[nH]n2)nc(Sc2ccc(S(=O)(=O)C(C)(C)c3cccc(Cl)c3F)cc2F)nc1N1CCOCC1] | XXX |
| 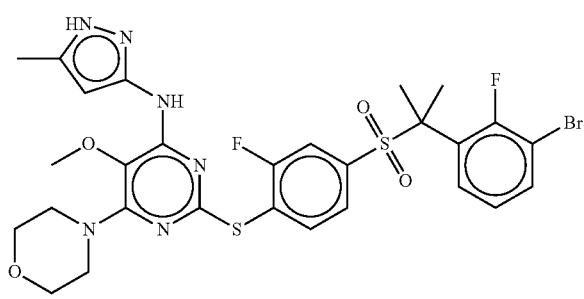 | XXX |
| 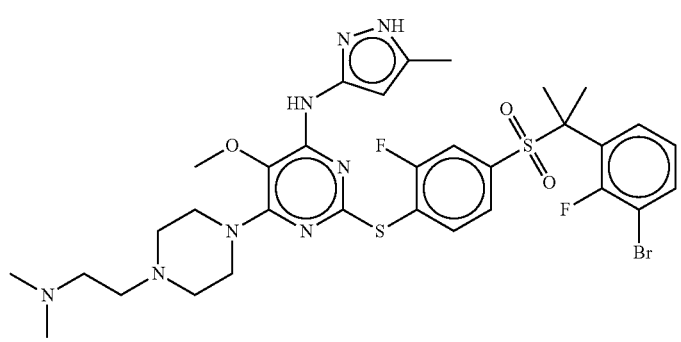 | XXX |

TABLE 1-continued
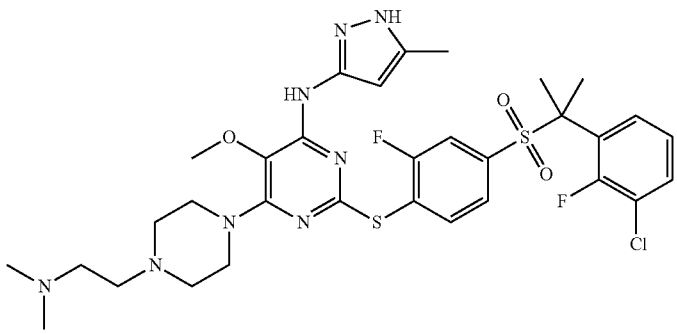 [SMILES: COc1c(Nc2cc(C)[nH]n2)nc(Sc2ccc(S(=O)(=O)C(C)(C)c3cccc(Cl)c3F)cc2F)nc1N1CCN(CCN(C)C)CC1] Activity XXX
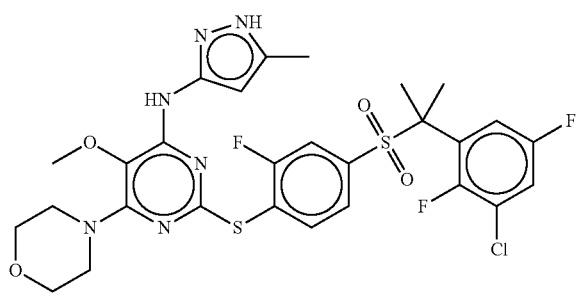 XXX
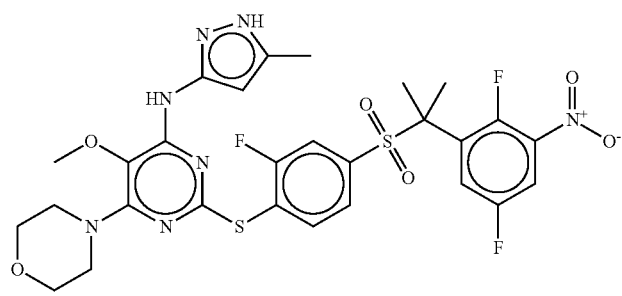 XXX
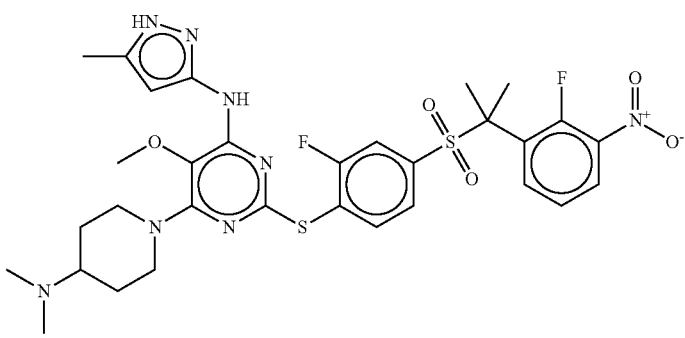 XXX
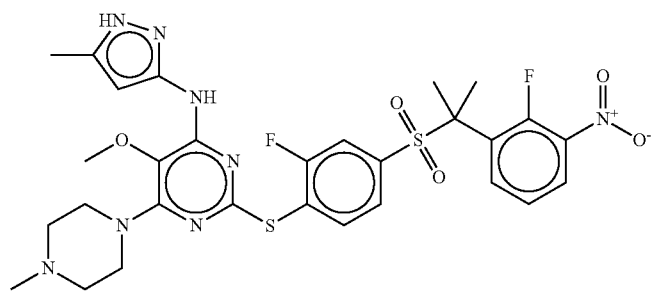 Activity XXX TABLE 1-continued
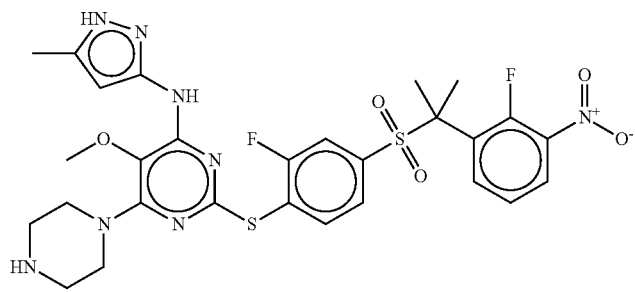 XXX
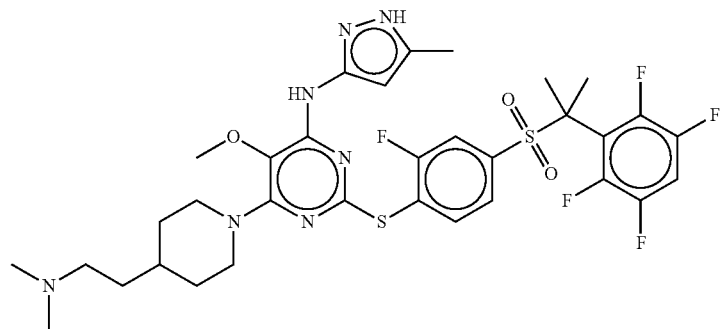 XXX
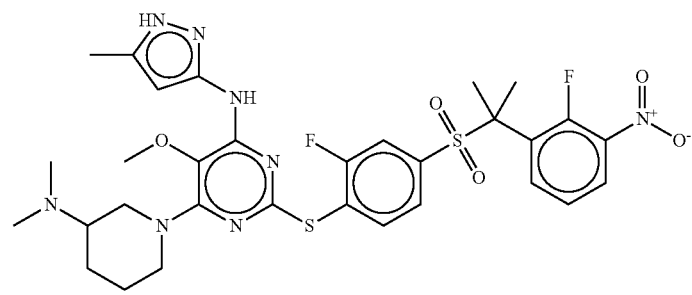 XXX
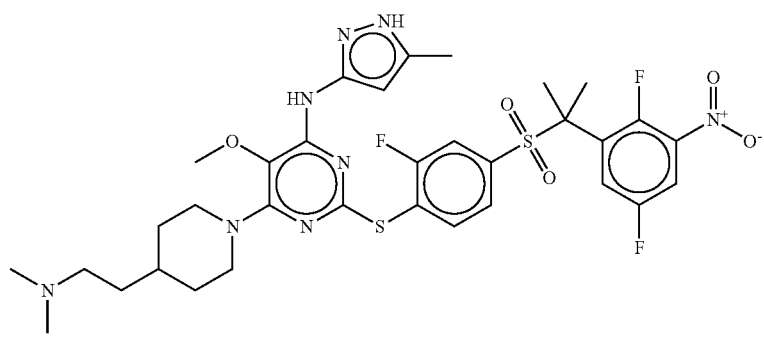 Activity XXX
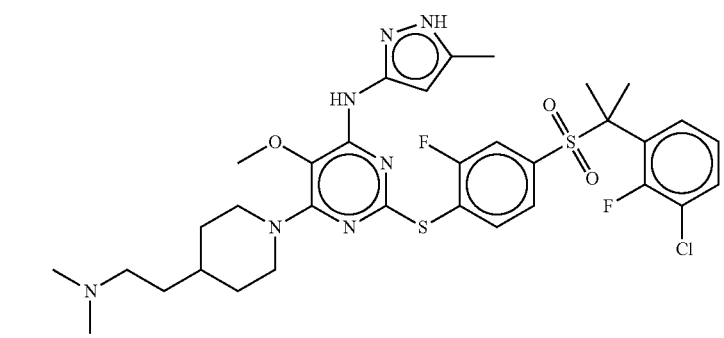 XXX TABLE 1-continued
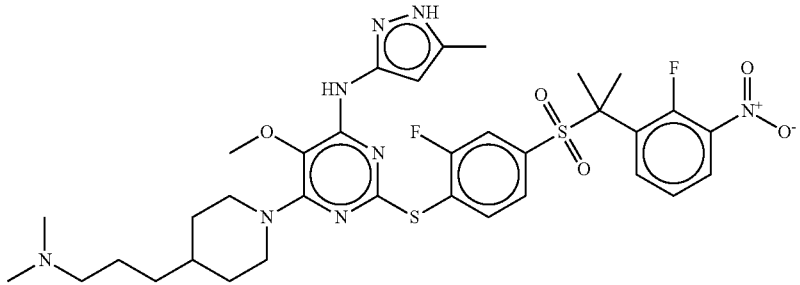 XXX
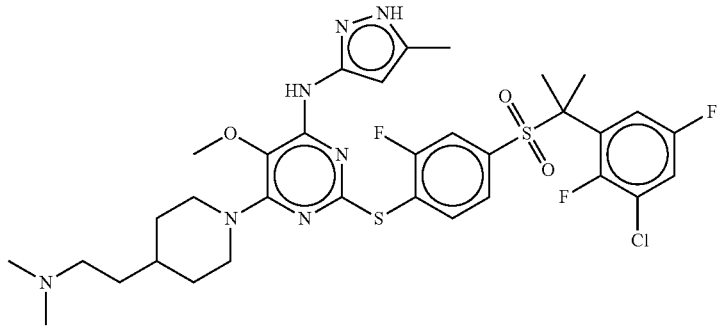 XXX
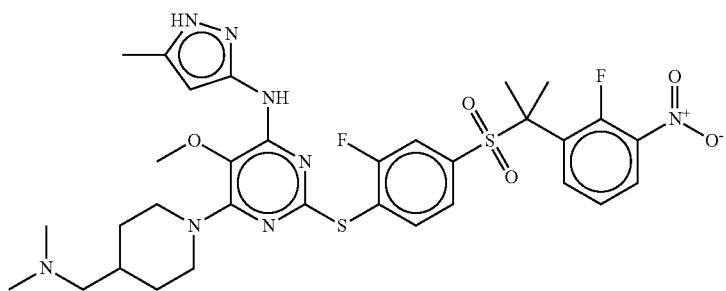 Activity XXX
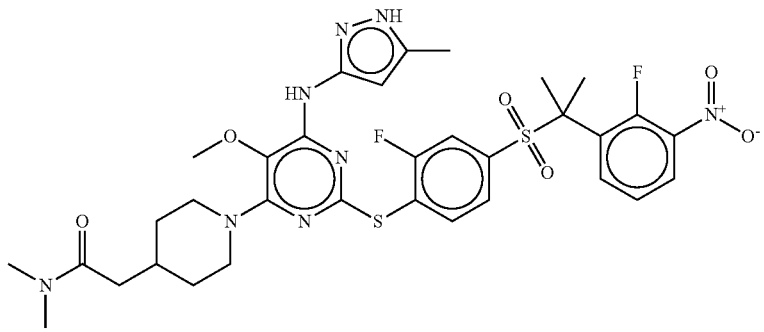 XXX
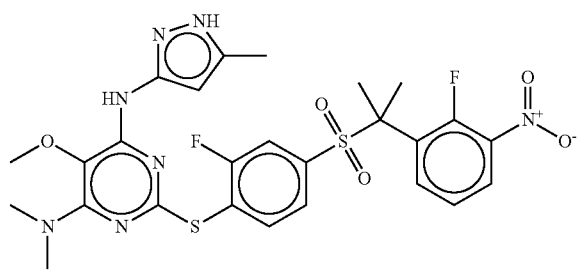 XXX TABLE 1-continued
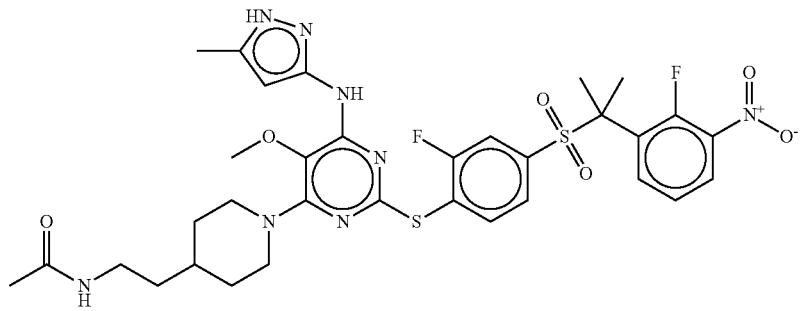
XXX
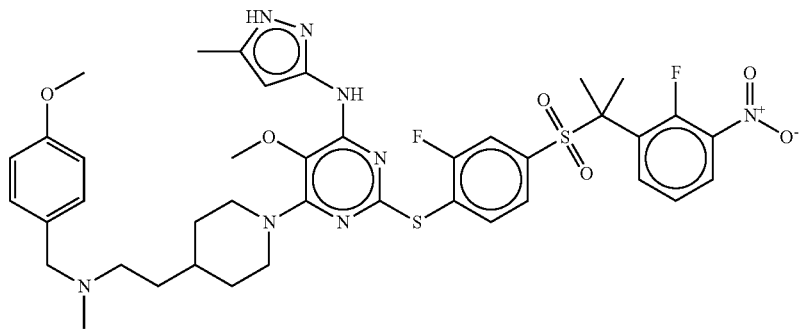
Activity XXX
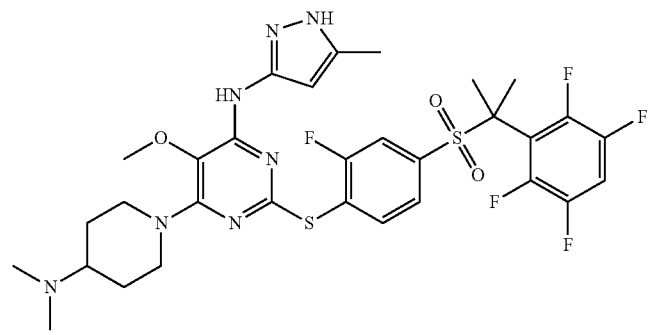 [SMILES: COc1c(Nc2cc(C)[nH]n2)nc(Sc2ccc(S(=O)(=O)C(C)(C)c3c(F)c(F)cc(F)c3F)cc2F)nc1N1CCC(N(C)C)CC1]
XXX
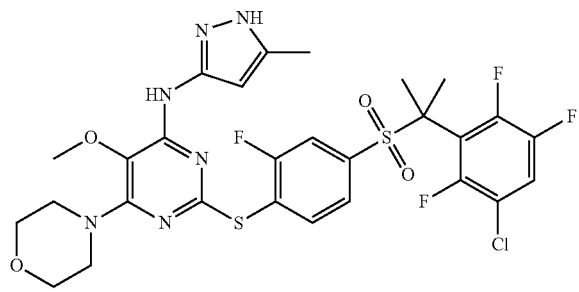 [SMILES: COc1c(Nc2cc(C)[nH]n2)nc(Sc2ccc(S(=O)(=O)C(C)(C)c3c(F)c(F)cc(Cl)c3F)cc2F)nc1N1CCOCC1]
XXX
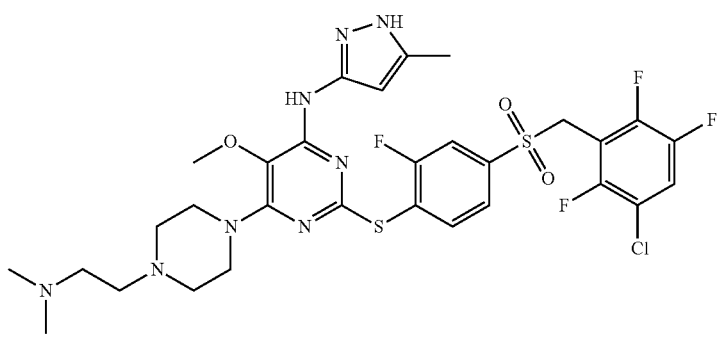
XXX

TABLE 1-continued
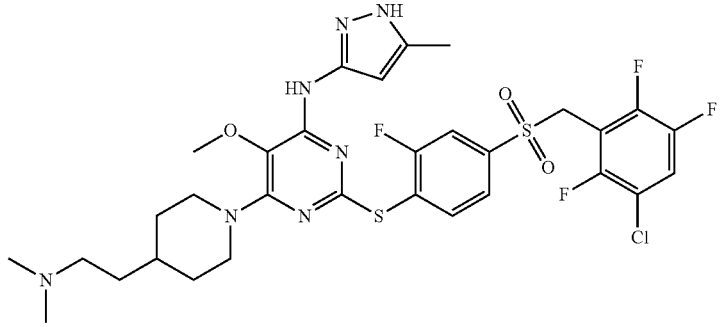 [SMILES: COc1c(Nc2cc(C)[nH]n2)nc(Sc2ccc(S(=O)(=O)Cc3c(F)c(F)cc(Cl)c3F)cc2F)nc1N1CCC(CCN(C)C)CC1] Activity XXX
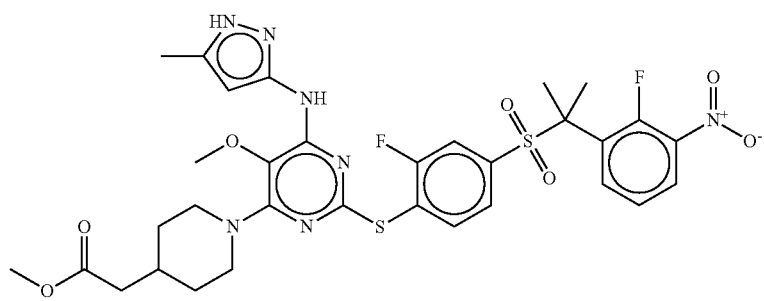 XXX
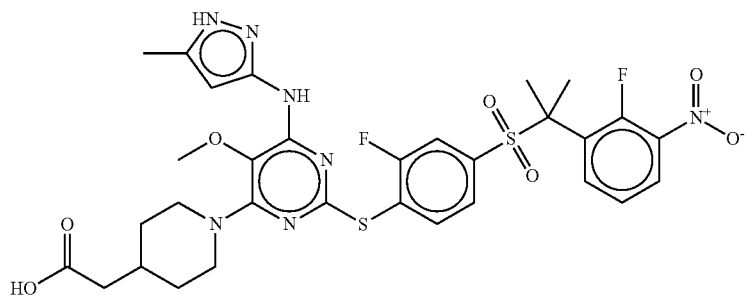 XXX
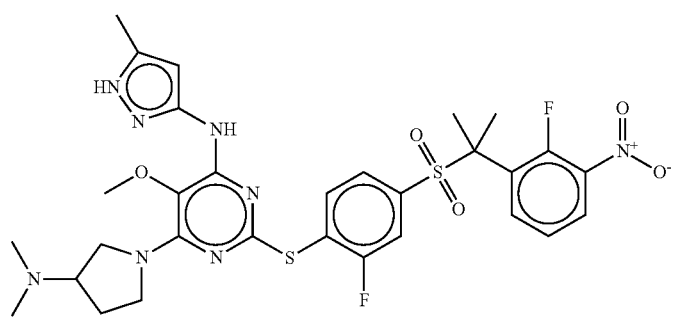 XXX
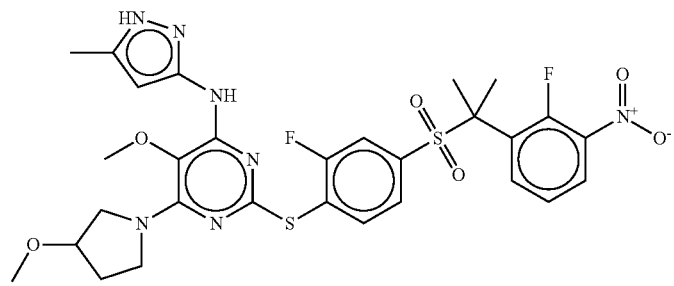 Activity XXX TABLE 1-continued
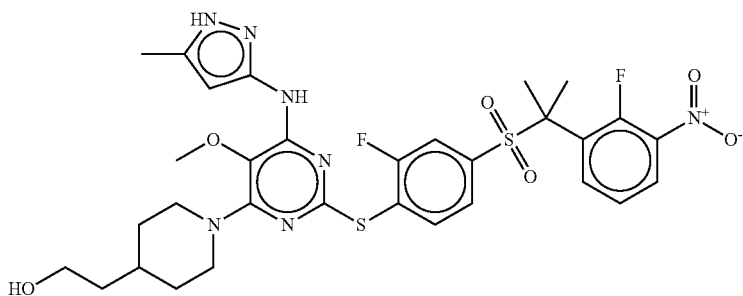 XXX
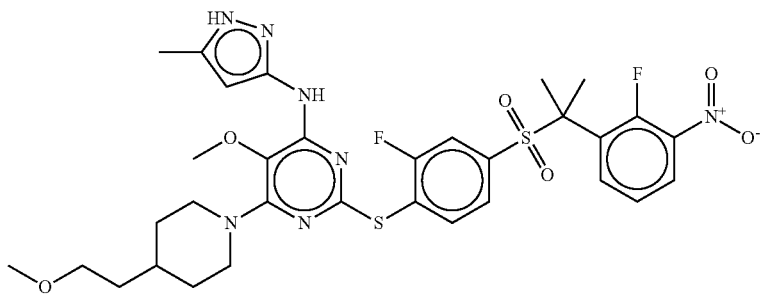 XXX
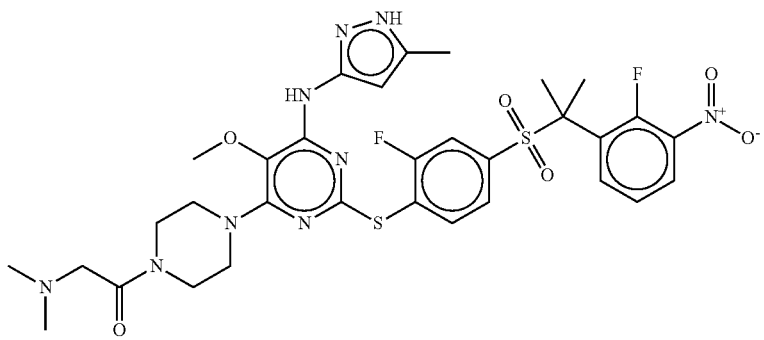 XXX
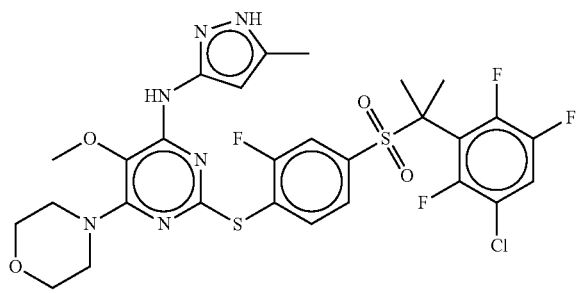 Activity XXX
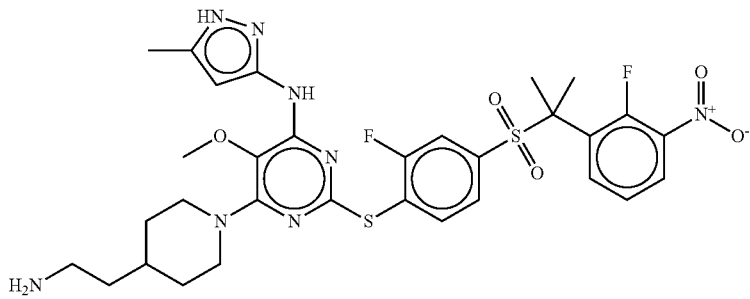 XXX TABLE 1-continued
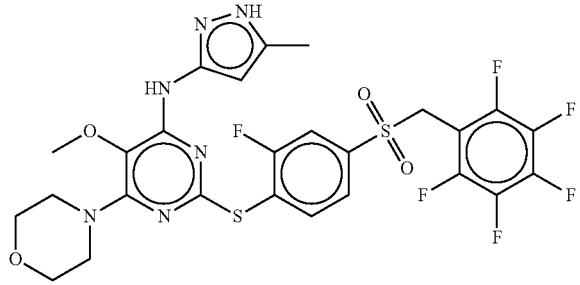 XXX
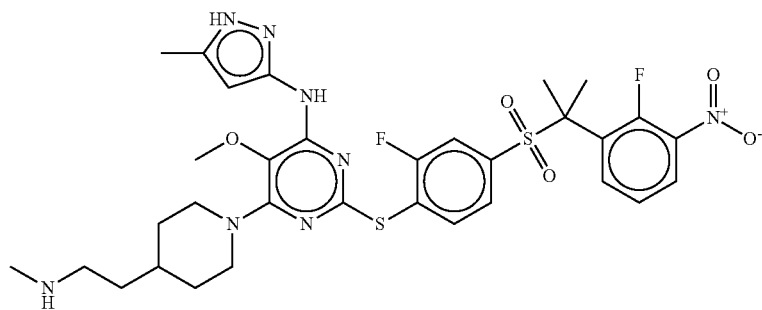 XXX
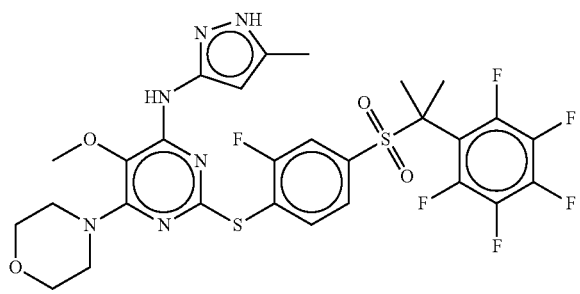 Activity XXX
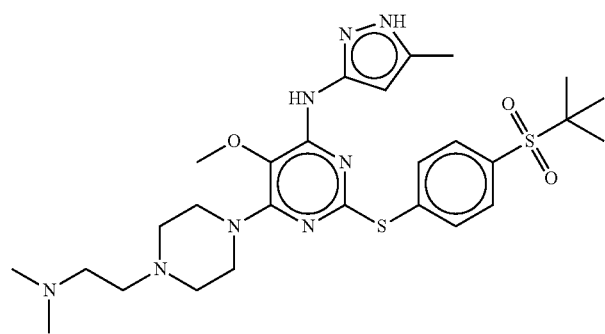 XXX
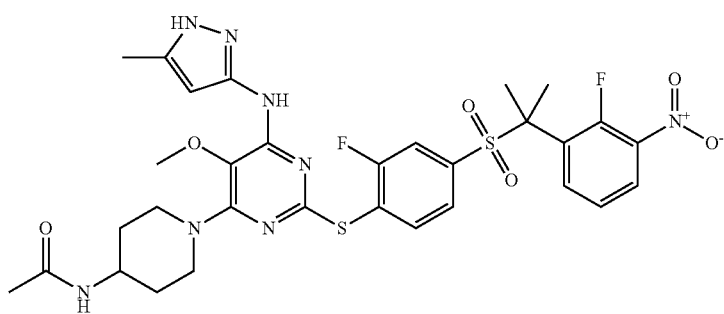 [SMILES: COc1c(Nc2cc(C)[nH]n2)nc(Sc2ccc(S(=O)(=O)C(C)(C)c3cccc([N+](=O)[O-])c3F)cc2F)nc1N1CCC(NC(C)=O)CC1] XXX TABLE 1-continued
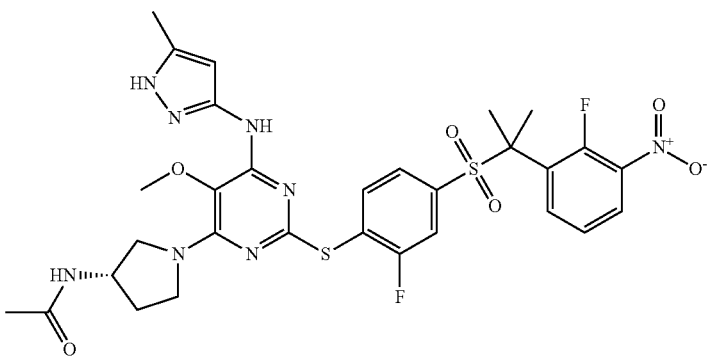 [SMILES: COc1c(Nc2cc(C)[nH]n2)nc(Sc2ccc(S(=O)(=O)C(C)(C)c3cccc([N+](=O)[O-])c3F)cc2F)nc1N1CC[C@H](NC(C)=O)C1]
XXX
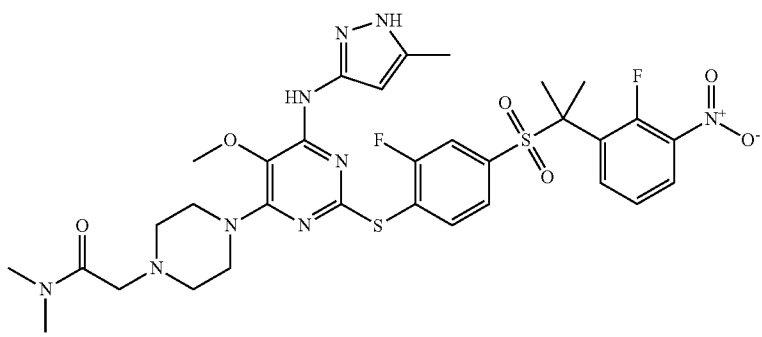 [SMILES: COc1c(Nc2cc(C)[nH]n2)nc(Sc2ccc(S(=O)(=O)C(C)(C)c3cccc([N+](=O)[O-])c3F)cc2F)nc1N1CCN(CC(=O)N(C)C)CC1]
Activity XXX
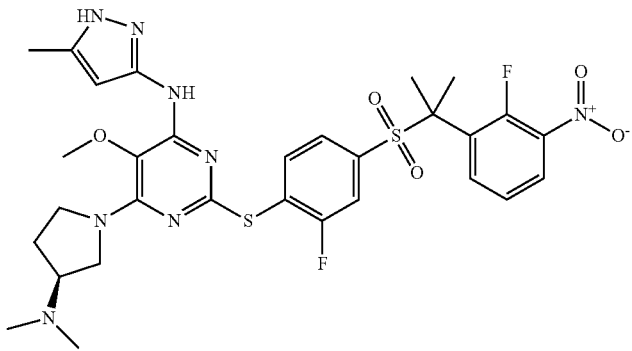 [SMILES: COc1c(Nc2cc(C)[nH]n2)nc(Sc2ccc(S(=O)(=O)C(C)(C)c3cccc([N+](=O)[O-])c3F)cc2F)nc1N1CC[C@H](N(C)C)C1]
XXX
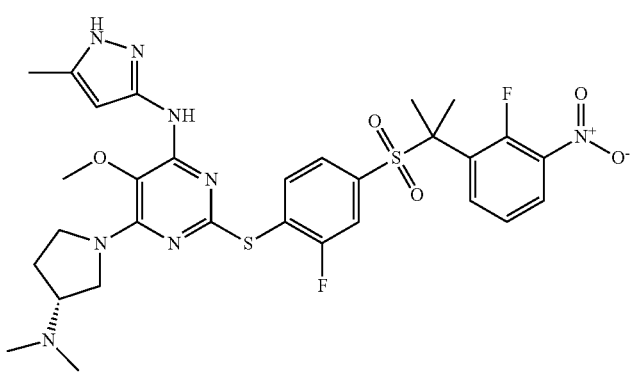 [SMILES: COc1c(Nc2cc(C)[nH]n2)nc(Sc2ccc(S(=O)(=O)C(C)(C)c3cccc([N+](=O)[O-])c3F)cc2F)nc1N1CC[C@@H](N(C)C)C1]
XXX TABLE 1-continued
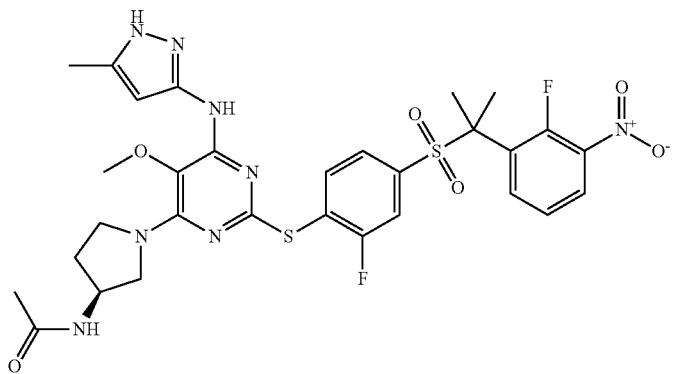 [SMILES: COc1c(Nc2cc(C)[nH]n2)nc(Sc2ccc(S(=O)(=O)C(C)(C)c3cccc([N+](=O)[O-])c3F)cc2F)nc1N1CC[C@H](NC(C)=O)C1] XXX
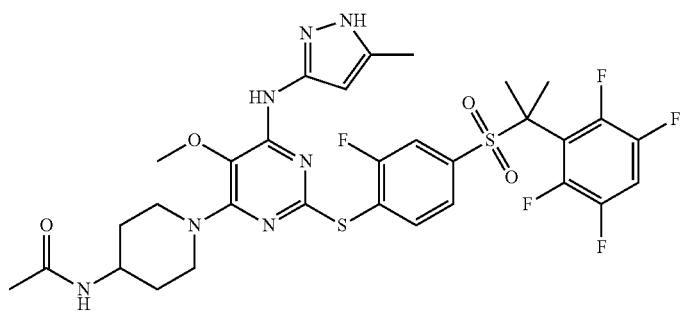 [SMILES: COc1c(Nc2cc(C)[nH]n2)nc(Sc2ccc(S(=O)(=O)C(C)(C)c3c(F)c(F)cc(F)c3F)cc2F)nc1N1CCC(NC(C)=O)CC1] Activity XXX
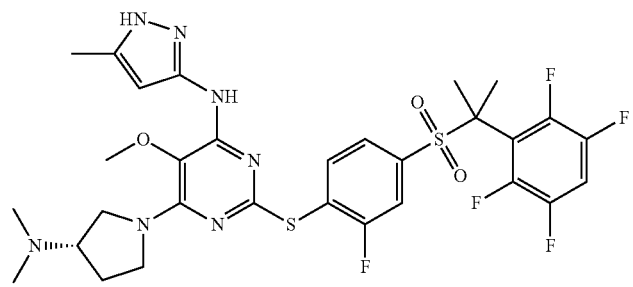 [SMILES: COc1c(Nc2cc(C)[nH]n2)nc(Sc2ccc(S(=O)(=O)C(C)(C)c3c(F)c(F)cc(F)c3F)cc2F)nc1N1CC[C@H](N(C)C)C1] XXX
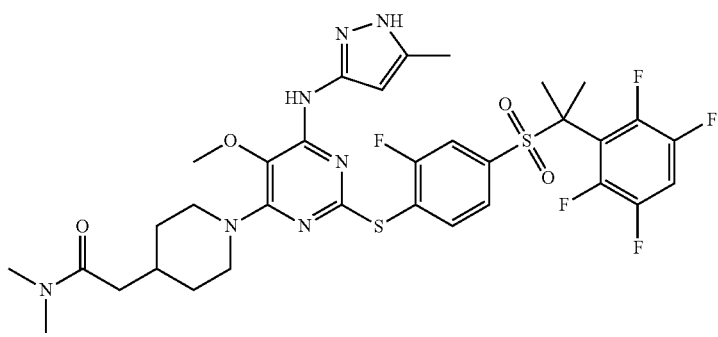 [SMILES: COc1c(Nc2cc(C)[nH]n2)nc(Sc2ccc(S(=O)(=O)C(C)(C)c3c(F)c(F)cc(F)c3F)cc2F)nc1N1CCC(CC(=O)N(C)C)CC1] XXX
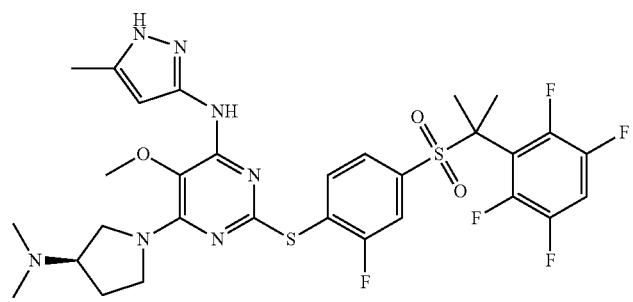 [SMILES: COc1c(Nc2cc(C)[nH]n2)nc(Sc2ccc(S(=O)(=O)C(C)(C)c3c(F)c(F)cc(F)c3F)cc2F)nc1N1CC[C@@H](N(C)C)C1] XXX TABLE 1-continued
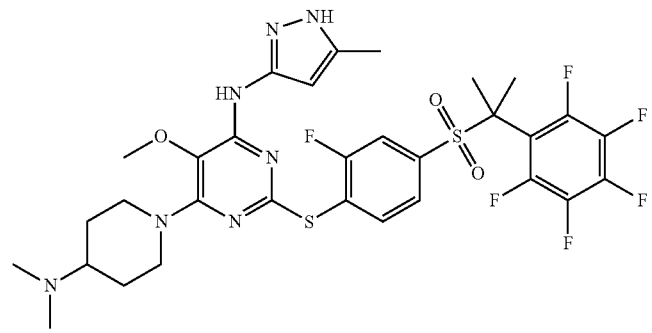 [SMILES: COc1c(Nc2cc(C)[nH]n2)nc(Sc2ccc(S(=O)(=O)C(C)(C)c3c(F)c(F)c(F)c(F)c3F)cc2F)nc1N1CCC(N(C)C)CC1] Activity XXX
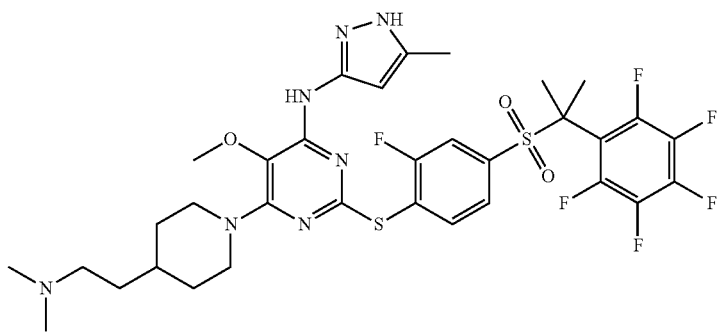 [SMILES: COc1c(Nc2cc(C)[nH]n2)nc(Sc2ccc(S(=O)(=O)C(C)(C)c3c(F)c(F)c(F)c(F)c3F)cc2F)nc1N1CCC(CCN(C)C)CC1] XXX
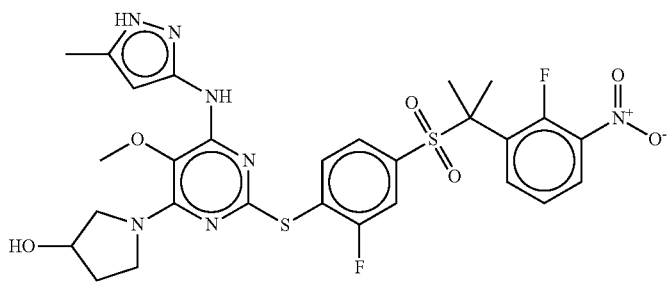 XXX
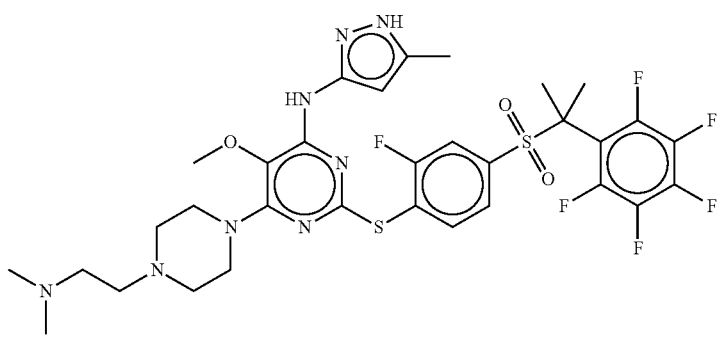 XXX
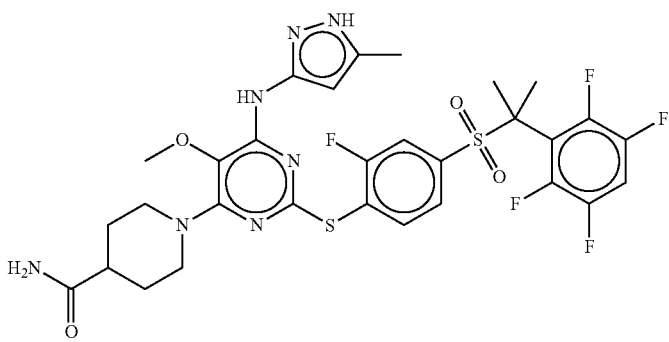 Activity XXX TABLE 1-continued
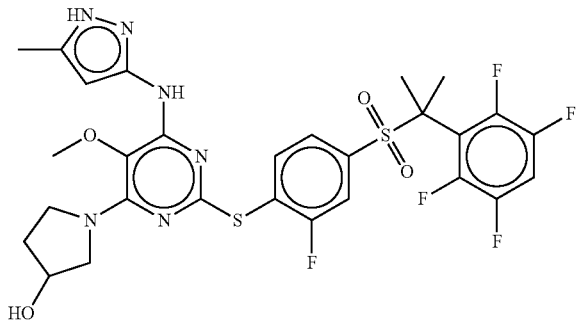
XXX
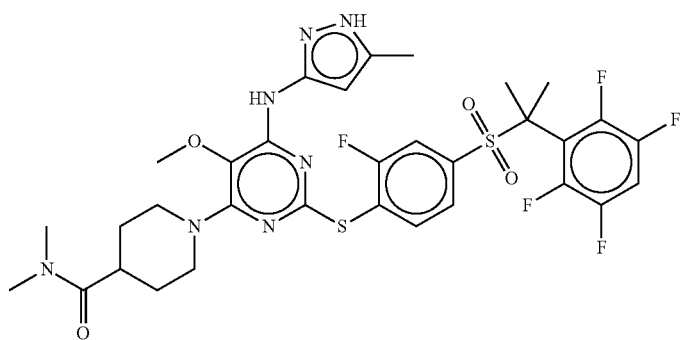
XXX
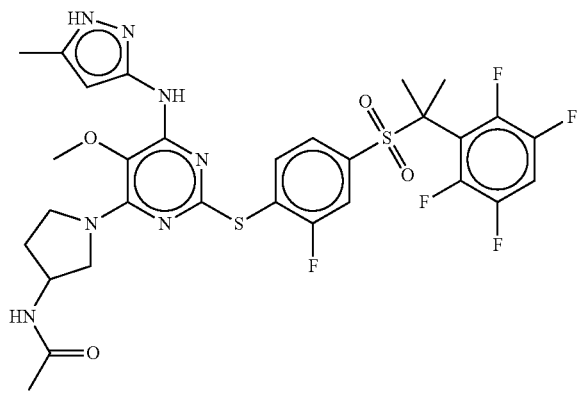
XXX
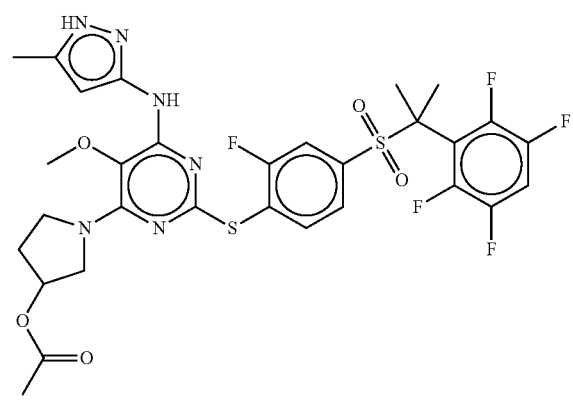
Activity XXX TABLE 1-continued
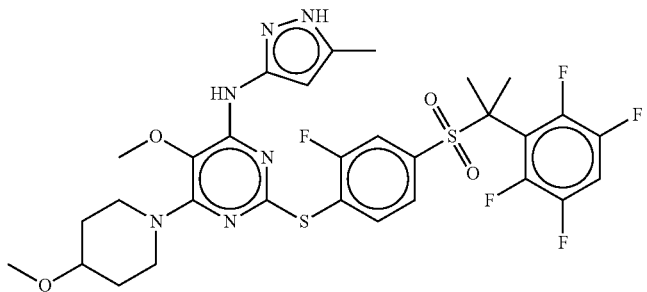 XXX
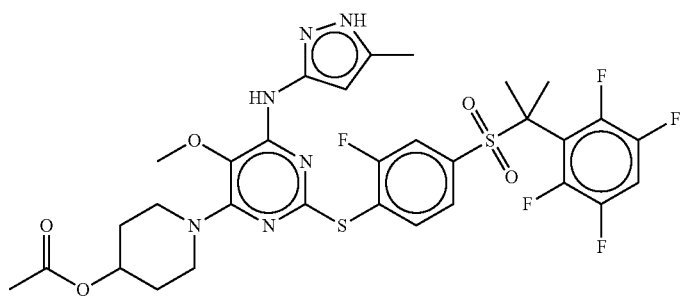 XXX
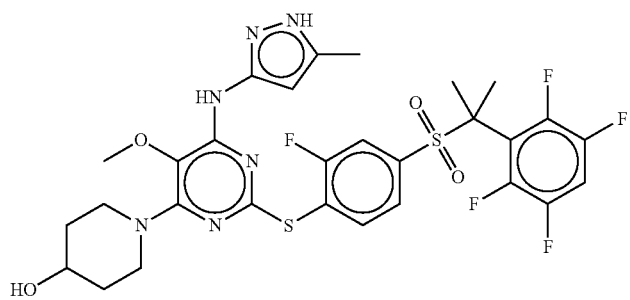 XXX
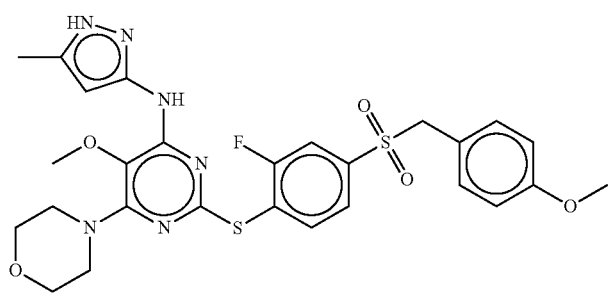 Activity XXX
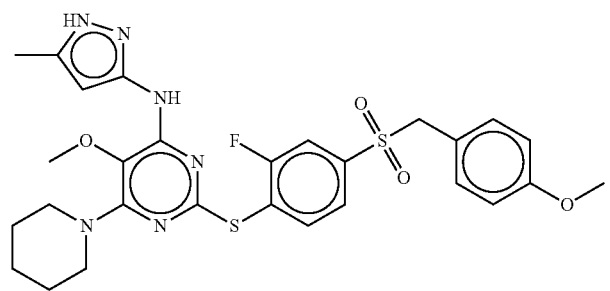 XXX TABLE 1-continued
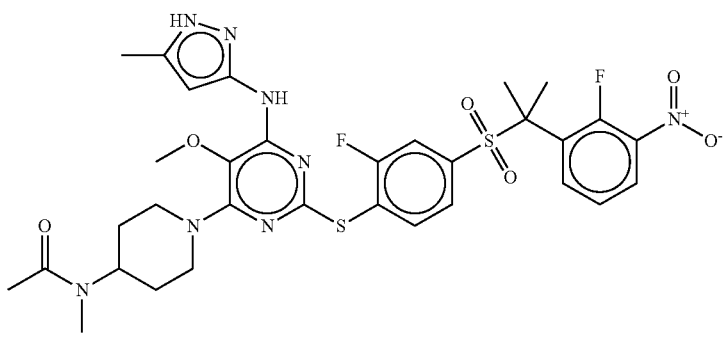
XXX
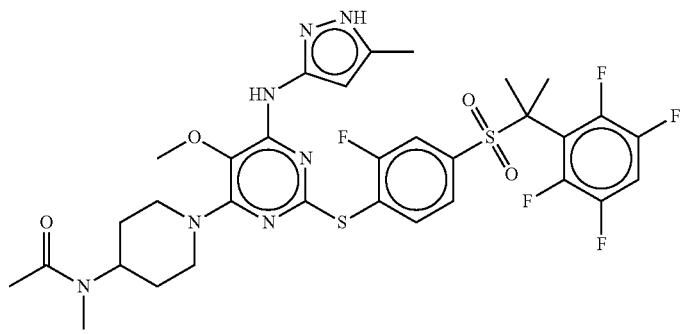
XXX
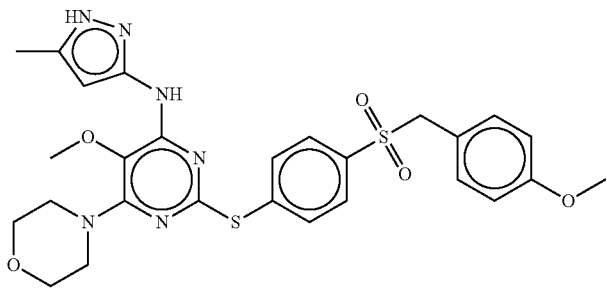
Activity XXX
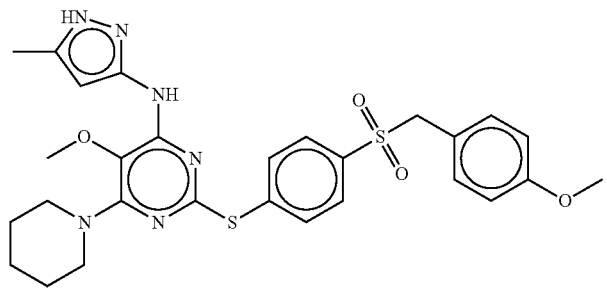
XXX
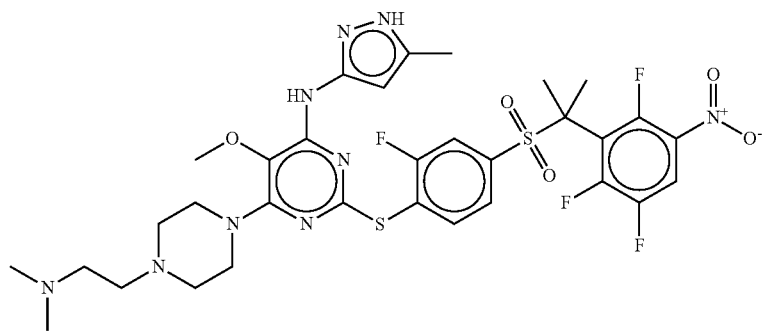
XXX TABLE 1-continued
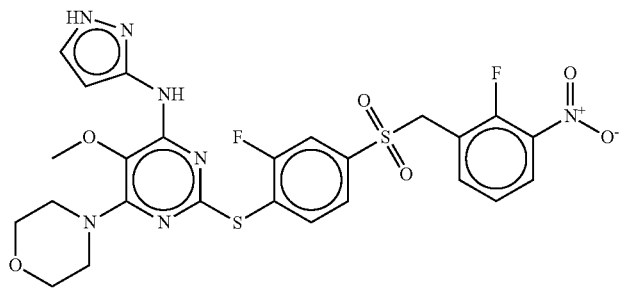 XXX
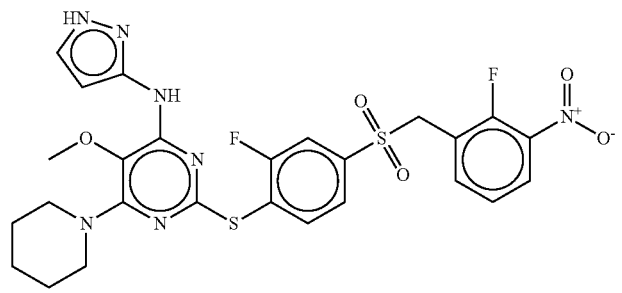 Activity XXX
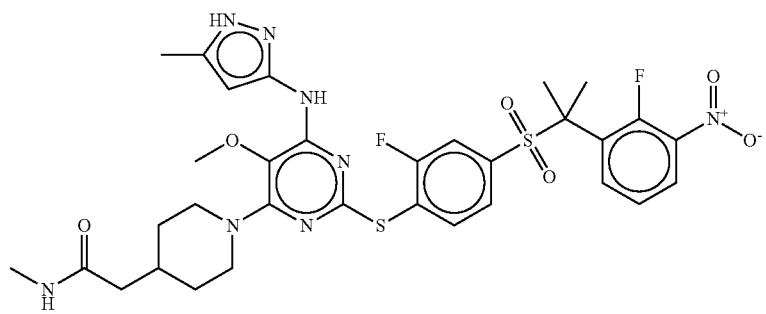 XXX
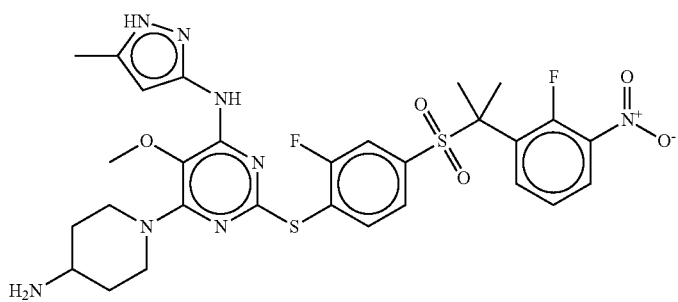 XXX
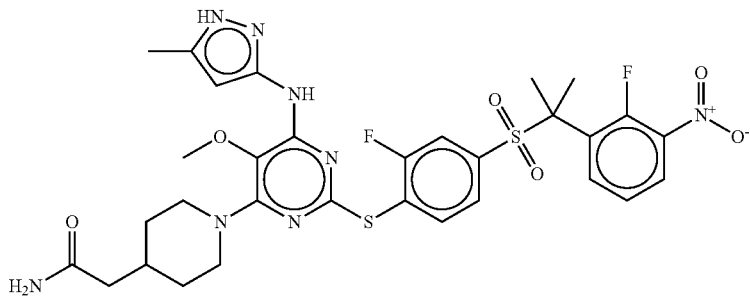 XXX TABLE 1-continued
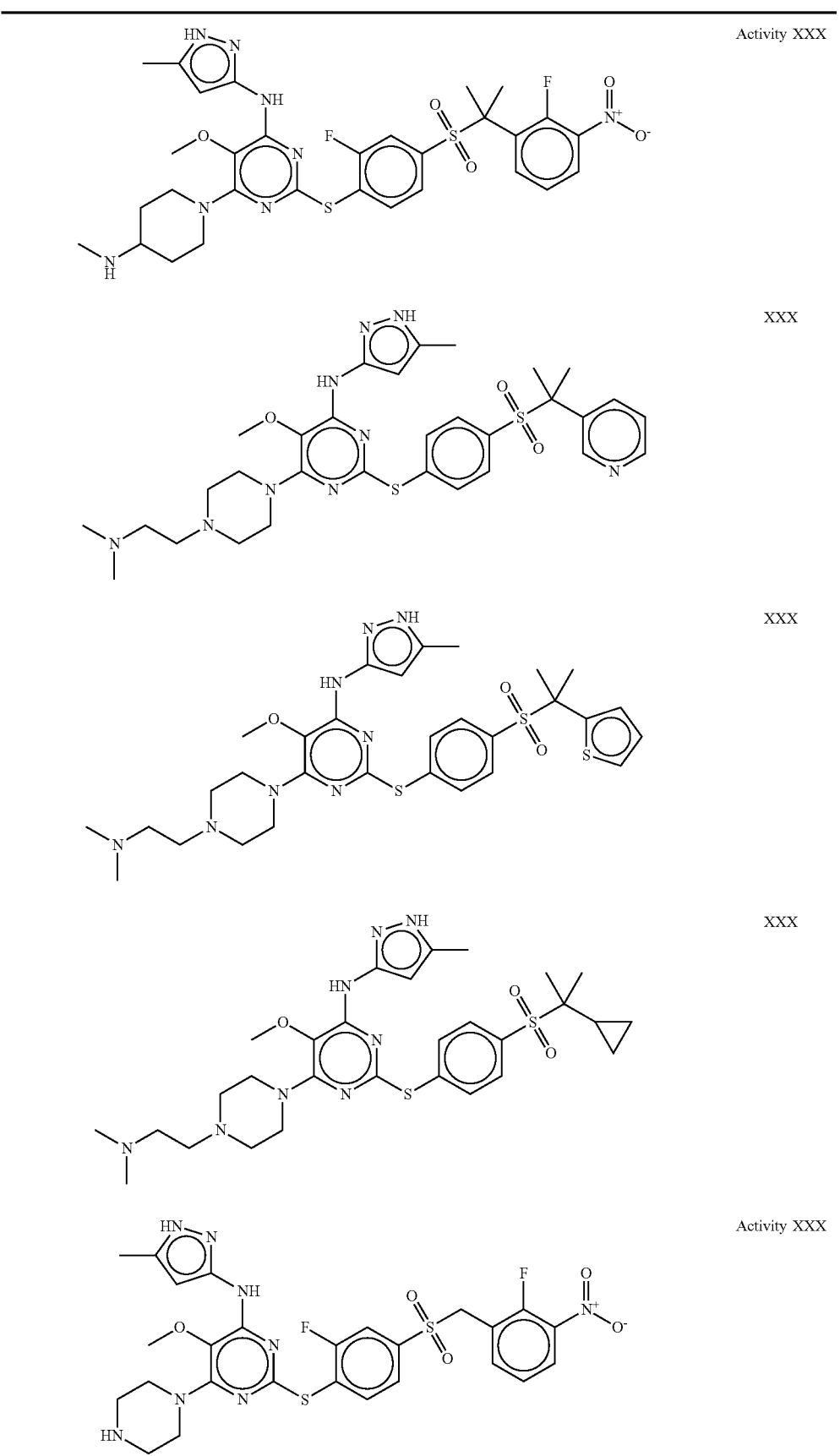
| | |
|---|---|
| | Activity XXX |
| | XXX |
| | XXX |
| | XXX |
| | Activity XXX |

TABLE 1-continued
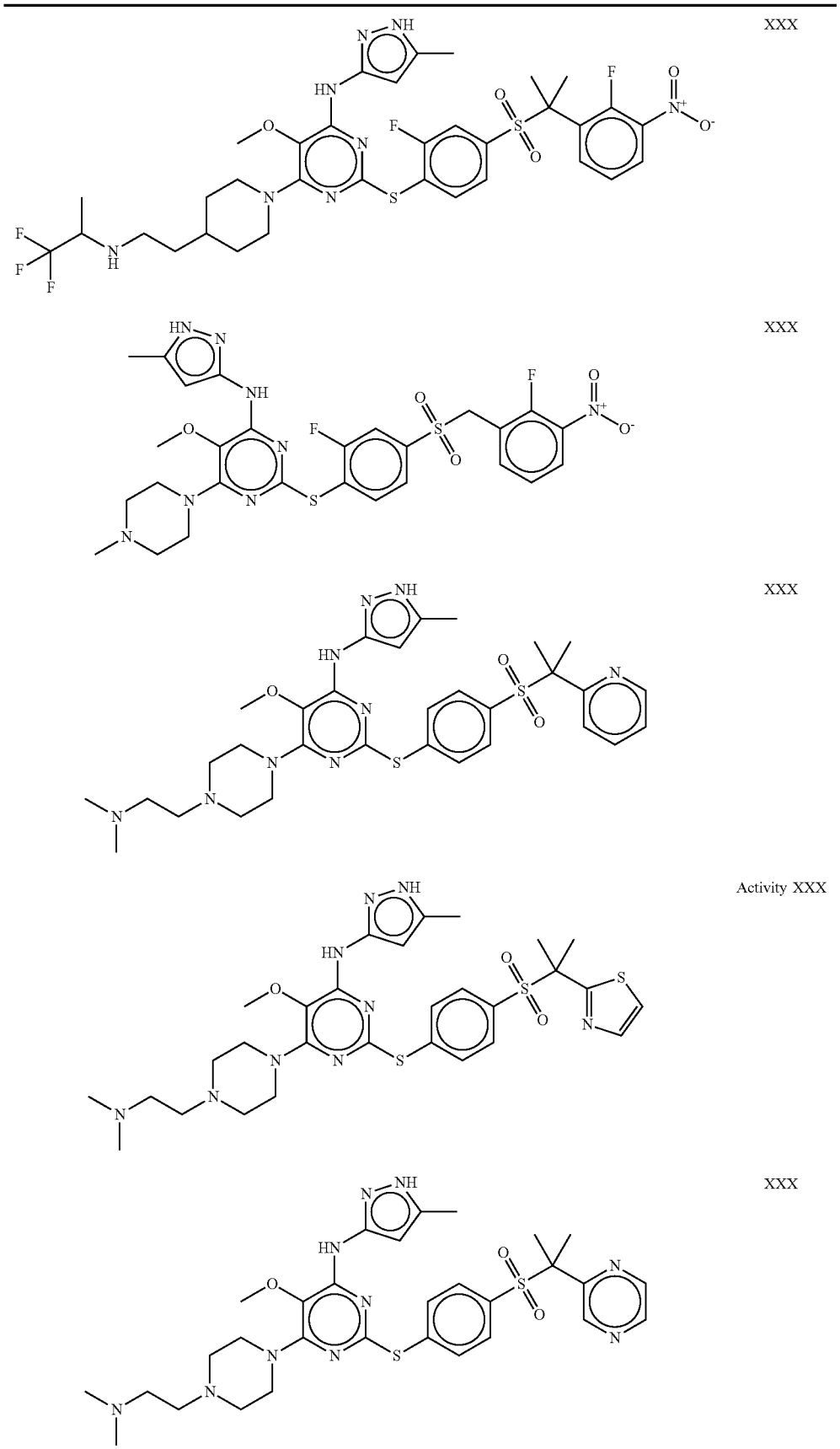

TABLE 1-continued
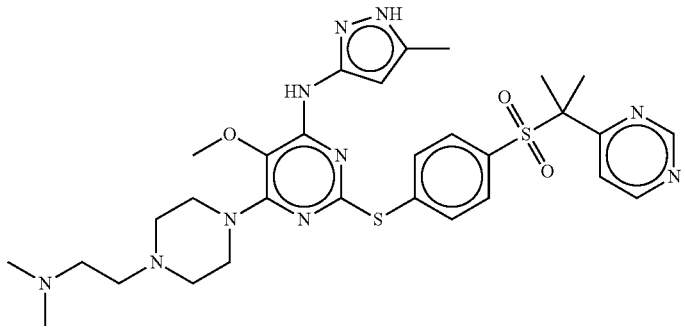 XXX
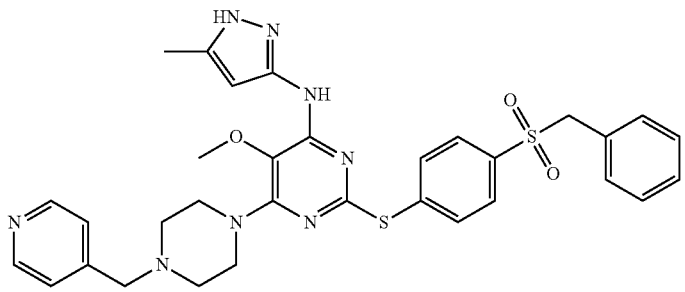 [SMILES: COc1c(Nc2cc(C)[nH]n2)nc(Sc2ccc(S(=O)(=O)Cc3ccccc3)cc2)nc1N1CCN(Cc2ccncc2)CC1] XXX
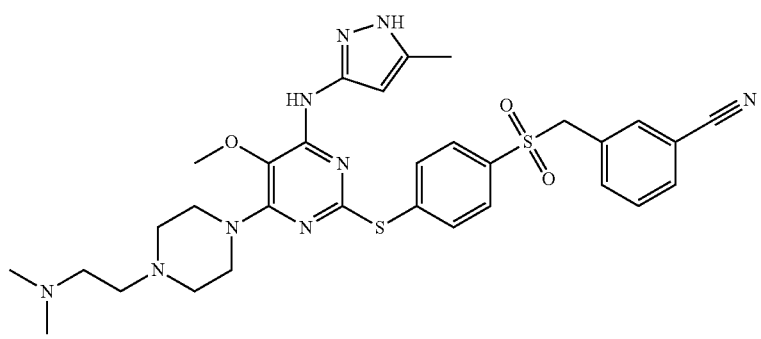 [SMILES: COc1c(Nc2cc(C)[nH]n2)nc(Sc2ccc(S(=O)(=O)Cc3cccc(C#N)c3)cc2)nc1N1CCN(CCN(C)C)CC1] Activity XXX
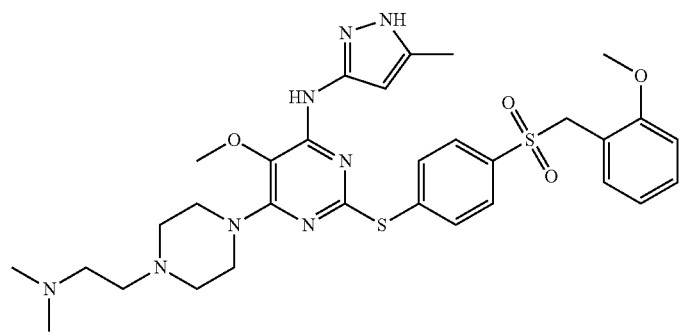 [SMILES: COc1ccccc1CS(=O)(=O)c1ccc(Sc2nc(Nc3cc(C)[nH]n3)c(OC)c(N3CCN(CCN(C)C)CC3)n2)cc1] XXX
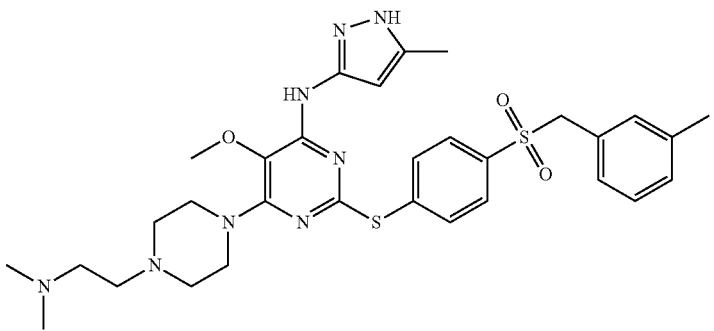 XXX TABLE 1-continued
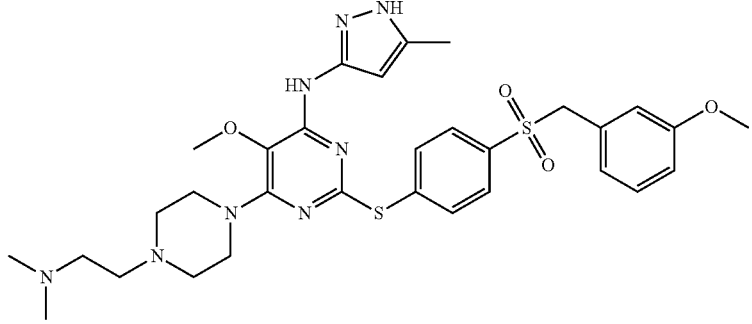
XXX
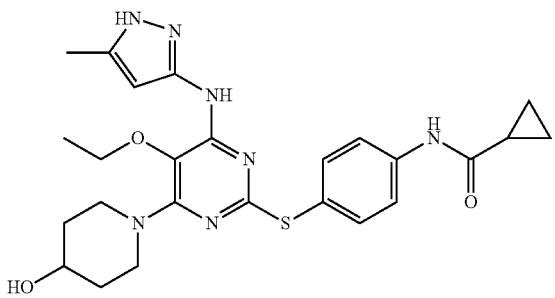 [SMILES: CCOc1c(Nc2cc(C)[nH]n2)nc(Sc2ccc(NC(=O)C3CC3)cc2)nc1N1CCC(O)CC1]
Activity XXX
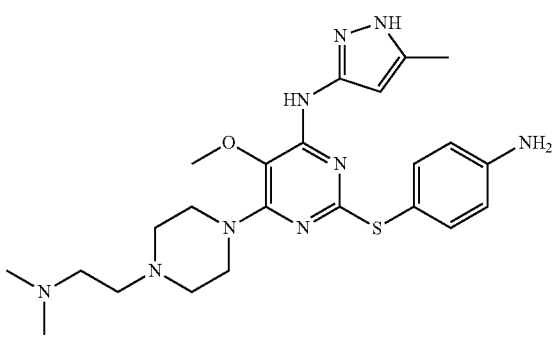 [SMILES: COc1c(Nc2cc(C)[nH]n2)nc(Sc2ccc(N)cc2)nc1N1CCN(CCN(C)C)CC1]
XX
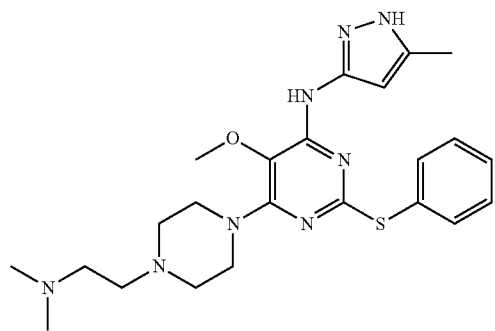 [SMILES: COc1c(Nc2cc(C)[nH]n2)nc(Sc2ccccc2)nc1N1CCN(CCN(C)C)CC1]
XX
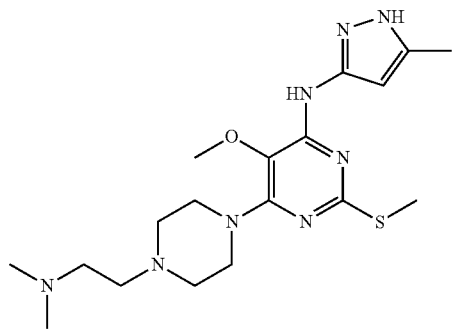
XX TABLE 1-continued
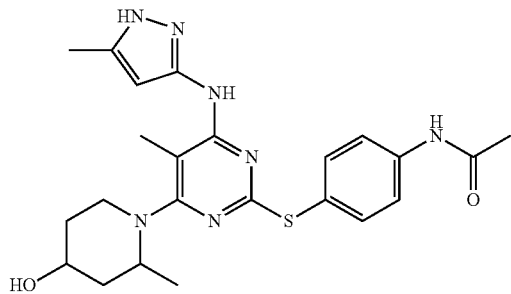 [SMILES: CC(=O)Nc1ccc(Sc2nc(Nc3cc(C)[nH]n3)c(C)c(N3CCC(O)CC3C)n2)cc1]
XXX
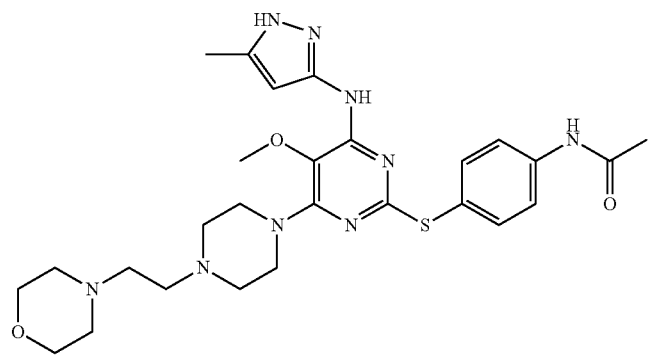 [SMILES: COc1c(Nc2cc(C)[nH]n2)nc(Sc2ccc(NC(C)=O)cc2)nc1N1CCN(CCN2CCOCC2)CC1]
Activity XXX
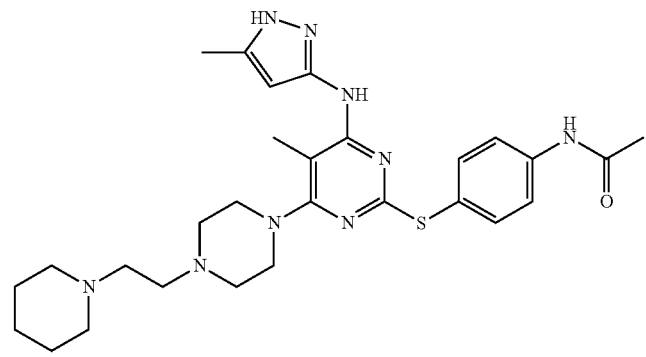 [SMILES: CC(=O)Nc1ccc(Sc2nc(Nc3cc(C)[nH]n3)c(C)c(N3CCN(CCN4CCCCC4)CC3)n2)cc1]
XXX
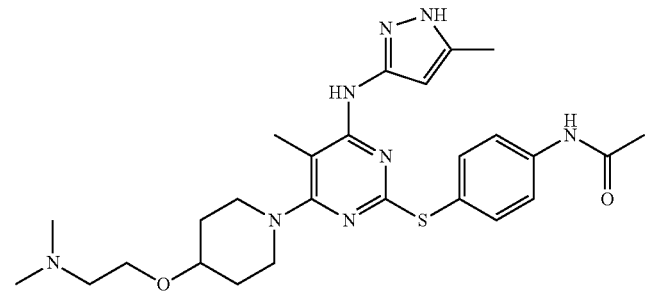 [SMILES: CC(=O)Nc1ccc(Sc2nc(Nc3cc(C)[nH]n3)c(C)c(N3CCC(OCCN(C)C)CC3)n2)cc1]
XXX
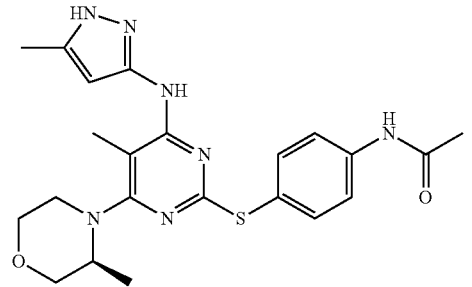 [SMILES: CC(=O)Nc1ccc(Sc2nc(Nc3cc(C)[nH]n3)c(C)c(N3CCOC[C@@H]3C)n2)cc1]
XXX TABLE 1-continued
| Structure | Activity |
|---|---|
| 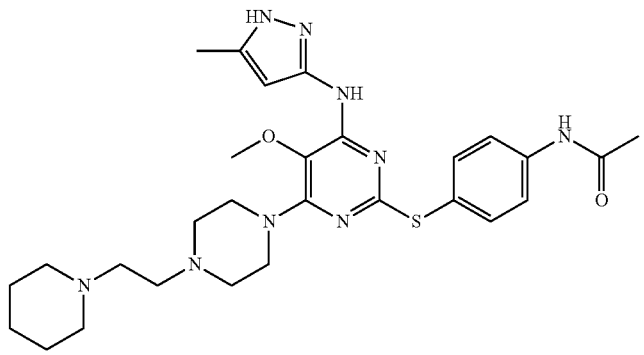 [SMILES: COc1c(Nc2cc(C)[nH]n2)nc(Sc2ccc(NC(C)=O)cc2)nc1N1CCN(CCN2CCCCC2)CC1] | XXX |
| 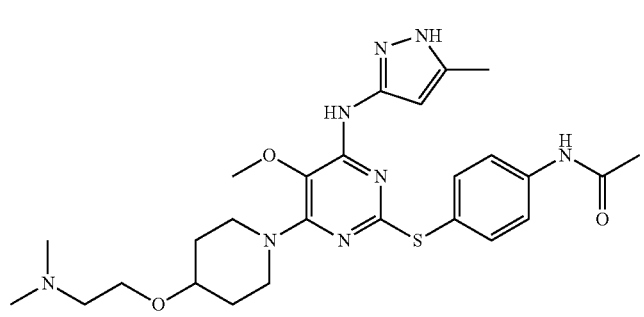 [SMILES: COc1c(Nc2cc(C)[nH]n2)nc(Sc2ccc(NC(C)=O)cc2)nc1N1CCC(OCCN(C)C)CC1] | XX |
| 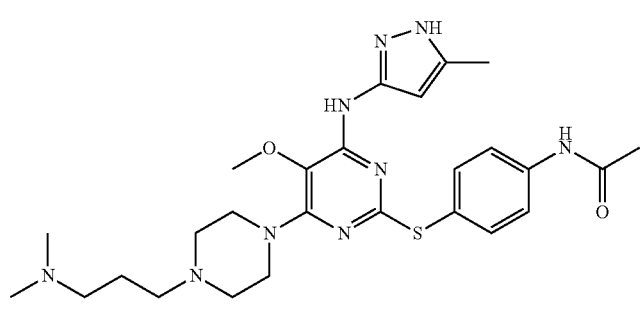 [SMILES: COc1c(Nc2cc(C)[nH]n2)nc(Sc2ccc(NC(C)=O)cc2)nc1N1CCN(CCCN(C)C)CC1] | XXX |
| 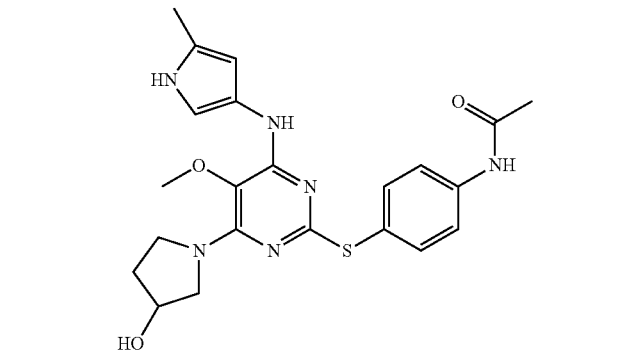 [SMILES: COc1c(Nc2c[nH]c(C)c2)nc(Sc2ccc(NC(C)=O)cc2)nc1N1CCC(O)C1] | XXX |

TABLE 1-continued
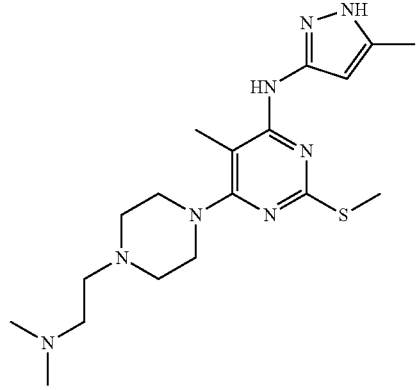 Activity XXX
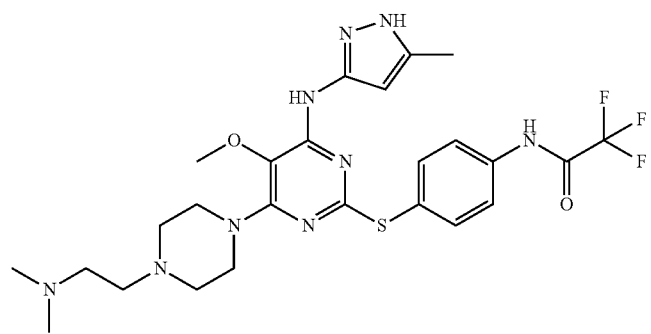 [SMILES: COc1c(Nc2cc(C)[nH]n2)nc(Sc2ccc(NC(=O)C(F)(F)F)cc2)nc1N1CCN(CCN(C)C)CC1] XXX
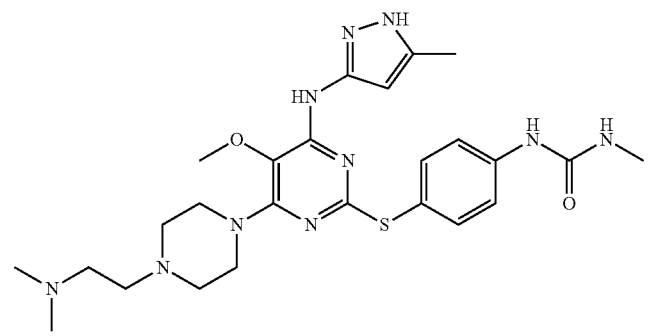 XXX
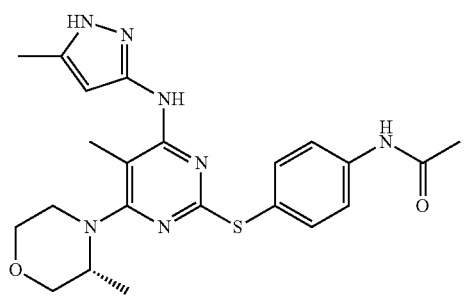 [SMILES: CC(=O)Nc1ccc(Sc2nc(Nc3cc(C)[nH]n3)c(C)c(N3CCOC[C@H]3C)n2)cc1] XXX TABLE 1-continued
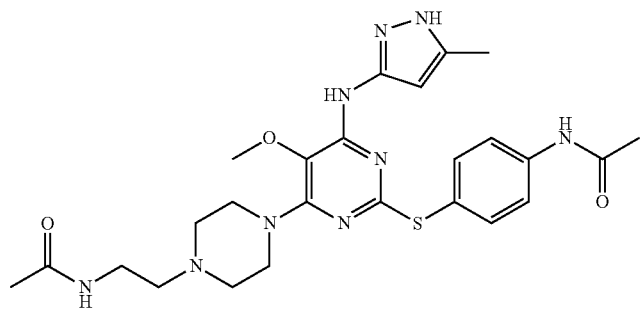 [SMILES: COc1c(Nc2cc(C)[nH]n2)nc(Sc2ccc(NC(C)=O)cc2)nc1N1CCN(CCNC(C)=O)CC1]
XXX
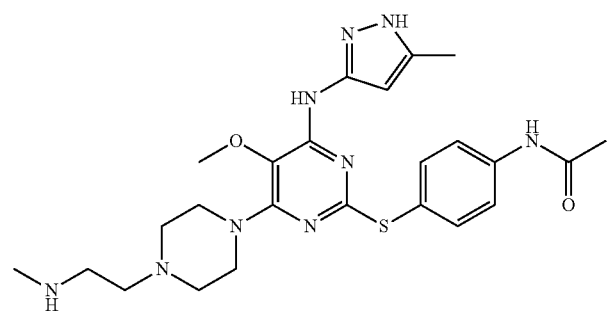 [SMILES: CNCCN1CCN(c2nc(Sc3ccc(NC(C)=O)cc3)nc(Nc3cc(C)[nH]n3)c2OC)CC1]
Activity XXX
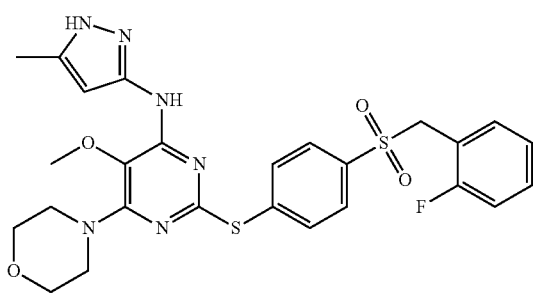 [SMILES: COc1c(Nc2cc(C)[nH]n2)nc(Sc2ccc(S(=O)(=O)Cc3ccccc3F)cc2)nc1N1CCOCC1]
XXX
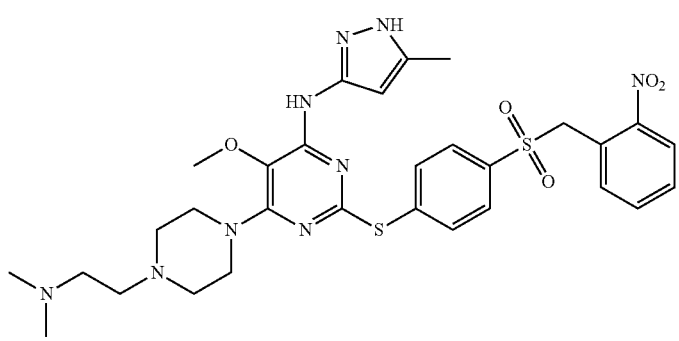
XXX
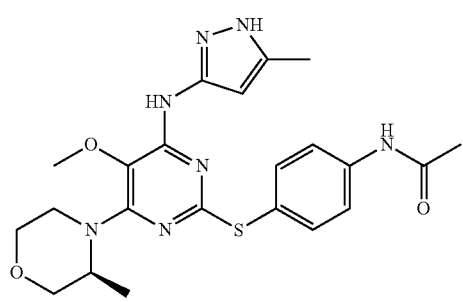 [SMILES: COc1c(Nc2cc(C)[nH]n2)nc(Sc2ccc(NC(C)=O)cc2)nc1N1CCOC[C@@H]1C]
XXX

TABLE 1-continued
| | |
|---|---|
| 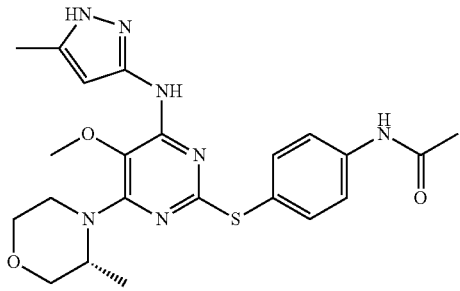 [SMILES: COc1c(Nc2cc(C)[nH]n2)nc(Sc2ccc(NC(C)=O)cc2)nc1N1CCOC[C@H]1C] | XXX |
| 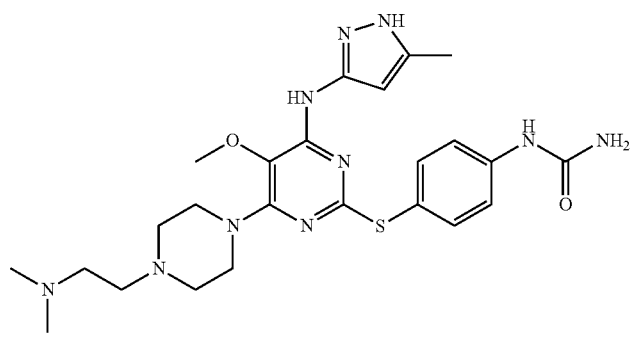 [SMILES: COc1c(Nc2cc(C)[nH]n2)nc(Sc2ccc(NC(N)=O)cc2)nc1N1CCN(CCN(C)C)CC1] | Activity XXX |
| 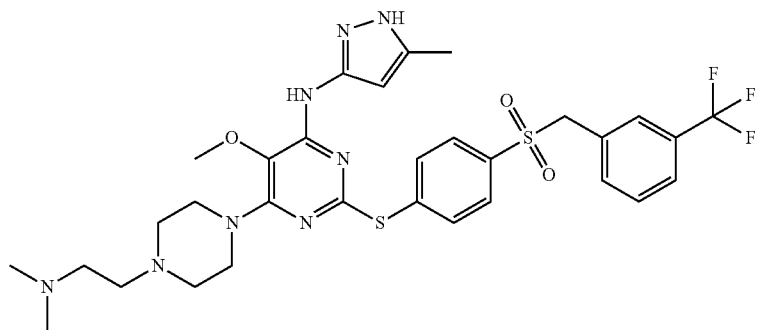 [SMILES: COc1c(Nc2cc(C)[nH]n2)nc(Sc2ccc(S(=O)(=O)Cc3cccc(C(F)(F)F)c3)cc2)nc1N1CCN(CCN(C)C)CC1] | XXX |
| 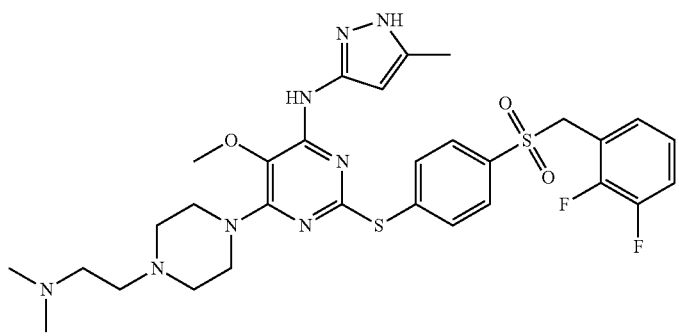 [SMILES: COc1c(Nc2cc(C)[nH]n2)nc(Sc2ccc(S(=O)(=O)Cc3cccc(F)c3F)cc2)nc1N1CCN(CCN(C)C)CC1] | XXX |
| 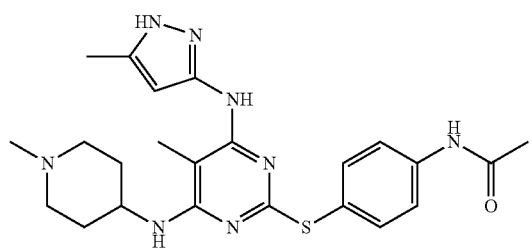 [SMILES: CC(=O)Nc1ccc(Sc2nc(Nc3cc(C)[nH]n3)c(C)c(NC3CCN(C)CC3)n2)cc1] | XXX |

TABLE 1-continued
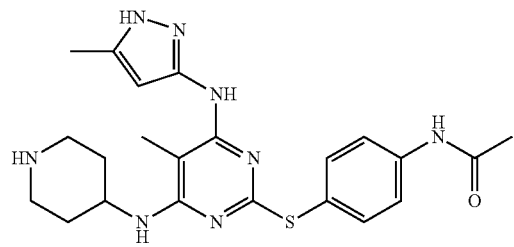 [SMILES: CC(=O)Nc1ccc(Sc2nc(Nc3cc(C)[nH]n3)c(C)c(NC3CCNCC3)n2)cc1] Activity XXX
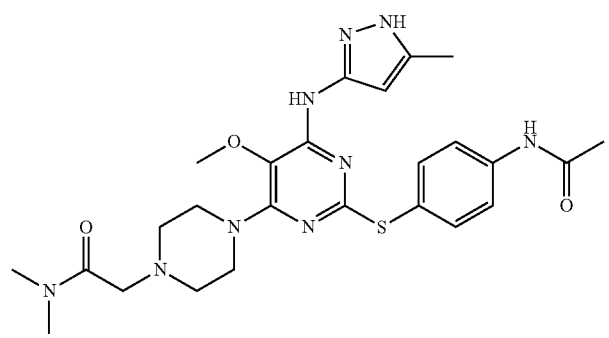 XXX
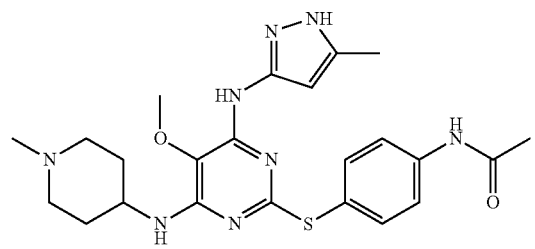 [SMILES: COc1c(Nc2cc(C)[nH]n2)nc(Sc2ccc(NC(C)=O)cc2)nc1NC1CCN(C)CC1] XXX
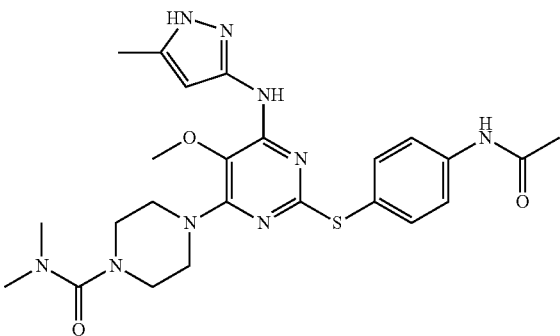 [SMILES: COc1c(Nc2cc(C)[nH]n2)nc(Sc2ccc(NC(C)=O)cc2)nc1N1CCN(C(=O)N(C)C)CC1] XXX
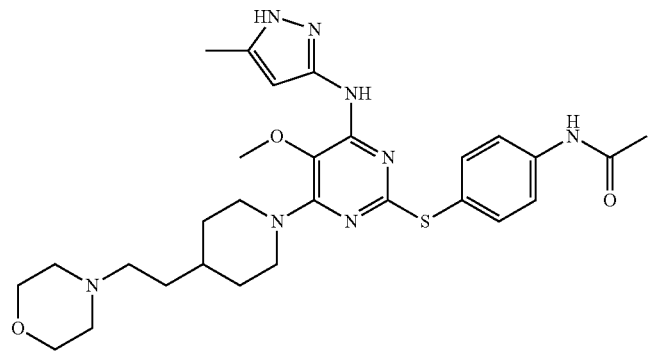 Activity XXX TABLE 1-continued
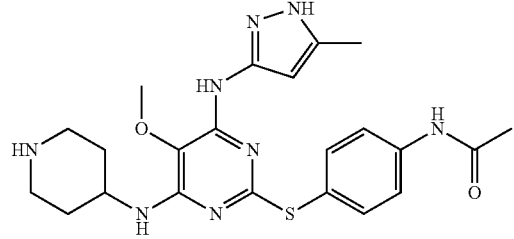 [SMILES: COc1c(Nc2cc(C)[nH]n2)nc(Sc2ccc(NC(C)=O)cc2)nc1NC1CCNCC1]
XXX
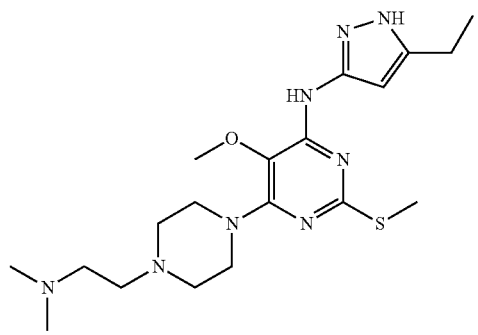 [SMILES: CCc1cc(Nc2nc(SC)nc(N3CCN(CCN(C)C)CC3)c2OC)n[nH]1]
XXX
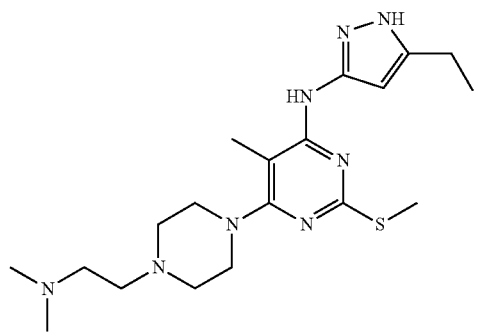 [SMILES: CCc1cc(Nc2nc(SC)nc(N3CCN(CCN(C)C)CC3)c2C)n[nH]1]
XXX
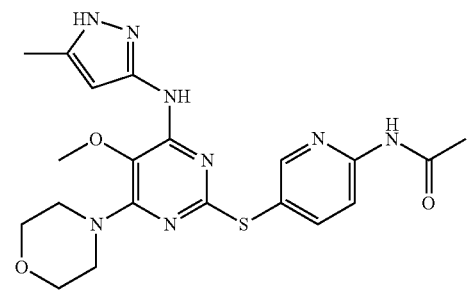 [SMILES: COc1c(Nc2cc(C)[nH]n2)nc(Sc2ccc(NC(C)=O)nc2)nc1N1CCOCC1]
XXX
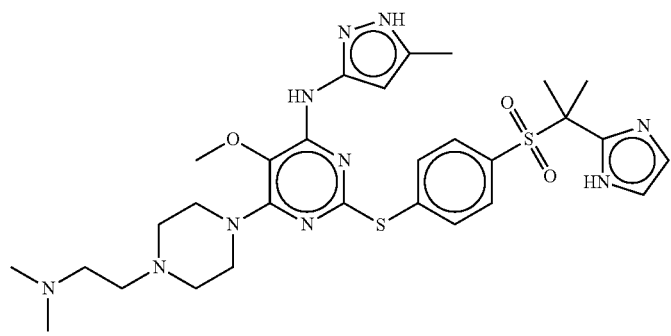
Activity XXX TABLE 1-continued
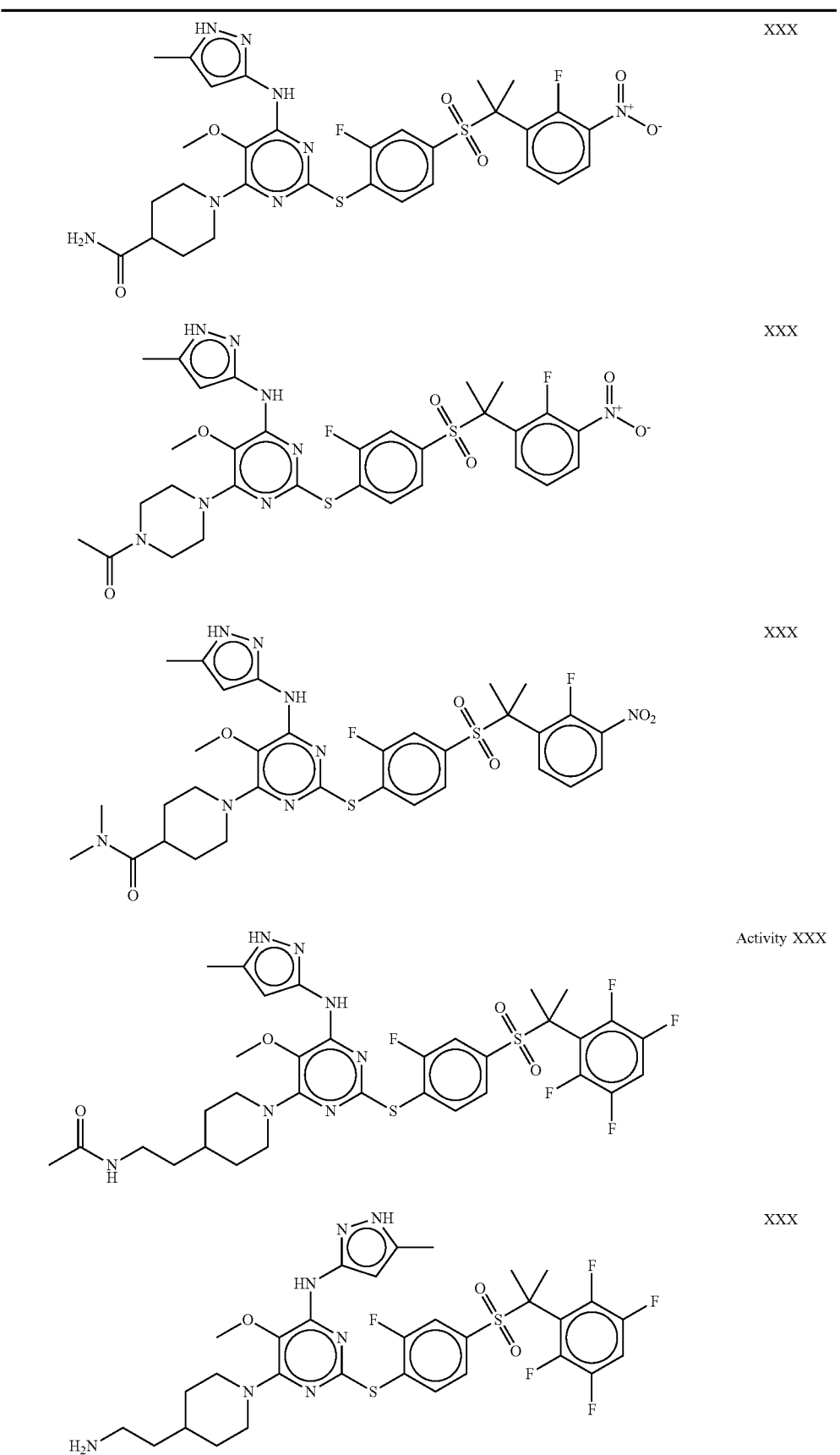
| | |
|---|---|
| | XXX |
| | XXX |
| | XXX |
| | Activity XXX |
| | XXX |

TABLE 1-continued
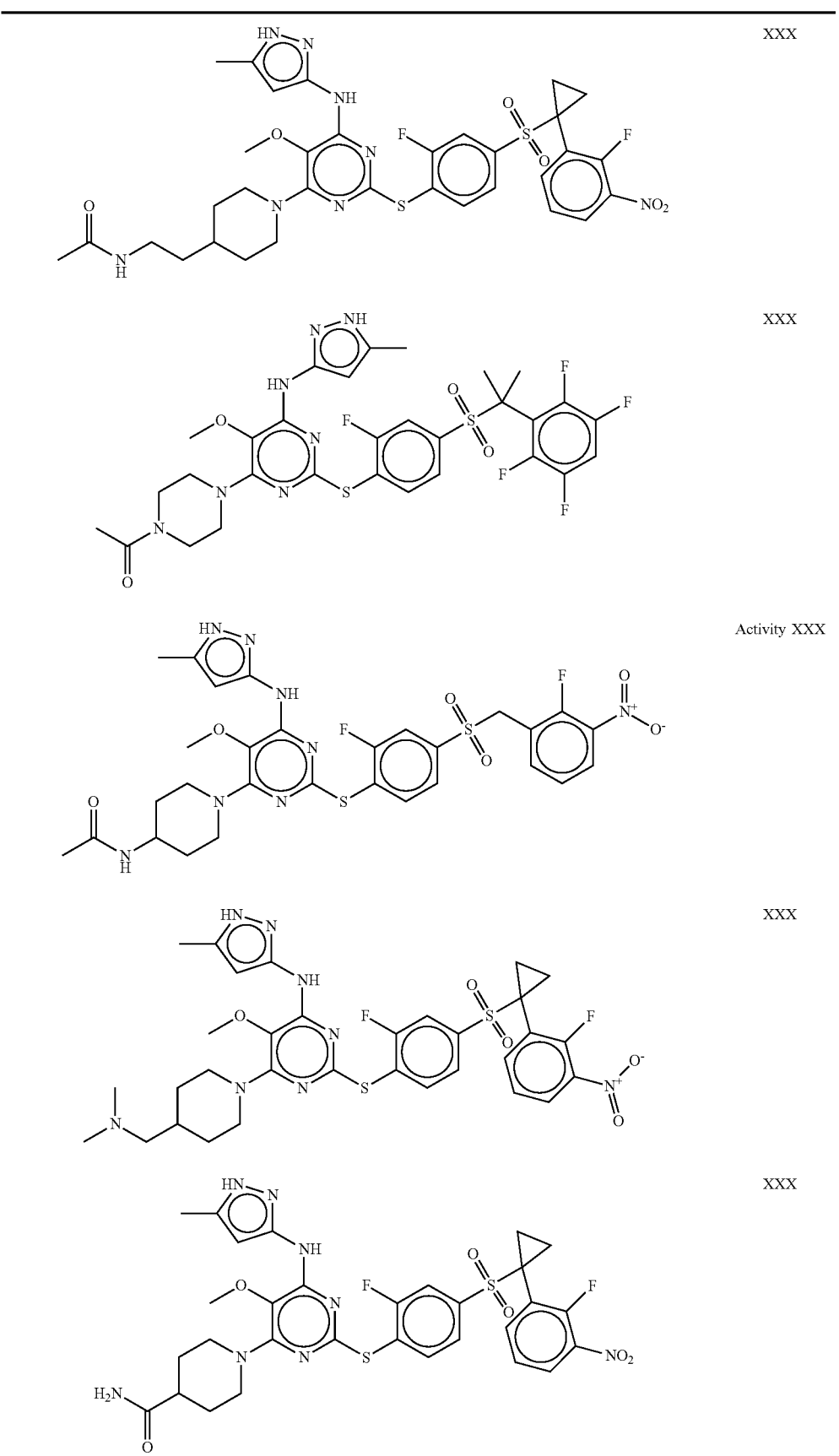
XXX
XXX
Activity XXX
XXX
XXX

TABLE 1-continued
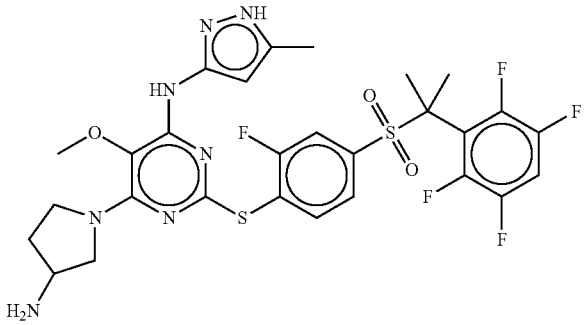 XXX
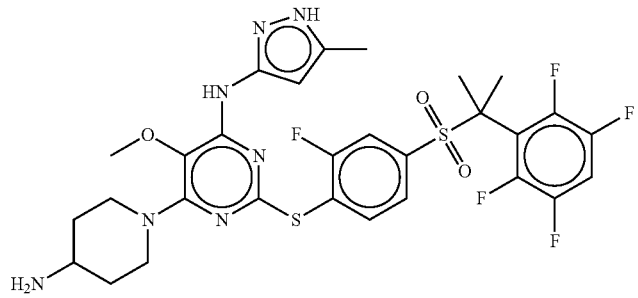 Activity XXX
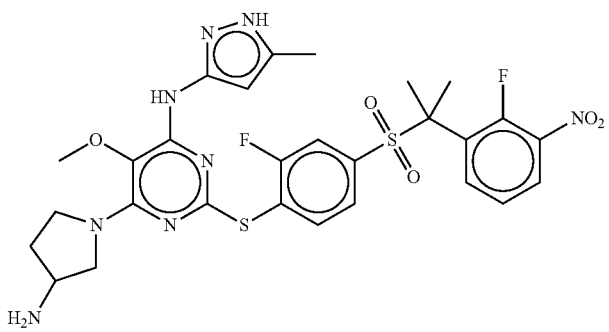 XXX
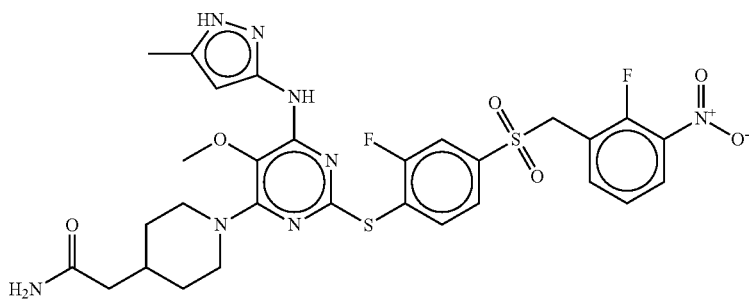 XXX
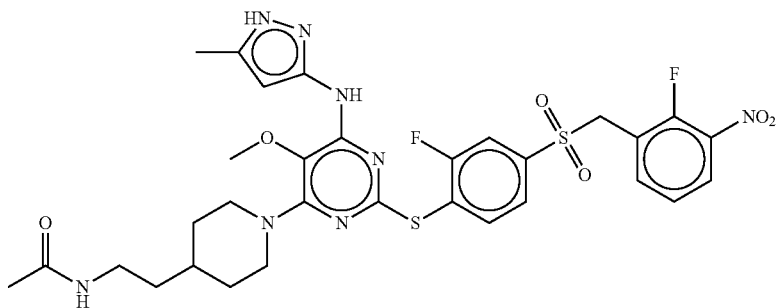 XXX TABLE 1-continued
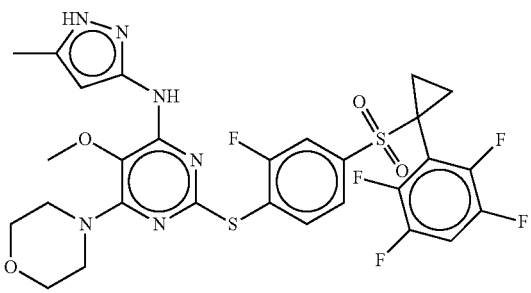
Activity XXX
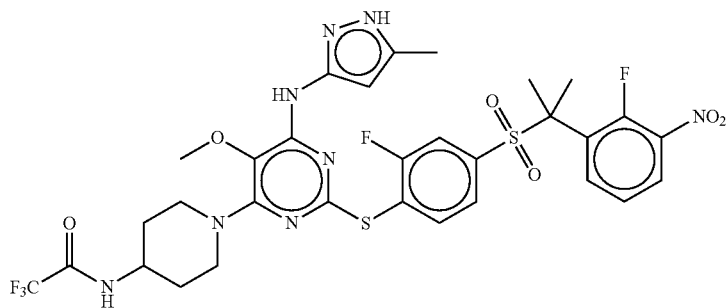
XXX
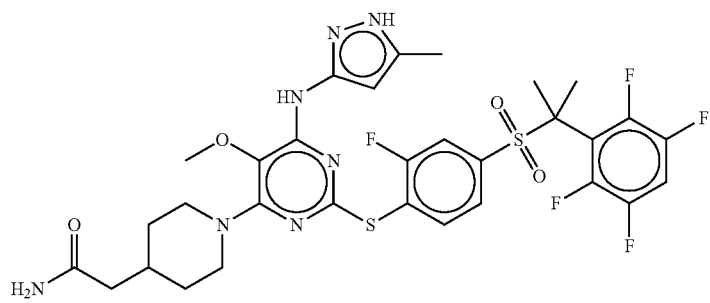
XXX
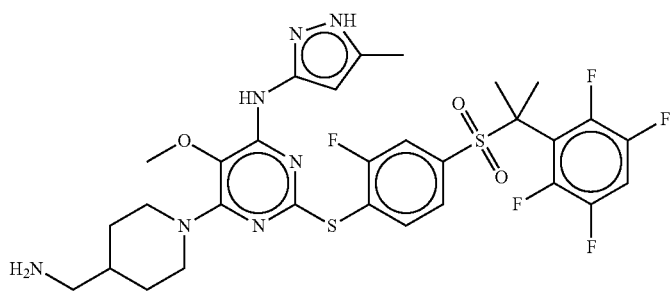
XXX
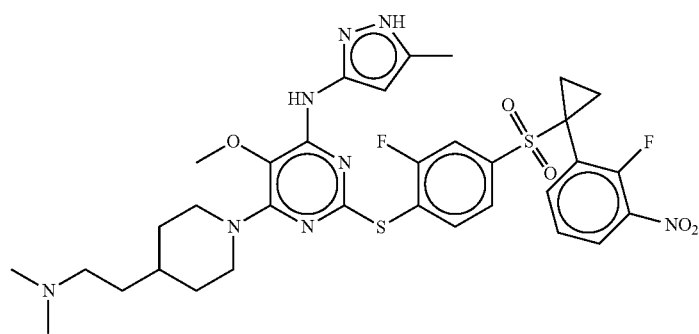
Activity XXX TABLE 1-continued
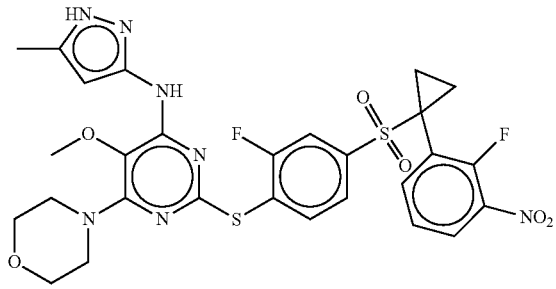 XXX
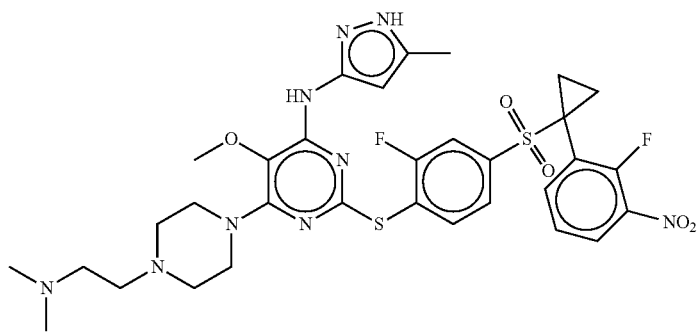 XXX
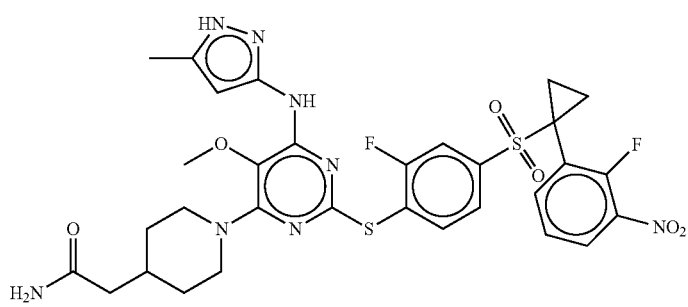 XXX
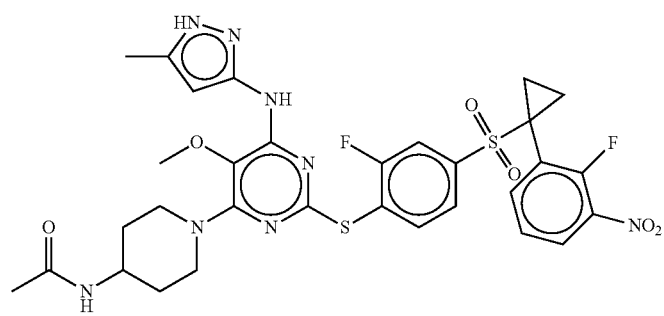 Activity XXX
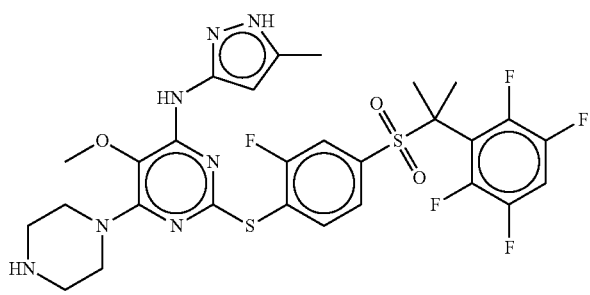 XXX TABLE 1-continued
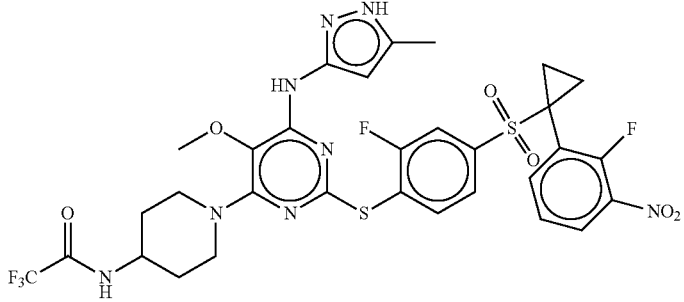 XXX
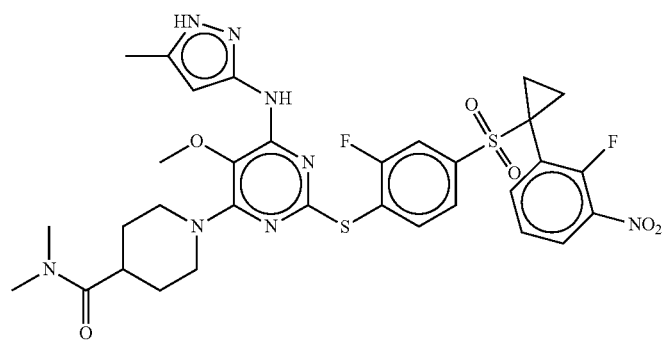 XXX
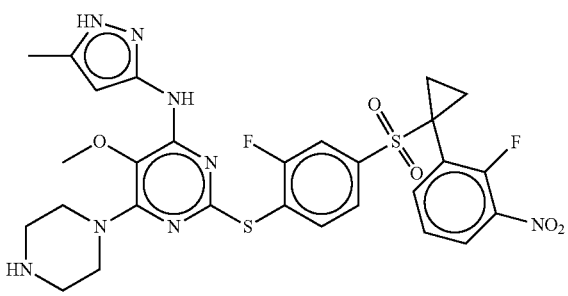 Activity XXX
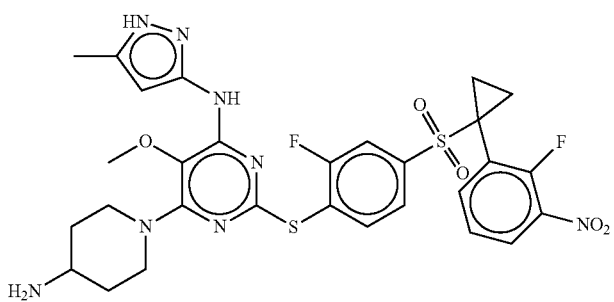 XXX
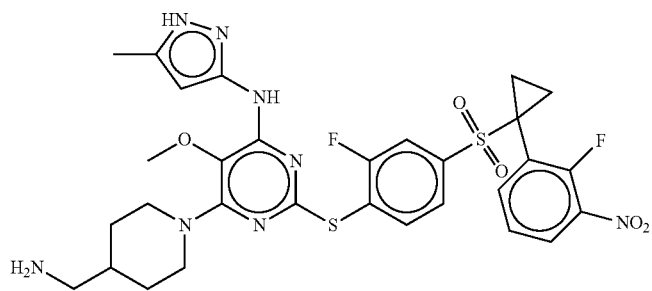 XXX TABLE 1-continued
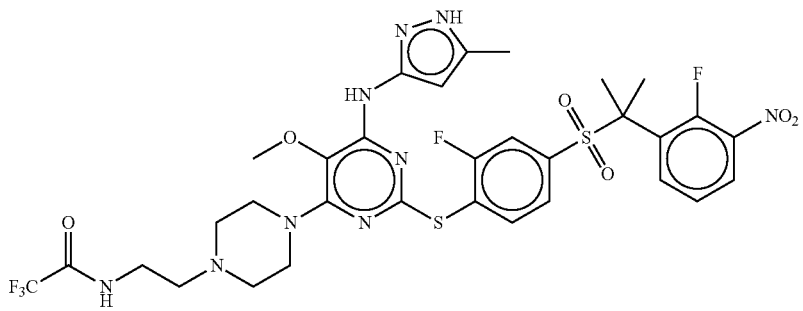
XXX
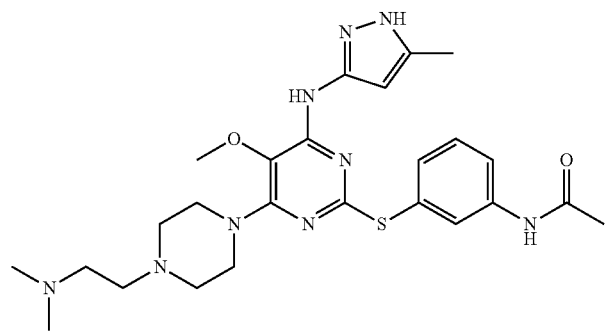 [SMILES: COc1c(Nc2cc(C)[nH]n2)nc(Sc2cccc(NC(C)=O)c2)nc1N1CCN(CCN(C)C)CC1]
Activity XXX
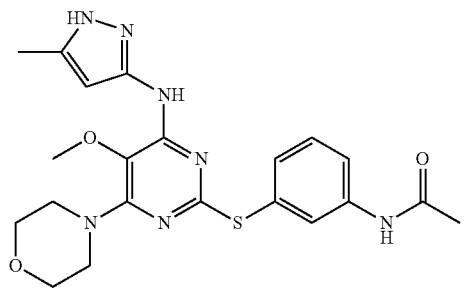 [SMILES: COc1c(Nc2cc(C)[nH]n2)nc(Sc2cccc(NC(C)=O)c2)nc1N1CCOCC1]
XXX
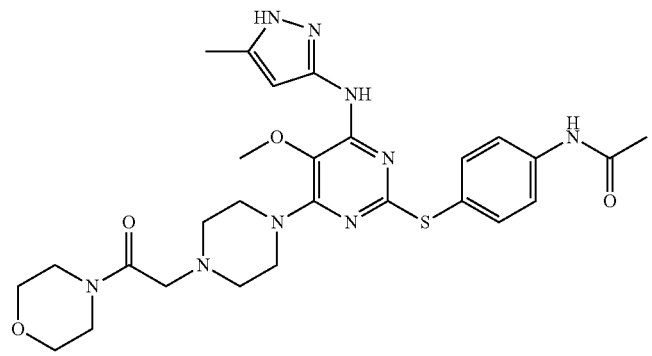 [SMILES: COc1c(Nc2cc(C)[nH]n2)nc(Sc2ccc(NC(C)=O)cc2)nc1N1CCN(CC(=O)N2CCOCC2)CC1]
XXX
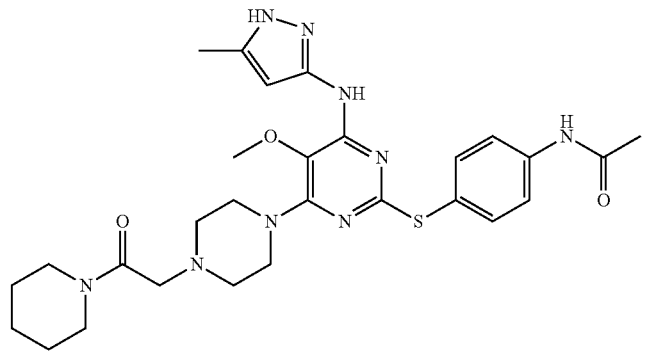 [SMILES: COc1c(Nc2cc(C)[nH]n2)nc(Sc2ccc(NC(C)=O)cc2)nc1N1CCN(CC(=O)N2CCCCC2)CC1]
XXX

TABLE 1-continued
| | |
|---|---|
| 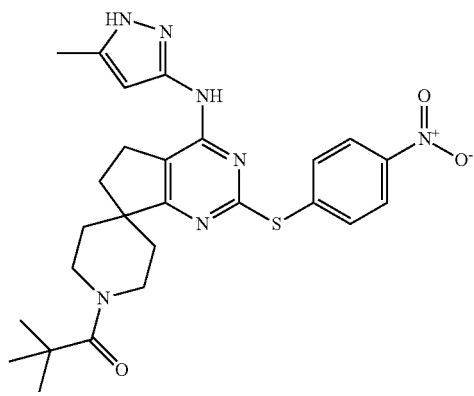 [SMILES: Cc1cc(Nc2nc(Sc3ccc([N+](=O)[O-])cc3)nc3c2CCC32CCN(C(=O)C(C)(C)C)CC2)n[nH]1] | Activity XXX |
| 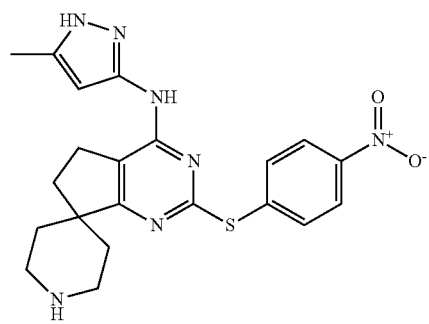 [SMILES: Cc1cc(Nc2nc(Sc3ccc([N+](=O)[O-])cc3)nc3c2CCC32CCNCC2)n[nH]1] | XXX |
| 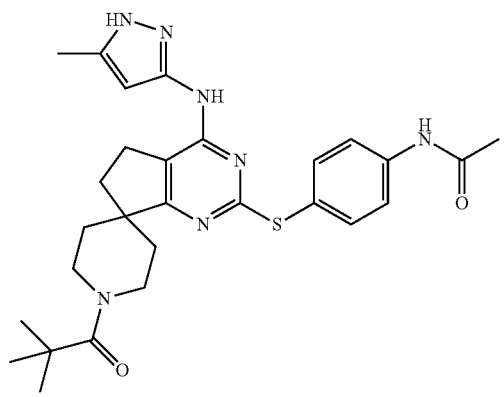 [SMILES: CC(=O)Nc1ccc(Sc2nc(Nc3cc(C)[nH]n3)c3c(n2)C2(CC3)CCN(C(=O)C(C)(C)C)CC2)cc1] | XXX |
| 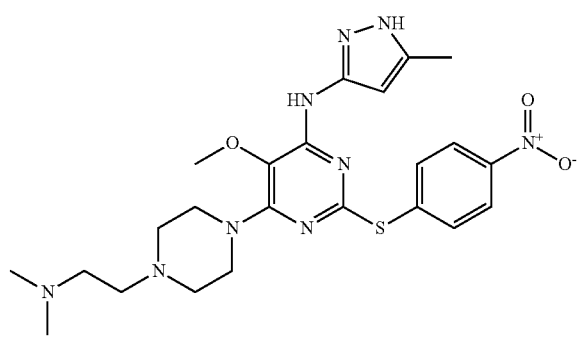 [SMILES: COc1c(Nc2cc(C)[nH]n2)nc(Sc2ccc([N+](=O)[O-])cc2)nc1N1CCN(CCN(C)C)CC1] | XXX |

TABLE 1-continued
| | |
|---|---|
| 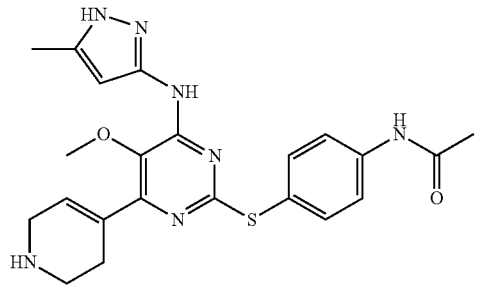 [SMILES: COc1c(Nc2cc(C)[nH]n2)nc(Sc2ccc(NC(C)=O)cc2)nc1C1=CCNCC1] | XXX |
| 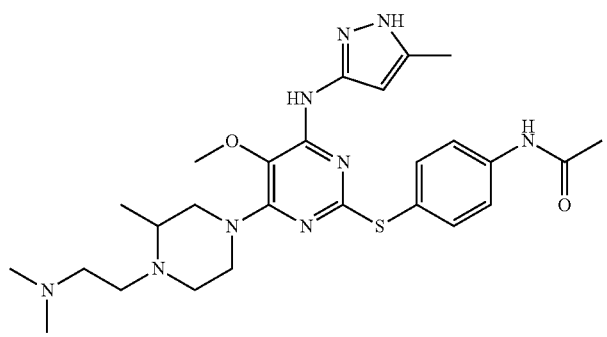 [SMILES: COc1c(Nc2cc(C)[nH]n2)nc(Sc2ccc(NC(C)=O)cc2)nc1N1CCN(CCN(C)C)C(C)C1] | Activity XXX |
| 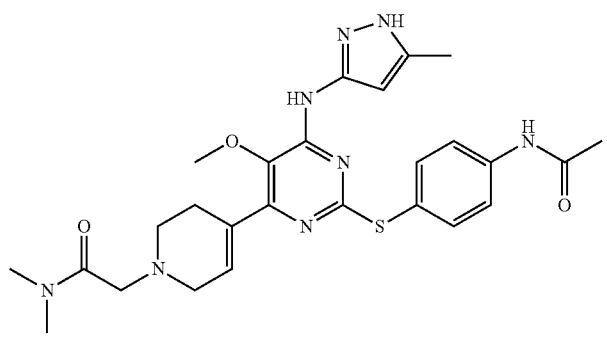 [SMILES: COc1c(Nc2cc(C)[nH]n2)nc(Sc2ccc(NC(C)=O)cc2)nc1C1=CCN(CC(=O)N(C)C)CC1] | XXX |
| 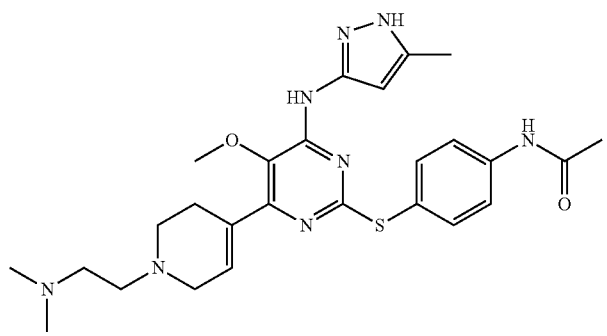 [SMILES: COc1c(Nc2cc(C)[nH]n2)nc(Sc2ccc(NC(C)=O)cc2)nc1C1=CCN(CCN(C)C)CC1] | XXX |
| 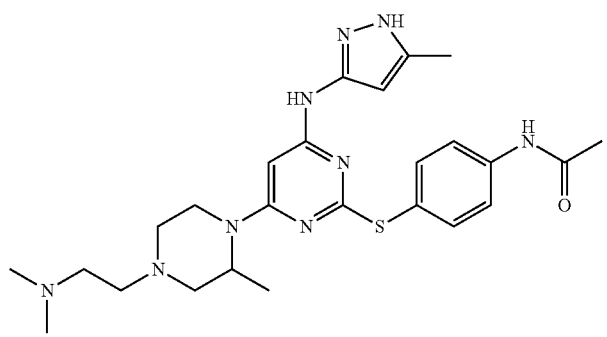 [SMILES: CC(=O)Nc1ccc(Sc2nc(Nc3cc(C)[nH]n3)cc(N3CCN(CCN(C)C)CC3C)n2)cc1] | XXX |

TABLE 1-continued
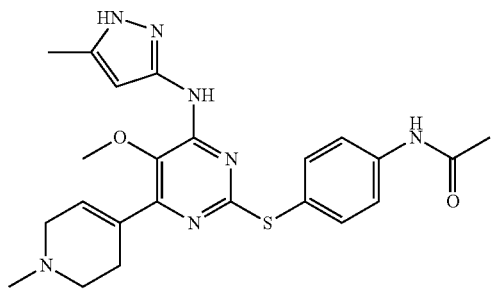 [SMILES: COc1c(Nc2cc(C)[nH]n2)nc(Sc2ccc(NC(C)=O)cc2)nc1C1=CCN(C)CC1]
Activity XXX
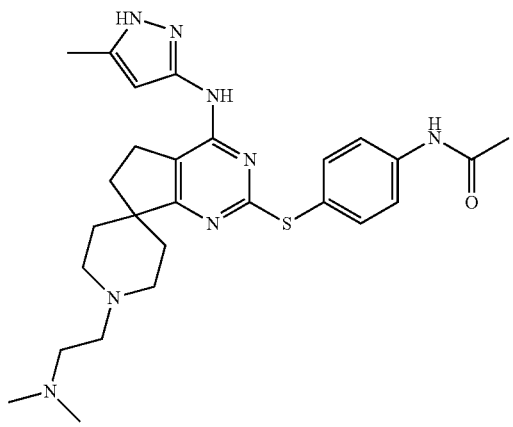 [SMILES: CC(=O)Nc1ccc(Sc2nc(Nc3cc(C)[nH]n3)c3c(n2)C2(CC3)CCN(CCN(C)C)CC2)cc1]
XXX
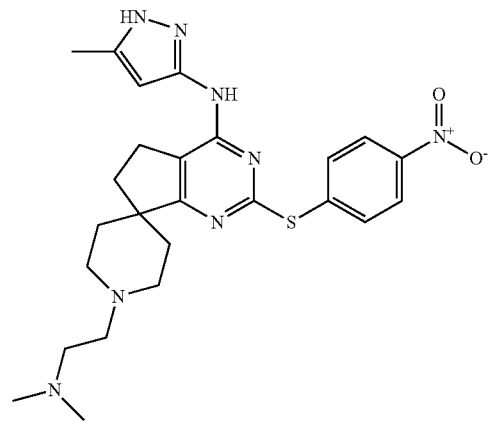 [SMILES: Cc1cc(Nc2nc(Sc3ccc([N+](=O)[O-])cc3)nc3c2CCC32CCN(CCN(C)C)CC2)n[nH]1]
XXX
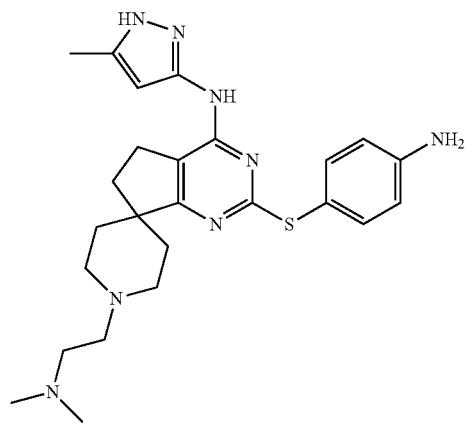 [SMILES: Cc1cc(Nc2nc(Sc3ccc(N)cc3)nc3c2CCC32CCN(CCN(C)C)CC2)n[nH]1]
XXX TABLE 1-continued
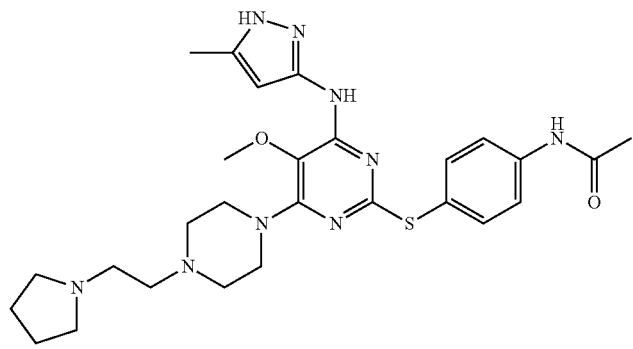 [SMILES: COc1c(Nc2cc(C)[nH]n2)nc(Sc2ccc(NC(C)=O)cc2)nc1N1CCN(CCN2CCCC2)CC1] XXX
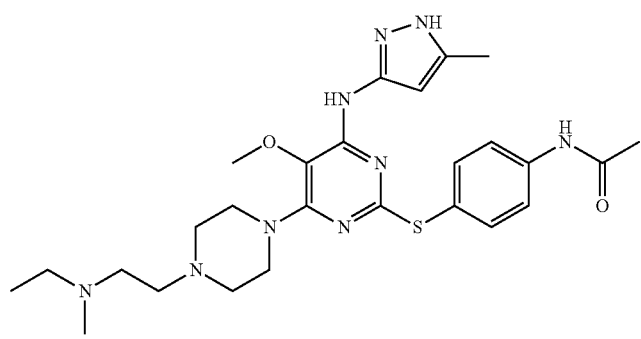 Activity XXX
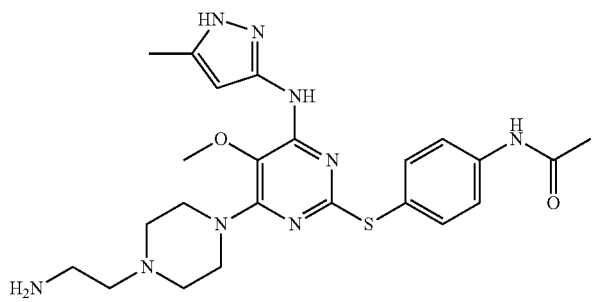 [SMILES: COc1c(Nc2cc(C)[nH]n2)nc(Sc2ccc(NC(C)=O)cc2)nc1N1CCN(CCN)CC1] XXX
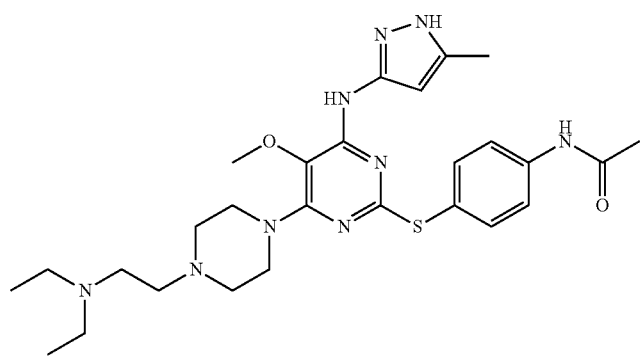 [SMILES: CCN(CC)CCN1CCN(c2nc(Sc3ccc(NC(C)=O)cc3)nc(Nc3cc(C)[nH]n3)c2OC)CC1] XXX TABLE 1-continued
| | |
|---|---|
| 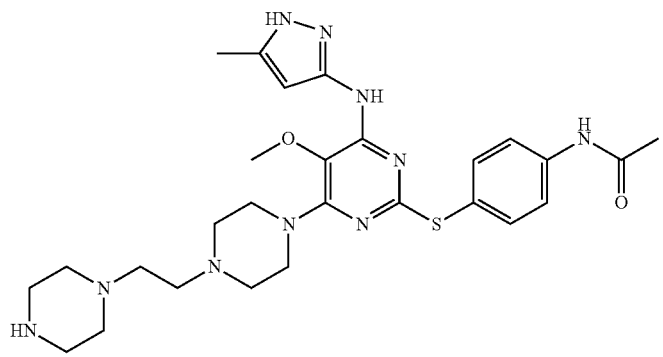 [SMILES: COc1c(Nc2cc(C)[nH]n2)nc(Sc2ccc(NC(C)=O)cc2)nc1N1CCN(CCN2CCNCC2)CC1] | XXX |
| 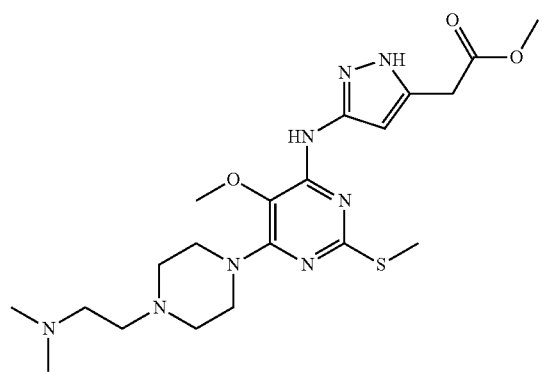 | Activity X |
| 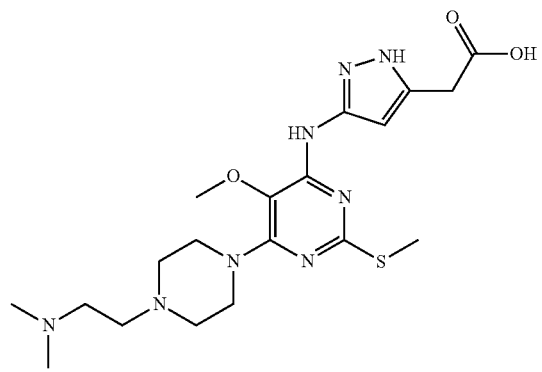 [SMILES: COc1c(Nc2cc(CC(=O)O)[nH]n2)nc(SC)nc1N1CCN(CCN(C)C)CC1] | X |
| 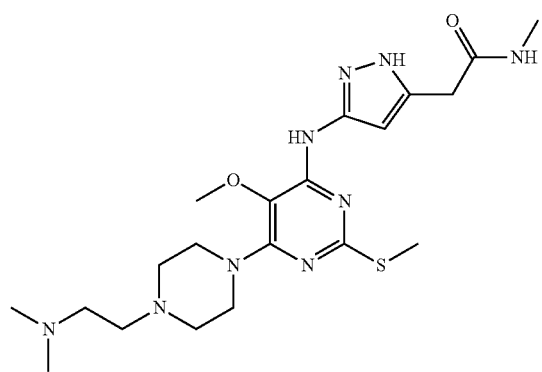 | X |

TABLE 1-continued
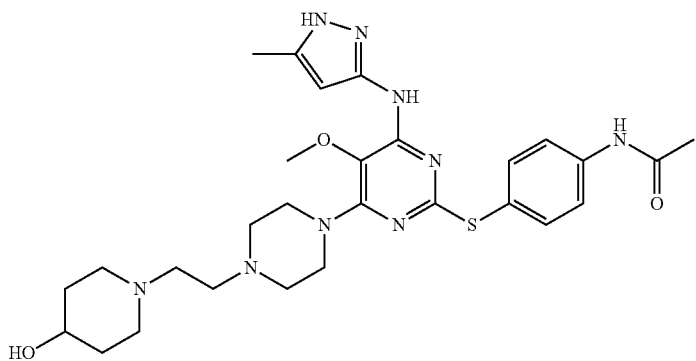 [SMILES: COc1c(Nc2cc(C)[nH]n2)nc(Sc2ccc(NC(C)=O)cc2)nc1N1CCN(CCN2CCC(O)CC2)CC1]
XX
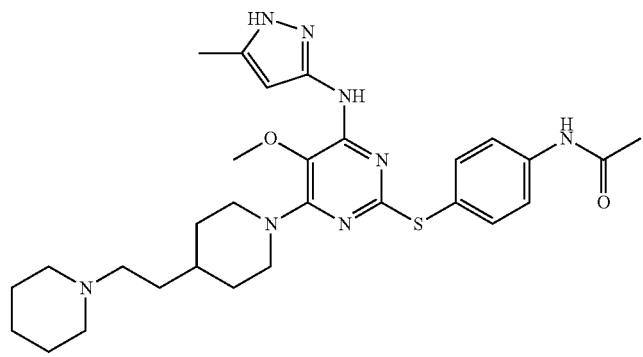 [SMILES: COc1c(Nc2cc(C)[nH]n2)nc(Sc2ccc(NC(C)=O)cc2)nc1N1CCC(CCN2CCCCC2)CC1]
Activity XX
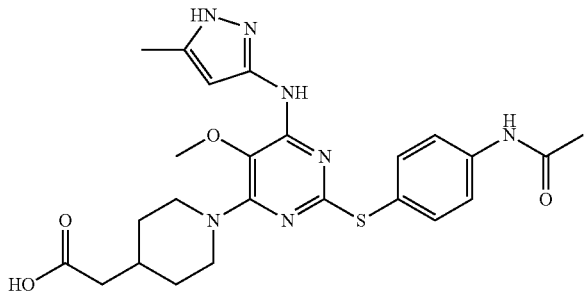
XXX
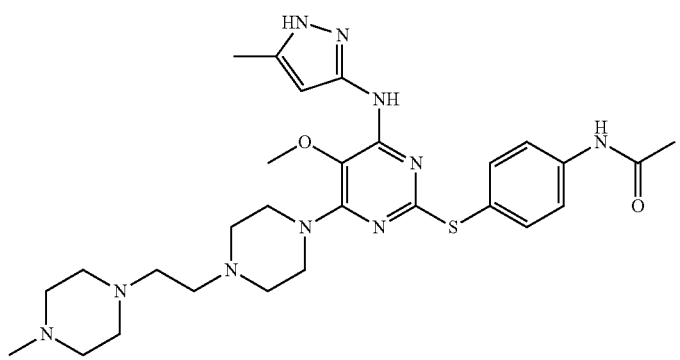
XXX TABLE 1-continued
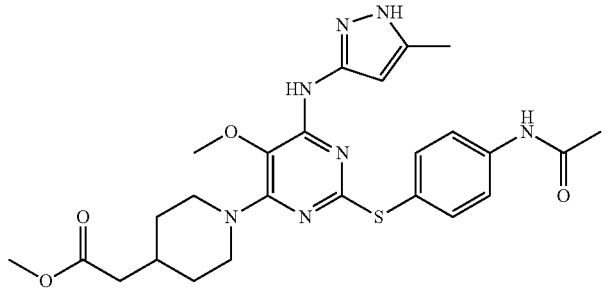 [SMILES: COC(=O)CC1CCN(c2nc(Sc3ccc(NC(C)=O)cc3)nc(Nc3cc(C)[nH]n3)c2OC)CC1]
XXX
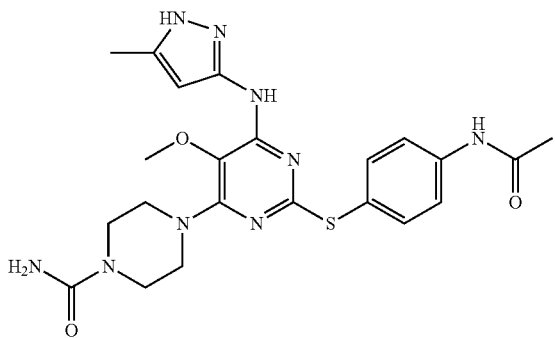 [SMILES: COc1c(Nc2cc(C)[nH]n2)nc(Sc2ccc(NC(C)=O)cc2)nc1N1CCN(C(N)=O)CC1]
Activity XXX
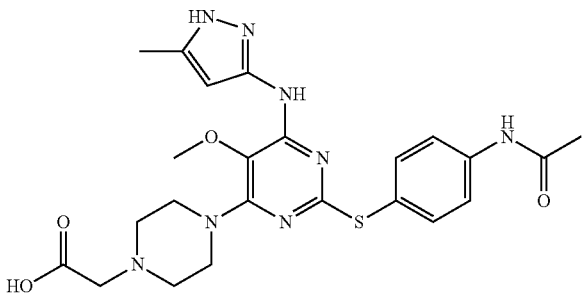 [SMILES: COc1c(Nc2cc(C)[nH]n2)nc(Sc2ccc(NC(C)=O)cc2)nc1N1CCN(CC(=O)O)CC1]
XXX
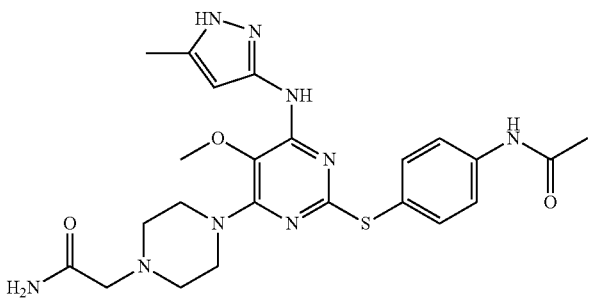
XXX
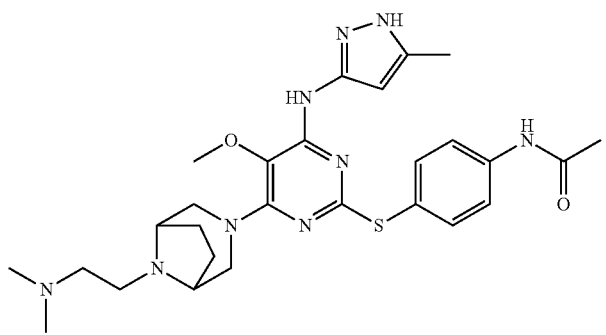 [SMILES: COc1c(Nc2cc(C)[nH]n2)nc(Sc2ccc(NC(C)=O)cc2)nc1N1CC2CCC(C1)N2CCN(C)C]
XXX TABLE 1-continued
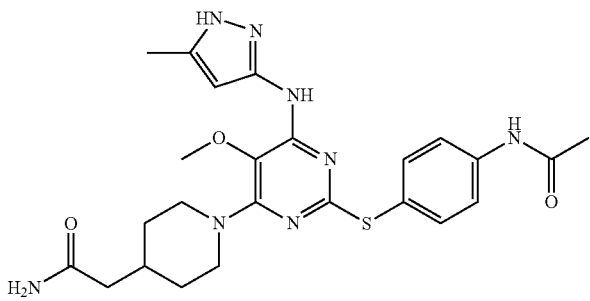 [SMILES: COc1c(Nc2cc(C)[nH]n2)nc(Sc2ccc(NC(C)=O)cc2)nc1N1CCC(CC(N)=O)CC1] Activity XXX
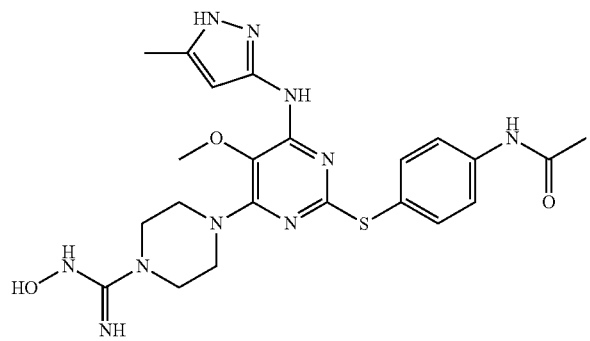 [SMILES: COc1c(Nc2cc(C)[nH]n2)nc(Sc2ccc(NC(C)=O)cc2)nc1N1CCN(C(=N)NO)CC1] XXX
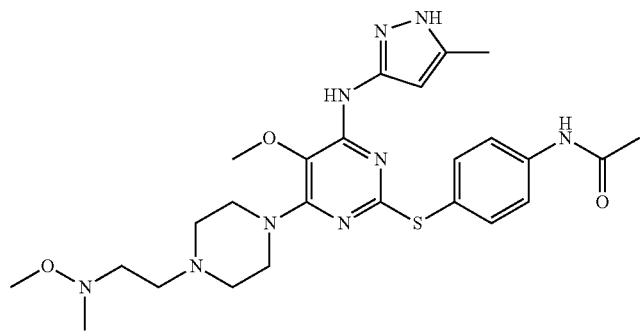 [SMILES: COc1c(Nc2cc(C)[nH]n2)nc(Sc2ccc(NC(C)=O)cc2)nc1N1CCN(CCN(C)OC)CC1] XXX
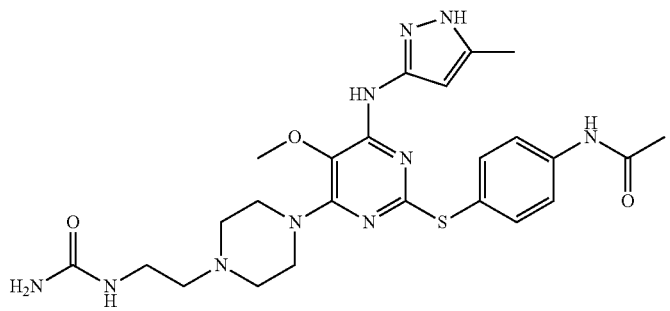 [SMILES: COc1c(Nc2cc(C)[nH]n2)nc(Sc2ccc(NC(C)=O)cc2)nc1N1CCN(CCNC(N)=O)CC1] XXX
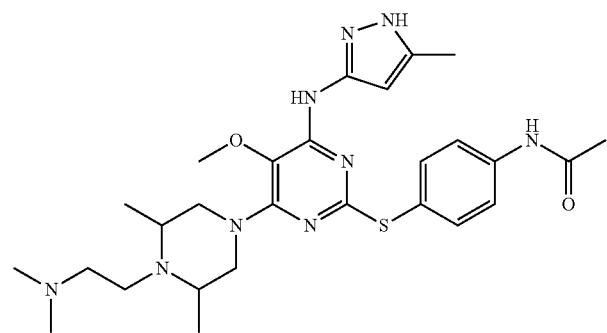 Activity XXX TABLE 1-continued
| | |
|---|---|
| 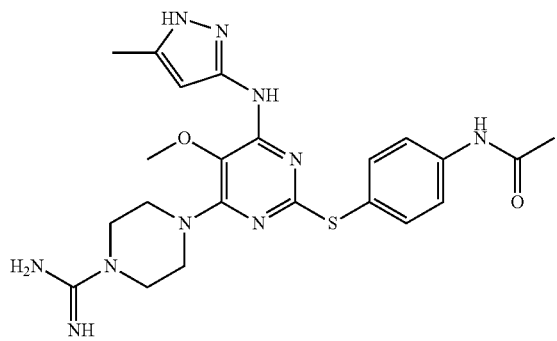 [SMILES: COc1c(Nc2cc(C)[nH]n2)nc(Sc2ccc(NC(C)=O)cc2)nc1N1CCN(C(=N)N)CC1] | XXX |
| 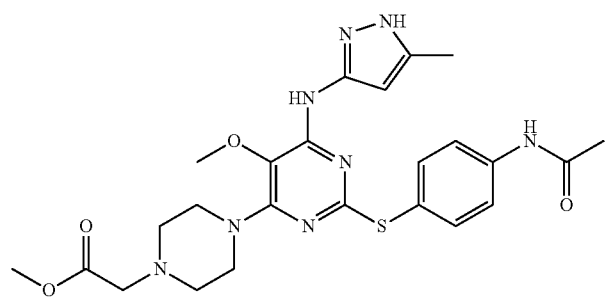 [SMILES: COC(=O)CN1CCN(c2nc(Sc3ccc(NC(C)=O)cc3)nc(Nc3cc(C)[nH]n3)c2OC)CC1] | XXX |
| 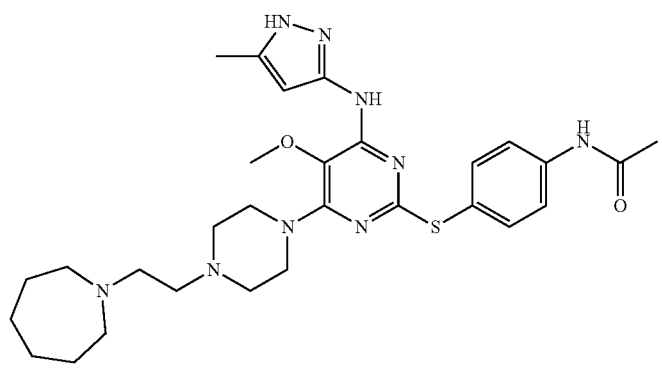 [SMILES: COc1c(Nc2cc(C)[nH]n2)nc(Sc2ccc(NC(C)=O)cc2)nc1N1CCN(CCN2CCCCCC2)CC1] | XXX |
| 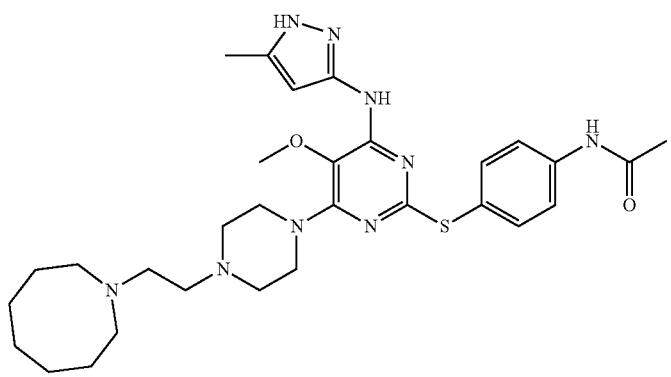 [SMILES: COc1c(Nc2cc(C)[nH]n2)nc(Sc2ccc(NC(C)=O)cc2)nc1N1CCN(CCN2CCCCCCC2)CC1] | Activity XXX |

TABLE 1-continued
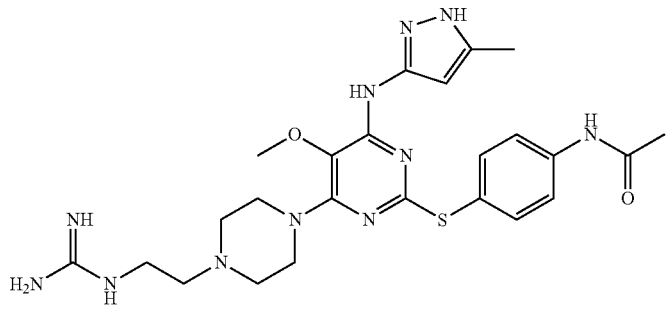 [SMILES: COc1c(Nc2cc(C)[nH]n2)nc(Sc2ccc(NC(C)=O)cc2)nc1N1CCN(CCNC(=N)N)CC1]
XXX
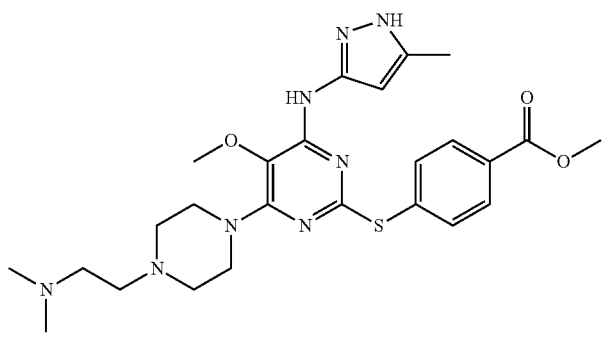
XXX
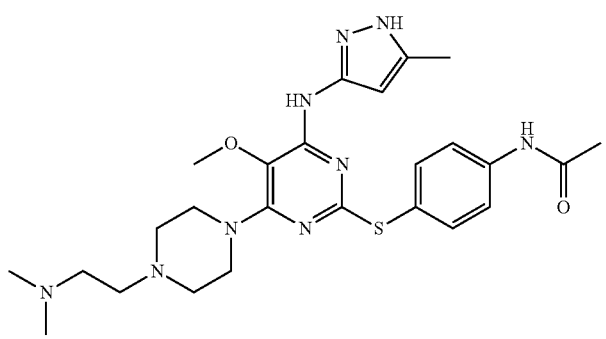
XXX
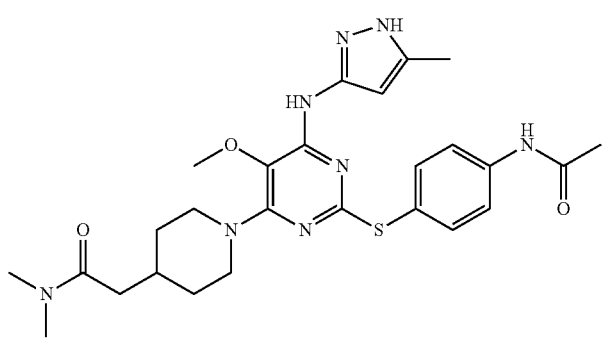 [SMILES: COc1c(Nc2cc(C)[nH]n2)nc(Sc2ccc(NC(C)=O)cc2)nc1N1CCC(CC(=O)N(C)C)CC1]
Activity XXX TABLE 1-continued
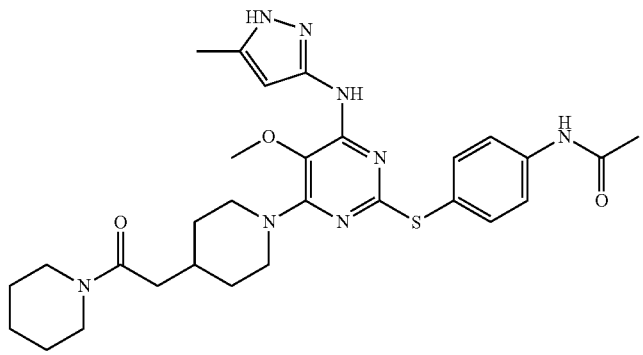 [SMILES: COc1c(Nc2cc(C)[nH]n2)nc(Sc2ccc(NC(C)=O)cc2)nc1N1CCC(CC(=O)N2CCCCC2)CC1] XXX
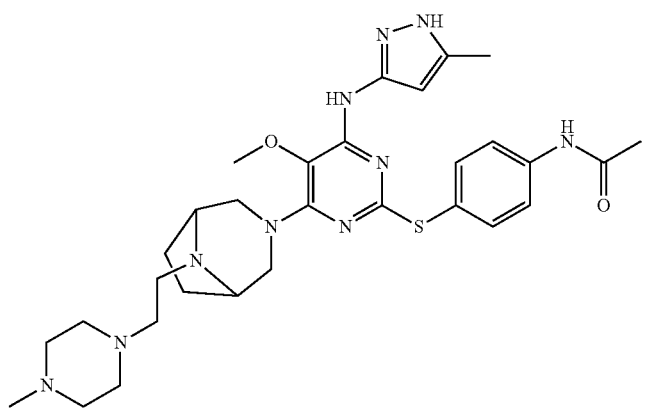 [SMILES: COc1c(Nc2cc(C)[nH]n2)nc(Sc2ccc(NC(C)=O)cc2)nc1N1CC2CCC(C1)N2CCN1CCN(C)CC1] XXX
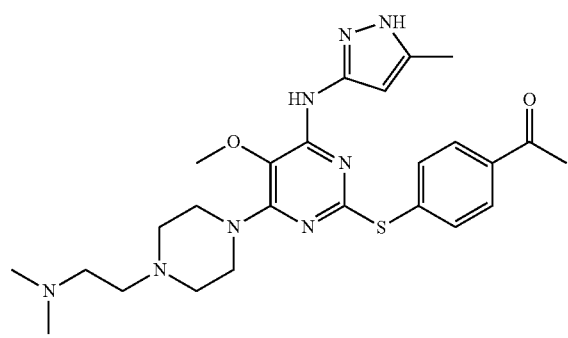 [SMILES: COc1c(Nc2cc(C)[nH]n2)nc(Sc2ccc(C(C)=O)cc2)nc1N1CCN(CCN(C)C)CC1] XXX
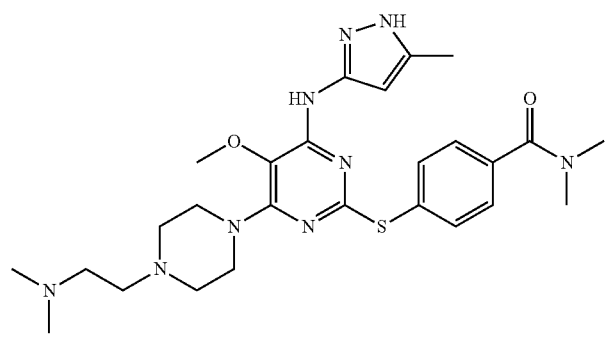 Activity XXX TABLE 1-continued
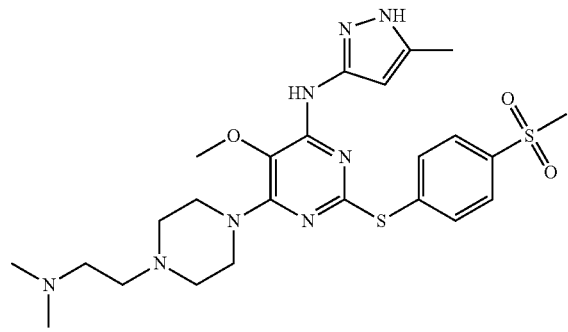
XXX
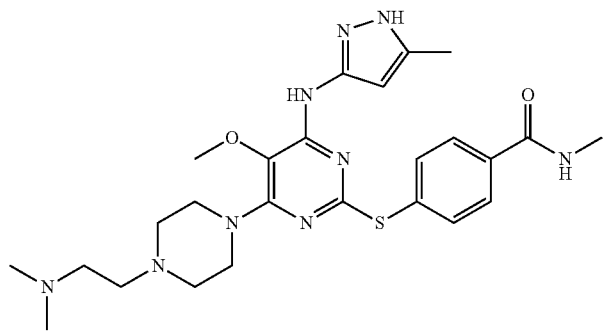
XXX
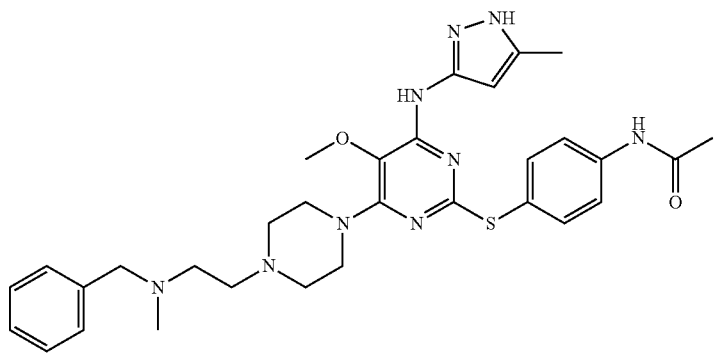 [SMILES: COc1c(Nc2cc(C)[nH]n2)nc(Sc2ccc(NC(C)=O)cc2)nc1N1CCN(CCN(C)Cc2ccccc2)CC1]
XXX
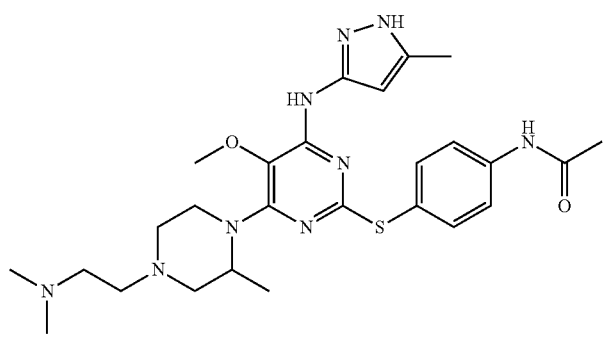 [SMILES: COc1c(Nc2cc(C)[nH]n2)nc(Sc2ccc(NC(C)=O)cc2)nc1N1CCN(CCN(C)C)CC1C]
Activity X TABLE 1-continued
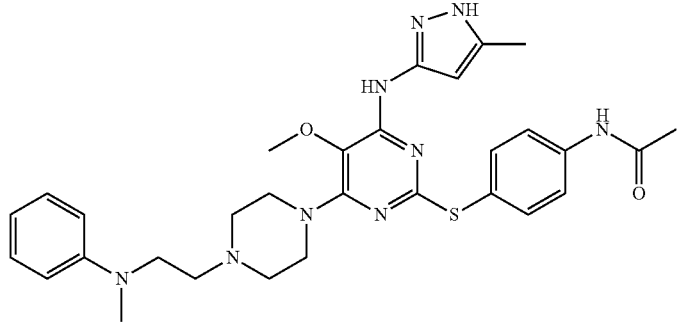 [SMILES: COc1c(Nc2cc(C)[nH]n2)nc(Sc2ccc(NC(C)=O)cc2)nc1N1CCN(CCN(C)c2ccccc2)CC1] XXX
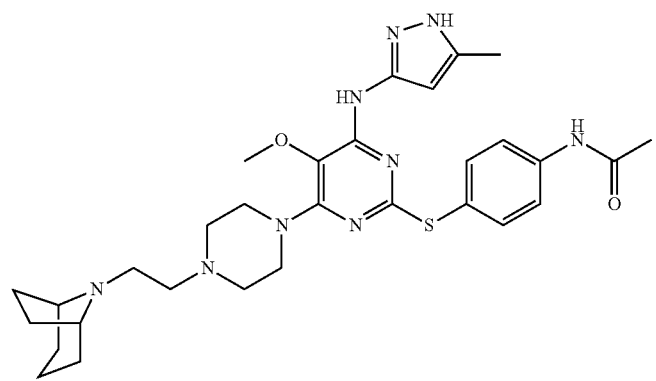 [SMILES: COc1c(Nc2cc(C)[nH]n2)nc(Sc2ccc(NC(C)=O)cc2)nc1N1CCN(CCN2C3CCCC2CC3)CC1] XXX
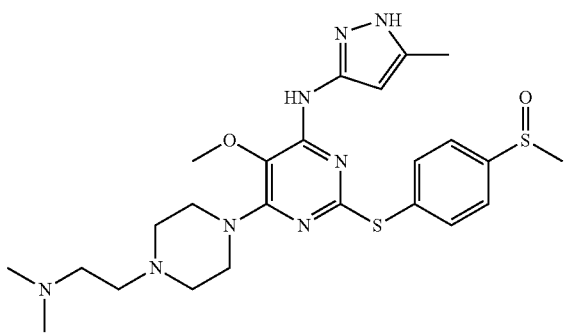 XXX
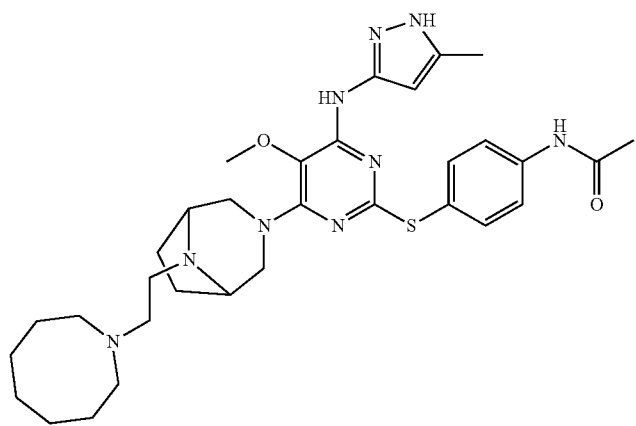 [SMILES: COc1c(Nc2cc(C)[nH]n2)nc(Sc2ccc(NC(C)=O)cc2)nc1N1CC2CCC(C1)N2CCN1CCCCCCC1] Activity XXX TABLE 1-continued
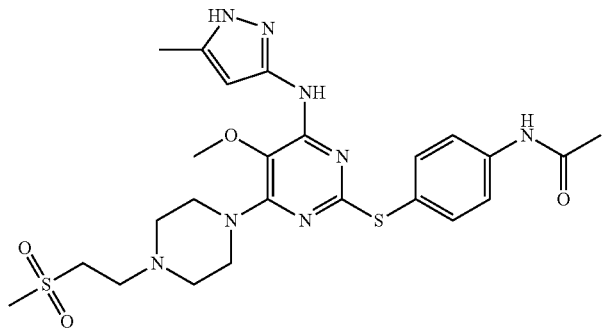 [SMILES: COc1c(Nc2cc(C)[nH]n2)nc(Sc2ccc(NC(C)=O)cc2)nc1N1CCN(CCS(C)(=O)=O)CC1] XXX
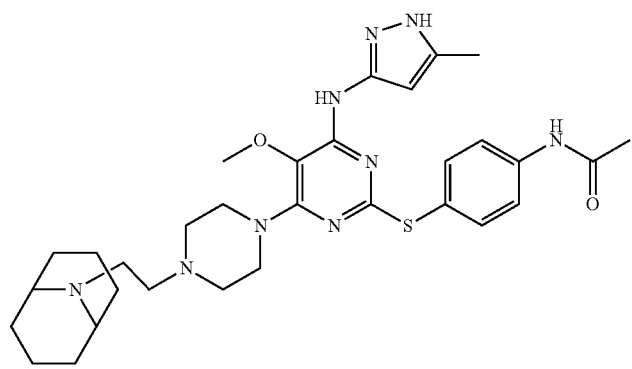 [SMILES: COc1c(Nc2cc(C)[nH]n2)nc(Sc2ccc(NC(C)=O)cc2)nc1N1CCN(CCN2C3CCCC2CCC3)CC1] XXX
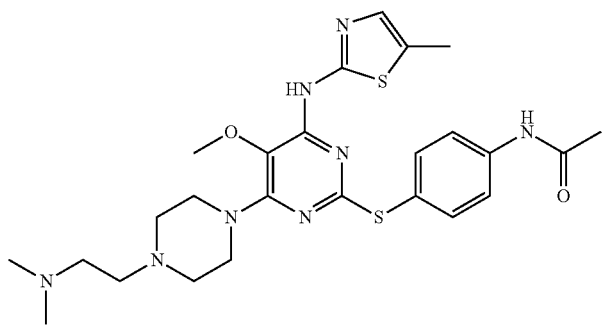 [SMILES: COc1c(Nc2ncc(C)s2)nc(Sc2ccc(NC(C)=O)cc2)nc1N1CCN(CCN(C)C)CC1] XXX
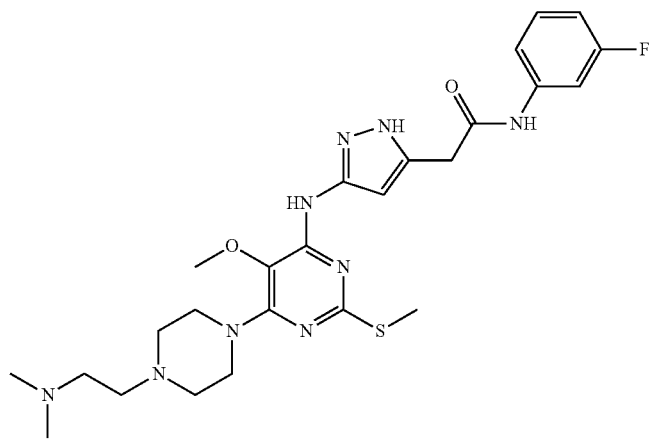 [SMILES: COc1c(Nc2cc(CC(=O)Nc3cccc(F)c3)[nH]n2)nc(SC)nc1N1CCN(CCN(C)C)CC1] Activity X TABLE 1-continued
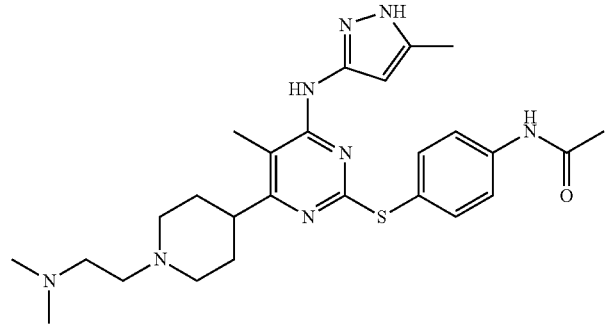 [SMILES: CC(=O)Nc1ccc(Sc2nc(Nc3cc(C)[nH]n3)c(C)c(C3CCN(CCN(C)C)CC3)n2)cc1] XXX
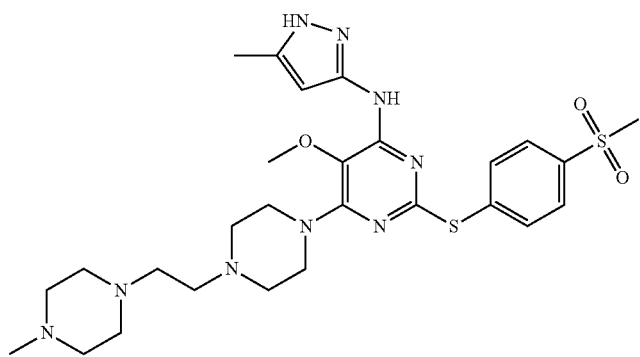 XXX
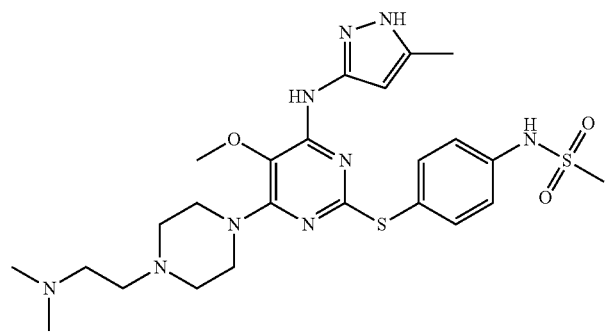 XXX
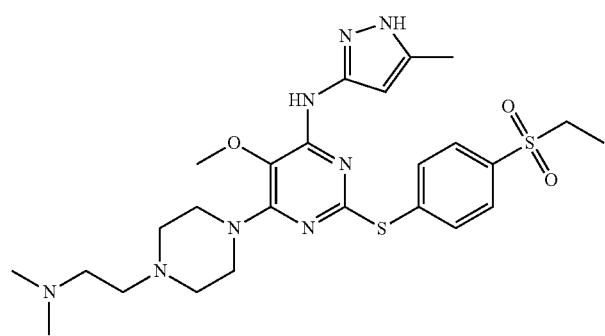 [SMILES: CCS(=O)(=O)c1ccc(Sc2nc(Nc3cc(C)[nH]n3)c(OC)c(N3CCN(CCN(C)C)CC3)n2)cc1] Activity XXX TABLE 1-continued
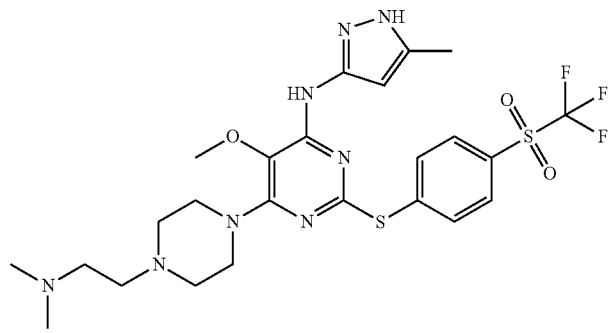 [SMILES: COc1c(Nc2cc(C)[nH]n2)nc(Sc2ccc(S(=O)(=O)C(F)(F)F)cc2)nc1N1CCN(CCN(C)C)CC1] XXX
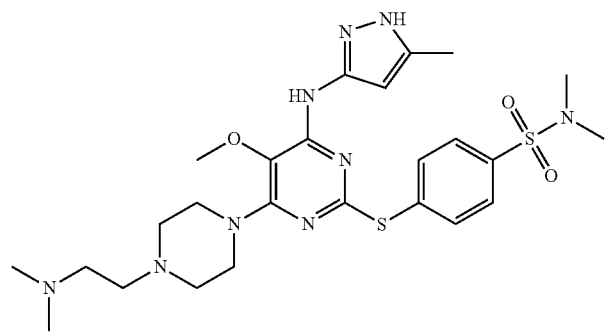 XXX
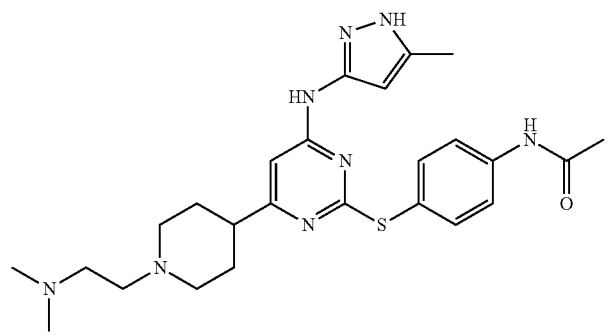 XX
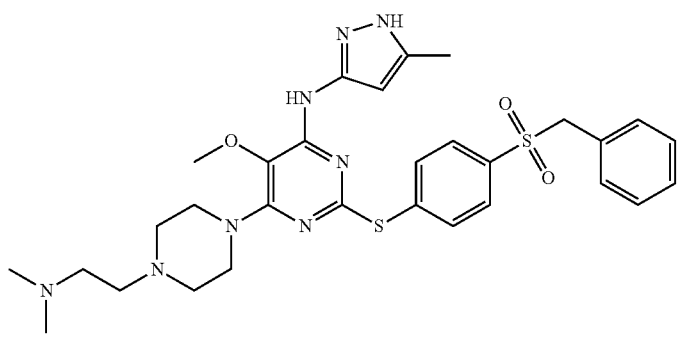 [SMILES: COc1c(Nc2cc(C)[nH]n2)nc(Sc2ccc(S(=O)(=O)Cc3ccccc3)cc2)nc1N1CCN(CCN(C)C)CC1] Activity XXX TABLE 1-continued
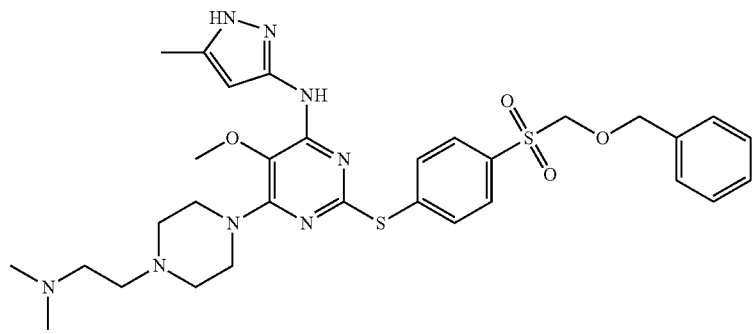 [SMILES: COc1c(Nc2cc(C)[nH]n2)nc(Sc2ccc(S(=O)(=O)COCc3ccccc3)cc2)nc1N1CCN(CCN(C)C)CC1]
XXX
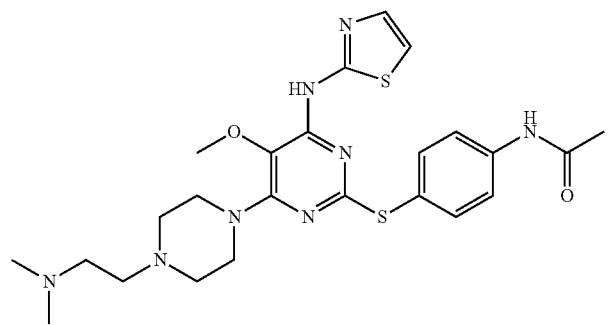 [SMILES: COc1c(Nc2nccs2)nc(Sc2ccc(NC(C)=O)cc2)nc1N1CCN(CCN(C)C)CC1]
XX
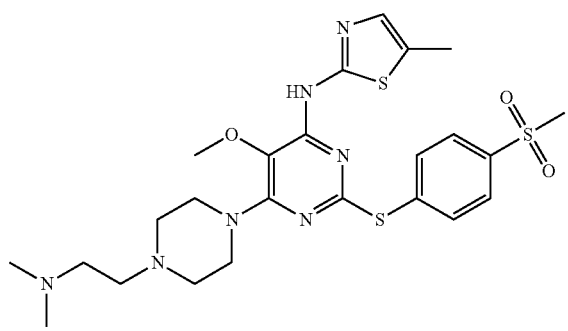
XXX
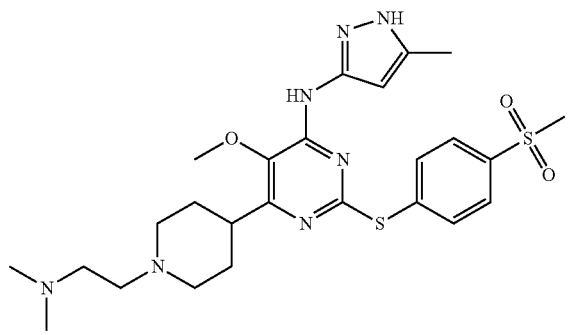
Activity XX TABLE 1-continued
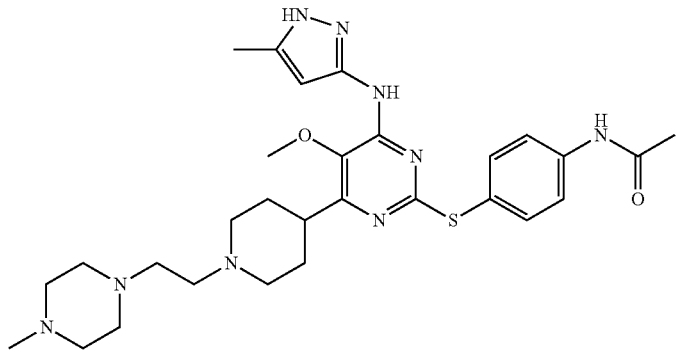
XXX
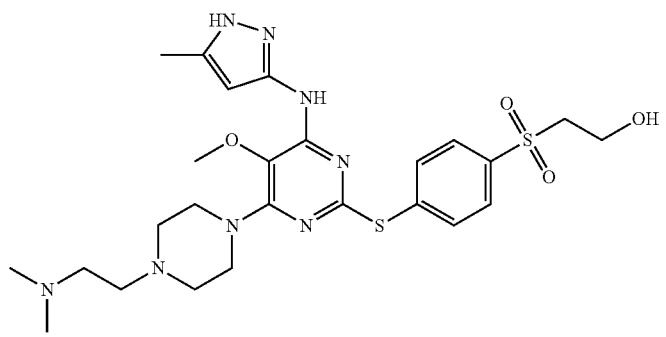 [SMILES: COc1c(Nc2cc(C)[nH]n2)nc(Sc2ccc(S(=O)(=O)CCO)cc2)nc1N1CCN(CCN(C)C)CC1]
XXX
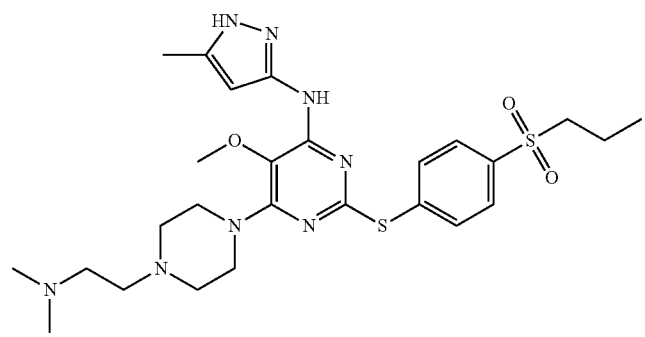 [SMILES: CCCS(=O)(=O)c1ccc(Sc2nc(Nc3cc(C)[nH]n3)c(OC)c(N3CCN(CCN(C)C)CC3)n2)cc1]
XXX
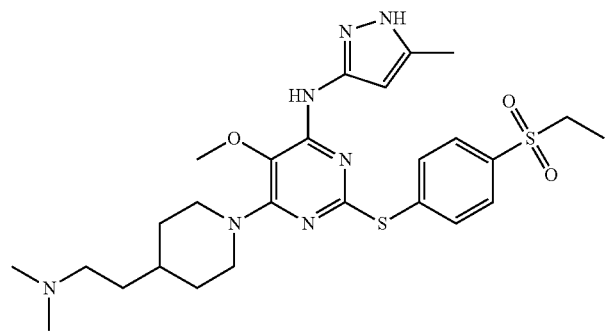
Activity XXX TABLE 1-continued
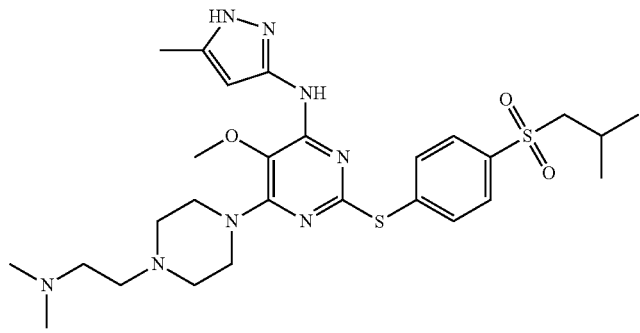 [SMILES: COc1c(Nc2cc(C)[nH]n2)nc(Sc2ccc(S(=O)(=O)CC(C)C)cc2)nc1N1CCN(CCN(C)C)CC1]
XXX
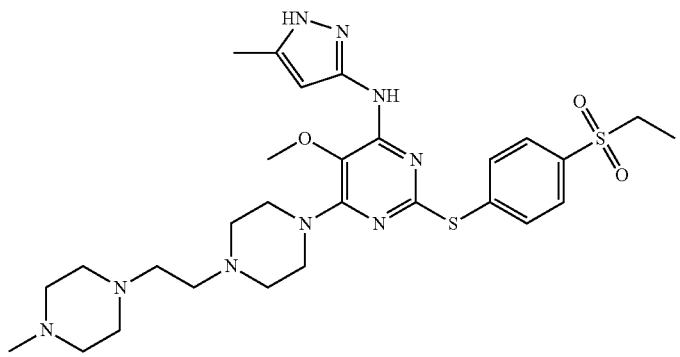 [SMILES: CCS(=O)(=O)c1ccc(Sc2nc(Nc3cc(C)[nH]n3)c(OC)c(N3CCN(CCN4CCN(C)CC4)CC3)n2)cc1]
XXX
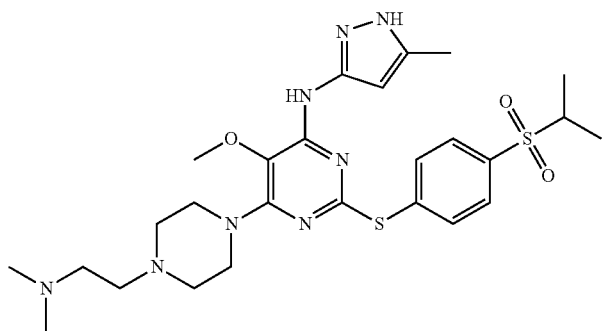
XXX
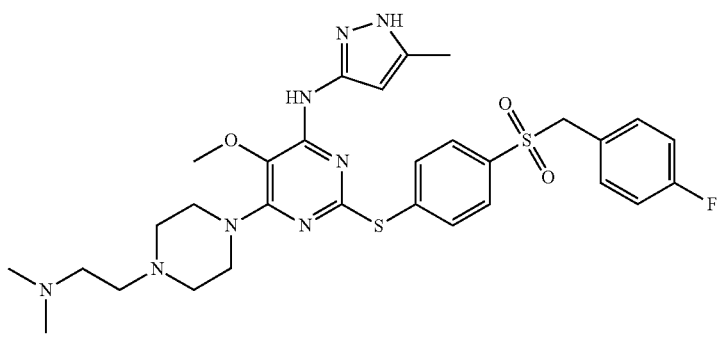 [SMILES: COc1c(Nc2cc(C)[nH]n2)nc(Sc2ccc(S(=O)(=O)Cc3ccc(F)cc3)cc2)nc1N1CCN(CCN(C)C)CC1]
Activity XXX TABLE 1-continued
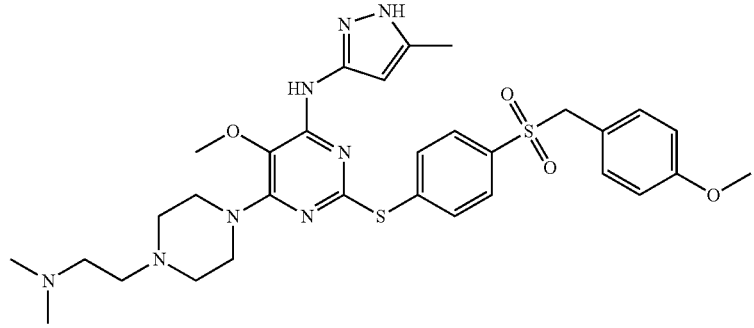
XXX
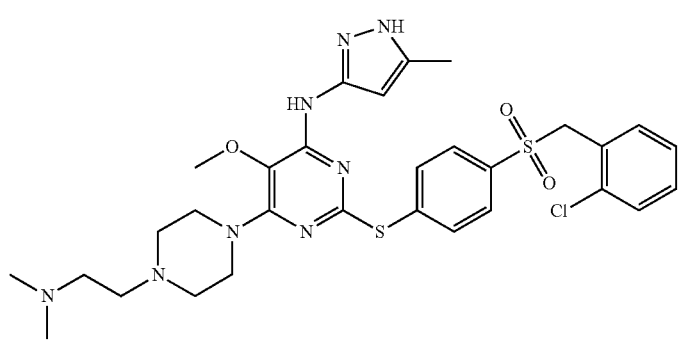 [SMILES: COc1c(Nc2cc(C)[nH]n2)nc(Sc2ccc(S(=O)(=O)Cc3ccccc3Cl)cc2)nc1N1CCN(CCN(C)C)CC1]
XXX
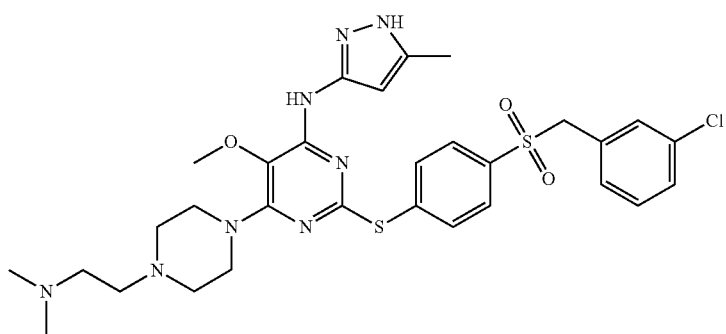 [SMILES: COc1c(Nc2cc(C)[nH]n2)nc(Sc2ccc(S(=O)(=O)Cc3cccc(Cl)c3)cc2)nc1N1CCN(CCN(C)C)CC1]
XXX
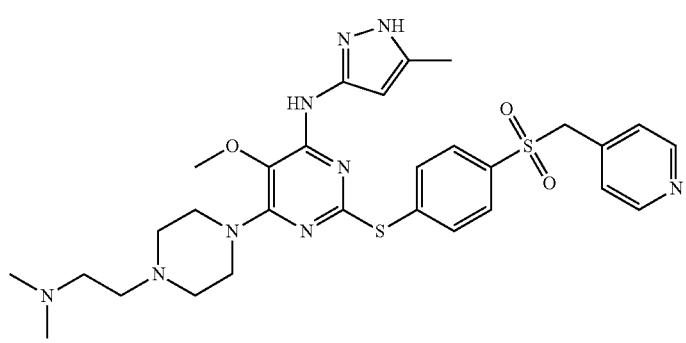 [SMILES: COc1c(Nc2cc(C)[nH]n2)nc(Sc2ccc(S(=O)(=O)Cc3ccncc3)cc2)nc1N1CCN(CCN(C)C)CC1]
Activity XXX TABLE 1-continued
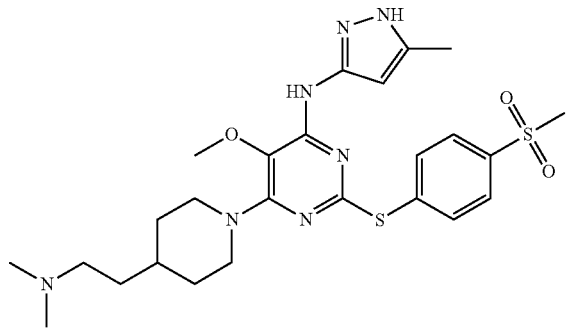 XXX
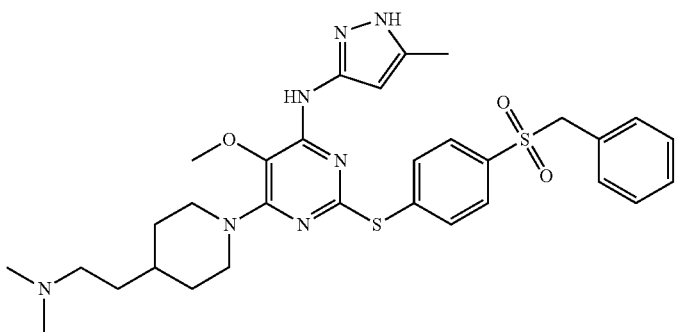 XXX
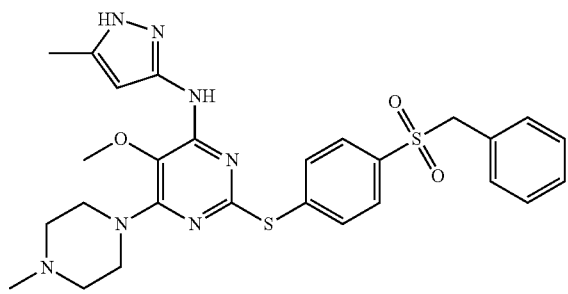 [SMILES: COc1c(Nc2cc(C)[nH]n2)nc(Sc2ccc(S(=O)(=O)Cc3ccccc3)cc2)nc1N1CCN(C)CC1] XXX
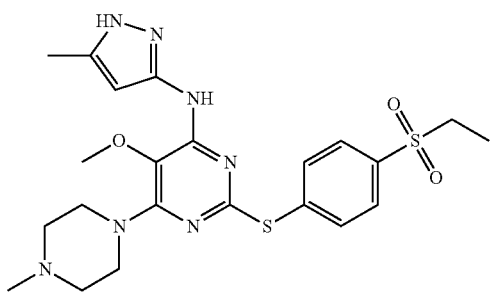 [SMILES: CCS(=O)(=O)c1ccc(Sc2nc(Nc3cc(C)[nH]n3)c(OC)c(N3CCN(C)CC3)n2)cc1] Activity XXX
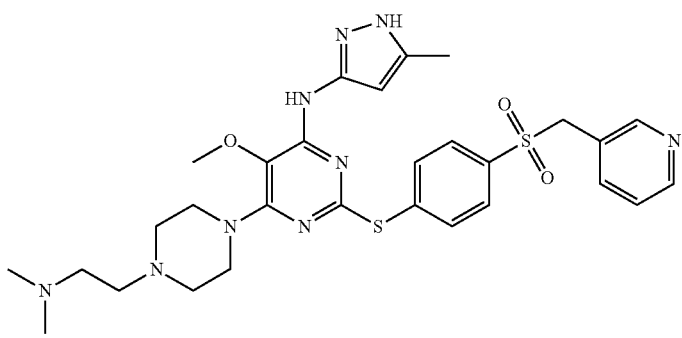 [SMILES: COc1c(Nc2cc(C)[nH]n2)nc(Sc2ccc(S(=O)(=O)Cc3cccnc3)cc2)nc1N1CCN(CCN(C)C)CC1] XXX TABLE 1-continued
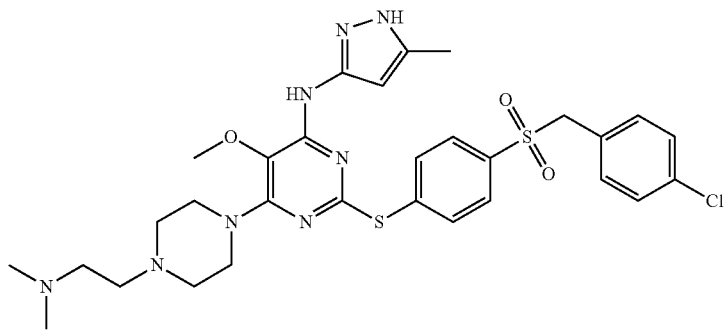 [SMILES: COc1c(Nc2cc(C)[nH]n2)nc(Sc2ccc(S(=O)(=O)Cc3ccc(Cl)cc3)cc2)nc1N1CCN(CCN(C)C)CC1]
XXX
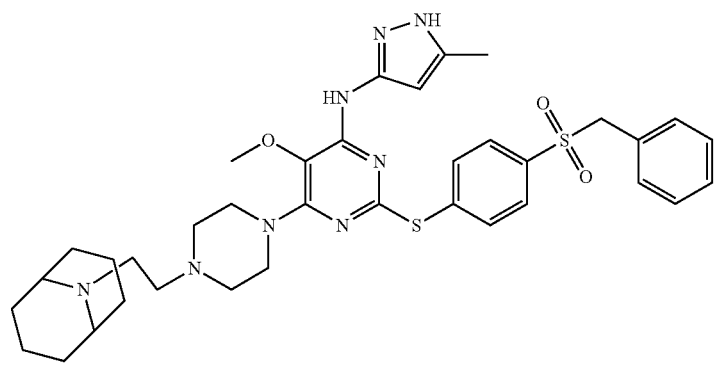 [SMILES: COc1c(Nc2cc(C)[nH]n2)nc(Sc2ccc(S(=O)(=O)Cc3ccccc3)cc2)nc1N1CCN(CCN2C3CCCC2CCC3)CC1]
XXX
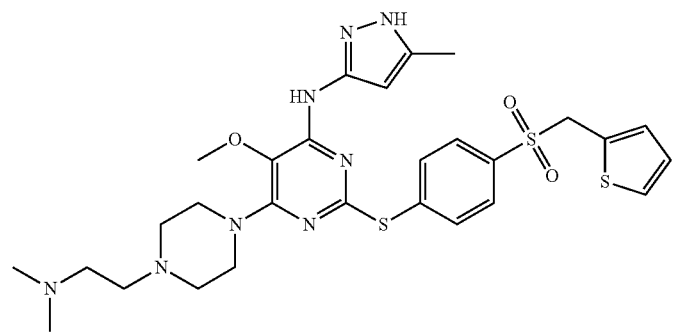 [SMILES: COc1c(Nc2cc(C)[nH]n2)nc(Sc2ccc(S(=O)(=O)Cc3cccs3)cc2)nc1N1CCN(CCN(C)C)CC1]
Activity XXX
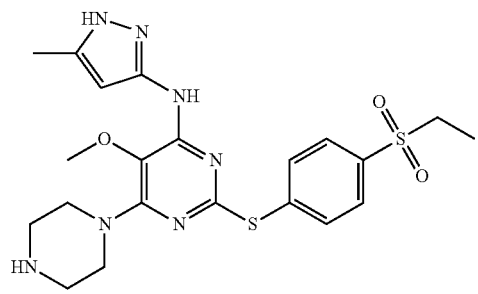 [SMILES: CCS(=O)(=O)c1ccc(Sc2nc(Nc3cc(C)[nH]n3)c(OC)c(N3CCNCC3)n2)cc1]
XXX
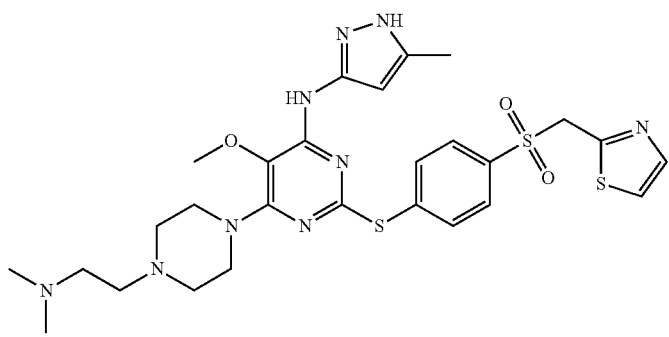
XXX TABLE 1-continued
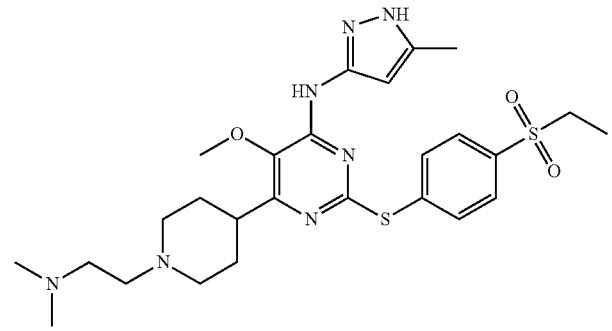 XXX
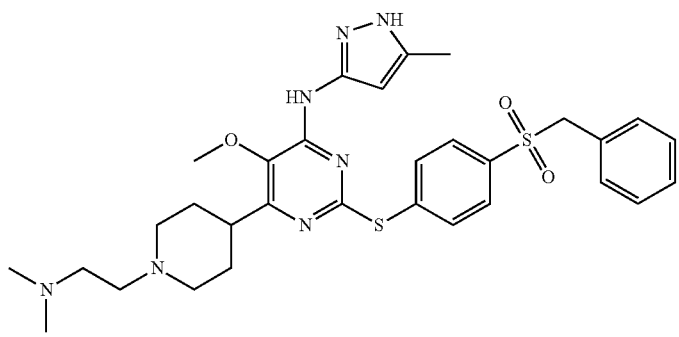 Activity XXX
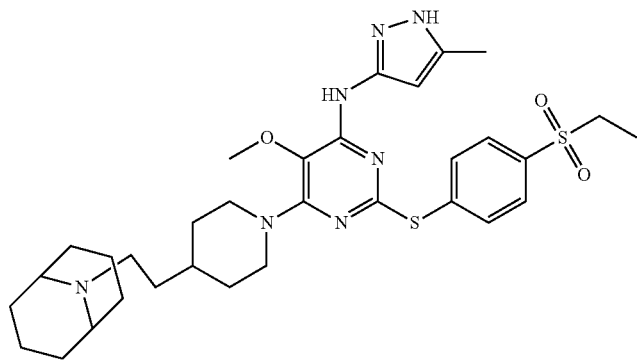 [SMILES: CCS(=O)(=O)c1ccc(Sc2nc(Nc3cc(C)[nH]n3)c(OC)c(N3CCC(CCN4C5CCCC4CCC5)CC3)n2)cc1] XXX
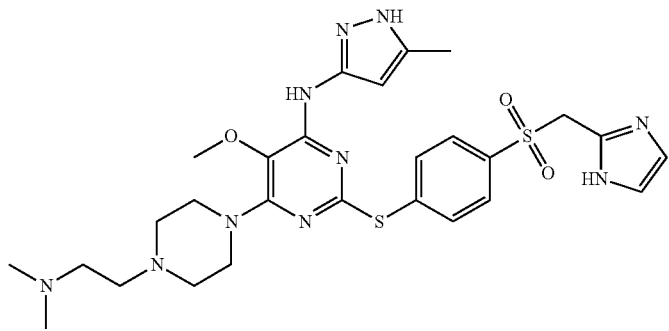 [SMILES: COc1c(Nc2cc(C)[nH]n2)nc(Sc2ccc(S(=O)(=O)Cc3ncc[nH]3)cc2)nc1N1CCN(CCN(C)C)CC1] XXX
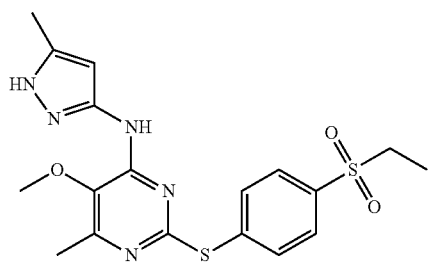 [SMILES: CCS(=O)(=O)c1ccc(Sc2nc(C)c(OC)c(Nc3cc(C)[nH]n3)n2)cc1] XXX TABLE 1-continued
| | |
|---|---|
| 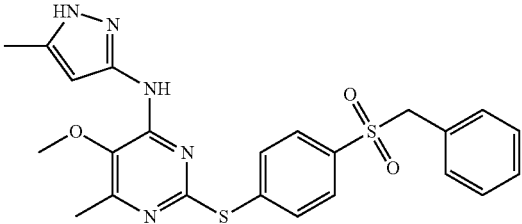 [SMILES: COc1c(C)nc(Sc2ccc(S(=O)(=O)Cc3ccccc3)cc2)nc1Nc1cc(C)[nH]n1] | Activity XXX |
| 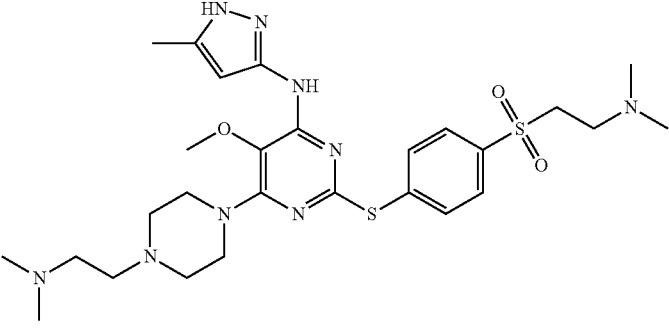 | XXX |
| 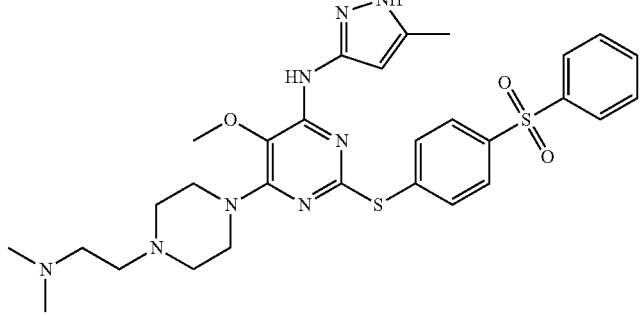 | XXX |
| 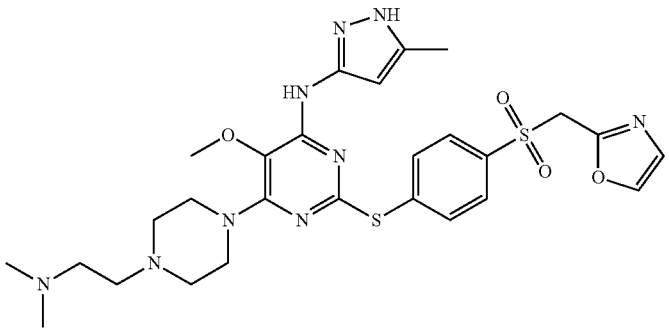 | XXX |
| 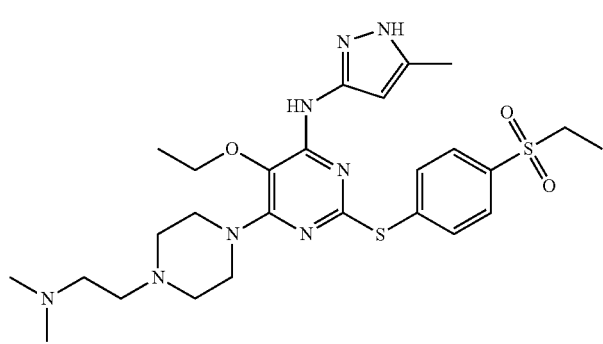 [SMILES: CCOc1c(Nc2cc(C)[nH]n2)nc(Sc2ccc(S(=O)(=O)CC)cc2)nc1N1CCN(CCN(C)C)CC1] | Activity XXX |

TABLE 1-continued
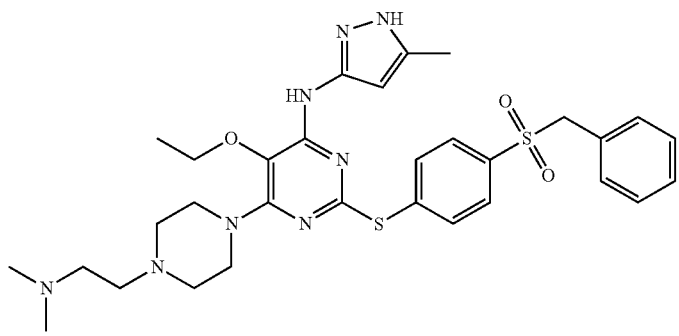
XXX
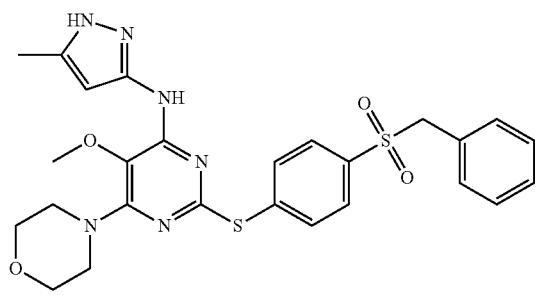 [SMILES: COc1c(Nc2cc(C)[nH]n2)nc(Sc2ccc(S(=O)(=O)Cc3ccccc3)cc2)nc1N1CCOCC1]
XXX
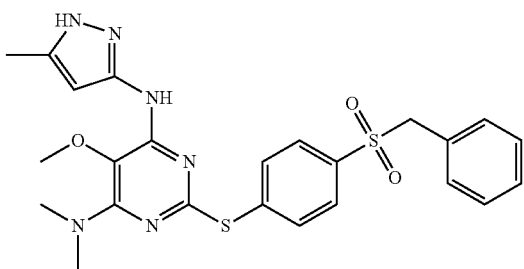 [SMILES: COc1c(Nc2cc(C)[nH]n2)nc(Sc2ccc(S(=O)(=O)Cc3ccccc3)cc2)nc1N(C)C]
XXX
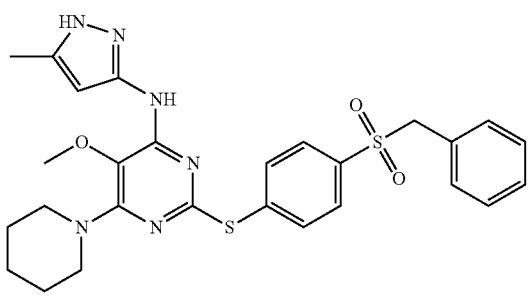 [SMILES: COc1c(Nc2cc(C)[nH]n2)nc(Sc2ccc(S(=O)(=O)Cc3ccccc3)cc2)nc1N1CCCCC1]
Activity XXX
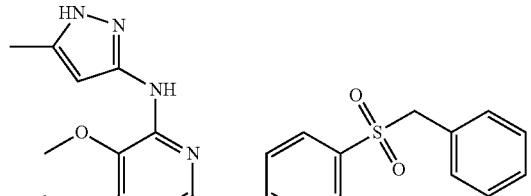
XXX TABLE 1-continued
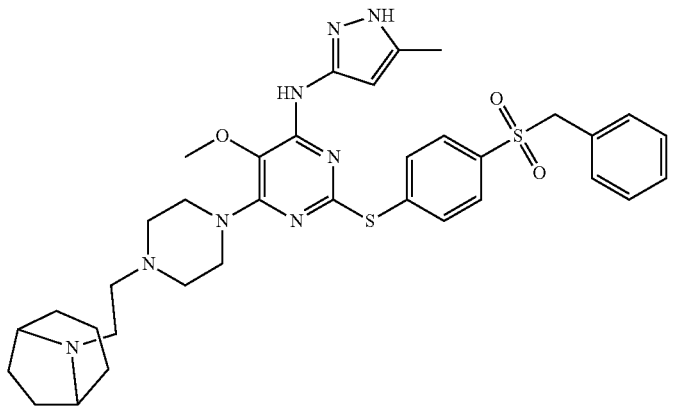 [SMILES: COc1c(Nc2cc(C)[nH]n2)nc(Sc2ccc(S(=O)(=O)Cc3ccccc3)cc2)nc1N1CCN(CCN2C3CCCC2CC3)CC1]
XXX
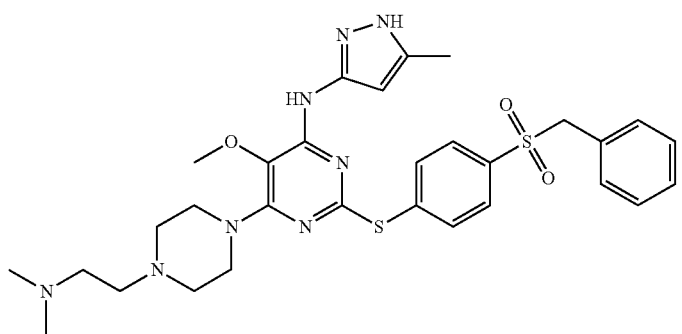
XXX
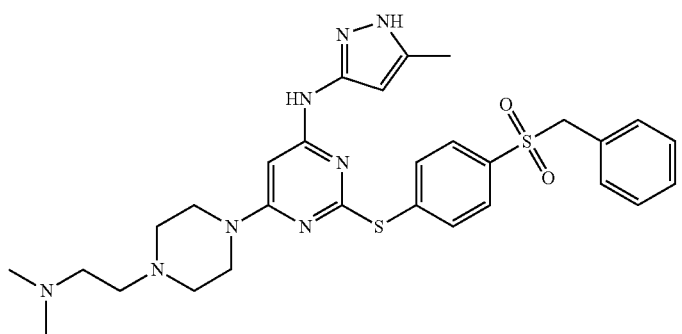 [SMILES: Cc1cc(Nc2cc(N3CCN(CCN(C)C)CC3)nc(Sc3ccc(S(=O)(=O)Cc4ccccc4)cc3)n2)n[nH]1]
Activity XXX
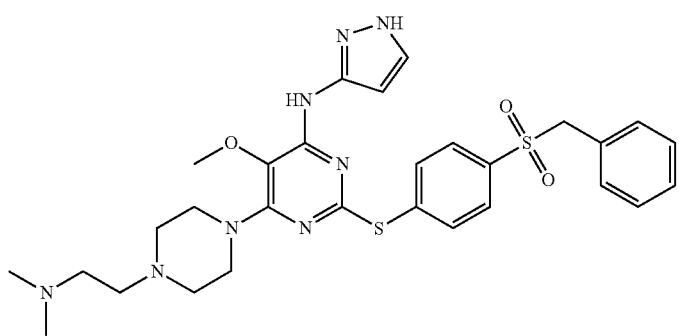 [SMILES: COc1c(Nc2cc[nH]n2)nc(Sc2ccc(S(=O)(=O)Cc3ccccc3)cc2)nc1N1CCN(CCN(C)C)CC1]
XXX

TABLE 1-continued
| Structure | Activity |
|---|---|
| 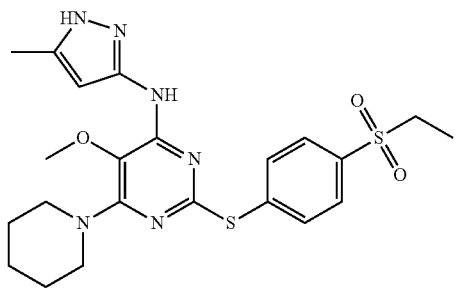 [SMILES: CCS(=O)(=O)c1ccc(Sc2nc(Nc3cc(C)[nH]n3)c(OC)c(N3CCCCC3)n2)cc1] | XXX |
| 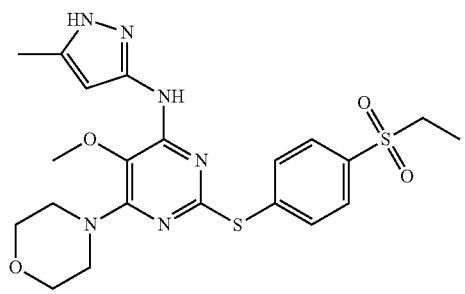 [SMILES: CCS(=O)(=O)c1ccc(Sc2nc(Nc3cc(C)[nH]n3)c(OC)c(N3CCOCC3)n2)cc1] | XXX |
| 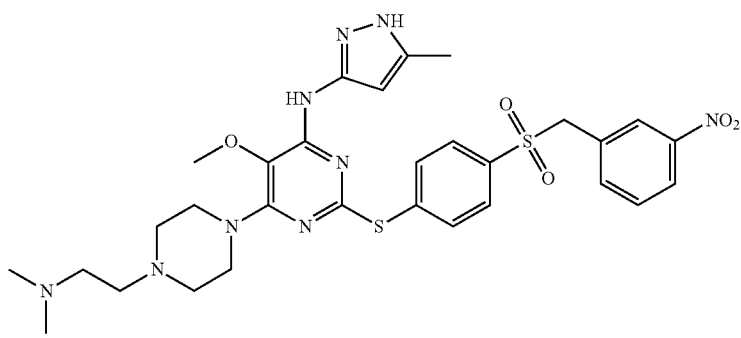 [SMILES: COc1c(Nc2cc(C)[nH]n2)nc(Sc2ccc(S(=O)(=O)Cc3cccc([N+](=O)[O-])c3)cc2)nc1N1CCN(CCN(C)C)CC1] | Activity XXX |
| 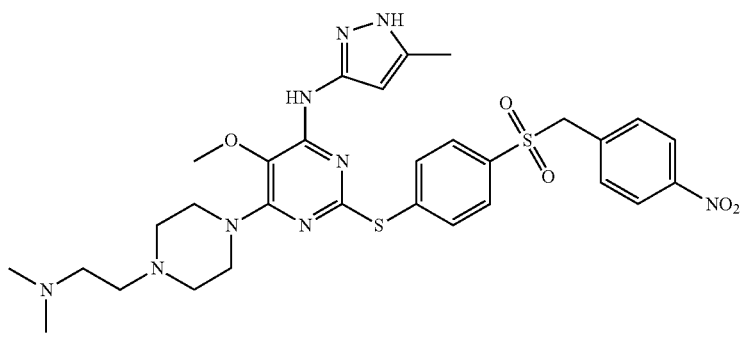 [SMILES: COc1c(Nc2cc(C)[nH]n2)nc(Sc2ccc(S(=O)(=O)Cc3ccc([N+](=O)[O-])cc3)cc2)nc1N1CCN(CCN(C)C)CC1] | XXX |
| 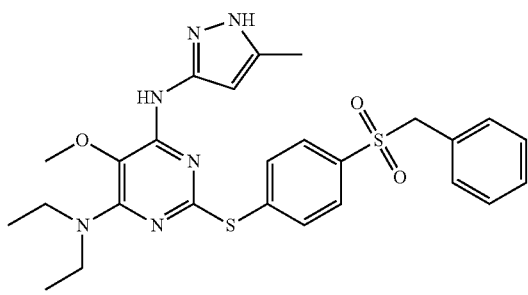 [SMILES: CCN(CC)c1nc(Sc2ccc(S(=O)(=O)Cc3ccccc3)cc2)nc(Nc2cc(C)[nH]n2)c1OC] | XXX |

TABLE 1-continued
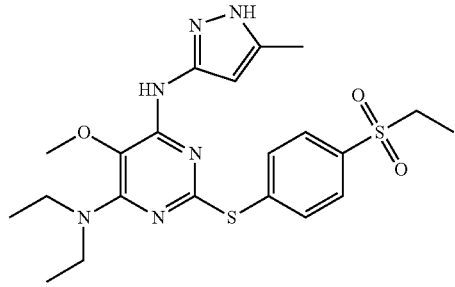 [SMILES: CCN(CC)c1nc(Sc2ccc(S(=O)(=O)CC)cc2)nc(Nc2cc(C)[nH]n2)c1OC] XXX
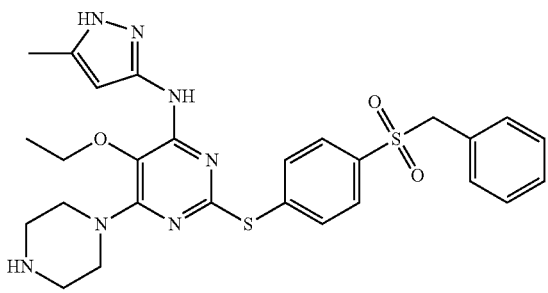 [SMILES: CCOc1c(Nc2cc(C)[nH]n2)nc(Sc2ccc(S(=O)(=O)Cc3ccccc3)cc2)nc1N1CCNCC1] Activity X
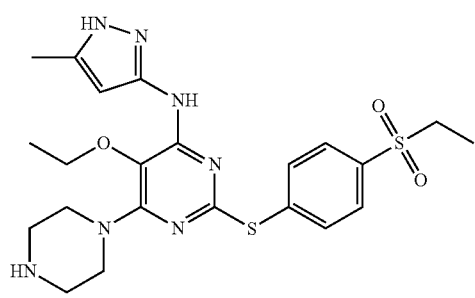 [SMILES: CCOc1c(Nc2cc(C)[nH]n2)nc(Sc2ccc(S(=O)(=O)CC)cc2)nc1N1CCNCC1] XXX
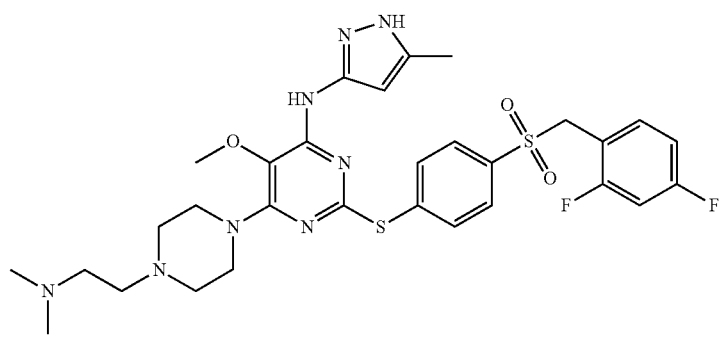 [SMILES: COc1c(Nc2cc(C)[nH]n2)nc(Sc2ccc(S(=O)(=O)Cc3ccc(F)cc3F)cc2)nc1N1CCN(CCN(C)C)CC1] XXX
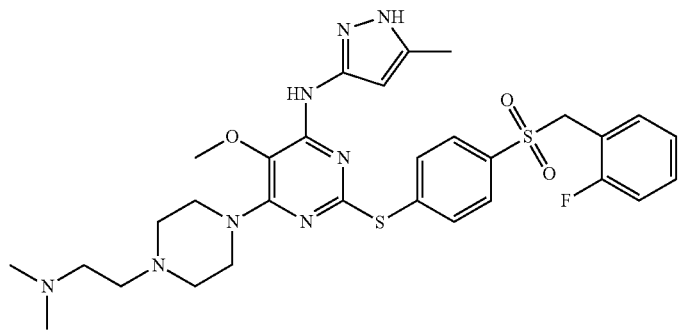 XXX TABLE 1-continued
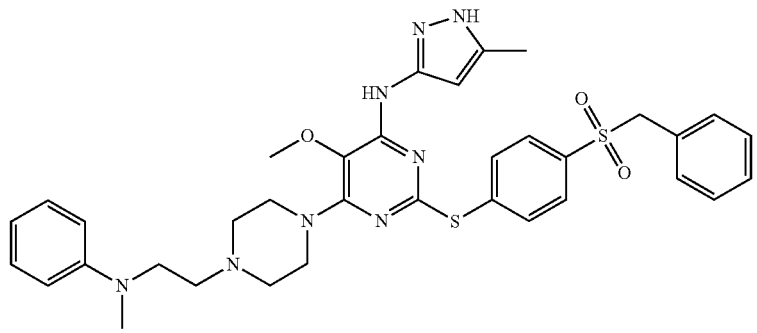 [SMILES: COc1c(Nc2cc(C)[nH]n2)nc(Sc2ccc(S(=O)(=O)Cc3ccccc3)cc2)nc1N1CCN(CCN(C)c2ccccc2)CC1]
Activity XXX
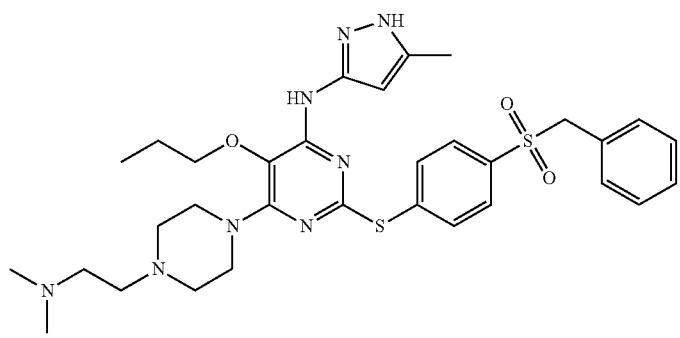 [SMILES: CCCOc1c(Nc2cc(C)[nH]n2)nc(Sc2ccc(S(=O)(=O)Cc3ccccc3)cc2)nc1N1CCN(CCN(C)C)CC1]
XXX
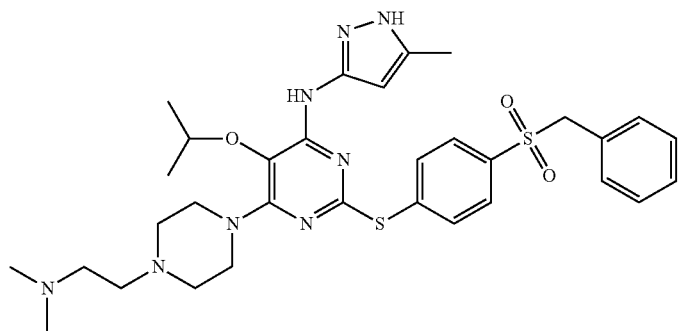 [SMILES: Cc1cc(Nc2nc(Sc3ccc(S(=O)(=O)Cc4ccccc4)cc3)nc(N3CCN(CCN(C)C)CC3)c2OC(C)C)n[nH]1]
XXX
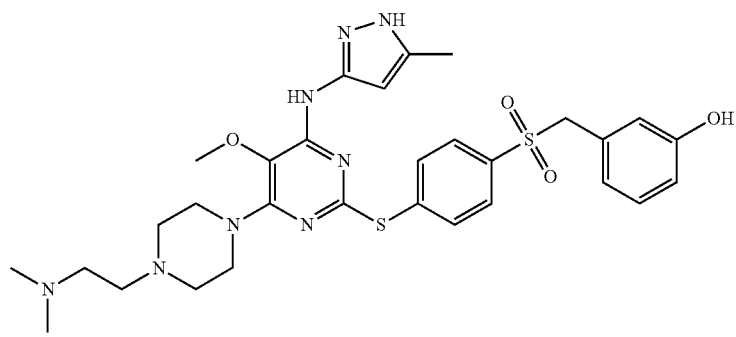 [SMILES: COc1c(Nc2cc(C)[nH]n2)nc(Sc2ccc(S(=O)(=O)Cc3cccc(O)c3)cc2)nc1N1CCN(CCN(C)C)CC1]
XXX TABLE 1-continued
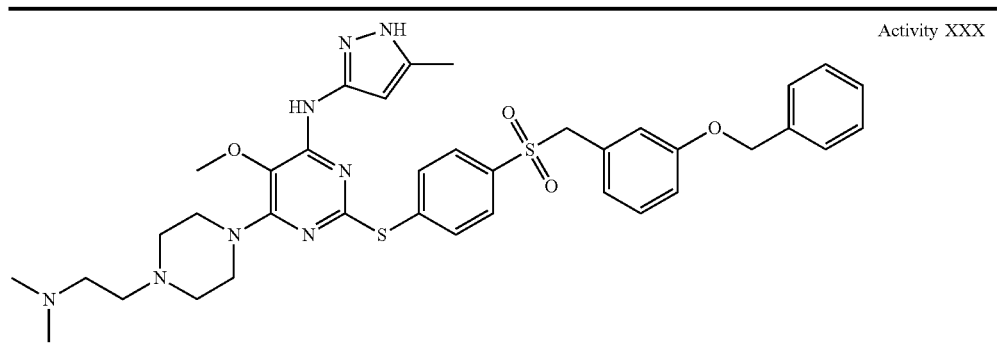
Activity XXX
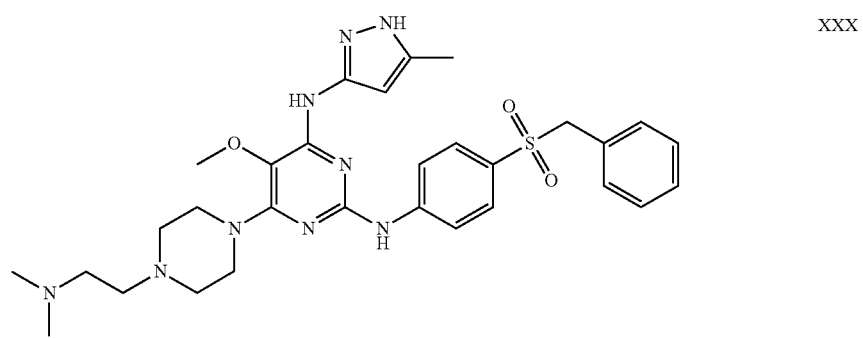
XXX
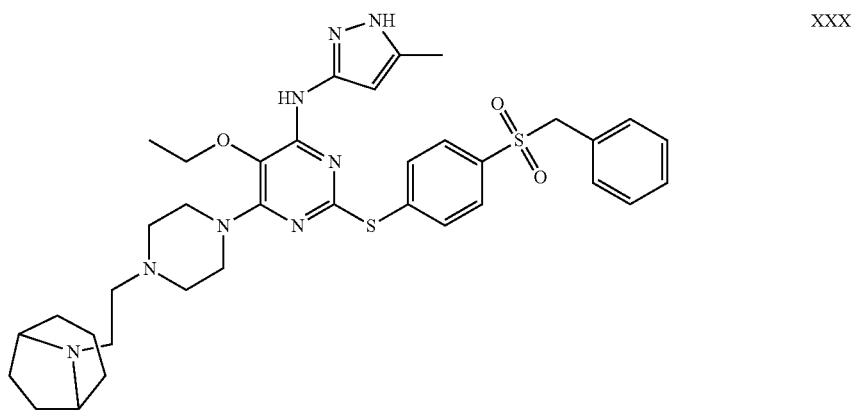
XXX
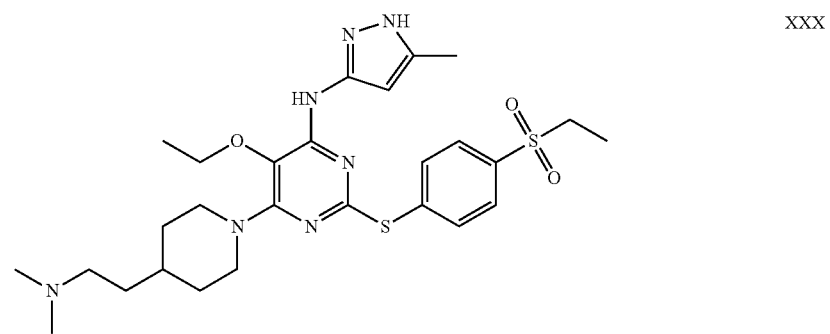
XXX TABLE 1-continued
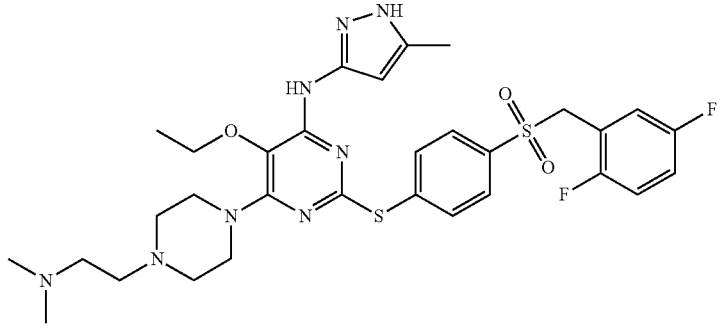 [SMILES: CCOc1c(Nc2cc(C)[nH]n2)nc(Sc2ccc(S(=O)(=O)Cc3cc(F)ccc3F)cc2)nc1N1CCN(CCN(C)C)CC1] Activity XXX
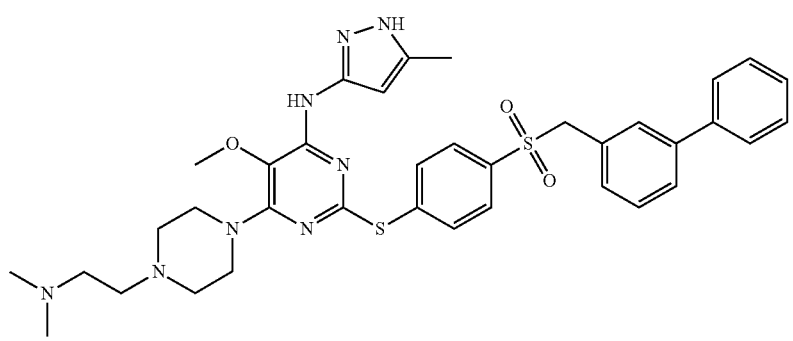 [SMILES: COc1c(Nc2cc(C)[nH]n2)nc(Sc2ccc(S(=O)(=O)Cc3cccc(-c4ccccc4)c3)cc2)nc1N1CCN(CCN(C)C)CC1] XXX
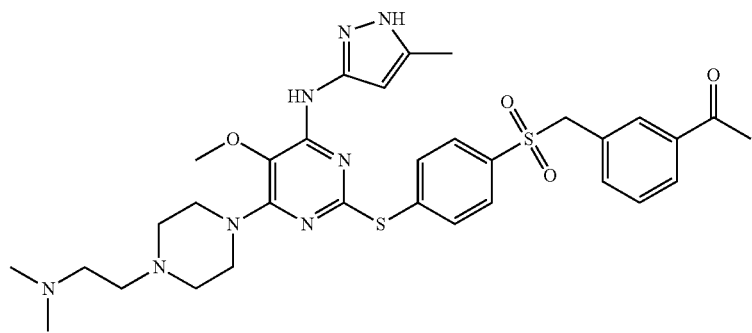 [SMILES: COc1c(Nc2cc(C)[nH]n2)nc(Sc2ccc(S(=O)(=O)Cc3cccc(C(C)=O)c3)cc2)nc1N1CCN(CCN(C)C)CC1] XXX
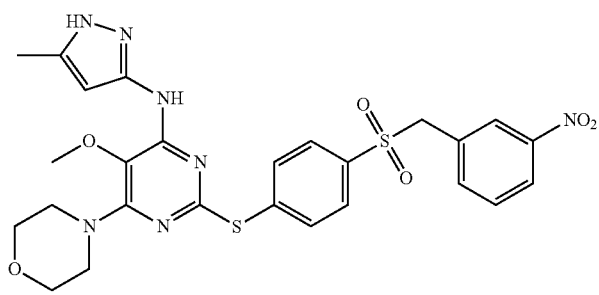 [SMILES: COc1c(Nc2cc(C)[nH]n2)nc(Sc2ccc(S(=O)(=O)Cc3cccc([N+](=O)[O-])c3)cc2)nc1N1CCOCC1] XXX
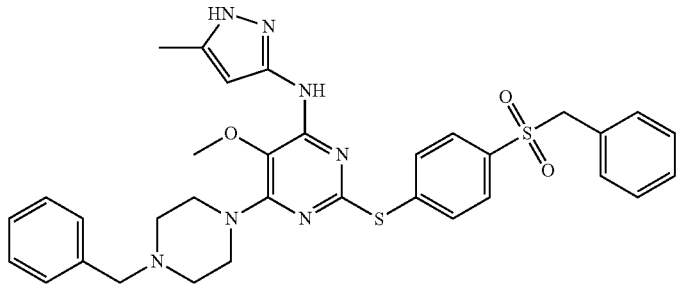 [SMILES: COc1c(Nc2cc(C)[nH]n2)nc(Sc2ccc(S(=O)(=O)Cc3ccccc3)cc2)nc1N1CCN(Cc2ccccc2)CC1] Activity XXX TABLE 1-continued

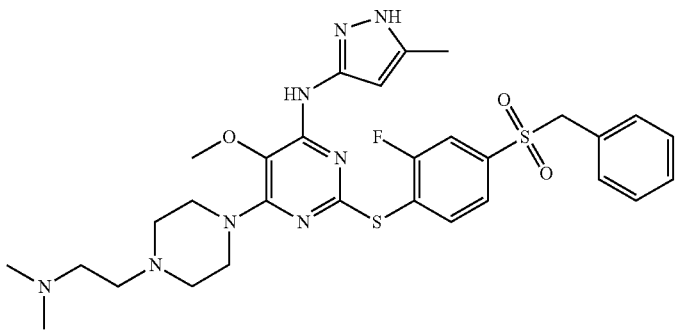 [SMILES: COc1c(Nc2cc(C)[nH]n2)nc(Sc2ccc(S(=O)(=O)Cc3ccccc3)cc2F)nc1N1CCN(CCN(C)C)CC1]

XXX

TABLE 2

Compound Names for exemplified compounds of formula (I), (II), and (III).
All compounds were confirmed by mass spectroscopy and by $^1$H and $^{13}$C NMR.

| No. | Chemical Name |
|---|---|
| 1 | N-(4-((4,5-dimethyl-6-((5-methyl-1H-pyrazol-3-yl)amino)pyrimidin-2-yl)thio)phenyl)cyclopropanecarboxamide |
| 2 | N-(4-((4-((5-methyl-1H-pyrazol-3-yl)amino)-6,7-dihydro-5H-cyclopenta[d]pyrimidin-2-yl)thio)phenyl)cyclopropanecarboxamide |
| 3 | N-(4-((4-methyl-6-((5-methyl-1H-pyrazol-3-yl)amino)pyrimidin-2-yl)thio)phenyl)cyclopropanecarboxamide |
| 4 | N-(4-((5-(hydroxymethyl)-4-((5-methyl-1H-pyrazol-3-yl)amino)-6-(4-methylpiperazin-1-yl)pyrimidin-2-yl)thio)phenyl)cyclopropanecarboxamide |
| 5 | N-(4-((5-ethyl-4-((5-methyl-1H-pyrazol-3-yl)amino)-6-(4-methylpiperazin-1-yl)pyrimidin-2-yl)thio)phenyl)cyclopropanecarboxamide |
| 6 | N-(4-((5-ethyl-4-methyl-6-((5-methyl-1H-pyrazol-3-yl)amino)pyrimidin-2-yl)thio)phenyl)cyclopropanecarboxamide |
| 7 | N-(4-((5-methoxy-4-((5-methyl-1H-pyrazol-3-yl)amino)-6-(4-methylpiperazin-1-yl)pyrimidin-2-yl)thio)phenyl)cyclopropanecarboxamide |
| 8 | N-(4-((5-methyl-4-((5-methyl-1H-pyrazol-3-yl)amino)-6-(4-methylpiperazin-1-yl)pyrimidin-2-yl)thio)phenyl)cyclopropanecarboxamide |
| 9 | N-(4-((5-methyl-4-((5-methyl-1H-pyrazol-3-yl)amino)-6-morpholinopyrimidin-2-yl)thio)phenyl)cyclopropanecarboxamide |
| 10 | N-(4-((4-(3,4-dimethylpiperazin-1-yl)-5-methyl-6-((5-methyl-1H-pyrazol-3-yl)amino)pyrimidin-2-yl)thio)phenyl)cyclopropanecarboxamide |
| 11 | N-(4-((4-(4-(2-(dimethylamino)ethyl)piperazin-1-yl)-5-methyl-6-((5-methyl-1H-pyrazol-3-yl)amino)pyrimidin-2-yl)thio)phenyl)cyclopropanecarboxamide |
| 12 | N-(4-((4-(4-(2-methoxyethyl)piperazin-1-yl)-5-methyl-6-((5-methyl-1H-pyrazol-3-yl)amino)pyrimidin-2-yl)thio)phenyl)cyclopropanecarboxamide |
| 13 | N-(4-((4-(4-acetylpiperazin-1-yl)-5-methyl-6-((5-methyl-1H-pyrazol-3-yl)amino)pyrimidin-2-yl)thio)phenyl)cyclopropanecarboxamide |
| 14 | N-(4-((4-(4-isopropylpiperazin-1-yl)-5-methyl-6-((5-methyl-1H-pyrazol-3-yl)amino)pyrimidin-2-yl)thio)phenyl)cyclopropanecarboxamide |
| 15 | N-(4-((4-(dimethylamino)-5-methyl-6-((5-methyl-1H-pyrazol-3-yl)amino)pyrimidin-2-yl)thio)phenyl)cyclopropanecarboxamide |
| 16 | N-(4-((4-(ethyl(methyl)amino)-5-methyl-6-((5-methyl-1H-pyrazol-3-yl)amino)pyrimidin-2-yl)thio)phenyl)cyclopropanecarboxamide |
| 17 | N-(4-((5-methoxy-4-methyl-6-((5-methyl-1H-pyrazol-3-yl)amino)pyrimidin-2-yl)thio)phenyl)cyclopropanecarboxamide |
| 18 | N-(4-((5-methyl-4-((5-methyl-1H-pyrazol-3-yl)amino)-6,7-dihydro-5H-cyclopenta[d]pyrimidin-2-yl)thio)phenyl)cyclopropanecarboxamide |
| 19 | N-(4-((4-((2-(dimethylamino)ethyl)(methyl)amino)-5-methyl-6-((5-methyl-1H-pyrazol-3-yl)amino)pyrimidin-2-yl)thio)phenyl)cyclopropanecarboxamide |
| 20 | N-(4-((4-((2-(dimethylamino)ethyl)amino)-5-methyl-6-((5-methyl-1H-pyrazol-3-yl)amino)pyrimidin-2-yl)thio)phenyl)cyclopropanecarboxamide |
| 21 | N-(4-((4-((2-methoxyethyl)(methyl)amino)-5-methyl-6-((5-methyl-1H-pyrazol-3-yl)amino)pyrimidin-2-yl)thio)phenyl)cyclopropanecarboxamide |
| 22 | N-(4-((4-((5-ethyl-1H-pyrazol-3-yl)amino)-5-methyl-6-(4-methylpiperazin-1-yl)pyrimidin-2-yl)thio)phenyl)cyclopropanecarboxamide |
| 23 | N-(4-((4-(1H-imidazol-1-yl)-5-methyl-6-((5-methyl-1H-pyrazol-3-yl)amino)pyrimidin-2-yl)thio)phenyl)cyclopropanecarboxamide |
| 24 | N-(4-((4-(diethylamino)-5-methyl-6-((5-methyl-1H-pyrazol-3-yl)amino)pyrimidin-2-yl)thio)phenyl)cyclopropanecarboxamide |
| 25 | N-(4-((4-chloro-5-methyl-6-((5-methyl-1H-pyrazol-3-yl)amino)pyrimidin-2-yl)thio)phenyl)cyclopropanecarboxamide |
| 26 | N-(4-((5-methoxy-4-((5-methyl-1H-pyrazol-3-yl)amino)-6-(piperazin-1-yl)pyrimidin-2-yl)thio)phenyl)cyclopropanecarboxamide |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 27 | N-(4-((5-methoxy-4-((5-methyl-1H-pyrazol-3-yl)amino)-6-morpholinopyrimidin-2-yl)thio)phenyl)cyclopropanecarboxamide |
| 28 | N-(4-((5-methyl-4-((5-methyl-1H-pyrazol-3-yl)amino)-6-(piperazin-1-yl)pyrimidin-2-yl)thio)phenyl)cyclopropanecarboxamide |
| 29 | N-(4-((5-methyl-4-(methyl(2-(methylamino)ethyl)amino)-6-((5-methyl-1H-pyrazol-3-yl)amino)pyrimidin-2-yl)thio)phenyl)cyclopropanecarboxamide |
| 30 | N-(4-((4-((1H-pyrazol-3-yl)amino)-5-methyl-6-(4-methylpiperazin-1-yl)pyrimidin-2-yl)thio)phenyl)cyclopropanecarboxamide |
| 31 | N-(4-((4-((5-methyl-1H-pyrazol-3-yl)amino)-6-(4-methylpiperazin-1-yl)-5-propoxypyrimidin-2-yl)thio)phenyl)cyclopropanecarboxamide |
| 31 | N-(4-((4-(diethylamino)-5-methoxy-6-((5-methyl-1H-pyrazol-3-yl)amino)pyrimidin-2-yl)thio)phenyl)cyclopropanecarboxamide |
| 33 | N-(4-((4-(dimethylamino)-5-methoxy-6-((5-methyl-1H-pyrazol-3-yl)amino)pyrimidin-2-yl)thio)phenyl)cyclopropanecarboxamide |
| 34 | N-(4-((4-(ethyl(methyl)amino)-5-methoxy-6-((5-methyl-1H-pyrazol-3-yl)amino)pyrimidin-2-yl)thio)phenyl)cyclopropanecarboxamide |
| 35 | N-(4-((5-(2-methoxyethoxy)-4-((5-methyl-1H-pyrazol-3-yl)amino)-6-(4-methylpiperazin-1-yl)pyrimidin-2-yl)thio)phenyl)cyclopropanecarboxamide |
| 36 | N-(4-((5-ethoxy-4-((5-methyl-1H-pyrazol-3-yl)amino)-6-(4-methylpiperazin-1-yl)pyrimidin-2-yl)thio)phenyl)cyclopropanecarboxamide |
| 37 | N-(4-((5-methoxy-4-((2-methoxyethyl)(methyl)amino)-6-((5-methyl-1H-pyrazol-3-yl)amino)pyrimidin-2-yl)thio)phenyl)cyclopropanecarboxamide |
| 38 | N-(4-((5-methyl-4-((5-methyl-1H-pyrazol-3-yl)amino)-6-(4-methylpiperazin-1-yl)pyrimidin-2-yl)thio)phenyl)cyclopentanecarboxamide |
| 39 | N-(4-((4-((2-(dimethylamino)ethyl)(methyl)amino)-5-methoxy-6-((5-methyl-1H-pyrazol-3-yl)amino)pyrimidin-2-yl)thio)phenyl)cyclopropanecarboxamide |
| 40 | N-(4-((4-((2-(dimethylamino)ethyl)amino)-5-methoxy-6-((5-methyl-1H-pyrazol-3-yl)amino)pyrimidin-2-yl)thio)phenyl)cyclopropanecarboxamide |
| 41 | N-(4-((4-(diethylamino)-6-((5-methyl-1H-pyrazol-3-yl)amino)-5-propoxypyrimidin-2-yl)thio)phenyl)cyclopropanecarboxamide |
| 42 | N-(4-((4-(isopropyl(methyl)amino)-5-methoxy-6-((5-methyl-1H-pyrazol-3-yl)amino)pyrimidin-2-yl)thio)phenyl)cyclopropanecarboxamide |
| 43 | N-(4-((4-(isopropylamino)-5-methoxy-6-((5-methyl-1H-pyrazol-3-yl)amino)pyrimidin-2-yl)thio)phenyl)cyclopropanecarboxamide |
| 44 | N-(4-((5-methoxy-4-((2-methoxyethyl)amino)-6-((5-methyl-1H-pyrazol-3-yl)amino)pyrimidin-2-yl)thio)phenyl)cyclopropanecarboxamide |
| 45 | N-(4-((5-methoxy-4-((5-methyl-1H-pyrazol-3-yl)amino)-6-(methylamino)pyrimidin-2-yl)thio)phenyl)cyclopropanecarboxamide |
| 46 | N-(4-((5-methoxy-4-((5-methyl-1H-pyrazol-3-yl)amino)-6-(piperidin-1-yl)pyrimidin-2-yl)thio)phenyl)cyclopropanecarboxamide |
| 47 | N-(4-((5-methoxy-4-(methyl(2-(methylamino)ethyl)amino)-6-((5-methyl-1H-pyrazol-3-yl)amino)pyrimidin-2-yl)thio)phenyl)cyclopropanecarboxamide |
| 48 | N-(4-((4-((2-methoxyethyl)amino)-5-methyl-6-((5-methyl-1H-pyrazol-3-yl)amino)pyrimidin-2-yl)thio)phenyl)cyclopropanecarboxamide |
| 49 | N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)cyclopropanecarboxamide |
| 50 | N-(4-((4-(4-acetylpiperazin-1-yl)-5-methoxy-6-((5-methyl-1H-pyrazol-3-yl)amino)pyrimidin-2-yl)thio)phenyl)cyclopropanecarboxamide |
| 51 | N-(4-((4-(4-ethylpiperazin-1-yl)-5-methoxy-6-((5-methyl-1H-pyrazol-3-yl)amino)pyrimidin-2-yl)thio)phenyl)cyclopropanecarboxamide |
| 52 | N-(4-((4-(4-isopropylpiperazin-1-yl)-5-methoxy-6-((5-methyl-1H-pyrazol-3-yl)amino)pyrimidin-2-yl)thio)phenyl)cyclopropanecarboxamide |
| 53 | N-(4-((4-(ethylamino)-5-methoxy-6-((5-methyl-1H-pyrazol-3-yl)amino)pyrimidin-2-yl)thio)phenyl)cyclopropanecarboxamide |
| 54 | N-(4-((4-(isopropyl(methyl)amino)-5-methyl-6-((5-methyl-1H-pyrazol-3-yl)amino)pyrimidin-2-yl)thio)phenyl)cyclopropanecarboxamide |
| 55 | N-(4-((5-methoxy-4-(4-(2-methoxyethyl)piperazin-1-yl)-6-((5-methyl-1H-pyrazol-3-yl)amino)pyrimidin-2-yl)thio)phenyl)cyclopropanecarboxamide |
| 56 | N-(4-((5-methyl-4-((5-methyl-1H-pyrazol-3-yl)amino)-6,7-dihydro-5H-cyclopenta[d]pyrimidin-2-yl)thio)phenyl)acetamide |
| 57 | N-(4-((5-methyl-4-((5-methyl-1H-pyrazol-3-yl)amino)-6,7-dihydro-5H-cyclopenta[d]pyrimidin-2-yl)thio)phenyl)cyclopentanecarboxamide |
| 58 | N-(4-((5-methyl-4-((5-methyl-1H-pyrazol-3-yl)amino)-6-(methylamino)pyrimidin-2-yl)thio)phenyl)cyclopropanecarboxamide |
| 59 | N-(4-((5-methyl-4-((5-methyl-1H-pyrazol-3-yl)amino)-6-(piperidin-1-yl)pyrimidin-2-yl)thio)phenyl)cyclopropanecarboxamide |
| 60 | N-(4-((4-((2-methoxyethyl)(methyl)amino)-5-methyl-6-((5-methyl-1H-pyrazol-3-yl)amino)pyrimidin-2-yl)thio)phenyl)acetamide |
| 61 | N-(4-((4-((2-methoxyethyl)amino)-5-methyl-6-((5-methyl-1H-pyrazol-3-yl)amino)pyrimidin-2-yl)thio)phenyl)acetamide |
| 62 | N-(4-((4-(4-(tert-butyl)piperazin-1-yl)-5-methoxy-6-((5-methyl-1H-pyrazol-3-yl)amino)pyrimidin-2-yl)thio)phenyl)cyclopropanecarboxamide |
| 63 | N-(4-((4-(dimethylamino)-5-methyl-6-((5-methyl-1H-pyrazol-3-yl)amino)pyrimidin-2-yl)thio)phenyl)acetamide |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 64 | N-(4-((4-(ethyl(methyl)amino)-5-methyl-6-((5-methyl-1H-pyrazol-3-yl)amino)pyrimidin-2-yl)thio)phenyl)acetamide |
| 65 | N-(4-((4-(ethylamino)-5-methyl-6-((5-methyl-1H-pyrazol-3-yl)amino)pyrimidin-2-yl)thio)phenyl)cyclopropanecarboxamide |
| 66 | N-(4-((4-(isopropylamino)-5-methyl-6-((5-methyl-1H-pyrazol-3-yl)amino)pyrimidin-2-yl)thio)phenyl)cyclopropanecarboxamide |
| 67 | N-(4-((5-methyl-4-((5-methyl-1H-pyrazol-3-yl)amino)-6-(4-methylpiperazin-1-yl)pyrimidin-2-yl)thio)phenyl)butyramide |
| 68 | N-(4-((5-methyl-4-((5-methyl-1H-pyrazol-3-yl)amino)-6-(piperidin-1-yl)pyrimidin-2-yl)thio)phenyl)acetamide |
| 69 | N-(4-((4-(4-acetylpiperazin-1-yl)-5-methoxy-6-((5-methyl-1H-pyrazol-3-yl)amino)pyrimidin-2-yl)thio)phenyl)cyclopentanecarboxamide |
| 70 | N-(4-((4-(diethylamino)-5-methoxy-6-((5-methyl-1H-pyrazol-3-yl)amino)pyrimidin-2-yl)thio)phenyl)cyclopentanecarboxamide |
| 71 | N-(4-((4-(dimethylamino)-5-methoxy-6-((5-methyl-1H-pyrazol-3-yl)amino)pyrimidin-2-yl)thio)phenyl)cyclopentanecarboxamide |
| 72 | N-(4-((4-(ethyl(methyl)amino)-5-methoxy-6-((5-methyl-1H-pyrazol-3-yl)amino)pyrimidin-2-yl)thio)phenyl)cyclopentanecarboxamide |
| 73 | N-(4-((5-methoxy-4-((2-methoxyethyl)(methyl)amino)-6-((5-methyl-1H-pyrazol-3-yl)amino)pyrimidin-2-yl)thio)phenyl)cyclopentanecarboxamide |
| 74 | N-(4-((5-methoxy-4-((2-methoxyethyl)amino)-6-((5-methyl-1H-pyrazol-3-yl)amino)pyrimidin-2-yl)thio)phenyl)cyclopentanecarboxamide |
| 75 | N-(4-((5-methoxy-4-((5-methyl-1H-pyrazol-3-yl)amino)-6-(piperidin-1-yl)pyrimidin-2-yl)thio)phenyl)cyclopentanecarboxamide |
| 76 | N-(4-((5-methoxy-4-((5-methyl-1H-pyrazol-3-yl)amino)-6-morpholinopyrimidin-2-yl)thio)phenyl)cyclopentanecarboxamide |
| 77 | N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)cyclopentanecarboxamide N-(4-((4-(diethylamino)-5-ethoxy-6-((5-methyl-1H-pyrazol-3-yl)amino)pyrimidin-2-yl)thio)phenyl)cyclopropanecarboxamide |
| 78 | N-(4-((4-(dimethylamino)-5-ethoxy-6-((5-methyl-1H-pyrazol-3-yl)amino)pyrimidin-2-yl)thio)phenyl)cyclopropanecarboxamide |
| 79 | N-(4-((5-ethoxy-4-((5-methyl-1H-pyrazol-3-yl)amino)-6-(piperazin-1-yl)pyrimidin-2-yl)thio)phenyl)cyclopropanecarboxamide |
| 80 | N-(4-((5-ethoxy-4-((5-methyl-1H-pyrazol-3-yl)amino)-6-(piperidin-1-yl)pyrimidin-2-yl)thio)phenyl)cyclopropanecarboxamide |
| 81 | N-(4-((5-ethoxy-4-((5-methyl-1H-pyrazol-3-yl)amino)-6-morpholinopyrimidin-2-yl)thio)phenyl)cyclopropanecarboxamide |
| 82 | N-(4-((5-ethoxy-4-(ethyl(methyl)amino)-6-((5-methyl-1H-pyrazol-3-yl)amino)pyrimidin-2-yl)thio)phenyl)cyclopropanecarboxamide |
| 83 | N-(4-((5-methoxy-4-((5-methyl-1H-pyrazol-3-yl)amino)-6-(4-methylpiperazin-1-yl)pyrimidin-2-yl)thio)phenyl)cyclopentanecarboxamide |
| 84 | N-(4-((5-methoxy-4-((5-methyl-1H-pyrazol-3-yl)amino)-6-(piperazin-1-yl)pyrimidin-2-yl)thio)phenyl)cyclopentanecarboxamide |
| 85 | N-(4-((5-methoxy-4-(4-(2-methoxyethyl)piperazin-1-yl)-6-((5-methyl-1H-pyrazol-3-yl)amino)pyrimidin-2-yl)thio)phenyl)cyclopentanecarboxamide |
| 86 | N-(4-((4-(4-(2-(dimethylamino)ethyl)piperazin-1-yl)-5-ethoxy-6-((5-methyl-1H-pyrazol-3-yl)amino)pyrimidin-2-yl)thio)phenyl)cyclopropanecarboxamide |
| 87 | N-(4-((4-(4-acetylpiperazin-1-yl)-5-ethoxy-6-((5-methyl-1H-pyrazol-3-yl)amino)pyrimidin-2-yl)thio)phenyl)cyclopropanecarboxamide |
| 88 | N-(4-((4-(diethylamino)-5-ethoxy-6-((5-methyl-1H-pyrazol-3-yl)amino)pyrimidin-2-yl)thio)phenyl)cyclopropanecarboxamide |
| 89 | N-(4-((4-(dimethylamino)-5-ethoxy-6-((5-methyl-1H-pyrazol-3-yl)amino)pyrimidin-2-yl)thio)phenyl)cyclopropanecarboxamide |
| 90 | N-(4-((5-ethoxy-4-((2-methoxyethyl)(methyl)amino)-6-((5-methyl-1H-pyrazol-3-yl)amino)pyrimidin-2-yl)thio)phenyl)cyclopropanecarboxamide |
| 91 | N-(4-((5-ethoxy-4-((2-methoxyethyl)amino)-6-((5-methyl-1H-pyrazol-3-yl)amino)pyrimidin-2-yl)thio)phenyl)cyclopropanecarboxamide |
| 92 | N-(4-((5-ethoxy-4-((5-methyl-1H-pyrazol-3-yl)amino)-6-(piperazin-1-yl)pyrimidin-2-yl)thio)phenyl)cyclopropanecarboxamide |
| 93 | N-(4-((5-ethoxy-4-(4-(2-methoxyethyl)piperazin-1-yl)-6-((5-methyl-1H-pyrazol-3-yl)amino)pyrimidin-2-yl)thio)phenyl)cyclopropanecarboxamide |
| 94 | N-(4-((5-ethoxy-4-(ethyl(methyl)amino)-6-((5-methyl-1H-pyrazol-3-yl)amino)pyrimidin-2-yl)thio)phenyl)cyclopropanecarboxamide |
| 95 | 3-(5-fluoro-2-methylpyridin-4-yl)-6-(4-(2-(piperidin-1-yl)ethoxy)phenyl)pyrazolo[1,5-a]pyrimidine |
| 96 | N-(4-((4-(4-(3-(dimethylamino)propanoyl)piperazin-1-yl)-5-methoxy-6-((5-methyl-1H-pyrazol-3-yl)amino)pyrimidin-2-yl)thio)phenyl)cyclopropanecarboxamide |
| 97 | N-(4-((4-(4-(cyclopropylmethyl)piperazin-1-yl)-5-methoxy-6-((5-methyl-1H-pyrazol-3-yl)amino)pyrimidin-2-yl)thio)phenyl)cyclopropanecarboxamide |
| 98 | N-(4-((4-(4-(dimethylglycyl)piperazin-1-yl)-5-methoxy-6-((5-methyl-1H-pyrazol-3-yl)amino)pyrimidin-2-yl)thio)phenyl)cyclopropanecarboxamide |
| 99 | N-(4-((5-ethoxy-4-((5-methyl-1H-pyrazol-3-yl)amino)-6-(piperazin-1-yl)pyrimidin-2-yl)thio)phenyl)acetamide |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 100 | N-(4-((5-ethoxy-4-((5-methyl-1H-pyrazol-3-yl)amino)-6-(piperidin-1-yl)pyrimidin-2-yl)thio)phenyl)acetamide |
| 101 | N-(4-((5-methoxy-4-((5-methyl-1H-pyrazol-3-yl)amino)-6-(4-(1-methylpiperidin-4-yl)piperazin-1-yl)pyrimidin-2-yl)thio)phenyl)cyclopropanecarboxamide |
| 102 | N-(4-((5-methoxy-4-((5-methyl-1H-pyrazol-3-yl)amino)-6-(4-(2-(methylamino)ethyl)piperazin-1-yl)pyrimidin-2-yl)thio)phenyl)cyclopropanecarboxamide |
| 103 | N-(4-((5-methoxy-4-((5-methyl-1H-pyrazol-3-yl)amino)-6-(4-phenylpiperazin-1-yl)pyrimidin-2-yl)thio)phenyl)cyclopropanecarboxamide |
| 104 | N-(4-((5-methoxy-4-(4-(2-methoxyacetyl)piperazin-1-yl)-6-((5-methyl-1H-pyrazol-3-yl)amino)pyrimidin-2-yl)thio)phenyl)cyclopropanecarboxamide |
| 105 | N-(4-((5-methoxy-4-(4-(3-methoxypropanoyl)piperazin-1-yl)-6-((5-methyl-1H-pyrazol-3-yl)amino)pyrimidin-2-yl)thio)phenyl)cyclopropanecarboxamide (1:1:1:1:1:1:1:1:1) |
| 106 | N-(4-((4-(4-(2-(dimethylamino)ethyl)piperazin-1-yl)-5-ethoxy-6-((5-methyl-1H-pyrazol-3-yl)amino)pyrimidin-2-yl)thio)phenyl)acetamide |
| 107 | N-(4-((4-(4-acetylpiperazin-1-yl)-5-ethoxy-6-((5-methyl-1H-pyrazol-3-yl)amino)pyrimidin-2-yl)thio)phenyl)acetamide |
| 108 | N-(4-((4-(diethylamino)-5-ethoxy-6-((5-methyl-1H-pyrazol-3-yl)amino)pyrimidin-2-yl)thio)phenyl)acetamide |
| 109 | N-(4-((4-(diethylamino)-5-ethoxy-6-((5-methyl-1H-pyrazol-3-yl)amino)pyrimidin-2-yl)thio)phenyl)cyclopentanecarboxamide |
| 110 | N-(4-((5-ethoxy-4-((5-methyl-1H-pyrazol-3-yl)amino)-6-(piperazin-1-yl)pyrimidin-2-yl)thio)phenyl)cyclopentanecarboxamide |
| 111 | N-(4-((5-ethoxy-4-((5-methyl-1H-pyrazol-3-yl)amino)-6-(piperidin-1-yl)pyrimidin-2-yl)thio)phenyl)cyclopentanecarboxamide |
| 112 | N-(4-((5-ethoxy-4-((5-methyl-1H-pyrazol-3-yl)amino)-6-morpholinopyrimidin-2-yl)thio)phenyl)acetamide |
| 113 | N-(4-((5-ethoxy-4-((5-methyl-1H-pyrazol-3-yl)amino)-6-morpholinopyrimidin-2-yl)thio)phenyl)cyclopentanecarboxamide |
| 114 | N-(4-((5-ethoxy-4-(4-(2-methoxyethyl)piperazin-1-yl)-6-((5-methyl-1H-pyrazol-3-yl)amino)pyrimidin-2-yl)thio)phenyl)acetamide |
| 115 | N-(4-((5-ethoxy-4-(ethyl(methyl)amino)-6-((5-methyl-1H-pyrazol-3-yl)amino)pyrimidin-2-yl)thio)phenyl)acetamide |
| 116 | N-(4-((4-(4-(2-(dimethylamino)ethyl)piperazin-1-yl)-5-ethoxy-6-((5-methyl-1H-pyrazol-3-yl)amino)pyrimidin-2-yl)thio)phenyl)cyclopentanecarboxamide |
| 117 | N-(4-((4-(4-(3-(dimethylamino)propanoyl)piperazin-1-yl)-5-ethoxy-6-((5-methyl-1H-pyrazol-3-yl)amino)pyrimidin-2-yl)thio)phenyl)cyclopropanecarboxamide |
| 118 | N-(4-((4-(4-acetylpiperazin-1-yl)-5-ethoxy-6-((5-methyl-1H-pyrazol-3-yl)amino)pyrimidin-2-yl)thio)phenyl)cyclopentanecarboxamide |
| 119 | N-(4-((5-ethoxy-4-(4-(2-methoxyacetyl)piperazin-1-yl)-6-((5-methyl-1H-pyrazol-3-yl)amino)pyrimidin-2-yl)thio)phenyl)cyclopropanecarboxamide |
| 120 | N-(4-((5-ethoxy-4-(4-(2-methoxyethyl)piperazin-1-yl)-6-((5-methyl-1H-pyrazol-3-yl)amino)pyrimidin-2-yl)thio)phenyl)cyclopentanecarboxamide |
| 121 | N-(4-((5-ethoxy-4-(4-(3-methoxypropanoyl)piperazin-1-yl)-6-((5-methyl-1H-pyrazol-3-yl)amino)pyrimidin-2-yl)thio)phenyl)cyclopropanecarboxamide |
| 122 | N-(4-((5-ethoxy-4-(ethyl(methyl)amino)-6-((5-methyl-1H-pyrazol-3-yl)amino)pyrimidin-2-yl)thio)phenyl)cyclopentanecarboxamide |
| 123 | N-(4-((5-ethyl-4-((5-methyl-1H-pyrazol-3-yl)amino)-6,7-dihydro-5H-cyclopenta[d]pyrimidin-2-yl)thio)phenyl)cyclopropanecarboxamide |
| 124 | N-(4-((5-methoxy-4-((5-methyl-1H-pyrazol-3-yl)amino)-6-(piperidin-4-ylamino)pyrimidin-2-yl)thio)phenyl)cyclopropanecarboxamide |
| 125 | N-(4-((5-methyl-4-((5-methyl-1H-pyrazol-3-yl)amino)-6-(4-methylpiperazin-1-yl)pyrimidin-2-yl)thio)phenyl)acetamide |
| 126 | N-(4-((5-methyl-4-((5-methyl-1H-pyrazol-3-yl)amino)-6-(4-methylpiperazin-1-yl)pyrimidin-2-yl)thio)phenyl)cyclobutanecarboxamide |
| 127 | N-(4-((4-(4-(cyclopropylmethyl)piperazin-1-yl)-5-ethoxy-6-((5-methyl-1H-pyrazol-3-yl)amino)pyrimidin-2-yl)thio)phenyl)cyclopentanecarboxamide |
| 128 | N-(4-((4-(4-(cyclopropylmethyl)piperazin-1-yl)-5-ethoxy-6-((5-methyl-1H-pyrazol-3-yl)amino)pyrimidin-2-yl)thio)phenyl)cyclopropanecarboxamide |
| 129 | N-(4-((4-(4-(dimethylglycyl)piperazin-1-yl)-5-ethoxy-6-((5-methyl-1H-pyrazol-3-yl)amino)pyrimidin-2-yl)thio)phenyl)cyclopentanecarboxamide |
| 130 | N-(4-((4-(4-(dimethylglycyl)piperazin-1-yl)-5-ethoxy-6-((5-methyl-1H-pyrazol-3-yl)amino)pyrimidin-2-yl)thio)phenyl)cyclopropanecarboxamide |
| 131 | N-(4-((5-ethoxy-4-((5-methyl-1H-pyrazol-3-yl)amino)-6-(4-(1-methylpiperidin-4-yl)piperazin-1-yl)pyrimidin-2-yl)thio)phenyl)cyclopentanecarboxamide |
| 132 | N-(4-((5-ethoxy-4-((5-methyl-1H-pyrazol-3-yl)amino)-6-(4-(1-methylpiperidin-4-yl)piperazin-1-yl)pyrimidin-2-yl)thio)phenyl)cyclopropanecarboxamide |
| 133 | N-(4-((5-ethoxy-4-((5-methyl-1H-pyrazol-3-yl)amino)-6-(4-(piperidin-4-yl)piperazin-1-yl)pyrimidin-2-yl)thio)phenyl)cyclopropanecarboxamide |
| 134 | N-(4-((5-ethoxy-4-((5-methyl-1H-pyrazol-3-yl)amino)-6-(4-methylpiperazin-1-yl)pyrimidin-2-yl)thio)phenyl)acetamide |
| 135 | N-(4-((5-ethoxy-4-(4-(2-methoxyacetyl)piperazin-1-yl)-6-((5-methyl-1H-pyrazol-3-yl)amino)pyrimidin-2-yl)thio)phenyl)cyclopentanecarboxamide |
| 136 | N-(4-((5-ethoxy-4-(4-(3-methoxypropanoyl)piperazin-1-yl)-6-((5-methyl-1H-pyrazol-3-yl)amino)pyrimidin-2-yl)thio)phenyl)cyclopentanecarboxamide |

TABLE 2-continued

Compound Names for exemplified compounds of formula (I), (II), and (III).
All compounds were confirmed by mass spectroscopy and by $^1$H and $^{13}$C NMR.

| No. | Chemical Name |
| --- | --- |
| 137 | N-(4-((5-methoxy-4-((5-methyl-1H-pyrazol-3-yl)amino)-6-((1-methylpiperidin-4-yl)amino)pyrimidin-2-yl)thio)phenyl)cyclopropanecarboxamide |
| 138 | N-(4-((4-(4-(2-(dimethylamino)ethyl)piperazin-1-yl)-5-methyl-6-((5-methyl-1H-pyrazol-3-yl)amino)pyrimidin-2-yl)thio)phenyl)acetamide |
| 139 | N-(4-((4-(4-(2-(dimethylamino)ethyl)piperazin-1-yl)-5-methyl-6-((5-methyl-1H-pyrazol-3-yl)amino)pyrimidin-2-yl)thio)phenyl)cyclopentanecarboxamide |
| 140 | N-(4-((4-(4-(2-methoxyethyl)piperazin-1-yl)-5-methyl-6-((5-methyl-1H-pyrazol-3-yl)amino)pyrimidin-2-yl)thio)phenyl)acetamide |
| 141 | N-(4-((4-(4-acetylpiperazin-1-yl)-5-methyl-6-((5-methyl-1H-pyrazol-3-yl)amino)pyrimidin-2-yl)thio)phenyl)acetamide |
| 142 | N-(4-((4-(dimethylamino)-5-ethoxy-6-((5-methyl-1H-pyrazol-3-yl)amino)pyrimidin-2-yl)thio)phenyl)acetamide |
| 143 | N-(4-((4-(dimethylamino)-5-ethoxy-6-((5-methyl-1H-pyrazol-3-yl)amino)pyrimidin-2-yl)thio)phenyl)cyclopentanecarboxamide |
| 144 | N-(4-((5-ethoxy-4-((5-methyl-1H-pyrazol-3-yl)amino)-6-(4-(piperidin-4-yl)piperazin-1-yl)pyrimidin-2-yl)thio)phenyl)cyclopentanecarboxamide |
| 145 | N-(4-((5-ethoxy-4-((5-methyl-1H-pyrazol-3-yl)amino)-6-(4-methylpiperazin-1-yl)pyrimidin-2-yl)thio)phenyl)cyclopentanecarboxamide |
| 146 | N-(4((5-methyl-4-((5-methyl-1H-pyrazol-3-yl)amino)-6-(4-(1-methylpiperidin-4-yl)piperazin-1-yl)pyrimidin-2-yl)thio)phenyl)acetamide |
| 147 | N-(4-((5-methyl-4-((5-methyl-1H-pyrazol-3-yl)amino)-6-(piperazin-1-yl)pyrimidin-2-yl)thio)phenyl)acetamide |
| 148 | N-(4-((5-methyl-4-((5-methyl-1H-pyrazol-3-yl)amino)-6-morpholinopyrimidin-2-yl)thio)phenyl)acetamide |
| 149 | N-(4-((4-(4-(2-methoxyacetyl)piperazin-1-yl)-5-methyl-6-((5-methyl-1H-pyrazol-3-yl)amino)pyrimidin-2-yl)thio)phenyl)acetamide |
| 150 | N-(4-((4-(4-(2-methoxyethyl)piperazin-1-yl)-5-methyl-6-((5-methyl-1H-pyrazol-3-yl)amino)pyrimidin-2-yl)thio)phenyl)cyclopentanecarboxamide |
| 151 | N-(4-((4-(4-(3-(dimethylamino)propanoyl)piperazin-1-yl)-5-ethoxy-6-((5-methyl-1H-pyrazol-3-yl)amino)pyrimidin-2-yl)thio)phenyl)cyclopentanecarboxamide |
| 152 | N-(4-((4-(4-(3-(dimethylamino)propanoyl)piperazin-1-yl)-5-methyl-6-((5-methyl-1H-pyrazol-3-yl)amino)pyrimidin-2-yl)thio)phenyl)acetamide |
| 153 | N-(4-((4-(4-acetylpiperazin-1-yl)-5-methyl-6-((5-methyl-1H-pyrazol-3-yl)amino)pyrimidin-2-yl)thio)phenyl)cyclopentanecarboxamide |
| 154 | N-(4-((4-(isopropyl(methyl)amino)-5-methyl-6-((5-methyl-1H-pyrazol-3-yl)amino)pyrimidin-2-yl)thio)phenyl)acetamide |
| 155 | N-(4-((5-(ethylthio)-4-((5-methyl-1H-pyrazol-3-yl)amino)-6-(4-methylpiperazin-1-yl)pyrimidin-2-yl)thio)phenyl)cyclopropanecarboxamide |
| 156 | N-(4-((5-methoxy-4-((5-methyl-1H-pyrazol-3-yl)amino)-6-(piperidin-1-yl)pyrimidin-2-yl)thio)phenyl)acetamide |
| 157 | N-(4-((5-methyl-4-((5-methyl-1H-pyrazol-3-yl)amino)-6-(4-(1-methylpiperidin-4-yl)piperazin-1-yl)pyrimidin-2-yl)thio)phenyl)cyclopentanecarboxamide |
| 158 | N-(4-((5-methyl-4-((5-methyl-1H-pyrazol-3-yl)amino)-6-(piperazin-1-yl)pyrimidin-2-yl)thio)phenyl)cyclopentanecarboxamide |
| 159 | N-(4-((5-methyl-4-((5-methyl-1H-pyrazol-3-yl)amino)-6-morpholinopyrimidin-2-yl)thio)phenyl)cyclopentanecarboxamide |
| 160 | N-(4-((4-((5-methyl-1H-pyrazol-3-yl)amino)-6-(4-methylpiperazin-1-yl)-5-(methylthio)pyrimidin-2-yl)thio)phenyl)cyclopropanecarboxamide |
| 161 | N-(4-((4-(4-(2-methoxyacetyl)piperazin-1-yl)-5-methyl-6-((5-methyl-1H-pyrazol-3-yl)amino)pyrimidin-2-yl)thio)phenyl)cyclopentanecarboxamide |
| 162 | N-(4-((4-(4-hydroxypiperidin-1-yl)-5-methyl-6-((5-methyl-1H-pyrazol-3-yl)amino)pyrimidin-2-yl)thio)phenyl)acetamide |
| 163 | N-(4-((4-(diethylamino)-5-methyl-6-((5-methyl-1H-pyrazol-3-yl)amino)pyrimidin-2-yl)thio)phenyl)cyclopentanecarboxamide |
| 164 | N-(4-((4-(dimethylamino)-5-methyl-6-((5-methyl-1H-pyrazol-3-yl)amino)pyrimidin-2-yl)thio)phenyl)cyclopentanecarboxamide |
| 165 | N-(4-((4-(ethyl(methyl)amino)-5-methyl-6-((5-methyl-1H-pyrazol-3-yl)amino)pyrimidin-2-yl)thio)phenyl)cyclopentanecarboxamide |
| 166 | N-(4-((4-(isopropyl(methyl)amino)-5-methyl-6-((5-methyl-1H-pyrazol-3-yl)amino)pyrimidin-2-yl)thio)phenyl)cyclopentanecarboxamide |
| 167 | N-(4-((5-methyl-4-((5-methyl-1H-pyrazol-3-yl)amino)-6-(piperidin-1-yl)pyrimidin-2-yl)thio)phenyl)cyclopentanecarboxamide |
| 168 | N-(4-((5-methyl-4-((5-methyl-1H-pyrazol-3-yl)amino)-6-(pyrrolidin-1-yl)pyrimidin-2-yl)thio)phenyl)acetamide |
| 169 | methyl (4-((5-methyl-4-((5-methyl-1H-pyrazol-3-yl)amino)-6-(piperidin-1-yl)pyrimidin-2-yl)thio)phenyl)carbamate |
| 170 | N-(4-((4-(azepan-1-yl)-5-methyl-6-((5-methyl-1H-pyrazol-3-yl)amino)pyrimidin-2-yl)thio)phenyl)acetamide |
| 171 | N-(4-((5-chloro-4-((5-methyl-1H-pyrazol-3-yl)amino)-6-(4-methylpiperazin-1-yl)pyrimidin-2-yl)thio)phenyl)acetamide |
| 172 | N-(4-((5-chloro-4-((5-methyl-1H-pyrazol-3-yl)amino)-6-(4-methylpiperazin-1-yl)pyrimidin-2-yl)thio)phenyl)cyclopropanecarboxamide |
| 173 | 1-methyl-3-(4-((5-methyl-4-((5-methyl-1H-pyrazol-3-yl)amino)-6-(piperidin-1-yl)pyrimidin-2-yl)thio)phenyl)urea |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 174 | 2-((4-aminophenyl)thio)-5-methyl-N-(5-methyl-1H-pyrazol-3-yl)-6-(piperidin-1-yl)pyrimidin-4-amine |
| 175 | 5-methyl-N-(5-methyl-1H-pyrazol-3-yl)-2-(methylthio)-6-(piperidin-1-yl)pyrimidin-4-amine |
| 176 | 5-methyl-N-(5-methyl-1H-pyrazol-3-yl)-2-(phenylthio)-6-(piperidin-1-yl)pyrimidin-4-amine |
| 177 | 5-methyl-N-(5-methyl-1H-pyrazol-3-yl)-6-(piperidin-1-yl)-2-(p-tolylthio)pyrimidin-4-amine |
| 178 | N-(4-((4-(3,6-dihydropyridin-1(2H)-yl)-5-methyl-6-((5-methyl-1H-pyrazol-3-yl)amino)pyrimidin-2-yl)thio)phenyl)acetamide |
| 179 | N-(4-((4-(4,4-difluoropiperidin-1-yl)-5-methyl-6-((5-methyl-1H-pyrazol-3-yl)amino)pyrimidin-2-yl)thio)phenyl)acetamide |
| 180 | N-(4-((4-(4-fluoro-3,6-dihydropyridin-1(2H)-yl)-5-methyl-6-((5-methyl-1H-pyrazol-3-yl)amino)pyrimidin-2-yl)thio)phenyl)acetamide |
| 181 | N-(4-((4-(4-fluoropiperidin-1-yl)-5-methyl-6-((5-methyl-1H-pyrazol-3-yl)amino)pyrimidin-2-yl)thio)phenyl)acetamide |
| 182 | N-(4-((5-chloro-4-((5-methyl-1H-pyrazol-3-yl)amino)-6-(piperidin-1-yl)pyrimidin-2-yl)thio)phenyl)acetamide |
| 183 | N-(4-((5-ethoxy-4-((5-methyl-1H-pyrazol-3-yl)amino)-6-(4-(1-methylpiperidin-4-yl)piperazin-1-yl)pyrimidin-2-yl)thio)phenyl)acetamide |
| 184 | N-(4-((5-methoxy-4-((5-methyl-1H-pyrazol-3-yl)amino)-6-(4-(1-methylpiperidin-4-yl)piperazin-1-yl)pyrimidin-2-yl)thio)phenyl)acetamide |
| 185 | N-(4-((5-methoxy-4-((5-methyl-1H-pyrazol-3-yl)amino)-6-(4-methylpiperazin-1-yl)pyrimidin-2-yl)thio)phenyl)acetamide |
| 186 | N-(4-((5-methyl-4-((5-methyl-1H-pyrazol-3-yl)amino)-6-(4-methylpiperidin-1-yl)pyrimidin-2-yl)thio)phenyl)acetamide |
| 187 | 2-((4-(dimethylamino)phenyl)thio)-5-methyl-N-(5-methyl-1H-pyrazol-3-yl)-6-(piperidin-1-yl)pyrimidin-4-amine |
| 188 | 5-methyl-N-(5-methyl-1H-pyrazol-3-yl)-2-((4-(methylamino)phenyl)thio)-6-(piperidin-1-yl)pyrimidin-4-amine |
| 189 | N-(4-((4-((5-methyl-1H-pyrazol-3-yl)amino)-6-(piperidin-1-yl)pyrimidin-2-yl)thio)phenyl)acetamide |
| 190 | N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)acetamide |
| 191 | N-(4-((4-(4-acetylpiperazin-1-yl)-5-methoxy-6-((5-methyl-1H-pyrazol-3-yl)amino)pyrimidin-2-yl)thio)phenyl)acetamide |
| 192 | N-(4-((4-(azepan-1-yl)-5-methoxy-6-((5-methyl-1H-pyrazol-3-yl)amino)pyrimidin-2-yl)thio)phenyl)acetamide |
| 193 | N-(4-((4-(diethylamino)-5-methoxy-6-((5-methyl-1H-pyrazol-3-yl)amino)pyrimidin-2-yl)thio)phenyl)acetamide |
| 194 | N-(4-((4-(dimethylamino)-5-methoxy-6-((5-methyl-1H-pyrazol-3-yl)amino)pyrimidin-2-yl)thio)phenyl)acetamide |
| 195 | N-(4-((4-(ethyl(methyl)amino)-5-methoxy-6-((5-methyl-1H-pyrazol-3-yl)amino)pyrimidin-2-yl)thio)phenyl)acetamide |
| 196 | N-(4-((5-methoxy-4-((5-methyl-1H-pyrazol-3-yl)amino)-6-(4-methylpiperidin-1-yl)pyrimidin-2-yl)thio)phenyl)acetamide |
| 197 | N-(4-((5-methoxy-4-((5-methyl-1H-pyrazol-3-yl)amino)-6-(piperazin-1-yl)pyrimidin-2-yl)thio)phenyl)acetamide |
| 198 | N-(4-((5-methoxy-4-((5-methyl-1H-pyrazol-3-yl)amino)-6-(pyrrolidin-1-yl)pyrimidin-2-yl)thio)phenyl)acetamide |
| 199 | N-(4-((5-methoxy-4-((5-methyl-1H-pyrazol-3-yl)amino)-6-morpholinopyrimidin-2-yl)thio)phenyl)acetamide |
| 200 | N-(4-((5-methoxy-4-(4-(2-methoxyethyl)piperazin-1-yl)-6-((5-methyl-1H-pyrazol-3-yl)amino)pyrimidin-2-yl)thio)phenyl)acetamide |
| 201 | N-(4-((4-(3,6-dihydropyridin-1(2H)-yl)-5-methoxy-6-((5-methyl-1H-pyrazol-3-yl)amino)pyrimidin-2-yl)thio)phenyl)acetamide |
| 202 | N-(4-((4-(4,4-difluoropiperidin-1-yl)-5-methoxy-6-((5-methyl-1H-pyrazol-3-yl)amino)pyrimidin-2-yl)thio)phenyl)acetamide |
| 203 | N-(4-((4-(4-acetylpiperidin-1-yl)-5-methoxy-6-((5-methyl-1H-pyrazol-3-yl)amino)pyrimidin-2-yl)thio)phenyl)acetamide |
| 204 | N-(4-((4-(4-aminopiperidin-1-yl)-5-methoxy-6-((5-methyl-1H-pyrazol-3-yl)amino)pyrimidin-2-yl)thio)phenyl)acetamide |
| 205 | N-(4-((4-(4-ethylpiperazin-1-yl)-5-methyl-6-((5-methyl-1H-pyrazol-3-yl)amino)pyrimidin-2-yl)thio)phenyl)acetamide |
| 206 | N-(4-((4-(4-fluoro-3,6-dihydropyridin-1(2H)-yl)-5-methoxy-6-((5-methyl-1H-pyrazol-3-yl)amino)pyrimidin-2-yl)thio)phenyl)acetamide |
| 207 | N-(4-((4-(4-fluoropiperidin-1-yl)-5-methoxy-6-((5-methyl-1H-pyrazol-3-yl)amino)pyrimidin-2-yl)thio)phenyl)acetamide |
| 208 | N-(4-((4-(4-hydroxypiperidin-1-yl)-5-methoxy-6-((5-methyl-1H-pyrazol-3-yl)amino)pyrimidin-2-yl)thio)phenyl)acetamide |
| 209 | N-(4-((4-(isopropyl(methyl)amino)-5-methoxy-6-((5-methyl-1H-pyrazol-3-yl)amino)pyrimidin-2-yl)thio)phenyl)acetamide |
| 210 | 6-(4-(2-(dimethylamino)ethyl)piperazin-1-yl)-5-methoxy-N-(5-methyl-1H-pyrazol-3-yl)-2-((4-((2-(thiazol-2-yl)propan-2-yl)sulfonyl)phenyl)thio)pyrimidin-4-amine |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 211 | N-(4-((5-methoxy-4-(4-(2-methoxyacetyl)piperazin-1-yl)-6-((5-methyl-1H-pyrazol-3-yl)amino)pyrimidin-2-yl)thio)phenyl)acetamide |
| 212 | N-(4-((5-methyl-4-((5-methyl-1H-pyrazol-3-yl)amino)-6-(2-methylpiperidin-1-yl)pyrimidin-2-yl)thio)phenyl)acetamide |
| 213 | N-(4-((4-(4-(2-(dimethylamino)ethyl)piperidin-1-yl)-5-methyl-6-((5-methyl-1H-pyrazol-3-yl)amino)pyrimidin-2-yl)thio)phenyl)acetamide |
| 214 | N-(4-((4-(4-(dimethylamino)piperidin-1-yl)-5-methoxy-6-((5-methyl-1H-pyrazol-3-yl)amino)pyrimidin-2-yl)thio)phenyl)acetamide |
| 215 | N-(4-((4-(4-ethylpiperazin-1-yl)-5-methoxy-6-((5-methyl-1H-pyrazol-3-yl)amino)pyrimidin-2-yl)thio)phenyl)acetamide |
| 216 | N-(4-((4-(4-isobutyrylpiperazin-1-yl)-5-methoxy-6-((5-methyl-1H-pyrazol-3-yl)amino)pyrimidin-2-yl)thio)phenyl)acetamide |
| 217 | N-(4-((5-methoxy-4-((5-methyl-1H-pyrazol-3-yl)amino)-6-(2-methylpiperidin-1-yl)pyrimidin-2-yl)thio)phenyl)acetamide |
| 218 | N-(4-((5-methoxy-4-((5-methyl-1H-pyrazol-3-yl)amino)-6-(4-propionylpiperazin-1-yl)pyrimidin-2-yl)thio)phenyl)acetamide |
| 219 | 1-(5-methyl-6-((5-methyl-1H-pyrazol-3-yl)amino)-2-(methylthio)pyrimidin-4-yl)piperidin-4-ol |
| 220 | 5-methyl-N-(5-methyl-1H-pyrazol-3-yl)-2-(methylthio)-6-morpholinopyrimidin-4-amine |
| 221 | N-(4-((4-(4-(dimethylglycyl)piperazin-1-yl)-5-methoxy-6-((5-methyl-1H-pyrazol-3-yl)amino)pyrimidin-2-yl)thio)phenyl)acetamide |
| 222 | N-(4-((4-(4-(dimethylglycyl)piperazin-1-yl)-5-methyl-6-((5-methyl-1H-pyrazol-3-yl)amino)pyrimidin-2-yl)thio)phenyl)acetamide |
| 223 | N-(4-((4-(4-acetylpiperidin-1-yl)-5-methyl-6-((5-methyl-1H-pyrazol-3-yl)amino)pyrimidin-2-yl)thio)phenyl)acetamide |
| 224 | N-(4-((4-(4-isobutyrylpiperazin-1-yl)-5-methyl-6-((5-methyl-1H-pyrazol-3-yl)amino)pyrimidin-2-yl)thio)phenyl)acetamide |
| 225 | N-(4-((4-(4-isopropylpiperazin-1-yl)-5-methoxy-6-((5-methyl-1H-pyrazol-3-yl)amino)pyrimidin-2-yl)thio)phenyl)acetamide |
| 226 | N-(4-((4-(4-isopropylpiperazin-1-yl)-5-methyl-6-((5-methyl-1H-pyrazol-3-yl)amino)pyrimidin-2-yl)thio)phenyl)acetamide |
| 227 | N-(4-((5-methoxy-4-((5-methyl-1H-pyrazol-3-yl)amino)-6-(4-(methylglycyl)piperazin-1-yl)pyrimidin-2-yl)thio)phenyl)acetamide |
| 228 | N-(4-((5-methyl-4-((5-methyl-1H-pyrazol-3-yl)amino)-6-(4-(methylamino)piperidin-1-yl)pyrimidin-2-yl)thio)phenyl)acetamide |
| 229 | N-(4-((5-methyl-4-((5-methyl-1H-pyrazol-3-yl)amino)-6-(4-(methylglycyl)piperazin-1-yl)pyrimidin-2-yl)thio)phenyl)acetamide |
| 230 | N-(4-((5-methyl-4-((5-methyl-1H-pyrazol-3-yl)amino)-6-(4-propionylpiperazin-1-yl)pyrimidin-2-yl)thio)phenyl)acetamide |
| 231 | N-(4-((4-(4-(dimethylamino)piperidin-1-yl)-5-methyl-6-((5-methyl-1H-pyrazol-3-yl)amino)pyrimidin-2-yl)thio)phenyl)acetamide |
| 232 | N-(4-((4-(4-aminopiperidin-1-yl)-5-methyl-6-((5-methyl-1H-pyrazol-3-yl)amino)pyrimidin-2-yl)thio)phenyl)acetamide |
| 233 | N-(4-((4-(4-hydroxy-4-methylpiperidin-1-yl)-5-methyl-6-((5-methyl-1H-pyrazol-3-yl)amino)pyrimidin-2-yl)thio)phenyl)acetamide |
| 234 | N-(4-((4-(diethylamino)-5-methyl-6-((5-methyl-1H-pyrazol-3-yl)amino)pyrimidin-2-yl)thio)phenyl)acetamide |
| 235 | 1-(4-((4-(4-hydroxypiperidin-1-yl)-5-methyl-6-((5-methyl-1H-pyrazol-3-yl)amino)pyrimidin-2-yl)thio)phenyl)-3-methylurea |
| 236 | 1-methyl-3-(4-((5-methyl-4-((5-methyl-1H-pyrazol-3-yl)amino)-6-morpholinopyrimidin-2-yl)thio)phenyl)urea |
| 237 | 1-(5-methyl-6-((5-methyl-1H-pyrazol-3-yl)amino)-2-(phenylthio)pyrimidin-4-yl)piperidin-4-ol |
| 238 | 5-methyl-N-(5-methyl-1H-pyrazol-3-yl)-6-(piperidin-1-yl)-2-(p-tolyloxy)pyrimidin-4-amine |
| 239 | 5-methyl-N-(5-methyl-1H-pyrazol-3-yl)-6-morpholino-2-(phenylthio)pyrimidin-4-amine |
| 240 | $N^4$-isopropyl-$N^4$,5-dimethyl-$N^6$-(5-methyl-1H-pyrazol-3-yl)-2-(phenylthio)pyrimidine-4,6-diamine |
| 241 | N-(4-((4-(4-(2-(dimethylamino)ethyl)piperidin-1-yl)-5-methoxy-6-((5-methyl-1H-pyrazol-3-yl)amino)pyrimidin-2-yl)thio)phenyl)acetamide |
| 242 | 1-(4-((4-(4-(2-methoxyacetyl)piperazin-1-yl)-5-methyl-6-((5-methyl-1H-pyrazol-3-yl)amino)pyrimidin-2-yl)thio)phenyl)-3-methylurea |
| 243 | 1-(4-((4-(isopropyl(methyl)amino)-5-methyl-6-((5-methyl-1H-pyrazol-3-yl)amino)pyrimidin-2-yl)thio)phenyl)-3-methylurea |
| 244 | 1-(4-(2-((4-aminophenyl)thio)-5-methyl-6-((5-methyl-1H-pyrazol-3-yl)amino)pyrimidin-4-yl)piperazin-1-yl)-2-methoxyethan-1-one |
| 245 | 2-methoxy-1-(4-(5-methyl-6-((5-methyl-1H-pyrazol-3-yl)amino)-2-(phenylthio)pyrimidin-4-yl)piperazin-1-yl)ethan-1-one |
| 246 | 1-(2-((4-aminophenyl)thio)-5-methyl-6-((5-methyl-1H-pyrazol-3-yl)amino)pyrimidin-4-yl)piperidin-4-ol |
| 247 | 6-(1-(2-(dimethylamino)ethyl)piperidin-4-yl)-2-((4-(ethylsulfonyl)phenyl)thio)-5-methoxy-N-(5-methyl-1H-pyrazol-3-yl)pyrimidin-4-amine |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 248 | 6-(4-(2-(8-azabicyclo[3.2.1]octan-8-yl)ethyl)piperazin-1-yl)-2-((4-(benzylsulfonyl)phenyl)thio)-5-methoxy-N-(5-methyl-1H-pyrazol-3-yl)pyrimidin-4-amine |
| 249 | 6-(4-(2-(9-azabicyclo[3.3.1]nonan-9-yl)ethyl)piperidin-1-yl)-2-((4-(ethylsulfonyl)phenyl)thio)-5-methoxy-N-(5-methyl-1H-pyrazol-3-yl)pyrimidin-4-amine |
| 250 | 6-(4-(2-(dimethylamino)ethyl)piperazin-1-yl)-5-methoxy-N-(5-methyl-1H-pyrazol-3-yl)-2-((4-((2-(pyrimidin-4-yl)propan-2-yl)sulfonyl)phenyl)thio)pyrimidin-4-amine |
| 251 | 6-(4-(2-(dimethylamino)ethyl)piperazin-1-yl)-2-((4-((2-(dimethylamino)ethyl)sulfonyl)phenyl)thio)-5-methoxy-N-(5-methyl-1H-pyrazol-3-yl)pyrimidin-4-amine |
| 252 | 6-(4-(2-(dimethylamino)ethyl)piperazin-1-yl)-5-ethoxy-2-((4-(ethylsulfonyl)phenyl)thio)-N-(5-methyl-1H-pyrazol-3-yl)pyrimidin-4-amine |
| 253 | 6-(4-(2-(dimethylamino)ethyl)piperazin-1-yl)-5-methoxy-N-(5-methyl-1H-pyrazol-3-yl)-2-((4-((oxazol-2-ylmethyl)sulfonyl)phenyl)thio)pyrimidin-4-amine |
| 254 | 6-(4-(2-(dimethylamino)ethyl)piperazin-1-yl)-5-methoxy-N-(5-methyl-1H-pyrazol-3-yl)-2-((4-((thiazol-2-ylmethyl)sulfonyl)phenyl)thio)pyrimidin-4-amine |
| 255 | 6-(4-(2-(dimethylamino)ethyl)piperazin-1-yl)-5-methoxy-N-(5-methyl-1H-pyrazol-3-yl)-2-((4-(phenylsulfonyl)phenyl)thio)pyrimidin-4-amine |
| 256 | 2-((4-((2,4-difluorobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 257 | 2-((4-(benzylsulfonyl)phenyl)thio)-5-ethoxy-N-(5-methyl-1H-pyrazol-3-yl)-6-(piperazin-1-yl)pyrimidin-4-amine |
| 258 | 2-((4-(benzylsulfonyl)phenyl)thio)-5-methoxy-6-(4-(2-(methyl(phenyl)amino)ethyl)piperazin-1-yl)-N-(5-methyl-1H-pyrazol-3-yl)pyrimidin-4-amine |
| 259 | 2-((4-(benzylsulfonyl)phenyl)thio)-6-(4-(2-(dimethylamino)ethyl)piperazin-1-yl)-5-isopropoxy-N-(5-methyl-1H-pyrazol-3-yl)pyrimidin-4-amine |
| 260 | 2-((4-(benzylsulfonyl)phenyl)thio)-6-(4-(2-(dimethylamino)ethyl)piperazin-1-yl)-5-methoxy-N-(1H-pyrazol-3-yl)pyrimidin-4-amine |
| 261 | 2-((4-(benzylsulfonyl)phenyl)thio)-6-(4-(2-(dimethylamino)ethyl)piperazin-1-yl)-5-methyl-N-(5-methyl-1H-pyrazol-3-yl)pyrimidin-4-amine |
| 262 | 2-((4-(benzylsulfonyl)phenyl)thio)-6-(4-(2-(dimethylamino)ethyl)piperazin-1-yl)-N-(5-methyl-1H-pyrazol-3-yl)-5-propoxypyrimidin-4-amine |
| 263 | 2-((4-(benzylsulfonyl)phenyl)thio)-6-(4-(2-(dimethylamino)ethyl)piperazin-1-yl)-N-(5-methyl-1H-pyrazol-3-yl)pyrimidin-4-amine |
| 264 | 2-((4-(benzylsulfonyl)phenyl)thio)-$N^4$,$N^4$-diethyl-5-methoxy-$N^6$-(5-methyl-1H-pyrazol-3-yl)pyrimidine-4,6-diamine |
| 265 | 2-((4-(ethylsulfonyl)phenyl)thio)-5-methoxy-N-(5-methyl-1H-pyrazol-3-yl)-6-(piperidin-1-yl)pyrimidin-4-amine |
| 266 | 2-((4-(ethylsulfonyl)phenyl)thio)-5-methoxy-N-(5-methyl-1H-pyrazol-3-yl)-6-morpholinopyrimidin-4-amine |
| 267 | 5-ethoxy-2-((4-(ethylsulfonyl)phenyl)thio)-N-(5-methyl-1H-pyrazol-3-yl)-6-(piperazin-1-yl)pyrimidin-4-amine |
| 268 | 6-(4-(2-(dimethylamino)ethyl)piperazin-1-yl)-2-((4-((2-fluorobenzyl)sulfonyl)phenyl)thio)-5-methoxy-N-(5-methyl-1H-pyrazol-3-yl)pyrimidin-4-amine |
| 269 | 6-(4-(2-(dimethylamino)ethyl)piperazin-1-yl)-5-methoxy-N-(5-methyl-1H-pyrazol-3-yl)-2-((4-((3-nitrobenzyl)sulfonyl)phenyl)thio)pyrimidin-4-amine |
| 270 | 6-(4-(2-(dimethylamino)ethyl)piperazin-1-yl)-5-methoxy-N-(5-methyl-1H-pyrazol-3-yl)-2-((4-((4-nitrobenzyl)sulfonyl)phenyl)thio)pyrimidin-4-amine |
| 271 | $N^4$,$N^4$-diethyl-2-((4-(ethylsulfonyl)phenyl)thio)-5-methoxy-$N^6$-(5-methyl-1H-pyrazol-3-yl)pyrimidine-4,6-diamine |
| 272 | 1-(3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)phenyl)ethan-1-one |
| 273 | 1-(2-(4-(2-((4-(benzylsulfonyl)phenyl)thio)-5-methoxy-6-((5-methyl-1H-pyrazol-3-yl)amino)pyrimidin-4-yl)piperazin-1-yl)ethyl)piperidin-4-ol |
| 274 | 3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)phenol |
| 275 | 2-((4-((2,3-difluorobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 276 | 2-((4-((2,5-difluorobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 277 | 2-((4-((2-fluorobenzyl)sulfonyl)phenyl)thio)-5-methoxy-N-(5-methyl-1H-pyrazol-3-yl)-6-morpholinopyrimidin-4-amine |
| 278 | 2-((4-((3-(benzyloxy)benzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 279 | 2-((4-(([1,1'-biphenyl]-3-ylmethyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 280 | 2-((4-(benzylsulfonyl)phenyl)thio)-5-methoxy-N-(5-methyl-1H-pyrazol-3-yl)-6-(4-(2-(piperidin-1-yl)ethyl)piperazin-1-yl)pyrimidin-4-amine |
| 281 | 2-((4-(benzylsulfonyl)phenyl)thio)-6-(4-(2-(2,6-dimethylpiperidin-1-yl)ethyl)piperazin-1-yl)-5-methoxy-N-(5-methyl-1H-pyrazol-3-yl)pyrimidin-4-amine |
| 282 | 5-methoxy-N-(5-methyl-1H-pyrazol-3-yl)-6-morpholino-2-((4-(((3-nitrobenzyl)sulfonyl)phenyl)thio)pyrimidin-4-amine |
| 283 | 6-(4-(2-(8-azabicyclo[3.2.1]octan-8-yl)ethyl)piperazin-1-yl)-2-((4-(benzylsulfonyl)phenyl)thio)-5-ethoxy-N-(5-methyl-1H-pyrazol-3-yl)pyrimidin-4-amine |
| 284 | 6-(4-(2-(dimethylamino)ethyl)piperazin-1-yl)-5-methoxy-N-(5-methyl-1H-pyrazol-3-yl)-2-((4-(((2-nitrobenzyl)sulfonyl)phenyl)thio)pyrimidin-4-amine |
| 285 | 6-(4-(2-(dimethylamino)ethyl)piperazin-1-yl)-5-methoxy-N-(5-methyl-1H-pyrazol-3-yl)-2-((4-((3-(trifluoromethyl)benzyl)sulfonyl)phenyl)thio)pyrimidin-4-amine |
| 286 | 6-(4-(2-(dimethylamino)ethyl)piperidin-1-yl)-5-ethoxy-2-((4-(ethylsulfonyl)phenyl)thio)-N-(5-methyl-1H-pyrazol-3-yl)pyrimidin-4-amine |
| 287 | N$^2$-(4-(benzylsulfonyl)phenyl)-6-(4-(2-(dimethylamino)ethyl)piperazin-1-yl)-5-methoxy-N$^4$-(5-methyl-1H-pyrazol-3-yl)pyrimidine-2,4-diamine |
| 288 | 3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzonitrile |
| 289 | (R)-2-((4-(benzylsulfonyl)phenyl)thio)-5-methoxy-N-(5-methyl-1H-pyrazol-3-yl)-6-(2-methylmorpholino)pyrimidin-4-amine |
| 290 | 2-((4-(benzylsulfonyl)-2-fluorophenyl)thio)-6-(4-(2-(dimethylamino)ethyl)piperazin-1-yl)-5-methoxy-N-(5-methyl-1H-pyrazol-3-yl)pyrimidin-4-amine |
| 291 | 2-((4-(benzylsulfonyl)phenyl)thio)-5-methoxy-N-(5-methyl-1H-pyrazol-3-yl)-6-(4-(1-methylpiperidin-4-yl)piperazin-1-yl)pyrimidin-4-amine |
| 292 | 2-((4-(benzylsulfonyl)phenyl)thio)-5-methoxy-N-(5-methyl-1H-pyrazol-3-yl)-6-(4-(2-(4-methylpiperazin-1-yl)ethyl)piperidin-1-yl)pyrimidin-4-amine |
| 293 | 2-((4-(benzylsulfonyl)phenyl)thio)-5-methoxy-N-(5-methyl-1H-pyrazol-3-yl)-6-(4-(2-(pyrrolidin-1-yl)ethyl)piperazin-1-yl)pyrimidin-4-amine |
| 294 | 2-((4-(benzylsulfonyl)phenyl)thio)-5-methoxy-N-(5-methyl-1H-pyrazol-3-yl)-6-(4-(4-methylpiperazin-1-yl)piperidin-1-yl)pyrimidin-4-amine |
| 295 | 2-((4-(benzylsulfonyl)phenyl)thio)-5-methoxy-N-(5-methyl-1H-pyrazol-3-yl)-6-(4-(pyridin-4-ylmethyl)piperazin-1-yl)pyrimidin-4-amine |
| 296 | 6-(4-(1-benzylpiperidin-4-yl)piperazin-1-yl)-2-((4-(benzylsulfonyl)phenyl)thio)-5-methoxy-N-(5-methyl-1H-pyrazol-3-yl)pyrimidin-4-amine |
| 297 | 6-(4-(2-(azepan-1-yl)ethyl)piperazin-1-yl)-2-((4-(benzylsulfonyl)phenyl)thio)-5-methoxy-N-(5-methyl-1H-pyrazol-3-yl)pyrimidin-4-amine |
| 298 | 6-(4-(2-(dimethylamino)ethyl)piperazin-1-yl)-5-methoxy-2-((4-((2-methoxybenzyl)sulfonyl)phenyl)thio)-N-(5-methyl-1H-pyrazol-3-yl)pyrimidin-4-amine |
| 299 | 6-(4-(2-(dimethylamino)ethyl)piperazin-1-yl)-5-methoxy-2-((4-((3-methoxybenzyl)sulfonyl)phenyl)thio)-N-(5-methyl-1H-pyrazol-3-yl)pyrimidin-4-amine |
| 300 | 6-(4-(2-(dimethylamino)ethyl)piperazin-1-yl)-5-methoxy-N-(5-methyl-1H-pyrazol-3-yl)-2-((4-((3-methylbenzyl)sulfonyl)phenyl)thio)pyrimidin-4-amine |
| 301 | 6-(4-benzylpiperazin-1-yl)-2-((4-(benzylsulfonyl)phenyl)thio)-5-methoxy-N-(5-methyl-1H-pyrazol-3-yl)pyrimidin-4-amine |
| 302 | methyl 3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzoate |
| 303 | 3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzamide |
| 304 | N-(2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)phenyl)acetamide |
| 305 | 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzonitrile |
| 306 | (R)-2-((4-(benzylsulfonyl)phenyl)thio)-5-methoxy-N-(5-methyl-1H-pyrazol-3-yl)-6-(3-methylmorpholino)pyrimidin-4-amine |
| 307 | (S)-2-((4-(benzylsulfonyl)phenyl)thio)-5-methoxy-N-(5-methyl-1H-pyrazol-3-yl)-6-(2-methylmorpholino)pyrimidin-4-amine |
| 308 | (S)-2-((4-(benzylsulfonyl)phenyl)thio)-5-methoxy-N-(5-methyl-1H-pyrazol-3-yl)-6-(3-methylmorpholino)pyrimidin-4-amine |
| 309 | 2-((4-((2-(dimethylamino)benzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 310 | 2-((4-(([1,1'-biphenyl]-2-ylmethyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 311 | 2-((4-(benzylsulfonyl)phenyl)thio)-6-(8-oxa-3-azabicyclo[3.2.1]octan-3-yl)-5-methoxy-N-(5-methyl-1H-pyrazol-3-yl)pyrimidin-4-amine |
| 312 | 6-(4-(2-(azetidin-1-yl)ethyl)piperazin-1-yl)-2-((4-(benzylsulfonyl)phenyl)thio)-5-methoxy-N-(5-methyl-1H-pyrazol-3-yl)pyrimidin-4-amine |
| 313 | 6-(4-(2-(benzyl(methyl)amino)ethyl)piperazin-1-yl)-5-methoxy-2-((4-((3-methoxybenzyl)sulfonyl)phenyl)thio)-N-(5-methyl-1H-pyrazol-3-yl)pyrimidin-4-amine |
| 314 | 6-(4-(2-(dimethylamino)ethyl)piperazin-1-yl)-2-((4-((2-fluoro-3-nitrobenzyl)sulfonyl)phenyl)thio)-5-methoxy-N-(5-methyl-1H-pyrazol-3-yl)pyrimidin-4-amine |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 315 | 6-(4-(2-(dimethylamino)ethyl)piperazin-1-yl)-2-((4-((3-fluorobenzyl)sulfonyl)phenyl)thio)-5-methoxy-N-(5-methyl-1H-pyrazol-3-yl)pyrimidin-4-amine |
| 316 | 6-(4-(2-(dimethylamino)ethyl)piperazin-1-yl)-5-methoxy-N-(5-methyl-1H-pyrazol-3-yl)-2-((4-((2-(trifluoromethyl)benzyl)sulfonyl)phenyl)thio)pyrimidin-4-amine |
| 317 | 6-(4-(2-(dimethylamino)ethyl)piperazin-1-yl)-5-methoxy-N-(5-methyl-1H-pyrazol-3-yl)-2-((4-((2-methylbenzyl)sulfonyl)phenyl)thio)pyrimidin-4-amine |
| 318 | 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzoic acid |
| 319 | 3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzoic acid |
| 320 | methyl 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzoate |
| 321 | 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)-N,N-dimethylbenzamide |
| 322 | 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzamide |
| 323 | 3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)-N,N-dimethylbenzamide |
| 324 | N-(3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)phenyl)acetamide |
| 325 | (R)-5-methoxy-N-(5-methyl-1H-pyrazol-3-yl)-6-(2-methylmorpholino)-2-((4-((3-nitrobenzyl)sulfonyl)phenyl)thio)pyrimidin-4-amine |
| 326 | (R)-5-methoxy-N-(5-methyl-1H-pyrazol-3-yl)-6-(3-methylmorpholino)-2-((4-((3-nitrobenzyl)sulfonyl)phenyl)thio)pyrimidin-4-amine |
| 327 | (S)-5-methoxy-N-(5-methyl-1H-pyrazol-3-yl)-6-(2-methylmorpholino)-2-((4-((3-nitrobenzyl)sulfonyl)phenyl)thio)pyrimidin-4-amine |
| 328 | (S)-5-methoxy-N-(5-methyl-1H-pyrazol-3-yl)-6-(3-methylmorpholino)-2-((4-((3-nitrobenzyl)sulfonyl)phenyl)thio)pyrimidin-4-amine |
| 329 | 2-((4-((3-(dimethylamino)benzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 330 | 2-((4-(benzylsulfonyl)-2-chlorophenyl)thio)-6-(4-(2-(dimethylamino)ethyl)piperazin-1-yl)-5-methoxy-N-(5-methyl-1H-pyrazol-3-yl)pyrimidin-4-amine |
| 331 | 2-((4-(benzylsulfonyl)phenyl)thio)-5-methoxy-N-(5-methyl-1H-pyrazol-3-yl)-6-(4-(piperidin-4-yl)piperazin-1-yl)pyrimidin-4-amine |
| 332 | 6-(4-(2-(8-azabicyclo[3.2.1]octan-8-yl)ethyl)piperidin-1-yl)-2-((4-(benzylsulfonyl)phenyl)thio)-5-methoxy-N-(5-methyl-1H-pyrazol-3-yl)pyrimidin-4-amine |
| 333 | 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)-6-nitrobenzonitrile |
| 334 | 1-(2-((4-((2-fluoro-3-nitrobenzyl)sulfonyl)phenyl)thio)-5-methoxy-6-((5-methyl-1H-pyrazol-3-yl)amino)pyrimidin-4-yl)piperidin-4-ol |
| 335 | (S)-2-((2-fluoro-4-((3-nitrobenzyl)sulfonyl)phenyl)thio)-5-methoxy-N-(5-methyl-1H-pyrazol-3-yl)-6-(3-methylmorpholino)pyrimidin-4-amine |
| 336 | 2-((2-fluoro-4-((2-fluoro-3-nitrobenzyl)sulfonyl)phenyl)thio)-5-methoxy-N-(5-methyl-1H-pyrazol-3-yl)-6-morpholinopyrimidin-4-amine |
| 337 | 2-((2-fluoro-4-((3-nitrobenzyl)sulfonyl)phenyl)thio)-5-methoxy-N-(5-methyl-1H-pyrazol-3-yl)-6-morpholinopyrimidin-4-amine |
| 338 | 2-((4-((2-chloro-3-nitrobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 339 | 2-((4-((2-fluoro-3-nitrobenzyl)sulfonyl)phenyl)thio)-5-methoxy-N-(5-methyl-1H-pyrazol-3-yl)-6-(piperidin-1-yl)pyrimidin-4-amine |
| 340 | 2-((4-((2-fluoro-3-nitrobenzyl)sulfonyl)phenyl)thio)-5-methoxy-N-(5-methyl-1H-pyrazol-3-yl)-6-morpholinopyrimidin-4-amine |
| 341 | 6-(4-(2-(dimethylamino)ethyl)piperazin-1-yl)-2-((2-fluoro-4-((2-fluoro-3-nitrobenzyl)sulfonyl)phenyl)thio)-5-methoxy-N-(5-methyl-1H-pyrazol-3-yl)pyrimidin-4-amine |
| 342 | 6-(4-(2-(dimethylamino)ethyl)piperazin-1-yl)-2-((2-fluoro-4-((3-nitrobenzyl)sulfonyl)phenyl)thio)-5-methoxy-N-(5-methyl-1H-pyrazol-3-yl)pyrimidin-4-amine |
| 343 | 6-(4-(2-(dimethylamino)ethyl)piperazin-1-yl)-2-((4-((2-fluoro-5-nitrobenzyl)sulfonyl)phenyl)thio)-5-methoxy-N-(5-methyl-1H-pyrazol-3-yl)pyrimidin-4-amine |
| 344 | 6-(4-(2-(dimethylamino)ethyl)piperazin-1-yl)-2-((4-((3-fluoro-5-nitrobenzyl)sulfonyl)phenyl)thio)-5-methoxy-N-(5-methyl-1H-pyrazol-3-yl)pyrimidin-4-amine |
| 345 | 6-(4-(2-(dimethylamino)ethyl)piperazin-1-yl)-5-methoxy-2-((4-((2-methoxy-3-nitrobenzyl)sulfonyl)phenyl)thio)-N-(5-methyl-1H-pyrazol-3-yl)pyrimidin-4-amine |
| 346 | 6-(4-(2-(dimethylamino)ethyl)piperazin-1-yl)-5-methoxy-2-((4-((2-methoxy-5-nitrobenzyl)sulfonyl)phenyl)thio)-N-(5-methyl-1H-pyrazol-3-yl)pyrimidin-4-amine |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 347 | 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)-6-nitrophenol |
| 348 | (R)-2-((2-fluoro-4-((2-fluoro-3-nitrobenzyl)sulfonyl)phenyl)thio)-5-methoxy-N-(5-methyl-1H-pyrazol-3-yl)-6-(3-methylmorpholino)pyrimidin-4-amine |
| 349 | (R)-2-((2-fluoro-4-((3-nitrobenzyl)sulfonyl)phenyl)thio)-5-methoxy-N-(5-methyl-1H-pyrazol-3-yl)-6-(3-methylmorpholino)pyrimidin-4-amine |
| 350 | (S)-2-((2-chloro-4-(ethylsulfonyl)phenyl)thio)-5-methoxy-N-(5-methyl-1H-pyrazol-3-yl)-6-(3-methylmorpholino)pyrimidin-4-amine |
| 351 | 2-((2-chloro-4-(ethylsulfonyl)phenyl)thio)-5-methoxy-N-(5-methyl-1H-pyrazol-3-yl)-6-(4-methylpiperazin-1-yl)pyrimidin-4-amine |
| 352 | 2-((2-chloro-4-(ethylsulfonyl)phenyl)thio)-5-methoxy-N-(5-methyl-1H-pyrazol-3-yl)-6-morpholinopyrimidin-4-amine |
| 353 | 2-((2-chloro-4-(ethylsulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 354 | 2-((2-chloro-4-(ethylsulfonyl)phenyl)thio)-6-(4-(2-(dimethylamino)ethyl)piperidin-1-yl)-5-methoxy-N-(5-methyl-1H-pyrazol-3-yl)pyrimidin-4-amine |
| 355 | 2-((2-chloro-4-(methylsulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 356 | 2-((2-chloro-4-(methylsulfonyl)phenyl)thio)-6-(4-(2-(dimethylamino)ethyl)piperidin-1-yl)-5-methoxy-N-(5-methyl-1H-pyrazol-3-yl)pyrimidin-4-amine |
| 357 | 6-(3-oxa-8-azabicyclo[3.2.1]octan-8-yl)-5-methoxy-N-(5-methyl-1H-pyrazol-3-yl)-2-((4-((3-nitrobenzyl)sulfonyl)phenyl)thio)pyrimidin-4-amine |
| 358 | 6-(4-(2-(dimethylamino)ethyl)piperazin-1-yl)-2-((2-fluoro-4-(methylsulfonyl)phenyl)thio)-5-methoxy-N-(5-methyl-1H-pyrazol-3-yl)pyrimidin-4-amine |
| 359 | 6-(4-(2-(dimethylamino)ethyl)piperazin-1-yl)-2-((4-(ethylsulfonyl)-2-fluorophenyl)thio)-5-methoxy-N-(5-methyl-1H-pyrazol-3-yl)pyrimidin-4-amine |
| 360 | 6-(4-(2-(dimethylamino)ethyl)piperidin-1-yl)-2-((2-fluoro-4-(methylsulfonyl)phenyl)thio)-5-methoxy-N-(5-methyl-1H-pyrazol-3-yl)pyrimidin-4-amine |
| 361 | 6-(4-(2-(dimethylamino)ethyl)piperidin-1-yl)-2-((4-(ethylsulfonyl)-2-fluorophenyl)thio)-5-methoxy-N-(5-methyl-1H-pyrazol-3-yl)pyrimidin-4-amine |
| 362 | 6-(4-(2-(dimethylamino)ethyl)piperazin-1-yl)-5-methoxy-N-(5-methyl-1H-pyrazol-3-yl)-2-((4-((2-(pyrazin-2-yl)propan-2-yl)sulfonyl)phenyl)thio)pyrimidin-4-amine |
| 363 | (R)-(4-(5-methoxy-6-((5-methyl-1H-pyrazol-3-yl)amino)-2-((4-((3-nitrobenzyl)sulfonyl)phenyl)thio)pyrimidin-4-yl)morpholin-3-yl)methanol |
| 364 | (R)-2-((2-chloro-4-(ethylsulfonyl)phenyl)thio)-5-methoxy-N-(5-methyl-1H-pyrazol-3-yl)-6-(3-methylmorpholino)pyrimidin-4-amine |
| 365 | (R)-2-((4-((2-fluoro-3-nitrobenzyl)sulfonyl)phenyl)thio)-5-methoxy-N-(5-methyl-1H-pyrazol-3-yl)-6-(3-methylmorpholino)pyrimidin-4-amine |
| 366 | (R)-6-(3-ethylmorpholino)-5-methoxy-N-(5-methyl-1H-pyrazol-3-yl)-2-((4-((3-nitrobenzyl)sulfonyl)phenyl)thio)pyrimidin-4-amine |
| 367 | (S)-2-((4-((2-fluoro-3-nitrobenzyl)sulfonyl)phenyl)thio)-5-methoxy-N-(5-methyl-1H-pyrazol-3-yl)-6-(3-methylmorpholino)pyrimidin-4-amine |
| 368 | (S)-2-((4-(ethylsulfonyl)-2-fluorophenyl)thio)-5-methoxy-N-(5-methyl-1H-pyrazol-3-yl)-6-(3-methylmorpholino)pyrimidin-4-amine |
| 369 | 2-((2-chloro-4-(ethylsulfonyl)phenyl)thio)-5-methoxy-N-(5-methyl-1H-pyrazol-3-yl)-6-(piperidin-1-yl)pyrimidin-4-amine |
| 370 | 2-((2-fluoro-4-(methylsulfonyl)phenyl)thio)-5-methoxy-N-(5-methyl-1H-pyrazol-3-yl)-6-(piperidin-1-yl)pyrimidin-4-amine |
| 371 | 2-((2-fluoro-4-(methylsulfonyl)phenyl)thio)-5-methoxy-N-(5-methyl-1H-pyrazol-3-yl)-6-morpholinopyrimidin-4-amine |
| 372 | 2-((4-((2,3-difluorobenzyl)sulfonyl)phenyl)thio)-5-methoxy-N-(5-methyl-1H-pyrazol-3-yl)-6-(piperidin-1-yl)pyrimidin-4-amine |
| 373 | 2-((4-(ethylsulfonyl)-2-fluorophenyl)thio)-5-methoxy-N-(5-methyl-1H-pyrazol-3-yl)-6-(piperidin-1-yl)pyrimidin-4-amine |
| 374 | 2-((4-(ethylsulfonyl)-2-fluorophenyl)thio)-5-methoxy-N-(5-methyl-1H-pyrazol-3-yl)-6-morpholinopyrimidin-4-amine |
| 375 | 5-methoxy-N-(5-methyl-1H-pyrazol-3-yl)-2-((4-(methylsulfonyl)phenyl)thio)-6-(piperidin-1-yl)pyrimidin-4-amine |
| 376 | 6-(3-ethylmorpholino)-5-methoxy-N-(5-methyl-1H-pyrazol-3-yl)-2-((4-((3-nitrobenzyl)sulfonyl)phenyl)thio)pyrimidin-4-amine |
| 377 | 1-(2-((2-fluoro-4-((1-(2-fluoro-3-nitrophenyl)cyclopropyl)sulfonyl)phenyl)thio)-5-methoxy-6-((5-methyl-1H-pyrazol-3-yl)amino)pyrimidin-4-yl)-N,N-dimethylpiperidine-4-carboxamide compound |
| 378 | 1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)-N,N-dimethylpiperidine-4-carboxamide |
| 379 | 1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidine-4-carboxamide |
| 380 | 2,2,2-trifluoro-N-(1-(2-((2-fluoro-4-((1-(2-fluoro-3-nitrophenyl)cyclopropyl)sulfonyl)phenyl)thio)-5-methoxy-6-((5-methyl-1H-pyrazol-3-yl)amino)pyrimidin-4-yl)piperidin-4-yl)acetamide |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 381 | 2,2,2-trifluoro-N-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)acetamide |
| 382 | 2,2,2-trifluoro-N-(2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)ethyl)acetamide |
| 383 | 2-(1-(2-((2-fluoro-4-((1-(2-fluoro-3-nitrophenyl)cyclopropyl)sulfonyl)phenyl)thio)-5-methoxy-6-((5-methyl-1H-pyrazol-3-yl)amino)pyrimidin-4-yl)piperidin-4-yl)acetamide |
| 384 | 2-(1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidin-4-yl)acetamide |
| 385 | 2-(1-(2-((2-fluoro-4-((2-fluoro-3-nitrobenzyl)sulfonyl)phenyl)thio)-5-methoxy-6-((5-methyl-1H-pyrazol-3-yl)amino)pyrimidin-4-yl)piperidin-4-yl)acetamide |
| 386 | N-(1-(2-((2-fluoro-4-((1-(2-fluoro-3-nitrophenyl)cyclopropyl)sulfonyl)phenyl)thio)-5-methoxy-6-((5-methyl-1H-pyrazol-3-yl)amino)pyrimidin-4-yl)piperidin-4-yl)acetamide |
| 387 | N-(1-(2-((2-fluoro-4-((2-fluoro-3-nitrobenzyl)sulfonyl)phenyl)thio)-5-methoxy-6-((5-methyl-1H-pyrazol-3-yl)amino)pyrimidin-4-yl)piperidin-4-yl)acetamide |
| 388 | N-(2-(1-(2-((2-fluoro-4-((1-(2-fluoro-3-nitrophenyl)cyclopropyl)sulfonyl)phenyl)thio)-5-methoxy-6-((5-methyl-1H-pyrazol-3-yl)amino)pyrimidin-4-yl)piperidin-4-yl)ethyl)acetamide |
| 389 | N-(2-(1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidin-4-yl)ethyl)acetamide |
| 390 | N-(2-(1-(2-((2-fluoro-4-((2-fluoro-3-nitrobenzyl)sulfonyl)phenyl)thio)-5-methoxy-6-((5-methyl-1H-pyrazol-3-yl)amino)pyrimidin-4-yl)piperidin-4-yl)ethyl)acetamide |
| 391 | 1-(4-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperazin-1-yl)ethan-1-one |
| 392 | 1-(4-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperazin-1-yl)ethan-1-one |
| 393 | 2-((2-fluoro-4-((1-(2,3,5,6-tetrafluorophenyl)cyclopropyl)sulfonyl)phenyl)thio)-5-methoxy-N-(5-methyl-1H-pyrazol-3-yl)-6-morpholinopyrimidin-4-amine |
| 394 | 2-((2-fluoro-4-((1-(2-fluoro-3-nitrophenyl)cyclopropyl)sulfonyl)phenyl)thio)-5-methoxy-N-(5-methyl-1H-pyrazol-3-yl)-6-(piperazin-1-yl)pyrimidin-4-amine |
| 395 | 2-((2-fluoro-4-((1-(2-fluoro-3-nitrophenyl)cyclopropyl)sulfonyl)phenyl)thio)-5-methoxy-N-(5-methyl-1H-pyrazol-3-yl)-6-morpholinopyrimidin-4-amine |
| 396 | 2-((2-fluoro-4-((2-(2,3,5,6-tetrafluorophenyl)propan-2-yl)sulfonyl)phenyl)thio)-5-methoxy-N-(5-methyl-1H-pyrazol-3-yl)-6-(piperazin-1-yl)pyrimidin-4-amine |
| 397 | 2-((4-((2-(1H-imidazol-2-yl)propan-2-yl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 398 | 6-(3-aminopyrrolidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 399 | 6-(3-aminopyrrolidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 400 | 6-(4-(2-(dimethylamino)ethyl)piperazin-1-yl)-2-((2-fluoro-4-((1-(2-fluoro-3-nitrophenyl)cyclopropyl)sulfonyl)phenyl)thio)-5-methoxy-N-(5-methyl-1H-pyrazol-3-yl)pyrimidin-4-amine |
| 401 | 6-(4-(2-(dimethylamino)ethyl)piperidin-1-yl)-2-((2-fluoro-4-((1-(2-fluoro-3-nitrophenyl)cyclopropyl)sulfonyl)phenyl)thio)-5-methoxy-N-(5-methyl-1H-pyrazol-3-yl)pyrimidin-4-amine |
| 402 | 6-(4-(2-aminoethyl)piperidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 403 | 6-(4-(aminomethyl)piperidin-1-yl)-2-((2-fluoro-4-((1-(2-fluoro-3-nitrophenyl)cyclopropyl)sulfonyl)phenyl)thio)-5-methoxy-N-(5-methyl-1H-pyrazol-3-yl)pyrimidin-4-amine |
| 404 | 6-(4-(aminomethyl)piperidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 405 | 6-(4-(aminomethyl)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 406 | 6-(4-aminopiperidin-1-yl)-2-((2-fluoro-4-((1-(2-fluoro-3-nitrophenyl)cyclopropyl)sulfonyl)phenyl)thio)-5-methoxy-N-(5-methyl-1H-pyrazol-3-yl)pyrimidin-4-amine |
| 407 | 6-(4-aminopiperidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 408 | 6-(4-aminopiperidin-1-yl)-2-((2-fluoro-4-((2-fluoro-3-nitrobenzyl)sulfonyl)phenyl)thio)-5-methoxy-N-(5-methyl-1H-pyrazol-3-yl)pyrimidin-4-amine |
| 409 | 6-(4-(2-(dimethylamino)ethyl)piperazin-1-yl)-5-methoxy-N-(5-methyl-1H-pyrazol-3-yl)-2-((4-((2,3,6-trifluorobenzyl)sulfonyl)phenyl)thio)pyrimidin-4-amine |
| 410 | 2-fluoro-3-(((3-fluoro-4-((5-methoxy-4-((5-methyl-1H-pyrazol-3-yl)amino)-6-morpholinopyrimidin-2-yl)thio)phenyl)sulfonyl)methyl)benzonitrile |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 411 | (S)-(4-(5-methoxy-6-((5-methyl-1H-pyrazol-3-yl)amino)-2-((4-((3-nitrobenzyl)sulfonyl)phenyl)thio)pyrimidin-4-yl)morpholin-3-yl)methanol |
| 412 | (S)-2-((2-fluoro-4-((2-fluoro-3-nitrobenzyl)sulfonyl)phenyl)thio)-5-methoxy-N-(5-methyl-1H-pyrazol-3-yl)-6-(3-methylmorpholino)pyrimidin-4-amine |
| 413 | (S)-2-((2-fluoro-4-(methylsulfonyl)phenyl)thio)-5-methoxy-N-(5-methyl-1H-pyrazol-3-yl)-6-(3-methylmorpholino)pyrimidin-4-amine |
| 414 | (S)-2-((4-((2,3-difluorobenzyl)sulfonyl)-2-fluorophenyl)thio)-5-methoxy-N-(5-methyl-1H-pyrazol-3-yl)-6-(3-methylmorpholino)pyrimidin-4-amine |
| 415 | 2-((2-fluoro-4-((2,3,5,6-tetrafluorobenzyl)sulfonyl)phenyl)thio)-5-methoxy-N-(5-methyl-1H-pyrazol-3-yl)-6-morpholinopyrimidin-4-amine |
| 416 | 2-((2-fluoro-4-((2-fluoro-3-(trifluoromethyl)benzyl)sulfonyl)phenyl)thio)-5-methoxy-N-(5-methyl-1H-pyrazol-3-yl)-6-morpholinopyrimidin-4-amine |
| 417 | 2-((2-fluoro-4-((2-fluoro-3-nitrobenzyl)sulfonyl)phenyl)thio)-5-methoxy-N-(5-methyl-1H-pyrazol-3-yl)-6-(piperidin-1-yl)pyrimidin-4-amine |
| 418 | 2-((4-((2,3-difluorobenzyl)sulfonyl)-2-fluorophenyl)thio)-5-methoxy-N-(5-methyl-1H-pyrazol-3-yl)-6-(piperidin-1-yl)pyrimidin-4-amine |
| 419 | 2-((4-((2,3-difluorobenzyl)sulfonyl)-2-fluorophenyl)thio)-5-methoxy-N-(5-methyl-1H-pyrazol-3-yl)-6-morpholinopyrimidin-4-amine |
| 420 | 2-((4-((2,3-difluorobenzyl)sulfonyl)-2-fluorophenyl)thio)-6-(4-(2-(dimethylamino)ethyl)piperazin-1-yl)-5-methoxy-N-(5-methyl-1H-pyrazol-3-yl)pyrimidin-4-amine |
| 421 | 2-((4-((3-bromo-2-fluorobenzyl)sulfonyl)-2-fluorophenyl)thio)-5-methoxy-N-(5-methyl-1H-pyrazol-3-yl)-6-morpholinopyrimidin-4-amine |
| 422 | 2-((4-((3-chloro-2-fluorobenzyl)sulfonyl)-2-fluorophenyl)thio)-5-methoxy-N-(5-methyl-1H-pyrazol-3-yl)-6-morpholinopyrimidin-4-amine |
| 423 | 6-(4-(2-(dimethylamino)ethyl)piperazin-1-yl)-2-((2-fluoro-4-((2,3,6-trifluorobenzyl)sulfonyl)phenyl)thio)-5-methoxy-N-(5-methyl-1H-pyrazol-3-yl)pyrimidin-4-amine |
| 424 | methyl 2-fluoro-3-(((3-fluoro-4-((5-methoxy-4-((5-methyl-1H-pyrazol-3-yl)amino)-6-morpholinopyrimidin-2-yl)thio)phenyl)sulfonyl)methyl)benzoate |
| 425 | 2-fluoro-3-(((3-fluoro-4-((5-methoxy-4-((5-methyl-1H-pyrazol-3-yl)amino)-6-morpholinopyrimidin-2-yl)thio)phenyl)sulfonyl)methyl)-N,N-dimethylbenzamide |
| 426 | 2-fluoro-3-(((3-fluoro-4-((5-methoxy-4-((5-methyl-1H-pyrazol-3-yl)amino)-6-morpholinopyrimidin-2-yl)thio)phenyl)sulfonyl)methyl)benzamide |
| 427 | 3-fluoro-N-(2-fluoro-3-nitrophenyl)-4-((5-methoxy-4-((5-methyl-1H-pyrazol-3-yl)amino)-6-morpholinopyrimidin-2-yl)thio)benzamide |
| 428 | (S)-(4-(2-((2-fluoro-4-((2-fluoro-3-nitrobenzyl)sulfonyl)phenyl)thio)-5-methoxy-6-((5-methyl-1H-pyrazol-3-yl)amino)pyrimidin-4-yl)morpholin-3-yl)methanol |
| 429 | (E)-2-((2-fluoro-4-(2-fluoro-3-nitrostyryl)phenyl)thio)-5-methoxy-N-(5-methyl-1H-pyrazol-3-yl)-6-morpholinopyrimidin-4-amine |
| 430 | 2-((2-fluoro-4-((2-fluoro-3-iodobenzyl)sulfonyl)phenyl)thio)-5-methoxy-N-(5-methyl-1H-pyrazol-3-yl)-6-morpholinopyrimidin-4-amine |
| 431 | 2-((2-fluoro-4-((2-fluoro-3-nitrophenyl)ethynyl)phenyl)thio)-5-methoxy-N-(5-methyl-1H-pyrazol-3-yl)-6-morpholinopyrimidin-4-amine |
| 432 | 2-((2-fluoro-4-((3-nitrophenyl)sulfonyl)phenyl)thio)-5-methoxy-N-(5-methyl-1H-pyrazol-3-yl)-6-morpholinopyrimidin-4-amine |
| 433 | 2-((2-fluoro-4-((fluoro(2-fluoro-3-nitrophenyl)methyl)sulfonyl)phenyl)thio)-5-methoxy-N-(5-methyl-1H-pyrazol-3-yl)-6-morpholinopyrimidin-4-amine |
| 434 | 2-((2-fluoro-4-(2-fluoro-3-nitrophenethyl)phenyl)thio)-5-methoxy-N-(5-methyl-1H-pyrazol-3-yl)-6-morpholinopyrimidin-4-amine |
| 435 | 2-((4-((3-amino-2-fluorobenzyl)sulfonyl)-2-fluorophenyl)thio)-5-methoxy-N-(5-methyl-1H-pyrazol-3-yl)-6-morpholinopyrimidin-4-amine |
| 436 | 2-((4-((3-bromo-2-fluorobenzyl)sulfonyl)-2-fluorophenyl)thio)-5-methoxy-N-(5-methyl-1H-pyrazol-3-yl)-6-(piperidin-1-yl)pyrimidin-4-amine |
| 437 | 6-(4-(2-(dimethylamino)ethyl)piperazin-1-yl)-2-((2-fluoro-4-((fluoro(2-fluoro-3-nitrophenyl)methyl)sulfonyl)phenyl)thio)-5-methoxy-N-(5-methyl-1H-pyrazol-3-yl)pyrimidin-4-amine |
| 438 | 2-fluoro-3-nitrophenyl 3-fluoro-4-((5-methoxy-4-((5-methyl-1H-pyrazol-3-yl)amino)-6-morpholinopyrimidin-2-yl)thio)benzoate |
| 439 | 2-(2-fluoro-3-nitrophenyl)-N-(3-fluoro-4-((5-methoxy-4-((5-methyl-1H-pyrazol-3-yl)amino)-6-morpholinopyrimidin-2-yl)thio)phenyl)acetamide |
| 440 | 2-fluoro-N-(3-fluoro-4-((5-methoxy-4-((5-methyl-1H-pyrazol-3-yl)amino)-6-morpholinopyrimidin-2-yl)thio)phenyl)-3-nitrobenzamide |
| 441 | 3-fluoro-4-((5-methoxy-4-((5-methyl-1H-pyrazol-3-yl)amino)-6-morpholinopyrimidin-2-yl)thio)-N-(3-nitrophenyl)benzenesulfonamide |
| 442 | 2-fluoro-3-(((3-fluoro-4-((5-methoxy-4-((5-methyl-1H-pyrazol-3-yl)amino)-6-(piperidin-1-yl)pyrimidin-2-yl)thio)phenyl)sulfonyl)methyl)benzonitrile |
| 443 | 2-fluoro-3-(fluoro((3-fluoro-4-((5-methoxy-4-((5-methyl-1H-pyrazol-3-yl)amino)-6-morpholinopyrimidin-2-yl)thio)phenyl)sulfonyl)methyl)benzonitrile |
| 444 | 3-(((4-((4-(2-(dimethylamino)ethyl)piperazin-1-yl)-5-methoxy-6-((5-methyl-1H-pyrazol-3-yl)amino)pyrimidin-2-yl)thio)-3-fluorophenyl)sulfonyl)methyl)-2-fluorobenzonitrile |
| 445 | 2-(2-fluoro-3-nitrophenyl)-1-(3-fluoro-4-((5-methoxy-4-((5-methyl-1H-pyrazol-3-yl)amino)-6-morpholinopyrimidin-2-yl)thio)phenyl)ethan-1-one |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 446 | ((3S)-4-(2-((2-fluoro-4-((fluoro(2-fluoro-3-nitrophenyl)methyl)sulfonyl)phenyl)thio)-5-methoxy-6-((5-methyl-1H-pyrazol-3-yl)amino)pyrimidin-4-yl)morpholin-3-yl)methanol |
| 447 | (R)-(1-(2-((2-fluoro-4-((2-fluoro-3-nitrobenzyl)sulfonyl)phenyl)thio)-5-methoxy-6-((5-methyl-1H-pyrazol-3-yl)amino)pyrimidin-4-yl)piperidin-2-yl)methanol |
| 448 | 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-(piperidin-1-yl)pyrimidin-4-amine |
| 449 | 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-morpholinopyrimidin-4-amine |
| 450 | 2-((2-fluoro-4-(7-nitrobenzofuran-2-yl)phenyl)thio)-5-methoxy-N-(5-methyl-1H-pyrazol-3-yl)-6-morpholinopyrimidin-4-amine |
| 451 | 6-(4-(2-(dimethylamino)ethyl)piperazin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 452 | 6-(4-(2-(dimethylamino)ethyl)piperidin-1-yl)-2-((2-fluoro-4-((2-fluoro-3-nitrobenzyl)sulfonyl)phenyl)thio)-5-methoxy-N-(5-methyl-1H-pyrazol-3-yl)pyrimidin-4-amine |
| 453 | 6-(4-(2-(dimethylamino)ethyl)piperidin-1-yl)-2-((2-fluoro-4-((fluoro(2-fluoro-3-nitrophenyl)methyl)sulfonyl)phenyl)thio)-5-methoxy-N-(5-methyl-1H-pyrazol-3-yl)pyrimidin-4-amine |
| 454 | (S)-(4-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)morpholin-3-yl)methanol |
| 455 | 2-((2-fluoro-4-((2-(2,3,5,6-tetrafluoro-4-methylphenyl)propan-2-yl)sulfonyl)phenyl)thio)-5-methoxy-N-(5-methyl-1H-pyrazol-3-yl)-6-morpholinopyrimidin-4-amine |
| 456 | 2-((2-fluoro-4-((2-(2,3,5,6-tetrafluorophenyl)propan-2-yl)sulfonyl)phenyl)thio)-5-methoxy-N-(5-methyl-1H-pyrazol-3-yl)-6-morpholinopyrimidin-4-amine |
| 457 | 2-((2-fluoro-4-((2-fluoro-3-nitrophenethyl)sulfonyl)phenyl)thio)-5-methoxy-N-(5-methyl-1H-pyrazol-3-yl)-6-morpholinopyrimidin-4-amine |
| 458 | 2-((2-fluoro-4-((fluoro(2,3,5,6-tetrafluorophenyl)methyl)sulfonyl)phenyl)thio)-5-methoxy-N-(5-methyl-1H-pyrazol-3-yl)-6-morpholinopyrimidin-4-amine |
| 459 | 2-((4-((2-(2,5-difluoro-3-nitrophenyl)propan-2-yl)sulfonyl)-2-fluorophenyl)thio)-5-methoxy-N-(5-methyl-1H-pyrazol-3-yl)-6-morpholinopyrimidin-4-amine |
| 460 | 2-((4-((2-(3-bromo-2-fluorophenyl)propan-2-yl)sulfonyl)-2-fluorophenyl)thio)-5-methoxy-N-(5-methyl-1H-pyrazol-3-yl)-6-morpholinopyrimidin-4-amine |
| 461 | 2-((4-((2-(3-bromo-2-fluorophenyl)propan-2-yl)sulfonyl)-2-fluorophenyl)thio)-6-(4-(2-(dimethylamino)ethyl)piperazin-1-yl)-5-methoxy-N-(5-methyl-1H-pyrazol-3-yl)pyrimidin-4-amine |
| 462 | 2-((4-((2-(3-chloro-2,5-difluorophenyl)propan-2-yl)sulfonyl)-2-fluorophenyl)thio)-5-methoxy-N-(5-methyl-1H-pyrazol-3-yl)-6-morpholinopyrimidin-4-amine |
| 463 | 2-((4-((2-(3-chloro-2-fluorophenyl)propan-2-yl)sulfonyl)-2-fluorophenyl)thio)-5-methoxy-N-(5-methyl-1H-pyrazol-3-yl)-6-morpholinopyrimidin-4-amine |
| 464 | 2-((4-((2-(3-chloro-2-fluorophenyl)propan-2-yl)sulfonyl)-2-fluorophenyl)thio)-6-(4-(2-(dimethylamino)ethyl)piperazin-1-yl)-5-methoxy-N-(5-methyl-1H-pyrazol-3-yl)pyrimidin-4-amine |
| 465 | 2-((4-((difluoro(2,3,5,6-tetrafluorophenyl)methyl)sulfonyl)-2-fluorophenyl)thio)-5-methoxy-N-(5-methyl-1H-pyrazol-3-yl)-6-morpholinopyrimidin-4-amine |
| 466 | 6-(4-(2-(dimethylamino)ethyl)piperazin-1-yl)-2-((2-fluoro-4-((2-(2,3,5,6-tetrafluoro-4-methylphenyl)propan-2-yl)sulfonyl)phenyl)thio)-5-methoxy-N-(5-methyl-1H-pyrazol-3-yl)pyrimidin-4-amine |
| 467 | 6-(4-(2-(dimethylamino)ethyl)piperazin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 468 | 6-(4-(2-(dimethylamino)ethyl)piperazin-1-yl)-2-((2-fluoro-4-((fluoro(2,3,5,6-tetrafluorophenyl)methyl)sulfonyl)phenyl)thio)-5-methoxy-N-(5-methyl-1H-pyrazol-3-yl)pyrimidin-4-amine |
| 469 | 6-(4-(2-(dimethylamino)ethyl)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 470 | 2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)-N,N-dimethylacetamide |
| 471 | N-(2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)ethyl)acetamide |
| 472 | 2-((2-fluoro-4-((2-(2-fluoro-3-nitrophenyl)propan-2-yl)sulfonyl)phenyl)thio)-5-methoxy-6-(4-(2-((4-methoxybenzyl)(methyl)amino)ethyl)piperidin-1-yl)-N-(5-methyl-1H-pyrazol-3-yl)pyrimidin-4-amine |
| 473 | 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-(4-methylpiperazin-1-yl)pyrimidin-4-amine |
| 474 | 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-(piperazin-1-yl)pyrimidin-4-amine |
| 475 | 2-((2-fluoro-4-((2-(2-fluoro-3-nitrophenyl)propan-2-yl)sulfonyl)phenyl)thio)-5-methoxy-$N^4$,$N^4$-dimethyl-$N^6$-(5-methyl-1H-pyrazol-3-yl)pyrimidine-4,6-diamine |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 476 | 2-((4-((2-(2,5-difluoro-3-nitrophenyl)propan-2-yl)sulfonyl)-2-fluorophenyl)thio)-6-(4-(2-(dimethylamino)ethyl)piperidin-1-yl)-5-methoxy-N-(5-methyl-1H-pyrazol-3-yl)pyrimidin-4-amine |
| 477 | 2-((4-((2-(3-chloro-2,5-difluorophenyl)propan-2-yl)sulfonyl)-2-fluorophenyl)thio)-6-(4-(2-(dimethylamino)ethyl)piperidin-1-yl)-5-methoxy-N-(5-methyl-1H-pyrazol-3-yl)pyrimidin-4-amine |
| 478 | 2-((4-((2-(3-chloro-2-fluorophenyl)propan-2-yl)sulfonyl)-2-fluorophenyl)thio)-6-(4-(2-(dimethylamino)ethyl)piperidin-1-yl)-5-methoxy-N-(5-methyl-1H-pyrazol-3-yl)pyrimidin-4-amine |
| 479 | 2-((4-((3-chloro-2,5,6-trifluorobenzyl)sulfonyl)-2-fluorophenyl)thio)-5-methoxy-N-(5-methyl-1H-pyrazol-3-yl)-6-morpholinopyrimidin-4-amine |
| 480 | 6-(3-(dimethylamino)piperidin-1-yl)-2-((2-fluoro-4-(2-((2-fluoro-3-nitrophenyl)propan-2-yl)sulfonyl)phenyl)thio)-5-methoxy-N-(5-methyl-1H-pyrazol-3-yl)pyrimidin-4-amine |
| 481 | 6-(4-((dimethylamino)methyl)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 482 | 6-(4-(2-(dimethylamino)ethyl)piperidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 483 | 6-(4-(3-(dimethylamino)propyl)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 484 | 6-(4-(dimethylamino)piperidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 485 | 6-(4-(dimethylamino)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 486 | 2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)acetic acid |
| 487 | methyl 2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)acetate |
| 488 | 2-(dimethylamino)-1-(4-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperazin-1-yl)ethan-1-one |
| 489 | 2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)ethan-1-ol |
| 490 | 2-((2-fluoro-4-(((perfluorophenyl)methyl)sulfonyl)phenyl)thio)-5-methoxy-N-(5-methyl-1H-pyrazol-3-yl)-6-morpholinopyrimidin-4-amine |
| 491 | 2-((2-fluoro-4-((2-(2-fluoro-3-nitrophenyl)propan-2-yl)sulfonyl)phenyl)thio)-5-methoxy-6-(3-methoxypyrrolidin-1-yl)-N-(5-methyl-1H-pyrazol-3-yl)pyrimidin-4-amine |
| 492 | 2-((2-fluoro-4-((2-(2-fluoro-3-nitrophenyl)propan-2-yl)sulfonyl)phenyl)thio)-5-methoxy-6-(4-(2-methoxyethyl)piperidin-1-yl)-N-(5-methyl-1H-pyrazol-3-yl)pyrimidin-4-amine |
| 493 | 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-(4-(2-(methylamino)ethyl)piperidin-1-yl)pyrimidin-4-amine |
| 494 | 2-((2-fluoro-4-((2-(perfluorophenyl)propan-2-yl)sulfonyl)phenyl)thio)-5-methoxy-N-(5-methyl-1H-pyrazol-3-yl)-6-morpholinopyrimidin-4-amine |
| 495 | 2-((4-((2-(3-chloro-2,5,6-trifluorophenyl)propan-2-yl)sulfonyl)-2-fluorophenyl)thio)-5-methoxy-N-(5-methyl-1H-pyrazol-3-yl)-6-morpholinopyrimidin-4-amine |
| 496 | 2-((4-((3-chloro-2,5,6-trifluorobenzyl)sulfonyl)-2-fluorophenyl)thio)-6-(4-(2-(dimethylamino)ethyl)piperazin-1-yl)-5-methoxy-N-(5-methyl-1H-pyrazol-3-yl)pyrimidin-4-amine |
| 497 | 2-((4-((3-chloro-2,5,6-trifluorobenzyl)sulfonyl)-2-fluorophenyl)thio)-6-(4-(2-(dimethylamino)ethyl)piperidin-1-yl)-5-methoxy-N-(5-methyl-1H-pyrazol-3-yl)pyrimidin-4-amine |
| 498 | 6-(3-(dimethylamino)pyrrolidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 499 | 6-(4-(2-aminoethyl)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 500 | (S)-N-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)pyrrolidin-3-yl)acetamide |
| 501 | 2-(1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidin-4-yl)-N,N-dimethylacetamide |
| 502 | 2-(4-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperazin-1-yl)-N,N-dimethylacetamide |
| 503 | N-(1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidin-4-yl)acetamide |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 504 | N-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)acetamide |
| 505 | 1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)pyrrolidin-3-ol |
| 506 | (R)-6-(3-(dimethylamino)pyrrolidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 507 | (R)-6-(3-(dimethylamino)pyrrolidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 508 | (S)-6-(3-(dimethylamino)pyrrolidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 509 | (S)-6-(3-(dimethylamino)pyrrolidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 510 | 2-((4-(tert-butylsulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 511 | 6-(4-(2-(dimethylamino)ethyl)piperazin-1-yl)-2-((2-fluoro-4-((2-(perfluorophenyl)propan-2-yl)sulfonyl)phenyl)thio)-5-methoxy-N-(5-methyl-1H-pyrazol-3-yl)pyrimidin-4-amine |
| 512 | 6-(4-(2-(dimethylamino)ethyl)piperidin-1-yl)-2-((2-fluoro-4-((2-(perfluorophenyl)propan-2-yl)sulfonyl)phenyl)thio)-5-methoxy-N-(5-methyl-1H-pyrazol-3-yl)pyrimidin-4-amine |
| 513 | 6-(4-(dimethylamino)piperidin-1-yl)-2-((2-fluoro-4-((2-(perfluorophenyl)propan-2-yl)sulfonyl)phenyl)thio)-5-methoxy-N-(5-methyl-1H-pyrazol-3-yl)pyrimidin-4-amine |
| 514 | 1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidin-4-yl acetate |
| 515 | 1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)pyrrolidin-3-yl acetate |
| 516 | 1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)-N,N-dimethylpiperidine-4-carboxamide |
| 517 | 1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidine-4-carboxamide |
| 518 | N-(1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidin-4-yl)-N-methylacetamide |
| 519 | N-(1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)pyrrolidin-3-yl)acetamide |
| 520 | N-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)-N-methylacetamide |
| 521 | 1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidin-4-ol |
| 522 | 1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)pyrrolidin-3-ol |
| 523 | 2-((2-fluoro-4-((2-(2,3,5,6-tetrafluorophenyl)propan-2-yl)sulfonyl)phenyl)thio)-5-methoxy-6-(4-methoxypiperidin-1-yl)-N-(5-methyl-1H-pyrazol-3-yl)pyrimidin-4-amine |
| 524 | 2-((2-fluoro-4-((4-methoxybenzyl)sulfonyl)phenyl)thio)-5-methoxy-N-(5-methyl-1H-pyrazol-3-yl)-6-(piperidin-1-yl)pyrimidin-4-amine |
| 525 | 2-((2-fluoro-4-((4-methoxybenzyl)sulfonyl)phenyl)thio)-5-methoxy-N-(5-methyl-1H-pyrazol-3-yl)-6-morpholinopyrimidin-4-amine |
| 526 | 5-methoxy-2-((4-((4-methoxybenzyl)sulfonyl)phenyl)thio)-N-(5-methyl-1H-pyrazol-3-yl)-6-(piperidin-1-yl)pyrimidin-4-amine |
| 527 | 5-methoxy-2-((4-((4-methoxybenzyl)sulfonyl)phenyl)thio)-N-(5-methyl-1H-pyrazol-3-yl)-6-morpholinopyrimidin-4-amine |
| 528 | 6-(4-(2-(dimethylamino)ethyl)piperazin-1-yl)-2-((2-fluoro-4-((2-(2,3,6-trifluoro-5-nitrophenyl)propan-2-yl)sulfonyl)phenyl)thio)-5-methoxy-N-(5-methyl-1H-pyrazol-3-yl)pyrimidin-4-amine |
| 529 | 2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)-N-methylacetamide |
| 530 | 2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)acetamide |
| 531 | 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-(4-(2-((1,1,1-trifluoropropan-2-yl)amino)ethyl)piperidin-1-yl)pyrimidin-4-amine |
| 532 | 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-(4-(methylamino)piperidin-1-yl)pyrimidin-4-amine |
| 533 | 2-((2-fluoro-4-((2-fluoro-3-nitrobenzyl)sulfonyl)phenyl)thio)-5-methoxy-6-(piperidin-1-yl)-N-(1H-pyrazol-3-yl)pyrimidin-4-amine |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 534 | 2-((2-fluoro-4-((2-fluoro-3-nitrobenzyl)sulfonyl)phenyl)thio)-5-methoxy-6-morpholino-N-(1H-pyrazol-3-yl)pyrimidin-4-amine |
| 535 | 2-((2-fluoro-4-((2-fluoro-3-nitrobenzyl)sulfonyl)phenyl)thio)-5-methoxy-N-(5-methyl-1H-pyrazol-3-yl)-6-(4-methylpiperazin-1-yl)pyrimidin-4-amine |
| 536 | 2-((2-fluoro-4-((2-fluoro-3-nitrobenzyl)sulfonyl)phenyl)thio)-5-methoxy-N-(5-methyl-1H-pyrazol-3-yl)-6-(piperazin-1-yl)pyrimidin-4-amine |
| 537 | 2-((4-((2-cyclopropylpropan-2-yl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 538 | 6-(4-(2-(dimethylamino)ethyl)piperazin-1-yl)-5-methoxy-N-(5-methyl-1H-pyrazol-3-yl)-2-((4-((2-(pyridin-3-yl)propan-2-yl)sulfonyl)phenyl)thio)pyrimidin-4-amine |
| 539 | 6-(4-(2-(dimethylamino)ethyl)piperazin-1-yl)-5-methoxy-N-(5-methyl-1H-pyrazol-3-yl)-2-((4-((2-(thiophen-2-yl)propan-2-yl)sulfonyl)phenyl)thio)pyrimidin-4-amine |
| 540 | 6-(4-aminopiperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 541 | 1-(5-methyl-6-((5-methyl-1H-pyrazol-3-yl)amino)-2-(p-tolylthio)pyrimidin-4-yl)piperidin-4-ol |
| 542 | 2-((4-aminophenyl)thio)-5-methyl-N-(5-methyl-1H-pyrazol-3-yl)-6-morpholinopyrimidin-4-amine |
| 543 | 2-((4-aminophenyl)thio)-N$^4$-isopropyl-N$^4$,5-dimethyl-N$^6$-(5-methyl-1H-pyrazol-3-yl)pyrimidine-4,6-diamine |
| 544 | N$^4$-isopropyl-N$^4$,5-dimethyl-N$^6$-(5-methyl-1H-pyrazol-3-yl)-2-(methylthio)pyrimidine-4,6-diamine |
| 545 | N-(4-((4-((2-hydroxyethyl)(isopropyl)amino)-5-methyl-6-((5-methyl-1H-pyrazol-3-yl)amino)pyrimidin-2-yl)thio)phenyl)acetamide |
| 546 | N-(4-((4-(ethyl(isopropyl)amino)-5-methyl-6-((5-methyl-1H-pyrazol-3-yl)amino)pyrimidin-2-yl)thio)phenyl)acetamide |
| 547 | N-(4-((4-(isopropyl(2-methoxyethyl)amino)-5-methyl-6-((5-methyl-1H-pyrazol-3-yl)amino)pyrimidin-2-yl)thio)phenyl)acetamide |
| 548 | N-(4-((5-chloro-2-(4-hydroxypiperidin-1-yl)-6-((5-methyl-1H-pyrazol-3-yl)amino)pyrimidin-4-yl)thio)phenyl)acetamide |
| 549 | N-(4-((5-chloro-4-(4-hydroxypiperidin-1-yl)-6-((5-methyl-1H-pyrazol-3-yl)amino)pyrimidin-2-yl)thio)phenyl)acetamide |
| 550 | 2-methoxy-1-(4-(5-methyl-6-((5-methyl-1H-pyrazol-3-yl)amino)-2-(p-tolylthio)pyrimidin-4-yl)piperazin-1-yl)ethan-1-one |
| 551 | 5-methyl-N-(5-methyl-1H-pyrazol-3-yl)-6-morpholino-2-(p-tolylthio)pyrimidin-4-amine |
| 552 | N-(4-((4-(4-hydroxypiperidin-1-yl)-5-methoxy-6-((5-methyl-1H-pyrazol-3-yl)amino)pyrimidin-2-yl)thio)phenyl)cyclopropanecarboxamide |
| 553 | N-(4-((4-(4-hydroxypiperidin-1-yl)-5-methyl-6-((5-methyl-1H-pyrazol-3-yl)amino)pyrimidin-2-yl)thio)phenyl)cyclopropanecarboxamide |
| 554 | N-(4-((5-ethoxy-4-(4-hydroxypiperidin-1-yl)-6-((5-methyl-1H-pyrazol-3-yl)amino)pyrimidin-2-yl)thio)phenyl)acetamide |
| 555 | N-(4-((5-methyl-4-((5-methyl-1H-pyrazol-3-yl)amino)-6-(4-(2-morpholinoethyl)piperazin-1-yl)pyrimidin-2-yl)thio)phenyl)acetamide |
| 556 | 2-methoxy-1-(4-(5-methyl-6-((5-methyl-1H-pyrazol-3-yl)amino)-2-(methylthio)pyrimidin-4-yl)piperazin-1-yl)ethan-1-one |
| 557 | 1-(5-ethoxy-6-((5-methyl-1H-pyrazol-3-yl)amino)-2-(methylthio)pyrimidin-4-yl)piperidin-4-ol |
| 558 | 5-ethoxy-N-(5-methyl-1H-pyrazol-3-yl)-2-(methylthio)-6-(piperidin-1-yl)pyrimidin-4-amine |
| 559 | 5-ethoxy-N-(5-methyl-1H-pyrazol-3-yl)-6-(4-methylpiperazin-1-yl)-2-(methylthio)pyrimidin-4-amine |
| 560 | 6-(4-(2-(dimethylamino)ethyl)piperazin-1-yl)-5-ethoxy-N-(5-methyl-1H-pyrazol-3-yl)-2-(methylthio)pyrimidin-4-amine |
| 561 | N$^4$-isopropyl-N$^4$,5-dimethyl-N$^6$-(5-methyl-1H-pyrazol-3-yl)-2-(p-tolylthio)pyrimidine-4,6-diamine |
| 562 | (S)-N-(4-((5-methyl-4-((5-methyl-1H-pyrazol-3-yl)amino)-6-(3-methylmorpholino)pyrimidin-2-yl)thio)phenyl)acetamide |
| 563 | N-(4-((4-(3-hydroxy-8-azabicyclo[3.2.1]octan-8-yl)-5-methoxy-6-((5-methyl-1H-pyrazol-3-yl)amino)pyrimidin-2-yl)thio)phenyl)acetamide |
| 564 | N-(4-((4-(3-hydroxy-8-azabicyclo[3.2.1]octan-8-yl)-5-methyl-6-((5-methyl-1H-pyrazol-3-yl)amino)pyrimidin-2-yl)thio)phenyl)acetamide |
| 565 | N-(4-((4-(4-(2-(dimethylamino)ethoxy)piperidin-1-yl)-5-methyl-6-((5-methyl-1H-pyrazol-3-yl)amino)pyrimidin-2-yl)thio)phenyl)acetamide |
| 566 | N-(4-((4-(4-hydroxy-2-methylpiperidin-1-yl)-5-methyl-6-((5-methyl-1H-pyrazol-3-yl)amino)pyrimidin-2-yl)thio)phenyl)acetamide |
| 567 | N-(4-((5-ethoxy-4-(4-hydroxypiperidin-1-yl)-6-((5-methyl-1H-pyrazol-3-yl)amino)pyrimidin-2-yl)thio)phenyl)cyclopropanecarboxamide |
| 568 | N-(4-((5-methoxy-4-((5-methyl-1H-pyrazol-3-yl)amino)-6-(4-(2-morpholinoethyl)piperazin-1-yl)pyrimidin-2-yl)thio)phenyl)acetamide |
| 569 | N-(4-((5-methyl-4-((5-methyl-1H-pyrazol-3-yl)amino)-6-(4-(2-(piperidin-1-yl)ethyl)piperazin-1-yl)pyrimidin-2-yl)thio)phenyl)acetamide |
| 570 | 2-((4-aminophenyl)thio)-6-(4-(2-(dimethylamino)ethyl)piperazin-1-yl)-5-methoxy-N-(5-methyl-1H-pyrazol-3-yl)pyrimidin-4-amine |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 571 | 6-(4-(2-(dimethylamino)ethyl)piperazin-1-yl)-5-methoxy-N-(5-methyl-1H-pyrazol-3-yl)-2-(methylthio)pyrimidin-4-amine |
| 572 | 6-(4-(2-(dimethylamino)ethyl)piperazin-1-yl)-5-methoxy-N-(5-methyl-1H-pyrazol-3-yl)-2-(phenylthio)pyrimidin-4-amine |
| 573 | (R)-N-(4-((5-methyl-4-((5-methyl-1H-pyrazol-3-yl)amino)-6-(3-methylmorpholino)pyrimidin-2-yl)thio)phenyl)acetamide |
| 574 | N-(4-((4-(3-hydroxypyrrolidin-1-yl)-5-methoxy-6-((5-methyl-1H-pyrazol-3-yl)amino)pyrimidin-2-yl)thio)phenyl)acetamide |
| 575 | N-(4-((4-(4-(2-(dimethylamino)ethoxy)piperidin-1-yl)-5-methoxy-6-((5-methyl-1H-pyrazol-3-yl)amino)pyrimidin-2-yl)thio)phenyl)acetamide |
| 576 | N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)-2,2,2-trifluoroacetamide |
| 577 | N-(4-((4-(4-(2-acetamidoethyl)piperazin-1-yl)-5-methoxy-6-((5-methyl-1H-pyrazol-3-yl)amino)pyrimidin-2-yl)thio)phenyl)acetamide |
| 578 | N-(4-((4-(4-(3-(dimethylamino)propyl)piperazin-1-yl)-5-methoxy-6-((5-methyl-1H-pyrazol-3-yl)amino)pyrimidin-2-yl)thio)phenyl)acetamide |
| 579 | N-(4-((5-methoxy-4-((5-methyl-1H-pyrazol-3-yl)amino)-6-(4-(2-(methylamino)ethyl)piperazin-1-yl)pyrimidin-2-yl)thio)phenyl)acetamide |
| 580 | N-(4-((5-methoxy-4-((5-methyl-1H-pyrazol-3-yl)amino)-6-(4-(2-(piperidin-1-yl)ethyl)piperazin-1-yl)pyrimidin-2-yl)thio)phenyl)acetamide |
| 581 | 1-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)-3-methylurea |
| 582 | 6-(4-(2-(dimethylamino)ethyl)piperazin-1-yl)-5-methyl-N-(5-methyl-1H-pyrazol-3-yl)-2-(methylthio)pyrimidin-4-amine |
| 583 | (R)-N-(4-((5-methoxy-4-((5-methyl-1H-pyrazol-3-yl)amino)-6-(3-methylmorpholino)pyrimidin-2-yl)thio)phenyl)acetamide |
| 584 | (S)-N-(4-((5-methoxy-4-((5-methyl-1H-pyrazol-3-yl)amino)-6-(3-methylmorpholino)pyrimidin-2-yl)thio)phenyl)acetamide |
| 585 | 2-(4-(2-((4-acetamidophenyl)thio)-5-methoxy-6-((5-methyl-1H-pyrazol-3-yl)amino)pyrimidin-4-yl)piperazin-1-yl)-N,N-dimethylacetamide |
| 586 | 4-(2-((4-acetamidophenyl)thio)-5-methoxy-6-((5-methyl-1H-pyrazol-3-yl)amino)pyrimidin-4-yl)-N,N-dimethylpiperazine-1-carboxamide |
| 587 | N-(4-((5-methoxy-4-((5-methyl-1H-pyrazol-3-yl)amino)-6-((1-methylpiperidin-4-yl)amino)pyrimidin-2-yl)thio)phenyl)acetamide |
| 588 | N-(4-((5-methoxy-4-((5-methyl-1H-pyrazol-3-yl)amino)-6-(4-(2-morpholinoethyl)piperidin-1-yl)pyrimidin-2-yl)thio)phenyl)acetamide |
| 589 | N-(4-((5-methyl-4-((5-methyl-1H-pyrazol-3-yl)amino)-6-((1-methylpiperidin-4-yl)amino)pyrimidin-2-yl)thio)phenyl)acetamide |
| 590 | N-(4-((5-methyl-4-((5-methyl-1H-pyrazol-3-yl)amino)-6-(piperidin-4-ylamino)pyrimidin-2-yl)thio)phenyl)acetamide |
| 591 | 1-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)urea |
| 592 | N-(3-((4-(4-(2-(dimethylamino)ethyl)piperazin-1-yl)-5-methoxy-6-((5-methyl-1H-pyrazol-3-yl)amino)pyrimidin-2-yl)thio)phenyl)acetamide |
| 593 | N-(3-((5-methoxy-4-((5-methyl-1H-pyrazol-3-yl)amino)-6-morpholinopyrimidin-2-yl)thio)phenyl)acetamide |
| 594 | N-(4-((4-((5-methyl-1H-pyrazol-3-yl)amino)-1'-pivaloyl-5,6-dihydrospiro[cyclopenta[d]pyrimidine-7,4'-piperidin]-2-yl)thio)phenyl)acetamide |
| 595 | N-(4-((5-methoxy-4-((5-methyl-1H-pyrazol-3-yl)amino)-6-(1,2,3,6-tetrahydropyridin-4-yl)pyrimidin-2-yl)thio)phenyl)acetamide |
| 596 | N-(4-((5-methoxy-4-((5-methyl-1H-pyrazol-3-yl)amino)-6-(4-(2-morpholino-2-oxoethyl)piperazin-1-yl)pyrimidin-2-yl)thio)phenyl)acetamide |
| 597 | N-(4-((5-methoxy-4-((5-methyl-1H-pyrazol-3-yl)amino)-6-(4-(2-oxo-2-(piperidin-1-yl)ethyl)piperazin-1-yl)pyrimidin-2-yl)thio)phenyl)acetamide |
| 598 | N-(4-((5-methoxy-4-((5-methyl-1H-pyrazol-3-yl)amino)-6-(piperidin-4-ylamino)pyrimidin-2-yl)thio)phenyl)acetamide |
| 599 | N-(5-((5-methoxy-4-((5-methyl-1H-pyrazol-3-yl)amino)-6-morpholinopyrimidin-2-yl)thio)pyridin-2-yl)acetamide |
| 600 | 2,2-dimethyl-1-(4-((5-methyl-1H-pyrazol-3-yl)amino)-2-((4-nitrophenyl)thio)-5,6-dihydrospiro[cyclopenta[d]pyrimidine-7,4'-piperidin]-1'-yl)propan-1-one |
| 601 | 6-(4-(2-(dimethylamino)ethyl)piperazin-1-yl)-5-methoxy-N-(5-methyl-1H-pyrazol-3-yl)-2-((4-nitrophenyl)thio)pyrimidin-4-amine |
| 602 | 6-(4-(2-(dimethylamino)ethyl)piperazin-1-yl)-N-(5-ethyl-1H-pyrazol-3-yl)-5-methoxy-2-(methylthio)pyrimidin-4-amine |
| 603 | 6-(4-(2-(dimethylamino)ethyl)piperazin-1-yl)-N-(5-ethyl-1H-pyrazol-3-yl)-5-methyl-2-(methylthio)pyrimidin-4-amine |
| 604 | N-(5-methyl-1H-pyrazol-3-yl)-2-((4-nitrophenyl)thio)-5,6-dihydrospiro[cyclopenta[d]pyrimidine-7,4'-piperidin]-4-amine |
| 605 | 2-(4-(2-((4-acetamidophenyl)thio)-5-methoxy-6-((5-methyl-1H-pyrazol-3-yl)amino)pyrimidin-4-yl)-3,6-dihydropyridin-1(2H)-yl)-N,N-dimethylacetamide |
| 606 | N-(4-((1'-(2-(dimethylamino)ethyl)-4-((5-methyl-1H-pyrazol-3-yl)amino)-5,6-dihydrospiro[cyclopenta[d]pyrimidine-7,4'-piperidin]-2-yl)thio)phenyl)acetamide |
| 607 | N-(4-((4-(1-(2-(dimethylamino)ethyl)-1,2,3,6-tetrahydropyridin-4-yl)-5-methoxy-6-((5-methyl-1H-pyrazol-3-yl)amino)pyrimidin-2-yl)thio)phenyl)acetamide |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 608 | N-(4-((4-(4-(2-(diethylamino)ethyl)piperazin-1-yl)-5-methoxy-6-((5-methyl-1H-pyrazol-3-yl)amino)pyrimidin-2-yl)thio)phenyl)acetamide |
| 609 | N-(4-((4-(4-(2-(dimethylamino)ethyl)-2-methylpiperazin-1-yl)-6-((5-methyl-1H-pyrazol-3-yl)amino)pyrimidin-2-yl)thio)phenyl)acetamide |
| 610 | N-(4-((4-(4-(2-(dimethylamino)ethyl)-3-methylpiperazin-1-yl)-5-methoxy-6-((5-methyl-1H-pyrazol-3-yl)amino)pyrimidin-2-yl)thio)phenyl)acetamide |
| 611 | N-(4-((4-(4-(2-(ethyl(methyl)amino)ethyl)piperazin-1-yl)-5-methoxy-6-((5-methyl-1H-pyrazol-3-yl)amino)pyrimidin-2-yl)thio)phenyl)acetamide |
| 612 | N-(4-((4-(4-(2-aminoethyl)piperazin-1-yl)-5-methoxy-6-((5-methyl-1H-pyrazol-3-yl)amino)pyrimidin-2-yl)thio)phenyl)acetamide |
| 613 | N-(4-((5-methoxy-4-((5-methyl-1H-pyrazol-3-yl)amino)-6-(4-(2-(piperazin-1-yl)ethyl)piperazin-1-yl)pyrimidin-2-yl)thio)phenyl)acetamide |
| 614 | N-(4-((5-methoxy-4-((5-methyl-1H-pyrazol-3-yl)amino)-6-(4-(2-(pyrrolidin-1-yl)ethyl)piperazin-1-yl)pyrimidin-2-yl)thio)phenyl)acetamide |
| 615 | N-(4-((5-methoxy-4-(1-methyl-1,2,3,6-tetrahydropyridin-4-yl)-6-((5-methyl-1H-pyrazol-3-yl)amino)pyrimidin-2-yl)thio)phenyl)acetamide |
| 616 | 1'-(2-(dimethylamino)ethyl)-N-(5-methyl-1H-pyrazol-3-yl)-2-((4-nitrophenyl)thio)-5,6-dihydrospiro[cyclopenta[d]pyrimidine-7,4'-piperidin]-4-amine |
| 617 | 2-((4-aminophenyl)thio)-1'-(2-(dimethylamino)ethyl)-N-(5-methyl-1H-pyrazol-3-yl)-5,6-dihydrospiro[cyclopenta[d]pyrimidine-7,4'-piperidin]-4-amine 2-(1-(2-((4-acetamidophenyl)thio)-5-methoxy-6-((5-methyl-1H-pyrazol-3-yl)amino)pyrimidin-4-yl)piperidin-4-yl)acetic acid |
| 618 | 2-(3-((6-(4-(2-(dimethylamino)ethyl)piperazin-1-yl)-5-methoxy-2-(methylthio)pyrimidin-4-yl)amino)-1H-pyrazol-5-yl)acetic acid |
| 619 | 2-(4-(2-((4-acetamidophenyl)thio)-5-methoxy-6-((5-methyl-1H-pyrazol-3-yl)amino)pyrimidin-4-yl)piperazin-1-yl)acetic acid |
| 620 | methyl 2-(1-(2-((4-acetamidophenyl)thio)-5-methoxy-6-((5-methyl-1H-pyrazol-3-yl)amino)pyrimidin-4-yl)piperidin-4-yl)acetate |
| 621 | methyl 2-(3-((6-(4-(2-(dimethylamino)ethyl)piperazin-1-yl)-5-methoxy-2-(methylthio)pyrimidin-4-yl)amino)-1H-pyrazol-5-yl)acetate |
| 622 | 2-(1-(2-((4-acetamidophenyl)thio)-5-methoxy-6-((5-methyl-1H-pyrazol-3-yl)amino)pyrimidin-4-yl)piperidin-4-yl)acetamide |
| 623 | 2-(3-((6-(4-(2-(dimethylamino)ethyl)piperazin-1-yl)-5-methoxy-2-(methylthio)pyrimidin-4-yl)amino)-1H-pyrazol-5-yl)-N-methylacetamide |
| 624 | 2-(4-(2-((4-acetamidophenyl)thio)-5-methoxy-6-((5-methyl-1H-pyrazol-3-yl)amino)pyrimidin-4-yl)piperazin-1-yl)acetamide |
| 625 | 4-(2-((4-acetamidophenyl)thio)-5-methoxy-6-((5-methyl-1H-pyrazol-3-yl)amino)pyrimidin-4-yl)piperazine-1-carboxamide |
| 626 | N-(4-((4-(4-(2-(4-hydroxypiperidin-1-yl)ethyl)piperazin-1-yl)-5-methoxy-6-((5-methyl-1H-pyrazol-3-yl)amino)pyrimidin-2-yl)thio)phenyl)acetamide |
| 627 | N-(4-((4-(4-(N-hydroxycarbamimidoyl)piperazin-1-yl)-5-methoxy-6-((5-methyl-1H-pyrazol-3-yl)amino)pyrimidin-2-yl)thio)phenyl)acetamide |
| 628 | N-(4-((4-(8-(2-(dimethylamino)ethyl)-3,8-diazabicyclo[3.2.1]octan-3-yl)-5-methoxy-6-((5-methyl-1H-pyrazol-3-yl)amino)pyrimidin-2-yl)thio)phenyl)acetamide |
| 629 | N-(4-((5-methoxy-4-((5-methyl-1H-pyrazol-3-yl)amino)-6-(4-(2-(4-methylpiperazin-1-yl)ethyl)piperazin-1-yl)pyrimidin-2-yl)thio)phenyl)acetamide |
| 630 | N-(4-((5-methoxy-4-((5-methyl-1H-pyrazol-3-yl)amino)-6-(4-(2-(piperidin-1-yl)ethyl)piperidin-1-yl)pyrimidin-2-yl)thio)phenyl)acetamide |
| 631 | methyl 2-(4-(2-((4-acetamidophenyl)thio)-5-methoxy-6-((5-methyl-1H-pyrazol-3-yl)amino)pyrimidin-4-yl)piperazin-1-yl)acetate |
| 632 | methyl 4-((4-(4-(2-(dimethylamino)ethyl)piperazin-1-yl)-5-methoxy-6-((5-methyl-1H-pyrazol-3-yl)amino)pyrimidin-2-yl)thio)benzoate |
| 633 | 2-(1-(2-((4-acetamidophenyl)thio)-5-methoxy-6-((5-methyl-1H-pyrazol-3-yl)amino)pyrimidin-4-yl)piperidin-4-yl)-N,N-dimethylacetamide |
| 634 | 4-((4-(4-(2-(dimethylamino)ethyl)piperazin-1-yl)-5-methoxy-6-((5-methyl-1H-pyrazol-3-yl)amino)pyrimidin-2-yl)thio)-N,N-dimethylbenzamide |
| 635 | N-(4-((4-(1-(2-(dimethylamino)ethyl)piperidin-4-yl)-5-methoxy-6-((5-methyl-1H-pyrazol-3-yl)amino)pyrimidin-2-yl)thio)phenyl)acetamide |
| 636 | N-(4-((4-(4-(2-(azepan-1-yl)ethyl)piperazin-1-yl)-5-methoxy-6-((5-methyl-1H-pyrazol-3-yl)amino)pyrimidin-2-yl)thio)phenyl)acetamide |
| 637 | N-(4-((4-(4-(2-(azocan-1-yl)ethyl)piperazin-1-yl)-5-methoxy-6-((5-methyl-1H-pyrazol-3-yl)amino)pyrimidin-2-yl)thio)phenyl)acetamide |
| 638 | N-(4-((4-(4-(2-(dimethylamino)ethyl)-3,5-dimethylpiperazin-1-yl)-5-methoxy-6-((5-methyl-1H-pyrazol-3-yl)amino)pyrimidin-2-yl)thio)phenyl)acetamide |
| 639 | N-(4-((4-(4-(2-guanidinoethyl)piperazin-1-yl)-5-methoxy-6-((5-methyl-1H-pyrazol-3-yl)amino)pyrimidin-2-yl)thio)phenyl)acetamide |
| 640 | N-(4-((4-(4-carbamimidoylpiperazin-1-yl)-5-methoxy-6-((5-methyl-1H-pyrazol-3-yl)amino)pyrimidin-2-yl)thio)phenyl)acetamide |
| 641 | N-(4-((5-methoxy-4-((5-methyl-1H-pyrazol-3-yl)amino)-6-(4-(2-oxo-2-(piperidin-1-yl)ethyl)piperidin-1-yl)pyrimidin-2-yl)thio)phenyl)acetamide |
| 642 | N-(4-((5-methoxy-4-((5-methyl-1H-pyrazol-3-yl)amino)-6-(4-(2-ureidoethyl)piperazin-1-yl)pyrimidin-2-yl)thio)phenyl)acetamide |
| 643 | N-(4-((5-methoxy-4-((5-methyl-1H-pyrazol-3-yl)amino)-6-(8-(2-(4-methylpiperazin-1-yl)ethyl)-3,8-diazabicyclo[3.2.1]octan-3-yl)pyrimidin-2-yl)thio)phenyl)acetamide |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 644 | N-(4-((5-methoxy-4-(4-(2-(methoxy(methyl)amino)ethyl)piperazin-1-yl)-6-((5-methyl-1H-pyrazol-3-yl)amino)pyrimidin-2-yl)thio)phenyl)acetamide |
| 645 | 1-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)ethan-1-one |
| 646 | 2-(3-((6-(4-(2-(dimethylamino)ethyl)piperazin-1-yl)-5-methoxy-2-(methylthio)pyrimidin-4-yl)amino)-1H-pyrazol-5-yl)-N-(3-fluorophenyl)acetamide |
| 647 | 4-((4-(4-(2-(dimethylamino)ethyl)piperazin-1-yl)-5-methoxy-6-((5-methyl-1H-pyrazol-3-yl)amino)pyrimidin-2-yl)thio)-N-methylbenzamide |
| 648 | N-(4-((4-(1-(2-(dimethylamino)ethyl)piperidin-4-yl)-5-methyl-6-((5-methyl-1H-pyrazol-3-yl)amino)pyrimidin-2-yl)thio)phenyl)acetamide |
| 649 | N-(4-((4-(4-(2-((1R,5S)-8-azabicyclo[3.2.1]octan-8-yl)ethyl)piperazin-1-yl)-5-methoxy-6-((5-methyl-1H-pyrazol-3-yl)amino)pyrimidin-2-yl)thio)phenyl)acetamide |
| 650 | N-(4-((4-(4-(2-(9-azabicyclo[3.3.1]nonan-9-yl)ethyl)piperazin-1-yl)-5-methoxy-6-((5-methyl-1H-pyrazol-3-yl)amino)pyrimidin-2-yl)thio)phenyl)acetamide |
| 651 | N-(4-((4-(4-(2-(benzyl(methyl)amino)ethyl)piperazin-1-yl)-5-methoxy-6-((5-methyl-1H-pyrazol-3-yl)amino)pyrimidin-2-yl)thio)phenyl)acetamide |
| 652 | N-(4-((4-(4-(2-(dimethylamino)ethyl)-2-methylpiperazin-1-yl)-5-methoxy-6-((5-methyl-1H-pyrazol-3-yl)amino)pyrimidin-2-yl)thio)phenyl)acetamide |
| 653 | N-(4-((4-(4-(2-(dimethylamino)ethyl)piperazin-1-yl)-5-methoxy-6-((5-methylthiazol-2-yl)amino)pyrimidin-2-yl)thio)phenyl)acetamide |
| 654 | N-(4-((4-(8-(2-(azocan-1-yl)ethyl)-3,8-diazabicyclo[3.2.1]octan-3-yl)-5-methoxy-6-((5-methyl-1H-pyrazol-3-yl)amino)pyrimidin-2-yl)thio)phenyl)acetamide |
| 655 | N-(4-((5-methoxy-4-((5-methyl-1H-pyrazol-3-yl)amino)-6-(4-(2-(methylsulfonyl)ethyl)piperazin-1-yl)pyrimidin-2-yl)thio)phenyl)acetamide |
| 656 | N-(4-((5-methoxy-4-(4-(2-(methyl(phenyl)amino)ethyl)piperazin-1-yl)-6-((5-methyl-1H-pyrazol-3-yl)amino)pyrimidin-2-yl)thio)phenyl)acetamide |
| 657 | N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)methanesulfonamide |
| 658 | 5-methoxy-N-(5-methyl-1H-pyrazol-3-yl)-6-(4-(2-(4-methylpiperazin-1-yl)ethyl)piperazin-1-yl)-2-((4-(methylsulfonyl)phenyl)thio)pyrimidin-4-amine |
| 659 | 6-(4-(2-(dimethylamino)ethyl)piperazin-1-yl)-5-methoxy-N-(5-methyl-1H-pyrazol-3-yl)-2-((4-(methylsulfinyl)phenyl)thio)pyrimidin-4-amine |
| 660 | 6-(4-(2-(dimethylamino)ethyl)piperazin-1-yl)-5-methoxy-N-(5-methyl-1H-pyrazol-3-yl)-2-((4-(methylsulfonyl)phenyl)thio)pyrimidin-4-amine |
| 661 | 2-(3-((6-(4-(2-(dimethylamino)ethyl)piperazin-1-yl)-5-methoxy-2-(methylthio)pyrimidin-4-yl)amino)-1H-pyrazol-5-yl)-N-(3-fluorophenyl)acetamide |
| 662 | 4-((4-(4-(2-(dimethylamino)ethyl)piperazin-1-yl)-5-methoxy-6-((5-methyl-1H-pyrazol-3-yl)amino)pyrimidin-2-yl)thio)-N-methylbenzamide |
| 663 | N-(4-((4-(1-(2-(dimethylamino)ethyl)piperidin-4-yl)-5-methyl-6-((5-methyl-1H-pyrazol-3-yl)amino)pyrimidin-2-yl)thio)phenyl)acetamide |
| 664 | N-(4-((4-(4-(2-((1R,5S)-8-azabicyclo[3.2.1]octan-8-yl)ethyl)piperazin-1-yl)-5-methoxy-6-((5-methyl-1H-pyrazol-3-yl)amino)pyrimidin-2-yl)thio)phenyl)acetamide |
| 665 | N-(4-((4-(4-(2-(9-azabicyclo[3.3.1]nonan-9-yl)ethyl)piperazin-1-yl)-5-methoxy-6-((5-methyl-1H-pyrazol-3-yl)amino)pyrimidin-2-yl)thio)phenyl)acetamide |
| 666 | N-(4-((4-(4-(2-(benzyl(methyl)amino)ethyl)piperazin-1-yl)-5-methoxy-6-((5-methyl-1H-pyrazol-3-yl)amino)pyrimidin-2-yl)thio)phenyl)acetamide |
| 667 | N-(4-((4-(4-(2-(dimethylamino)ethyl)-2-methylpiperazin-1-yl)-5-methoxy-6-((5-methyl-1H-pyrazol-3-yl)amino)pyrimidin-2-yl)thio)phenyl)acetamide |
| 668 | N-(4-((4-(4-(2-(dimethylamino)ethyl)piperazin-1-yl)-5-methoxy-6-((5-methylthiazol-2-yl)amino)pyrimidin-2-yl)thio)phenyl)acetamide |
| 669 | N-(4-((4-(8-(2-(azocan-1-yl)ethyl)-3,8-diazabicyclo[3.2.1]octan-3-yl)-5-methoxy-6-((5-methyl-1H-pyrazol-3-yl)amino)pyrimidin-2-yl)thio)phenyl)acetamide |
| 670 | N-(4-((5-methoxy-4-((5-methyl-1H-pyrazol-3-yl)amino)-6-(4-(2-(methylsulfonyl)ethyl)piperazin-1-yl)pyrimidin-2-yl)thio)phenyl)acetamide |
| 671 | N-(4-((5-methoxy-4-(4-(2-(methyl(phenyl)amino)ethyl)piperazin-1-yl)-6-((5-methyl-1H-pyrazol-3-yl)amino)pyrimidin-2-yl)thio)phenyl)acetamide |
| 672 | N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)methanesulfonamide |
| 673 | 5-methoxy-N-(5-methyl-1H-pyrazol-3-yl)-6-(4-(2-(4-methylpiperazin-1-yl)ethyl)piperazin-1-yl)-2-((4-(methylsulfonyl)phenyl)thio)pyrimidin-4-amine |
| 674 | 6-(4-(2-(dimethylamino)ethyl)piperazin-1-yl)-5-methoxy-N-(5-methyl-1H-pyrazol-3-yl)-2-((4-(methylsulfinyl)phenyl)thio)pyrimidin-4-amine |
| 675 | 6-(4-(2-(dimethylamino)ethyl)piperazin-1-yl)-5-methoxy-N-(5-methyl-1H-pyrazol-3-yl)-2-((4-(methylsulfonyl)phenyl)thio)pyrimidin-4-amine |
| 676 | 2-((4-((2-chlorobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 677 | 2-((4-((3-chlorobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 678 | 2-((4-((4-chlorobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 679 | 2-((4-(benzylsulfonyl)phenyl)thio)-5-methoxy-N-(5-methyl-1H-pyrazol-3-yl)-6-(4-methylpiperazin-1-yl)pyrimidin-4-amine |
| 680 | 2-((4-(benzylsulfonyl)phenyl)thio)-6-(4-(2-(dimethylamino)ethyl)piperidin-1-yl)-5-methoxy-N-(5-methyl-1H-pyrazol-3-yl)pyrimidin-4-amine |

TABLE 2-continued

Compound Names for exemplified compounds of formula (I), (II), and (III).
All compounds were confirmed by mass spectroscopy and by $^1$H and $^{13}$C NMR.

| No. | Chemical Name |
|---|---|
| 681 | 2-((4-(ethylsulfonyl)phenyl)thio)-5-methoxy-N-(5-methyl-1H-pyrazol-3-yl)-6-(4-(2-(4-methylpiperazin-1-yl)ethyl)piperazin-1-yl)pyrimidin-4-amine |
| 682 | 2-((4-(ethylsulfonyl)phenyl)thio)-5-methoxy-N-(5-methyl-1H-pyrazol-3-yl)-6-(4-methylpiperazin-1-yl)pyrimidin-4-amine |
| 683 | 2-((4-(ethylsulfonyl)phenyl)thio)-5-methoxy-N-(5-methyl-1H-pyrazol-3-yl)-6-(piperazin-1-yl)pyrimidin-4-amine |
| 684 | 6-(4-(2-(9-azabicyclo[3.3.1]nonan-9-yl)ethyl)piperazin-1-yl)-2-((4-(benzylsulfonyl)phenyl)thio)-5-methoxy-N-(5-methyl-1H-pyrazol-3-yl)pyrimidin-4-amine |
| 685 | 6-(4-(2-(dimethylamino)ethyl)piperazin-1-yl)-2-((4-((4-fluorobenzyl)sulfonyl)phenyl)thio)-5-methoxy-N-(5-methyl-1H-pyrazol-3-yl)pyrimidin-4-amine |
| 686 | 6-(4-(2-(dimethylamino)ethyl)piperazin-1-yl)-2-((4-(isopropylsulfonyl)phenyl)thio)-5-methoxy-N-(5-methyl-1H-pyrazol-3-yl)pyrimidin-4-amine |
| 687 | 6-(4-(2-(dimethylamino)ethyl)piperazin-1-yl)-5-methoxy-2-((4-((4-methoxybenzyl)sulfonyl)phenyl)thio)-N-(5-methyl-1H-pyrazol-3-yl)pyrimidin-4-amine |
| 688 | 6-(4-(2-(dimethylamino)ethyl)piperazin-1-yl)-5-methoxy-N-(5-methyl-1H-pyrazol-3-yl)-2-((4-((pyridin-3-ylmethyl)sulfonyl)phenyl)thio)pyrimidin-4-amine |
| 689 | 6-(4-(2-(dimethylamino)ethyl)piperazin-1-yl)-5-methoxy-N-(5-methyl-1H-pyrazol-3-yl)-2-((4-((pyridin-4-ylmethyl)sulfonyl)phenyl)thio)pyrimidin-4-amine |
| 690 | 6-(4-(2-(dimethylamino)ethyl)piperazin-1-yl)-5-methoxy-N-(5-methyl-1H-pyrazol-3-yl)-2-((4-((thiophen-2-ylmethyl)sulfonyl)phenyl)thio)pyrimidin-4-amine |
| 691 | 6-(4-(2-(dimethylamino)ethyl)piperidin-1-yl)-5-methoxy-N-(5-methyl-1H-pyrazol-3-yl)-2-((4-(methylsulfonyl)phenyl)thio)pyrimidin-4-amine |
| 692 | 2-((4-(((1H-imidazol-2-yl)methyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 693 | 2-((4-(benzylsulfonyl)phenyl)thio)-5-methoxy-6-methyl-N-(5-methyl-1H-pyrazol-3-yl)pyrimidin-4-amine |
| 694 | 2-((4-(benzylsulfonyl)phenyl)thio)-5-methoxy-N-(5-methyl-1H-pyrazol-3-yl)-6-(4-(2-(4-methylpiperazin-1-yl)ethyl)piperazin-1-yl)pyrimidin-4-amine |
| 695 | 2-((4-(benzylsulfonyl)phenyl)thio)-5-methoxy-N-(5-methyl-1H-pyrazol-3-yl)-6-(piperidin-1-yl)pyrimidin-4-amine |
| 696 | 2-((4-(benzylsulfonyl)phenyl)thio)-5-methoxy-N-(5-methyl-1H-pyrazol-3-yl)-6-morpholinopyrimidin-4-amine |
| 697 | 2-((4-(benzylsulfonyl)phenyl)thio)-5-methoxy-$N^4$,$N^4$-dimethyl-$N^6$-(5-methyl-1H-pyrazol-3-yl)pyrimidine-4,6-diamine |
| 698 | 2-((4-(benzylsulfonyl)phenyl)thio)-6-(1-(2-(dimethylamino)ethyl)piperidin-4-yl)-5-methoxy-N-(5-methyl-1H-pyrazol-3-yl)pyrimidin-4-amine |
| 699 | 2-((4-(benzylsulfonyl)phenyl)thio)-6-(4-(2-(dimethylamino)ethyl)piperazin-1-yl)-5-ethoxy-N-(5-methyl-1H-pyrazol-3-yl)pyrimidin-4-amine |
| 700 | 2-((4-(ethylsulfonyl)phenyl)thio)-5-methoxy-6-methyl-N-(5-methyl-1H-pyrazol-3-yl)pyrimidin-4-amine |

Example 2—Synthetic Examples

Synthesis of 2-((2-fluoro-4-((2-fluoro-3-nitrobenzyl)sulfonyl)phenyl)thio)-5-methoxy-N-(5-methyl-1H-pyrazol-3-yl)-6-morpholinopyrimidin-4-amine (14)

Scheme 1:

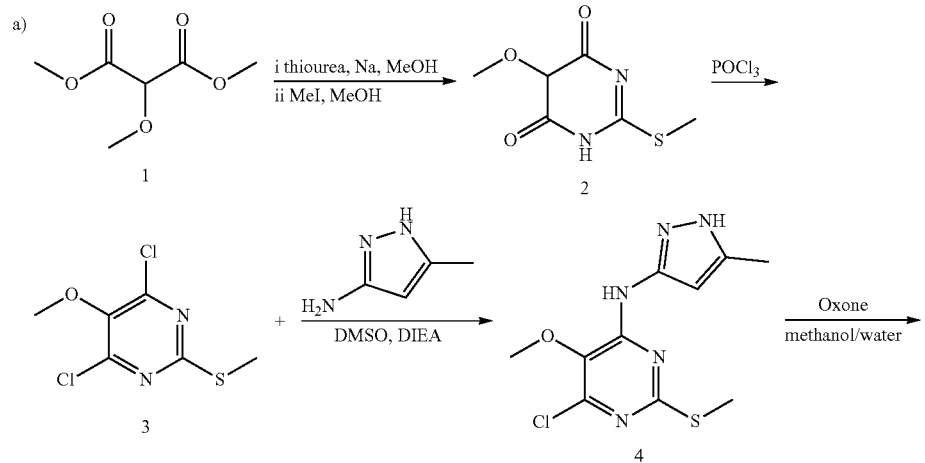

-continued
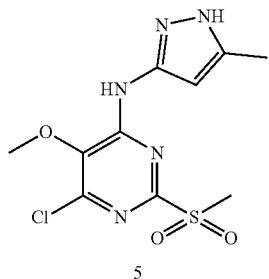
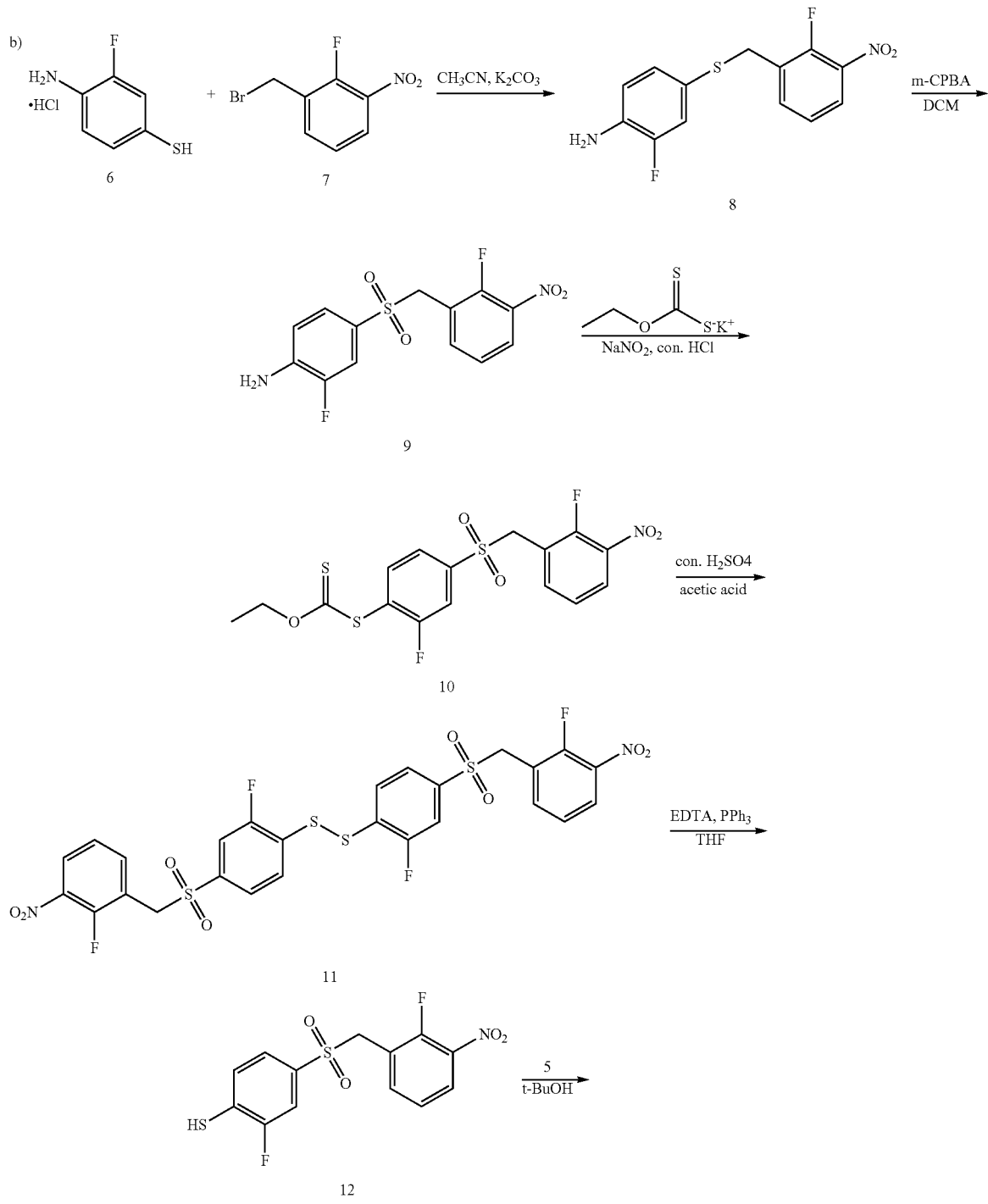

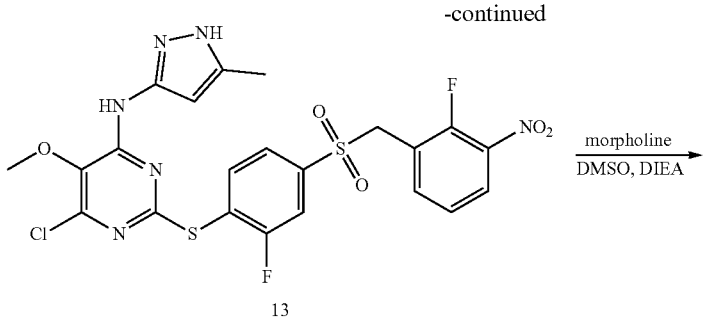

13

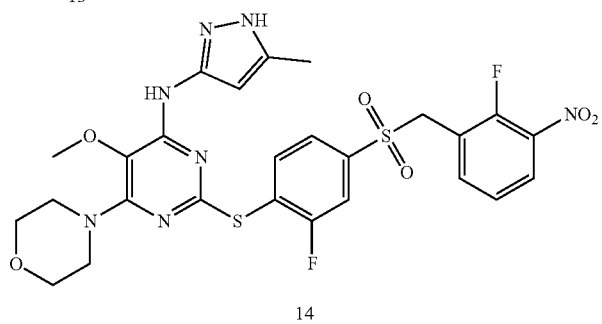

14

Synthetic Procedures for Scheme 1

Synthesis of Compound 2: A solution of 1 (45.1 g, 0.28 mol, 1.0 eq.) and thiourea (21.3 g, 0.28 mol, 1.0 eq) in methanol (200 mL) was maintained at 23° C. for 20 min. before the addition of a sodium methoxide solution [Na (6.44 g, 0.28 mol, 1.0 eq) in methanol (100 mL)]. After the addition was complete, the mixture was heated at reflux for 24 h, allowed to cool to 23° C. and iodomethane (47.7 g, 0.336 mol, 1.2 eq) was added dropwise. The resulting mixture was stirred at 23° C. overnight, and concentrated. The residue was triturated with water (50 mL) and filtered. The collected solid was washed with water (50 mL) and dried in vacuo to afford 2 (38.0 g, 72.5% yield).

Synthesis of Compound 3: A mixture of 2 (38.0 g, 0.202 mmol) in phosphorus oxychloride (300 mL) was heated at reflux for 3 h, then cooled and concentrated. The residue was poured slowly into warm water (40° C.) with vigorous stirring. After the addition was complete, the mixture was extracted with EtOAc (2×300 mL) and the combined organic layers were dried ($Na_2SO_4$) and concentrated. The residue was purified by flash column chromatography (PE/EA=30/1, v/v) to afford 3 (42.0 g, 93% yield).

Synthesis of Compound 4: A solution of 3 (42.0 g, 0.187 mol, 1.0 eq.), 5-methyl-1H-pyrazol-3-amine (21.7 g, 0.224 mol, 1.2 eq) and DIEA (49 mL, 0.28 mol, 1.5 eq) in DMSO (400 mL) was heated at 80° C. for 24 h, then allowed to warm to 23° C. The reaction mixture was poured into water with stirring. The resulting precipitate was collected by filtration, washed with water, triturated with DCM (100 mL) and dried in vacuo to provide 4 (38.5 g, 72.3% yield).

Synthesis of Compound 5: To a solution of 4 (38.5 g, 0.135 mol, 1.0 eq.) in MeOH (800 mL) was added a solution of oxone (170 g, 0.277 mol, 2.05 eq.) in water (400 mL) dropwise at 0° C. After the addition was complete, the mixture was stirred for 3 h at 23° C. and filtered. The collected solid was washed with methanol and added to a solution of sat. aqueous $NaHCO_3$ (500 mL) and water (500 mL). The mixture was stirred at 23° C. for 0.5 h before the solids were collected by filtration. The filtrate was neutralized to pH=7-8 with sat. $NaHCO_3$ and the resulting solids were collected by filtration. The combined solids were washed with water (50 mL) and dried in vacuo to afford 5 (39.2 g, 91.7% yield).

Synthesis of Compound 8: To a solution of 6 (63.5 g, 0.354 mol, 1.2 eq.) and 7 (68.9 g, 0.295 mol, 1.0 eq) in acetonitrile (1 L) was added $K_2CO_3$ (122 g, 0.885 mol, 3.0 eq) at 23° C. The resulting mixture was stirred at 23° C. overnight and filtered. The filtrate was concentrated and the residue was purified by flash column (PE/EA=4/1, v/v) to afford 8 (78.4 g, 89.9% yield).

Synthesis of Compound 9: To a solution of 8 (78.4 g, 0.265 mol, 1.0 eq.) in DCM (1 L) was added mCPBA (114 g, 0.662 mol, 2.5 eq) at 0° C. The resulting mixture was stirred at 23° C. for 2 days and filtered. The collected solid was triturated with 1N NaOH, filtered and dried in vacuo to afford 9 (59.8 g, 68.9% yield).

Synthesis of Compound 10: 9 (59.8 g, 0.182 mol, 1.0 eq.) was added to a solution of 12N hydrochloric acid (300 mL), water (300 mL) and acetonitrile (600 mL). To the mixture was added a solution of $NaNO_2$ (15 g, 0.218 mol, 1.2 eq.) in water (20 mL) dropwise at 0° C. The resulting mixture was stirred at 0° C. for 0.5 h, then a solution of potassium ethylxanthate (73 g, 0.456 mol, 2.5 eq.) in water (30 mL) was added dropwise while maintaining the internal temperature below 5° C. After the addition was complete, the resulting mixture was allowed to warm to 23° C. over 0.5 h, extracted with EtOAc (3×300 mL) and the combined organic layers were dried ($Na_2SO_4$) and concentrated. The residue was purified by flash column (PE/EA=2/1, v/v) to afford 10 (50.4 g, 63.8% yield).

Synthesis of Compound 11: A mixture of 10 (50.4 g, 0.116 mol) in 18M $H_2SO_4$ (200 mL) and acetic acid (300 mL) was heated at 100° C. overnight, cooled, poured into water (500 mL) and then filtered. The collected solid was dried in vacuo to afford crude 11 (43.2 g), which was used in the next step without further purification.

Synthesis of Compound 12: A mixture of 11 (43.2 g, 62.8 mmol, 1.0 eq), $PPh_3$ (24.7 g, 94.2 mmol, 1.5 eq) and EDTA (1.83 g, 6.28 mmol, 0.1 eq) in THF (900 mL) and water (300 mL) was stirred at 23° C. for 0.5 h under an inert atmosphere, then evaporated to remove most of THF. The residue was extracted with EtOAc (2×300 mL) and the combined organic layers were dried ($Na_2SO_4$) and concentrated. The residue was purified by flash column (PE/EA=2/1, v/v) to afford 12 (31.0 g, 71.6% yield).

Synthesis of Compound 13: A mixture of 5 (10.0 g, 31.5 mmol, 1.0 eq) and 12 (16.3 g, 47.2 mmol, 1.5 eq) in t-BuOH (1.6 L) was heated at reflux for 2 days under an inert atmosphere, then cooled and concentrated. The residue was purified by prep-HPLC to afford 13 (5.14 g, 28% yield).

Synthesis of Compound 14: A mixture of 13 (10 mg, 0.017 mmol, 1.0 eq), morpholine (1.7 mg, 0.020 mmol, 1.2 eq) and DIEA (3.3 mg, 0.0255 mmol, 1.5 eq) in DMSO (1 mL) was heated at 80° C. overnight, then cooled and poured into water (20 mL). The mixture was extracted with DCM (2×15 mL) and the combined organic layers were dried (Na$_2$SO$_4$) and concentrated. The residue was purified by prep-HPLC to afford 14 (4.7 mg, 43% yield). LRMS: 634 [M+1]$^+$ m/z calculated 634.1, found 634.1. $^1$H NMR (400 MHz, CD$_3$OD): δ 8.11 (t, 1H), 7.88 (t, 1H), 7.67-7.74 (m, 2H), 7.61 (d, 1H), 7.39-7.43 (t, 1H), 5.99 (s, 1H), 4.82 (s, 2H), 3.63-3.66 (m, 7H), 3.51-3.53 (m, 4H), 3.32 (s, 3H).

Synthesis of 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-morpholinopyrimidin-4-amine (16)

Scheme 2:

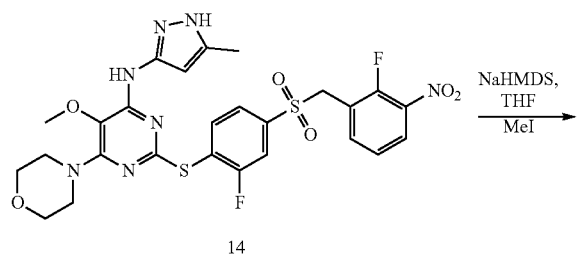

14

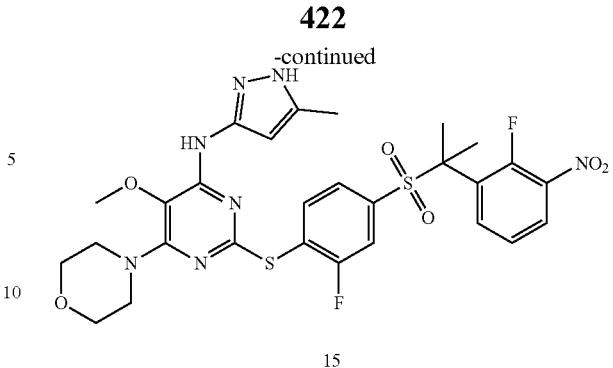

15

Synthesis of Compound 15: To a solution of 14 (0.3 g, 0.474 mmol, 1.0 eq.) in THF (10 mL) was added a solution of NaHMDS (2 M in THF, 16 mL, 3.2 mmol, 6.8 eq) dropwise at −78 OC. After the addition was complete, the resulting solution was maintained at −78° C. for 1 h prior to the dropwise addition of MeI (1.0 g, 7.04 mmol, 14.9 eq). The resulting solution was maintained at −78° C. for another 4 h before being quenched with sat. NH$_4$Cl (sat.) and extracted with EtOAc (2×20 mL). The combined organic layers were dried (Na$_2$SO$_4$) and concentrated to afford 15 (48 mg, 15% yield).

LRMS: 662 [M+1]$^+$ m/z calculated 662.2, found 662.2. $^1$H NMR (300 MHz, CD$_3$OD): δ 8.05-8.06 (m, 1H), 7.80-7.87 (m, 2H), 7.38-7.43 (m, 3H), 5.63 (s, 1H), 3.69-3.74 (m, 4H), 3.67 (s, 3H), 3.54-3.58 (m, 4H), 2.15 (s, 3H), 1.95 (dd, 6H).

Synthesis of N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)acetamide (19)

Scheme 3:

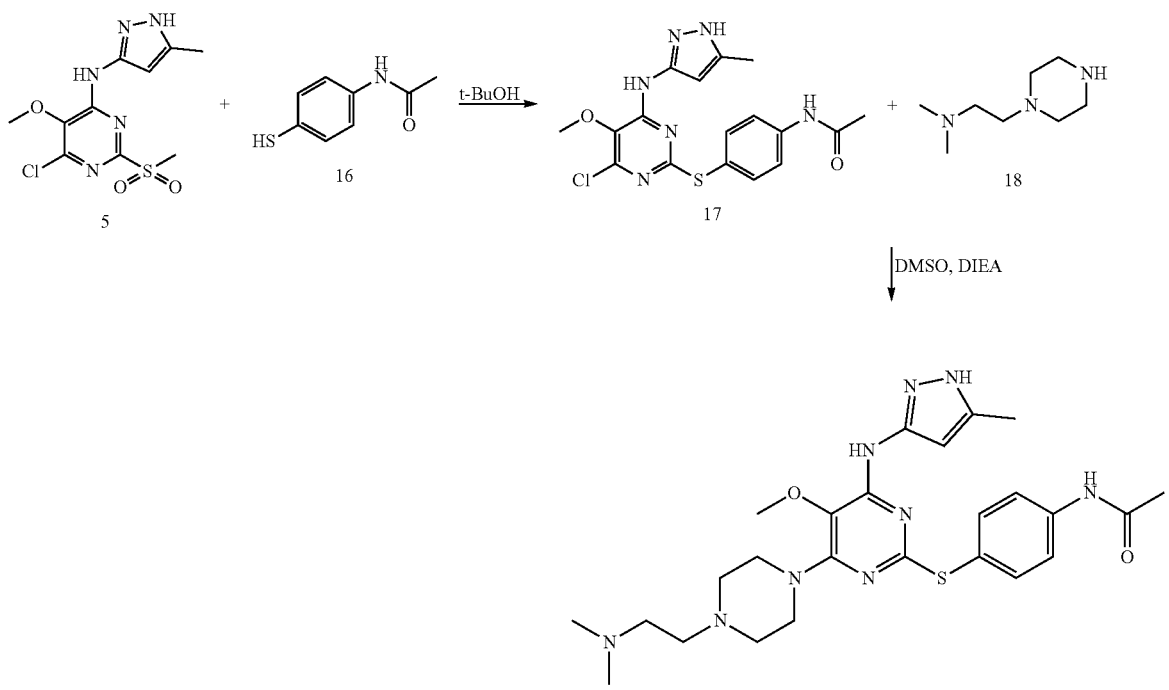

Synthesis of Compound 17: A solution of 5 (7.1 g, 22.4 mmol, 1.0 eq) and 16 (5.6 g, 33.6 mmol, 1.5 eq) in t-BuOH (500 mL) was heated at reflux for 2 days under an inert atmosphere before being cooled and evaporated. The residue was purified by prep-HPLC to afford 17 (6.1 g, 67% yield).

Synthesis of Compound 19: A solution of 17 (1.38 g, 3.4 mmol, 1.0 eq), 18 (1.07 g, 6.8 mmol, 2 eq) and DIEA (0.88 g, 6.8 mmol, 2.0 eq) in DMSO (5 mL) was heated at 80° C. for 2 days and then cooled and poured into water. The mixture was extracted with a mixture of DCM and MeOH (1:20, 2×15 mL). The combined organic layers were dried ($Na_2SO_4$) and concentrated. The residue was purified by flash column chromatography (DCM/MeOH=10/1, v/v) to afford 19 (1.1 g, 61% yield). LRMS: 526 [M+1]$^+$ m/z calculated 526.3, found 526.3. $^1$H NMR (400 MHz, DMSO-d6): δ 11.72 (brs, 1H), 10.16 (s, 1H), 8.30 (brs, 1H), 7.70 (d, 2H), 7.48 (d, 2H), 5.40 (s, 1H), 3.52 (s, 3H), 3.43-3.49 (m, 4H), 2.45-2.49 (m, 4H), 2.33-2-41 (m, 2H), 2.14 (s, 6H), 2.07 (s, 3H), 1.98 (s, 3H).

Synthesis of (2-{2-Fluoro-4-[1-(2-fluoro-3-nitro-phenyl)-cyclopropanesulfonyl]-phenylsulfanyl}-5-methoxy-6-morpholin-4-yl-pyrimidin-4-yl)-(5-methyl-1H-pyrazol-3-yl)-amine (25)

Scheme 4:

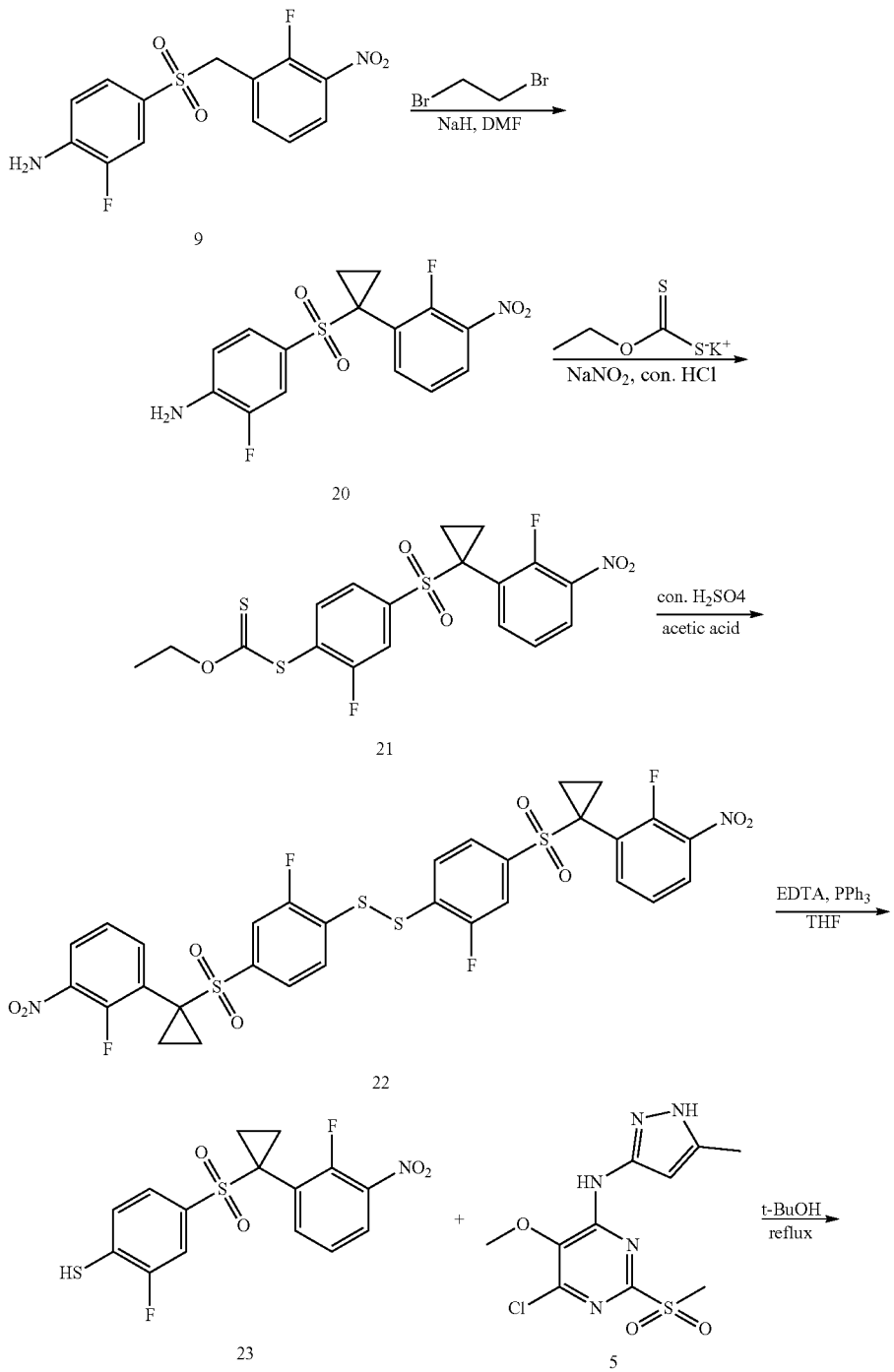

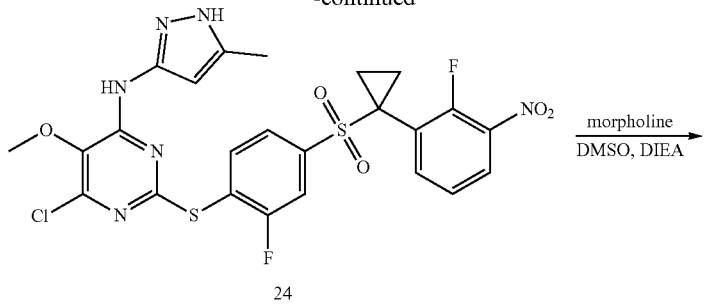

24

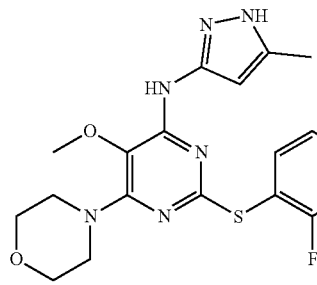

25

Synthesis of Compound 20. NaH ((60%, 12.0 g, 0.302 mol, 4.5 eq) was added to a solution of 9 (22.0 g, 0.067 mol, 1.0 eq) in DMF (2000 mL) at 0° C. The mixture was stirred at 0° C. for 1 h before the dropwise addition of 1,2-dibromoethane (22 mL, 0.175 mol, 2.6 eq). The resulting mixture was stirred for an additional 1 h at 0° C. before being poured onto ice-water (3000 mL) and extracted with DCM (3×200 mL). The combined organic layers were washed with brine (200 mL), dried ($Na_2SO_4$) and concentrated. The residue was purified by flash column chromatography (PE/EA=2/1, v/v) to give 20 (9.4 g, 40% yield).

Synthesis of Compound 21. To a solution of 20 (5.0 g, 0.014 mol, 1.0 eq), 12 N hydrochloric acid (25 mL), water (25 mL) and acetonitrile (50 mL) at 0° C. was added a solution of $NaNO_2$ (1.45 g, 0.021 mol, 1.5 eq) in water (2 mL), dropwise, while maintaining the internal temperature below 5° C. The resulting suspension was stirred at 0° C. for 0.5 h before the dropwise addition of a solution of potassium ethylxanthate (5.6 g, 0.035 mol, 2.5 eq) in water (3 mL), while maintaining the internal temperature below 5° C. The resulting solution was maintained at 0° C. for 0.5 h before being extracted with EtOAc (3×25 mL). The combined organic layers were dried ($Na_2SO_4$) and concentrated. The residue was purified by flash column chromatography (PE/EA=4/1, v/v) to provide 21 (3.0 g, 46% yield).

Synthesis of Compound 22. A solution of 21 (3.0 g, 6.5 mmol), concentrated $H_2SO_4$ (20 mL) and acetic acid (40 mL) was heated at 100° C. for 16 h before being cooled, poured into water (50 mL) and filtered. The collected residue was dried in vacuo to afford crude 22 (3.5 g), which was used in the next step without further purification.

Synthesis of Compound 23. A solution of 22 (3.5 g, 4.73 mmol, 1.0 eq), $PPh_3$ (1.86 g, 7.10 mmol, 1.5 eq) and EDTA (137 mg, 0.47 mmol, 0.1 eq) in THF (30 mL) and water (6 mL) was maintained at 25° C. for 2 h before being concentrated and extracted with EtOAc (2×30 mL). The combined organic layers were dried ($Na_2SO_4$) and concentrated. The residue was purified by flash column chromatography (DCM/MeOH=20/1, v/v) to give 23 (2.1 g, 88% yield).

Synthesis of Compound 24. A solution of 5 (1.5 g, 4.72 mmol, 1.0 eq) and 23 (2.1 g, 5.66 mmol, 1.2 eq) in t-BuOH (700 mL) was maintained at reflux for 48 h before being concentrated. The residue was purified by flash column chromatography (DCM/MeOH=20/1, v/v) to provide 24 (1.8 g, 63% yield).

Synthesis of Compound 25. A solution of 24 (60 mg, 0.099 mmol, 1.0 eq), morpholine (10 mg, 0.115 mmol, 1.2 eq) and DIEA (19 mg, 0.145 mmol, 1.5 eq) in DMSO (2 mL) was maintained at 80° C. for 16 h before being cooled and poured into water (20 mL). The resulting mixture was extracted with DCM (2×15 mL) and the combined organic layers were dried ($Na_2SO_4$) and concentrated. The residue was purified by prep-HPLC to afford 25 (38 mg, 58% yield). LR-MS: 660 $[M+1]^+$ m/z calculated 660.1, found 660.1. $^1$H NMR (400 MHz, $CD_3OD$): δ 8.08 (t, 1H), 7.83 (t, 1H), 7.55 (t, 1H), 7.40-7.45 (m, 2H), 7.31 (t, 1H), 5.60 (s, 1H), 3.68 (t, 4H), 3.65 (s, 3H), 3.55 (t, 4H), 2.13 (s, 3H), 2.08 (t, 2H), 1.48 (t, 2H).

Example 3. Reversible Centriole Depletion with a Plk4 Inhibitor

Abstract. Supernumerary centrosomes are a common feature of human cancers. To test the importance of centrosomes in the proliferation of normal and cancerous human cells, we developed centrinone, a specific reversible inhibitor of Plk4—the kinase that initiates centriole assembly. Centrinone enables routine centrosome depletion from human and other vertebrate cells. Centrosome loss irreversibly arrested normal cells in a senescence-like G1 state via a p53-dependent mechanism that was independent of DNA damage/stress/Hippo signaling, extended mitotic duration, or segregation errors. In contrast, cancer cell lines with normal or amplified centrosome numbers could proliferate indefinitely following centrosome loss. Upon centrinone washout, each cancer cell line returned to an intrinsic centrosome number 'set point'. Thus, cells with cancer-associated mutations fundamentally differ from normal cells in their response to centrosome loss.

Results and Discussion

Centrioles template assembly of cilia and recruit pericentriolar material to form centrosomes (1,2). Centriole duplication is tightly controlled so that mitotic cells have precisely two centrosomes (3,4). Supernumerary centrosomes are prevalent in cancer and have been postulated to contribute to tumorigenesis (5-7), perhaps by promoting chromosomal instability (8,9) or increasing cellular invasiveness (10). However, whether cancer cells become dependent upon extra centrosomes for proliferation is unknown.

Figure 1B:
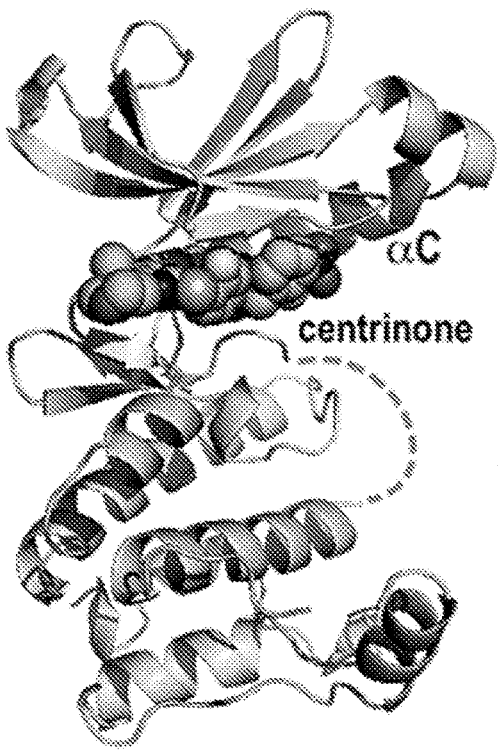
Figure 1C:
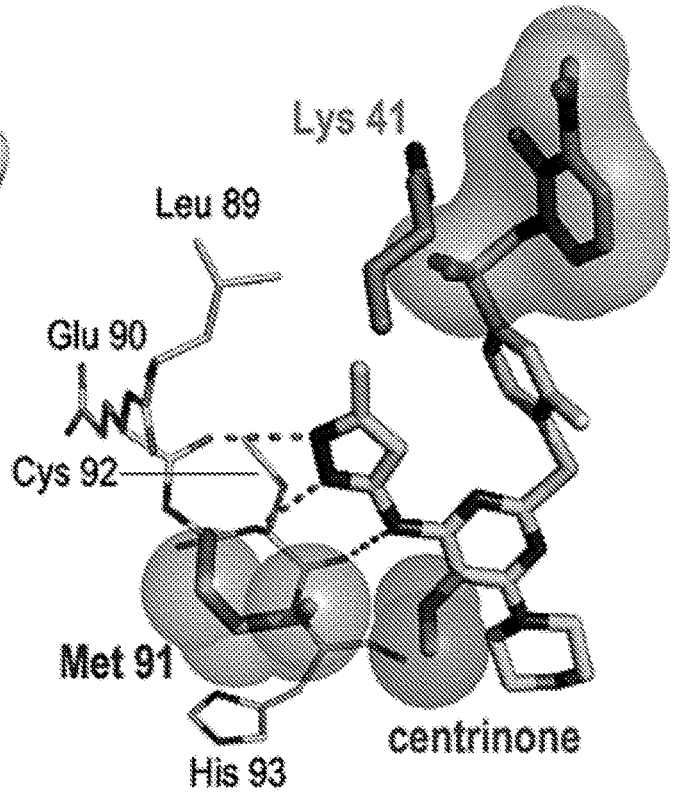
Figure 5A:
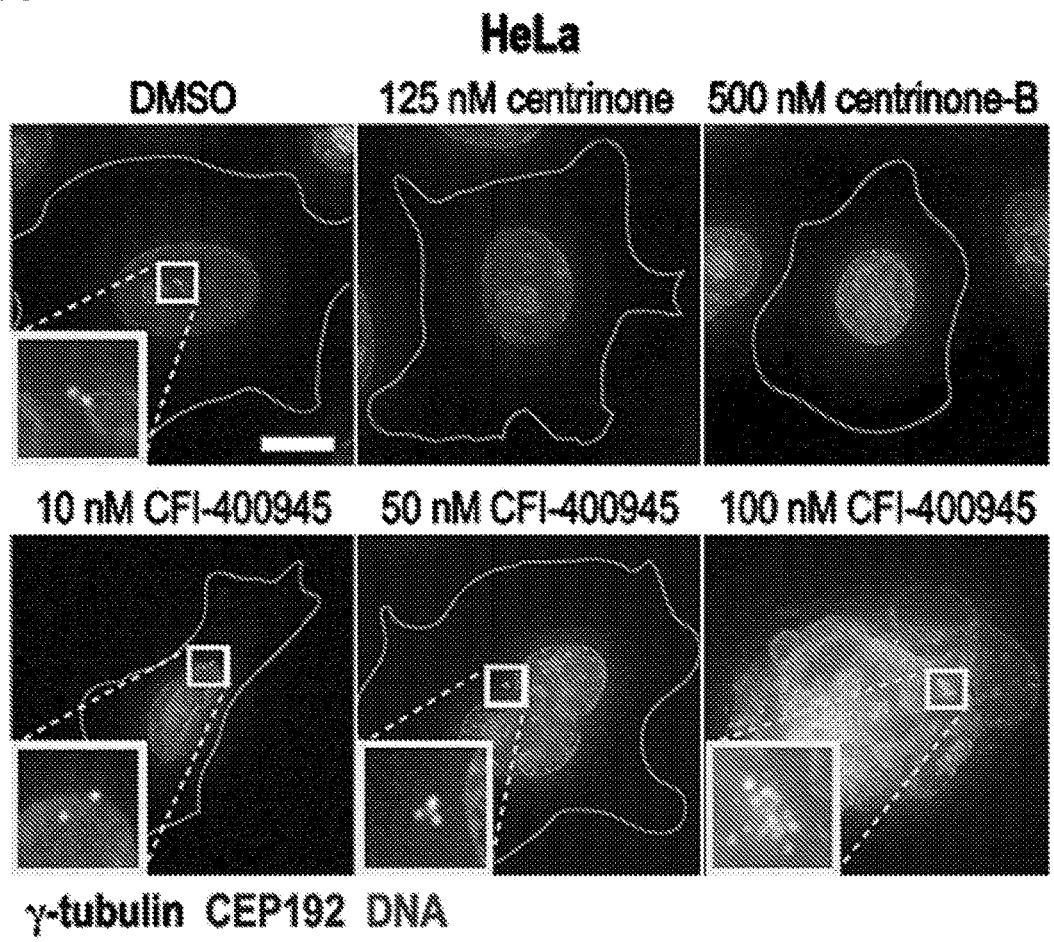
FIGS. 5A-5C. CFI-400945 is a non-selective Plk4 inhibitor that does not deplete centrioles from cells. Treatment of HeLa cells with 50 or 100 nM CFI-400945 causes centrosome amplification, likely due to partial blockade of Plk4 autophosphorylation-mediated degradation (52). At these concentrations, CFI-400945-treated cells also become grossly multinuclear (see examples in A) and stop dividing, presumably due to Aurora B inhibition (18,19).
Figure 5B:
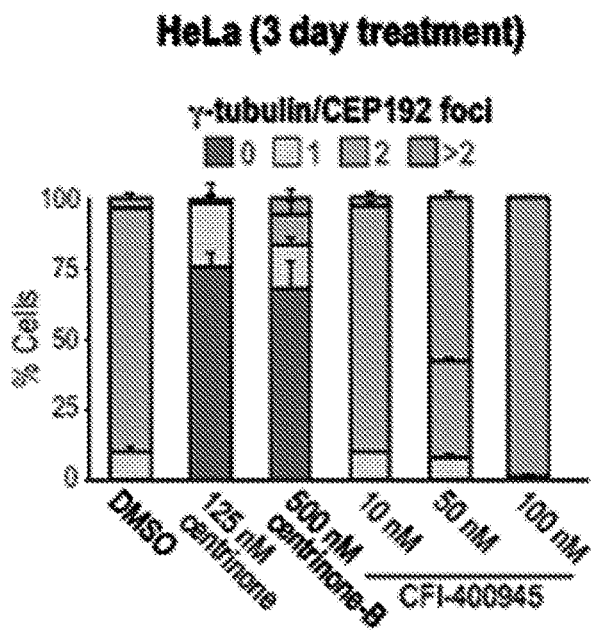
Figure 5C:
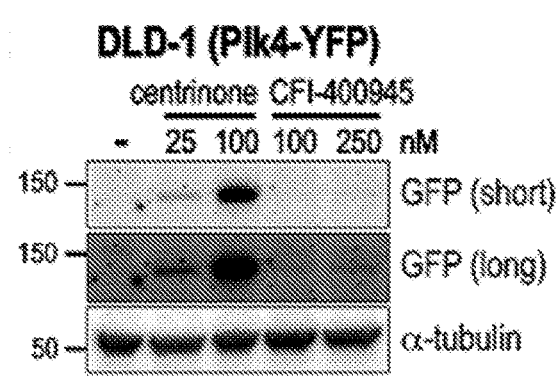
Figure 6A:
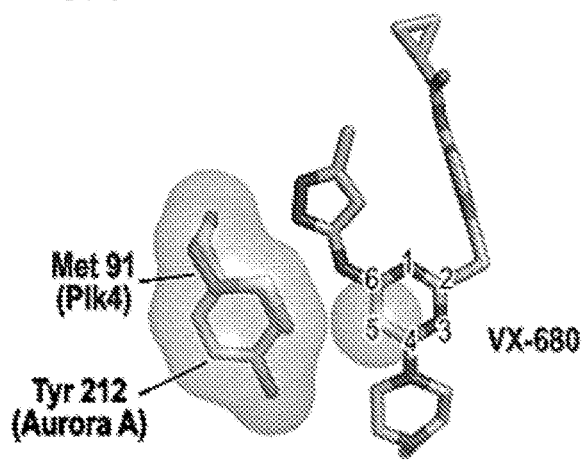
FIGS. 6A-6E. Centrinone is a selective Plk4 inhibitor that depletes centrioles from cells.
Figure 6B:
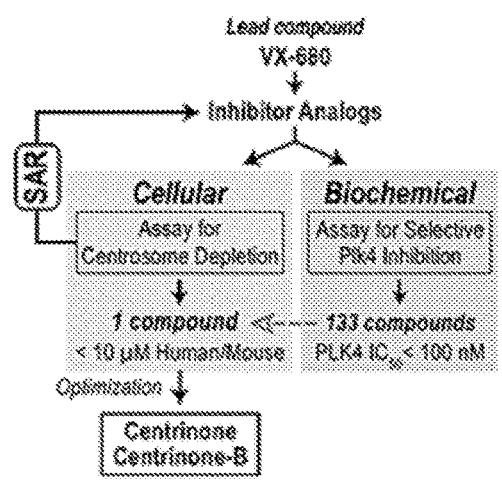
Figure 6C:
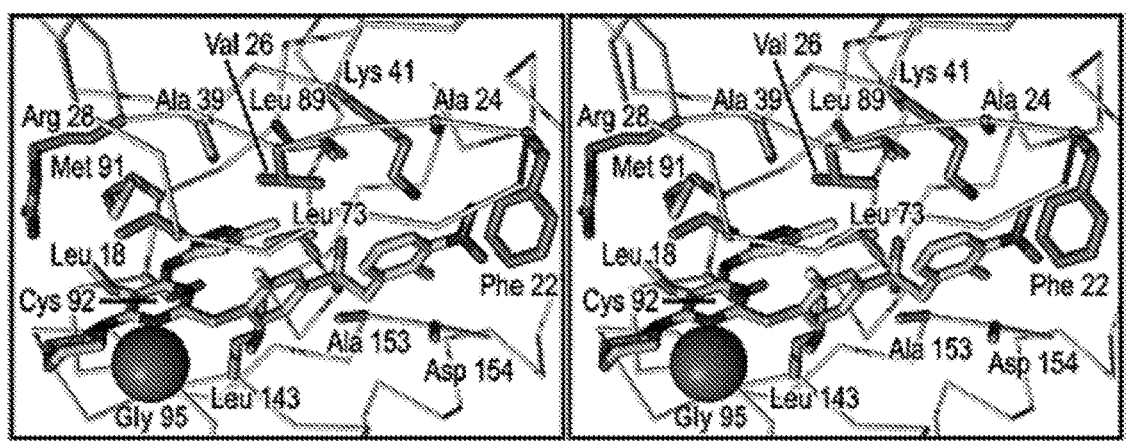
Figure 6D:
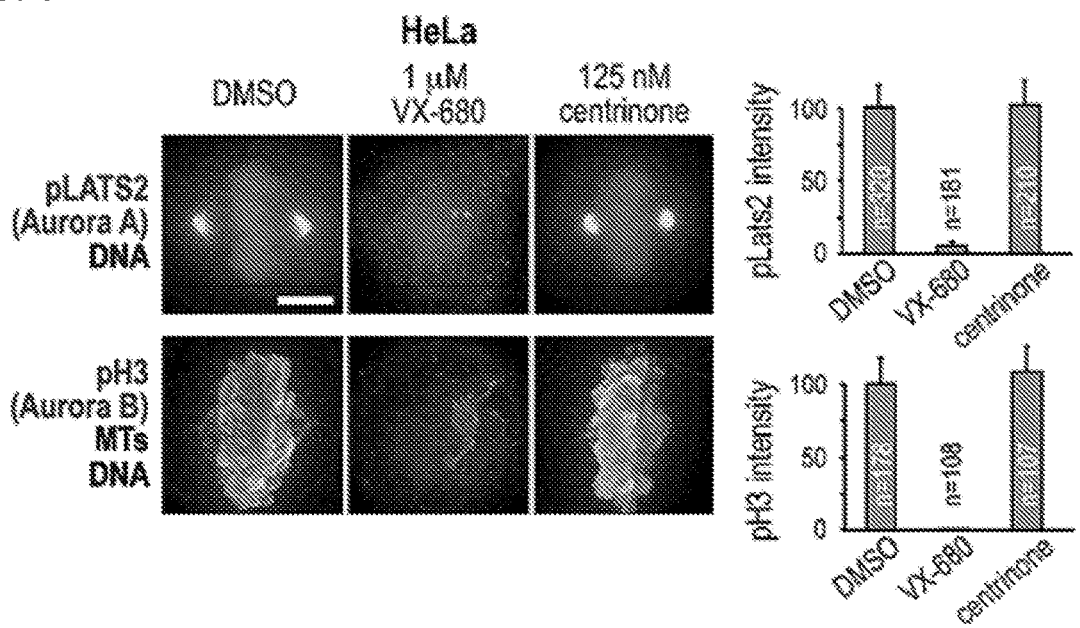

Centriole assembly is controlled by the Polo family kinase Plk4 (11-15). Of all compounds previously reported to bind Plk4, only CFI-400945 and related analogs exhibit any in vitro Plk4 selectivity (16-20), and none prevent centriole assembly in cells. CFI-400945 also induces centrosome amplification and phenotypes associated with Aurora B inhibition (FIGS. 5A-5C (18)). Therefore, to develop a selective Plk4 inhibitor with in vivo efficacy, we chose the pan-Aurora kinase inhibitor VX-680, which also inhibits Plk4 (16,17,20), as a template (FIGS. 6A-6B). Motivated by modeling, we introduced a methoxy substituent at the VX-680 C5 position (shading in FIG. 1A) to target the relatively unique hinge methionine in Plk4 (Met 91) (FIG. 6B) and generated a compound with ~15-fold in vitro preference for Plk4 over Aurora A. From an additional 390 analogs synthesized and characterized, 133 (34%) had $IC_{50}s \leq 100$ nM for Plk4 in vitro, but only one, LCR-015 (in which the VX-680 cyclopropylamide was replaced with a benzylsulfone; orange shading in FIG. 1A), depleted centrosomes in NIH/3T3 and HCT-116 cells at concentrations <10 μM (FIG. 6A). Optimization of LCR-015 produced two highly selective Plk4 inhibitors with robust cellular activity: centrinone (LCR-263; $K_i$=0.16 nM in vitro; centrosome depletion at 100 nM) and centrinone-B (LCR-323; $K_i$=0.6 nM in vitro; centrosome depletion at 500 nM) (FIG. 1A). A 2.65 Å centrinone/Plk4 kinase domain co-crystal structure (FIG. 1B-1C; Table 3) revealed that the benzylsulfone moiety required for cellular activity (FIGS. 1A, 1C) wraps around the catalytic lysine (Lys 41) and forms hydrophobic contacts with Asp 154 of the DFG motif (FIG. 1C; FIG. 6C), suppressing transition to the active state. Both centrinones were >1000-fold selective for Plk4 versus Aurora A/B (FIG. 1A; Table 4) in vitro and did not affect cellular Aurora A or B substrate phosphorylation at concentrations that deplete centrosomes (FIG. 6D). In vitro screening against 442 human kinases (16) at ~500×$K_i$ and subsequent dose response analysis indicated high selectivity (Table 5), particularly against mitotic kinases. While we report data obtained with centrinone, key results were replicated with centrinone-B.

TABLE 3

Data collection and refinement statistics.

| Data collection | Centrinone/Plk4 kinase domain |
|---|---|
| Resolution (Å) | 62.9-2.65 |
| Space Group | I23 |
| Unit Cell Dimensions (a, b, c) Å | 125.8, 125.8, 125.8 |
| Unit cell Angles (α, β, γ) ° | 90, 90, 90 |
| I/σ (last shell) | 30.4 (1.7) |
| $^aR_{sym}$ (last shell) | 0.102 (2.423) |
| $^bR_{meas}$ (last shell) | 0.104 (2.478) |
| $^cCC_{1/2}$ (last shell) | 1.000 (0.632) |
| Completeness (last shell) % | 100.0 (100.0) |
| Number of reflections | 217426 |
| Unique | 9793 |
| Multiplicity (last shell) | 22.2 (22.5) |
| Refinement | |
| Resolution (Å) | 62.9-2.65 (3.04-2.65) |
| Number of reflections | |
| Working | 9313 |
| Free | 469 |
| $^dR_{work}$ (last shell) (%) | 19.92 (25.26) |
| $^dR_{free}$ (last shell) (%) | 26.95 (36.54) |
| Structure/Stereochemistry | |
| Number of atoms | 1750 |
| Solvent | 43 |
| Ligand | 12 |
| r.m.s.d. bond lengths (Å) | 0.008 |
| r.m.s.d. bond angles (°) | 1.389 |
| Average B-Factor | 47.07 |
| Protein Data Bank ID$^e$ | 4YUR |

$^aR_{sym} = \Sigma\Sigma j |I_j - \langle I \rangle|/\Sigma I_j$, where $I_j$ is the intensity measurement for reflection j and $\langle I \rangle$ is the mean intensity for multiply recorded reflections.

$^bR_{meas} = \Sigma_h [\sqrt{(n/(n-1))} \Sigma_j [I_{hj} - \langle I_h \rangle]]/\Sigma_{hj} \langle I_h \rangle$, where $I_{hj}$ is a single intensity measurement for reflection h, $\langle I_h \rangle$ is the average intensity measurement for multiply recorded reflections, and n is the number of observations of reflection h.

$^cCC_{1/2}$ is the Pearson correlation coefficient between the average measured intensities of two randomly-assigned half-sets of the measurements of each unique reflection (63). $CC_{1/2}$ is considered significant above a value of ~0.15.

$^dR_{work, free} = \Sigma ||F_{obs}| - |F_{calc}||/|F_{obs}|$, where the working and free R-factors are calculated using the working and free reflection sets, respectively.

$^e$Coordinates and structure factors have been deposited with the Protein Data Bank (World Wide Web pdb.org) with the noted accession code.

TABLE 4

$K_i$ values and selectivities of centrinone, centrinone-B and VX-680 for inhibitor-resistant mutant Plk4 (G95L) and Aurora A/B. Selectivity is defined as $K_i$(kinase)/$K_i$(Plk4).

| | $K_i$ (nM) | | | Plk4 selectivity | | |
|---|---|---|---|---|---|---|
| Kinase | Centrinone | Centrinone-B | VX-680 | Centrinone | Centrinone-B | VX-680 |
| Plk4 | 0.16 | 0.59 | 7.66 | — | — | — |
| Plk4 (G95L) | 68.57 | 497.53 | 9291.67 | 432 | 847 | 1213 |
| Aurora A | 171.00 | 1239.00 | 0.65 | 1078 | 2108 | 0.08 |
| Aurora B | 436.76 | 5597.14 | 3.36 | 2754 | 9523 | 0.44 |

TABLE 5

$K_i$ values and selectivities of centrinone and centrinone-B for the top 7 identified off-targets from DiscoveRx kinome profiling. Selectivity is defined as $K_i$(kinase)/$K_i$(Plk4).

| Kinase | $K_i$ (nM) Centrinone | $K_i$ (nM) Centrinone-B | Plk4 selectivity Centrinone | Plk4 selectivity Centrinone-B |
|---|---|---|---|---|
| Plk4 | 0.16 | 0.59 | — | — |
| TNK1 | 1.38 | 6.04 | 9 | 10 |
| LRRK2 | 2.08 | 7.66 | 13 | 13 |
| ROS/ROS1 | 2.77 | 90.07 | 18 | 153 |
| FLT4/VEGFR3 | 6.29 | 58.04 | 40 | 99 |
| RET | 13.92 | 195.25 | 88 | 332 |
| JAK2 | >150 | >500 | >938 | >847 |
| SRPK1 | >150 | >500 | >938 | >847 |

Figure 1D:
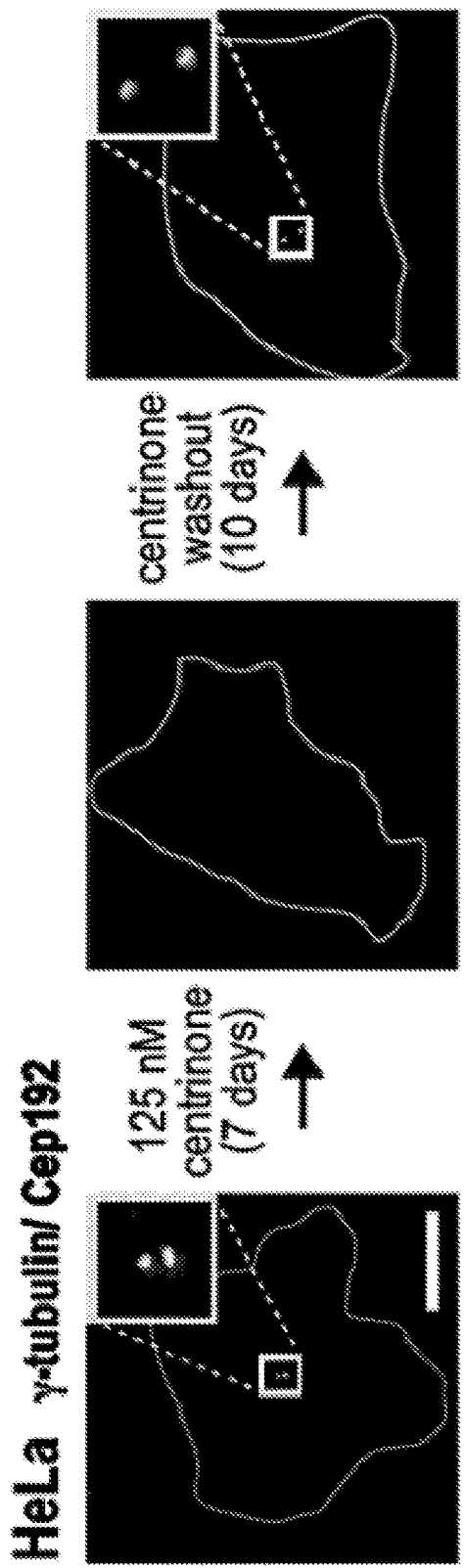
Figure 1D:
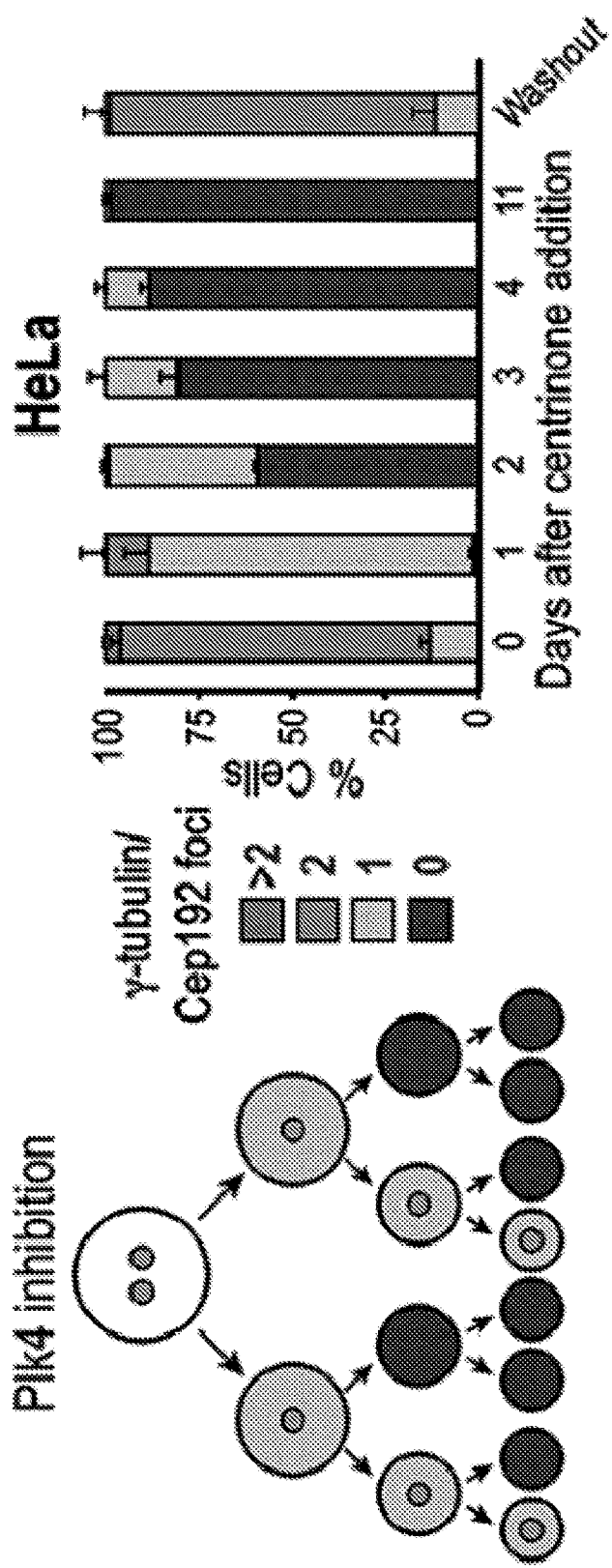
Figure 1E:
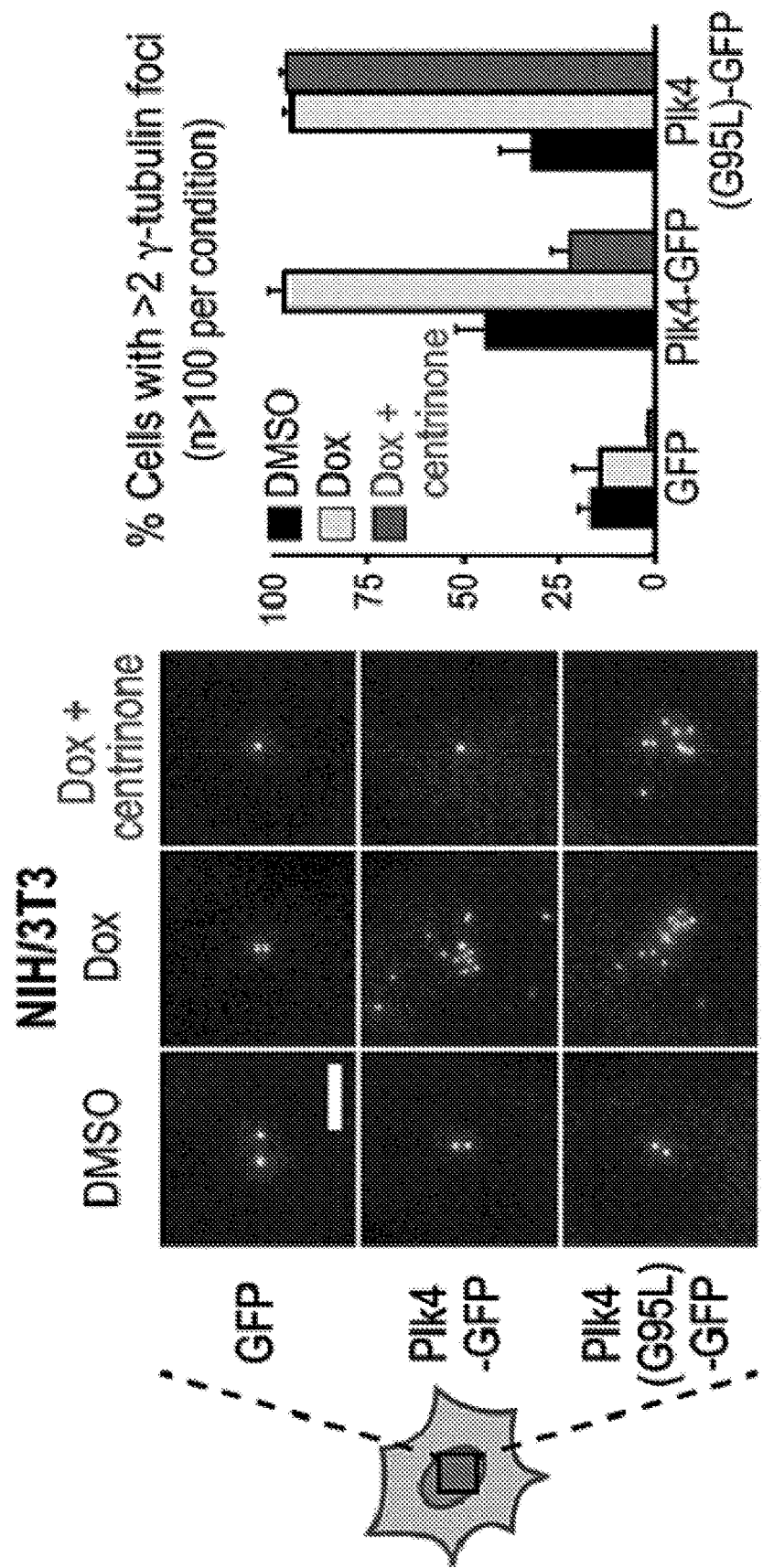
Figure 6E:
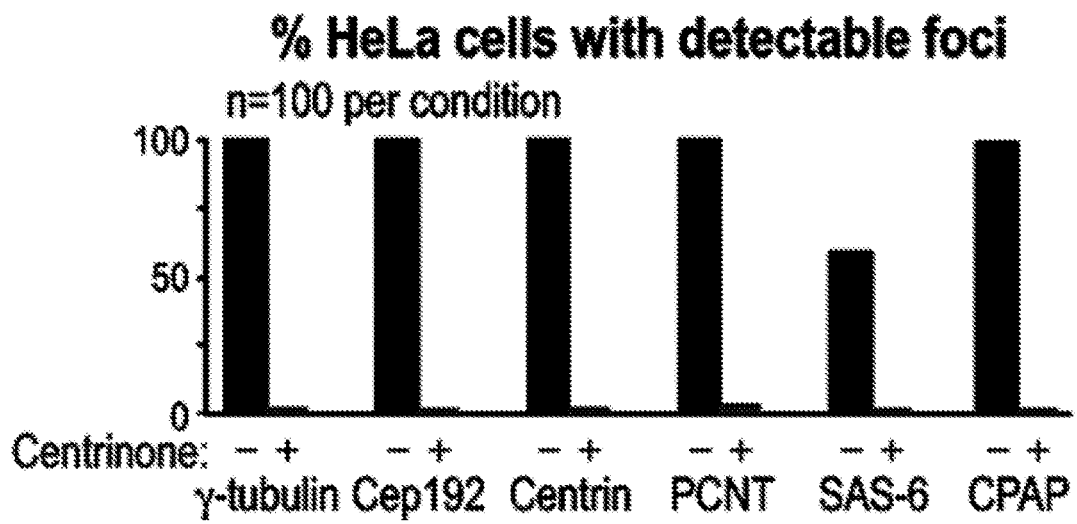
Figure 7A:
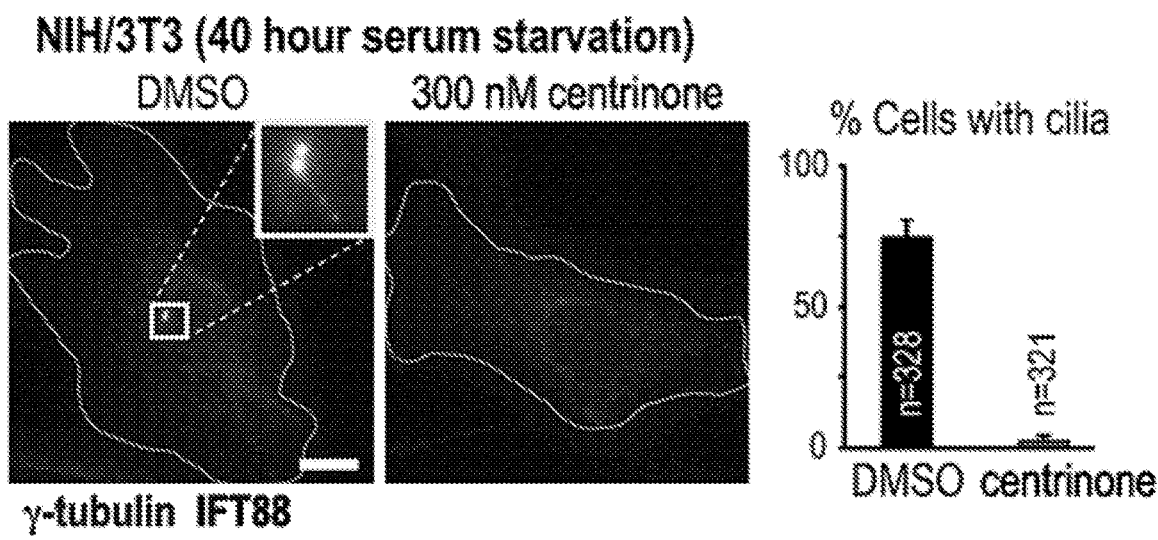
FIGS. 7A-7C. Centrinone prevents assembly of primary cilia and centrosomal microtubule-organizing centers but Golgi organization is largely normal.
Figure 7B:
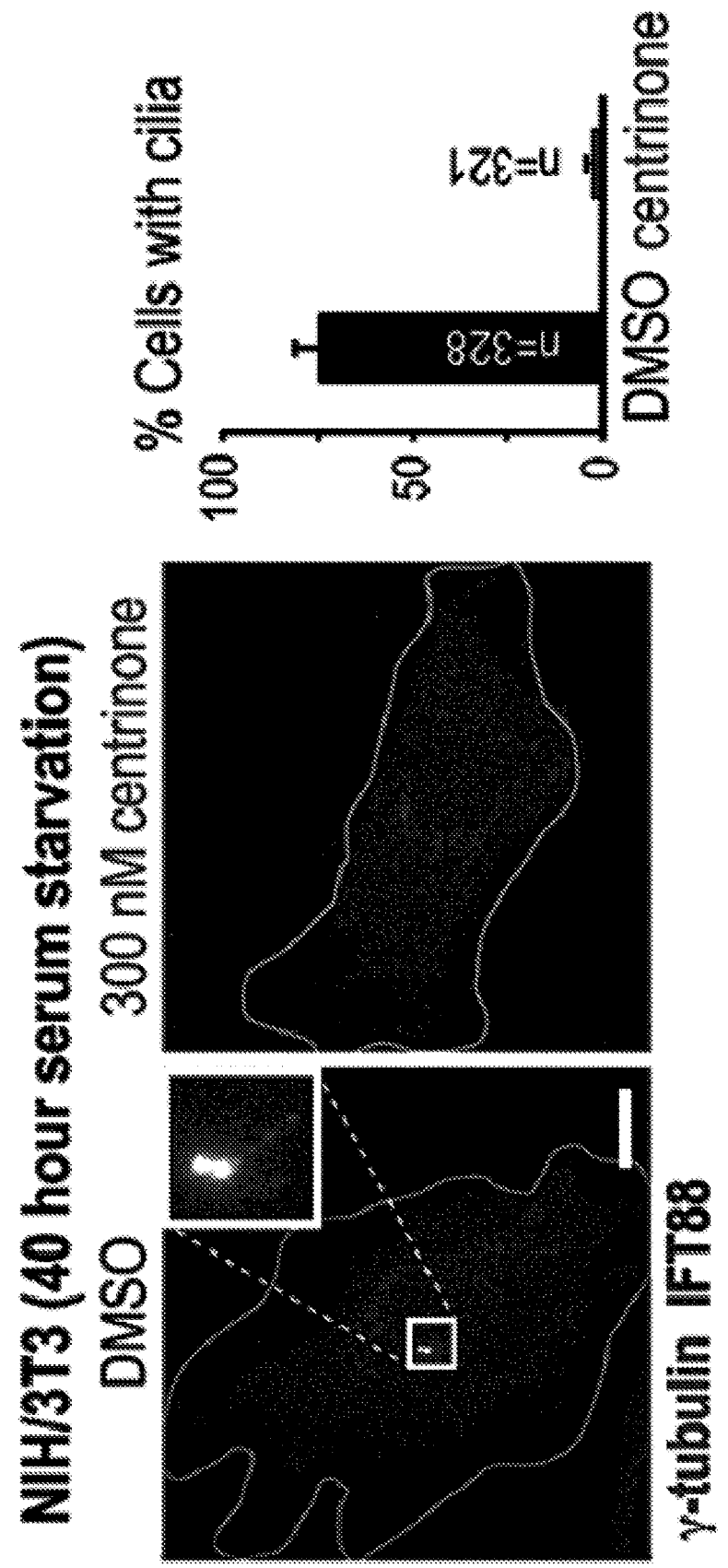
Figure 7C:
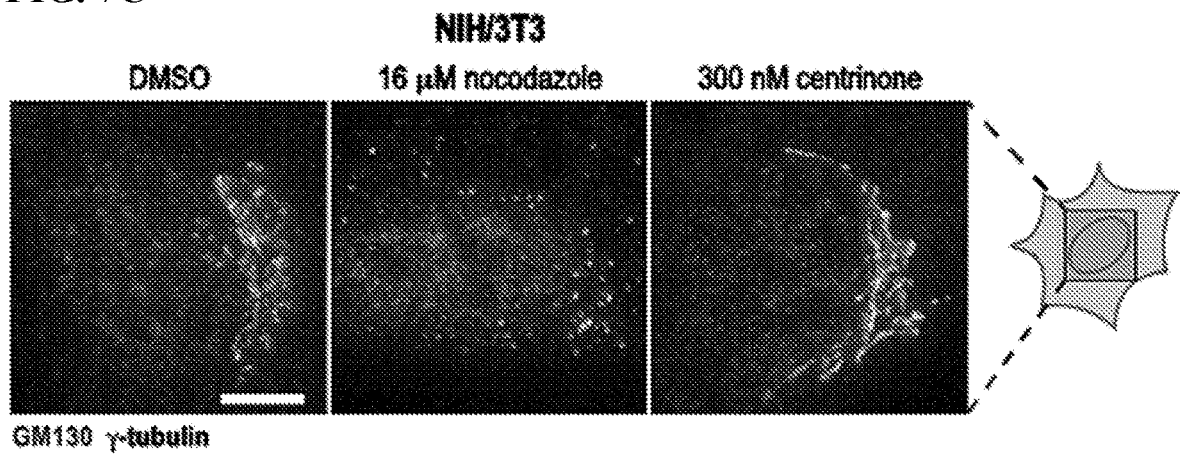
Figure 8A:
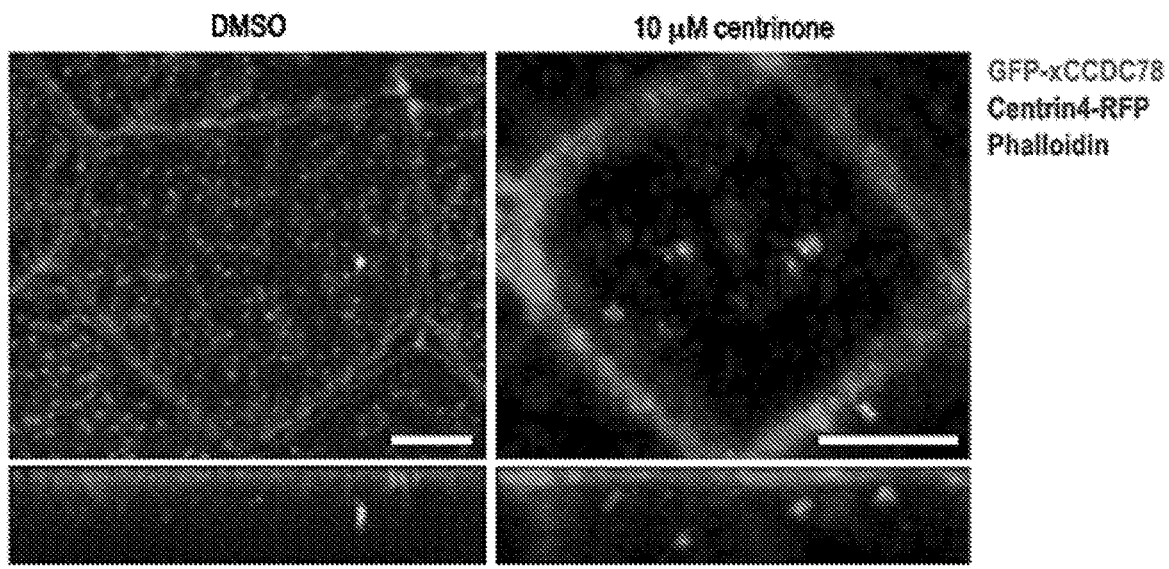
FIGS. 8A-8B. Centrinone inhibits centriole assembly in Xenopus multiciliated cells. Dexamethasone-induced Multicilin expression leads to the formation of ectopic multiciliated cells that cover the entire ectoderm in Xenopus embryos (50). These cells contain numerous centrioles that are primarily generated from structures called deuterosomes that are marked by xCCDC78 and also recruit Plk4 (51).
Figure 8B:
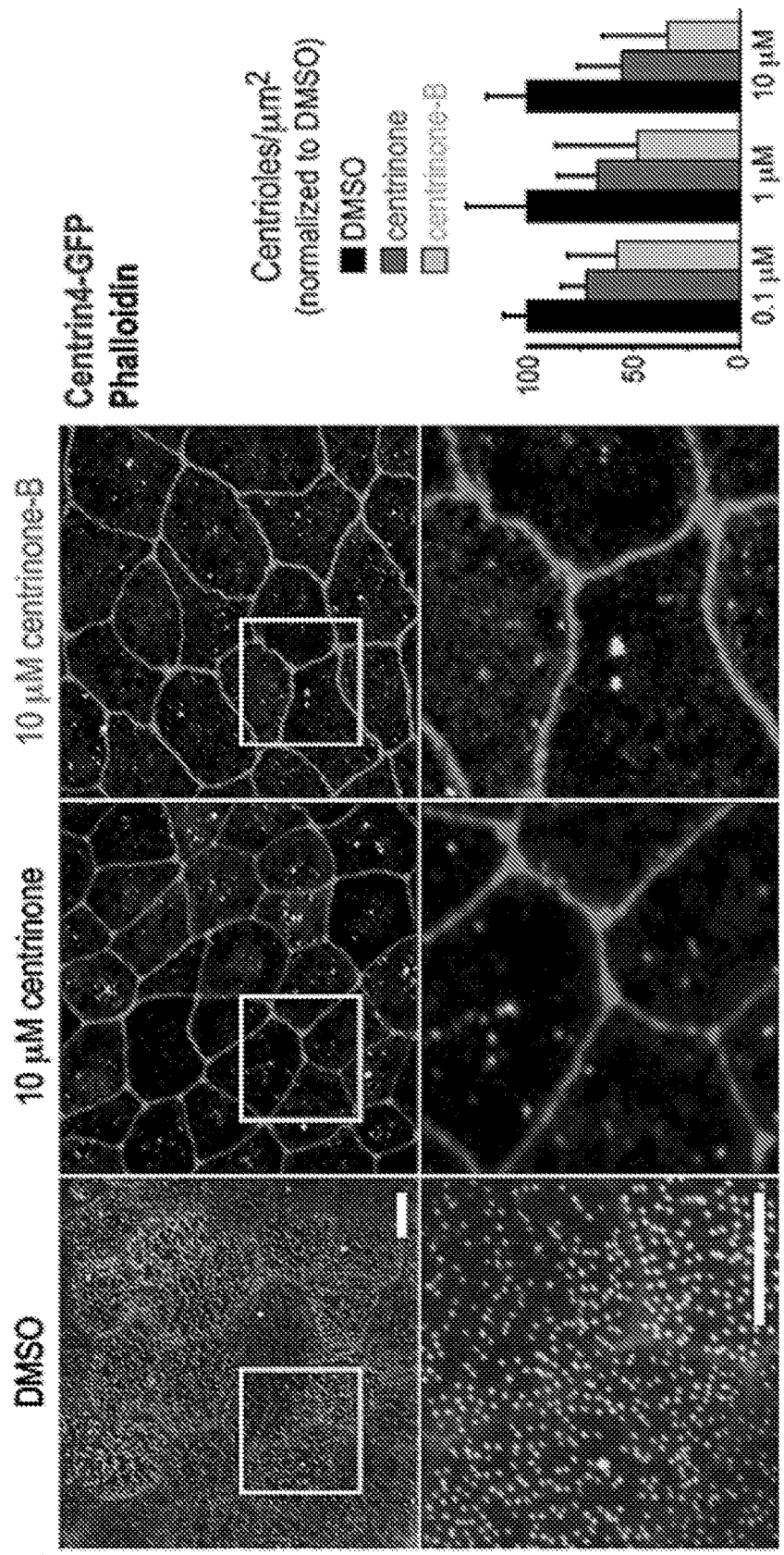
Figure 9A:
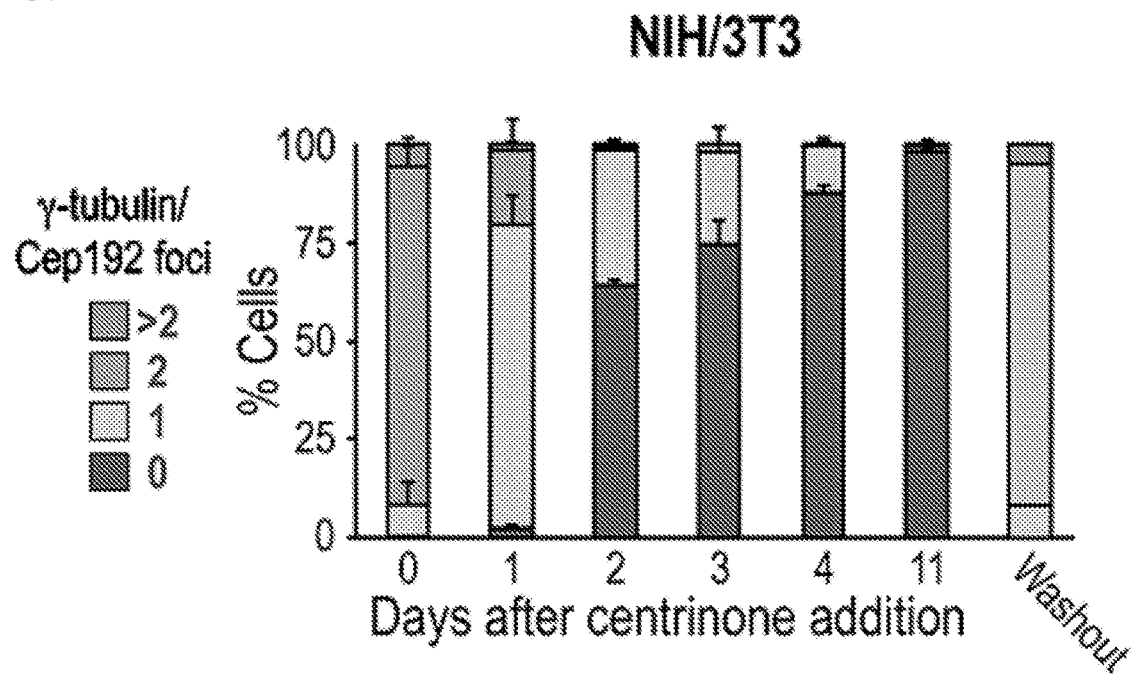
FIGS. 9A-9B. HeLa and NIH/3T3 cells proliferate indefinitely without centrosomes.
Figure 9B:
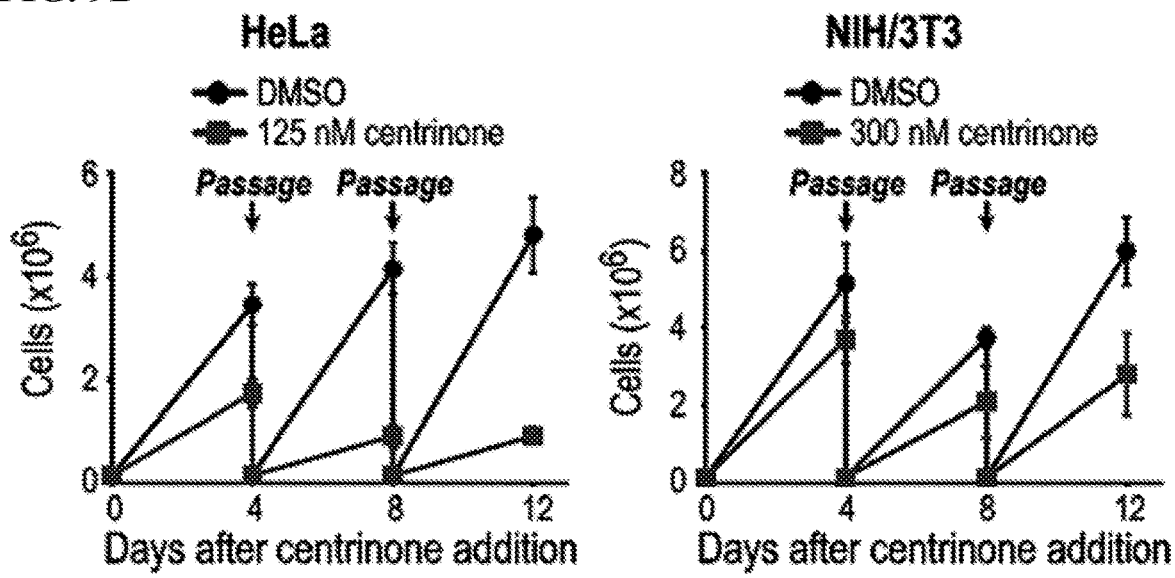

Plk4 inhibition prevents new centriole assembly without disassembling pre-existing centrioles (11,12,14). Consistent with this, centrinone treatment of HeLa cells led to a progressive reduction in foci containing centriolar and pericentriolar material markers at each round of cell division, until most cells lacked centrioles/centrosomes (FIG. 1D; FIG. 6E). Centriole loss prevented formation of primary cilia and resulted in absence of focal microtubule organization during recovery from nocodazole treatment (FIGS. 7A-7B). Golgi organization was unaffected (FIG. 7C), consistent with its ability to nucleate microtubules independently of centrosomes (21). Centriole loss was fully reversible; 10 days following centrinone washout, all cells exhibited normal centrosome numbers (FIG. 1D). Treatment with centrinone reduced centriole number in multiciliated Xenopus epithelial cells, indicating that Plk4 also controls centriole amplification in differentiated cells (FIGS. 8A-8B). To confirm that these effects were due to Plk4 inhibition, we generated a Plk4 mutant (G95L) with wild-type biochemical activity that sterically hindered centrinone binding ($K_i$, mutant/$K_i$, wild-type >400, Table 4; FIG. 6C). Treatment with centrinone blocked centriole amplification in cells overexpressing wild-type, but not G95L, Plk4 (FIG. 1E), confirming that centrinone prevents centriole assembly by inhibiting Plk4.

Figure 2A:
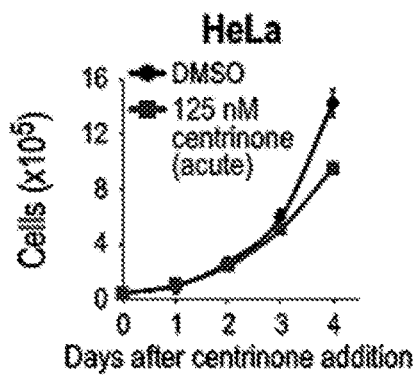
FIGS. 2A-2G. Transformed cells proliferate indefinitely in the absence of centrosomes.
Figure 2A:
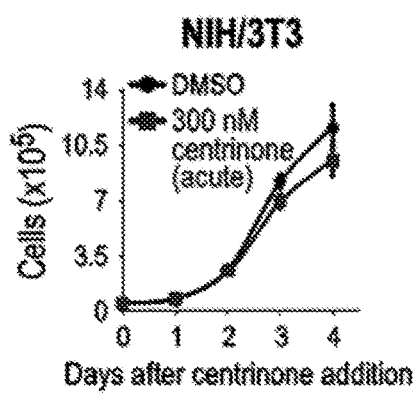
Figure 2B:
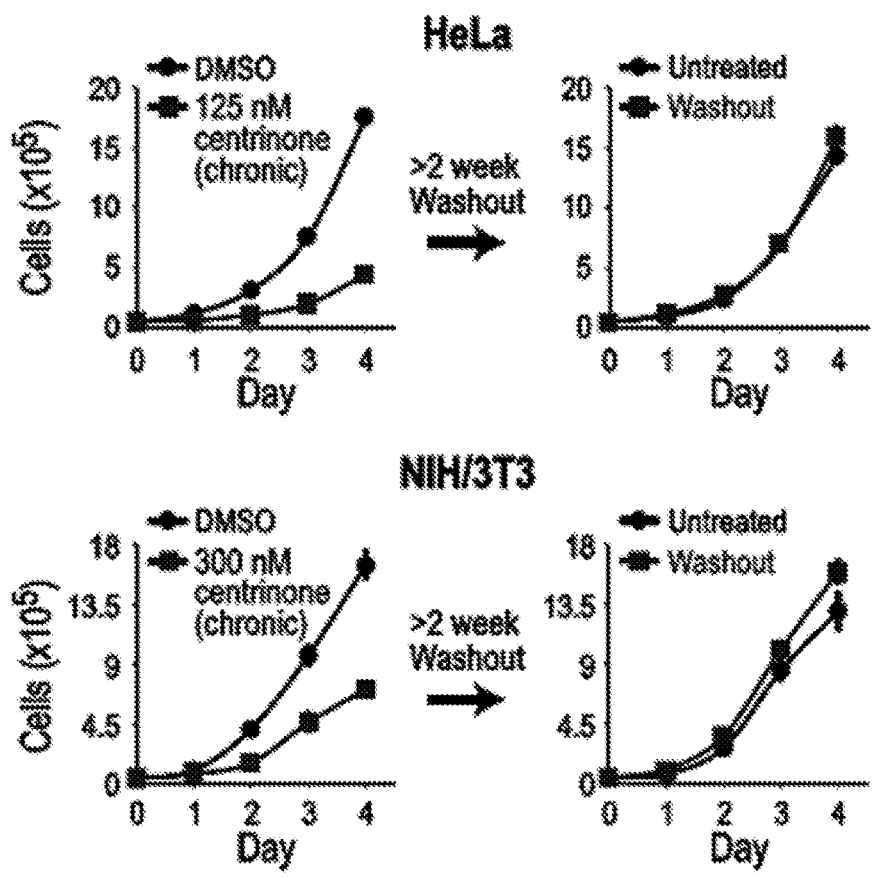
Figure 10A:
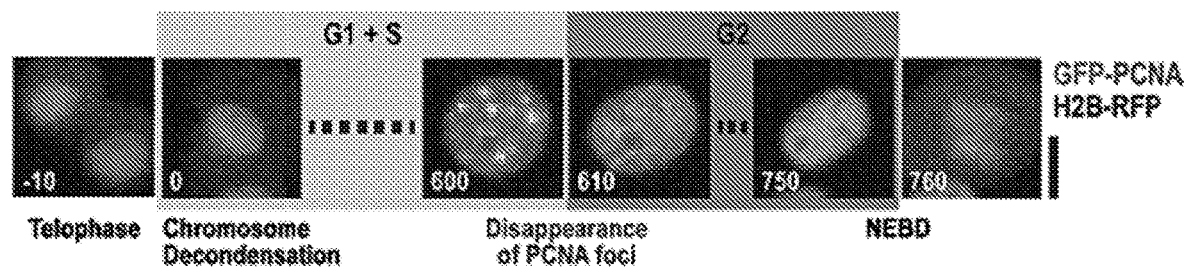
FIGS. 10A-10D. Centrosome loss does not affect interphase duration but leads to an increase in apoptotic cell death. To determine how centrosome removal led to a reduction in population growth, we first analyzed whether centrosome-less cells exhibit altered progression through interphase. We measured the duration of G1+S and G2 in control and centrosome-less HeLa and NIH/3T3 cells engineered to co-express GFP-PCNA and H2B-RFP. The H2B-RFP enables monitoring chromosome decondensation and nuclear envelope breakdown (NEBD), which mark the M/G1 and G2/M transitions, respectively. GFP-PCNA localizes to nuclear foci representing sites of active DNA replication that form during S-phase and persist until the S/G2 boundary (56), enabling assessment of the end of S phase.
Figure 10B:
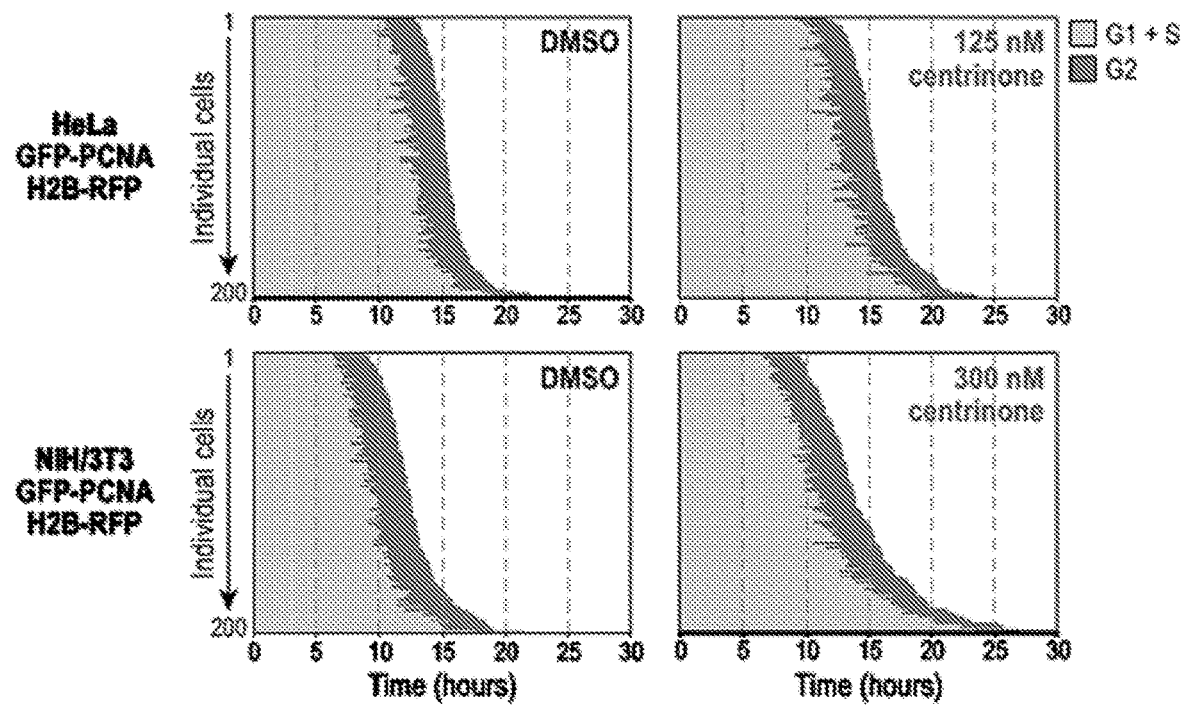
Figure 10C:
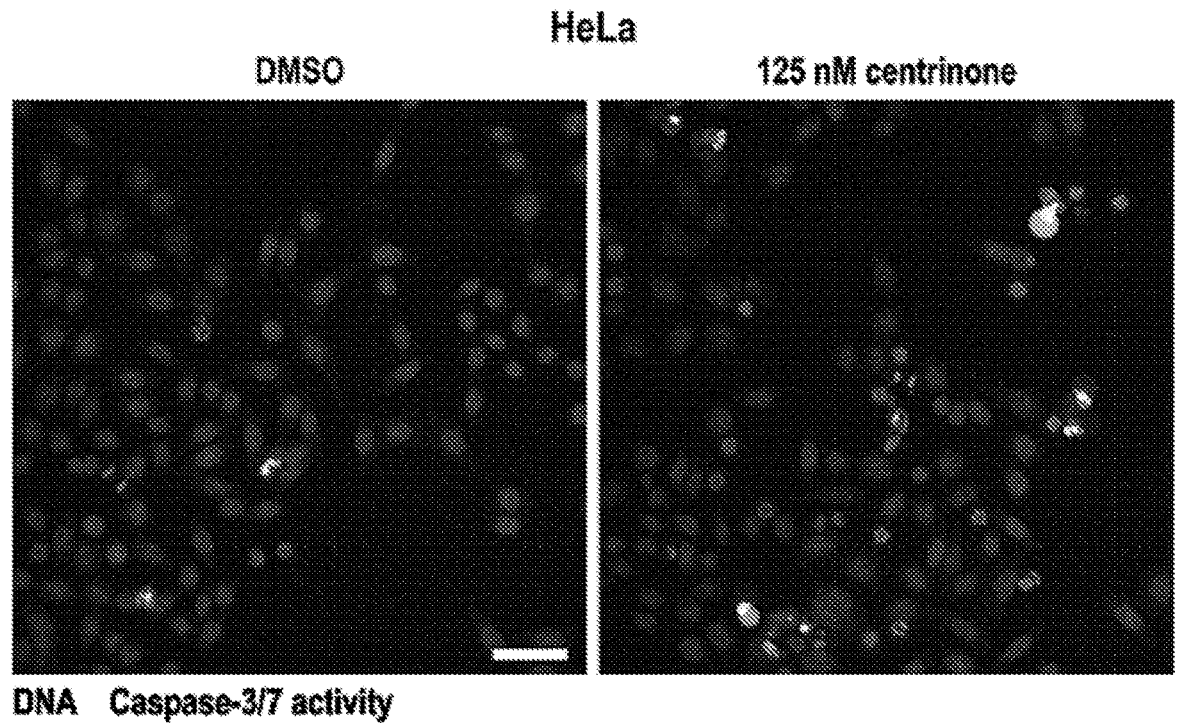
Figure 10D:
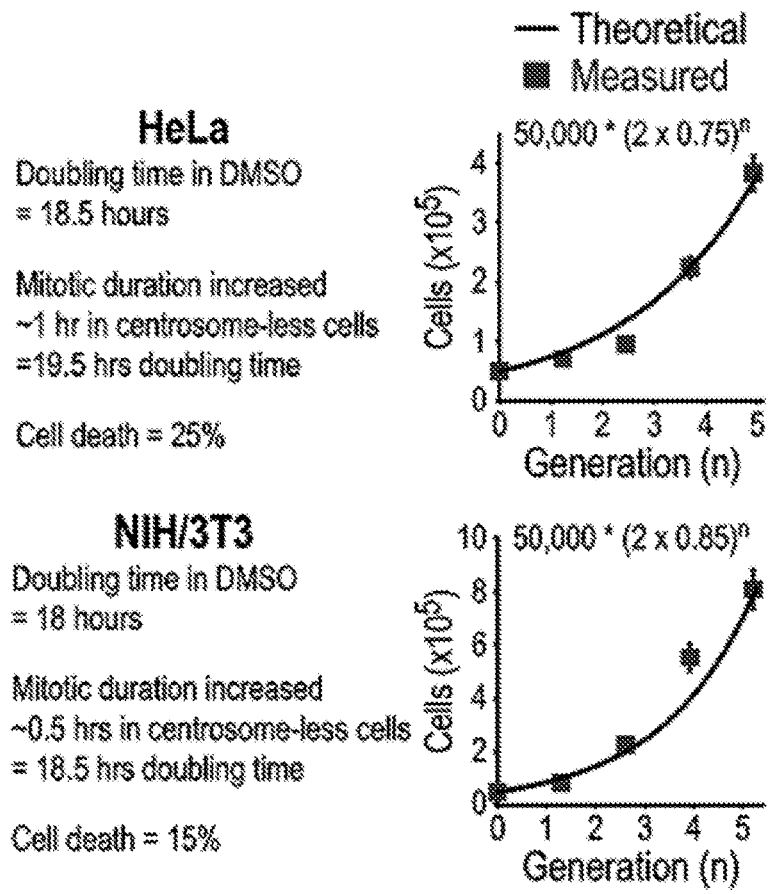
Figure 11A:
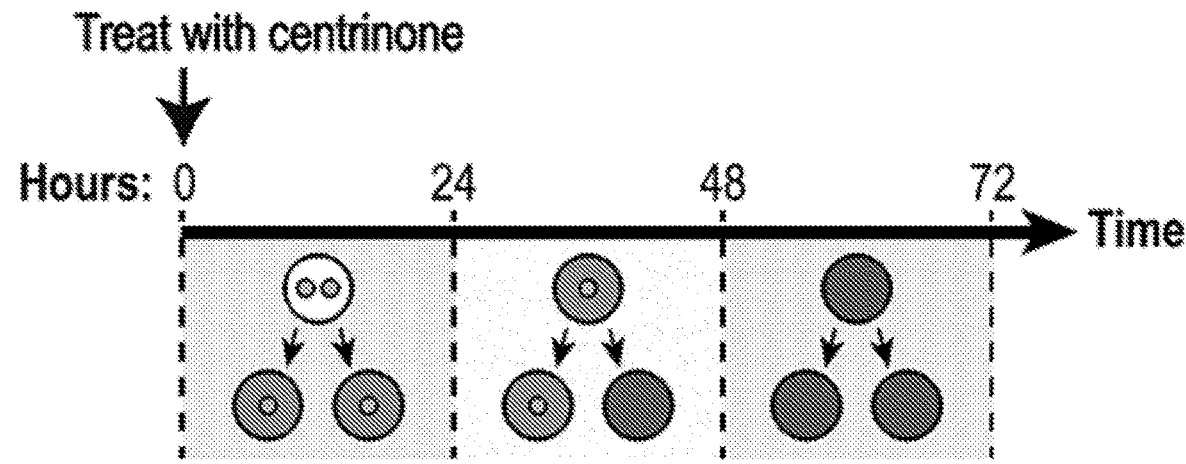
FIGS. 11A-11C. Centrosome loss slows spindle assembly and leads to mitotic errors.
Figure 11B:
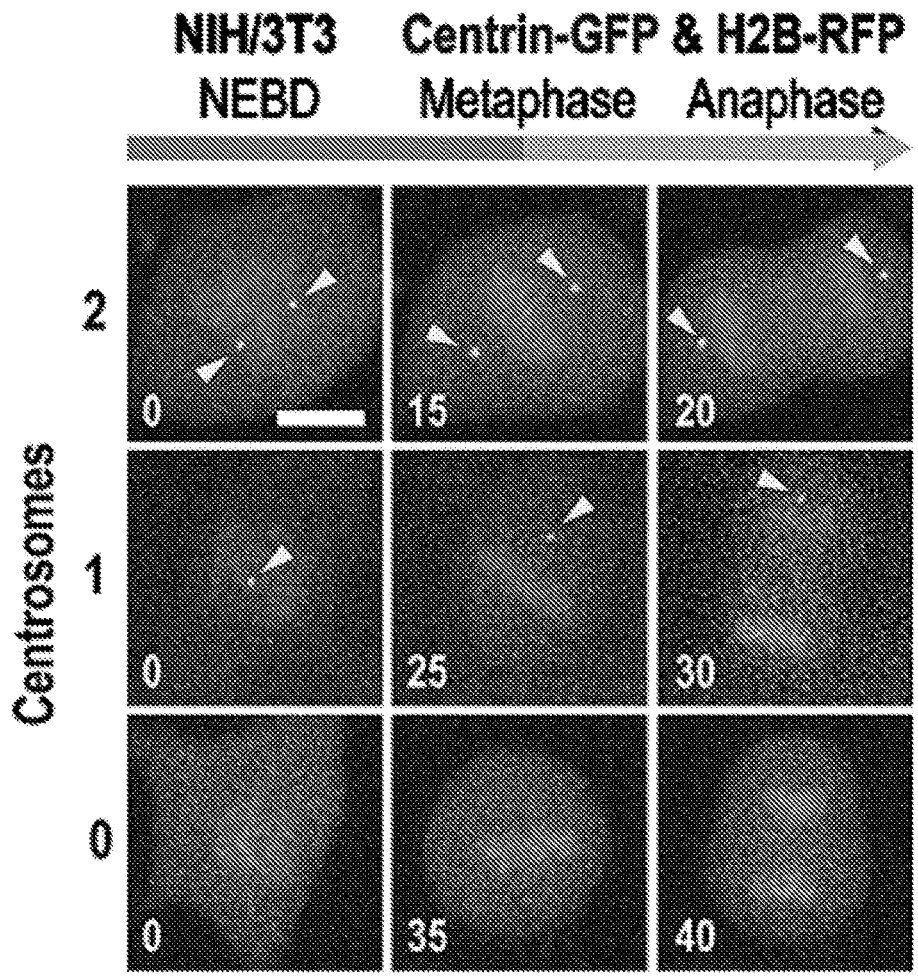
Figure 11C:
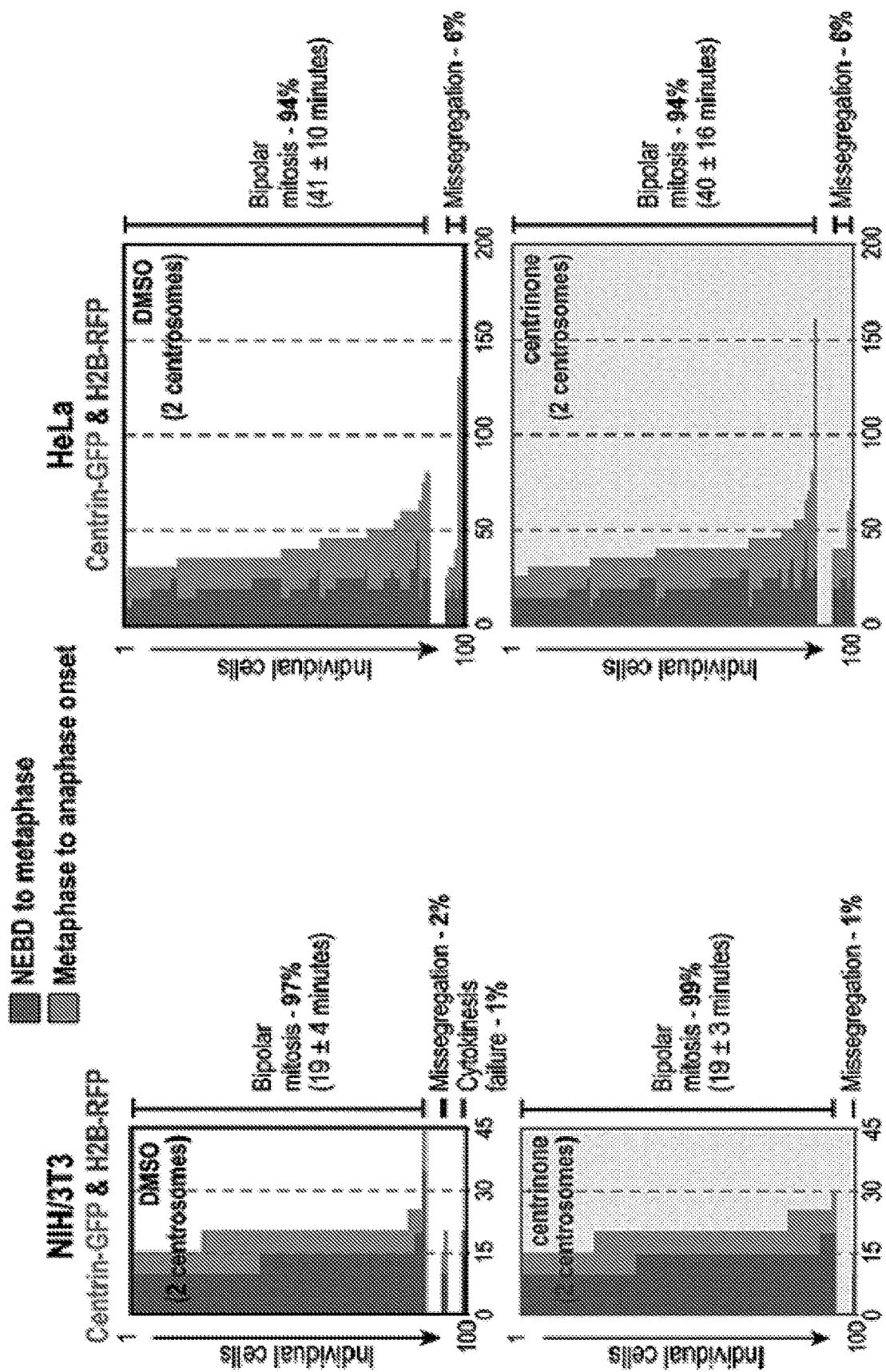
Figure 11C:
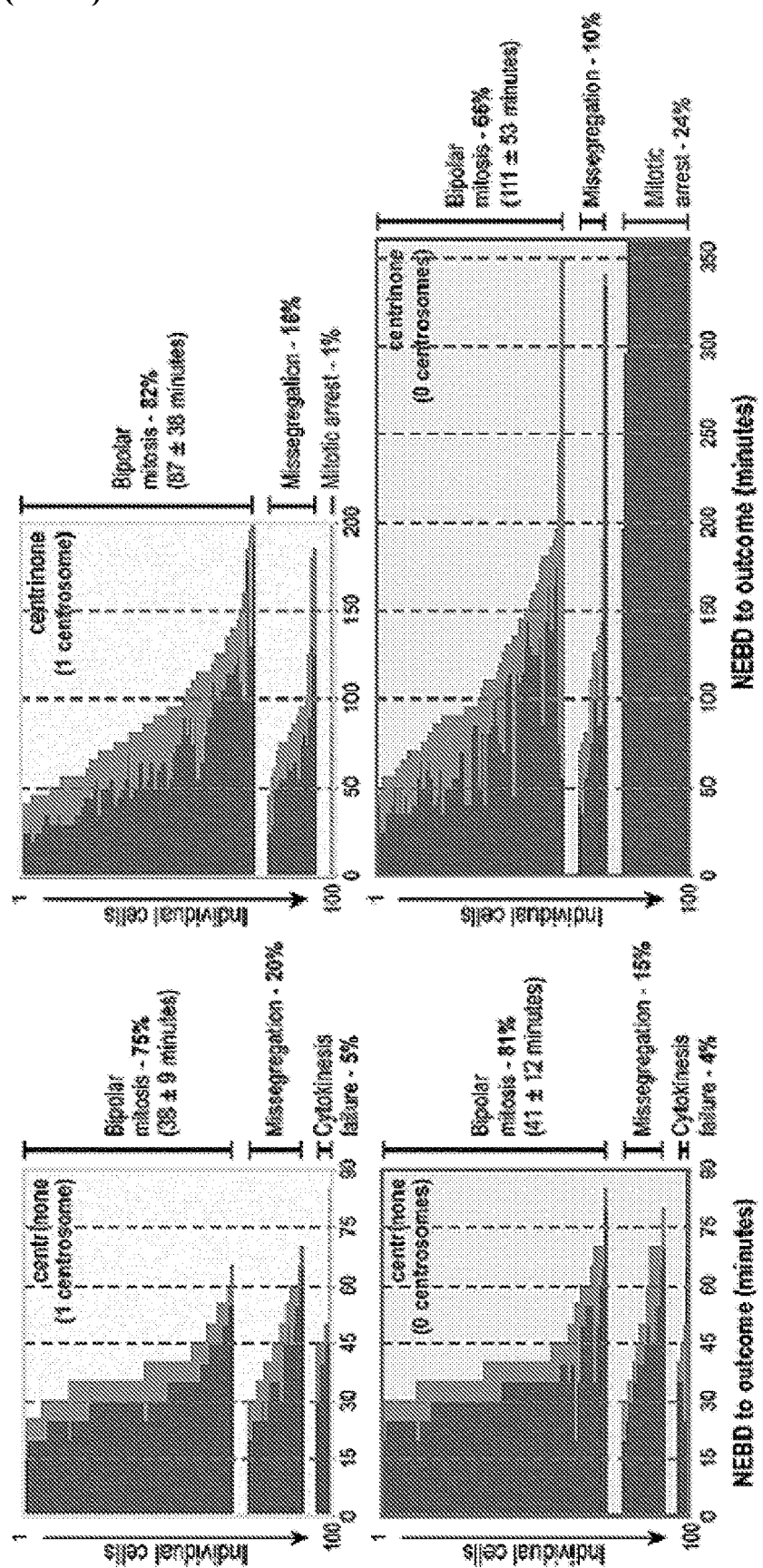
Figure 12:
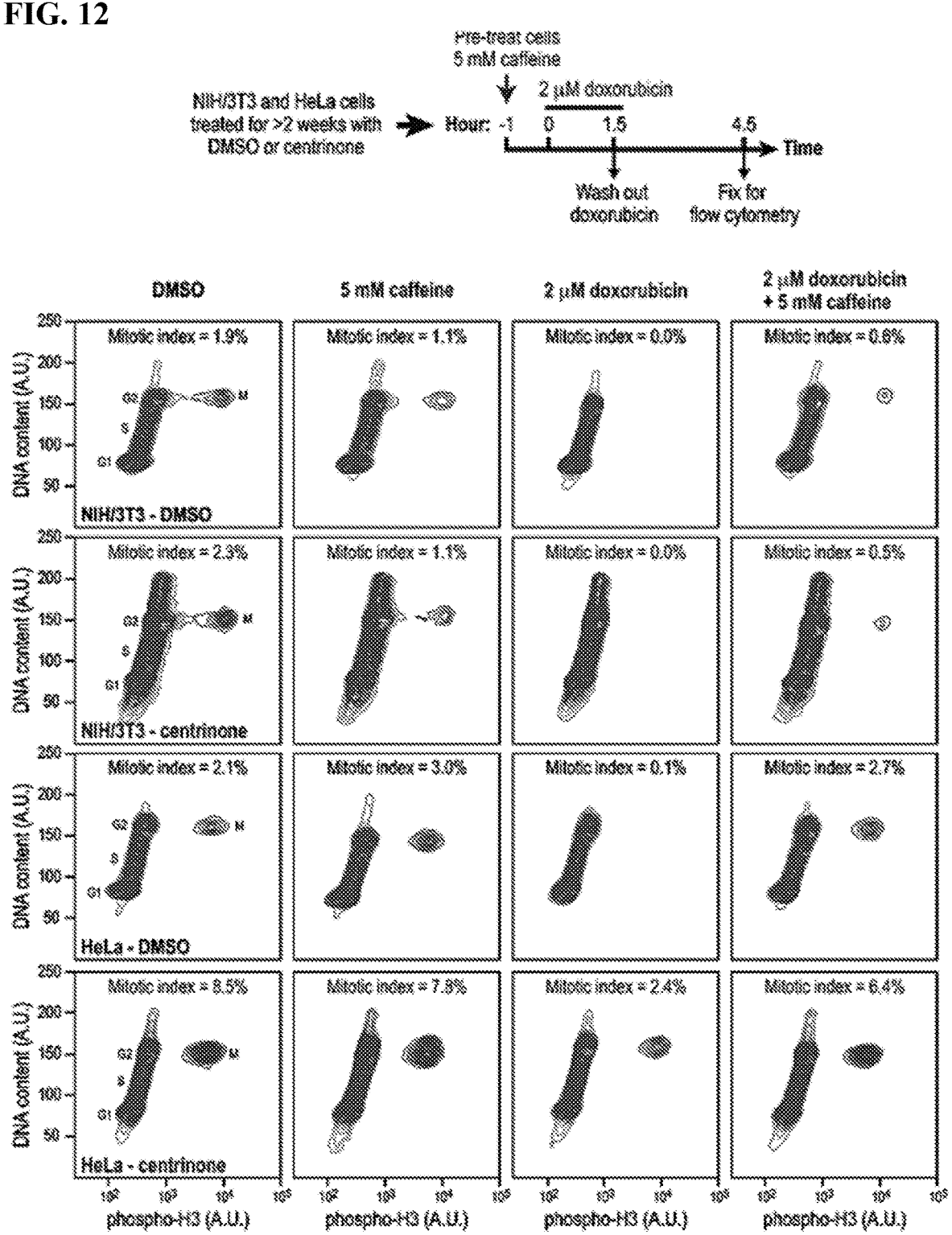
FIG. 12. Cells maintain an intact DNA damage response in the absence of centrosomes. NIH/3T3 and HeLa cells were subjected to the schematized experimental protocol. Double-stranded DNA breaks were induced by treatment of cells with doxorubicin. DNA content analysis was used to measure the proportion of cells in mitosis, based on phospho-H3(S10) staining. In the presence of an intact G2 DNA damage checkpoint, the mitotic index of the population is reduced because cells that would have entered mitosis are arrested prior to mitotic entry, whereas cells already in mitosis can exit. Treatment of cells with 5 mM caffeine was used as a positive control for bypass of the DNA damage checkpoint. The mitotic index of centrinone-treated HeLa cells does not fall completely to zero after being challenged with doxorubicin because 24% of centrosome-less HeLa cells undergo a persistent mitotic arrest (see FIGS. 11A-11C).

For the first two days after centrinone addition, when cells retained 2 or 1 centrosomes, the proliferation of HeLa and NIH/3T3 cells was identical to controls; this was followed by a decrease in proliferation rate coincident with the appearance of centrosome-less cells (FIG. 2A, FIG. 1D, FIG. 9A-9B). Long-term treated cells continued to proliferate at the slower rate, and returned to the control rate after washout-mediated centrosome recovery (FIG. 2B). Measurement by single-cell imaging in cells co-expressing GFP-PCNA and H2B-RFP, revealed that G1+S and G2 durations were not substantially different in centrosome-less cells compared to controls (FIG. 2D, FIGS. 10A-10D). Imaging of cells co-expressing Centrin-GFP and H2B-RFP revealed that mitotic duration was increased by ~20 minutes in centrosome-less NIH/3T3 cells and by ~1 hour in HeLa cells (FIGS. 11A-11C). Consistent with prior work (22,23), centrosome loss increased the frequency of mitotic errors (FIG. 2E; FIGS. 11A-11C), resulting in cell death (FIG. 2F; FIG. 10C) that quantitatively explained the reduced proliferation following centrosome removal (FIG. 10D). Centrosome-less NIH/3T3 and HeLa cells arrested in response to DNA damage and also retained the ability to bypass this arrest when treated with caffeine (FIG. 12).

Figure 2C:
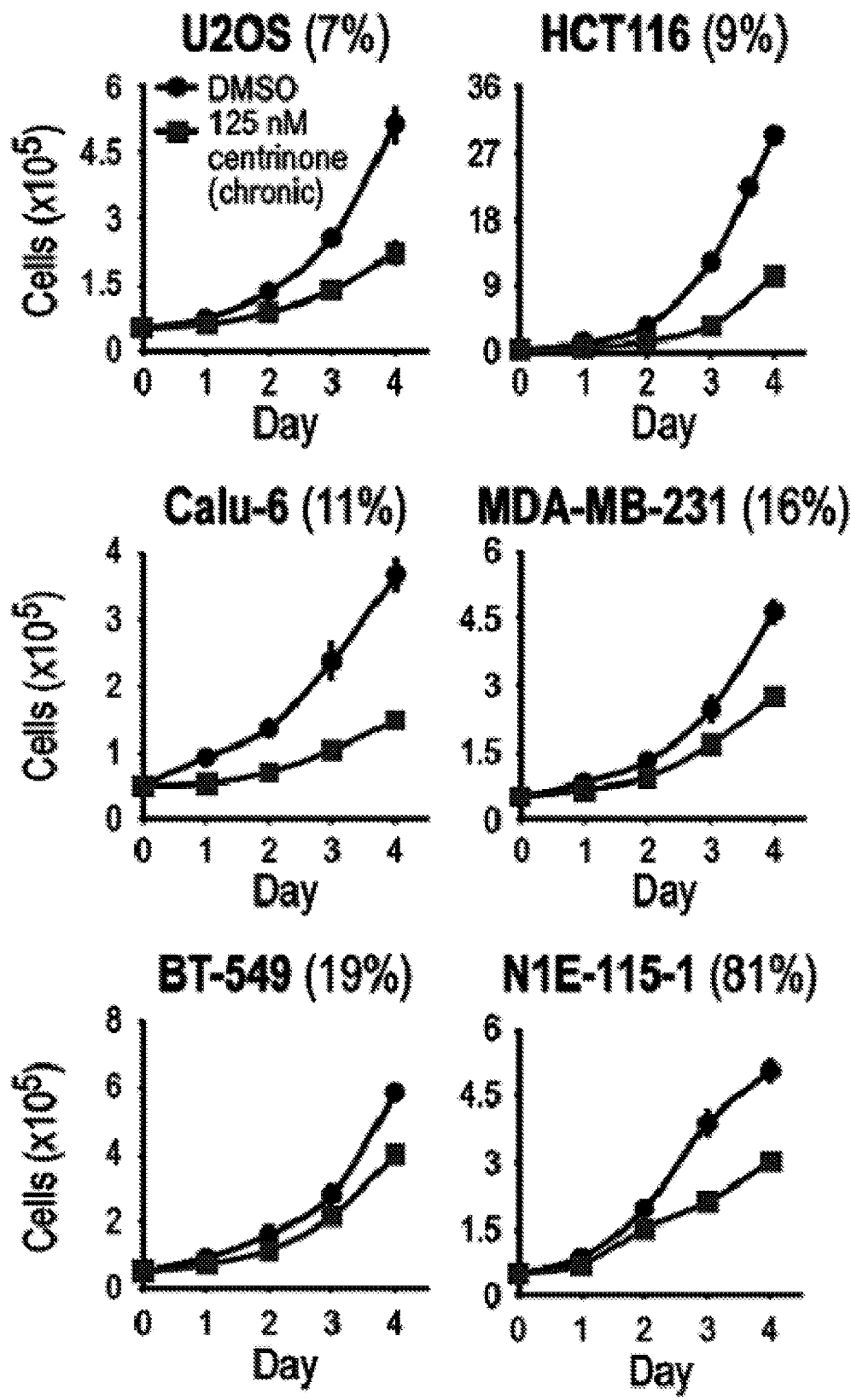
Figure 2D:
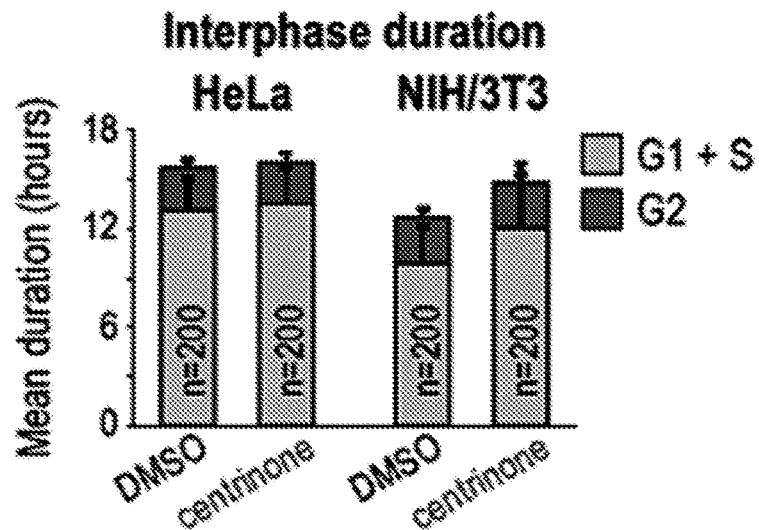
Figure 2E:
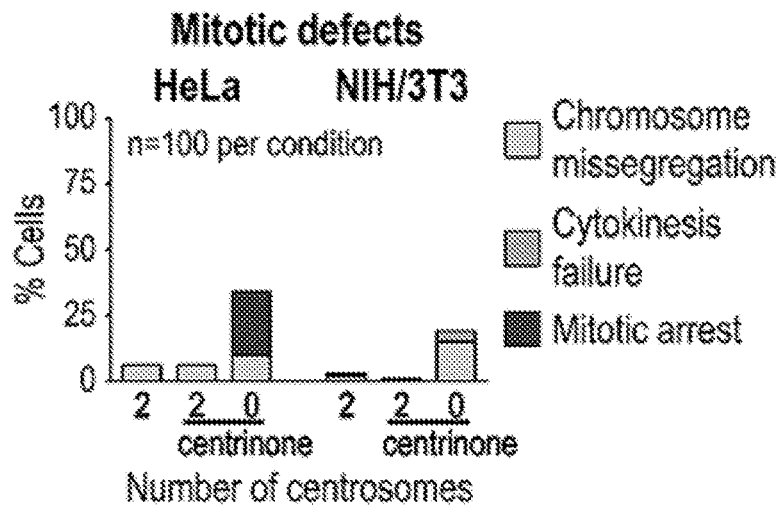
Figure 2F:
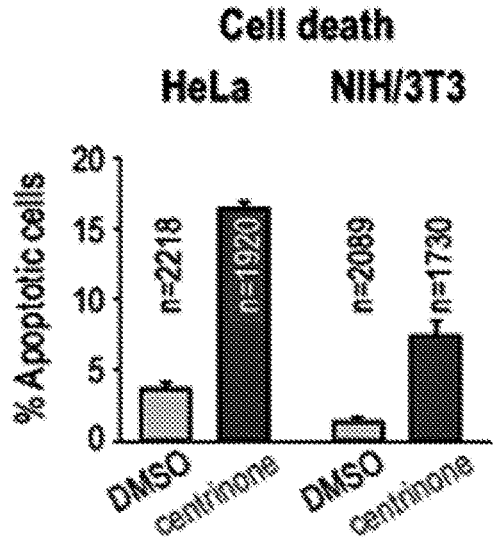

To determine whether centriole depletion is preferentially deleterious to cell lines possessing supernumerary centrosomes, we analyzed the basal level of centrosome amplification across a panel of 19 cell lines that continued to proliferate after centrinone treatment (Table 6). Nine lines spanning a range of amplification levels (HeLa 4%, NIH/3T3 6%, U2OS 7%, HCT116 9%, Calu-6 11%, MDA-MB-231 16%, BT-549 19% and N1E-115-1 81%) were depleted of centrosomes and their proliferation rate was compared to DMSO-treated controls (FIGS. 2A,2C). We observed no correlation between basal centrosome amplification state and proliferation after centrosome depletion, indicating that cells with multiple centrosomes are not addicted to them.

TABLE 6

Cell lines that proliferate in the absence of centrosomes. Cell lines are ordered by the degree of centrosome amplification (percentage of cells with >2 γ-tubulin/Cep192 foci) in untreated cells.

| CELL LINE | ORIGIN | CENTROSOME AMPLIFICATION (%) | p53 and CDKN2A STATUS |
|---|---|---|---|
| CT26.WT[a] | Colon carcinoma | 2 | CDKN2A deleted |
| U-138 MG | Glioblastoma | 3 | p53 mutated |
| HeLa | Cervical carcinoma | 4 | p53 degraded (HPV) |
| Ca Ski | Cervical carcinoma | 4 | p53 degraded (HPV) |
| SW837 | Rectal carcinoma | 4 | p53 mutated |
| DLD-1 | Colon carcinoma | 5 | p53 mutated |
| NCI-H358 | Lung carcinoma | 5 | p53 mutated |
| SJSA-1 | Osteosarcoma | 5 | p53 degraded (MDM2 amplification) |
| MCF 10A | Breast epithelial | 5 | CDKN2A deleted |
| LNCaP | Prostate carcinoma | 5 | Wild-type |
| NIH/3T3[a] | Embryonic fibroblast | 6 | CDKN2A deleted |
| C-33 A | Cervical carcinoma | 6 | p53 mutated |
| LOX IMVI | Melanoma | 6 | CDKN2A deleted |
| U2OS | Osteosarcoma | 7 | CDKN2A silenced |
| HCT116 | Colon carcinoma | 9 | CDKN2A silenced |
| Calu-6 | Lung carcinoma | 11 | p53 mutated |
| MDA-MB-231 | Breast carcinoma | 16 | p53 mutated |
| BT-549 | Breast carcinoma | 19 | p53 mutated |
| RD | Rhabdomyosarcoma | 22 | p53 mutated |
| B16-F10[a] | Melanoma | 27 | CDKN2A deleted |
| N1E-115-1[a] | Neuroblastoma | 81 | Not known |

Figure 2G:
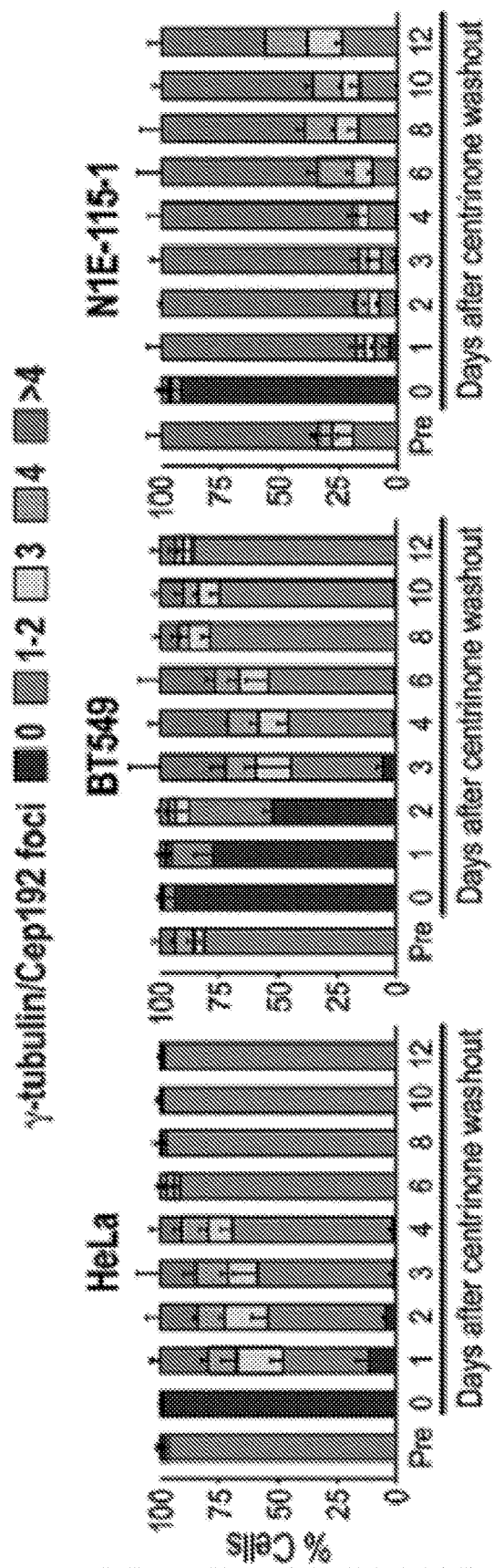
Figure 13A:
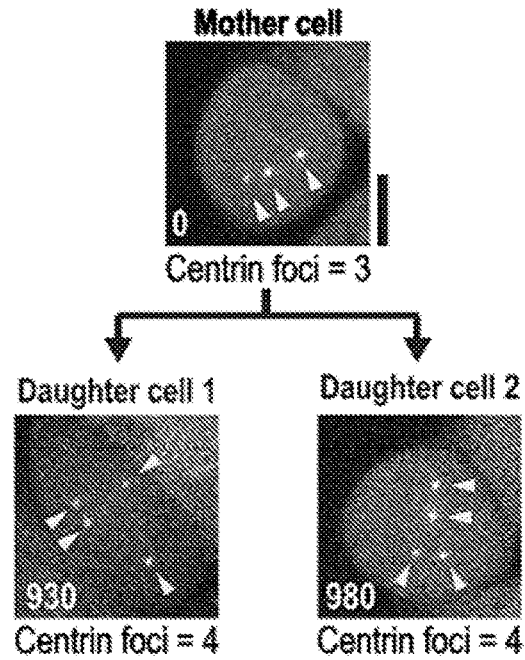
FIGS. 13A-13D. Centriole number set points arise from a dynamic equilibrium between centriole overduplication and removal of cells with extra centrioles.
Figure 13B:
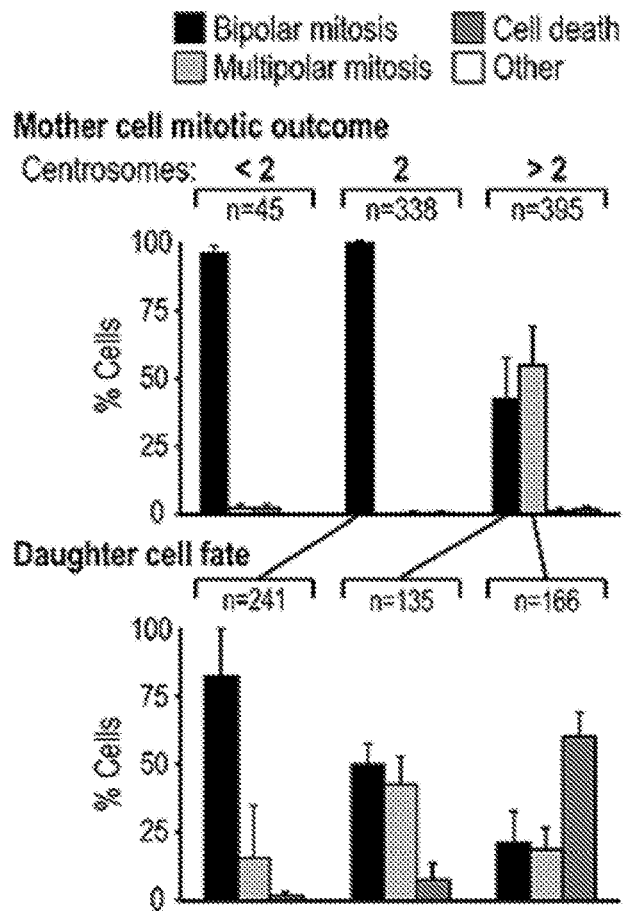
Figure 13C:
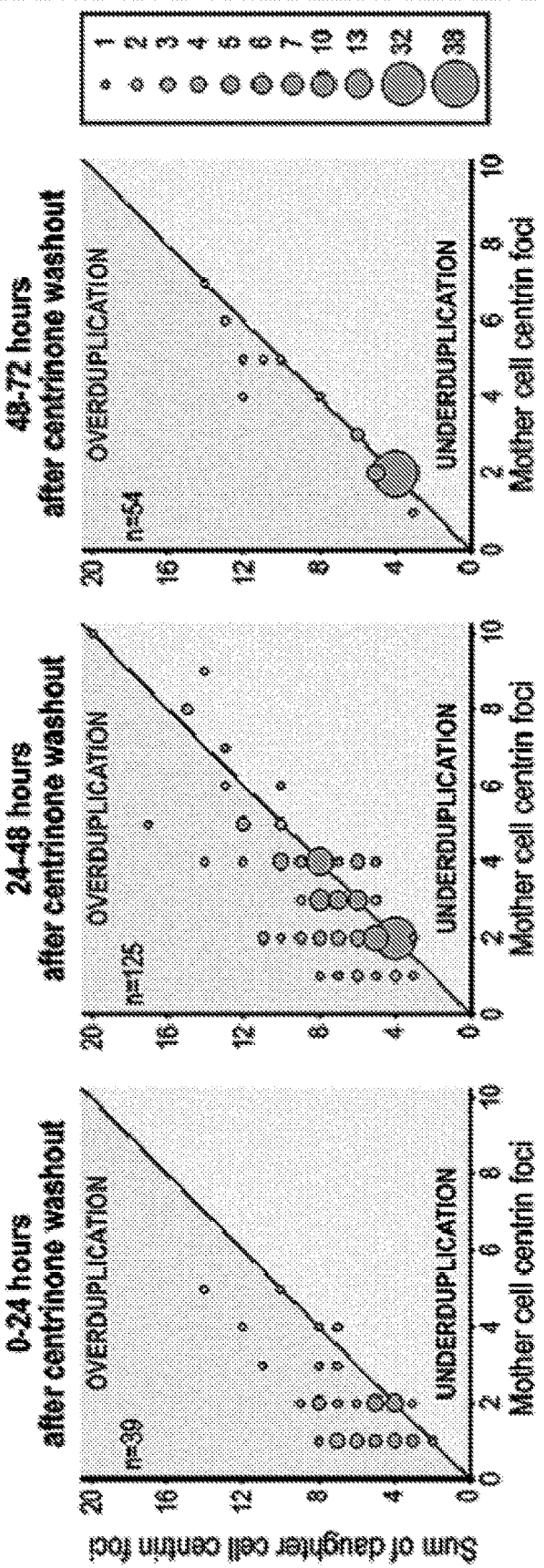
Figure 13D:
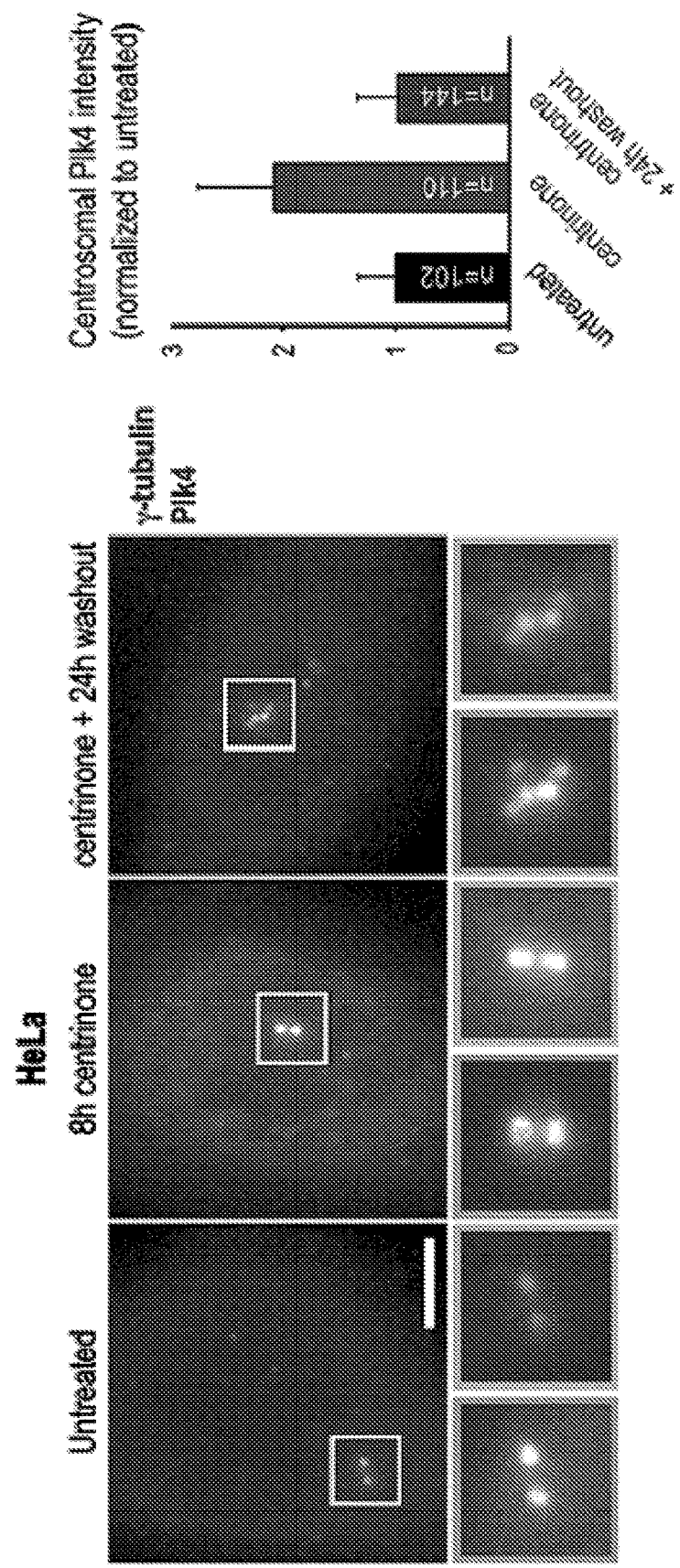

To study the origins of centrosome amplification within cancer cell lines, we depleted centrosomes from three cell lines that normally exhibit low (HeLa; 4%), medium (BT549; 19%), or high (N1E-115-1; 81%) amplification (FIG. 2G). We then washed out centrinone and counted centrosomes at regular intervals. In all three lines, centrinone washout triggered an initial wave of centrosome overduplication (FIG. 2G; FIGS. 13A, 13C) due to the lack of copy number control during de novo assembly and elevated Plk4 levels resulting from inhibition of autophosphorylation-mediated degradation (FIG. 5C, FIG. 13D). This wave of overduplication was followed by a gradual return to a centrosome number distribution similar to that prior to depletion (FIG. 2G). Live imaging of HeLa cells revealed that recovery of the original distribution occurred by removal of cells with supernumerary centrosomes via multipolar mitoses with death of the resulting progeny (FIG.

13B). Thus, each cancer cell line has an intrinsic centrosome number distribution or "set point" that is independent of pre-existing centrosomes and reflects a dynamic equilibrium between ongoing overduplication and selection against cells with extra centrosomes.

Figure 3A:
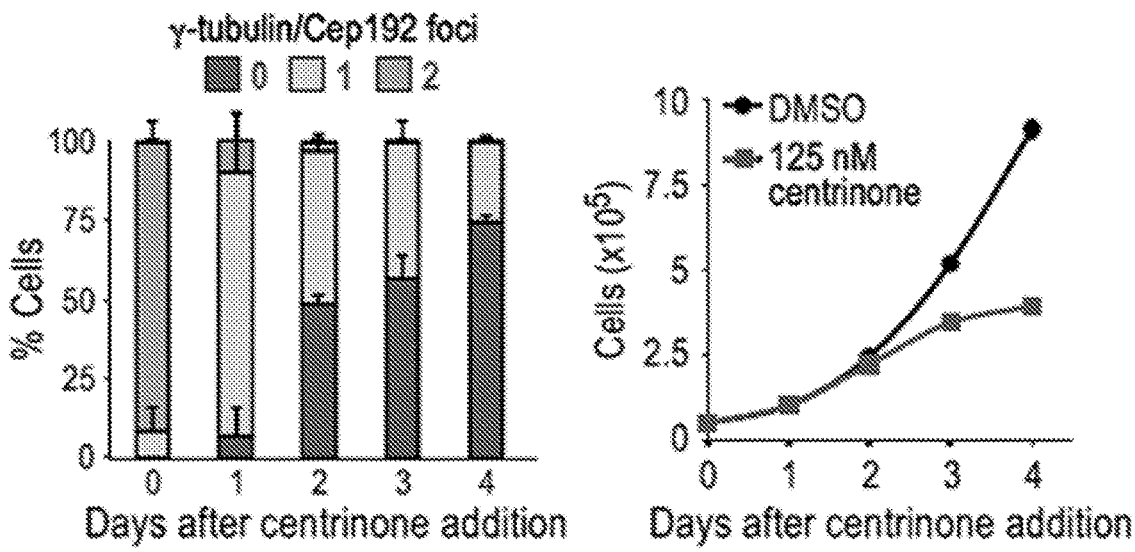
FIGS. 3A-3E. Centrosome loss triggers a p53-dependent arrest in normal cells.
Figure 3B:
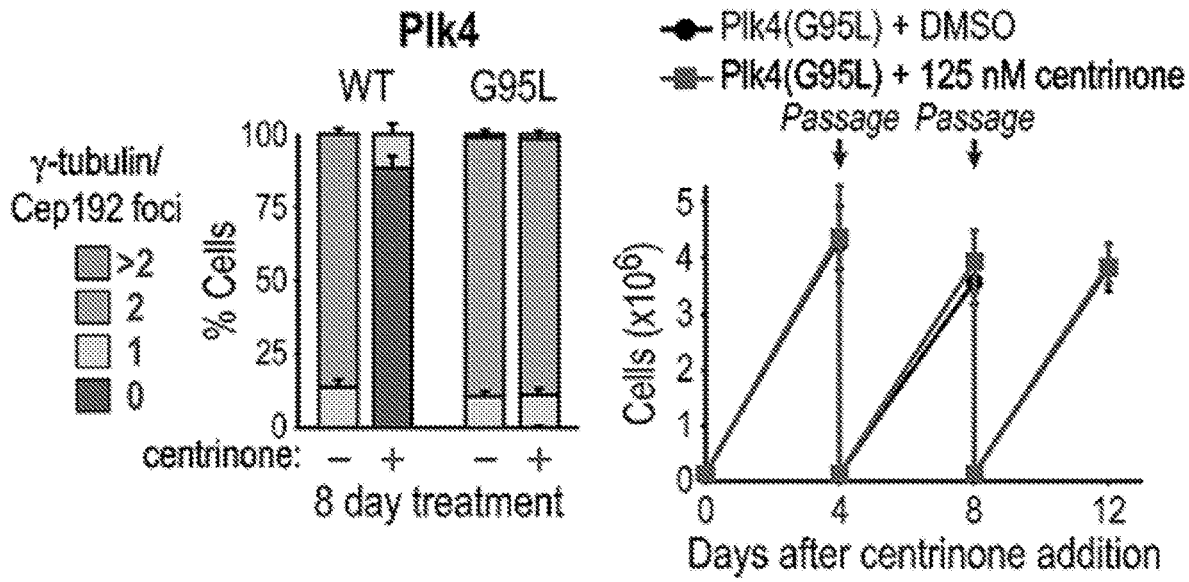
Figure 14A:
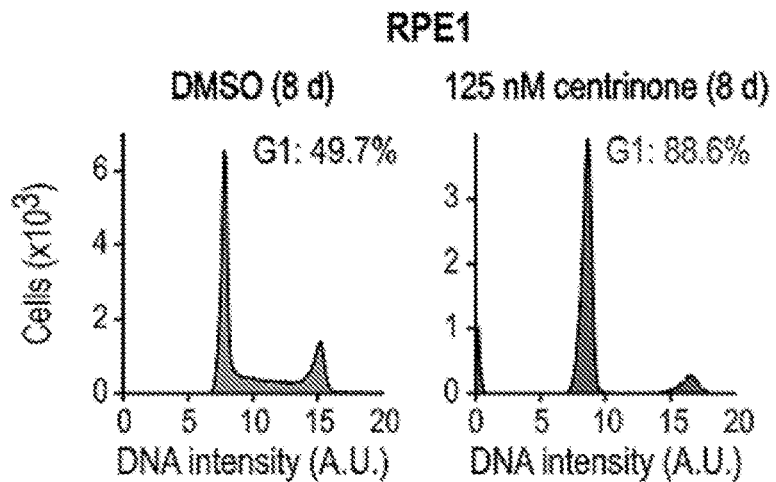
FIGS. 14A-14F. Centrosome loss triggers a p53-dependent arrest in normal cells within two to three cell cycles.
Figure 14B:
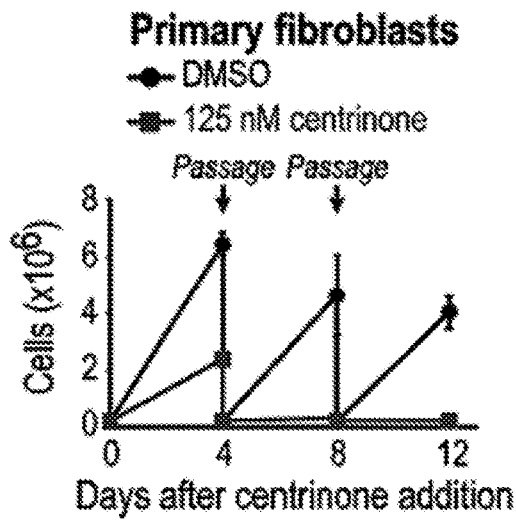
Figure 14C:
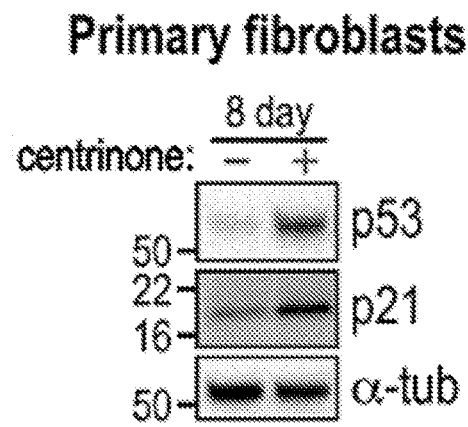
Figure 14D:
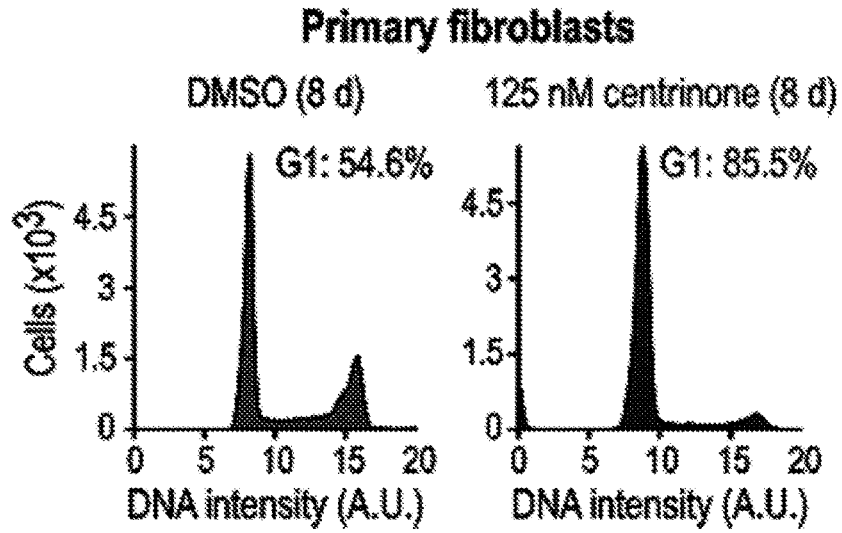
Figure 15:
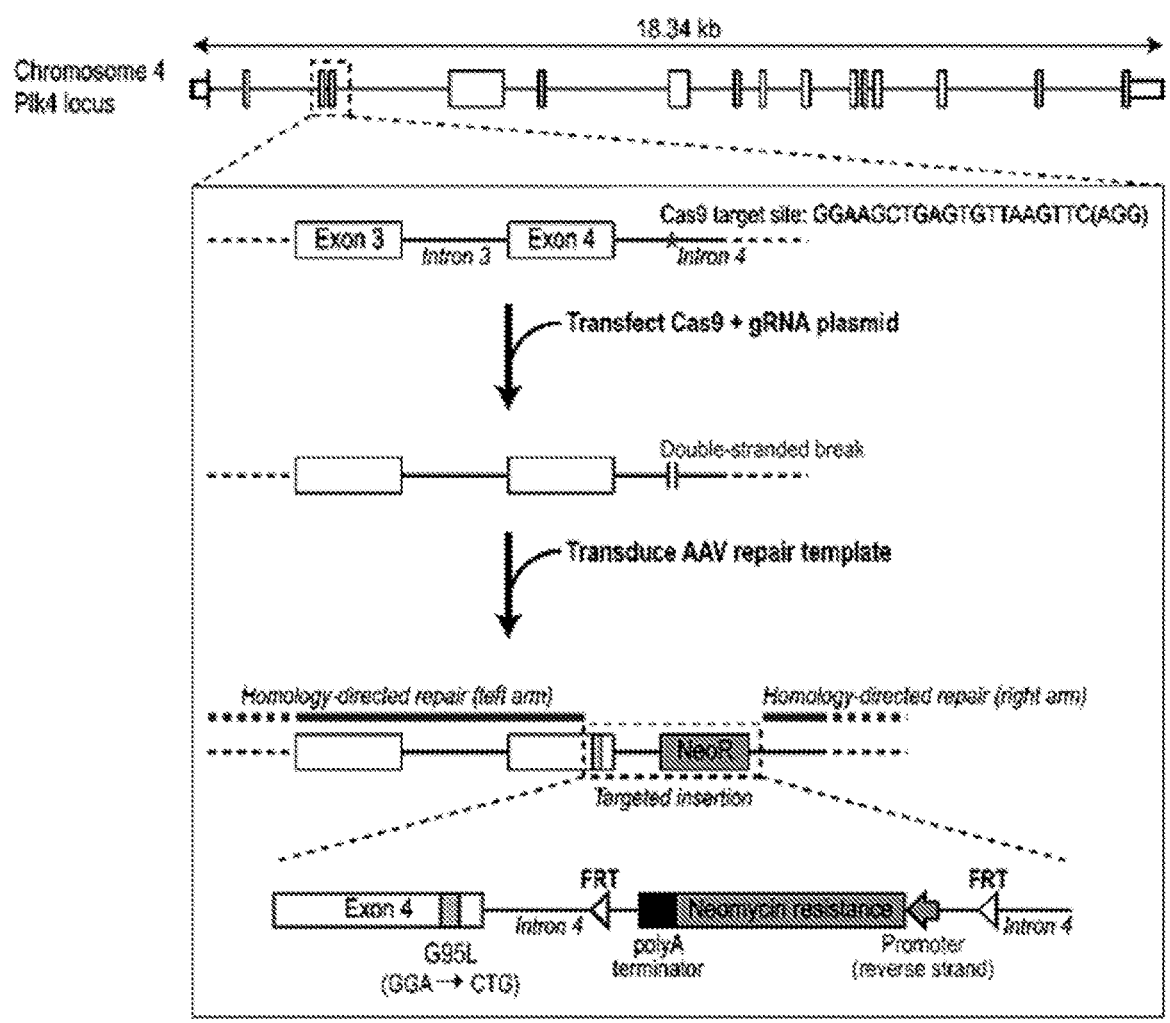
FIG. 15. Generation of RPE1 cells with a centrinone-resistant (G95L) Plk4 knock-in. The codon for residue G95 is located in exon 4 of the Plk4 locus. A Cas9 recognition site within the intronic region between exons 4 and 5 was targeted to generate a double-stranded DNA break. AAV-mediated homology-directed repair was used to introduce the G95L point mutation into exon 4, together with a neomycin resistance cassette in the intron. The resistance cassette, driven by its own promoter on the anti-sense strand, enabled selection of clones positive for the knock-in. Homozygosity of the point mutation was verified by PCR and sequencing of genomic DNA at the locus.

To determine if centrosomes are required for the proliferation of normal human cells, we analyzed the effect of centrosome depletion in three cell lines and three primary cell cultures. Prior work in RPE1 cells showed that transient centrosome removal did not block passage through the subsequent G1/S transition (24), but the effect of multi-generational centrosome removal could not be analyzed because S-phase entry triggered de novo centriole assembly. Using centrinone to persistently block centriole assembly in RPE1 cells, we found that centrosome loss coincided with a plateau in cell number (FIG. 3A). A 12-day passaging assay and flow cytometry showed that centrosome depletion led to cell cycle arrest in G1 (FIG. 3E, FIG. 14A); an identical arrest was observed following centrosome depletion in three primary cell cultures and two other lines lacking cancer-associated mutations (Table 7; FIGS. 14B, 14D). Centrinone treatment did not lead to centrosome loss or proliferation arrest in RPE1 cells where both endogenous PLK4 alleles were engineered to express the centrinone-resistant G95L mutant (FIG. 3B, FIG. 15), indicating that the arrest is triggered by centrosome loss due to Plk4 inhibition.

TABLE 7

Cell lines and primary cell cultures that arrest in response to centrosome depletion. Cell lines are ordered by the degree of centrosome amplification (percentage of cells with >2 γ-tubulin/Cep192 foci) in untreated cells.

| CELL LINE | ORIGIN | CENTROSOME AMPLIFICATION (%) | p53 STATUS |
|---|---|---|---|
| | Primary dermal fibroblast | 0 | Wild-type |
| | Primary umbilical vein endothelial | 0 | Wild-type |
| | Primary mammary epithelial | 0 | Wild-type |
| BJ-5ta | Foreskin fibroblast | 0 | Wild-type |
| RPE1 | Retinal pigment epithelial | 1 | Wild-type |
| IMR-90 | Lung fibroblast | 3 | Wild-type |

Figure 3C:
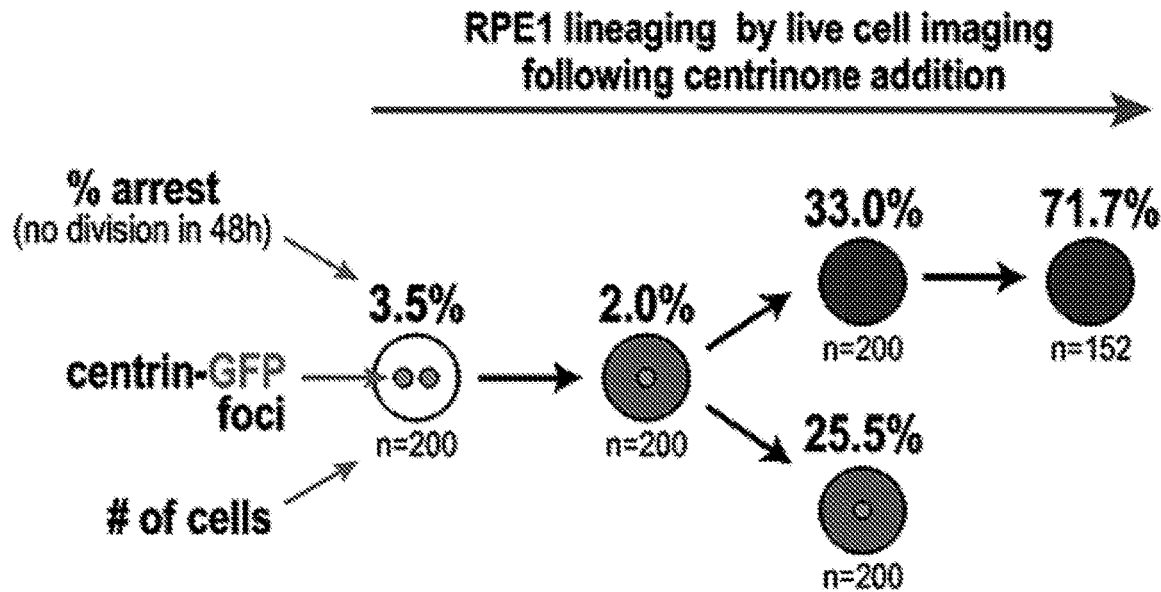

The potent G1 arrest in the absence of centrosomes was in contrast to the normal progression through G1/S observed following transient centrosome removal (24). To address this difference, we employed live-cell imaging to lineage RPE1 cells co-expressing centrin-GFP and H2B-RFP following acute centrinone treatment (FIG. 3C). Pioneer 1-centrosome mothers divided at normal frequency but a significant fraction of their 1- and 0-centrosome progeny arrested (25.5 & 33.0%, respectively). The majority (70%) of the progeny of pioneer 0-centrosome mothers arrested. The fact that 1-centrosome progeny of 1-centrosome mothers arrest indicates that cells detect loss of even a single centrosome. Thus, penetrant G1 arrest requires 1-2 cell cycles following centrosome removal, explaining why it was not observed following transient centrosome ablation. We speculate that progressive arrest, rather than an immediate block when one or both centrosomes are absent, allows for rescue by the de novo centriole assembly pathway.

Figure 3D:
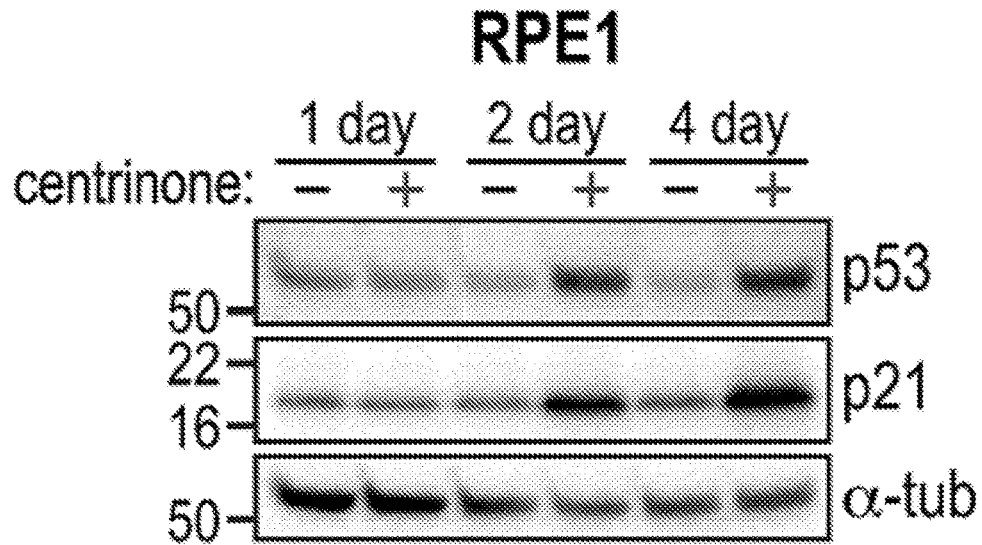
Figure 3E:
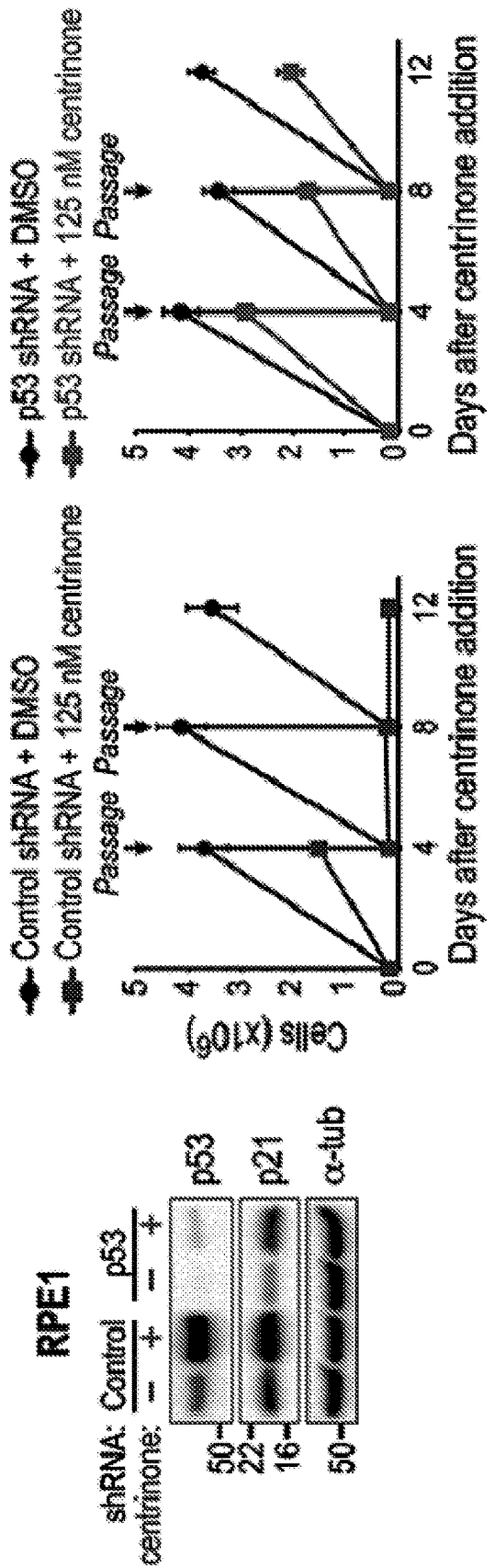
Figure 4A:
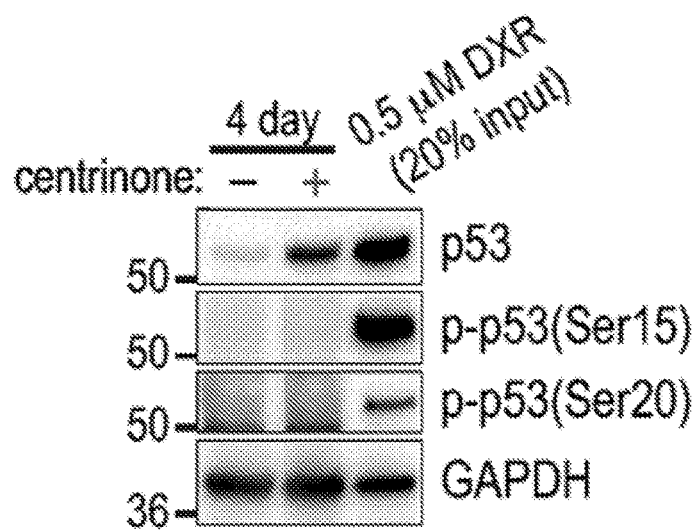
FIGS. 4A-4G. The irreversible G1 arrest following centrosome loss occurs via an unidentified mechanism.
Figure 4B:
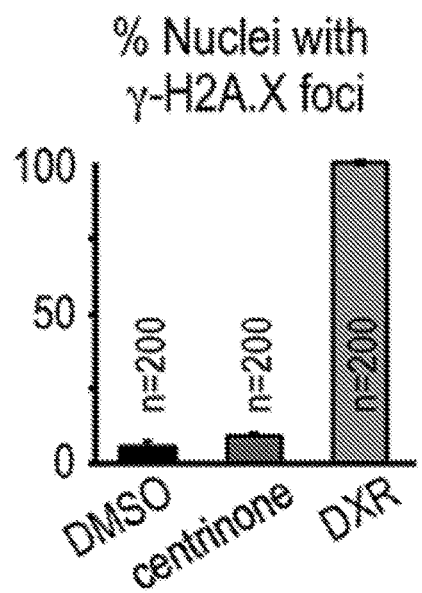
Figure 4C:
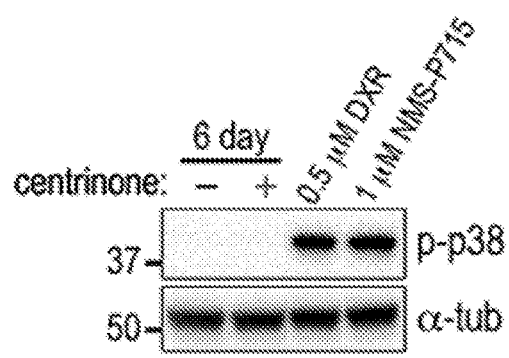
Figure 4D:
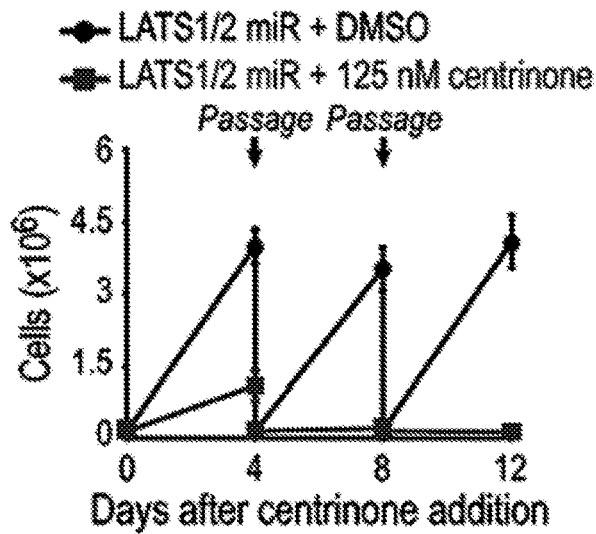
Figure 14E:
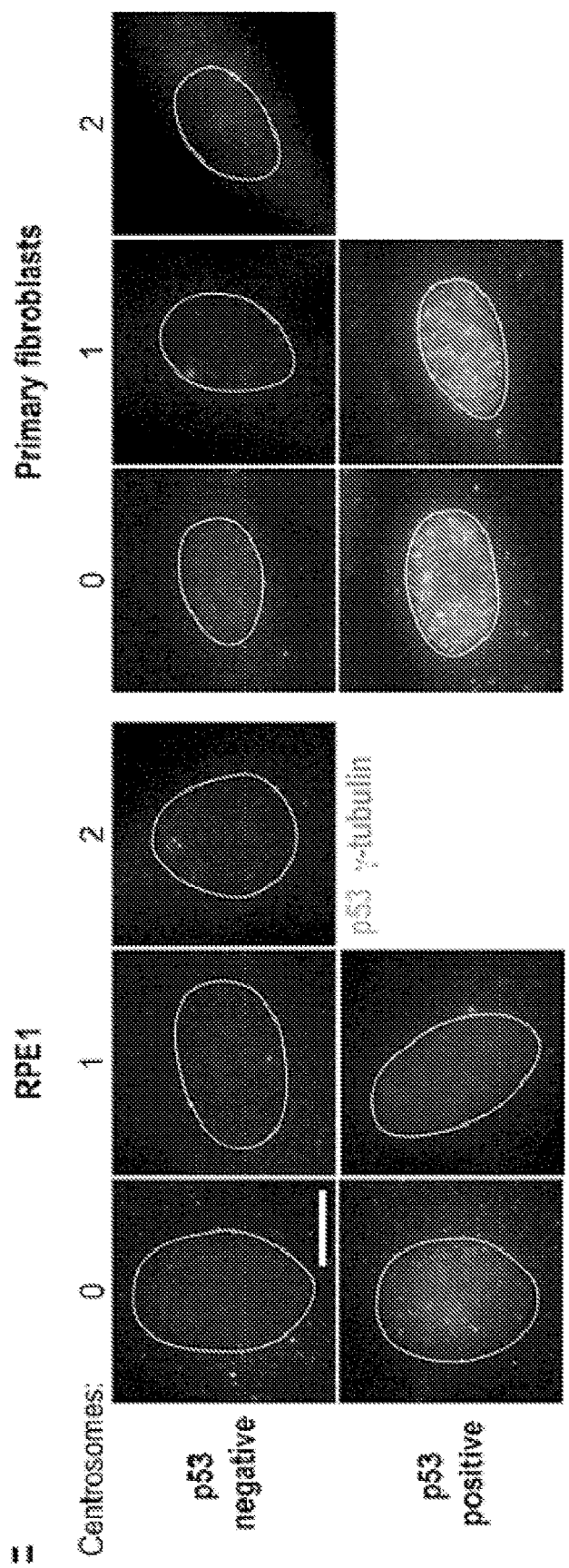
Figure 14F:
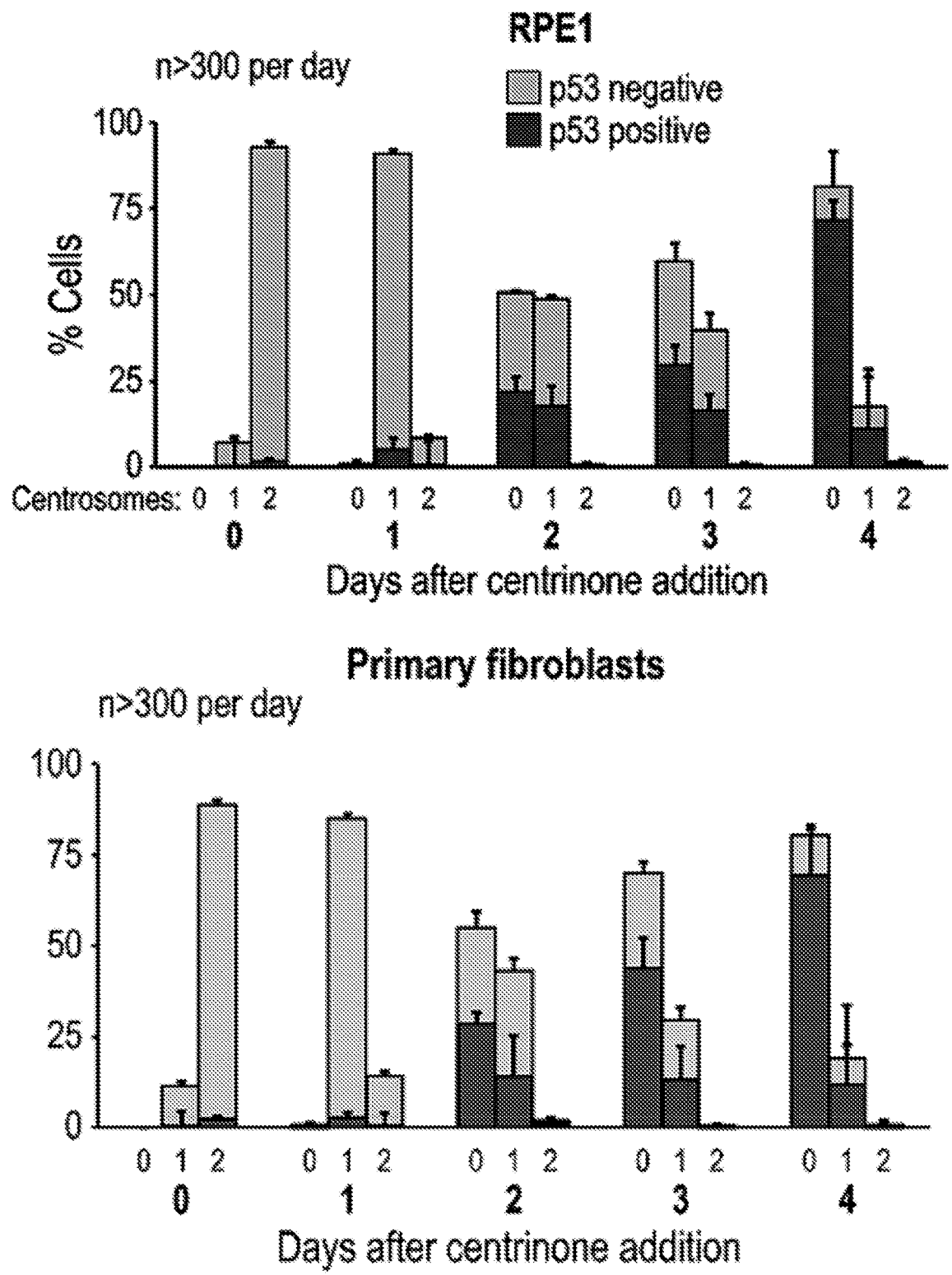
Figure 16A:
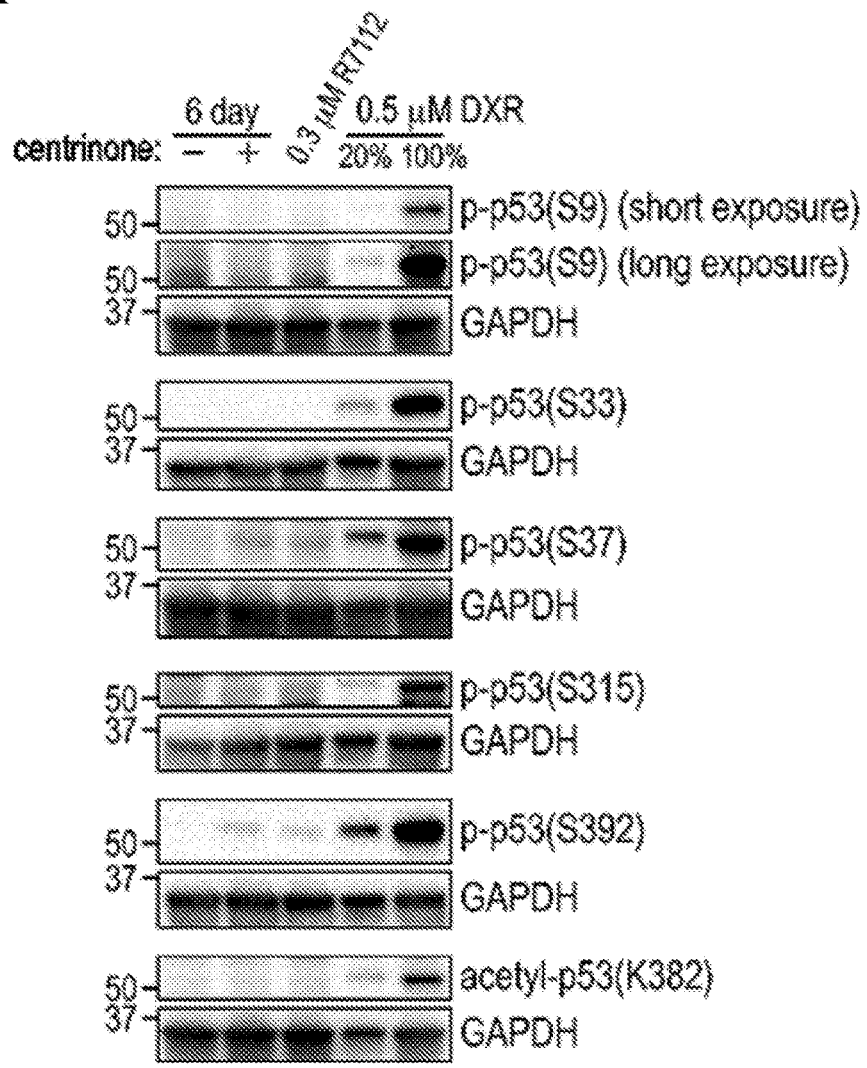
FIGS. 16A-16F. Arrest after centrosome loss is not related to DNA damage or stress.
Figure 16B:
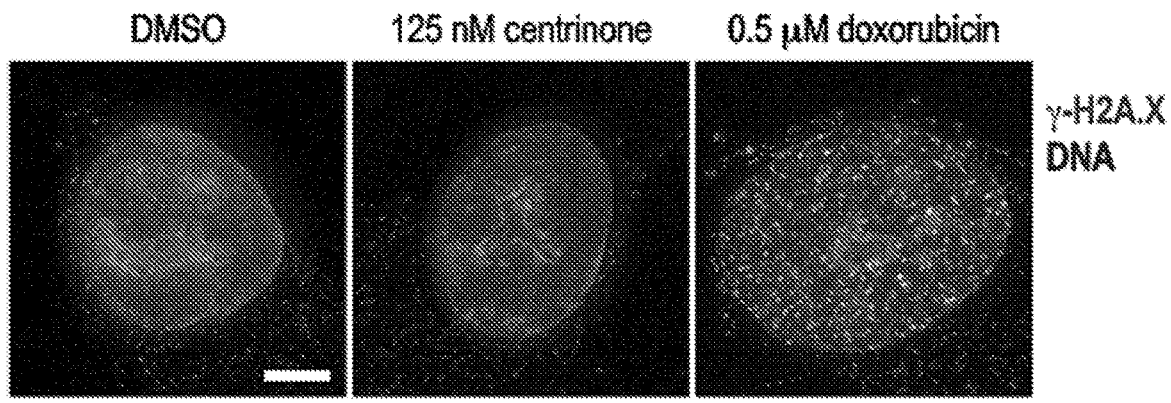
Figure 16C:
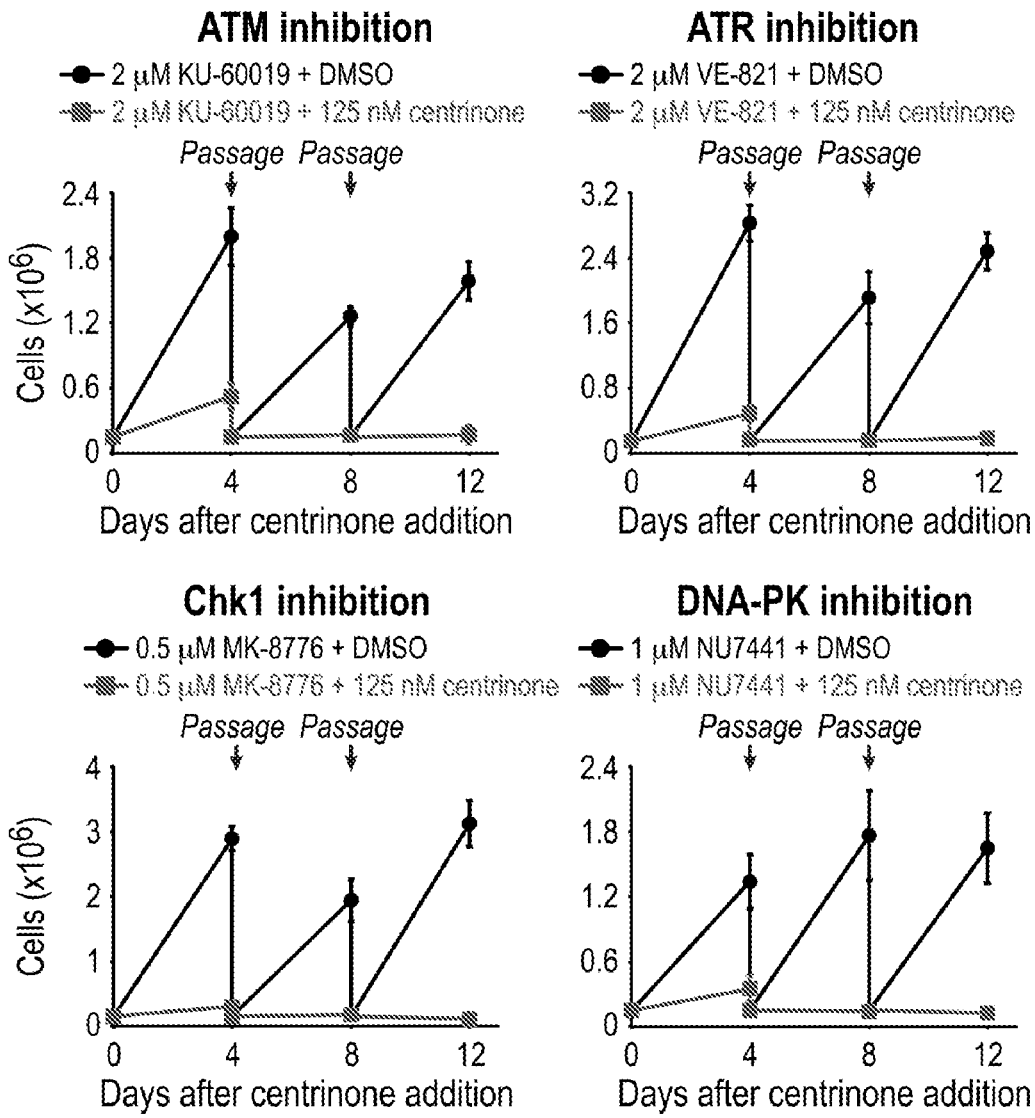
Figure 16D:
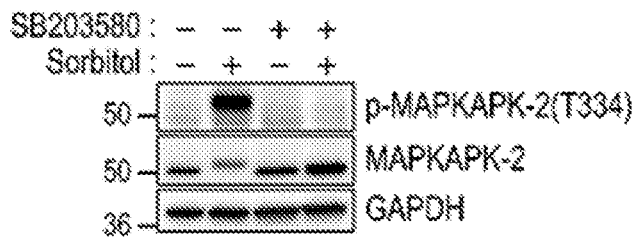
Figure 16E:
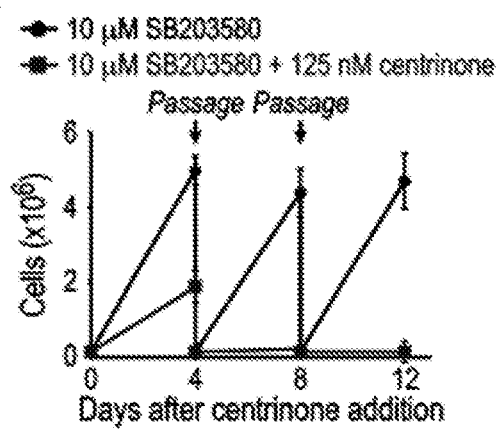
Figure 16F:
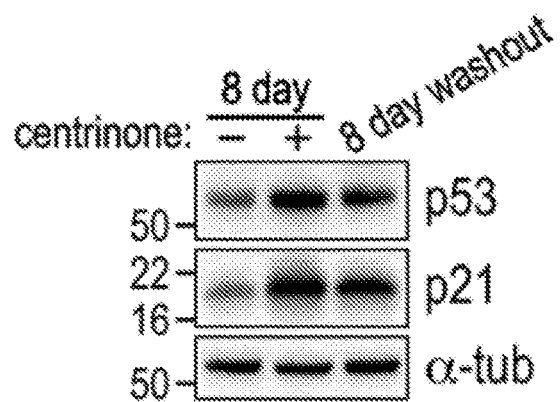
Figure 17A:
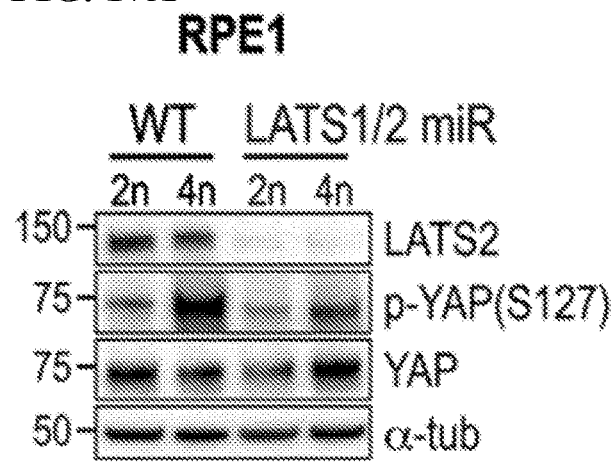
FIGS. 17A-17C. Arrest after centrosome loss is not related to the Hippo signaling pathway. Cytokinesis failure has been shown to trigger activation of the Hippo signaling pathway and subsequent cell cycle arrest (27). A key step in the activation of Hippo signaling is phosphorylation of YAP by LATS2 kinase.
Figure 17B:
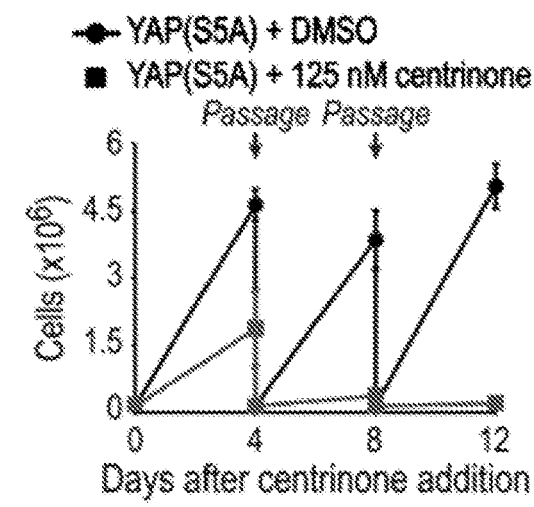
Figure 17C:
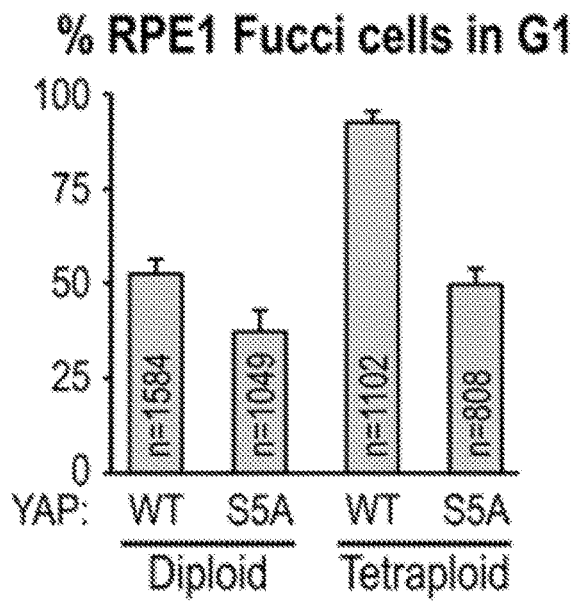

Of the cell lines we identified that continue to proliferate in the absence of centrosomes, eleven have mutations in or suppress expression of p53 (Table 6), suggesting that the arrest is p53-dependent. Consistent with this, immunoblot analysis showed increased levels of p53 and its downstream effector p21 following centrosome depletion (FIG. 3D; FIG. 14C), fixed analysis in RPE1 cells and primary fibroblasts revealed that this p53 increase paralleled arrest observed in the lineaging analysis (FIGS. 14E, 14F), and shRNA-mediated p53 depletion in RPE1 cells allowed indefinite proliferation in the absence of centrosomes (FIG. 3E). Three lines of evidence indicate that the p53-dependent arrest was not a consequence of DNA damage. First, no post-translational modifications were observed at eight p53 residues associated with DNA damage signaling (S9, S15, S20, S33, S37, S315, S392 phosphorylation and K382 acetylation; FIG. 4A; FIG. 16A (25,26)). Second, γ-H2A.X foci, which mark sites of double-stranded DNA breaks, were not elevated in centrinone-treated cells (FIG. 4B, FIG. 16B). Third, chemical inhibition of the DNA damage response kinases ATM, ATR, Chk1 and DNA-PK had no effect on the proliferation arrest induced by centrosome loss (FIG. 16C). The G1 arrest induced by centrosome loss was also not due to stress signaling; p38 stress kinase, activated by both doxorubicin-induced DNA damage and chromosome missegregation (induced by Mps1 inhibition), was not activated by centrosome loss (FIG. 4C), and a p38 inhibitor had no effect on the G1 arrest (FIGS. 16D,16E). Knockdown of LATS2 or expression of constitutively-active (S5A) YAP, both recently shown to bypass a Hippo pathway-mediated arrest resulting from cytokinesis failure (27), also did not bypass the arrest due to centrosome loss (FIG. 4D, FIGS. 17A-17C).

Figure 4E:
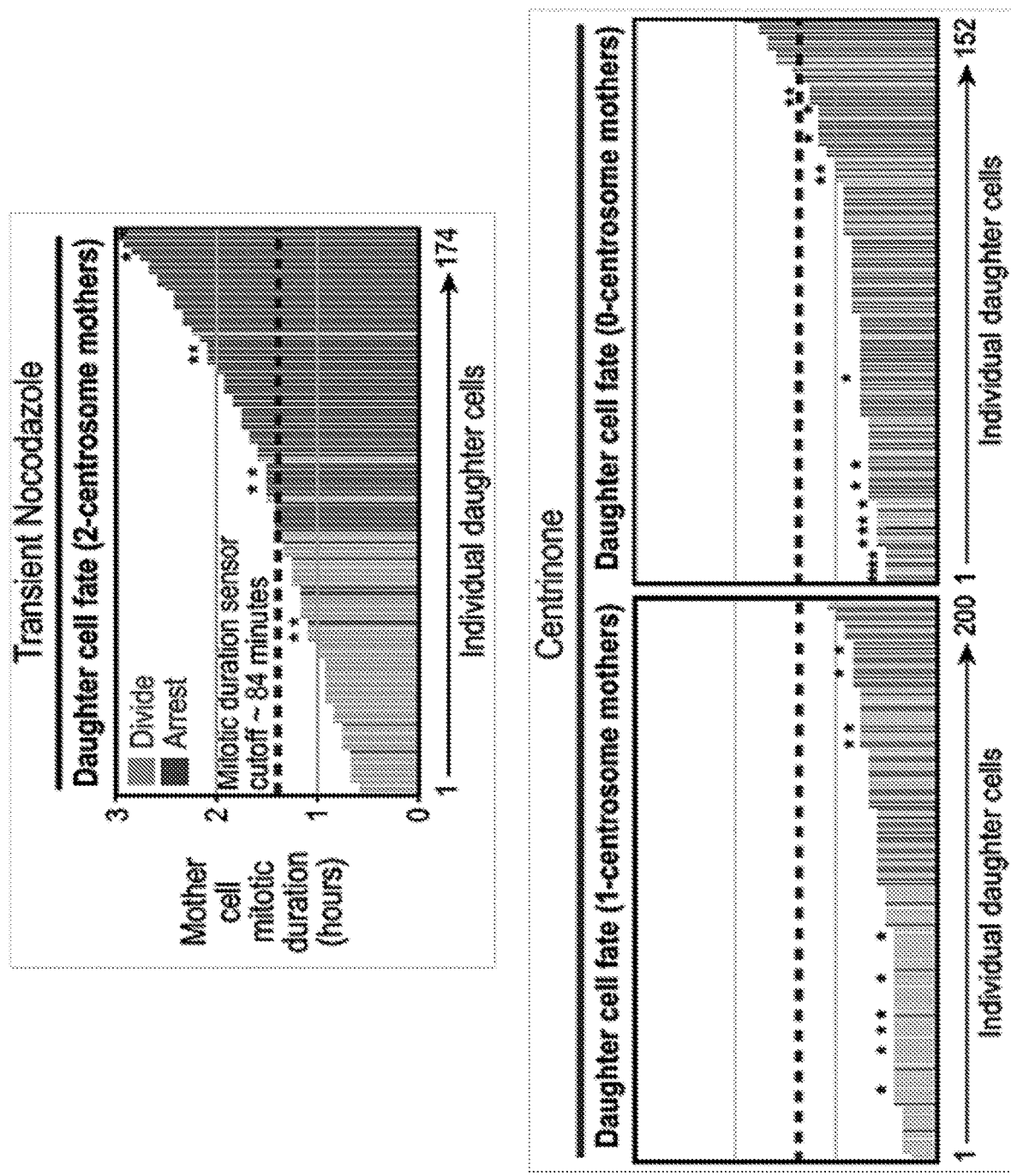
Figure 18A:
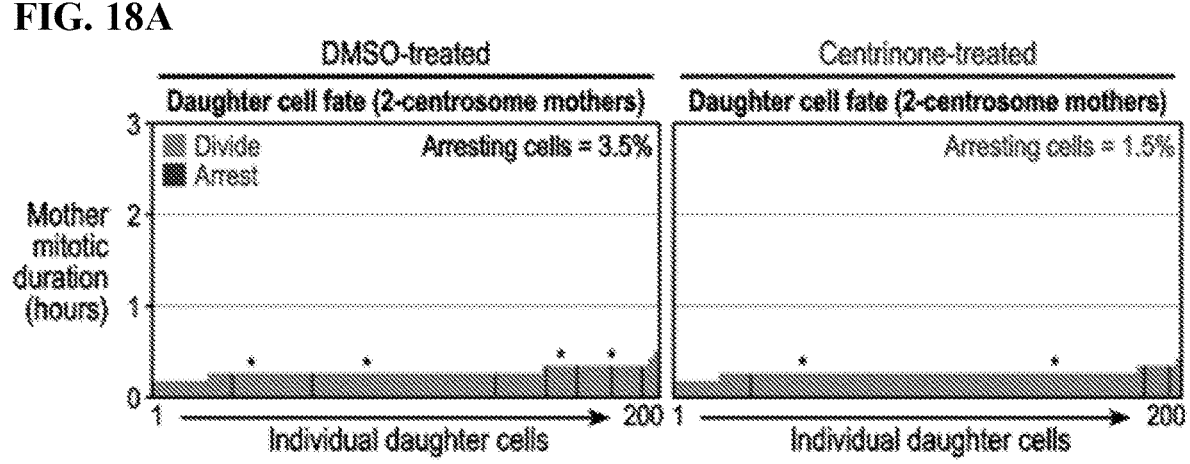
FIGS. 18A-18B. Arrest after centrosome loss is not related to the mitotic duration sensor or chromosome missegregation. Analysis of daughter cell fate in RPE1 cells expressing centrin-GFP and H2B-RFP. Vertical bars represent measurements from individual daughter cells (N=2). The height of each bar is the time their mother spent in prometaphase.
Figure 18B:
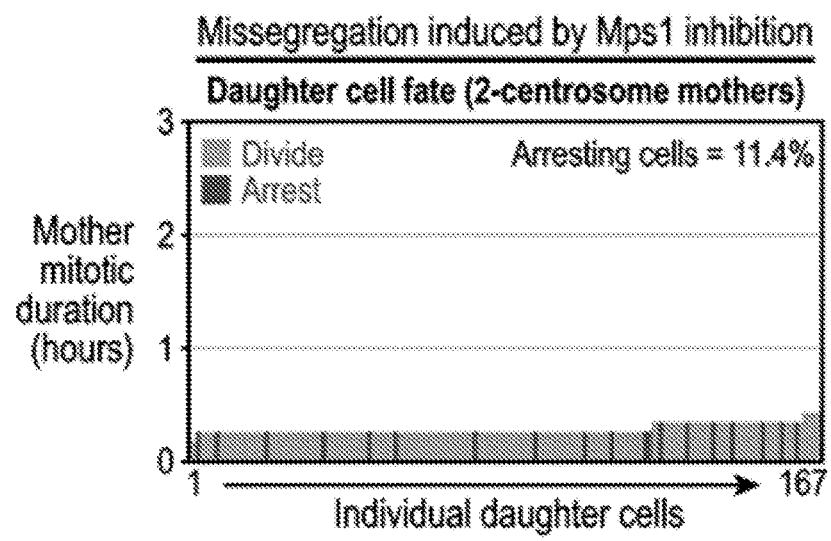

When mitosis is artificially prolonged beyond ~90 minutes in RPE1 cells (unperturbed duration ~20 minutes), a mitotic duration sensor arrests the resulting progeny in G1 in a p53-dependent manner ((28), FIG. 4E, left panel). A recent study of Sas4−/− mouse embryos proposed that centriole loss delays mitosis and activates the sensor, triggering p53-dependent apoptosis (29,30). To test this idea, we correlated the mitotic duration of mother cells with daughter cell fate during the course of centrosome depletion (FIG. 4E; FIG. 18A). All 1-centrosome mothers and 87% of 0-centrosome mothers spent less time in mitosis than the duration sensor timing cutoff (dashed black line in FIG. 4E), with most completing this step in significantly less time. There was no correlation between mitotic duration in the mother cell and daughter cell fate. Thus, the G1 arrest triggered by centrosome loss is not a result of extended mitotic duration. In addition, chromosome missegregation was observed only in a minority of cells (FIG. 4E, asterisks), suggesting that aneuploidy resulting from centrosome loss was not the cause of the arrest. Consistent with this, following deliberate induction of chromosome missegregation via Mps1 inhibition, only 11% of the progeny of mothers with visible missegregation arrested in G1 (FIG. 18B).

Figure 4F:
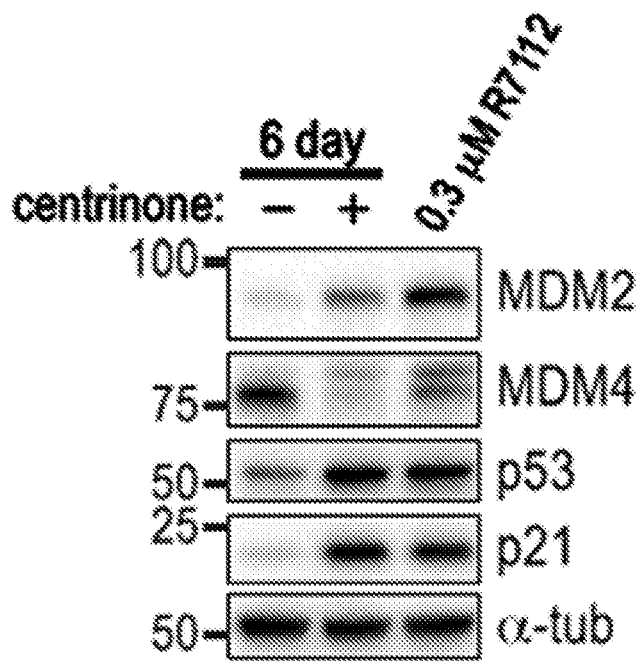
Figure 4G:
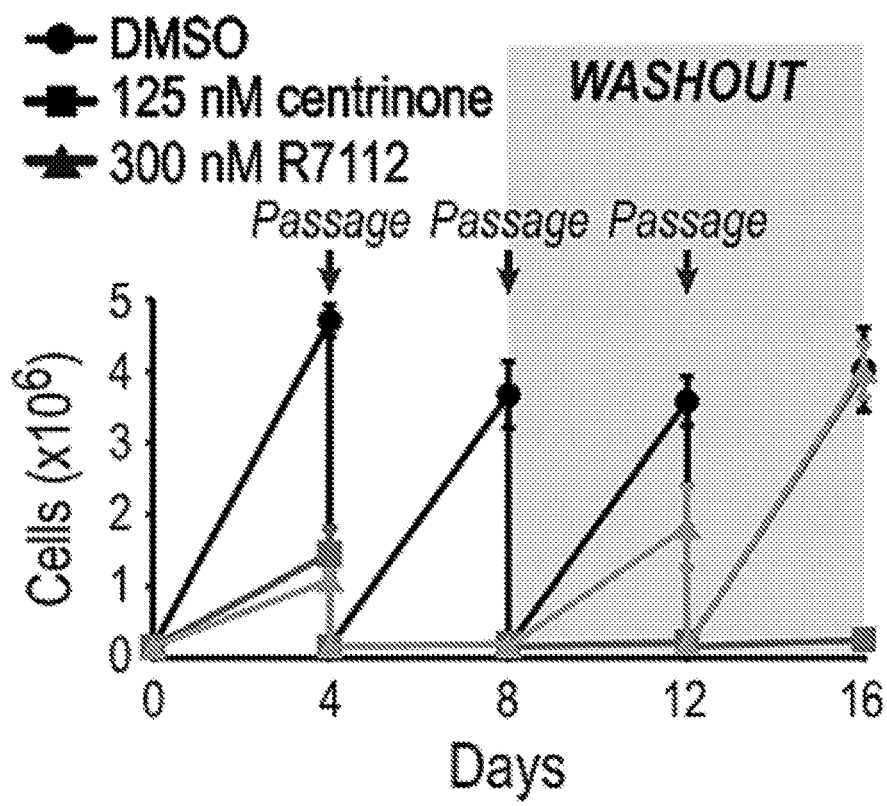

Our results indicate that the p53-mediated G1 arrest following centrosome loss is not due to any previously described signaling mechanism. Instead, centrosome loss resembles the effect of chemically blocking the interaction between p53 and MDM2, the E3 ubiquitin ligase that targets p53 for degradation (31). Both centrosome loss and treatment with the Mdm2 inhibitor R7112 raised p53 levels without genotoxic stress, and led to increased MDM2 and decreased MDM4 levels (FIG. 4F). However, while R7112 washout led to resumption of proliferation, centrinone washout did not (FIG. 4G), even though arrested cells remained viable for >3 weeks. This difference could result from centrosomes being necessary to suppress p53 levels and new centriole assembly requiring S-phase entry. Effectively, this would trap centrosome-less G1-arrested cells in a "Catch-22" situation, unable to reduce p53 levels and enter S-phase because they lack centrosomes, while at the same time are unable to form new centrosomes because they cannot enter S-phase.

In summary, the specific, reversible Plk4 inhibitor centrinone enables an organelle knockout and should prove broadly useful for analysis of centrioles/centrosomes. Centrinone treatment revealed that centrosomes are essential for the proliferation of normal human cells, settling a long debate and highlighting an important difference from *Drosophila* (32). In their absence, a centrosome loss sensor arrests cells in G1 in a p53-dependent manner distinct from previously described signaling mechanisms. In addition to preventing the proliferation of centrosome-less cells, the centrosome loss sensor may also serve a physiological function. As centrosome inactivation is coincident with differentiation in many contexts (33-35), we speculate that it may not only be important to form specialized microtubule arrays, but may also function as a barrier restricting cell cycle re-entry. Cancer-derived cell lines, irrespective of their basal amplification state, continue to proliferate without centrosomes, albeit with substantially reduced mitotic fidelity. The differential effect of centrosome removal on normal cells and cells with cancer-associated mutations suggests the possibility of combining centrosome depletion with other perturbations to selectively target dividing cancer cells.

Materials and Methods

Centrinones. Centrinone (LCR-263) and centrinone-B (LCR-323) were synthesized by Sundia Meditech, Shanghai, China.

Centrinone (LCR-263):

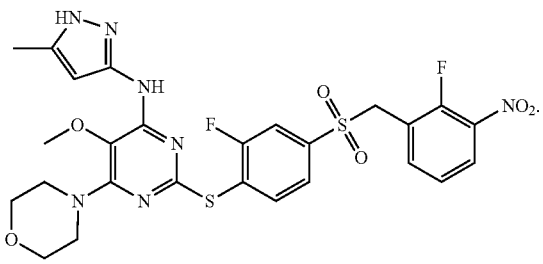 [SMILES: COc1c(Nc2cc(C)[nH]n2)nc(Sc2ccc(S(=O)(=O)Cc3cccc([N+](=O)[O-])c3F)cc2F)nc1N1CCOCC1]

2-((2-fluoro-4-((2-fluoro-3-nitrobenzyl)sulfonyl)phenyl) thio)-5-methoxy-N-(5-methyl-1H-pyrazol-3-yl)-6-morpholinopyrimidin-4-amine was prepared by Sundia Meditech, Shanghai, China. $^1$H NMR (400 MHz, CD$_3$OD): δ 8.11 (t, 1H), 7.88 (t, 1H), 7.67-7.74 (m, 2H), 7.61 (d, 1H), 7.39-7.43 (t, 1H), 5.99 (s, 1H), 4.82 (s, 2H), 3.63-3.66 (m, 7H), 3.51-3.53 (m, 4H), 3.32 (s, 3H). $^{13}$C NMR (100 MHz, DMSO-d6): δ 168.12, 165.61, 165.00, 159.54, 157.93, 150.85, 146.05, 145.93, 144.29, 143.24, 142.55, 132.20, 130.69, 130.13, 129.70, 127.90, 124.13, 120.93, 100.45, 71.33, 64.03, 59.32, 51.39, 16.23. HRMS(ESI) m/z for C$_{26}$H$_{26}$F$_2$N$_7$O$_6$S$_2$ [M+1]$^+$ calculated 634.1354, found 634.1367.

Centrinone-B (LCR-323):

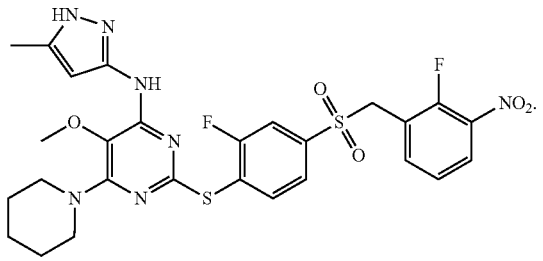 [SMILES: COc1c(Nc2cc(C)[nH]n2)nc(Sc2ccc(S(=O)(=O)Cc3cccc([N+](=O)[O-])c3F)cc2F)nc1N1CCCCC1]

2-((2-fluoro-4-((2-fluoro-3-nitrobenzyl)sulfonyl)phenyl) thio)-5-methoxy-N-(5-methyl-1H-pyrazol-3-yl)-6-(piperidin-1-yl)pyrimidin-4-amine was prepared by Sundia Meditech, Shanghai, China. $^1$H NMR (400 MHz, CD$_3$OD): δ 8.07-8.12 (m, 1H), 7.88 (t, 1H), 7.60-7.65 (m, 2H), 7.36 (t, 1H), 5.68 (s, 1H), 4.79 (s, 2H), 3.62 (s, 3H), 3.51-3.53 (m, 4H), 2.14 (s, 3H), 1.56-1.64 (m, 6H). $^{13}$C NMR (100 MHz, DMSO-d6): δ 162.88, 160.38, 159.52, 154.21, 152.64, 145.87, 140.63, 140.45, 139.03, 138.02, 137.30, 126.95, 125.50, 124.90, 124.38, 122.06, 118.89, 115.55, 95.10, 58.60, 54.01, 46.49, 25.49, 24.15, 11.02. HRMS(ESI) m/z for C$_{27}$H$_{28}$F$_2$N$_7$O$_5$S$_2$ [M+1]$^+$ calculated 632.1561, found 632.1548.

Chemical inhibitors. CFI-400945 (0.01-0.1 μM) and R7112 (0.3 μM) were synthesized by Sundia Meditech. The following chemical inhibitors were purchased from commercial sources, with their working concentrations indicated in parentheses: VX-680 (1 μM; Selleck Chem); nocodazole (0.08-16 μM; Sigma-Aldrich); doxorubicin (0.5-2 μM; Sigma-Aldrich); SB203580 (10 μM; LC Labs); KU-60019 (2 μM; Selleck Chem); VE-821 (2 μM; Selleck Chem); MK-8776 (0.5 μM; Selleck Chem); NU7441 (1 μM; Tocris); AZ3146 (2 μM; Tocris); NMS-P715 (1 μM; EMD Millipore).

Antibodies. Antibodies against Cep192, SAS-6 and Plk4 were generated by injecting GST fusions of Cep192 aa 1-211, SAS-6 aa 501-657 and Plk4 aa 814-970, respectively, into rabbits. Antibodies were affinity-purified using standard procedures (36). Cep192 and SAS-6 antibodies were used at 0.5 μg/ml. The Plk4 antibody was used at 1 μg/ml.

The following antibodies were purchased from commercial sources, with their working concentrations indicated in parentheses: GTU-88 (anti-γ-tubulin; 1:1000; Sigma-Aldrich); anti-centrin-1 (1 μg/ml; Abcam); anti-pericentrin (1 μg/ml; Abcam); anti-CPAP (1:400; ProteinTech); anti-IFT-88 (1:100; ProteinTech); anti-GM130 (1 μg/ml; Abcam); anti-GFP (0.4 μg/ml; Roche); anti-LATS2 (1 μg/ml; Abcam); anti-p-LATS2(Ser83) (1:500; Cyclex); anti-p-H3(Ser10) (1:100; Cell Signaling); Alexa488-conjugated anti-p-H3(Ser10) (1:200; Cell Signaling); anti-YAP (0.5 μg/ml; Santa Cruz); anti-p-YAP(Ser127) (1:1000; Cell Signaling); YL1/2 (anti-tubulin; 1:500; Abcam); anti-p-p38 (Thr180/Tyr182) (1:1000; Cell Signaling); anti-MAPKAPK-2 (1:1000; Cell Signaling); anti-p-MAPKAPK-2 (Thr334) (1:1000; Cell Signaling); anti-p53 (1:100; Calbiochem); anti-p-p53(Ser9) (1:1000; Cell Signaling); anti-p-p53(Ser15) (1:250; MBL); anti-p-p53(Ser20) (1:1000; Abcam); anti-p-p53(Ser33) (1:1000; Cell Signaling); anti-p-p53(Ser37) (1:1000; Cell Signaling); anti-p-p53 (Ser315) (1:1000; Cell Signaling); anti-p-p53(Ser392) (1:1000; Cell Signaling); anti-acetyl-p53(Lys382) (1:1000; Cell Signaling); anti-p21 (1:1000; Cell Signaling); anti-MDM2 (1:1000; Millipore); anti-γ-H2A.X (1 μg/ml; Abcam); DM1A (anti-α-tubulin; 1:1000; Sigma-Aldrich); anti-GAPDH (1:1000; Cell Signaling). Secondary antibodies were purchased from Jackson Immunoresearch.

Kinase assays. All kinase assays were performed in Corning #3674 white 384-well plates. Plk4 assays used equal volumes of: (1) purified 6×His-tagged human Plk4 kinase domain (aa 2-275) (expressed in *E. coli* and purified via Ni-NTA affinity chromatography) in 20 mM Tris pH 7.5, 100 mM NaCl, 10% glycerol, 1 mM DTT; (2) 2× reaction buffer consisting of 50 mM HEPES pH 8.5, 20 mM MgCl$_2$, 1 mM DTT, 0.2 mg/ml BSA, 16 μM ATP, and 200 μM A-All substrate (amino acid sequence: TPSDSLIYDDGLS; 17). The Plk4 concentration in the final reaction was 2.5-10 nM with a final pH of 8.0. Inhibitors arrayed in dose response were added from DMSO stocks using a V&P 384-pintool head mounted on a Beckman Multimek chassis. Reactions were allowed to proceed for 4-16 hours at 25° C. Detection was performed using ADP-Glo reagent (Promega), following manufacturer's instructions. Luminescence was measured on an Infinite M1000 plate reader (Tecan). Data were fit using Prism (GraphPad) and $K_i$s were calculated from $IC_{50}$ data using the Cheng and Prusoff equation (37) or the Copeland formalism for tight-binding inhibitors (38).

Aurora A assays used 1 nM purified human Aurora A (Millipore) in 25 mM Tris pH 7.5, 75 mM NaCl, 10 mM $MgCl_2$, 135 mM Sucrose, 0.5 mM DTT, 0.1 mg/ml BSA, 0.015% Brij 35+35 µM ATP+400 µM Kemptide substrate (amino acid sequence: LRRASLG)+inhibitors arrayed in dose response (added as described above). Reactions were incubated for 1 hour at 25° C. Detection, measurement and data analysis were performed as described above.

Aurora B and other radiometric kinase assays were performed by Reaction Biology (Malvern, Pa.). Kinome profiling of centrinone and centrinone-B was performed by DiscoveRx (San Diego, Calif.).

Crystal structure of centrinone-bound Plk4. Human Plk4 (aa 2-275) was cloned into pET42 with an N-terminal GST-6×His tag. The fusion protein was co-expressed with λ-phosphatase (cloned into pCDF-Duet1 (Novagen)) in *E. coli* BL21 Rosetta2(DE3) cells (Novagen) and purified by affinity chromatography with Ni-NTA Superflow resin (Qiagen) followed by glutathione Sepharose 4 Fast Flow (GE) using standard methods. The tag was cleaved with Turbo3C protease (ETON), and removed using glutathione Sepharose. The untagged protein was further purified by size-exclusion chromatography on a GE Superdex 75 16/600 column. The final eluate (in 20 mM Tris pH 7.5, 100 mM NaCl, 0.5 mM TCEP) was incubated with 100 µM centrinone overnight on ice, then concentrated to ~8 mg/mL using Amicon Ultra 10K MWCO concentrators (Millipore).

Plk4(2-275)+centrinone was crystallized by sitting drop vapor diffusion using a reservoir buffer consisting of 0.1 M HEPES pH 7.5, 0.2 M $MgCl_2$, 30% PEG-400 at 24° C. 0.2 µL protein solution was mixed with 0.1 µL reservoir buffer using a Mosquito pipettor (TTP Labtech) and sealed in a chamber containing 70 µL of reservoir solution. After 8 months, a single cubic crystal (~30 µm edge) was transferred to a cryoprotectant containing 0.1 M HEPES pH 7.5, 0.2 M $MgCl_2$, 32.5% PEG 400, 100 µM centrinone, and flash-frozen in liquid nitrogen.

X-ray diffraction data were measured at the NE-CAT beamline 24-ID-E at the Advanced Photon Source at Argonne National Laboratory and processed with XDS (39) and AIMLESS from the CCP4 suite (40). The structure was determined by molecular replacement using PHASER (41) and sequential searches with the large and then the small lobe of the kinase domain model of the AMP-PNP complex (PDB: 3COK). Refinement was performed using PHENIX (42) interspersed with iterative cycles of rebuilding using Moloc (43). Figures were made using PyMol (Schrödinger).

Cell lines. Primary cells and cell lines were obtained from the ATCC, with the exception of N1E-115-1 (Sigma-Aldrich), Tet-On 3G NIH/3T3 (Clontech), DLD-1 Plk4-YFP (gift from A. Holland and D. Cleveland) and RPE1 Fucci YAP (WT and S5A; gifts from N. Ganem and D. Pellman). Cells were generally maintained in ATCC-recommended complete growth media+100 U/mL penicillin+100 ag/mL streptomycin. Compounds were added to and maintained in complete growth medium unless otherwise specified.

For generation of Plk4-GFP inducible NIH/3T3 cells, a mouse Plk4 cDNA C-terminally fused to eGFP was cloned into the lentiviral vector pLVX-TRE3G (Clontech). The G95L point mutation was generated by Quikchange mutagenesis (Agilent Technologies). Plasmids were transfected into HEK-293T cells using the Lenti-X HTX packaging system (Clontech), following manufacturer's instructions. 48 hours after transfection, virus-containing culture supernatant was harvested and added to the growth medium of Tet-On 3G NIH/3T3 cells (Clontech)+8 µg/ml polybrene (EMD Millipore). Multiple clones were isolated by direct trypsinization of single colonies, and all showed similar behavior in the centriole overduplication assay (see below).

For generation of cell lines co-expressing centrin-GFP and H2B-RFP, a human centrin-GFP construct was purchased from Origene. This plasmid and lentivirus packaging vectors (pCAG-HIVgp and pCMV-VSV-G-RSV-Rev from Hiroyuki Miyoshi, RIKEN BioResource Center) were co-transfected into HEK-293T cells using Fugene HD (Promega). Virus was harvested as described above and added to the growth media of cells +5-10 ☐µg/ml polybrene. A pBABE-Puro vector encoding human histone H2B C-terminally fused to mRFP1.3 was obtained from the laboratory of Don Cleveland. This plasmid and pBSK-VSV-G were co-transfected into the packaging cell line GP2-293 (Clontech) using Fugene HD. Virus was harvested as described above and added to the growth media of unsorted centrin-GFP-expressing cells +5-10 lag/ml polybrene. Populations of each cell line expressing both transgenes at moderate levels were selected by FACS.

For generation of HeLa and NIH/3T3 lines co-expressing GFP-PCNA and H2B-RFP, cells were transduced with an H2B-RFP retrovirus as described above. An MGC collection human PCNA cDNA was engineered as an N-terminal eGFP fusion and cloned into pBABE-Hygro. Retroviral production and transduction was performed as described for H2B-RFP above. Populations of each cell line expressing both transgenes at moderate levels were selected by FACS.

For generation of RPE1 cells with a Plk4(G95L) knock-in, we targeted the intronic region between exons 4 and 5 of the Plk4 locus with a gRNA sequence (GGAAGCTGAGT-GTTAAGTTC, SEQ ID NO: 1) cloned into pX458 (a gift from Feng Zhang; Addgene plasmid #48138; 44). A repair template was cloned to introduce the G95L point mutation, as well as a neomycin resistance cassette within the intronic region (see FIG. 15). RPE1 cells were transfected with the Cas9/gRNA plasmid, then transduced with adeno-associated virus coding for the repair template using previously described methods (45). Cells were selected in 96-well plates for 2 weeks using 0.5 mg/ml Geneticin (Life Technologies). Positive clones homozygous for the G95L knock-in were identified by PCR and sequencing of genomic DNA.

For generation of RPE1 cells expressing a constitutive LATS1/LATS2 microRNA, the pLenti-EmGFP-LATS1/2KD plasmid was used (a gift from Yutaka Hata; Addgene plasmid #52085; 46). Lentiviral generation and transduction were performed as described above. Transduced cells were selected by FACS based on GFP fluorescence.

For generation of RPE1 cells expressing a constitutive p53 shRNA, lentivirus coding for either Glu4 control or p53 shRNA were gifts from Quan Zhu and Inder Verma. Lentiviral transduction were performed as described above. Transduced cells were used directly in experiments as the transduction efficiency was >95% for both control and p53 shRNA lentiviruses.

Centriole depletion assay for compound screening. 1,500 NIH/3T3 cells or 3,500 HCT116 cells were seeded into 96-well SCREENSTAR microplates (Greiner) and treated with inhibitors in dose response, added from DMSO stocks. After 3 days, cells were fixed directly in the wells with 100% methanol (−20° C., 10 minutes). The fixed cells were washed with PBS and stained with primary antibodies against γ-tubulin and, for a subset of compounds, Cep192. Cells were then stained with Alexa-488 donkey anti-mouse and Alexa-647 goat anti-rabbit secondary antibodies. Cells were imaged using either a Model 500 LumaScope (Etaluma) or an EVOS FL (Advanced Microscopy Group/Life Technologies), and centriole depletion was determined by scoring the percentage of cells without visible γ-tubulin/Cep192 foci.

Quantification of centrosome numbers from fixed samples. Cells were seeded onto poly-D-lysine-coated coverslips (Neuvitro) in 12-well plates at least 8 hours before fixation. At the required timepoints for each experiment, cells were washed once with PBS and fixed in 100% methanol (−20° C., 5 minutes). Fixed cells were washed with PBS, blocked with PBS+4% BSA+0.1% Triton X-100, and stained with primary antibodies against γ-tubulin and Cep192, which localize to the pericentriolar material and proximal to the outer centriole wall, respectively (47, 48). Alexa488-labeled anti-mouse secondary antibody (against anti-γ-tubulin) and Alexa647-labeled anti-rabbit secondary antibody (against anti-Cep192) were both used at 1.5 jag/mL. Samples were mounted onto slides with Prolong Gold antifade reagent (Life Technologies). Images of fixed interphase cells were acquired on a Nikon Eclipse E800 with a 60×1.4 NA PlanApo objective and ORCA-ER camera (Hamamatsu) using Metamorph software (Molecular Devices). Quantification of foci was performed manually. A focus was defined as a bona-fide centrosome if it was positive for both γ-tubulin and Cep192 (true for >95% of foci).

Microtubule regrowth assay. NIH/3T3 cells were treated with DMSO or 300 nM centrinone for >2 weeks prior to the start of the experiment. Cells were seeded onto coverslips in 12-well plates and treated with 16 μM nocodazole for 4 hours to depolymerize microtubules. Wells were washed 6 times with PBS to remove the nocodazole, and fresh, pre-warmed medium was added to each well. After 5 minutes of recovery, cells were fixed with 100% methanol (−20° C., 5 minutes) and stained with antibodies against γ-tubulin and α-tubulin. Coverslips were mounted onto slides and imaged on a DeltaVision microscope (Applied Precision) with a 60×1.42 NA PlanApo objective and CoolSnap camera (Photometrics). Image deconvolution was performed in softWoRx (Applied Precision) and subsequent processing was performed in ImageJ (NIH).

Cilia formation assay in NIH/3T3 cells. NIH/3T3 cells were treated with DMSO or 300 nM centrinone for >2 weeks prior to the start of the experiment. Cells were seeded onto coverslips and starved for 40 hours by replacing their media with DMEM+0.5% defined bovine serum. Cells were then washed with PBS, fixed with 100% methanol (−20° C., 5 minutes), stained with antibodies against γ-tubulin and IFT-88, and mounted onto slides. Image acquisition and deconvolution were performed on the DeltaVision system, as above. Subsequent image processing was performed in ImageJ.

Multiciliation assay in *Xenopus* embryos. *Xenopus* embryos were obtained by in vitro fertilization using standard protocols (49) approved by the Northwestern University Institutional Animal Care and Use Committee. Fertilized *Xenopus* embryos were injected with mRNA encoding the centriole marker Centrin4-GFP (333 pg/embryo) and a Dexamethasone-inducible Multicilin (hGR 3'MCI; 160 pg/embryo) (50, 51). Embryos were allowed to develop to stage 10.5-11 and were then treated with a combination of Dexamethosone (20 OM) and either DMSO, centrinone or centrinone-B. Drug treatments were performed in 0.5× Marc's Modified Ringers (2.5 mM HEPES, 55 mM NaCl, 1 mM KCl, 0.5 mM $MgCl_2$, 1 mM $CaCl_2$, 1 mM $NaHCO_3$, pH 7.8) with 4% Ficoll to facilitate solubility. Embryos were treated for 13 hours at room temperature, fixed in 4% paraformaldehyde and treated with the actin stain phalloidin. Confocal image stacks were collected using a Nikon AIR microscope and centriole numbers were manually quantified in Nikon Elements software. For each condition, centriole numbers were quantified from approximately 100 cells from at least 3 embryos.

Centriole overduplication assay. Tet-On 3G NIH/3T3 cells (Clontech) stably transduced with GFP, Plk4-GFP or Plk4(G95L)-GFP were seeded onto coverslips in a 12-well plate at 30,000 cells/well. Transgene expression was induced with 1 μg/ml doxycycline. At the same time, cells were treated with DMSO or 300 nM centrinone. Treated cells were incubated for 40 hours, and then washed with PBS and fixed in 100% methanol (−20° C., 5 minutes). Fixed samples were stained for γ-tubulin and Cep192, and mounted onto slides. Image acquisition and deconvolution were performed on the DeltaVision system equipped with a 100×1.3 NA U-PlanApo objective. Subsequent image processing was performed in ImageJ.

Quantification of Aurora A and Aurora B activity. HeLa cells were seeded onto coverslips, and allowed to settle for 16 hours. Cells were then treated with DMSO, 125 nM centrinone or 1 μM VX-680 for 7 hours. For quantification of Aurora A activity, treated cells were fixed in 100% methanol (−20° C., 5 minutes) and stained with anti-p-LATS2(Ser83) and Hoechst 33342. 5×1 m z-sections of metaphase cells (or in the case of VX-680-treatment, cells with condensed DNA) were acquired on the DeltaVision system with the 60×1.42 NA PlanApo objective. Stacks were projected and transferred to ImageJ for analysis. The integrated signal from a 1×1 μm box centered on each centrosome was measured. For background subtraction, a 1×1 μm box in the cytoplasm was used. Mean values of measurements were normalized to the DMSO-treated condition. For quantification of Aurora B activity, treated cells were fixed in 4% paraformaldehyde for 15 minutes at room temperature, then permeabilized with PBS+0.25% Triton X-100 for 5 minutes. Fixed cells were stained with anti-p-H3(Ser10), anti-α-tubulin, and Hoechst 33342. 5×1 μm z-sections were acquired as above and projected. The DNA signal was used to threshold and define a binary mask, which was then transferred to the p-H3 channel. The mean intensity of this region was measured in the p-H3 channel. For background subtraction, the masked region was expanded by 20 pixels, and the mean intensity of the peripheral region was used. Mean values of measurements were normalized to the DMSO-treated condition.

Proliferation assays. For each condition, cells were seeded in triplicate into 6-well plates at 50,000 cells/well. Compounds were added at the indicated concentrations. At 24-hour intervals, 3 wells were harvested per condition. Cell counting was performed using a TC10 automated cell counter (Bio-Rad). Results are from 3 independent experiments.

Passaging assays. Cells were seeded into 10 cm tissue culture plates at 150,000 (HeLa, NIH/3T3 and RPE1) or 200,000 cells/plate (primary fibroblasts). Compounds were added at the indicated concentrations. At 4-day intervals, cells were harvested, counted using a TC10 cell counter, and re-seeded into new plates at the densities above. Results are from 2 independent experiments.

Analysis of cell cycle progression. HeLa and NIH/3T3 cells co-expressing GFP-PCNA and H2B-RFP were treated with DMSO or centrinone (125 nM for HeLa, 300 nM for NIH/3T3) for >2 weeks prior to the start of the experiment.

Cells were seeded into 96-well cycloolefin plates (Greiner Bio-One) at 4000 cells/well, 8-10 hours before imaging. Movies were acquired on a CV1000 spinning disk confocal system (Yokogawa Electric Corporation) with a 20×0.75 NA U-PlanApo objective and 512×512 EM-CCD camera (Hamamatsu). The imaging chamber was maintained at 37° C. and 5% $CO_2$. Image acquisition and data analysis were performed using CellVoyager software. 12-24 fields/well were imaged, with duplicate wells for each condition. 3×4 μm z-sections in the GFP (20% power, 100 ms, 25% gain) and RFP (25% power, 100 ms, 25% gain) channels were captured in each field, at 10-minute intervals for 48 hours. Cells were manually tracked from the beginning of G1 (chromosome decondensation) to the beginning of the next mitosis (nuclear envelope breakdown). GFP-PCNA foci appear in the nucleus during mid- to late-S-phase, and the first frame in which these foci are no longer visible was defined as the beginning of G2 phase. Results represent combined measurements of 200 cells per condition from 2 independent experiments.

Analysis of mitosis and daughter cell fate. HeLa, NIH/3T3 and RPE1 cells co-expressing centrin-GFP and H2B-RFP were treated with DMSO or centrinone (125 nM for HeLa and RPE1, 300 nM for NIH/3T3) beginning 2 days, 1 day or immediately prior to imaging to capture 0-, 1-, and 2-centrosome mitoses, respectively. Cells were seeded into 96-well cycloolefin plates at 5000 cells/well, 8-10 hours before imaging. Movies were acquired on the CV1000 with a 40×0.95 NA U-PlanApo objective. The imaging chamber was maintained at 37° C. and 5% $CO_2$. Image acquisition and data analysis were performed using CellVoyager software. 20 fields/well were imaged. For HeLa and NIH/3T3 cells, 5×2 μm z-sections in the GFP (25% power, 125 ms, 30% gain) and RFP (25% power, 100 ms, 30% gain) channels were captured in each field, at 5-minute intervals for 24 hours. For RPE1 cells, 5×2 μm z-sections in the GFP (20% power, 100 ms, 30% gain) and RFP (25% power, 100 ms, 30% gain) channels were captured in each field, at 5-minute intervals for 8 hours. To track RPE1 daughter cell fate, imaging was then switched to 3×4 μm z-sections in the RFP channel only, at 10-minute intervals for 48 hours. Mitosis was measured from nuclear envelope breakdown to anaphase onset (or arrest). Results represent combined measurements of 100 mother cells per condition from 2-4 independent experiments.

To study the correlation between mother cell prometaphase duration and daughter cell fate, RPE1 cells co-expressing centrin-GFP and H2B-RFP were seeded into 96-well cycloolefin plates at 5000 cells/well, 8-10 hours before imaging. Cells were treated with 80 nM nocodazole and immediately imaged on the CV1000 system with a 40×0.95 NA U-PlanApo objective. The imaging chamber was maintained at 37° C. and 5% $CO_2$. 20 fields/well were imaged. 5×2 Lm z-sections in the GFP (20% power, 100 ms, 30% gain) and RFP (25% power, 100 ms, 30% gain) channels were captured in each field, at 5-minute intervals for 6 hours. The plate was then removed from the microscope, and wells were washed 6 times with warm medium. The plate was returned to the microscope, and imaging was resumed, capturing 3×4 Lm z-sections in the RFP channel only, at 10-minute intervals for 50 hours. To study the effect of chromosome missegregation on daughter cell fate, cells were treated with 1 LM NMS-P715 to inhibit the spindle assembly checkpoint kinase Mps1, then imaged as described above. Only mitotic events with clear missegregation (lagging chromosomes and subsequent formation of daughter cells with micronuclei) were analyzed. For both experiments, results represent combined measurements of 100 mother cells from 2 independent experiments.

Live imaging of centriole recovery. HeLa cells co-expressing centrin-GFP and H2B-RFP were treated with 125 nM centrinone for >2 weeks prior to the start of the experiment. Centrinone was washed out 39 hours, 15 hours, or immediately prior to imaging to obtain data within a large time window of centriole recovery. Cells were seeded into 96-well cycloolefin plates at 5000 cells/well, 8-10 hours before imaging. Movies were acquired on the CV1000 with a 40×0.95 NA U-PlanApo objective. The imaging chamber was maintained at 37° C. and 5% $CO_2$. Image acquisition and data analysis were performed using CellVoyager software. 20 fields/well were imaged. 5×2 Lm z-sections in the GFP (25% power, 125 ms, 30% gain) and RFP (25% power, 100 ms, 30% gain) channels were captured in each field, at 10-minute intervals for 72 hours. For each cell, centrin foci were counted at nuclear envelope breakdown, when the centrosomes maximally separate from each other. Results represent combined measurements of 300 mother cells from 3 independent experiments.

Apoptosis Assay. HeLa and NIH/3T3 cells were treated with DMSO or centrinone (125 nM for HeLa, 300 nM for NIH/3T3) for 8 days prior to the start of the experiment. Cells were seeded into 96-well cycloolefin plates (Greiner Bio-One) 20 hours before imaging. 30 minutes before imaging, cells were stained with NucRed Live 647 (Life Technologies) and CellEvent Caspase-3/7 Green Reagent (Life Technologies) to mark DNA and apoptotic cells, respectively. Images were acquired on a CV7000 spinning disk confocal system (Yokogawa Electric Corporation) with a 20×0.75 NA U-PlanApo objective and 2560×2160 sCMOS camera (Andor) at 2×2 binning. The imaging chamber was maintained at 37° C. and 5% $CO_2$. Image acquisition and data analysis were performed using CV7000 software. 9 fields/well were imaged, with triplicate wells for each condition. 10×2 μm z-sections in the green (25% power, 100 ms, 2.2× gain) and far-red (30% power, 200 ms, 2.2× gain) channels were captured in each field. The percentage of apoptotic cells was calculated by manual counting of cells positively or negatively staining with the fluorescent caspase reporter. Results represent combined measurements from 2 independent experiments.

Flow cytometry. Cells were seeded into 15 cm tissue culture plates such that each plate was 50-80% confluent at the time of harvesting. Cells were de-adhered by trypsinization and pelleted in 15 ml tubes by centrifugation. Each pellet was resuspended in 0.3 mL PBS, and 0.7 mL ice-cold 100% ethanol was added to the tube while gently vortexing. Fixed cells were stored at 4° C. for up to 2 weeks. For DNA content analysis, fixed cells were pelleted, washed twice with PBS, and resuspended in 0.5 mL PBS+2% BSA and Alexa488-conjugated anti-p-H3(Ser10) antibody. Samples were incubated for 1 hour at 4° C., then washed twice with PBS+2% BSA. Pellets were resuspended in 1 mL PBS+2% BSA, 10 μg/ml propidium iodide (Sigma-Aldrich), 500 g/ml RNAse A (Thermo Scientific). Samples were incubated at 37° C. for 30 minutes, then transferred to 12×75 mm tubes for analysis. Data were acquired using FACSDiva software on a LSR II flow cytometer (BD Biosciences). 50,000 cells were analyzed per condition. Cell cycle fitting was performed using ModFit LT (Verity Software House).

DNA Damage Checkpoint Assay. HeLa and NIH/3T3 cells were treated with DMSO or centrinone (125 nM for Hela, 300 nM for NIH/3T3) for >2 weeks prior to the start of the experiment. Cells were seeded into 10 cm tissue culture plates at 30-40% confluence 24 hours before the experiment. For the positive control, cells were pre-treated with 5 mM caffeine (Sigma-Aldrich) for 1 hour before beginning the experiment. Cells were treated with 2 µM doxorubicin for 90 minutes, then washed twice with PBS and allowed to recover in fresh medium for 3 hours (with 5 mM caffeine, where indicated). Cells were then harvested and processed for flow cytometry as described above.

γ-H2A.X staining. RPE1 cells were treated with DMSO or 125 nM centrinone for 4 days. Cells were either seeded onto coverslips for staining, or harvested for cell extracts (see below). Cells treated for 16 hours with 0.5 µM doxorubicin were used as a positive control for DNA damage induction. Coverslips with cells were fixed in 100% methanol (−20° C., 5 minutes) and stained with antibodies against γ-H2A.X, γ-tubulin, and Hoechst 33342. Coverslips were mounted onto slides and imaged on the DeltaVision system at 100× magnification. Cells with γ-H2A.X foci in the nucleus were manually counted for each condition.

MAPKAPK-2 activation assay. RPE1 cells on 10 cm plates were treated with DMSO or 10 µM SB203580 for 2 hours prior to induction of stress. To induce osmotic stress, the growth medium was replaced with 0.5 M sorbitol (with DMSO or 10 µM SB203580) for 45 minutes before harvesting for Western blotting (see below).

Plk4 stabilization assay. Expression was induced in Plk4-YFP DLD-1 cells using 1 µg/ml doxycycline. At the same time, cells were treated with the indicated concentrations of compounds. Cells were incubated for 24 hours before harvesting for Western blotting (see below).

Western blotting. Asynchronously growing cells from 10 cm plates were harvested at 50-80% confluence and lysed by sonication in RIPA buffer+protease and phosphatase inhibitor cocktail (Thermo Scientific). Cell extracts were stored at −80° C. until use. Before use, concentrations of extracts were normalized using a Bio-Rad Protein Assay (Bio-Rad). For every sample, 25-50 µg protein/lane was run on Mini-PROTEAN gels (Bio-Rad), and transferred to PVDF membranes using a TransBlot Turbo system (Bio-Rad).

For p53, p-p53(S33), p-p53(S392), p-p38(T180/Y182), acetyl-p53(K382), LATS2, YAP, MDM2, MAPKAPK-2 and GFP, blocking and antibody incubations were performed in TBS-T+5% non-fat dry milk. For p-YAP(S127), p-p53(S9), p-p53(S15), p-p53(S20), p-p53(S37), p-p53(S315), p21 and p-MAPKAPK-2(T334), blocking and antibody incubations were performed in TBS-T+5% BSA. Detection was performed using HRP-conjugated secondary antibodies (GE Healthcare) with WesternBright Sirius (Advansta) or SuperSignal West Femto (Thermo Scientific) substrates. Membranes were imaged on a ChemiDoc MP system (Bio-Rad). Membranes were stripped and reprobed with antibodies against α-tubulin or GAPDH as loading controls.

Tetraploid cell arrest assay. RPE1 Fucci cells expressing wild-type or constitutively-active (S5A) YAP were seeded into a 96-well cycloolefin plate at 3000 cells/well, 16 hours before treatment. Cells were treated with DMSO or 4 LM cytochalasin D (Sigma-Aldrich) for 24 hours, then washed 5 times with warm medium. 12 hours after drug washout, the plate was imaged on the CV1000 system with a 10×0.4 NA U-PlanApo objective. Image acquisition and data analysis were performed using CellVoyager software. 4 fields/well were imaged, with 12 wells for each condition. 4×4 Lm z-sections in the GFP (25% power, 100 ms, 30% gain) and RFP (30% power, 150 ms, 60% gain) channels were captured in each field. Tetraploid cells were identified as cells with two nuclei. The number of cells in G1 (red nuclei, expressing hCdt-1-mCherry) and S/G2 (green nuclei, expressing hGem-Azami-Green) was quantified, and the percentage of cells in G1 calculated.

References and Notes (Example 3)

Each reference cited herein is incorporated by reference in its entirety and for all purposes. References for Example 3 follow: (1) A. Drummond, Cilia functions in development. Current opinion in cell biology 24, 24-30 (2012); (2) H. Schatten, The mammalian centrosome and its functional significance. Histochemistry and cell biology 129, 667-686 (2008); (3) D. A. Brito, S. M. Gouveia, M. Bettencourt-Dias, Deconstructing the centriole: structure and number control. Current opinion in cell biology 24, 4-13 (2012); (4) E. N. Firat-Karalar, T. Stearns, The centriole duplication cycle. Philosophical transactions of the Royal Society of London. Series B, Biological sciences 369, (2014); (5) T. Boveri, Zur Frage der Entstehung maligner Tumoren. (Cold Spring Harbor Laboratory Press, 1914), pp. 82; (6) S. A. Godinho, D. Pellman, Causes and consequences of centrosome abnormalities in cancer. Philosophical transactions of the Royal Society of London. Series B, Biological sciences 369, (2014); (7) E. A. Nigg, L. Cajanek, C. Arquint, The centrosome duplication cycle in health and disease. FEBS letters 588, 2366-2372 (2014); (8) N. J. Ganem, S. A. Godinho, D. Pellman, A mechanism linking extra centrosomes to chromosomal instability. Nature 460, 278-282 (2009); (9) W. T. Silkworth, I. K. Nardi, L. M. Scholl, D. Cimini, Multipolar spindle pole coalescence is a major source of kinetochore mis-attachment and chromosome mis-segregation in cancer cells. PloS one 4, e6564 (2009); (10) S. A. Godinho et al., Oncogene-like induction of cellular invasion from centrosome amplification. Nature 510, 167-171 (2014); (11) M. Bettencourt-Dias et al., SAK/PLK4 is required for centriole duplication and flagella development. Current biology: CB 15, 2199-2207 (2005); (12) R. Habedanck, Y. D. Stierhof, C. J. Wilkinson, E. A. Nigg, The Polo kinase Plk4 functions in centriole duplication. Nature cell biology 7, 1140-1146 (2005); (13) J. Kleylein-Sohn et al., Plk4-induced centriole biogenesis in human cells. Developmental cell 13, 190-202 (2007); (14) K. F. O'Connell et al., The C. elegans zyg-1 gene encodes a regulator of centrosome duplication with distinct maternal and paternal roles in the embryo. Cell 105, 547-558 (2001); (15) N. Peel, N. R. Stevens, R. Basto, J. W. Raff, Overexpressing centriole-replication proteins in vivo induces centriole overduplication and de novo formation. Current biology: CB 17, 834-843 (2007); (16) M. I. Davis et al., Comprehensive analysis of kinase inhibitor selectivity. Nature biotechnology 29, 1046-1051 (2011); (17) E. F. Johnson, K. D. Stewart, K. W. Woods, V. L. Giranda, Y. Luo, Pharmacological and functional comparison of the polo-like kinase family: insight into inhibitor and substrate specificity. Biochemistry 46, 9551-9563 (2007); (18) J. M. Mason et al., Functional characterization of CFI-400945, a Polo-like kinase 4 inhibitor, as a potential anticancer agent. Cancer cell 26, 163-176 (2014); (19) P. B. Sampson et al., The discovery of Polo-like kinase 4 inhibitors: identification of (1R,2S).2-(3-((E).4-(((cis).2,6-dimethylmorpholino)methyl) styryl). 1H.indazol-6-yl)-5'-methoxyspiro[cyclopropane-1,3'-indolin]-2'-one (CFI-400945) as a potent, orally active antitumor agent. Journal of medicinal chemistry 58, 147-169 (2015); (20) D. A. Sloane et al., Drug-resistant aurora A mutants for cellular target validation of the small molecule kinase inhibitors MLN8054 and MLN8237. ACS chemical biology 5, 563-576 (2010); (21) R. M. Rios, The centrosome-Golgi apparatus nexus. Philosophical transactions of the Royal Society of London.

Series B, Biological sciences 369, (2014); (22) A. Khodjakov, C. L. Rieder, Centrosomes enhance the fidelity of cytokinesis in vertebrates and are required for cell cycle progression. The Journal of cell biology 153, 237-242 (2001); (23) J. H. Sir et al., Loss of centrioles causes chromosomal instability in vertebrate somatic cells. The Journal of cell biology 203, 747-756 (2013); (24) Y. Uetake et al., Cell cycle progression and de novo centriole assembly after centrosomal removal in untransformed human cells. The Journal of cell biology 176, 173-182 (2007); (25) L. M. Jenkins, S. R. Durell, S. J. Mazur, E. Appella, p53 N-terminal phosphorylation: a defining layer of complex regulation. Carcinogenesis 33, 1441-1449 (2012); (26) N. D. Lakin, S. P. Jackson, Regulation of p53 in response to DNA damage. Oncogene 18, 7644-7655 (1999); (27) N. J. Ganem et al., Cytokinesis failure triggers hippo tumor suppressor pathway activation. *Cell* 158, 833-848 (2014); (28) Y. Uetake, G. Sluder, Prolonged prometaphase blocks daughter cell proliferation despite normal completion of mitosis. Current biology: CB 20, 1666-1671 (2010); (29) H. Bazzi, K. V. Anderson, Acentriolar mitosis activates a p53-dependent apoptosis pathway in the mouse embryo. Proceedings of the National Academy of Sciences of the United States of America 111, E1491-1500 (2014); (30) D. Izquierdo, W. J. Wang, K. Uryu, M. F. Tsou, Stabilization of cartwheel-less centrioles for duplication requires CEP295-mediated centriole-to-centrosome conversion. Cell reports 8, 957-965 (2014); (31) H. Shen, C. G. Maki, Pharmacologic activation of p53 by small-molecule MDM2 antagonists. Current pharmaceutical design 17, 560-568 (2011); (32) R. Basto et al., Flies without centrioles. Cell 125, 1375-1386 (2006); (33) F. Bartolini, G. G. Gundersen, Generation of noncentrosomal microtubule arrays. Journal of cell science 119, 4155-4163 (2006); (34) M. Stiess et al., Axon extension occurs independently of centrosomal microtubule nucleation. *Science* 327, 704-707 (2010); (35) K. D. Sumigray, T. Lechler, Control of cortical microtubule organization and desmosome stability by centrosomal proteins. Bioarchitecture 1, 221-224 (2011); (36) E. Harlow, D. Lane, Antibodies: A Laboratory Manual. (Cold Spring Harbor Laboratory Press, 1988); (37) Y. Cheng, W. H. Prusoff, Relationship between the inhibition constant (K1) and the concentration of inhibitor which causes 50 percent inhibition (I50) of an enzymatic reaction. Biochemical pharmacology 22, 3099-3108 (1973); (38) R. A. Copeland et al., Recombinant human dihydroorotate dehydrogenase: expression, purification, and characterization of a catalytically functional truncated enzyme. Archives of biochemistry and biophysics 323, 79-86 (1995); (39) W. Kabsch, Xds. Acta crystallographica. Section D, Biological crystallography 66, 125-132 (2010); (40) M. D. Winn et al., Overview of the CCP4 suite and current developments. Acta crystallographica. Section D, Biological crystallography 67, 235-242 (2011); (41) A. J. MαCoy et al., Phaser crystallographic software. Journal of applied crystallography 40, 658-674 (2007); (42) P. D. Adams et al., PHENIX: a comprehensive Python-based system for macromolecular structure solution. Acta crystallographica. Section D, Biological crystallography 66, 213-221 (2010); (43) K. Muller et al., MOLOC: A molecular modeling program. Bull. Soc. Chim. Belg. 97, 655-667 (1988); (44) F. A. Ran et al., Genome engineering using the CRISPR-Cas9 system. Nature protocols 8, 2281-2308 (2013); (45) E. Berdougo, M. E. Terret, P. V. Jallepalli, Functional dissection of mitotic regulators through gene targeting in human somatic cells. Methods in molecular biology 545, 21-37 (2009); (46) Z. Yang et al., Screening with a novel cell-based assay for TAZ activators identifies a compound that enhances myogenesis in C2C12 cells and facilitates muscle repair in a muscle injury model. Molecular and cellular biology 34, 1607-1621 (2014); (47) S. Lawo, M. Hasegan, G. D. Gupta, L. Pelletier, Subdiffraction imaging of centrosomes reveals higher-order organizational features of pericentriolar material. Nature cell biology 14, 1148-1158 (2012); (48) K. F. Sonnen, L. Schermelleh, H. Leonhardt, E. A. Nigg, 3D-structured illumination microscopy provides novel insight into architecture of human centrosomes. Biology open 1, 965-976 (2012); (49) H. L. Sive, R. M. Grainger, R. M. Harland, Early Development of *Xenopus laevis*. (Cold Spring Harbor Laboratory Press, 2000); (50) J. L. Stubbs, E. K. Vladar, J. D. Axelrod, C. Kintner, Multicilin promotes centriole assembly and ciliogenesis during multiciliate cell differentiation. Nature cell biology 14, 140-147 (2012); (51) D. A. Klos Dehring et al., Deuterosome-mediated centriole biogenesis. Developmental cell 27, 103-112 (2013); (52) S. Zitouni, C. Nabais, S. C. Jana, A. Guerrero, M. Bettencourt-Dias, Polo-like kinases: structural variations lead to multiple functions. Nature reviews. Molecular cell biology 15, 433-452 (2014); (53) A. J. Holland, W. Lan, S. Niessen, H. Hoover, D. W. Cleveland, Polo-like kinase 4 kinase activity limits centrosome overduplication by autoregulating its own stability. The Journal of cell biology 188, 191-198 (2010); (54) I. Akritopoulou-Zanze, P. J. Hajduk, Kinase-targeted libraries: the design and synthesis of novel, potent, and selective kinase inhibitors. Drug discovery today 14, 291-297 (2009); (55) M. Kothe et al., Selectivity-determining residues in Plk1. Chemical biology & drug design 70, 540-546 (2007); (56) H. Leonhardt et al., Dynamics of DNA replication factories in living cells. The Journal of cell biology 149, 271-280 (2000); (57) G. J. Gorbsky, Cohesion fatigue. Current biology: CB 23, R986-988 (2013); (58) Y. Higashimoto et al., Human p53 is phosphorylated on serines 6 and 9 in response to DNA damage-inducing agents. The Journal of biological chemistry 275, 23199-23203 (2000); (59) S. Y. Shieh, M. Ikeda, Y. Taya, C. Prives, DNA damage-induced phosphorylation of p53 alleviates inhibition by MDM2. Cell 91, 325-334 (1997); (60) K. Sakaguchi et al., DNA damage activates p53 through a phosphorylation-acetylation cascade. Genes & development 12, 2831-2841 (1998); (61) J. P. Blaydes et al., Stoichiometric phosphorylation of human p53 at Ser315 stimulates p53-dependent transcription. The Journal of biological chemistry 276, 4699-4708 (2001); (62) M. L. Cox, D. W. Meek, Phosphorylation of serine 392 in p53 is a common and integral event during p53 induction by diverse stimuli. Cellular signalling 22, 564-571 (2010); (63) P. A. Karplus, K. Diederichs, Linking crystallographic model and data quality. Science 336, 1030-1033 (2012);

VI. Embodiments

Embodiment P1

A compound having the formula:

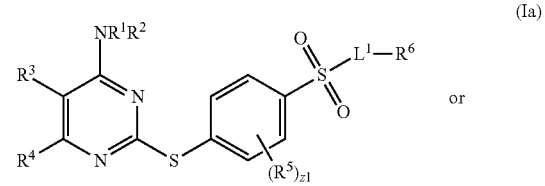

or

-continued

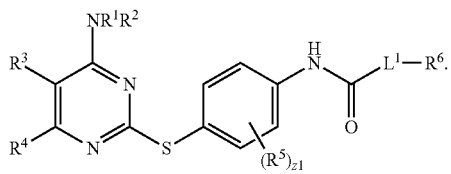

(Ib)

L¹ is a bond, —C(O)—, —C(O)O—, —O—, —S—, —NR¹³—, —C(O)NR¹³—, —NR¹³C(O)—, —S(O)₂—, —S(O)NR¹³—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. R¹ is hydrogen, halogen, —N₃, —CF₃, —CCl₃, —CBr₃, —CI₃, —CN, —COR$^{1A}$, —OR$^{1A}$, —NR$^{1A}$R$^{1B}$, —C(O)OR$^{1A}$, —C(O)NR$^{1A}$R$^{1B}$, —NO₂, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R² is hydrogen, halogen, —N₃, —CF₃, —CCl₃, —CBr₃, —CI₃, —CN, —COR$^{2A}$, —OR$^{2A}$, —NR$^{2A}$R$^{2B}$, —C(O)OR$^{2A}$, —C(O)N$_R$$^{2A}$R$^{2B}$, —NO₂, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R³ is hydrogen, halogen, —N₃, —CF₃, —CCl₃, —CBr₃, —CI₃, —CN, —COR$^{3A}$, —OR$^{3A}$, —NR$^{3A}$R$^{3B}$, —C(O)OR$^{3A}$, —C(O)NR$^{3A}$R$^{3B}$, —NO₂, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R⁴ is hydrogen, halogen, —N₃, —CF₃, —CCl₃, —CBr₃, —CI₃, —CN, —COR$^{4A}$, —OR$^{4A}$, —NR$^{4A}$R$^{4B}$, —C(O)OR$^{4A}$, —C(O)NR$^{4A}$R$^{4B}$, —NO₂, —SR$^{4A}$, —S(O)$_{n4}$R$^{4A}$, —S(O)$_{n4}$OR$^{4A}$, —S(O)$_{n4}$NR$^{4A}$R$^{4B}$, —NHNR$^{4A}$R$^{4B}$, —ONR$^{4A}$R$^{4B}$, —NHC(O)NHNR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R³ and R⁴ are optionally combined to form a substituted or unsubstituted cycloalkyl, substituted or unsubstituted heterocycloalkyl, substituted or unsubstituted aryl, or substituted or unsubstituted heteroaryl. R⁵ is independently hydrogen, halogen, —N₃, —CF₃, —CCl₃, —CBr₃, —CI₃, —CN, —COR$^{5A}$, —OR$^{5A}$, —NR$^{5A}$R$^{5B}$, —C(O)OR$^{5A}$, —C(O)NR$^{5A}$R$^{5B}$, —NO₂, —SR$^{5A}$, —S(O)$_{n5}$R$^{5A}$, —S(O)$_{n5}$OR$^{5A}$, —S(O)$_{n5}$NR$^{5A}$R$^{5B}$, —NHNR$^{5A}$R$^{5B}$, —ONR$^{5A}$R$^{5B}$, —NHC(O)NHNR$^{5A}$R$^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R⁶ is hydrogen, oxo, halogen, —N₃, —CF₃, —CCl₃, —CBr₃, —CI₃, —CN, —CHO, —OR$^{6A}$, —NR$^{6A}$R$^{6B}$, —C(O)OR$^{6A}$, —C(OC(O)NR$^{6A}$R$^{6B}$, —NO₂, —SR$^{6A}$, —S(O)$_{n6}$R$^{6A}$, —S(O)$_{n6}$OR$^{6A}$, —S(O)$_{n6}$NR$^{6A}$R$^{6B}$, —NHNR$^{6A}$R$^{6B}$, —ONR$^{6A}$R$^{6B}$, —NHC(O)NHNR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n1, n2, n3, n4, n5, and n6 are independently 1 or 2. z1 is 1, 2, 3, or 4. R$^{1A}$, R$^{1B}$, R$^{2A}$, R$^{2B}$, R$^{3A}$, R$^{3B}$, R$^{4A}$, R$^{4B}$, R$^{5A}$, R$^{5B}$, R$^{6A}$, R$^{6B}$, and R¹³ are independently hydrogen, oxo, halogen, —CF₃, —CN, —OH, —NH₂, —COOH, —CONH₂, —COH, —COCH₃, —NO₂, —SH, —S(O)₂Cl, —S(O)₃H, —S(O)₄H, —S(O)₂NH₂, —NHNH₂, —ONH₂, —NHC(O)NHNH₂, —NHC(O)NH₂, —NHS(O)₂H, —NHC(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The compound is not VX-680.

Embodiment P2

The compound of embodiment 1, wherein said compound has the formula:

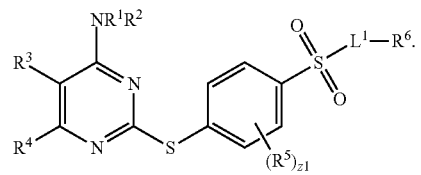

(Ia)

Embodiment P3

The compound of embodiment 1, wherein R³ is hydrogen, halogen, —N₃, —CF₃, —CCl₃, —CBr₃, —CI₃, —CN, —COR$^{3A}$, —OR$^{3A}$, —NR$^{3A}$R$^{3B}$, —C(O)OR$^{3A}$, —C(O)NR$^{3A}$R$^{3B}$, —NO₂, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, or substituted or unsubstituted alkyl, or optionally combined with R⁴ to form a substituted or unsubstituted cycloalkyl; and R$^{3A}$, R$^{3B}$, R$^{3C}$, are independently hydrogen, oxo, halogen, —CF₃, —OH, —NH₂, —COOH, —CONH₂, substituted or unsubstituted alkyl, or substituted or unsubstituted aryl.

Embodiment P4

The compound of any one of embodiments 1 to 3, wherein R³ is hydrogen, halogen, —OR$^{3A}$, or substituted or unsubstituted alkyl; and R$^{3A}$ is substituted or unsubstituted alkyl.

Embodiment P5

The compound of any one of embodiments 1 to 4, wherein R³ is —OR$^{3A}$; and R$^{3A}$ is substituted or unsubstituted alkyl.

Embodiment P6

The compound of any one of embodiments 1 to 5, wherein R³ is —OCH₃.

Embodiment P7

The compound of any one of embodiments 1 to 3, wherein $R^3$ and $R^4$ together form a substituted or unsubstituted cycloalkyl.

Embodiment P8

The compound of any one of embodiments 1 to 6, wherein $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P9

The compound of any one of embodiments 1 to 8, wherein $R^4$ is substituted or unsubstituted cycloalkyl, substituted or unsubstituted heterocycloalkyl, substituted or unsubstituted aryl, or substituted or unsubstituted heteroaryl.

Embodiment P10

The compound of any one of embodiments 1 to 9, wherein $R^4$ is substituted or unsubstituted 5 to 8 membered heterocycloalkyl.

Embodiment P11

The compound of any one of embodiments 1 to 10, wherein $R^4$ is substituted or unsubstituted 5 to 8 membered heterocycloalkyl having at least one ring nitrogen.

Embodiment P12

The compound of any one of embodiments 1 to 11, wherein $R^4$ is substituted or unsubstituted piperidinyl, substituted or unsubstituted piperazinyl, substituted or unsubstituted morpholino, or substituted or unsubstituted pyrrolidinyl.

Embodiment P13

The compound of any one of embodiments 1 to 9, wherein $R^4$ is $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl. $R^{40}$ is independently hydrogen, oxo, halogen, $-N_3$, $-CF_3$, $-CCl_3$, $-CBr_3$, $-CI_3$, $-CN$, $-COR^{40A}$, $-OR^{40A}$, $-NR^{40A}R^{40B}$, $-C(O)OR^{40A}$, $-C(O)NR^{40A}R^{40B}$, $-NO_2$, $-SR^{40A}$, $-S(O)_2R^{40A}$, $-S(O)_2OR^{40A}$, $-S(O)_2NR^{40A}R^{40B}$, $-NHNR^{40A}R^{40B}$, $-ONR^{40A}R^{40B}$, $-NHC(O)NHNR^{40A}R^{40B}$, $R^{40A}$-substituted or unsubstituted alkyl, $R^{40A}$-substituted or unsubstituted heteroalkyl, $R^{40A}$-substituted or unsubstituted cycloalkyl, $R^{40A}$-substituted or unsubstituted heterocycloalkyl, $R^{40A}$-substituted or unsubstituted aryl, or $R^{40A}$-substituted or unsubstituted heteroaryl. $R^{40A}$ is independently hydrogen, oxo, halogen, $-N_3$, $-CF_3$, $-CCl_3$, $-CBr_3$, $-CI_3$, $-CN$, $-OR^{41}$, $-NR^{41}R^{40C}$, $-COR^{41}$, $-COOR^{41}$, $-CONR^{41}R^{40C}$, $-NO_2$, $-SR^{41}$, $-S(O)_2R^{41}$, $-S(O)_3R^{41}$, $-S(O)_2NR^{41}R^{40C}$, $S(O)_4R^{41}$, $-NHNR^{41}R^{40C}$, $-ONR^{41}R^{40C}$, $-NHC(O)NHNR^{41}R^{40C}$, $-NHC(O)NR^{41}R^{40C}$, $-NHS(O)_2R^{41}$, $-NHC(O)R^{41}$, $-NHC(O)-OR^{41}$, $-NHOR^{41}$, $-OCF_3$, $-OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl. $R^{40B}$ is independently hydrogen, oxo, halogen, $-N_3$, $-CF_3$, $-CCl_3$, $-CBr_3$, $-CI_3$, $-CN$, $-OR^{45}$, $-NR^{45}R^{40D}$, $-COR^{45}$, $-COOR^{45}$, $-CONR^{45}R^{40D}$, $-NO_2$, $-SR^{45}$, $-S(O)_2R^{45}$, $-S(O)_3R^{45}$, $-S(O)_4R^{45}$, $-S(O)_2NR^{45}R^{40D}$, $-NHNR^{45}R^{40D}$, $-ONR^{45}R^{40D}$, $-NHC(O)NHNR^{45}R^{40D}$, $-NHC(O)NR^{45}R^{40D}$, $-NHS(O)_2R^{45}$, $-NHC(O)R^{45}$, $-NHC(O)-OR^{45}$, $-NHOR^{45}$, $-OCF_3$, $-OCHF_2$, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl. $R^{40C}$, $R^{40D}$, $R^{41}$ and $R^{45}$ are independently hydrogen, oxo, halogen, $-N_3$, $-CF_3$, $-CCl_3$, $-CBr_3$, $-CI_3$, $-CN$, $-OH$, $-NH_2$, $-COOH$, $-CONH_2$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl.

Embodiment P14

The compound of embodiment 13, wherein $R^4$ is $R^{40}$-substituted or unsubstituted heterocycloalkyl.

Embodiment P15

The compound of embodiment 14, wherein $R^4$ is $R^{40}$-substituted or unsubstituted piperidinyl, $R^{40}$-substituted or unsubstituted piperazinyl, or $R^{40}$-substituted or unsubstituted morpholino, or $R^{40}$-substituted or unsubstituted pyrrolidinyl.

Embodiment P16

The compound of embodiment 15, wherein $R^4$ is $R^{40}$-substituted or unsubstituted piperidinyl, $R^{40}$-substituted or unsubstituted piperazinyl, or $R^{40}$-substituted or unsubstituted pyrrolidinyl.

Embodiment P17

The compound of any one of embodiments 1 to 6, wherein $R^4$ is $-NR^{4A}R^{4B}$ wherein $R^{4A}$ is hydrogen, $R^{41}$-substituted or unsubstituted alkyl, or $R^{41}$-substituted or unsubstituted heteroalkyl; $R^{4B}$ is hydrogen, $R^{45}$-substituted or unsubstituted alkyl, or $R^{45}$-substituted or unsubstituted heteroalkyl; $R^{41}$ is independently hydrogen, halogen, $CF_3$, $-OR^{41A}$, $-NR^{41A}R^{41B}$, $R^{42}$-substituted or unsubstituted alkyl, $R^{42}$-substituted or unsubstituted heteroalkyl, or $R^{42}$-substituted or unsubstituted aryl; $R^{45}$ is independently hydrogen, halogen, $CF_3$, $-OR^{45A}$, $-NR^{45A}R^{45B}$, $R^{46}$-substituted or unsubstituted alkyl, $R^{46}$-substituted or unsubstituted heteroalkyl, or $R^{46}$-substituted or unsubstituted aryl; $R^{41A}$, $R^{41B}$, $R^{45A}$, and $R^{45B}$, are independently hydrogen or unsubstituted $C_1$-$C_5$ alkyl; and $R^{42}$ and $R^{46}$ are independently oxo, halogen, $-N_3$, $-CF_3$, $-CCl_3$, $-CBr_3$, $-CI_3$, $-CN$, $-OH$, $-NH_2$, $-COOH$, $-CONH_2$, $-COH$, $-COCH_3$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, unsubstituted alkyl, unsubstituted heteroalkyl, cycloalkyl, unsubstituted heterocycloalkyl, unsubstituted aryl, or unsubstituted heteroaryl.

Embodiment P18

The compound of embodiment 1 having formula:

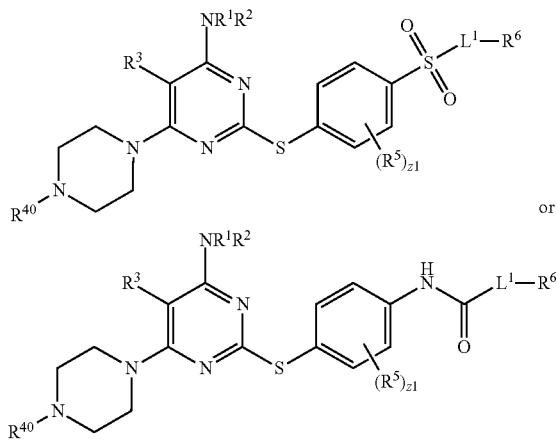

or wherein $R^{40}$ is hydrogen, halogen, —$N_3$, —$CF_3$, —$CCl_3$, —$CBr_3$, —$CI_3$, —CN, —$COR^{40A}$, —$OR^{40A}$, —$NR^{40A}R^{40B}$, —$C(O)OR^{40}$, —$C(O)NR^{40A}R^{40B}$, —$NO_2$, —SH, —$S(O)_2H$, —$S(O)_2OH$, —$S(O)_2NH_2$, —$NHNH_2$, —$ONH_2$, —$NHC(O)NHNR^{40A}R^{40B}$, $R^{40A}$-substituted or unsubstituted alkyl, $R^{40A}$-substituted or unsubstituted heteroalkyl, $R^{40A}$-substituted or unsubstituted cycloalkyl, $R^{40A}$-substituted or unsubstituted heterocycloalkyl, $R^{40A}$-substituted or unsubstituted aryl, or $R^{40A}$-substituted or unsubstituted heteroaryl; $R^{40A}$ is hydrogen, oxo, halogen, —$N_3$, —$CF_3$, —$CCl_3$, —$CBr_3$, —$CI_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl; $R^{40B}$ is hydrogen, oxo, halogen, —$N_3$, —$CF_3$, —$CCl_3$, —$CBr_3$, —$CI_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, $R^{45}$-substituted or unsubstituted alkyl, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl; and $R^{41}$ and $R^{45}$ are independently hydrogen, oxo, halogen, —$N_3$, —$CF_3$, —$CCl_3$, —$CBr_3$, —$CI_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

Embodiment P19

The compound of any one of embodiments 1 to 18, wherein $R^5$ is hydrogen, —Cl, or —F; and z1 is 1 or 2.

Embodiment P20

The compound of any one of embodiments 1 to 19, wherein $L^1$ is a bond, —C(O)—, —C(O)O—, —O—, —S—, —$NR^{13}$—, —$C(O)NR^{13}$—, —$NR^3C(O)$—, —$S(O)_2$—, —$S(O)NR^{13}$—, $R^{13}$-substituted or unsubstituted alkylene, $R^{13}$-substituted or unsubstituted heteroalkylene; and $R^{13}$ is hydrogen or substituted or unsubstituted alkyl.

Embodiment P21

The compound of any one of embodiments 1 to 20, wherein L is a bond or substituted or unsubstituted alkylene.

Embodiment P22

The compound of any one of embodiments 1 to 21, wherein $L^1$ is substituted or unsubstituted $C_1$-$C_5$ alkylene.

Embodiment P23

The compound of any one of embodiments 1 to 22, wherein $L^1$ is $R^{13}$-substituted or unsubstituted alkylene; and $R^{13}$ is hydrogen, halogen, or substituted or unsubstituted alkyl.

Embodiment P24

The compound of embodiment 23, wherein $R^{13}$ is unsubstituted alkyl.

Embodiment P25

The compound of embodiment 1, wherein said compound has the formula:

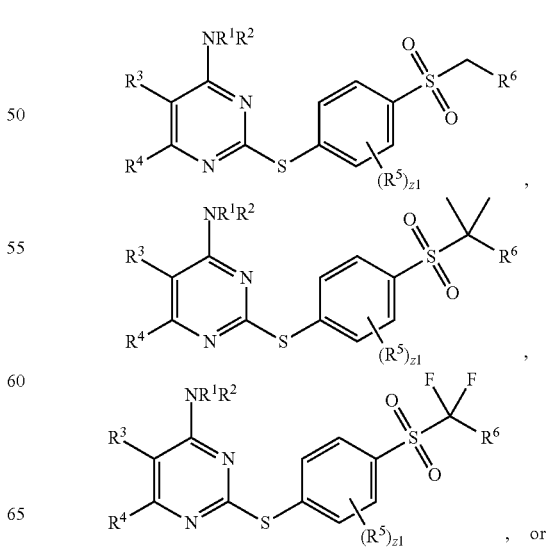

, or

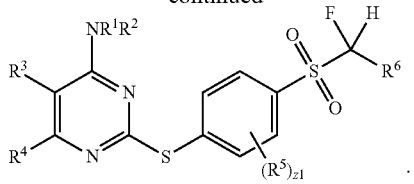

Embodiment P26

The compound of embodiment 1, wherein said compound has the formula:

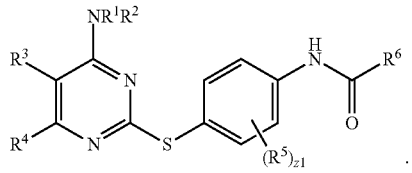

Embodiment P27

The compound of any one of embodiments 1 to 26, wherein $R^6$ is hydrogen, —$CF_3$, —$NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P28

The compound of any one of embodiments 1 to 27, wherein $R^6$ is substituted or unsubstituted cycloalkyl, substituted or unsubstituted heterocycloalkyl, substituted or unsubstituted aryl, or substituted or unsubstituted heteroaryl.

Embodiment P29

The compound of any one of embodiments 1 to 28, wherein $R^6$ is substituted or unsubstituted 3 to 6 membered cycloalkyl.

Embodiment P30

The compound of any one of embodiments 1 to 29, wherein $R^6$ is substituted or unsubstituted 3 to 6 membered heterocycloalkyl.

Embodiment P31

The compound of any one of embodiments 1 to 30, wherein $R^6$ is substituted or unsubstituted aryl.

Embodiment P32

The compound of any one of embodiments 1 to 31, wherein $R^6$ is $R^{60}$-substituted or unsubstituted aryl; and $R^{60}$ is independently hydrogen, halogen, —$N_3$, —$CF_3$, —$CCl_3$, —$CBr_3$, —$CI_3$, —CN, —$COR^{61}$, —$OR^{60A}$, —$NR^{60A}R^{60B}$, —$C(O)OR^{60A}$, —$C(O)NR^{60A}R^{60B}$, —$NO_2$, —$SR^{60A}$, —$S(O)_2H$, —$S(O)_2OH$, —$S(O)_2NH_2$, —$NHNH_2$, —$ONH_2$, —$NHC(O)NHNR^{60A}R^{6B}$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl. $R^{60A}$ is independently hydrogen, halogen, —$NO_2$, —$CF_3$, —CN, —$COR^{61}$, $R^{61}$-substituted or unsubstituted alkyl, $R^{61}$-substituted or unsubstituted heteroalkyl, or $R^{61}$-substituted or unsubstituted aryl. $R^{61}$ is independently hydrogen, halogen, —$N_3$, —$CF_3$, —$CCl_3$, —$CBr_3$, —$CI_3$, —CN, —$COR^{61A}$, —$OR^{61A}NR^{61A}R^{61B}$, —$C(O)OR^{61A}$, —$C(O)NR^{61A}R^{61B}$, —$NO_2$, —$SR^{61A}$, —$S(O)_2R^{61A}$, —$S(O)_2OR^{61A}$, —$S(O)_2NR^{61A}R^{61B}$, —$NHNR^{61A}R^{61B}$, —$ONR^{61A}R^{61B}$, —$NHC(O)NHNR^{61A}R^{61B}$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl. $R^{60B}$, $R^{61A}$, $R^{61B}$, and $R^{62}$ is independently hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

Embodiment P33

The compound of embodiment 32, wherein $R^6$ is $R^{60}$-substituted or unsubstituted heteroaryl; and $R^{60}$ is independently halogen, —$CF_3$, —$NR^{60A}R^{60B}$, —$NO_2$, $R^{61}$-substituted or unsubstituted alkyl, or $R^{61}$-substituted or unsubstituted heteroalkyl; $R^{61}$ is independently hydrogen or unsubstituted alkyl.

Embodiment P34

The compound of embodiment 28, wherein $R^6$ is unsubstituted thiophenyl, unsubstituted thiazolyl, unsubstituted imidazolyl, or unsubstituted oxazolyl.

Embodiment P35

The compound of embodiment 1 having the formula:

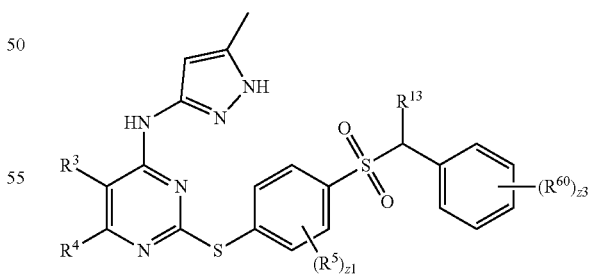

wherein $R^{60}$ is independently hydrogen, halogen, —$N_3$, —$CF_3$, —$CCl_3$, —$CBr_3$, —$CI_3$, —CN, —$COR^{61}$, —$OR^{60A}$, —$NR^{60A}R^{60B}$, —$C(O)OR^{60A}$, —$C(O)NR^{60A}R^{60B}$, —$NO_2$, —$SR^{60A}$, —$S(O)_2H$, —$S(O)_2OH$, —$S(O)_2NH_2$, —$NHNH_2$, —$ONH_2$, —$NHC(O)NHNR^{60A}R^{6B}$, $R^{61}$-substituted or unsubstituted alkyl, $R^{61}$-substituted or unsubstituted heteroalkyl, $R^{61}$-substituted or unsubstituted cycloalkyl, $R^{61}$- substituted or unsubstituted heterocycloalkyl, $R^{61}$-substituted or unsubstituted aryl, or $R^{61}$-substituted or unsubstituted heteroaryl; $R^{60A}$ is independently hydrogen, halogen, —$NO_2$, —$CF_3$, —CN, —$COR^{61}$, $R^{61}$—Substituted or unsubstituted alkyl, $R^{61}$-substituted or unsubstituted heteroalkyl, or $R^{61}$-substituted or unsubstituted aryl; $R^{61}$ is independently hydrogen, halogen, —$N_3$, —$CF_3$, —$CCl_3$, —$CBr_3$, —$CI_3$, —CN, —$COR^{61A}$, —$OR^{61A}$, —$NR^{61A}R^{61B}$, —$C(O)OR^{61A}$, —$C(O)NR^{61A}R^{61B}$, —$NO_2$, —$SR^{61A}$, —$S(O)_2H$, —$S(O)_2OH$, —$S(O)_2NH_2$, —$NHNH_2$, —$ONH_2$, —$NHC(O)NHNR^{61A}R^{61B}$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl; $R^{60B}$, $R^{61A}$, $R^{61B}$, and $R^{62}$ are independently hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)_NH2$, —$NHS(O)_2H$, —$NHC(O)H$, —$NHC(O)$—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl; and z3 is an integer of 0, 1, 2, 3, 4, or 5.

Embodiment P36

The compound of embodiment 1 having the formula:

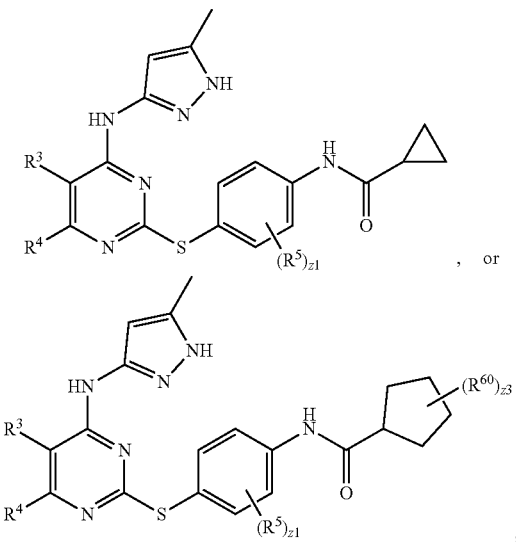

, or

Wherein $R^{60}$ is independently hydrogen, halogen, —$N_3$, —$CF_3$, —$CCl_3$, —$CBr_3$, —$CI_3$, —CN, —$COR^{61}$, —$OR^{64}$, —$NR^{60A}R^{60B}$, —$C(O)OR^{60A}$, —$C(O)NR^{60A}R^{60B}$, —$NO_2$, —$SR^{60A}$, —$S(O)_2H$, —$S(O)_2OH$, —$S(O)_2NH_2$, —$NHNH_2$, —$ONH_2$, —$NHC(O)NHNR^{60A}R^{60B}$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl; $R^{60A}$ is independently hydrogen, halogen, —$NO_2$, —$CF_3$, —CN, —$COR^{61}$, $R^{61}$-substituted or unsubstituted alkyl, $R^{61}$-substituted or unsubstituted heteroalkyl, or $R^{61}$-substituted or unsubstituted aryl; $R^{61}$ is independently hydrogen, halogen, or unsubstituted alkyl; $R^{60B}$ is independently hydrogen halogen, or unsubstituted alkyl; and z3 is an integer of 0, 1, 2, 3, 4, or 5.

Embodiment P37

A compound having the formula:

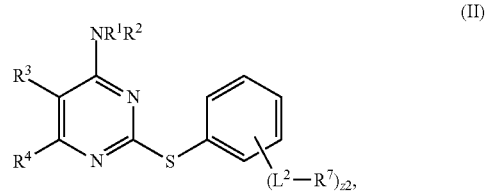

(II)

$L^1$ is a bond, —C(O)—, —C(O)O—, —O—, —S—, —$NR^{13}$—, —$C(O)NR^{13}$—, —$NR^{13}C(O)$—, —$S(O)_2$—, —$S(O)NR^{13}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ is independently a bond, —C(O)—, —C(O)O—, —O—, —S—, —$NR^{14}$—, —$C(O)NR^{14}$—, —$NR^{14}C(O)$—, —$S(O)_2$—, —$S(O)NR^{14}$-substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, —$N_3$, —$CF_3$, —$CCl_3$, —$CBr_3$, —$CI_3$, —CN, —$COR^{1A}$, —$OR^{1A}$, —$NR^{1A}R^{1B}$, —$C(O)OR^{1A}$, —$C(O)NR^{1A}R^{1B}$, —$NO_2$, —$SR^{1A}$, —$S(O)_{n1}R^{1A}$, —$S(O)_{n1}OR^{1A}$, —$S(O)_{n1}NR^{1A}R^{1B}$, —$NHNR^{1A}R^{1B}$, —$ONR^{1A}R^{1B}$, —$NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, —$N_3$, —$CF_3$, —$CCl_3$, —$CBr_3$, —$CI_3$, —CN, —$COR^{2A}$, —$OR^{2A}$, —$NR^{2A}R^{2B}$, —$C(O)OR^{2A}$, —$C(O)NR^{2A}R^{2B}$, —$NO_2$, —$SR^{2A}$, —$S(O)_{n2}R^{2A}$, —$S(O)_{n2}OR^{2A}$, —$S(O)_{n2}NR^{2A}R^{2B}$, —$NHNR^{2A}R^{2B}$, —$ONR^{2A}R^{2B}$, —$NHC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is halogen, —$N_3$, —$CF_3$, —$CCl_3$, —$CBr_3$, —$CI_3$, —CN, —$COR^{3A}$, —$OR^{3A}$, —$NR^{3A}R^{3B}$, —$C(O)OR^{3A}$, —$C(O)NR^{3A}R^{3B}$, —$NO_2$, —$SR^{3A}$, —$S(O)_{n3}R^{3A}$, —$S(O)_{n3}OR^{3A}$, —$S(O)_{n3}NR^{3A}R^{3B}$, —$NHNR^{3A}R^{3B}$, —$ONR^{3A}R^{3B}$, —$NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is halogen, —$N_3$, —$CF_3$, —$CCl_3$, —$CBr_3$, —$CI_3$, —CN, —$COR^{4A}$, —$OR^{4A}$, —$NR^{4A}R^{4B}$, —$C(O)OR^{4A}$, —$C(O)NR^{4A}R^{4B}$, —$NO_2$, —$SR^{4A}$, —$S(O)_{n4}R^{4A}$, —$S(O)_{n4}OR^{4A}$, —$S(O)_{n4}NR^{4A}R^{4B}$, —$NHNR^{4A}R^{4B}$, —$ONR^{4A}R^{4B}$, —$NHC(O)NHNR^{4A}R^{4B}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is independently hydrogen, oxo, halogen, —$N_3$, —$CF_3$, —$CCl_3$, —$CBr_3$, —$CI_3$, —CN, —$COR^{7A}$, —$OR^{7A}$, —$NR^{7A}R^{7B}$, —C(O)

$OR^{7A}$, —C(O)$NR^{7A}R^{7B}$, —$NO_2$, —$SR^{7A}$, —S(O)$_{n7}R^{7A}$, —S(O)$_{n7}OR^{7A}$, —S(O)$_{n7}NR^{7A}R^{7B}$, —$NHNR^{7A}R^{7B}$, —$ONR^{7A}R^{7B}$, —NHC(O)$NHNR^{7A}R^{7B}$, -$L^1$-$R^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is hydrogen, oxo, halogen, —$N_3$, —$CF_3$, —$CCl_3$, —$CBr_3$, —$CI_3$, —CN, —CHO, —$OR^{6A}$, —$NR^{6A}R^{6B}$, —C(O)$OR^{6A}$, —C(O)$NR^{6A}R^{6B}$, —$NO_2$, —$SR^{6A}$, —S(O)$_{n6}R^{6A}$, —S(O)$_{n6}OR^{6A}$, —S(O)$_6NR^{6A}R^{6B}$, —$NHNR^{6A}R^{6B}$, —$ONR^{6A}R^{6B}$, —NHC(O)$NHNR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n1, n2, n3, n4, n6, and n7 are independently 1 or 2. z2 is 1, 2, 3, 4, or 5. $R^{1A}$, $R^{1B}$, $R^{2A}$, $R^{2B}$, $R^{3A}$, $R^{3B}$, $R^{4A}$, $R^{4B}$, $R^{6A}$, $R^{6B}$, $R^{7A}$, $R^{7B}$, $R^{13}$, and $R^{14}$ are independently hydrogen, oxo, halogen, —$CF_3$, —CN, —OH, —$NH_2$, —COOH, —$CONH_2$, —COH, —$COCH_3$, —$NO_2$, —SH, —S(O)$_2$Cl, —S(O)$_3$H, —S(O)$_4$H, —S(O)$_2NH_2$, —$NHNH_2$, —$ONH_2$, —NHC(O)$NHNH_2$, —NHC(O)$NH_2$, —NHS(O)$_2$H, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The compound is not VX-680.

Embodiment P38

The compound of embodiment 37, wherein $R^3$ is halogen, —$OR^{3A}$, or substituted or unsubstituted alkyl; and $R^{3A}$ is substituted or unsubstituted alkyl.

Embodiment P39

The compound of embodiment 37, wherein $R^3$ is —$OR^{3A}$; and $R^{3A}$ is substituted or unsubstituted alkyl.

Embodiment P40

The compound of any one of embodiments 37 to 39, wherein $R^3$ is —$OCH_3$.

Embodiment P41

The compound of embodiment 37, wherein $R^3$ and $R^4$ together form a substituted or unsubstituted cycloalkyl.

Embodiment P42

The compound of embodiment 37, wherein $R^4$ is substituted or unsubstituted cycloalkyl, substituted or unsubstituted heterocycloalkyl, substituted or unsubstituted aryl, or substituted or unsubstituted heteroaryl.

Embodiment P43

The compound of any one of embodiments 37 to 42, wherein $R^4$ is substituted or unsubstituted 5 or 6 membered heterocycloalkyl.

Embodiment P44

The compound of any one of embodiments 37 to 43, wherein $R^4$ is substituted or unsubstituted piperidinyl, substituted or unsubstituted piperazinyl, or substituted or unsubstituted morpholino, or substituted or unsubstituted pyrrolidinyl.

Embodiment P45

The compound of any one of embodiments 37 to 42, wherein $R^4$ is $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl; $R^{40}$ is independently hydrogen, oxo, halogen, —$N_3$, —$CF_3$, —$CCl_3$, —$CBr_3$, —$CI_3$, —CN, —$COR^{40A}$, —$OR^{40A}$, —$NR^{40A}R^{40B}$, —C(O)$OR^{40A}$, —C(O)$NR^{40A}R^{40B}$, —$NO_2$, —$SR^{40A}$, —S(O)$_2R^{40A}$, —S(O)$_2$ $OR^{40A}$, —S(O)$_2NR^{40A}R^{40B}$, —$NHNR^{40A}R^{40B}$, —$ONR^{40A}R^{40B}$, —NHC(O)$NHNR^{40A}R^{40B}$, $R^{40A}$-substituted or unsubstituted alkyl, $R^{40A}$-substituted or unsubstituted heteroalkyl, $R^{40A}$-substituted or unsubstituted cycloalkyl, $R^{40A}$-substituted or unsubstituted heterocycloalkyl, $R^{40A}$-substituted or unsubstituted aryl, or $R^{40A}$-substituted or unsubstituted heteroaryl. $R^{40A}$ is independently hydrogen, oxo, halogen, —$N_3$, —$CF_3$, —$CCl_3$, —$CBr_3$, —$CI_3$, —CN, —$OR^{41}$, —$NR^{41}R^{40C}$, —$COR^{41}$, —$COOR^{41}$, —$CONR^{41}R^{40C}$, —$NO_2$, —$SR^{41}$, —S(O)$_2R^{41}$, —S(O)$_3R^{41}$, —S(O)$_2NR^{41}R^{40C}$, S(O)$_4R^{41}$, —$NHNR^{41}R^{40C}$, —$ONR^{41}R^{40C}$, —NHC(O)$NHNR^{41}R^{40C}$, —NHC(O)$NR^{41}R^{40C}$, —NHS(O)$_2R^{41}$, —NHC(O)$R^{41}$, —NHC(O)—$OR^{41}$, —$NHOR^{41}$, —$OCF_3$, —$OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl. $R^{40B}$ is independently hydrogen, oxo, halogen, —$N_3$, —$CF_3$, —$CCl_3$, —$CBr_3$, —$CI_3$, —CN, —$OR^{45}$, —$NR^{45}R^{40D}$, —$COR^{45}$, —$COOR^{45}$, —$CONR^{45}R^{40D}$, —$NO_2$, —$SR^{45}$, —S(O)$_2R^{45}$, —S(O)$_3R^{45}$, —S(O)$_4R^{45}$, —S(O)$_2NR^{45}R^{40D}$, —$NHNR^{40D}R^{40D}$, —$ONR^{45}R^{40D}$, —NHC(O)$NHNR^{45}R^{40D}$, —NHC(O)$NR^{45}R^{40D}$, —NHS(O)$_2R^{45}$, —NHC(O)$R^{45}$, —NHC(O)—$OR^{45}$, —$NHOR^{45}$, —$OCF_3$, —$OCHF_2$, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl. $R^{40C}$, $R^{40D}$, $R^{41}$ and $R^{45}$ are independently hydrogen, oxo, halogen, —$N_3$, —$CF_3$, —$CCl_3$, —$CBr_3$, —$CI_3$, —CN, —OH, —$NH_2$, —COOH, —$CONH_2$, —$NO_2$, —SH, —S(O)$_2$Cl, —S(O)$_3$H, —S(O)$_4$H, —S(O)$_2NH_2$, —$NHNH_2$, —$ONH_2$, —NHC(O)$NHNH_2$, —NHC(O)$NH_2$, —NHS(O)$_2$H, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

Embodiment P46

The compound of embodiment 45, wherein $R^4$ is $R^{40}$-substituted or unsubstituted heterocycloalkyl.

Embodiment P47

The compound of embodiment 45, wherein $R^4$ is $R^{40}$-substituted or unsubstituted piperidinyl, $R^{40}$-substituted or unsubstituted piperazinyl, or $R^{40}$-substituted or unsubstituted morpholino, or $R^{40}$-substituted or unsubstituted pyrrolidinyl.

Embodiment P48

A compound having the formula:

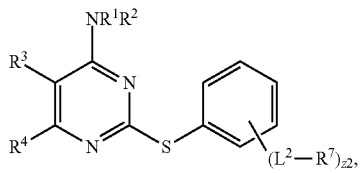

(II)

$L^1$ is a bond, —C(O)—, —C(O)O—, —O—, —S—, —NR$^{13}$—, —C(O)NR$^3$—, —NR$^{13}$C(O)—, —S(O)$_2$—, —S(O)NR$^{13}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ is independently a bond, —C(O)—, —C(O)O—, —O—, —S—, —NR$^{14}$—, —C(O)NR$^{14}$—, —NR$^{14}$C(O)—, —S(O)$_2$—, —S(O)NR$^{14}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, —N$_3$, —CF$_3$, —CCl$_3$, —CBr$_3$, —CI$_3$, —CN, —COR$^{1A}$, —OR$^{1A}$, —NR$^{1A}$R$^{1B}$, —C(O)OR$^{1A}$, —C(O)NR$^{1A}$R$^{1B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, —N$_3$, —CF$_3$, —CCl$_3$, —CBr$_3$, —CI$_3$, —CN, —COR$^{2A}$, —OR$^{2A}$, —NR$^{2A}$R$^{2B}$, —C(O)OR$^{2A}$, —C(O)NR$^{2A}$R$^{2B}$, —NO$_2$, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is —N$_3$, —CF$_3$, —CCl$_3$, —CBr$_3$, —CI$_3$, —CN, —COR$^{3A}$, —OR$^{3A}$, —NR$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, —N$_3$, —CF$_3$, —CCl$_3$, —CBr$_3$, —CI$_3$, —CN, —COR$^{4A}$, —OR$^{4A}$, —NR$^{4A}$R$^{4B}$, —C(O)OR$^{4A}$, —C(O)NR$^{4A}$R$^{4B}$, —NO$_2$, —SR$^{4A}$, —S(O)$_{n4}$R$^{4A}$, —S(O)$_{n4}$OR$^{4A}$, —S(O)$_{n4}$NR$^{4A}$R$^{4B}$, —NHNR$^{4A}$R$^{4B}$, —ONR$^{4A}$R$^{4B}$, —NHC(O)NHNR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is independently hydrogen, oxo, halogen, —N$_3$, —CF$_3$, —CCl$_3$, —CBr$_3$, —CI$_3$, —CN, —COR$^{7A}$, —OR$^{7A}$, —NR$^{7A}$R$^{7B}$, —C(O)OR$^{7A}$, —C(O)NR$^{7A}$R$^{7B}$, —NO$_2$, —SR$^{1A}$, —S(O)$_{n7}$R$^{7A}$, —S(O)$_{n7}$OR$^{7A}$, —S(O)$_{n7}$NR$^{7A}$R$^{7B}$, —NHNR$^{7A}$R$^{7B}$, —ONR$^{7A}$R$^{7B}$, —NHC(O)NHNR$^{7A}$R$^{7B}$, -L$^1$-R$^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is hydrogen, oxo, halogen, —N$_3$, —CF$_3$, —CCl$_3$, —CBr$_3$, —CI$_3$, —CN, —CHO, —OR$^{6A}$, —NR$^{6A}$R$^{6B}$, —C(O)OR$^{6A}$, —C(O)NR$^{6A}$R$^{6B}$, —NO$_2$, —SR$^{6A}$, —S(O)$_{n6}$R$^{6A}$, —S(O)$_{n6}$OR$^{6A}$, —S(O)$_{n6}$NR$^{6A}$R$^{6B}$, —NHNR$^{6A}$R$^{6B}$, —ONR$^{6A}$R$^{6B}$, —NHC(O)NHNR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n1, n2, n3, n4, n6, and n7 are independently 1 or 2. z2 is 1, 2, 3, 4, or 5. $R^{1A}$, $R^{1B}$, $R^{2A}$, $R^{2B}$, $R^{3A}$, $R^{3B}$ $R^{4A}$, $R^{4B}$, $R^{6A}$, $R^{6B}$, $R^{7A}$, $R^{7B}$, $R^{13}$, and $R^{14}$ are independently hydrogen, oxo, halogen, —CF$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The compound is not VX-680.

Embodiment P49

The compound of embodiment 48, wherein $R^3$ is —OR$^{3A}$; and $R^{3A}$ is substituted or unsubstituted alkyl.

Embodiment P50

The compound of any one of embodiments 48 to 49, wherein $R^3$ is —OCH$_3$.

Embodiment P51

The compound of any one of embodiments 48 to 50, wherein $R^3$ and $R^4$ together form a substituted or unsubstituted cycloalkyl.

Embodiment P52

The compound of any one of embodiments 48 to 51, wherein $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P53

The compound of any one of embodiments 48 to 52, wherein $R^4$ is substituted or unsubstituted cycloalkyl, substituted or unsubstituted heterocycloalkyl, substituted or unsubstituted aryl, or substituted or unsubstituted heteroaryl.

Embodiment P54

The compound of any one of embodiments 48 to 53, wherein $R^4$ is substituted or unsubstituted 5 or 6 membered heterocycloalkyl.

Embodiment P55

The compound of any one of embodiments 48 to 54, wherein $R^4$ is substituted or unsubstituted piperidinyl, substituted or unsubstituted piperazinyl, or substituted or unsubstituted morpholino.

Embodiment P56

The compound of any one of embodiments 48 to 53, wherein $R^4$ is $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl. $R^{40}$ is independently hydrogen, oxo, halogen, $-N_3$, $-CF_3$, $-CCl_3$, $-CBr_3$, $-CI_3$, $-CN$, $-COR^{40A}$, $-OR^{40A}$, $-NR^{40A}R^{40B}$, $-C(O)OR^{40A}$, $-C(O)NR^{40A}R^{40B}$, $-NO_2$, $-SR^{40A}$, $-S(O)_2R^{40A}$, $-S(O)_2OR^{40A}$, $-S(O)_2NR^{40A}R^{40B}$, $-NHNR^{40A}R^{40B}$, $-ONR^{40A}R^{40B}$, $-NHC(O)NHNR^{40A}R^{40B}$, $R^{40A}$-substituted or unsubstituted alkyl, $R^{40A}$-substituted or unsubstituted heteroalkyl, $R^{40A}$-substituted or unsubstituted cycloalkyl, $R^{40A}$-substituted or unsubstituted heterocycloalkyl, $R^{40A}$-substituted or unsubstituted aryl, or $R^{40A}$-substituted or unsubstituted heteroaryl. $R^{40A}$ is independently hydrogen, oxo, halogen, $-N_3$, $-CF_3$, $-CCl_3$, $-CBr_3$, $-CI_3$, $-CN$, $-OR^{41}$, $-NR^{41}R^{40C}$, $-COR^{41}$, $-COOR^{41}$, $-CONR^{41}R^{40C}$, $-NO_2$, $-SR^{41}$, $-S(O)_2R^{41}$, $-S(O)_3R^{41}$, $-S(O)_2NR^{41}R^{40C}$, $S(O)_4R^{41}$, $NHNR^{41}R^{40C}$, $-ONR^{41}R^{40C}$, $-NHC(O)NHNR^{41}R^{40C}$, $-NHC(O)NR^{41}R^{40C}$, $-NHS(O)_2R^{41}$, $-NHC(O)R^{41}$, $-NHC(O)-OR^{41}$, $-NHOR^{41}$, $-OCF_3$, $-OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl. $R^{40B}$ is independently hydrogen, oxo, halogen, $-N_3$, $-CF_3$, $-CCl_3$, $-CBr_3$, $-CI_3$, $-CN$, $-OR^{45}$, $-NR^{45}R^{40D}$, $-COR^{45}$, $-COOR^{45}$, $-CONR^{45}R^{40D}$, $-NO_2$, $-SR^{45}$, $-S(O)_2R^{45}$, $-S(O)_3R^{45}$, $-S(O)_4R^{45}$, $-S(O)_2NR^{45}R^{40D}$, $-NHNR^{45}R^{40D}$, $-ONR^{45}R^{40D}$, $-NHC(O)NHNR^{45}R^{40D}$, $-NHC(O)NR^{45}R^{40D}$, $-NHS(O)_2R^{45}$, $-NHC(O)R^{45}$, $-NHC(O)-OR^{45}$, $-NHOR^{45}$, $-OCF_3$, $-OCHF_2$, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl. $R^{40C}$, $R^{40D}$, $R^{41}$ and $R^{45}$ are independently hydrogen, oxo, halogen, $-N_3$, $-CF_3$, $-CCl_3$, $-CBr_3$, $-CI_3$, $-CN$, $-OH$, $-NH_2$, $-COOH$, $-CONH_2$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl.

Embodiment P57

The compound embodiment 56, wherein $R^4$ is $R^{40}$-substituted or unsubstituted piperidinyl, $R^{40}$-substituted or unsubstituted piperazinyl, or $R^{40}$-substituted or unsubstituted morpholino, or $R^{40}$-substituted or unsubstituted pyrrolidinyl.

Embodiment P58

The compound of any one of embodiments 37 to 57, wherein $L^1$ is a bond, $-C(O)-$, $-C(O)O-$, $-O-$, $-S-$, $-NR^{13}-$, $-C(O)NR^{13}-$, $-NR^{13}C(O)-$, $-S(O)_2-$, $-S(O)NR^{13}-$, substituted or unsubstituted alkylene, substituted or unsubstituted heteroalkylene; and $R^{13}$ is hydrogen or substituted or unsubstituted alkyl.

Embodiment P59

The compound of any one of embodiments 37 to 58, wherein $L^2$ is independently a bond, $-C(O)-$, $-C(O)O-$, $-O-$, $-S-$, $-NR^{14}-$, $-C(O)NR^{14}-$, $-NR^{14}C(O)-$, $-S(O)-$, $-S(O)_2-$, $-S(O)NR^{14}-$, or substituted or unsubstituted alkylene; and $R^{14}$ is hydrogen, halogen, $-N_3$, $-CF_3$, $-CCl_3$, $-CBr_3$, $-CI_3$, $-CN$, $-COH$, $-OH$, $-NH_2$, $-C(O)OH$, $-C(O)NH_2$, $-NO_2$, $-SH$, $-S(O)_2H$, $-S(O)_2OH$, $-S(O)_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P60

The compound of any one of embodiments 37 to 59, wherein $L^2$ is independently a bond, $-C(O)NH-$, $-NHC(O)-$, or $-S(O)_2-$.

Embodiment P61

The compound of any one of embodiments 37 to 60, wherein -$L^2$-$R^7$ is hydrogen or $-I$, $-Cl$, or $-Br$.

Embodiment P62

The compound of any one of embodiments 37 to 61, wherein $L^2$ is $-C(O)NH-$, $-NHC(O)-$, or $-S(O)_2-$ and $R^7$ is -$L^1$-$R^6$.

Embodiment P63

The compound of any one of embodiments 37 to 62, wherein $L^1$ is a bond or substituted or unsubstituted alkylene.

Embodiment P64

The compound of any one of embodiments 37 to 63, wherein $L^1$ is substituted or unsubstituted $C_1$-$C_5$ alkylene.

Embodiment P65

The compound of any one of embodiments 37 to 64, wherein $L^1$ is $R^{13}$-substituted or unsubstituted alkylene; and $R^{13}$ is hydrogen, halogen, or substituted or unsubstituted alkyl.

Embodiment P66

The compound of any one of embodiments 37 to 65, wherein $R^7$ is substituted or unsubstituted alkyl.

Embodiment P67

The compound of any one of embodiments 37 to 66, wherein $R^6$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P68

The compound of any one of embodiments 37 to 67, wherein $R^6$ is substituted or unsubstituted heterocycloalkyl, substituted or unsubstituted aryl, or substituted or unsubstituted heteroaryl.

Embodiment P69

The compound of any one of embodiments 37 to 68, wherein $R^6$ is substituted or unsubstituted 3 to 6 membered heterocycloalkyl.

Embodiment P70

The compound of any one of embodiments 37 to 69, wherein $R^6$ is substituted or unsubstituted aryl.

Embodiment P71

The compound of any one of embodiments 37 to 70, wherein $R^6$ is $R^{60}$-substituted or unsubstituted aryl; and $R^{60}$ is independently hydrogen, halogen, —$N_3$, —$CF_3$, —$CCl_3$, —$CBr_3$, —$CI_3$, —CN, —$COR^{61}$, —$OR^{60A}$, —$NR^{60A}R^{60B}$, —$C(O)OR^{60A}$, —$C(O)NR^{60A}R^{60B}$, —$NO_2$, —$SR^{60A}$, —$S(O)_2H$, —$S(O)_2OH$, —$S(O)_2NH_2$, —$NHNH_2$, —$ONH_2$, —$NHC(O)NHNR^{60A}R^{60B}$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl. $R^{60A}$ is independently hydrogen, halogen, —$NO_2$, —$CF_3$, —CN, —$COR^{61}$, $R^{61}$-substituted or unsubstituted alkyl, $R^{61}$-substituted or unsubstituted heteroalkyl, or $R^{61}$-substituted or unsubstituted aryl. $R^{61}$ is independently hydrogen, halogen, —$N_3$, —$CF_3$, —$CCl_3$, —$CBr_3$, —$CI_3$, —CN, —$COR^{61A}$, —$OR^{61A}NR^{61A}R^{61B}$, —$C(O)OR^{61A}$, —$C(O)NR^{61A}R^{61B}$, —$NO_2$, —$SR^{61A}$, —$S(O)_2R^{61A}$, —$S(O)_2OR^{61A}$, —$S(O)_2NR^{61A}R^{61B}$, —$NHNR^{61A}R^{61B}$, —$ONR^{61A}R^{61B}$, —$NHC(O)NHNR^{61A}R^{61B}$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl. $R^{60B}$, $R^{61A}$, $R^{61B}$, and $R^{62}$ is independently hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

Embodiment P72

The compound of any one of embodiments 37 to 71, wherein $R^6$ is $R^{60}$-substituted or unsubstituted aryl; and $R^{60}$ is hydrogen, halogen, or —$NO_2$.

Embodiment P73

The compound of any one of embodiments 37 to 72, wherein z2 is 1, 2, or 3.

Embodiment P74

The compound of any one of embodiments 37 to 73, wherein said compound has the formula:

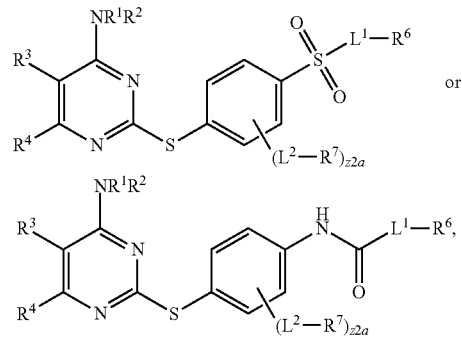

wherein z2a is 0, 1, 2, 3, or 4.

Embodiment P75

The compound of embodiment 74, wherein z2a is 0 or 1.

Embodiment P76

The compound of embodiment 74, wherein -$L^2$-$R^7$ is —Cl or —F; and z2a is 1 or 2.

Embodiment P77

The compound of any one of embodiments 1 to 76, wherein $R^1$ is hydrogen, halogen, —$N_3$, —$CF_3$, —$CCl_3$, —$CBr_3$, —$CI_3$, —CN, —$COR^{1A}$, —$OR^{1A}$, —$NR^{1A}R^{1B}$, —$C(O)OR^{1A}$, —$C(O)NR^{1A}R^{1B}$, —$NO_2$, —$SR^{1A}$, —$S(O)_{n1}R^{1A}$, —$S(O)_{n1}OR^{1A}$, —$S(O)_{n1}NR^{1A}R^{1B}$, —$NHNR^{1A}R^{1B}$, —$ONR^{1A}R^{1B}$, —$NHC(O)NHNR^{1A}R^{1B}$; and $R^{1A}$ and $R^{1B}$ are independently hydrogen, oxo, halogen, —$CF_3$, —OH, —$NH_2$, —COOH, —$CONH_2$, substituted or unsubstituted alkyl, or substituted or unsubstituted aryl.

Embodiment P78

The compound of any one of embodiments 1 to 77, wherein $R^1$ is hydrogen.

Embodiment P79

The compound of any one of embodiments 1 to 78, wherein $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P80

The compound of any one of embodiments 1 to 79, wherein $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P81

The compound of any one of embodiments 1 to 80, wherein $R^2$ is substituted or unsubstituted cycloalkyl, substituted or unsubstituted heterocycloalkyl, substituted or unsubstituted aryl, or substituted or unsubstituted heteroaryl.

Embodiment P82

The compound of any one of embodiments 1 to 81, wherein $R^2$ is substituted or unsubstituted heterocycloalkyl, substituted or unsubstituted aryl, or substituted or unsubstituted heteroaryl.

Embodiment P83

The compound of any one of embodiments 1 to 82, wherein $R^2$ is substituted or unsubstituted heteroaryl.

Embodiment P84

The compound of any one of embodiments 1 to 83, wherein $R^2$ is $R^{2A}$-substituted or unsubstituted heteroaryl; and $R^{2A}$ is —$N_3$, —$CF_3$, —$CCl_3$, —$CBr_3$, —$CI_3$, —CN, —OH, —$NH_2$, —C(O)OH, —C(O)$NH_2$, —$NO_2$, —SH, substituted or unsubstituted alkyl, substituted or unsubstituted heteroalkyl.

Embodiment P85

The compound of any one of embodiments 1 to 84, wherein $R^2$ is substituted or unsubstituted furanyl, substituted or unsubstituted pyrrolyl, substituted or unsubstituted thiophenyl, substituted or unsubstituted imidazoyl, substituted or unsubstituted pyrazolyl, substituted or unsubstituted oxazoyl, substituted or unsubstituted isoxazolyl, substituted or unsubstituted thiazolyl, substituted or unsubstituted pyridinyl, substituted or unsubstituted pyrazinyl, substituted or unsubstituted pyrimidinyl, or substituted or unsubstituted pyridazinyl.

Embodiment P86

The compound of any one of embodiments 1 to 85, wherein $R^2$ is substituted or unsubstituted pyrazolyl.

Embodiment P87

The compound of any one of embodiments 1 to 86, wherein $R^2$ is $R^{2A}$-substituted or unsubstituted pyrazolyl; and $R^{2A}$ is —$CF_3$, —$CCl_3$, —$CBr_3$, —$CI_3$, —CN, —OH, —$NH_2$, —C(O)OH, —C(O)$NH_2$, —$NO_2$, substituted or unsubstituted alkyl, or substituted or unsubstituted heteroalkyl.

Embodiment P88

A method of inhibiting a PLK4 kinase, said method comprising contacting said PLK4 kinase with a compound of any one of embodiments 1 to 87, and allowing said compound to bind to said PLK4 kinase, thereby inhibiting said PLK4 kinase.

Embodiment P89

A method of treating cancer in a subject in need thereof, said method comprising administering to said subject a therapeutically effective amount of a compound having the formula of any one of embodiments 1 to 87.

Embodiment P90

The method of embodiment 89, wherein said cancer is basal cell carcinoma, medulloblastoma, pancreatic cancer, small cell lung cancer, gastric cancer, colon cancer, or chondrosarcoma.

Embodiment P91

A method of treating cancer in a subject in need thereof, said method comprising administering to said subject a therapeutically effective amount of a compound having formula:

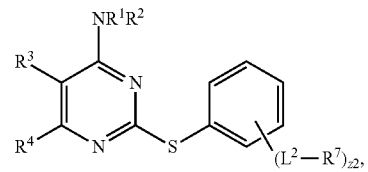

(II)

wherein; $L^1$ is a bond, —C(O)—, —C(O)O—, —O—, —S—, —$NR^{13}$—, —C(O)$NR^{13}$—, —$NR^{13}$C(O)—, —S(O)$_2$—, —S(O)$NR^{13}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^2$ is independently a bond, —C(O)—, —C(O)O—, —O—, —S—, —$NR^{14}$—, —C(O)$NR^{14}$—, —$NR^{14}$C(O)—, —S(O)$_2$—, —S(O)$NR^{14}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ is hydrogen, halogen, —$N_3$, —$CF_3$, —$CCl_3$, —$CBr_3$, —$CI_3$, —CN, —$COR^{1A}$, —$OR^{1A}$, —$NR^{1A}R^{1B}$, —C(O)$OR^{1A}$, —C(O)$NR^{1A}R^{1B}$, —$NO_2$, —$SR^{1A}$, —S(O)$_{n1}R^{1A}$, —S(O)$_{n1}OR^{1A}$, —S(O)$_{n1}NR^{1A}R^{1B}$, —$NHNR^{1A}R^{1B}$, —$ONR^{1A}R^{1B}$, —NHC(O)$NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, —$N_3$, —$CF_3$, —$CCl_3$, —$CBr_3$, —$CI_3$, —CN, —$COR^{2A}$, —$OR^{2A}$, —$NR^{2A}R^{2B}$, —C(O)$OR^{2A}$, —C(O)$NR^{2A}R^{2B}$, —$NO_2$, —$SR^{2A}$, —S(O)$_{n2}R^{2A}$, —S(O)$_{n2}OR^{2A}$, —S(O)$_{n2}NR^{2A}R^{2B}$, —$NHNR^{2A}R^{2B}$, —$ONR^{2A}R^{2B}$, —NHC(O)$NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is halogen, —$N_3$, —$CF_3$, —$CCl_3$, —$CBr_3$, —$CI_3$, —CN, —$COR^{3A}$, —$OR^{3A}$, —$NR^{3A}R^{3B}$, —C(O)$OR^{3A}$, —C(O)$NR^{3A}R^{3B}$, —$NO_2$, —$SR^{3A}$, —S(O)$_{n3}R^{3A}$, —S(O)$_{n3}OR^{3A}$, —S(O)$_{n3}NR^{3A}R^{3B}$, —$NHNR^{3A}R^{3B}$, —$ONR^{3A}R^{3B}$, —NHC(O)$NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, —$N_3$, —$CF_3$, —$CCl_3$, —$CBr_3$, —$CI_3$, —CN, —$COR^{4A}$, —$OR^{4A}$, —$NR^{4A}R^{4B}$, —$C(O)OR^{4A}$, —$C(O)NR^{4A}R^{4B}$, —$NO_2$, —$SR^{4A}$, —$S(O)_{n4}R^{4A}$, —$S(O)_{n4}OR^{4A}$, —$S(O)_{n4}NR^{4A}R^{4B}$, —$NHNR^{4A}R^{4B}$, —$ONR^{4A}R^{4B}$, —$NHC(O)NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is independently hydrogen, oxo, halogen, —$N_3$, —$CF_3$, —$CCl_3$, —$CBr_3$, —$CI_3$, —CN, —$COR^{7A}$, —$OR^{7A}$, —$NR^{7A}R^{7B}$, —$C(O)OR^{7A}$, —$C(O)NR^{7A}R^{7B}$, —$NO_2$, —$SR^{7A}$, —$S(O)_{n7}R^{7A}$, —$S(O)_{n7}R^{7A}$, —$S(O)_{n7}NR^{7A}R^{7B}$, —$NHNR^{7A}R^{7B}$, —$ONR^{7A}R^{7B}$, —$NHC(O)NHNR^{7A}R^{7B}$, -$L^1$-$R^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is hydrogen, oxo, halogen, —$N_3$, —$CF_3$, —$CCl_3$, —$CBr_3$, —$CI_3$, —CN, —CHO, —$OR^{6A}$, —$NR^{6A}R^{6B}$, —$C(O)OR^{6A}$, —$C(O)NR^{6A}R^{6B}$, —$NO_2$, —$SR^{6A}$, —$S(O)_{n6}R^{6A}$, —$S(O)_{n6}OR^{6A}$, —$S(O)_{n6}NR^{6A}R^{6B}$, —$NHNR^{6A}R^{6B}$, —$ONR^{6A}R^{6B}$, —$NHC(O)NHNR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n1, n2, n3, n4, n6, and n7 are independently 1 or 2; z2 is 1, 2, 3, 4, or 5; and $R^{1A}$, $R^{1B}$, $R^{2A}$, $R^{2B}$, $R^{3A}R^{3B}$, $R^{4A}$, $R^{4B}$, $R^{6A}$, $R^{6B}$, $R^{7A}$, $R^{7B}$, $R^{13}$, and $R^{14}$ are independently hydrogen, oxo, halogen, —$CF_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)OH$, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P92

The method of embodiment 91, wherein said cancer is basal cell carcinoma, medulloblastoma, pancreatic cancer, small cell lung cancer, gastric cancer, colon cancer, or chondrosarcoma.

Embodiment P93

A pharmaceutical composition comprising a compound of any one of embodiments 1 to 87 and a pharmaceutically acceptable excipient.

---

What is claimed is:

1. A compound having the formula:

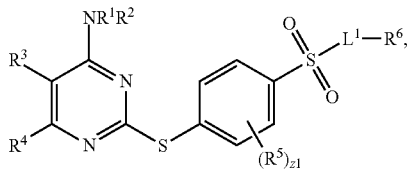

wherein:
L$^1$ is a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^1$ is halogen, —N$_3$, —CF$_3$, —CCl$_3$, —CBr$_3$, —Cl$_3$, —CN, —C(O)R$^{1A}$, —OR$^{1A}$, —NR$^{1A}$R$^{1B}$, —C(O)OR$^{1A}$, —C(O)NR$^{1A}$R$^{1B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is hydrogen, halogen, —N$_3$, —CF$_3$, —CCl$_3$, —CBr$_3$, —Cl$_3$, —CN, —C(O)R$^{2A}$, —OR$^{2A}$, —NR$^{2A}$R$^{2B}$, —C(O)OR$^{2A}$, —C(O)NR$^{2A}$R$^{2B}$, —NO$_2$, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is hydrogen, halogen, —N$_3$, —CF$_3$, —CCl$_3$, —CBr$_3$, —Cl$_3$, —C(O)R$^{3A}$, —OR$^{3A}$, —NR$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$ is hydrogen, halogen, —N$_3$, —CF$_3$, —CCl$_3$, —CBr$_3$, —Cl$_3$, —CN, —C(O)R$^{4A}$, —OR$^{4A}$, —NR$^{4A}$R$^{4B}$, —C(O)OR$^{4A}$, —C(O)NR$^{4A}$R$^{4B}$, —NO$_2$, —SR$^{4A}$, —S(O)$_{n4}$R$^{4A}$, —S(O)$_{n4}$OR$^{4A}$, —S(O)$_{n4}$NR$^{4A}$R$^{4B}$, —NHNR$^{4A}$R$^{4B}$, —ONR$^{4A}$R$^{4B}$, —NHC(O)NHNR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^3$ and R$^4$ are optionally combined to form a substituted or unsubstituted cycloalkyl, substituted or unsubstituted heterocycloalkyl, substituted or unsubstituted aryl, or substituted or unsubstituted heteroaryl;

R$^5$ is independently hydrogen, halogen, —N$_3$, —CF$_3$, —CCl$_3$, —CBr$_3$, —Cl$_3$, —CN, —C(O)R$^{5A}$, —OR$^{5A}$, —NR$^{5A}$R$^{5B}$, —C(O)OR$^{5A}$, —C(O)NR$^{5A}$R$^{5B}$, —NO$_2$, —SR$^{5A}$, —S(O)$_{n5}$R$^{5A}$, —S(O)$_{n5}$OR$^{5A}$, —S(O)$_{n5}$NR$^{5A}$R$^{5B}$, —NHNR$^{5A}$R$^{5B}$, —ONR$^{5A}$R$^{5B}$, —NHC(O)NHNR$^{5A}$R$^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^6$ is hydrogen, oxo, halogen, —N$_3$, —CF$_3$, —CCl$_3$, —CBr$_3$, —Cl$_3$, —CN, —CHO, —OR$^{6A}$, —NR$^{6A}$R$^{6B}$, —C(O)OR$^{6A}$, —C(O)NR$^{6A}$R$^{6B}$, —NO$_2$, —SR$^{6A}$, —S(O)$_{n6}$R$^{6A}$, —S(O)$_{n6}$OR$^{6A}$, —S(O)$_{n6}$NR$^{6A}$R$^{6B}$, —NHNR$^{6A}$R$^{6B}$, —ONR$^{6A}$R$^{6B}$, —NHC(O)NHNR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n1, n2, n3, n4, n5, and n6 are independently 1 or 2;
z1 is 1, 2, 3, or 4; and
R$^{1A}$, R$^{1B}$, R$^{2A}$, R$^{2B}$, R$^{3A}$, R$^{3B}$, R$^{4A}$, R$^{4B}$, R$^{5A}$, R$^{5B}$, R$^{6A}$, R$^{6B}$, and R$^{13}$ are independently hydrogen, oxo, halogen, —CF$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

2. The compound of claim 1, wherein
R$^3$ is hydrogen, halogen, —OR$^{3A}$, Or substituted or unsubstituted alkyl; and
R$^{3A}$ is substituted or unsubstituted alkyl; or
R$^3$ and R$^4$ together form a substituted or unsubstituted cycloalkyl.

3. The compound of claim 1, wherein
R$^4$ is R$^{40}$-substituted or unsubstituted cycloalkyl, R$^{40}$-substituted or unsubstituted heterocycloalkyl, R$^{40}$-substituted or unsubstituted aryl, or R$^{40}$-substituted or unsubstituted heteroaryl;
R$^{40}$ is independently hydrogen, oxo, halogen, —N$_3$, —CF$_3$, —CCl$_3$, —CBr$_3$, —Cl$_3$, —CN, —C(O)R$^{40A}$, —OR$^{40A}$, —NR$^{4A}$R$^{40B}$, —C(O)OR$^{40A}$, —C(O)NR$^{4A}$R$^{40B}$, —NO$_2$, —SR$^{40A}$, —S(O)$_2$R$^{40A}$, —S(O)$_2$OR$^{40A}$, —S(O)$_2$NR$^{40A}$R$^{40B}$, —NHNR$^{40A}$R$^{40B}$, —ONR$^{40A}$R$^{40B}$, —NHC(O)NHNR$^{40A}$R$^{40B}$, R$^{40A}$-substituted or unsubstituted alkyl, $R^{40A}$-substituted or unsubstituted heteroalkyl, $R^{40A}$-substituted or unsubstituted cycloalkyl, $R^{40A}$-substituted or unsubstituted heterocycloalkyl, $R^{40A}$-substituted or unsubstituted aryl, or $R^{40A}$-substituted or unsubstituted heteroaryl;

$R^{40A}$ is independently hydrogen, oxo, halogen, —$N_3$, —$CF_3$, —$CCl_3$, —$CBr_3$, —$CI_3$, —CN, —$OR^{41}$, —$NR^{41}R^{40C}$, —$C(O)R^{41}$, —$COOR^{41}$, —$CONR^{41}R^{40C}$, —$NO_2$, —$SR^{41}$, —$S(O)_2R^{41}$, —$S(O)_3R^{41}$, —$S(O)_2NR^{41}R^{40C}$, $S(O)_4R^{41}$, —$NHNR^{41}R^{40C}$, —$ONR^{41}R^{40C}$, —NHC(O)NHNR$^{41}R^{40C}$, —NHC(O)NR$^{41}R^{40C}$, —$NHS(O)_2R^{41}$, —$NHC(O)R^{41}$, —NHC(O)—$OR^{41}$, —$NHOR^{41}$, —$OCF_3$, —$OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl;

$R^{40B}$ is independently hydrogen, oxo, halogen, —$N_3$, —$CF_3$, —$CCl_3$, —$CBr_3$, —$CI_3$, —CN, —$OR^{45}$, —$NR^{45}R^{40D}$, —$C(O)R^{45}$, —$COOR^{45}$, —$CONR^{45}R^{40D}$, —$NO_2$, —$SR^{45}$, —$S(O)_2R^{45}$, —$S(O)_3R^{45}$, —$S(O)_4R^{45}$, —$S(O)_2NR^{45}R^{40D}$, —$NHNR^4R^{40D}$, —$ONR^{45}R^{40D}$, —NHC(O)NHNR$^{45}R^{40D}$, —NHC(O)NR$^{45}R^{40D}$, —$NHS(O)_2R^{45}$, —$NHC(O)R^{45}$, —NHC(O)—$OR^{45}$, —$NHOR^{45}$, —$OCF_3$, —$OCHF_2$, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl; and $R^{40C}$, $R^{40D}$, $R^{41}$ and $R^{45}$ are independently hydrogen, oxo, halogen, —$N_3$, —$CF_3$, —$CCl_3$, —$CBr_3$, —$CI_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

4. The compound of claim 3, wherein
$R^4$ is $R^{40}$-substituted or unsubstituted piperidinyl, $R^{40}$-substituted or unsubstituted piperazinyl, or $R^{40}$-substituted or unsubstituted morpholino, or $R^{40}$-substituted or unsubstituted pyrrolidinyl.

5. The compound of claim 1, wherein $R^4$ is —$NR^{4A}R^{4B}$ wherein:
$R^{4A}$ is hydrogen, $R^{41}$-substituted or unsubstituted alkyl, or $R^{41}$-substituted or unsubstituted heteroalkyl;
$R^{4B}$ is hydrogen, $R^{45}$-substituted or unsubstituted alkyl, or $R^{45}$-substituted or unsubstituted heteroalkyl;
$R^{41}$ is independently hydrogen, halogen, $CF_3$, —$OR^{41A}$, —$NR^{41A}R^{41B}$, $R^{42}$-substituted or unsubstituted alkyl, $R^{42}$-substituted or unsubstituted heteroalkyl, or $R^{42}$-substituted or unsubstituted aryl;
$R^{45}$ is independently hydrogen, halogen, $CF_3$, —$OR^{45A}$, —$NR^{45A}R^{45B}$, $R^{46}$-substituted or unsubstituted alkyl, $R^{46}$-substituted or unsubstituted heteroalkyl, or $R^{46}$-substituted or unsubstituted aryl;

$R^{41A}$, $R^{41B}$, $R^{45A}$, and $R^{45B}$ are independently hydrogen or unsubstituted $C_1$-$C_5$ alkyl; and $R^{42}$ and $R^{46}$ are independently oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

6. The compound of claim 1, wherein
$R^5$ is hydrogen, —Cl, or —F; and
z1 is 1 or 2.

7. The compound of claim 1, wherein
$L^1$ is $R^{13}$-substituted or unsubstituted alkylene; and
$R^{13}$ is hydrogen, halogen, or substituted or unsubstituted alkyl.

8. The compound of claim 1, wherein $R^6$ is hydrogen, —$CF_3$, —$NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

9. The compound of claim 1, wherein
$R^6$ is $R^{60}$-substituted or unsubstituted aryl; and
$R^{60}$ is independently hydrogen, halogen, —$N_3$, —$CF_3$, —$CCl_3$, —$CBr_3$, —$CI_3$, —CN, —$C(O)R^{61}$, —$OR^{60A}$, —$NR^{60A}R^{60B}$, —$C(O)OR^{60A}$, —$C(O)NR^{6A}R^{60B}$, —$NO_2$, —$SR^{60A}$, —$S(O)_2H$, —$S(O)_2OH$, —$S(O)_2NH_2$, —$NHNH_2$, —$ONH_2$, —$NHC(O)NHNR^{6A}R^{60B}$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl;

$R^{60A}$ is independently hydrogen, halogen, —$NO_2$, —$CF_3$, —CN, —$C(O)R^{61}$, $R^{61}$-substituted or unsubstituted alkyl, $R^{61}$-substituted or unsubstituted heteroalkyl, or $R^{61}$-substituted or unsubstituted aryl;

$R^{61}$ independently hydrogen, halogen, —$N_3$, —$CF_3$, —$CCl_3$, —$CBr_3$, —$CI_3$, —CN, —$C(O)R^{61A}$, —$OR^{61A}$, —$NR^{61A}R^{61B}$, —$C(O)OR^{61A}$, —$C(O)NR^{61A}R^{61B}$, —$NO_2$, —$SR^{61A}$, —$S(O)_2R^{61A}$, —$S(O)_2OR^{61A}$, —$S(O)_2NR^{61A}R^{61B}$, —$NHNR^{61A}R^{61B}$, —$ONR^{61A}R^{61B}$, —$NHC(O)NHNR^{61A}R^{61B}$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl; and $R^{60B}$, $R^{61A}$, $R^{61B}$, and $R^{62}$ is independently hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —NHC(O)NHNH$_2$, —NHC(O)NH$_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

10. The compound of claim 9 having the formula:

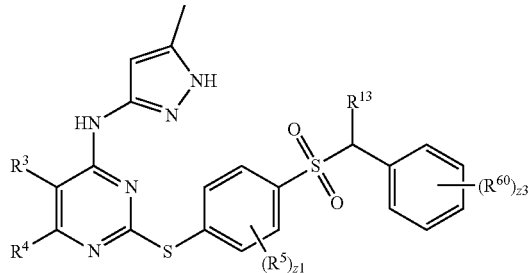

wherein z3 is an integer of 0, 1, 2, 3, 4 or 5.

11. The compound of claim 1, wherein $R^2$ is $R^{2A}$-substituted or unsubstituted cycloalkyl, $R^{2A}$-substituted or unsubstituted heterocycloalkyl, $R^{2A}$-substituted or unsubstituted aryl, or $R^{2A}$-substituted or unsubstituted heteroaryl; and $R^{2A}$ is $-N_3$, $-CF_3$, $-CCl_3$, $-CBr_3$, $-CI_3$, $-CN$, $-OH$, $-NH_2$, $-C(O)OH$, $-C(O)NH_2$, $-NO_2$, $-SH$, substituted or unsubstituted alkyl, or substituted or unsubstituted heteroalkyl.

12. A pharmaceutical composition comprising a compound of claim 1, and a pharmaceutically acceptable excipient.

13. A method of inhibiting a PLK4 kinase, said method comprising contacting said PLK4 kinase with a compound of claim 1, and allowing said compound to bind to said PLK4 kinase, thereby inhibiting said PLK4 kinase.

14. A method of treating cancer in a subject suffering from cancer, said method comprising administering to said subject a therapeutically effective amount of a compound having the formula of claim 1.

15. The method of claim 14, wherein said cancer is basal cell carcinoma, medulloblastoma, pancreatic cancer, small cell lung cancer, gastric cancer, colon cancer, or chondrosarcoma.

16. The compound of claim 1, wherein $R^3$ is hydrogen, halogen, $-N_3$, $-CF_3$, $-CCl_3$, $-CBr_3$, $-CI_3$, $-C(O)R^{3A}$, $-OR^{3A}$, $-NR^{3A}R^{3B}$, $-C(O)OR^{3A}$, $-C(O)NR^{3A}R^{3B}$, $-NO_2$, $-SR^{3A}$, $-S(O)_{n3}R^{3A}$, $-S(O)_{n3}OR^{3A}$, $-S(O)_{n3}NR^{3A}R^{3B}$, $-NHNR^{3A}R^{3B}$, $-ONR^{3A}R^{3B}$, $-NHC(O)NHNR^{3A}R^{3B}$, or substituted or unsubstituted alkyl, or optionally combined with $R^4$ to form a substituted or unsubstituted cycloalkyl; and $R^{3A}$, $R^{3B}$, and $R^{3C}$ are independently hydrogen oxo, halogen, $-CF_3$, $-OH$, $-NH_2$, $-COOH$, $-CONH_2$, substituted or unsubstituted alkyl, or substituted or unsubstituted aryl.

17. The compound of claim 1, wherein $R^4$ is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

18. The compound of claim 1, wherein $R^6$ is substituted or unsubstituted cycloalkyl, substituted or unsubstituted heterocycloalkyl, substituted or unsubstituted aryl, or substituted or unsubstituted heteroaryl.

19. The compound of claim 1, wherein $R^3$ is $-O-CH_3$.

20. The compound of claim 1, wherein $R^1$ is pyrazolyl.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
ggaagctgag tgttaagttc                                              20

<210> SEQ ID NO 2
<211> LENGTH: 970
<212> TYPE: PRT
<213> ORGANISM: Homo sapiens

<400> SEQUENCE: 2

Met Ala Thr Cys Ile Gly Glu Lys Ile Glu Asp Phe Lys Val Gly Asn
1               5                   10                  15

Leu Leu Gly Lys Gly Ser Phe Ala Gly Val Tyr Arg Ala Glu Ser Ile
                20                  25                  30

His Thr Gly Leu Glu Val Ala Ile Lys Met Ile Asp Lys Lys Ala Met
            35                  40                  45

Tyr Lys Ala Gly Met Val Gln Arg Val Gln Asn Glu Val Lys Ile His
        50                  55                  60

Cys Gln Leu Lys His Pro Ser Ile Leu Glu Leu Tyr Asn Tyr Phe Glu
65                  70                  75                  80

Asp Ser Asn Tyr Val Tyr Leu Val Leu Glu Met Cys His Asn Gly Glu
                85                  90                  95

Met Asn Arg Tyr Leu Lys Asn Arg Val Lys Pro Phe Ser Glu Asn Glu
                100                 105                 110
```

```
Ala Arg His Phe Met His Gln Ile Ile Thr Gly Met Leu Tyr Leu His
        115                 120                 125
Ser His Gly Ile Leu His Arg Asp Leu Thr Leu Ser Asn Leu Leu Leu
130                 135                 140
Thr Arg Asn Met Asn Ile Lys Ile Ala Asp Phe Gly Leu Ala Thr Gln
145                 150                 155                 160
Leu Lys Met Pro His Glu Lys His Tyr Thr Leu Cys Gly Thr Pro Asn
                165                 170                 175
Tyr Ile Ser Pro Glu Ile Ala Thr Arg Ser Ala His Gly Leu Glu Ser
                180                 185                 190
Asp Val Trp Ser Leu Gly Cys Met Phe Tyr Thr Leu Leu Ile Gly Arg
            195                 200                 205
Pro Pro Phe Asp Thr Asp Thr Val Lys Asn Thr Leu Asn Lys Val Val
210                 215                 220
Leu Ala Asp Tyr Glu Met Pro Ser Phe Leu Ser Ile Glu Ala Lys Asp
225                 230                 235                 240
Leu Ile His Gln Leu Leu Arg Arg Asn Pro Ala Asp Arg Leu Ser Leu
                245                 250                 255
Ser Ser Val Leu Asp His Pro Phe Met Ser Arg Asn Ser Ser Thr Lys
            260                 265                 270
Ser Lys Asp Leu Gly Thr Val Glu Asp Ser Ile Asp Ser Gly His Ala
        275                 280                 285
Thr Ile Ser Thr Ala Ile Thr Ala Ser Ser Ser Thr Ser Ile Ser Gly
    290                 295                 300
Ser Leu Phe Asp Lys Arg Arg Leu Leu Ile Gly Gln Pro Leu Pro Asn
305                 310                 315                 320
Lys Met Thr Val Phe Pro Lys Asn Lys Ser Ser Thr Asp Phe Ser Ser
                325                 330                 335
Ser Gly Asp Gly Asn Ser Phe Tyr Thr Gln Trp Gly Asn Gln Glu Thr
            340                 345                 350
Ser Asn Ser Gly Arg Gly Arg Val Ile Gln Asp Ala Glu Glu Arg Pro
        355                 360                 365
His Ser Arg Tyr Leu Arg Arg Ala Tyr Ser Ser Asp Arg Ser Gly Thr
    370                 375                 380
Ser Asn Ser Gln Ser Gln Ala Lys Thr Tyr Thr Met Glu Arg Cys His
385                 390                 395                 400
Ser Ala Glu Met Leu Ser Val Ser Lys Arg Ser Gly Gly Gly Glu Asn
                405                 410                 415
Glu Glu Arg Tyr Ser Pro Thr Asp Asn Asn Ala Asn Ile Phe Asn Phe
            420                 425                 430
Phe Lys Glu Lys Thr Ser Ser Ser Gly Ser Phe Glu Arg Pro Asp
        435                 440                 445
Asn Asn Gln Ala Leu Ser Asn His Leu Cys Pro Gly Lys Thr Pro Phe
    450                 455                 460
Pro Phe Ala Asp Pro Thr Pro Gln Thr Glu Thr Val Gln Gln Trp Phe
465                 470                 475                 480
Gly Asn Leu Gln Ile Asn Ala His Leu Arg Lys Thr Thr Glu Tyr Asp
                485                 490                 495
Ser Ile Ser Pro Asn Arg Asp Phe Gln Gly His Pro Asp Leu Gln Lys
            500                 505                 510
Asp Thr Ser Lys Asn Ala Trp Thr Asp Thr Lys Val Lys Lys Asn Ser
        515                 520                 525
```

```
Asp Ala Ser Asp Asn Ala His Ser Val Lys Gln Gln Asn Thr Met Lys
            530                 535                 540

Tyr Met Thr Ala Leu His Ser Lys Pro Glu Ile Ile Gln Gln Glu Cys
545                 550                 555                 560

Val Phe Gly Ser Asp Pro Leu Ser Glu Gln Ser Lys Thr Arg Gly Met
                565                 570                 575

Glu Pro Pro Trp Gly Tyr Gln Asn Arg Thr Leu Arg Ser Ile Thr Ser
            580                 585                 590

Pro Leu Val Ala His Arg Leu Lys Pro Ile Arg Gln Lys Thr Lys Lys
                595                 600                 605

Ala Val Val Ser Ile Leu Asp Ser Glu Glu Val Cys Val Glu Leu Val
610                 615                 620

Lys Glu Tyr Ala Ser Gln Glu Tyr Val Lys Glu Val Leu Gln Ile Ser
625                 630                 635                 640

Ser Asp Gly Asn Thr Ile Thr Ile Tyr Tyr Pro Asn Gly Gly Arg Gly
                645                 650                 655

Phe Pro Leu Ala Asp Arg Pro Ser Pro Thr Asp Asn Ile Ser Arg
                660                 665                 670

Tyr Ser Phe Asp Asn Leu Pro Glu Lys Tyr Trp Arg Lys Tyr Gln Tyr
                675                 680                 685

Ala Ser Arg Phe Val Gln Leu Val Arg Ser Lys Ser Pro Lys Ile Thr
690                 695                 700

Tyr Phe Thr Arg Tyr Ala Lys Cys Ile Leu Met Glu Asn Ser Pro Gly
705                 710                 715                 720

Ala Asp Phe Glu Val Trp Phe Tyr Asp Gly Val Lys Ile His Lys Thr
                725                 730                 735

Glu Asp Phe Ile Gln Val Ile Glu Lys Thr Gly Lys Ser Tyr Thr Leu
                740                 745                 750

Lys Ser Glu Ser Glu Val Asn Ser Leu Lys Glu Glu Ile Lys Met Tyr
                755                 760                 765

Met Asp His Ala Asn Glu Gly His Arg Ile Cys Leu Ala Leu Glu Ser
770                 775                 780

Ile Ile Ser Glu Glu Arg Lys Thr Arg Ser Ala Pro Phe Phe Pro
785                 790                 795                 800

Ile Ile Ile Gly Arg Lys Pro Gly Ser Thr Ser Ser Pro Lys Ala Leu
                805                 810                 815

Ser Pro Pro Pro Ser Val Asp Ser Asn Tyr Pro Thr Arg Glu Arg Ala
                820                 825                 830

Ser Phe Asn Arg Met Val Met His Ser Ala Ala Ser Pro Thr Gln Ala
                835                 840                 845

Pro Ile Leu Asn Pro Ser Met Val Thr Asn Glu Gly Leu Gly Leu Thr
                850                 855                 860

Thr Thr Ala Ser Gly Thr Asp Ile Ser Ser Asn Ser Leu Lys Asp Cys
865                 870                 875                 880

Leu Pro Lys Ser Ala Gln Leu Leu Lys Ser Val Phe Val Lys Asn Val
                885                 890                 895

Gly Trp Ala Thr Gln Leu Thr Ser Gly Ala Val Trp Gln Phe Asn
                900                 905                 910

Asp Gly Ser Gln Leu Val Val Gln Ala Gly Val Ser Ser Ile Ser Tyr
                915                 920                 925

Thr Ser Pro Asn Gly Gln Thr Thr Arg Tyr Gly Glu Asn Glu Lys Leu
                930                 935                 940
```

```
Pro Asp Tyr Ile Lys Gln Lys Leu Gln Cys Leu Ser Ser Ile Leu Leu
945                 950                 955                 960

Met Phe Ser Asn Pro Thr Pro Asn Phe His
                965                 970
```